United States Patent
Lerchen et al.

(10) Patent No.: US 10,744,205 B2
(45) Date of Patent: Aug. 18, 2020

(54) ANTIBODY DRUG CONJUGATES OF KINESIN SPINDEL PROTEIN (KSP) INHIBITORS WITH ANTI-CD123-ANTIBODIES

(71) Applicant: Bayer Pharma Aktiengesellschaft, Berlin (DE)

(72) Inventors: Hans-Georg Lerchen, Leverkusen (DE); Anne-Sophie Rebstock, Champagne au Mont d'Or (FR); Yolanda Cancho Grande, Leverkusen (DE); Sven Wittrock, Berlin (DE); Beatrix Stelte-Ludwig, Wülfrath (DE); Christoph Mahlert, Wuppertal (DE); Simone Greven, Dormagen (DE); Stephan Märsch, Cologne (DE); Dennis Kirchhoff, Berlin (DE)

(73) Assignee: Bayer Pharma Aktiengesellschaft, Berlin (DE)

( * ) Notice: Subject to any disclaimer, the term of this patent is extended or adjusted under 35 U.S.C. 154(b) by 0 days.

(21) Appl. No.: 15/739,134

(22) PCT Filed: Jun. 20, 2016

(86) PCT No.: PCT/EP2016/064133
§ 371 (c)(1),
(2) Date: Dec. 21, 2017

(87) PCT Pub. No.: WO2016/207098
PCT Pub. Date: Dec. 29, 2016

(65) Prior Publication Data
US 2018/0318437 A1    Nov. 8, 2018

(30) Foreign Application Priority Data

Jun. 23, 2015 (EP) .................... 15173479

(51) Int. Cl.
| | |
|---|---|
| *A61K 47/68* | (2017.01) |
| *A61K 31/4025* | (2006.01) |
| *A61K 38/00* | (2006.01) |
| *A61P 35/00* | (2006.01) |
| *C07D 207/33* | (2006.01) |
| *A61K 31/40* | (2006.01) |
| *C07K 16/28* | (2006.01) |
| *A61K 39/00* | (2006.01) |

(52) U.S. Cl.
CPC .......... *A61K 47/6803* (2017.08); *A61K 31/40* (2013.01); *A61K 31/4025* (2013.01); *A61K 47/6849* (2017.08); *A61K 47/6851* (2017.08); *A61P 35/00* (2018.01); *C07D 207/33* (2013.01); *C07K 16/2866* (2013.01); *A61K 2039/505* (2013.01); *A61K 2039/572* (2013.01); *C07K 2317/24* (2013.01); *C07K 2317/56* (2013.01); *C07K 2317/565* (2013.01); *C07K 2317/73* (2013.01); *C07K 2317/76* (2013.01); *C07K 2317/92* (2013.01)

(58) Field of Classification Search
CPC .... C07D 207/335; A61K 35/00; A61K 47/00; A61K 38/00; A61K 47/6803; A61K 31/4025; A61P 35/00; A61P 38/00
See application file for complete search history.

(56) References Cited

U.S. PATENT DOCUMENTS

| | | | |
|---|---|---|---|
| 10,022,453 B2 * | 7/2018 | Lerchen | ............... C07D 413/12 |
| 10,485,880 B2 | 11/2019 | Lerchen | |
| 2008/0193445 A1 | 8/2008 | Goetsch | |
| 2014/0322247 A1 | 10/2014 | Barsanti | |
| 2016/0346402 A1 | 12/2016 | Lerchen | |
| 2018/0015176 A1 | 1/2018 | Lerchen | |
| 2018/0169256 A1 | 6/2018 | Lerchen | |
| 2018/0185510 A1 | 7/2018 | Lerchen | |
| 2018/0318438 A1 | 11/2018 | Lerchen | |
| 2019/0077752 A1 | 3/2019 | Lerchen | |
| 2019/0262463 A1 | 8/2019 | Lerchen | |
| 2019/0328897 A1 | 10/2019 | Lerchen | |
| 2019/0330357 A1 | 10/2019 | Lerchen | |
| 2019/0351066 A1 | 11/2019 | Lerchen | |
| 2019/0365916 A1 | 12/2019 | Lerchen | |

FOREIGN PATENT DOCUMENTS

| | | | |
|---|---|---|---|
| CA | 2990411 A1 | 12/2016 | |
| CA | 3018630 A1 | 9/2017 | |
| EP | 2311879 A2 | 4/2011 | |

(Continued)

OTHER PUBLICATIONS

International Search Report and Written Opinion dated Sep. 19, 2016, for PCT Application No. PCT/EP2016/064133, filed on Jun. 20, 2016, 14 pages.

(Continued)

*Primary Examiner* — Venkataraman Balasubramanian

(74) *Attorney, Agent, or Firm* — Morrison & Foerster LLP

(57) ABSTRACT

The present application relates to novel binder drug conjugates (ADCs), to active metabolites of these ADCs, to processes for preparing these ADCs, to the use of these ADCs for the treatment and/or prophylaxis of diseases and to the use of these ADCs for preparing medicaments for treatment and/or prophylaxis of diseases, in particular hyperproliferative and/or angiogenic disorders such as, for example, cancer diseases. Such treatments can be effected as monotherapy or else in combination with other medicaments or further therapeutic measures.

28 Claims, 8 Drawing Sheets

Specification includes a Sequence Listing.

(56) References Cited

FOREIGN PATENT DOCUMENTS

| WO | WO-2008127735 A1 | * | 10/2008 | ......... C07K 16/2866 |
| WO | WO-2012021934 A1 | * | 2/2012 | ......... C07K 16/2866 |
| WO | WO-2013173820 A2 | * | 11/2013 | ......... C07K 16/2809 |
| WO | WO2014093640 A1 | | 6/2014 | |
| WO | WO2014151030 A1 | | 9/2014 | |
| WO | WO2014160160 A2 | | 10/2014 | |
| WO | WO2015054659 A1 | | 4/2015 | |
| WO | WO2015089449 A2 | | 6/2015 | |
| WO | WO-2015096982 A1 | * | 7/2015 | ........... C07D 403/12 |
| WO | WO2015096982 A1 | | 7/2015 | |
| WO | WO2015138615 A2 | | 9/2015 | |
| WO | WO2016020791 A1 | | 2/2016 | |
| WO | WO2016096610 A1 | | 6/2016 | |
| WO | WO2016207089 A1 | | 12/2016 | |
| WO | WO2016207090 A2 | | 12/2016 | |
| WO | WO2016207094 A1 | | 12/2016 | |
| WO | WO2016207098 A1 | | 12/2016 | |
| WO | WO2016207103 A1 | | 12/2016 | |
| WO | WO2016207104 A1 | | 12/2016 | |
| WO | WO2017162663 A1 | | 9/2017 | |
| WO | WO2017216028 A1 | | 12/2017 | |
| WO | WO2018114578 A1 | | 6/2018 | |
| WO | WO2018114798 A1 | | 6/2018 | |
| WO | WO2018114804 A1 | | 6/2018 | |

OTHER PUBLICATIONS

U.S. Appl. No. 16/472,682, filed Jun. 21, 2019, for Hans-Georg Lerchen et al, (Copy not attached) (U.S. Patent Application is not submitted herewith pursuant to the waiver of 37 C.F.R § 1.98(a)(2)(iii) issued by the Office on Sep. 21, 2004.).

U.S. Appl. No. 16/472,749, filed Jun. 21, 2019, for Hans-Georg Lerchen et al. (Copy not attached) (U.S. Patent Application is not submitted herewith pursuant to the waiver of 37 C.F.R § 1.98(a)(2)(iii) issued by the Office on Sep. 21, 2004.).

U.S. Appl. No. 15/739,471, filed Feb. 22, 2019, for Lerchen et al. (Copy not attached) (U.S. Patent Application is not submitted herewith pursuant to the waiver of 37 C.F.R § 1.98(a)(2)(iii) issued by the Office on Sep. 21, 2004.).

* cited by examiner

FIG. 1

<SEQ ID NO:1>
QVQLVQSGAEVKKPGASVKVSCKASGYTFTDYYMKWVRQAPGQGLEWMGDIIPSNGATFYAQKFQGRVTMTRDTSTS
TVYMELSSLRSEDTAVYYCARSHLLRASWFAYWGQGTLVTVSS

<SEQ ID NO:2>
DYYMK

<SEQ ID NO:3>
DIIPSNGATFYAQKFQG

<SEQ ID NO:4>
ARSHLLRASWFAY

<SEQ ID NO:5>
DIVMTQSPDSLAVSLGERATINCKSSQSLLNSGNQKNYLTWYQQKPGQPPKLLIYWASTRESGVPDRFSGSGSGTDF
TLTISSLQAEDVAVYYCQNDYSYPYTFGQGTKLEIK

<SEQ ID NO:6>
KSSQSLLNSGNQKNYLT

<SEQ ID NO:7>
WASTRES

<SEQ ID NO:8>
QNDYSYPYT

<SEQ ID NO:9>
QVQLVQSGAEVKKPGASVKVSCKASGYTFTDYYMKWVRQAPGQGLEWMGDIIPSNGATFYAQKFQGRVTMTRDTSTS
TVYMELSSLRSEDTAVYYCARSHLLRASWFAYWGQGTLVTVSSASTKGPSVFPLAPSSKSTSGGTAALGCLVKDYFP
EPVTVSWNSGALTSGVHTFPAVLQSSGLYSLSSVVTVPSSSLGTQTYICNVNHKPSNTKVDKKVEPKSCDKTHTCPP
CPAPELLGGPSVFLFPPKPKDTLMISRTPEVTCVVVDVSHEDPEVKFNWYVDGVEVHNAKTKPREEQYNSTYRVVSV
LTVLHQDWLNGKEYKCKVSNKALPAPIEKTISKAKGQPREPQVYTLPPSRDELTKNQVSLTCLVKGFYPSDIAVEWE
SNGQPENNYKTTPPVLDSDGSFFLYSKLTVDKSRWQQGNVFSCSVMHEALHNHYTQKSLSLSPG

<SEQ ID NO:10>
DIVMTQSPDSLAVSLGERATINCKSSQSLLNSGNQKNYLTWYQQKPGQPPKLLIYWASTRESGVPDRFSGSGSGTDF
TLTISSLQAEDVAVYYCQNDYSYPYTFGQGTKLEIKRTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

<SEQ ID NO:11>
QVQLVQSGAEVKKPGSSVKVSCKASGGTFSDYYMKWVRQAPGQGLEWMGDIIPSNGATFYAQKFQGRVTITADESTS
TAYMELSSLRSEDTAVYYCARSHLLRASWFAYWGQGTLVTVSS

<SEQ ID NO:12>
DYYMK

<SEQ ID NO:13>
DIIPSNGATFYAQKFQG

<SEQ ID NO:14>
ARSHLLRASWFAY

*FIG. 1 (continued)*

<SEQ ID NO:15>
DIVMTQSPDSLAVSLGERATINCESSQSLLNSGNQKNYLTWYQQKPGQPPKLLIYWASTRESGVPDRFSGSGSGTDF
TLTISSLQAEDVAVYYCQNDYSYPYTFGQGTKLEIK

<SEQ ID NO:16>
ESSQSLLNSGNQKNYLT

<SEQ ID NO:17>
WASTRES

<SEQ ID NO:18>
QNDYSYPYT

<SEQ ID NO:19>
QVQLVQSGAEVKKPGSSVKVSCKASGGTFSDYYMKWVRQAPGQGLEWMGDIIPSNGATFYAQKFQGRVTITADESTS
TAYMELSSLRSEDTAVYYCARSHLLRASWFAYWGQGTLVTVSSASTKGPSVFPLAPSSKSTSGGTAALGCLVKDYFP
EPVTVSWNSGALTSGVHTFPAVLQSSGLYSLSSVVTVPSSSLGTQTYICNVNHKPSNTKVDKKVEPKSCDKTHTCPP
CPAPELLGGPSVFLFPPKPKDTLMISRTPEVTCVVVDVSHEDPEVKFNWYVDGVEVHNAKTKPREEQYNSTYRVVSV
LTVLHQDWLNGKEYKCKVSNKALPAPIEKTISKAKGQPREPQVYTLPPSRDELTKNQVSLTCLVKGFYPSDIAVEWE
SNGQPENNYKTTPPVLDSDGSFFLYSKLTVDKSRWQQGNVFSCSVMHEALHNHYTQKSLSLSPG

<SEQ ID NO:20>
DIVMTQSPDSLAVSLGERATINCESSQSLLNSGNQKNYLTWYQQKPGQPPKLLIYWASTRESGVPDRFSGSGSGTDF
TLTISSLQAEDVAVYYCQNDYSYPYTFGQGTKLEIKRTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

<SEQ ID NO:21>
QVQLVQSGAEVKKPGSSVKVSCKASGGTFSDYYMKWVRQAPGQGLEWMGDIIPSNGATFYAQKFQGRVTITADESTS
TAYMELSSLRSEDTAVYYCARSHLLRASWFAYWGQGTLVTVSS

<SEQ ID NO:22>
DYYMK

<SEQ ID NO:23>
DIIPSNGATFYAQKFQG

<SEQ ID NO:24>
ARSHLLRASWFAY

<SEQ ID NO:25>
DIVMTQSPDSLAVSLGERATINCKSSQSLLNSGNQKNYLTWYQQKPGQPPKLLIYWASTRESGVPDRFSGSGSGTDF
TLTISSLQAEDVAVYYCQNDYSYPYTFGQGTKLEIK

<SEQ ID NO:26>
KSSQSLLNSGNQKNYLT

<SEQ ID NO:27>
WASTRES

<SEQ ID NO:28>
QNDYSYPYT

FIG. 1 (continued)

<SEQ ID NO:29>
QVQLVQSGAEVKKPGSSVKVSCKASGGTFSDYYMKWVRQAPGQGLEWMGDIIPSNGATFYAQKFQGRVTITADESTS
TAYMELSSLRSEDTAVYYCARSHLLRASWFAYWGQGTLVTVSSASTKGPSVFPLAPSSKSTSGGTAALGCLVKDYFP
EPVTVSWNSGALTSGVHTFPAVLQSSGLYSLSSVVTVPSSSLGTQTYICNVNHKPSNTKVDKKVEPKSCDKTHTCPP
CPAPELLGGPSVFLFPPKPKDTLMISRTPEVTCVVVDVSHEDPEVKFNWYVDGVEVHNAKTKPREEQYNSTYRVVSV
LTVLHQDWLNGKEYKCKVSNKALPAPIEKTISKAKGQPREPQVYTLPPSRDELTKNQVSLTCLVKGFYPSDIAVEWE
SNGQPENNYKTTPPVLDSDGSFFLYSKLTVDKSRWQQGNVFSCSVMHEALHNHYTQKSLSLSPG

<SEQ ID NO:30>
DIVMTQSPDSLAVSLGERATINCKSSQSLLNSGNQKNYLTWYQQKPGQPPKLLIYWASTRESGVPDRFSGSGSGTDF
TLTISSLQAEDVAVYYCQNDYSYPYTFGQGTKLEIKRTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

<SEQ ID NO:31>
QVQLQESGPGLVKPSQSLSLTCSVTDYSITSGYYWNWIRQFPGNKLEWMGYISYDGSNNYNPSLKNRISITRDTSKN
QFFLKLSSVTTEDTATYYCSRGEGFYFDSWGQGTTLTVSS

<SEQ ID NO:32>
SGYYWN

<SEQ ID NO:33>
YISYDGSNNYNPSLKN

<SEQ ID NO:34>
SRGEGFYFDS

<SEQ ID NO:35>
DIMMSQSPSSLAVSVGEKFTMTCKSSQSLFFGSTQKNYLAWYQQKPGQSPKLLIYWASTRESGVPDRFTGSGSGTDF
TLAISSVMPEDLAVYYCQQYYNYPWTFGGGTKLEIK

<SEQ ID NO:36>
KSSQSLFFGSTQKNYLA

<SEQ ID NO:37>
WASTRES

<SEQ ID NO:38>
QQYYNYPWT

<SEQ ID NO:39>
QVQLQESGPGLVKPSQSLSLTCSVTDYSITSGYYWNWIRQFPGNKLEWMGYISYDGSNNYNPSLKNRISITRDTSKN
QFFLKLSSVTTEDTATYYCSRGEGFYFDSWGQGTTLTVSSASTKGPSVFPLAPSSKSTSGGTAALGCLVKDYFPEPV
TVSWNSGALTSGVHTFPAVLQSSGLYSLSSVVTVPSSSLGTQTYICNVNHKPSNTKVDKKVEPKSCDKTHTCPPCPA
PELLGGPSVFLFPPKPKDTLMISRTPEVTCVVVDVSHEDPEVKFNWYVDGVEVHNAKTKPREEQYNSTYRVVSVLTV
LHQDWLNGKEYKCKVSNKALPAPIEKTISKAKGQPREPQVYTLPPSRDELTKNQVSLTCLVKGFYPSDIAVEWESNG
QPENNYKTTPPVLDSDGSFFLYSKLTVDKSRWQQGNVFSCSVMHEALHNHYTQKSLSLSPG

<SEQ ID NO:40>
DIMMSQSPSSLAVSVGEKFTMTCKSSQSLFFGSTQKNYLAWYQQKPGQSPKLLIYWASTRESGVPDRFTGSGSGTDF
TLAISSVMPEDLAVYYCQQYYNYPWTFGGGTKLEIKRTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

*FIG. 1 (continued)*

<SEQ ID NO:41>
KEDPNPPITNLRMKAKAQQLTWDLNRNVTDIECVKDADYSMPAVNNSYCQFGAISLCEVTNYTVRVANPPFSTWILF
PENSGKPWAGAENLTCWIHDVDFLSCSWAVGPGAPADVQYDLYLNVANRRQQYECLHYKTDAQGTRIGCRFDDISRL
SSGSQSSHILVRGRSAAFGIPCTDKFVVFSQIEILTPPNMTAKCNKTHSFMHWKMRSHFNRKFRYELQIQKRMQPVI
TEQVRDRTSFQLLNPGTYTVQIRARERVYEFLSAWSTPQRFECDQEEGANTRAWRTSLLIALGTLLALVCVFVICRR
YLVMQRLFPRIPHMKDPIGDSFQNDKLVVWEAGKAGLEECLVTEVQVVQKT

SEQ ID NO:42 (Polypeptide)
KEDPNPPITN LRMKAKAQQL TWDLNRNVTD IECVKDADYS MPAVNNSYCQ FGAISLCEVT NYTVRVANPP
FSTWILFPEN SGKPWAGAEN LTCWIHDVDF LSCSWAVGPG APADVQYDLY LNVANRRQQY ECLHYKTDAQ
GTRIGCRFDD ISRLSSGSQS SHILVRGRSA AFGIPCTDKF VVFSQIEILT PPNMTAKCNK THSFMHWKMR
SHFNRKFRYE LQIQKRMQPV ITEQVRDRTS FQLLNPGTYT VQIRARERVY EFLSAWSTPQ RFECDQEEGA
NTRAWR

FIG. 2

```
>TPP-5968 VH (PRT)
QVQLVQSGAEVKKPGASVKVSCKASGYTFTDYYMKWVRQAPGQGLEWMGDIIPSNGATFYAQKFQGRVTMTRDTSTSTVY
                        |---|                   |-----HCDR2-----|
                        HCDR1

MELSSLRSEDTAVYYCARSHLLRASWFAYWGQGTLVTVSS
              |---HCDR3---|

>TPP-5968 VL (PRT)
DIVMTQSPDSLAVSLGERATINCKSSQSLLNSGNQKNYLTWYQQKPGQPPKLLIYWASTRESGVPDRFSGSGSGTDFTLT
                   |--------LCDR1--------|                    |-----|
                                                                LCDR2

ISSLQAEDVAVYYCQNDYSYPYTFGQGTKLEIK
            |-LCDR3-|

>TPP-5968 Heavy Chain (PRT)
QVQLVQSGAEVKKPGASVKVSCKASGYTFTDYYMKWVRQAPGQGLEWMGDIIPSNGATFYAQKFQGRVTMTRDTSTSTVY
|-------------------------------------------------------------VH-------------------
                        |---|                   |-----HCDR2-----|
                        HCDR1

MELSSLRSEDTAVYYCARSHLLRASWFAYWGQGTLVTVSSASTKGPSVFPLAPSSKSTSGGTAALGCLVKDYFPEPVTVS
----------------------------------------|
              |-----HCDR3-----|

WNSGALTSGVHTFPAVLQSSGLYSLSSVVTVPSSSLGTQTYICNVNHKPSNTKVDKKVEPKSCDKTHTCPPCPAPELLGG

PSVFLFPPKPKDTLMISRTPEVTCVVVDVSHEDPEVKFNWYVDGVEVHNAKTKPREEQYNSTYRVVSVLTVLHQDWLNGK

EYKCKVSNKALPAPIEKTISKAKGQPREPQVYTLPPSRDELTKNQVSLTCLVKGFYPSDIAVEWESNGQPENNYKTTPPV

LDSDGSFFLYSKLTVDKSRWQQGNVFSCSVMHEALHNHYTQKSLSLSPG

>TPP-5968 Light Chain (PRT)
DIVMTQSPDSLAVSLGERATINCKSSQSLLNSGNQKNYLTWYQQKPGQPPKLLIYWASTRESGVPDRFSGSGSGTDFTLT
|------------------------------------------------------------VL--------------------
                   |-----LCDR1-----|                          |-----|
                                                                LCDR2

ISSLQAEDVAVYYCQNDYSYPYTFGQGTKLEIKRTVAAPSVFIFPPSDEQLKSGTASVVCLLNNFYPREAKVQWKVDNAL
-------------------------------|
            |-LCDR3-|

QSGNSQESVTEQDSKDSTYSLSSTLTLSKADYEKHKVYACEVTHQGLSSPVTKSFNRGEC
```

FIG. 2 (continued)

```
>TPP-5969 VH (PRT)
QVQLVQSGAEVKKPGSSVKVSCKASGGTFSDYYMKWVRQAPGQGLEWMGDIIPSNGATFYAQKFQGRVTITADESTSTAY
                            |---|                   |-----HCDR2-----|
                            HCDR1

MELSSLRSEDTAVYYCARSHLLRASWFAYWGQGTLVTVSS
              |---HCDR3---|

>TPP-5969 VL (PRT)
DIVMTQSPDSLAVSLGERATINCESSQSLLNSGNQKNYLTWYQQKPGQPPKLLIYWASTRESGVPDRFSGSGSGTDFTLT
                  |-----LCDR1-----|                    |-----|
                                                        LCDR2

ISSLQAEDVAVYYCQNDYSYPYTFGQGTKLEIK
            |-LCDR3-|

>TPP-5969 Heavy Chain (PRT)
QVQLVQSGAEVKKPGSSVKVSCKASGGTFSDYYMKWVRQAPGQGLEWMGDIIPSNGATFYAQKFQGRVTITADESTSTAY
|---------------------------------------------------------VH--------------------
                            |---|                   |--------HCDR2--------|
                            HCDR1

MELSSLRSEDTAVYYCARSHLLRASWFAYWGQGTLVTVSSASTKGPSVFPLAPSSKSTSGGTAALGCLVKDYFPEPVTVS
--------------------------------------|
              |-----HCDR3-----|

WNSGALTSGVHTFPAVLQSSGLYSLSSVVTVPSSSLGTQTYICNVNHKPSNTKVDKKVEPKSCDKTHTCPPCPAPELLGG

PSVFLFPPKPKDTLMISRTPEVTCVVVDVSHEDPEVKFNWYVDGVEVHNAKTKPREEQYNSTYRVVSVLTVLHQDWLNGK

EYKCKVSNKALPAPIEKTISKAKGQPREPQVYTLPPSRDELTKNQVSLTCLVKGFYPSDIAVEWESNGQPENNYKTTPPV

LDSDGSFFLYSKLTVDKSRWQQGNVFSCSVMHEALHNHYTQKSLSLSPG

>TPP-5969 Light Chain (PRT)
DIVMTQSPDSLAVSLGERATINCESSQSLLNSGNQKNYLTWYQQKPGQPPKLLIYWASTRESGVPDRFSGSGSGTDFTLT
|------------------------------------------------------VL----------------------
                  |-----LCDR1-----|                    |-----|
                                                        LCDR2

ISSLQAEDVAVYYCQNDYSYPYTFGQGTKLEIKRTVAAPSVFIFPPSDEQLKSGTASVVCLLNNFYPREAKVQWKVDNAL
--------------------------------|
            |-LCDR3-|

QSGNSQESVTEQDSKDSTYSLSSTLTLSKADYEKHKVYACEVTHQGLSSPVTKSFNRGEC
```

*FIG. 2 (continued)*

```
>TPP-5971 VH (PRT)
QVQLVQSGAEVKKPGSSVKVSCKASGGTFSDYYMKWVRQAPGQGLEWMGDIIPSNGATFYAQKFQGRVTITADESTSTAY
                              |---|                    |-----HCDR2-----|
                              HCDR1

MELSSLRSEDTAVYYCARSHLLRASWFAYWGQGTLVTVSS
            |---HCDR3---|

>TPP-5971 VL (PRT)
DIVMTQSPDSLAVSLGERATINCKSSQSLLNSGNQKNYLTWYQQKPGQPPKLLIYWASTRESGVPDRFSGSGSGTDFTLT
                    |-----LCDR1-----|                     |-----|
                                                            LCDR2

ISSLQAEDVAVYYCQNDYSYPYTFGQGTKLEIK
            |-LCDR3-|

>TPP-5971 Heavy Chain (PRT)
QVQLVQSGAEVKKPGSSVKVSCKASGGTFSDYYMKWVRQAPGQGLEWMGDIIPSNGATFYAQKFQGRVTITADESTSTAY
|----------------------------------------------------------VH----------------------
                              |-----|                    |--------HCDR2--------|
                              HCDR1

MELSSLRSEDTAVYYCARSHLLRASWFAYWGQGTLVTVSSASTKGPSVFPLAPSSKSTSGGTAALGCLVKDYFPEPVTVS
---------------------------------------|
            |-----HCDR3-----|

WNSGALTSGVHTFPAVLQSSGLYSLSSVVTVPSSSLGTQTYICNVNHKPSNTKVDKKVEPKSCDKTHTCPPCPAPELLGG

PSVFLFPPKPKDTLMISRTPEVTCVVVDVSHEDPEVKFNWYVDGVEVHNAKTKPREEQYNSTYRVVSVLTVLHQDWLNGK

EYKCKVSNKALPAPIEKTISKAKGQPREPQVYTLPPSRDELTKNQVSLTCLVKGFYPSDIAVEWESNGQPENNYKTTPPV

LDSDGSFFLYSKLTVDKSRWQQGNVFSCSVMHEALHNHYTQKSLSLSPG

>TPP-5971 Light Chain (PRT)
DIVMTQSPDSLAVSLGERATINCKSSQSLLNSGNQKNYLTWYQQKPGQPPKLLIYWASTRESGVPDRFSGSGSGTDFTLT
|--------------------------------------------------VL------------------------------
                    |-----LCDR1-----|                     |-----|
                                                            LCDR2

ISSLQAEDVAVYYCQNDYSYPYTFGQGTKLEIKRTVAAPSVFIFPPSDEQLKSGTASVVCLLNNFYPREAKVQWKVDNAL
------------------------------------|
            |-LCDR3-|

QSGNSQESVTEQDSKDSTYSLSSTLTLSKADYEKHKVYACEVTHQGLSSPVTKSFNRGEC
```

FIG. 2 (continued)

```
>TPP-6013 VH (PRT)
QVQLQESGPGLVKPSQSLSLTCSVTDYSITSGYYWNWIRQFPGNKLEWMGYISYDGSNNYNPSLKNRISITRDTSKNQFF
                        |----|                      |----HCDR2-----|
                        HCDR1

LKLSSVTTEDTATYYCSRGEGFYFDSWGQGTTLTVSS
              |-HCDR3--|

>TPP-6013 VL (PRT)
DIMMSQSPSSLAVSVGEKFTMTCKSSQSLFFGSTQKNYLAWYQQKPGQSPKLLIYWASTRESGVPDRFTGSGSGTDFTLA
                  |-----LCDR1-----|                  |-----|
                                                       LCDR2

ISSVMPEDLAVYYCQQYYNYPWTFGGGTKLEIK
              |-LCDR3-|

>TPP-6013 Heavy Chain (PRT)
QVQLQESGPGLVKPSQSLSLTCSVTDYSITSGYYWNWIRQFPGNKLEWMGYISYDGSNNYNPSLKNRISITRDTSKNQFF
|-----------------------------------------------------VH---------------------
                        |------|                      |-------HCDR2--------|
                        HCDR1

LKLSSVTTEDTATYYCSRGEGFYFDSWGQGTTLTVSSASTKGPSVFPLAPSSKSTSGGTAALGCLVKDYFPEPVTVSWNS
----------------------------------------|
              |-HCDR3--|

GALTSGVHTFPAVLQSSGLYSLSSVVTVPSSSLGTQTYICNVNHKPSNTKVDKKVEPKSCDKTHTCPPCPAPELLGGPSV

FLFPPKPKDTLMISRTPEVTCVVVDVSHEDPEVKFNWYVDGVEVHNAKTKPREEQYNSTYRVVSVLTVLHQDWLNGKEYK

CKVSNKALPAPIEKTISKAKGQPREPQVYTLPPSRDELTKNQVSLTCLVKGFYPSDIAVEWESNGQPENNYKTTPPVLDS

DGSFFLYSKLTVDKSRWQQGNVFSCSVMHEALHNHYTQKSLSLSPG

>TPP-6013 Light Chain (PRT)
DIMMSQSPSSLAVSVGEKFTMTCKSSQSLFFGSTQKNYLAWYQQKPGQSPKLLIYWASTRESGVPDRFTGSGSGTDFTLA
|----------------------------------------------------VL---------------------
                  |-----LCDR1-----|                  |-----|
                                                       LCDR2

ISSVMPEDLAVYYCQQYYNYPWTFGGGTKLEIKRTVAAPSVFIFPPSDEQLKSGTASVVCLLNNFYPREAKVQWKVDNAL
----------------------------------|
              |-LCDR3-|

QSGNSQESVTEQDSKDSTYSLSSTLTLSKADYEKHKVYACEVTHQGLSSPVTKSFNRGEC
```

ANTIBODY DRUG CONJUGATES OF KINESIN SPINDEL PROTEIN (KSP) INHIBITORS WITH ANTI-CD123-ANTIBODIES

CROSS REFERENCE TO RELATED APPLICATIONS

This application is the national stage of International Application No. PCT/EP2016/064133, filed internationally on Jun. 20, 2016, which claims the benefit of European Application No. 15173479.5, filed Jun. 23, 2015.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 777052018700SeqList.txt, date recorded: Dec. 21, 2017, size: 43 KB).

INTRODUCTION AND STATE OF THE ART

The invention relates to binder drug conjugates (ADCs) of kinesin spindle protein inhibitors, to active metabolites of these ADCs, to processes for preparing these ADCs, to the use of these ADCs for the treatment and/or prophylaxis of diseases and to the use of these ADCs for preparing medicaments for treatment and/or prevention of diseases, in particular hyperproliferative and/or angiogenic disorders such as, for example, cancer diseases. Such treatments can be effected as monotherapy or else in combination with other medicaments or further therapeutic measures.

Cancers are the consequence of uncontrolled cell growth of the most diverse tissues. In many cases the new cells penetrate into existing tissue (invasive growth), or they metastasize into remote organs. Cancers occur in a wide variety of different organs and often have tissue-specific courses. The term "cancer" as a generic term therefore describes a large group of defined diseases of different organs, tissue and cell types.

Some tumours at early stages can be removed by surgical and radiotherapy measures. Metastased tumours as a rule can only be treated palliatively by chemotherapeutics. The aim here is to achieve the optimum combination of an improvement in the quality of life and prolonging of life.

Conjugates of binder proteins with one or more active compound molecules are known, in particular in the form of antibody drug conjugates (ADCs) in which an internalising antibody directed against a tumour-associated antigen is covalently attached via a linker to a cytotoxic agent. Following introduction of the ADCs into the tumour cell and subsequent dissociation of the conjugate, either the cytotoxic agent itself or a cytotoxic metabolite formed therefrom is released within the tumour cell and can unfold its action therein directly and selectively. In this manner, in contrast to conventional chemotherapy, damage to normal tissue is contained in significantly narrower limits [see, for example, J. M. Lambert, Curr. Opin. Pharmacol. 5, 543-549 (2005); A. M. Wu and P. D. Senter, Nat. Biotechnol. 23, 1137-1146 (2005); P. D. Senter, Curr. Opin. Chem. Biol. 13, 235-244 (2009); L. Ducry and B. Stump, Bioconjugate Chem. 21, 5-13 (2010)]. Thus, WO2012/171020 describes ADCs in which a plurality of toxophor molecules are attached via a polymeric linker to an antibody. As possible toxophors, WO2012/171020 mentions, among others, the substances SB 743921, SB 715992 (Ispinesib), MK-0371, AZD8477, AZ3146 and ARRY-520.

The substances mentioned last are kinesin spindle protein inhibitors. Kinesin spindle protein (KSP, also known as Eg5, HsEg5, KNSL1 or KIF11) is a kinesin-like motorprotein which is essential for the bipolar mitotic spindle to function. Inhibition of KSP leads to mitotic arrest and, over a relatively long term, to apoptosis (Tao et al., Cancer Cell 2005 Jul. 8(1), 39-59). After the discovery of the first cell-permeable KSP inhibitor, monastrol, KSP inhibitors have established themselves as a class of novel chemotherapeutics (Mayer et al., Science 286: 971-974, 1999) and have been the subject of a number of patent applications (e.g. WO2006/044825; WO2006/002236; WO2005/051922; WO2006/060737; WO03/060064; WO03/040979; and WO03/049527). However, since KSP unfolds its action only during a relatively short period of time during the mitosis phase, KSP inhibitors have to be present in a sufficiently high concentration during this phase. WO2014/151030 discloses ADCs including certain KSP inhibitors.

SUMMARY OF THE INVENTION

Against this background it is an object of the present invention to provide substances which, after administration at a relatively low concentration, unfold apoptotic action and may therefore be of benefit for cancer therapy.

To achieve this object, the invention provides conjugates of an anti-CD123 antibody with compounds of the formula (I) below, where one or more of the compounds of the formula (I) are attached to the antibody via a linker L. The antibody is preferably a human, humanized or chimeric monoclonal antibody. Preference is given here to a chimeric or humanized anti-CD123 antibody derived from an antibody 7G3 or 12F1 originating from mice. Particular preference is given to the antibodies TPP-6013, TPP-5968, TPP-5969 and TPP-5971.

Formula (I)

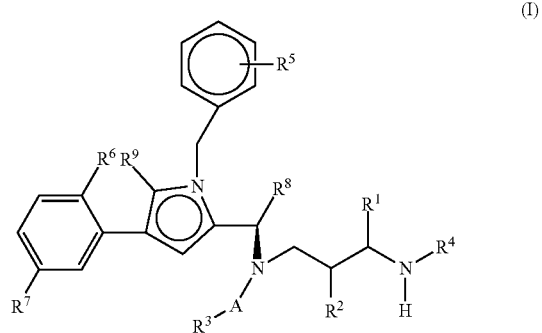

where
$R^1$ represents H, -L-#1, -MOD or $-(CH_2)_{0-3}Z$, where Z represents $-H$, $-NHY^3$, $-OY^3$, $-SY^3$, halogen, $-CO-NY^1Y^2$ or $-CO-OY^3$,
where $Y^1$ and $Y^2$ independently of one another represent H, $NH_2$, $-(CH_2CH_2O)_{0-3}-(CH_2)_{0-3}Z'$ (e.g. $-(CH_2)_{0-3}Z'$) or $-CH(CH_2W)Z'$, and $Y^3$ represents H or $-(CH_2)_{0-3}Z'$,
where Z' represents H, $NH_2$, $SO_3H$, COOH, $-NH-CO-CH_2-CH_2-CH(NH_2)COOH$ or $-(CO-NH-CHY^4)_{1-3}COOH$, where W represents H or OH, where $Y^4$ represents straight-chain or branched $C_{1-6}$ alkyl which is optionally substituted by —NHCONH$_2$, or represents aryl or benzyl which are optionally substituted by —NH$_2$;

$R^2$ represents H, -MOD, —CO—CHY$^4$—NHY$^5$ or —(CH$_2$)$_{0-3}$Z, where Z represents —H, halogen, —OY$^3$, —SY$^3$, NHY$^3$, —CO—NY$^1$Y$^2$ or —CO—OY$^3$, where $Y^1$ and $Y^2$ independently of one another represent H, NH$_2$ or —(CH$_2$)$_{0-3}$Z', and $Y^3$ represents H or —(CH$_2$)$_{0-3}$Z', where Z' represents H, SO$_3$H, NH$_2$ or COOH;

where $Y^4$ represents straight-chain or branched $C_{1-6}$-alkyl which is optionally substituted by —NHCONH$_2$, or represents aryl or benzyl which are optionally substituted by —NH$_2$, and $Y^5$ represents H or —CO—CHY$^6$—NH$_2$, where $Y^6$ represents straight-chain or branched $C_{1-6}$-alkyl;

$R^4$ represents H, -L-#1, -SG$_{lys}$-(CO)$_{0-1}$—R$^{4'}$, —CO—CHY$^4$—NHY$^5$ or —(CH$_2$)$_{0-3}$Z, where SG$_{lys}$ represents a group which can be cleaved by a lysosomal enzyme, in particular a group consisting of a di- or tripeptide, $R^{4'}$ represents a $C_{1-10}$-alkyl, $C_{5-10}$-aryl or $C_{6-10}$-aralkyl, $C_{5-10}$-heteroalkyl, $C_{1-10}$-alkyl-O—$C_{6-10}$-aryl, $C_{5-10}$-heterocycloalkyl, heteroaryl, heteroarylalkyl, heteroarylalkoxy, $C_{1-10}$-alkoxy, $C_{6-10}$-aryloxy or $C_{6-10}$-aralkoxy, $C_{5-10}$-heteroaralkoxy, $C_{1-10}$-alkyl-O—$C_{6-10}$-aryloxy, $C_{5-10}$-heterocycloalkoxy group which may be mono- or polysubstituted by —NH$_2$, —NH-alkyl, —N(alkyl)$_2$, NH—CO-alkyl, N(alkyl)-COalkyl, —SO$_3$H, —SO$_2$NH$_2$, —SO$_2$—N(alkyl)$_2$, —COOH, —CONH$_2$, —CON(alkyl)$_2$ or —OH, —H or a group —O$_x$—(CH$_2$CH$_2$O)$_v$—R$^{4''}$ (where x represents 0 or 1 and v represents a number from 1 to 20 and R$^{4''}$ represents —H, -alkyl (preferably $C_{1-12}$-alkyl), —CH$_2$—COOH, —CH$_2$—CH$_2$—COOH or —CH$_2$—CH$_2$—NH$_2$), where after cleavage a primary amine group is present (corresponds to R$^4$=H);

where Z represents —H, halogen, —OY$^3$, —SY$^3$, NHY$^3$, —CO—NY$^1$Y$^2$ or —CO—OY$^3$, where $Y^1$ and $Y^2$ independently of one another represent H, NH$_2$ or —(CH$_2$)$_{0-3}$Z', and $Y^3$ represents H or —(CH$_2$)$_{0-3}$Z', where Z' represents H, SO$_3$H, NH$_2$ or COOH;

where $Y^4$ represents straight-chain or branched $C_{1-6}$-alkyl which is optionally substituted by —NHCONH$_2$, or represents aryl or benzyl which are optionally substituted by —NH$_2$, and $Y^5$ represents H or —CO—CHY$^6$—NH$_2$, where $Y^6$ represents straight-chain or branched $C_{1-6}$-alkyl;

or $R^2$ and $R^4$ together (with formation of a pyrrolidine ring) represent —CH$_2$—CHR$^{11}$— or —CHR$^{11}$—CH$_2$—, where $R^{11}$ represents H, NH$_2$, SO$_3$H, COOH, SH, halogen (in particular F or Cl), $C_{1-4}$-alkyl, $C_{1-4}$-haloalkyl, $C_{1-4}$-alkoxy, hydroxyl-substituted $C_{1-4}$-alkyl, COO($C_{1-4}$-alkyl) or OH;

A represents CO, SO, SO$_2$, SO$_2$NH or CNNH$_2$;

$R^3$ represents -L-#1, -MOD or an optionally substituted alkyl, cycloalkyl, aryl, heteroaryl, heteroalkyl, heterocycloalkyl group, preferably -L-#1 or a $C_{1-10}$-alkyl, $C_{6-10}$-aryl or $C_{6-10}$-aralkyl, $C_{5-10}$-heteroalkyl, $C_{1-10}$-alkyl-O—$C_{6-10}$-aryl or $C_{5-10}$-heterocycloalkyl group which may be substituted by 1-3-OH groups, 1-3 halogen atoms, 1-3 halogenated alkyl groups (each having 1-3 halogen atoms), 1-3 O-alkyl groups, 1-3-SH groups, 1-3-S-alkyl groups, 1-3-O—CO-alkyl groups, 1-3-O—CO—NH-alkyl groups, 1-3-NH—CO-alkyl groups, 1-3-NH—CO—NH-alkyl groups, 1-3-S(O)$_n$-alkyl groups, 1-3-SO$_2$—NH-alkyl groups, 1-3-NH-alkyl groups, 1-3-N(alkyl)$_2$ groups, 1-3-NH$_2$ groups or 1-3-(CH$_2$)$_{0-3}$Z groups, where n represents 0, 1 or 2, Z represents —H, halogen, —OY$^3$, —SY$^3$, —NHY$^3$, —CO—NY$^1$Y$^2$ or —CO—OY$^3$, where $Y^1$ and $Y^2$ independently of one another represent H, NH$_2$ or —(CH$_2$)$_{0-3}$Z' and $Y^3$ represents H, —(CH$_2$)$_{0-3}$—CH(NHCOCH$_3$)Z', —(CH$_2$)$_{0-3}$—CH(NH$_2$)Z' or —(CH$_2$)$_{0-3}$Z', where Z' represents H, SO$_3$H, NH$_2$ or COOH (where "alkyl" preferably represents $C_{1-10}$-alkyl);

$R^5$ represents H, NH$_2$, NO$_2$, halogen (in particular F, Cl, Br), —CN, CF$_3$, —OCF$_3$, —CH$_2$F, —CH$_2$F, SH or —(CH$_2$)$_{0-3}$Z, where Z represents —H, —OY$^3$, —SY$^3$, halogen, NHY$^3$, —CO—NY$^1$Y$^2$ or —CO—OY$^3$, where $Y^1$ and $Y^2$ independently of one another represent H, NH$_2$ or —(CH$_2$)$_{0-3}$Z', and $Y^3$ represents H or —(CH$_2$)$_{0-3}$Z', where Z' represents H, SO$_3$H, NH$_2$ or COOH;

$R^6$ and $R^7$ independently of one another represent H, cyano, (optionally fluorinated) $C_{1-10}$-alkyl, (optionally fluorinated) $C_{2-10}$-alkenyl, (optionally fluorinated) $C_{2-10}$-alkynyl, hydroxy, NO$_2$, NH$_2$, COOH or halogen (in particular F, Cl, Br), $R^8$ represents (optionally fluorinated) $C_{1-10}$-alkyl, (optionally fluorinated) $C_{2-10}$-alkenyl, (optionally fluorinated) $C_{2-10}$-alkynyl, (optionally fluorinated) $C_{4-10}$-cycloalkyl or —(CH$_2$)$_{0-2}$—(HZ$^2$), where HZ$^2$ represents a 4- to 7-membered heterocycle having up to two heteroatoms selected from the group consisting of N, O and S, where each of these groups may be substituted by —OH, CO$_2$H or NH$_2$;

$R^9$ represents H, F, CH$_3$, CF$_3$, CH$_2$F or CHF$_2$;

where one of the substituents $R^1$, $R^3$ or $R^4$ represents or (in the case of $R^8$) contains -L-#1, L represents the linker and #1 represents the bond to the binder or derivative thereof, where -MOD represents —(NR$^{10}$)$_n$-(G1)$_o$-G2-G3, where $R^{10}$ represents H or $C_1$-$C_3$-alkyl;

G1 represents —NHCO— or —CONH— (where, if G1 represents —NHCO—, $R^{10}$ does not represent NH$_2$);

n represents 0 or 1;

o represents 0 or 1; and

G2 represents a straight-chain and/or branched hydrocarbon group which has 1 to 10 carbon atoms and which may be interrupted once or more than once by one or more of the groups —O—, —S—, —SO—, SO$_2$, —NRy-, —NRyCO—, CONRy-, —NRyNRy-, —SO$_2$NRyNRy-, —CONRyNRy- (where R$^y$ represents H, phenyl, $C_1$-$C_{10}$-alkyl, $C_2$-$C_{10}$-alkenyl or $C_2$-$C_{10}$-alkynyl, each of which may be substituted by NHCONH$_2$, —COOH, —OH, —NH$_2$, NH—CNNH$_2$, sulphonamide, sulphone, sulphoxide or sulphonic acid), —CO—, or —CR$^x$=N—O— (where Rx represents H, $C_1$-$C_3$-alkyl or phenyl), where the hydrocarbon chain including any side chains may be substituted by —NHCONH$_2$, —COOH, —OH, —NH$_2$, NH—CNNH$_2$, sulphonamide, sulphone, sulphoxide or sulphonic acid, G3 represents —H or —COOH, and where the group -MOD preferably has at least one group —COOH;

and the salts, solvates, salts of the solvates and epimers thereof.

The conjugates according to the invention can have chemically labile linkers, enzymatically labile linkers or stable linkers. Particular preference is given to stable linkers and linkers which can be cleaved by a protease.

The invention furthermore provides processes for preparing the conjugates according to the invention, and also precursors and intermediates for the preparation.

The preparation of the conjugates according to the invention regularly comprises the following steps:

preparation of a linker precursor which optionally carries protective groups and has a reactive group which is capable of coupling to the antibody;

conjugation of the linker precursor to the derivative, which optionally carries protective groups, of a KSP inhibitor of the formula (I), where in these formulae there is as yet no bond to a linker, giving a reactive KSP inhibitor/linker conjugate which optionally carries protective groups;

removal of any protective groups present in the KSP inhibitor/linker conjugate and conjugation of the antibody to the KSP inhibitor/linker conjugate, giving the antibody/KSP inhibitor conjugate according to the invention.

Attachment of the reactive group may also take place after the construction of an optionally protected KSP inhibitor/linker precursor conjugate.

Depending on the linker, succinimide-linked ADCs may, after conjugation, be converted according to Scheme 26 into the open-chain succinamides, which have an advantageous stability profile.

As illustrated above, conjugation of the linker precursor to a low-molecular-weight KSP inhibitor can be by substitution of a hydrogen atom at $R^1$, $R^3$ or $R^4$ in formula (I) by the linker. In the synthesis steps prior to the conjugation, any functional groups present may also be present in protected form. Prior to the conjugation step, these protective groups are removed by known methods of peptide chemistry. The conjugation can take place chemically by various routes, as shown in an exemplary manner in Schemes 20 to 31 in the examples. In particular, it is optionally possible to modify the low-molecular weight KSP inhibitor for conjugation to the linker, for example by introduction of protective groups or leaving groups to facilitate substitution.

In particular, the invention provides novel low-molecular-weight KSP inhibitors conjugated to an anti-CD123 antibody such as chimeric or humanized variants of 7G3 or 12F1. These KSP inhibitors or their antibody conjugates have the following general formula (II):

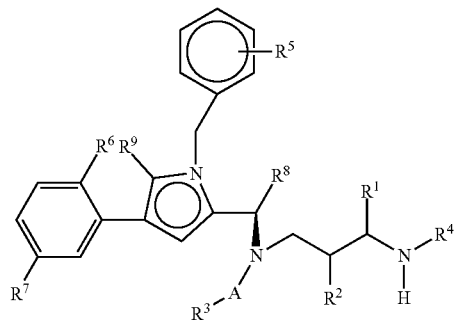

(II)

where
$R^1$ represents H, -L-BINDER, -MOD or —$(CH_2)_{0-3}$Z, where Z represents —H, —$NHY^3$, —$OY^3$, —$SY^3$, halogen, —CO—$NY^1Y^2$ or —CO—$OY^3$,
where
$Y^1$ and $Y^2$ independently of one another represent H, $NH_2$, —$(CH_2CH_2O)_{0-3}$—$(CH_2)_{0-3}$Z' (e.g. —$(CH_2)_{0-3}$Z') or —$CH(CH_2W)Z'$,
$Y^3$ represents H or —$(CH_2)_{0-3}$Z',
Z' represents H, $NH_2$, $SO_3H$, COOH, —NH—CO—$CH_2$—$CH_2$—$CH(NH_2)$COOH or —(CO—NH—$CHY^4$)_{1-3}$COOH;
W represents H or OH,
$Y^4$ represents straight-chain or branched $C_{1-6}$ alkyl which is optionally substituted by —NH—C(=O)—$NH_2$, or represents aryl or benzyl which are optionally substituted by —$NH_2$;
$R^2$ represents H, -MOD, —C(=O)—$CHY^4$—$NHY^5$ or —$(CH_2)_{0-3}$Z, or
$R^2$ and $R^4$ together (with formation of a pyrrolidine ring) represent —$CH_2$—$CHR^{11}$— or —$CHR^{11}$—$CH_2$—, where
$R^{11}$ represents —H, —$NH_2$, —$SO_3H$, —COOH, —SH, halogen (in particular F or Cl), $C_{1-4}$-alkyl, $C_{1-4}$-haloalkyl, $C_{1-4}$-alkoxy, hydroxyl-substituted $C_{1-4}$-alkyl, COO($C_{1-4}$-alkyl) or —OH;
Z represents —H, halogen, —$OY^3$, —$SY^3$, $NHY^3$, —CO—$NY^1Y^2$ or —CO—$OY^3$,
$Y^1$ and $Y^2$ independently of one another represent H, $NH_2$ or —$(CH_2)_{0-3}$Z', and $Y^3$ represents H or —$(CH_2)_{0-3}$Z', where Z' represents H, $SO_3H$, $NH_2$ or COOH;
where $Y^4$ represents straight-chain or branched $C_{1-6}$-alkyl which is optionally substituted by —$NHCONH_2$, or represents aryl or benzyl which are optionally substituted by —$NH_2$, and $Y^5$ represents H or —CO—$CHY^6$—$NH_2$, where $Y^6$ represents straight-chain or branched $C_{1-6}$-alkyl;
$R^4$ represents H, -L-BINDER, -$SG_{lys}$-(CO)$_{0-1}$—$R^{4'}$, —CO—$CHY^4$—$NHY^5$ or —$(CH_2)_{0-3}$Z,
where $SG_{lys}$ represents a group which can be cleaved by a lysosomal enzyme, in particular a group consisting of a di- or tripeptide, $R^{4'}$ represents a $C_{1-10}$-alkyl, $C_{5-10}$-aryl or $C_{6-10}$-aralkyl, $C_{5-10}$-heteroalkyl, $C_{1-10}$-alkyl-O—$C_{6-10}$-aryl, $C_{5-10}$-heterocycloalkyl, heteroaryl, heteroarylalkyl, heteroarylalkoxy, $C_{1-10}$-alkoxy, $C_{6-10}$-aryloxy or $C_{6-10}$-aralkoxy, $C_{5-10}$-heteroaralkoxy, $C_{1-10}$-alkyl-O—$C_{6-10}$-aryloxy, $C_{5-10}$-heterocycloalkoxy group which may be mono- or polysubstituted by —$NH_2$, —NH-alkyl, —N(alkyl)$_2$, NH—CO-alkyl, N(alkyl)-COalkyl, —$SO_3H$, —$SO_2NH_2$, —$SO_2$—N(alkyl)$_2$, —COOH, —$CONH_2$, —CON(alkyl)$_2$ or —OH, —H or a group —$O_x$—$(CH_2CH_2O)_v$—$R^{4''}$ (where x represents 0 or 1 and v represents a number from 1 to 20 and $R^{4''}$ represents —H, -alkyl (preferably $C_{1-12}$-alkyl), —$CH_2$—COOH, —$CH_2$—$CH_2$—COOH or —$CH_2$—$CH_2$—$NH_2$), where after cleavage a primary amine group is present (corresponds to $R^4$=H);
where Z represents —H, halogen, —$OY^3$, —$SY^3$, $NHY^3$, —CO—$NY^1Y^2$ or —CO—$OY^3$,
where $Y^1$ and $Y^2$ independently of one another represent H, $NH_2$ or —$(CH_2)_{0-3}$Z', and $Y^3$ represents H or —$(CH_2)_{0-3}$Z', where Z' represents H, $SO_3H$, $NH_2$ or COOH;
where $Y^4$ represents straight-chain or branched $C_{1-6}$-alkyl which is optionally substituted by —$NHCONH_2$, or represents aryl or benzyl which are optionally substituted by —$NH_2$, and $Y^5$ represents H or —CO—$CHY^6$—$NH_2$, where $Y^6$ represents straight-chain or branched $C_{1-6}$-alkyl;
or $R^2$ and $R^4$ together (with formation of a pyrrolidine ring) represent —$CH_2$—$CHR^{11}$— or —$CHR^{11}$—$CH_2$—,
where $R^{11}$ represents H, $NH_2$, $SO_3H$, COOH, SH, halogen (in particular F or Cl), $C_{1-4}$-alkyl, $C_{1-4}$-haloalkyl, $C_{1-4}$-alkoxy, hydroxyl-substituted $C_{1-4}$-alkyl, COO($C_{1-4}$-alkyl) or OH;
A represents —C(=O)—, —S(=O)—, —S(=O)$_2$—, —S(=O)$_2$—NH or —$CNNH_2$—;
$R^3$ represents -L-BINDER, -MOD or an optionally substituted alkyl, cycloalkyl, aryl, heteroaryl, heteroalkyl, heterocycloalkyl group, preferably -L-BINDER or a $C_{1-10}$-alkyl, $C_{6-10}$-aryl or $C_{6-10}$-aralkyl, $C_{5-10}$-heteroalkyl, $C_{1-10}$-alkyl-O—$C_{6-10}$-aryl or $C_{5-10}$-heterocycloalkyl group which may be substituted by 1-3-OH groups, 1-3 halogen atoms, 1-3 halogenated alkyl groups (each having 1-3 halogen atoms), 1-3 O-alkyl groups, 1-3-SH groups, 1-3-S-alkyl groups, 1-3-O—CO-alkyl groups, 1-3-O—

CO—NH-alkyl groups, 1-3-NH—CO-alkyl groups, 1-3-NH—CO—NH-alkyl groups, 1-3-S(O)$_n$-alkyl groups, 1-3-SO$_2$—NH-alkyl groups, 1-3-NH-alkyl groups, 1-3-N(alkyl)$_2$ groups, 1-3-NH$_2$ groups or 1-3-(CH$_2$)$_{0-3}$Z groups, where Z represents —H, halogen, —OY$^3$, —SY$^3$, —NHY$^3$, —CO—NY$^1$Y$^2$ or —CO—OY$^3$, where Y$^1$ and Y$^2$ independently of one another represent H, NH$_2$ or —(CH$_2$)$_{0-3}$Z' and Y$^3$ represents H, —(CH$_2$)$_{0-3}$—CH(NHCOCH$_3$)Z', —(CH$_2$)$_{0-3}$—CH(NH$_2$)Z' or —(CH$_2$)$_{0-3}$Z', where Z' represents H, SO$_3$H, NH$_2$ or COOH (where "alkyl" preferably represents C$_{1-10}$-alkyl);

n represents 0, 1 or 2,

R$^5$ represents H, NH$_2$, NO$_2$, halogen (in particular F, Cl, Br), —CN, CF$_3$, —OCF$_3$, —CH$_2$F, —CH$_2$F, SH or —(CH$_2$)$_{0-3}$Z, where Z represents —H, —OY$^3$, —SY$^3$, halogen, NHY$^3$, —CO—NY$^1$Y$^2$ or —CO—OY$^3$, where Y$^1$ and Y$^2$ independently of one another represent H, NH$_2$ or —(CH$_2$)$_{0-3}$Z', and Y$^3$ represents H or —(CH$_2$)$_{0-3}$Z', where Z' represents H, SO$_3$H, NH$_2$ or COOH;

R$^8$ represents (optionally fluorinated) C$_{1-10}$-alkyl, (optionally fluorinated) C$_{2-10}$-alkenyl, (optionally fluorinated) C$_{2-10}$-alkynyl, (optionally fluorinated) C$_{4-10}$-cycloalkyl or —(CH$_2$)$_{0-2}$—(HZ$^2$), where HZ$^2$ represents a 4- to 7-membered heterocycle having up to two heteroatoms selected from the group consisting of N, O and S (preferably oxetane), where each of these groups may be substituted by —OH, CO$_2$H or NH$_2$;

R$^9$ represents H, F, CH$_3$, CF$_3$, CH$_2$F or CHF$_2$;

where L represents a linker and BINDER represents an anti-CD123 antibody, where the binder may optionally be attached to a plurality of active compound molecules, where one representative of R$^1$, R$^3$ and R$^4$ represents -L-BINDER;

R$^6$ and R$^7$ independently of one another represent H, cyano, (optionally fluorinated) C$_{1-10}$-alkyl, (optionally fluorinated) C$_{2-10}$-alkenyl, (optionally fluorinated) C$_{2-10}$-alkynyl, hydroxy, NO$_2$, NH$_2$, COOH or halogen (in particular F, Cl, Br), where -MOD represents —(NR$^{10}$)$_n$-(G1)$_o$-G2-G3, where R$^{10}$ represents H or C$_1$-C$_3$-alkyl;

G1 represents —NHCO— or —CONH— (where, if G1 represents —NHCO—, R$^{10}$ does not represent NH$_2$);

n represents 0 or 1;

o represents 0 or 1; and

G2 represents a straight-chain and/or branched hydrocarbon group which has 1 to 10 carbon atoms and which may be interrupted once or more than once by one or more of the groups —O—, —S—, —SO—, SO$_2$, —NRy-, —NRyCO—, CONRy-, —NRyNRy-, —SO$_2$NRyNRy-, —CONRyNRy- (where R$^y$ represents H, phenyl, C$_1$-C$_{10}$-alkyl, C$_2$-C$_{10}$-alkenyl or C$_2$-C$_{10}$-alkynyl, each of which may be substituted by NHCONH$_2$, —COOH, —OH, —NH$_2$, NH—CNNH$_2$, sulphonamide, sulphone, sulphoxide or sulphonic acid), —CO—, —CR$^x$=N—O— (where Rx represents H, C$_1$-C$_3$-alkyl or phenyl), where the hydrocarbon chain including any side chains may be substituted by —NHCONH$_2$, —COOH, —OH, —NH$_2$, NH—CNNH$_2$, sulphonamide, sulphone, sulphoxide or sulphonic acid, G3 represents —H or —COOH, where the group -MOD preferably has at least one group —COOH; and the salts, solvates, salts of the solvates and epimers thereof.

DESCRIPTION OF THE FIGURES

FIG. 1 shows the sequence protocol.

FIG. 2 shows the annotated sequence of the antibodies. For each of the antibodies or antibody fragments, the CDR regions (HCDR1, HCDR2, HCDR3, LCDR1, LCDR2, LCDR3) and the variable regions (VH, VL) are emphasized.

DETAILED DESCRIPTION OF THE INVENTION

The invention provides conjugates of an anti-CD123 antibody with one or more active compound molecules, the active compound molecule being a kinesin spindle protein inhibitor (KSP inhibitor) attached to the antibody via a linker L.

The conjugate according to the invention can be represented by the general formula

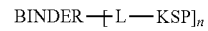

where BINDER represents the anti-CD123 antibody, L represents the linker, KSP represents the KSP inhibitor and n represents a number from 1 to 50, preferably from 1.2 to 20 and particularly preferably from 2 to 8. Here, n is the mean of the number of KSP inhibitor/linker conjugates per BINDER. Preferably, KSP-L has the formula (I) shown above. Furthermore, the linker is preferably attached to different amino acids of the antibody. Particular preference is given to binding to different cysteine residues of the binder. The anti-CD123 antibody is preferably a human, humanized or chimeric monoclonal antibody. Preference is given here to a chimeric or humanized anti-CD123 antibody derived from an antibody 7G3 or 12F1 originating from mice. Particular preference is given to the antibodies TPP-6013, TPP-5968, TPP-5969 and TPP-5971.

Antibodies which can be used according to the invention, KSP inhibitors which can be used according to the invention and linkers which can be used according to the invention which can be used in combination without any limitation are described below. In particular, the binders represented in each case as preferred or particularly preferred can be employed in combination with the KSP inhibitors represented in each case as preferred or particularly preferred, optionally in combination with the linkers represented in each case as preferred or particularly preferred.

KSP Inhibitors and their Binder Conjugates

Definitions

The term "substituted" means that one or more hydrogens at the atom or group referred to is/are replaced by a selection of the group mentioned, with the proviso that the normal valency of the atom referred to is not exceeded under the present circumstances. Combinations of substituents and/or variables are admissible.

The term "optionally substituted" means that the number of substituents may be equal to or different from zero. Unless indicated otherwise, optionally substituted groups may be substituted by as many optional substituents as can be accommodated by replacing a hydrogen atom by a non-hydrogen substituent at any available carbon or nitrogen or sulphur atom. Usually, the number of optional substituents (if present) may be 1, 2, 3, 4 or 5, in particular 1, 2 or 3.

As used herein, the term "once or more than once", for example in the definition of the substituents of the compounds of the general formulae of the present invention, means "1, 2, 3, 4 or 5, preferably 1, 2, 3 or 4, particularly preferably 1, 2 or 3, very particularly preferably 1 or 2".

If radicals in the compounds according to the invention are substituted, the radicals may, unless indicated otherwise, be mono- or polysubstituted. In the scope of the present invention, the meanings of all radicals which occur more than once are independent of one another. Substitution by one, two or three identical or different substituents is preferred. Substitution by one substituent is particularly preferred.

Alkyl

Alkyl represents a straight-chain or branched saturated monovalent hydrocarbon radical having 1 to 10 carbon atoms ($C_1$-$C_{10}$-alkyl), generally 1 to 6 ($C_1$-$C_6$-alkyl), preferably 1 to 4 ($C_1$-$C_4$-alkyl) and particularly preferably 1 to 3 carbon atoms ($C_1$-$C_3$-alkyl).

The following may be mentioned by way of example and as being preferred:
methyl-, ethyl-, propyl-, butyl-, pentyl-, hexyl-, isopropyl-, isobutyl-, sec-butyl, tert-butyl-, isopentyl-, 2-methylbutyl-, 1-methylbutyl-, 1-ethylpropyl-, 1,2-dimethylpropyl-, neopentyl-, 1,1-dimethylpropyl-, 4-methylpentyl-, 3-methylpentyl-, 2-methylpentyl-, 1-methylpentyl-, 2-ethylbutyl-, 1-ethylbutyl-, 3,3-dimethylbutyl-, 2,2-dimethylbutyl-, 1,1-dimethylbutyl-, 2,3-dimethylbutyl-, 1,3-dimethylbutyl- and 1,2-dimethylbutyl-.

Particular preference is given to a methyl-, ethyl-, propyl-, isopropyl- and tert-butyl radical.

Heteroalkyl

Heteroalkyl represents a straight-chain and/or branched hydrocarbon chain having 1 to 10 carbon atoms which may be interrupted once or more than once by one or more of the groups —O—, —S—, —C(=O)—, —S(=O)—, —S(=O)$_2$—, —NR$^y$—, —NR$^y$C(=O)—, —C(=O)—NR$^y$—, —NR$^y$NR$^y$—, —S(=O)$_2$—NR$^y$NR$^y$—, —C(=O)—NR$^y$NR$^y$—, —CR$^x$=N—O—, and where the hydrocarbon chain including side chains, if present, may be substituted by —NH—C(=O)—NH$_2$, —C(=O)—OH, —OH, —NH$_2$, —NH—C(=NNH$_2$)—, sulphonamide, sulphone, sulphoxide or sulphonic acid, Here, R$^y$ in each case represents —H, phenyl-, $C_1$-$C_{10}$-alkyl-, $C_2$-$C_{10}$-alkenyl- or $C_2$-$C_{10}$-alkynyl-, which for their part may each be substituted by —NH—C(=O)—NH$_2$, —C(=O)—OH, —OH, —NH$_2$, —NH—C(=NNH$_2$)—, sulphonamide, sulphone, sulphoxide or sulphonic acid.

Here, R$^x$ represents —H, $C_1$-$C_3$-alkyl- or phenyl-.

Alkenyl

Alkenyl represents a straight-chain or branched monovalent hydrocarbon chain having one or two double bonds and 2, 3, 4, 5, 6, 7, 8, 9 or 10 carbon atoms ($C_2$-$C_{10}$-alkenyl), in particular 2 or 3 carbon atoms ($C_2$-$C_3$-alkenyl), it being understood that, if the alkenyl group contains more than one double bond, the double bonds may be isolated from one another or conjugated to one another. The alkenyl group is, for example, an ethenyl (or vinyl), prop-2-en-1-yl (or "allyl"), prop-1-en-1-yl, but-3-enyl, but-2-enyl, but-1-enyl, pent-4-enyl, pent-3-enyl, pent-2-enyl, pent-1-enyl, hex-5-enyl, hex-4-enyl, hex-3-enyl, hex-2-enyl, hex-1-enyl, prop-1-en-2-yl (or "isopropenyl"), 2-methylprop-2-enyl, 1-methylprop-2-enyl, 2-methylprop-1-enyl, 1-methylprop-1-enyl, 3-methylbut-3-enyl, 2-methylbut-3-enyl, 1-methylbut-3-enyl, 3-methylbut-2-enyl, 2-methylbut-2-enyl, 1-methylbut-2-enyl, 3-methylbut-1-enyl, 2-methylbut-1-enyl, 1-methylbut-1-enyl, 1,1-dimethylprop-2-enyl, 1-ethylprop-1-enyl, 1-propylvinyl, 1-isopropylvinyl, 4-methylpent-4-enyl, 3-methylpent-4-enyl, 2-methylpent-4-enyl, 1-methylpent-4-enyl, 4-methylpent-3-enyl, 3-methylpent-3-enyl, 2-methylpent-3-enyl, 1-methylpent-3-enyl, 4-methylpent-2-enyl, 3-methylpent-2-enyl, 2-methylpent-2-enyl, 1-methylpent-2-enyl, 3-methylpent-1-enyl, 2-methylpent-1-enyl, 1-methylpent-1-enyl, 3-ethylbut-3-enyl, 2-ethylbut-3-enyl, 1-ethylbut-3-enyl, 3-ethylbut-2-enyl, 2-ethylbut-2-enyl, 1-ethylbut-2-enyl, 3-ethylbut-1-enyl, 2-ethylbut-1-enyl, 1-ethylbut-1-enyl, 2-propylprop-2-enyl, 1-propylprop-2-enyl, 2-isopropylprop-2-enyl, 1-isopropylprop-2-enyl, 2-propylprop-1-enyl, 1-propylprop-1-enyl, 2-isopropylprop-1-enyl, 1-isopropylprop-1-enyl, 3,3-dimethylprop-1-enyl, 1-(1,1-dimethylethyl)ethenyl, buta-1,3-dienyl, penta-1,4-dienyl or hexa-1-5-dienyl group. The group is in particular vinyl or allyl.

Alkynyl

Alkynyl represents a straight-chain or branched monovalent hydrocarbon chain having a triple bond and 2, 3, 4, 5, 6, 7, 8, 9 or 10 carbon atoms ($C_2$-$C_{10}$-alkynyl), in particular 2 or 3 carbon atoms ($C_2$-$C_3$-alkynyl). The $C_2$-$C_6$-alkynyl group is, for example, an ethynyl, prop-1-ynyl, prop-2-ynyl (or propargyl), but-1-ynyl, but-2-ynyl, but-3-ynyl, pent-1-ynyl, pent-2-ynyl, pent-3-ynyl, pent-4-ynyl, hex-1-ynyl, hex-2-ynyl, hex-3-ynyl, hex-4-ynyl, hex-5-ynyl, 1-methylprop-2-ynyl, 2-methylbut-3-ynyl, 1-methylbut-3-ynyl, 1-methylbut-2-ynyl, 3-methylbut-1-ynyl, 1-ethylprop-2-ynyl, 3-methylpent-4-ynyl, 2-methylpent-4-ynyl, 1-methylpent-4-ynyl, 2-methylpent-3-ynyl, 1-methylpent-3-ynyl, 4-methylpent-2-ynyl, 1-methylpent-2-ynyl, 4-methylpent-1-ynyl, 3-methylpent-1-ynyl, 2-ethylbut-3-ynyl, 1-ethylbut-3-ynyl, 1-ethylbut-2-ynyl, 1-propylprop-2-ynyl, 1-isopropylprop-2-ynyl, 2,2-dimethylbut-3-ynyl, 1,1-dimethylbut-3-ynyl, 1,1-dimethylbut-2-ynyl- or 3,3-dimethylbut-1-ynyl group. The alkynyl group is in particular ethynyl, prop-1-ynyl or prop-2-ynyl.

Cycloalkyl

Cycloalkyl represents a saturated monovalent mono- or bicyclic hydrocarbon radical having 3-12 carbon atoms ($C_3$-$C_{12}$-cycloalkyl).

Here, a monocyclic hydrocarbon radical represents a monovalent hydrocarbon radical having generally 3 to 10 ($C_3$-$C_{10}$-cycloalkyl), preferably 3 to 8 ($C_3$-$C_8$-cycloalkyl) and particularly preferably 3 to 7 ($C_3$-$C_7$-cycloalkyl) carbon atoms.

The following may be mentioned by way of example and as being preferred for a monocyclic hydrocarbon radical: cyclopropyl, cyclobutyl, cyclopentyl, cyclohexyl, cycloheptyl and cyclooctyl.

Particular preference is given to cyclopropyl, cyclobutyl, cyclopentyl, cyclohexyl and cycloheptyl.

Here, a bicyclic hydrocarbon radical represents a hydrocarbon radical having generally 3 to 12 carbon atoms ($C_3$-$C_{12}$-cycloalkyl), which is to be understood as a fusion of two saturated ring systems jointly sharing two directly adjacent atoms. The following may be mentioned by way of example and as being preferred for a bicyclic hydrocarbon radical: bicyclo[2.2.0]hexyl, bicyclo[3.3.0]octyl, bicyclo[4.4.0]decyl, bicyclo[5.4.0]undecyl, bicyclo[3.2.0]heptyl, bicyclo[4.2.0]octyl, bicyclo[5.2.0]nonyl, bicyclo[6.2.0]decyl, bicyclo[4.3.0]nonyl, bicyclo[5.3.0]decyl, bicyclo[6.3.0]undecyl and bicyclo[5.4.0]undecyl.

Heterocycloalkyl

Heterocycloalkyl represents a non-aromatic mono- or bicyclic ring system having one, two, three or four heteroatoms which may be identical or different. Heteroatoms present may be nitrogen atoms, oxygen atoms or sulphur atoms.

A monocyclic ring system in accordance with the present invention may have 3 to 8, preferably 4 to 7, particularly preferably 5 or 6, ring atoms.

The following may be mentioned by way of example and as being preferred for a heterocycloalkyl having 3 ring atoms:
aziridinyl.

The following may be mentioned by way of example and as being preferred for a heterocycloalkyl having 4 ring atoms:
azetidinyl, oxetanyl.

The following may be mentioned by way of example and as being preferred for a heterocycloalkyl having 5 ring atoms:
pyrrolidinyl, imidazolidinyl, pyrazolidinyl, pyrrolinyl, dioxolanyl and tetrahydrofuranyl.

The following may be mentioned by way of example and as being preferred for a heterocycloalkyl having 6 ring atoms:
piperidinyl, piperazinyl, morpholinyl, dioxanyl, tetrahydropyranyl and thiomorpholinyl.

The following may be mentioned by way of example and as being preferred for a heterocycloalkyl having 7 ring atoms:
azepanyl, oxepanyl, 1,3-diazepanyl, 1,4-diazepanyl.

The following may be mentioned by way of example and as being preferred for a heterocycloalkyl having 8 ring atoms:
oxocanyl, azocanyl.

From among monocyclic heterocycloalkyl, preference is given to 4- to 7-membered saturated heterocyclyl radicals having up to 2 heteroatoms from the group consisting of O, N and S.

Particular preference is given to morpholinyl, piperidinyl, pyrrolidinyl and tetrahydrofuranyl.

A bicyclic ring system having one, two, three or four heteroatoms, which may be identical or different, may, in accordance with the present invention, have 6 to 12, preferably 6 to 10, ring atoms, where one, two, three or four carbon atoms may be replaced by identical or different heteroatoms from the group consisting of O, N and S.

The following may be mentioned by way of example:
azabicyclo[3.3.0]octyl, azabicyclo[4.3.0]nonyl, diazabicyclo [4.3.0]nonyl, oxazabicyclo[4.3.0]nonyl, thiazabicyclo [4.3.0]nonyl or azabicyclo[4.4.0]decyl, and also radicals derived from further possible combinations according to the definitions.

Particular preference is given to perhydrocyclopenta[c] pyrrolyl, perhydrofuro[3,2-c]pyridinyl, perhydropyrrolo[1, 2-a]pyrazinyl, perhydropyrrolo[3,4-c]pyrrolyl and 3,4-methylenedioxyphenyl.

Aryl

Aryl is a monovalent mono- or bicyclic aromatic ring system which consists of carbon atoms. Examples are naphthyl and phenyl; preference is given to phenyl or a phenyl radical.

$C_6$-$C_{10}$-Aralkyl

In the context of the invention, $C_{6-10}$-aralkyl represents a monocyclic aromatic aryl, for example phenyl, which is attached to a $C_1$-$C_4$-alkyl group.

An exemplary $C_{6-10}$-aralkyl group is benzyl.

Heteroaryl

Heteroaryl is a monovalent monocyclic, bicyclic or tricyclic aromatic ring system having 5, 6, 7, 8, 9, 10, 11, 12, 13 or 14 ring systems (a "5- to 14-membered heteroaryl" group), in particular 5, 6, 9 or 10 ring atoms, which contains at least one ring heteroatom and optionally one, two or three further ring heteroatoms from the group consisting of N, O and S and which is attached via a ring carbon atom or optionally (the valency permitting) via a ring nitrogen atom.

The heteroaryl group may be a 5-membered heteroaryl group such as, for example, thienyl, furyl, pyrrolyl, oxazolyl, thiazolyl, imidazolyl, pyrazolyl, isoxazolyl, isothiazolyl, oxadiazolyl, triazolyl, thiadiazolyl or tetrazolyl; or a 6-membered heteroaryl group such as, for example, pyridinyl, pyridazinyl, pyrimidinyl, pyrazinyl or triazinyl; or a tricyclic heteroaryl group such as, for example, carbazolyl, acridinyl or phenazinyl; or a 9-membered heteroaryl group such as, for example, benzofuranyl, benzothienyl, benzoxazolyl, benzisoxazolyl, benzimidazolyl, benzothiazolyl, benzotriazolyl, indazolyl, indolyl, isoindolyl, indolizinyl or purinyl; or a 10-membered heteroaryl group such as, for example, quinolinyl, quinazolinyl, isoquinolinyl, cinnolinyl, phthalazinyl, quinoxalinyl or pteridinyl.

In general, and if not mentioned otherwise, the heteroaryl radicals include all possible isomeric forms thereof, for example tautomers and positional isomers with respect to the point of attachment to the remainder of the molecule. Thus, as an illustrative, non-including example, the term pyridinyl includes pyridin-2-yl, pyridin-3-yl and pyridin-4-yl; or the term thienyl includes thien-2-yl and thien-3-yl.

$C_5$-$C_{10}$-Heteroaryl

In the context of the invention, $C_{5-10}$-heteroaryl represents a mono- or bicyclic aromatic ring system having one, two, three or four heteroatoms which may be identical or different. Heteroatoms which may be present are: N, O, S, $S(=O)$ and/or $S(=O)_2$. The binding valency may be located at any aromatic carbon atom or at a nitrogen atom.

A monocyclic heteroaryl radical in accordance with the present invention has 5 or 6 ring atoms. Preference is given to heteroaryl radicals having one or two heteroatoms. Particular preference is given here to one or two nitrogen atoms.

Heteroaryl radicals having 5 ring atoms include, for example, the rings:
thienyl, thiazolyl, furyl, pyrrolyl, oxazolyl, imidazolyl, pyrazolyl, isoxazolyl, isothiazolyl, oxadiazolyl, triazolyl, tetrazolyl and thiadiazolyl.

Heteroaryl radicals having 6 ring atoms include, for example, the rings:
pyridinyl, pyridazinyl, pyrimidinyl, pyrazinyl and triazinyl.

A bicyclic heteroaryl radical in accordance with the present invention has 9 or 10 ring atoms.

Heteroaryl radicals having 9 ring atoms include, for example, the rings:
phthalidyl, thiophthalidyl, indolyl, isoindolyl, indazolyl, benzothiazolyl, benzofuryl, benzothienyl, benzimidazolyl, benzoxazolyl, azocinyl, indolizinyl, purinyl, indolinyl.

Heteroaryl radicals having 10 ring atoms include, for example, the rings:
isoquinolinyl, quinolinyl, quinolizinyl, quinazolinyl, quinoxalinyl, cinnolinyl, phthalazinyl, 1,7- and 1,8-naphthyridinyl, pteridinyl, chromanyl.

Heteroalkoxy

Heteroalkoxy represents a straight-chain and/or branched hydrocarbon chain having 1 to 10 carbon atoms which is attached to the remainder of the molecule via —O— and which may furthermore be interrupted once or more than once by one or more of the groups —O—, —S—, —C(=O)—, —S(=O)—, —S(=O)$_2$—, —NR$^y$—, —NR$^y$C(=O)—, —C(=O)—NR$^y$—, —NR$^y$NR$^y$—, —S(=O)$_2$—NR$^y$NR$^y$—, —C(=O)—NR$^y$NR$^y$—, —CR$^x$=N—O—, and where the hydrocarbon chain including the side chains, if present, may be substituted by —NH—C(=O)—NH$_2$, —C(=O)—OH, —OH, —NH$_2$, —NH—C(=NNH$_2$)—, sulphonamide, sulphone, sulphoxide or sulphonic acid.

Here, R$^y$ in each case represents —H, phenyl, C$_1$-C$_{10}$-alkyl, C$_2$-C$_{10}$-alkenyl or C$_2$-C$_{10}$-alkynyl, which for their part may in each case be substituted by —NH—C(=O)—NH$_2$, —C(=O)—OH, —OH, —NH$_2$, —NH—C(=NNH$_2$)—, sulphonamide, sulphone, sulphoxide or sulphonic acid.

Here, R$^x$ represents —H, C$_1$-C$_3$-alkyl or phenyl.

In the context of the invention, halogen or halogen atom represents fluorine (—F), chlorine (—Cl), bromine (—Br) or iodine (—I).

Fluoroalkyl, fluoroalkenyl and fluoroalkynyl mean that alkyl, alkenyl and alkynyl may be mono- or polysubstituted by fluorine.

The conjugation of the KSP inhibitor to the antibody can take place chemically by various routes, as shown in an exemplary manner in Schemes 20 to 31 in the examples. In particular, it is optionally possible to modify the low-molecular weight KSP inhibitor for the conjugation to the linker, for example by introducing protective groups or leaving groups to facilitate substitution (such that in the reaction said leaving group, and not a hydrogen atom, is substituted by the linker).

The KSP inhibitor—linker molecule obtained in this manner (where the linker has a reactive group for coupling to the binder) can then be reacted with the binder to give a binder conjugate according to the invention. In the experimental section, this procedure is illustrated in an exemplary manner by a large number of examples.

Other particularly preferred compounds have the formula (I) or (Ia) below:

Formula (I)

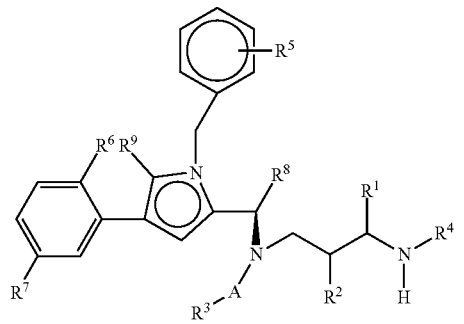

(I)

where

R$^1$ represents H, -L-#1, -MOD or —(CH$_2$)$_{0-3}$Z, where Z represents —H, —NHY$^3$, —OY$^3$, —SY$^3$, halogen, —CO—NY$^1$Y$^2$ or —CO—OY$^3$, where Y$^1$ and Y$^2$ independently of one another represent H, NH$_2$, —(CH$_2$CH$_2$O)$_{0-3}$—(CH$_2$)$_{0-3}$Z' (e.g. —(CH$_2$)$_{0-3}$Z') or —CH(CH$_2$W)Z', and Y$^3$ represents H or —(CH$_2$)$_{0-3}$Z', where Z' represents H, NH$_2$, SO$_3$H, COOH, —NH—CO—CH$_2$—CH$_2$—CH(NH$_2$)COOH or —(CO—NH—CHY$^4$)$_{1-3}$COOH, where W represents H or OH, where Y$^4$ represents straight-chain or branched C$_{1-6}$ alkyl which is optionally substituted by —NHCONH$_2$, or represents aryl or benzyl which are optionally substituted by —NH$_2$;

R$^2$ represents H, -MOD, —CO—CHY$^4$—NHY$^5$ or —(CH$_2$)$_{0-3}$Z, where Z represents —H, halogen, —OY$^3$, —SY$^3$, NHY$^3$, —CO—NY$^1$Y$^2$ or —CO—OY$^3$, where Y$^1$ and Y$^2$ independently of one another represent H, NH$_2$ or —(CH$_2$)$_{0-3}$Z', and Y$^3$ represents H or —(CH$_2$)$_{0-3}$Z', where Z' represents H, SO$_3$H, NH$_2$ or COOH;

where Y$^4$ represents straight-chain or branched C$_{1-16}$-alkyl which is optionally substituted by —NHCONH$_2$, or represents aryl or benzyl which are optionally substituted by —NH$_2$, and Y$^5$ represents H or —CO—CHY$^6$—NH$_2$, where Y$^6$ represents straight-chain or branched C$_{1-16}$-alkyl;

R$^4$ represents H, -L-#1, -SG$_{lys}$-(CO)$_{0-1}$—R$^{4'}$, —CO—CHY$^{4''}$—NHY$^5$ or —(CH$_2$)$_{0-3}$Z, where SG$_{lys}$ represents a group which can be cleaved by a lysosomal enzyme, in particular a group consisting of a di- or tripeptide, R$^{4'}$ represents a C$_{1-10}$-alkyl, C$_{5-10}$-aryl or C$_{6-10}$-aralkyl, C$_{5-10}$-heteroalkyl, C$_{1-10}$-alkyl-O—C$_{6-10}$-aryl, C$_{5-10}$-heterocycloalkyl, heteroaryl, heteroarylalkyl, heteroarylalkoxy, C$_{1-10}$-alkoxy, C$_{6-10}$-aryloxy or C$_{6-10}$-aralkoxy, C$_{5-10}$-heteroaralkoxy, C$_{1-10}$-alkyl-O—C$_{6-10}$-aryloxy, C$_{5-10}$-heterocycloalkoxy group which may be mono- or polysubstituted by —NH$_2$, —NH-alkyl, —N(alkyl)$_2$, NH—CO-alkyl, N(alkyl)-COalkyl, —SO$_3$H, —SO$_2$NH$_2$, —SO$_2$—N(alkyl)$_2$, —COOH, —CONH$_2$, —CON(alkyl)$_2$ or —OH, —H or a group —O$_x$—(CH$_2$CH$_2$O)$_v$—R$^{4''}$ (where x represents 0 or 1 and v represents a number from 1 to 20 and R$^{4''}$ represents —H, -alkyl (preferably C$_{1-12}$-alkyl), —CH$_2$—COOH, —CH$_2$—CH$_2$—COOH or —CH$_2$—NH$_2$);

where Z represents —H, halogen, —OY$^3$, —SY$^3$, NHY$^3$, —CO—NY$^1$Y$^2$ or —CO—OY$^3$, where Y$^1$ and Y$^2$ independently of one another represent H, NH$_2$ or —(CH$_2$)$_{0-3}$Z', and Y$^3$ represents H or —(CH$_2$)$_{0-3}$Z', where Z' represents H, SO$_3$H, NH$_2$ or COOH;

where Y$^4$ represents straight-chain or branched C$_{1-6}$-alkyl which is optionally substituted by —NHCONH$_2$, or represents aryl or benzyl which are optionally substituted by —NH$_2$, and Y$^5$ represents H or —CO—CHY$^6$—NH$_2$, where Y$^6$ represents straight-chain or branched C$_{1-6}$-alkyl;

or R$^2$ and R$^4$ together (with formation of a pyrrolidine ring) represent —CH$_2$—CHR$^{11}$— or —CHR$^{11}$—CH$_2$—, where R$^{11}$ represents H, NH$_2$, SO$_3$H, COOH, SH, halogen (in particular F or Cl), C$_{1-4}$-alkyl, C$_{1-4}$-haloalkyl, C$_{1-4}$-alkoxy, hydroxyl-substituted C$_{1-4}$-alkyl, COO(C$_{1-4}$-alkyl) or OH;

A represents CO, SO, SO$_2$, SO$_2$NH or CNNH$_2$;

R$^3$ represents -L-#1, -MOD or an optionally substituted alkyl, cycloalkyl, aryl, heteroaryl, heteroalkyl, heterocycloalkyl group, preferably a C$_{1-10}$-alkyl, C$_{6-10}$-aryl or C$_{6-10}$-aralkyl, C$_{5-10}$-heteroalkyl, C$_{1-10}$-alkyl-O—C$_{6-10}$-aryl or C$_{5-10}$-heterocycloalkyl group which may be substituted by 1-3-OH groups, 1-3 halogen atoms, 1-3 halogenated alkyl groups (each having 1-3 halogen atoms), 1-3 O-alkyl groups, 1-3-SH groups, 1-3-S-alkyl groups, 1-3-O—CO-alkyl groups, 1-3-O—CO—NH-alkyl groups, 1-3-NH—CO-alkyl groups, 1-3-NH—CO—NH-alkyl groups, 1-3-S(O)$_n$-alkyl groups, 1-3-SO$_2$—NH-alkyl groups, 1-3-NH-alkyl groups, 1-3-N(alkyl)$_2$ groups, 1-3-NH((CH$_2$CH$_2$O)1-20H) groups, 1-3-NH$_2$ groups or 1-3-(CH$_2$)$_{0-3}$Z groups, where n represents 0, 1 or 2, Z represents —H, halogen, —OY$^3$, —SY$^3$, —NHY$^3$, —CO—NY$^1$Y$^2$ or —CO—OY$^3$, where Y$^1$ and Y$^2$ independently of one another represent H, NH$_2$ or —(CH$_2$)$_{0-3}$Z' and Y$^3$ represents H, —(CH$_2$)$_{0-3}$—CH(NHCOCH$_3$)Z', —(CH$_2$)$_{0-3}$—CH(NH$_2$)Z' or —(CH$_2$)$_{0-3}$Z', where Z' represents H, SO$_3$H, NH$_2$ or COOH (where "alkyl" is preferably C$_{1-10}$-alkyl);

R$^5$ represents H, -MOD, NH$_2$, NO$_2$, halogen (in particular F, Cl, Br), —CN, CF$_3$, —OCF$_3$, —CH$_2$F, —CH$_2$F, SH or —(CH$_2$)$_{0-3}$Z, where Z represents —H, —OY$^3$, —SY$^3$, halogen, NHY$^3$, —CO—NY$^1$Y$^2$ or —CO—OY$^3$,
where Y$^1$ and Y$^2$ independently of one another represent H, NH$_2$ or —(CH$_2$)$_{0-3}$Z', and Y$^3$ represents H or —(CH$_2$)$_{0-3}$Z', where Z' represents H, SO$_3$H, NH$_2$ or COOH;
R$^6$ and R$^7$ independently of one another represent H, cyano, (optionally fluorinated) C$_{1-10}$-alkyl, (optionally fluorinated) C$_{2-10}$-alkenyl, (optionally fluorinated) C$_{2-10}$-alkynyl, hydroxy, NO$_2$, NH$_2$, COOH or halogen (in particular F, Cl, Br),
R$^8$ represents (optionally fluorinated) C$_{1-10}$-alkyl, (optionally fluorinated) C$_{2-10}$-alkenyl, (optionally fluorinated) C$_{2-10}$-alkynyl, (optionally fluorinated) C$_{4-10}$-cycloalkyl or —(CH$_2$)$_{0-2}$—(HZ$^2$), where HZ$^2$ represents a 4- to 7-membered heterocycle having up to two heteroatoms selected from the group consisting of N, O and S (preferably oxetane), where each of these groups may be substituted by —OH, CO$_2$H or NH$_2$;
where one of the substituents R$^1$, R$^3$ and R$^4$ represents -L-#1,
L represents the linker and #1 represents the bond to the antibody,
R$^9$ represents H, F, CH$_3$, CF$_3$, CH$_2$F or CHF$_2$;
where -MOD represents —(NR$^{10}$)$_n$-(G1)$_o$-G2-G3, where R$^{10}$ represents H or C$_1$-C$_3$-alkyl;
G1 represents —NHCO—, —CONH— or

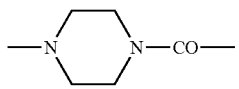

(where, if G1 represents —NHCO— or

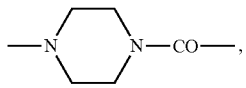

R$^{10}$ does not represent NH$_2$);
n represents 0 or 1;
o represents 0 or 1; and
G2 represents a straight-chain and/or branched hydrocarbon group which has 1 to 10 carbon atoms and which may be interrupted once or more than once by one or more of the groups —O—, —S—, —SO—, SO$_2$, —NRy-, —NRyCO—, CONRy-, —NRyNRy-, —SO$_2$NRyNRy-, —CONRyNRy- (where R$^y$ represents H, phenyl, C$_1$-C$_{10}$-alkyl, C$_2$-C$_{10}$-alkenyl or C$_2$-C$_{10}$-alkynyl, each of which may be substituted by NHCONH$_2$, —COOH, —OH, —NH$_2$, NH—CNNH$_2$, sulphonamide, sulphone, sulphoxide or sulphonic acid), —CO—, or —CR$^x$=N—O— (where Rx represents H, C$_1$-C$_3$-alkyl or phenyl), where the hydrocarbon chain including any side chains may be substituted by —NHCONH$_2$, —COOH, —OH, —NH$_2$, NH—CNNH$_2$, sulphonamide, sulphone, sulphoxide or sulphonic acid, where G3 represents —H or —COOH, and where the group -MOD preferably has at least one group —COOH;
and the salts, solvates, salts of the solvates and epimers thereof.
In a preferred embodiment of the formula (I), one of the substituents R$^1$ or R$^3$ represents -L-#1. In this embodiment it is particularly preferred if R$^4$ represents H or -SG$_{lys}$-(CO)$_{0-1}$—R$^{4'}$, where SG$_{lys}$ and R$^{4'}$ have the same meaning as above. In another preferred embodiment of the formula (I), the substituent R$^4$ represents -L-#1, where the linker is a linker which can be cleaved at the nitrogen atom which binds to R$^4$, so that a primary amino group is present after cleavage (corresponds to R$^4$=H). Such cleavable groups are described in detail below.
If R$^1$ does not represent H, the carbon atom to which R$^1$ binds is a stereocentre which may be present in the L and/or D configuration, preferably in the L configuration.
If R$^2$ does not represent H, the carbon atom to which R$^2$ binds is a stereocentre which may be present in the L and/or D configuration.

Formula (Ia)

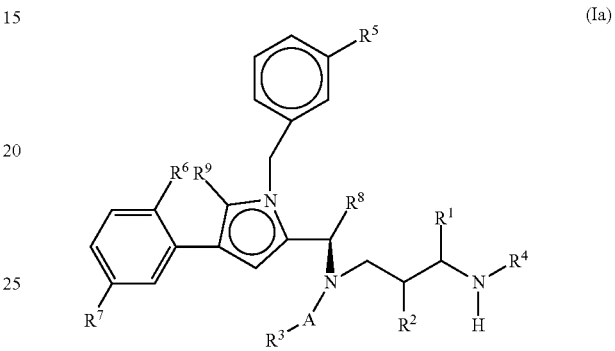

where
R$^1$ represents H, -L-#1 or —(CH$_2$)$_{0-3}$Z, where Z represents —H, —NHY$^3$, —OY$^3$, —SY$^3$, halogen, —CO—NY$^1$Y$^2$ or —CO—OY$^3$,
where Y$^1$ and Y$^2$ independently of one another represent H, NH$_2$, —(CH$_2$CH$_2$O)$_{0-3}$—(CH$_2$)$_{0-3}$Z' (e.g. —(CH$_2$)$_{0-3}$Z') or —CH(CH$_2$W)Z', and Y$^3$ represents H or —(CH$_2$)$_{0-3}$Z', where Z' represents H, NH$_2$, SO$_3$H, COOH, —NH—CO—CH$_2$—CH$_2$—CH(NH$_2$)COOH or —(CO—NH—CHY$^4$)$_{1-3}$COOH, where W represents H or OH;
where Y$^4$ represents straight-chain or branched C$_{1-6}$ alkyl which is optionally substituted by —NHCONH$_2$, or represents aryl or benzyl which are optionally substituted by —NH$_2$.
R$^2$ and R$^4$ independently of one another represent H, -SG$_{lys}$-(CO)$_{0-1}$—R$^{4'}$, —CO—CHY$^4$—NHY$^5$ or —(CH$_2$)$_{0-3}$Z,
where SG$_{lys}$ represents a group which can be cleaved by a lysosomal enzyme, in particular a group consisting of a di- or tripeptide, R$^{4'}$ represents a C$_{1-10}$-alkyl, C$_{5-10}$-aryl or C$_{6-10}$-aralkyl, C$_{5-10}$-heteroalkyl, C$_{1-10}$-alkyl-O—C$_{6-10}$-aryl, C$_{5-10}$-heterocycloalkyl, heteroaryl, heteroarylalkyl, heteroarylalkoxy, C$_{1-10}$-alkoxy, C$_{6-10}$-aryloxy or C$_{6-10}$-aralkoxy, C$_{5-10}$-heteroaralkoxy, C$_{1-10}$-alkyl-O—C$_{6-10}$-aryloxy, C$_{5-10}$-heterocycloalkoxy group which may be mono- or polysubstituted by —NH$_2$, —NH-alkyl, —N(alkyl)$_2$, NH—CO-alkyl, N(alkyl)-COalkyl, —SO$_3$H, —SO$_2$NH$_2$, —SO$_2$—N(alkyl)$_2$, —COOH, —CONH$_2$, —CON(alkyl)$_2$ or —OH, —H or a group —O$_x$—(CH$_2$CH$_2$O)$_v$—R$^{4''}$ (where x represents 0 or 1 and v represents a number from 1 to 20 and R$^{4''}$ represents —H, -alkyl (preferably C$_{1-12}$-alkyl), —CH$_2$—COOH, —CH$_2$—CH$_2$—COOH or —CH$_2$—CH$_2$—NH$_2$);
or R$^2$ and R$^4$ together represent (with formation of a pyrrolidine ring) —CH$_2$—CHR$^{11}$— or —CHR$^{11}$—CH$_2$—, where R$^{11}$ represents H, NH$_2$, SO$_3$H, COOH, SH, halogen (in particular F or Cl), C$_{1-4}$-alkyl, C$_{1-4}$-haloalkyl, C$_{1-4}$-alkoxy, hydroxyl-substituted C$_{1-4}$-alkyl, COO(C$_{1-4}$-alkyl) or OH; or R$^2$ represents H, —CO—CHY$^4$—NHY$^5$ or —(CH$_2$)$_{0-3}$Z and $R^4$ represents -L-#1 darstellt, and where Z represents —H, halogen, —$OY^3$, —$SY^3$, —$NHY^3$, —CO—$NY_1Y_2$ or —CO—$OY^3$,
where $Y^1$ and $Y^2$ independently of one another represent H, $NH_2$ or —$(CH_2)_{0-3}Z'$, and $Y^3$ represents H or —$(CH_2)_{0-3}Z'$, where $Z'$ represents H, $SO_3H$, $NH_2$ or COOH;
where $Y^4$ independently of one another represents straight-chain or branched $C_{1-6}$-alkyl which is optionally substituted by —$NHCONH_2$ or represents aryl or benzyl which are optionally substituted by —$NH_2$, where $Y^4$ represents straight-chain or branched $C_{1-6}$-alkyl which is optionally substituted by —$NHCONH_2$ or represents aryl or benzyl which are optionally substituted by —$NH_2$ and $Y^5$ represents H or —CO—$CHY^6$—$NH_2$, where $Y^6$ represents straight-chain or branched $C_{1-6}$-alkyl;
A represents CO, SO, $SO_2$, $SO_2NH$ or $CNNH_2$;
$R^3$ represents an optionally substituted alkyl, aryl, heteroaryl, heteroalkyl, heterocycloalkyl group, preferably -L-#1 or a $C_{1-10}$-alkyl, $C_{6-10}$-aryl or $C_{6-10}$-aralkyl, $C_{5-10}$-heteroalkyl, $C_{1-10}$-alkyl-O—$C_{6-10}$-aryl or $C_{5-10}$-heterocycloalkyl group which may be substituted by 1-3-OH groups, 1-3 halogen atoms, 1-3 halogenated alkyl groups (each having 1-3 halogen atoms), 1-3 O-alkyl groups, 1-3-SH groups, 1-3-S-alkyl groups, 1-3-O—CO-alkyl groups, 1-3-O—CO—NH-alkyl groups, 1-3-NH—CO-alkyl groups, 1-3-NH—CO—NH-alkyl groups, 1-3-$S(O)_n$-alkyl groups, 1-3-$SO_2$—NH-alkyl groups, 1-3-NH-alkyl groups, 1-3-N(alkyl)$_2$ groups, 1-3-$NH_2$ groups or 1-3-$(CH_2)_{0-3}Z$ groups, where n represents 0, 1 or 2, Z represents —H, halogen, —$OY^3$, —$SY^3$, —$NHY^3$, —CO—$NY^1Y^2$ or —CO—$OY^3$, where $Y^1$ and $Y^2$ independently of one another represent H, $NH_2$ or —$(CH_2)_{0-3}Z'$ and $Y^3$ represents H, —$(CH_2)_{0-3}$—CH(NHCOCH$_3$)$Z'$, —$(CH_2)_{0-3}$—CH(NH$_2$)$Z'$ or —$(CH_2)_{0-3}Z'$, where $Z'$ represents H, $SO_3H$, $NH_2$ or COOH (where "alkyl" preferably represents $C_{1-10}$-alkyl);
$R^5$ represents H, F, $NH_2$, $NO_2$, halogen, SH or —$(CH_2)_{0-3}Z$, where Z represents —H, halogen, —$OY^3$, —$SY^3$, $NHY^3$, —CO—$NY^1Y^2$ or —CO—$OY^3$,
where $Y^1$ and $Y^2$ independently of one another represent H, $NH_2$ or —$(CH_2)_{0-3}Z'$, and $Y^3$ represents H or —$(CH_2)_{0-3}Z'$, where $Z'$ represents H, $SO_3H$, $NH_2$ or COOH;
$R^6$ and $R^7$ independently of one another represent H, cyano, (optionally fluorinated) $C_{1-10}$-alkyl, (optionally fluorinated) $C_{2-10}$-alkenyl, (optionally fluorinated) $C_{2-10}$-alkynyl, hydroxy or halogen,
$R^8$ represents (optionally fluorinated) $C_{1-10}$-alkyl, (optionally fluorinated) $C_{4-10}$-cycloalkyl or optionally substituted oxetane; and
$R^9$ represents H, F, $CH_3$, $CF_3$, $CH_2F$ or $CHF_2$; and the salts, solvates, salts of the solvates and epimers thereof.

By substitution of a hydrogen atom at $R^1$, $R^3$ or $R^4$, it is possible to attach a compound of the formula (I) or (Ia) in which none of the substituents $R^1$, $R^3$ and $R^4$ represents -L-#1 to a linker in a manner known to the person skilled in the art. This gives conjugates of the formula (I) or (Ia) where one of the substituents $R^1$, $R^3$ or $R^4$ represents -L-#1, L represents the linker and #1 represents the bond to the antibody. If the KSP inhibitor according to formula (I) or (Ia) is conjugated with a binder, one of the substituents $R^1$, $R^3$ oder $R^4$ thus represents -L-#1, where L represents the linker and #1 represents the bond to the antibody. That is, in the case of the conjugates one of the substituents $R^1$, $R^3$ or $R^4$ represents -L-#1, where -L-#1 represents the bond to the antibody. The binder is preferably a human, humanized or chimeric monoclonal antibody or an antigen-binding fragment thereof. In a preferred embodiment of the formula (I) or (Ia), one of the substituents $R^1$ or $R^3$ represents -L-#1. In this embodiment it is particularly preferred if $R^4$ represents H or -$SG_{lys}$-$(CO)_{0-1}$—$R^{4'}$, where $SG_{lys}$ and $R^{4'}$ have the same meaning as above. In another preferred embodiment of the formula (I), the substituent $R^4$ represents -L-#1, where the linker is a linker which can be cleaved at the nitrogen atom which binds to $R^4$, so that a primary amino group is present after cleavage (corresponds to $R^4$=H). Such cleavable groups are described in detail below. Preference is given here to a chimeric or humanized anti-CD123 antibody derived from an antibody 7G3 or 12F1 originating from mice. Particular preference is given to the antibodies TPP-6013, TPP-5968, TPP-5969 and TPP-5971.

Instead of -L-#1, it is also possible for the group -L-#3 to be present in the compound, where L represents the linker and #3 represents the reactive group for binding to the antibody. Compounds comprising -L-#3 are reactive compounds which react with the antibody. #3 is preferably a group which reacts with an amino or thiol group with formation of a covalent bond, preferably with the cysteine residue in a protein. The cysteine residue in a protein may be present naturally in the protein, may be introduced by biochemical methods or, preferably, may be generated by prior reduction of disulphides of the binder.

For A, preference is given to CO (carbonyl).

Preferred for $R^1$ are -L-#1, H, —COOH, —$CONHNH_2$, —$(CH_2)_{1-3}NH_2$, —$CONZ''(CH_2)_{1-3}$ $NH_2$ and —$CONZ''CH_2COOH$, where $Z''$ represents H or $NH_2$.

Preferred for $R^2$ and $R^4$ is H, or $R^2$ and $R^4$ together (with formation of a pyrrolidine ring) represent —$CH_2$—$CHR^{11}$— or —$CHR^{11}$—$CH_2$—, where $R^{11}$ represents H or F. Also preferred for $R^4$ is -L-#1, where -L-#1 is a cleavable linker, preferably a linker which can be cleaved intracellularly by enzymes.

Preferred for $R^3$ is -L-#1 or $C_{1-10}$-alkyl-, which may optionally be substituted by —OH, O-alkyl, SH, S-alkyl, O—CO-alkyl, O—CO—NH-alkyl, NH—CO-alkyl, NH—CO—NH-alkyl, $S(O)_n$-alkyl, $SO_2$—NH— alkyl, NH-alkyl, N(alkyl)$_2$ or $NH_2$ (where alkyl is preferably $C_{1-3}$-alkyl).

Preferred for $R^5$ is H or F.

Preferred for $R^6$ and $R^7$, independently of one another, are H, (optionally fluorinated) $C_{1-3}$-alkyl, (optionally fluorinated) $C_{2-4}$-alkenyl, (optionally fluorinated) $C_{2-4}$-alkynyl, hydroxy or halogen.

Preferred for $R^8$ is a branched $C_{1-5}$-alkyl group, in particular a group of the formula —$C(CH_3)_2$—$(CH_2)_{0-2}$—$R_y$, where $R_y$ represents —H, —OH, $CO_2H$ or $NH_2$, or an (optionally fluorinated) $C_{5-7}$-cycloalkyl. Particular preference is given to a group of the formula —$C(CH_3)_3$ or a cyclohexyl group.

Preferred for $R^9$ is H or F.

Especially preferred are compounds of the formula (I) or (Ia) in which A represents CO (carbonyl);
$R^1$ represents H, -L-#1, —COOH, —$CONHNH_2$, —$(CH_2)_{1-3}NH_2$, —$CONZ''(CH_2)_{1-3}$ $NH_2$ or —$CONZ''CH_2COOH$, where $Z''$ represents H or $NH_2$;
$R^2$ and $R^4$ represent H or $R^2$ and $R^4$ together (with formation of a pyrrolidine ring) represent —$CH_2$—$CHR^{11}$— or —$CHR^{11}$—$CH_2$—, where $R^{11}$ represents H; or $R^4$ represents -L-#1 and $R^2$ represents H;
$R^3$ represents -L-#1 or a phenyl group which may be mono- or polysubstituted by halogen (in particular F) or optionally fluorinated $C_{1-3}$-alkyl, or represents an optionally fluorinated $C_{1-10}$-alkyl group which may optionally be substituted by —$OY^4$, —$SY^4$, —O—CO—$Y^4$, —O—CO—NH—$Y^4$, NH—CO—$Y^4$, —NH—CO—NH—$Y^4$, $S(O)$—$Y^4$ (where n represents 0, 1 or 2), —$SO_2$—NH—$Y^4$, NH—$Y^4$ or $N(Y^4)_2$, where $Y^4$ represents H, phenyl (optionally mono- or polysubstituted by halogen (in particular F) or optionally fluorinated $C_{1-3}$-alkyl), or alkyl (where the alkyl group may be substituted by —OH, —COOH, and/or —NHCO—$C_{1-3}$-alkyl and where alkyl preferably represents $C_{1-3}$-alkyl); where particularly preferably $R^3$ may be substituted by —OH, O-alkyl, SH, S-alkyl, O—CO-alkyl, O—CO—NH-alkyl, NH—CO-alkyl, NH—CO—NH-alkyl, $S(O)_n$-alkyl, $SO_2$—NH-alkyl, NH-alkyl, N(alkyl)$_2$ or NH$_2$ (where alkyl preferably means $C_{1-3}$-alkyl);

$R^5$ represents H or F;

$R^6$ and $R^7$ independently of one another represent H, (optionally fluorinated) $C_{1-3}$-alkyl, (optionally fluorinated) $C_{2-4}$-alkenyl, (optionally fluorinated) $C_{2-4}$-alkynyl, hydroxy or halogen;

$R^8$ represents a branched $C_{1-5}$-alkyl group or cyclohexyl; and $R^9$ represents H or F.

Furthermore, it is preferred when (alone or in combination)

$R^1$ represents -L-#1, COOH or H, $R^2$ and $R^4$ represent H or $R^2$ and $R^4$ together (with formation of a pyrrolidine ring) represent —CH$_2$—CHR$^{11}$— or —CHR$^{11}$—CH$_2$—, where $R^{11}$ represents H, or $R^4$ represents -L-#1 and $R^2$ represents H;

A represents CO, $R^3$ represents —(CH$_2$)OH, —CH(CH$_3$)OH, —CH$_2$SCH$_2$CH(COOH)NHCOCH$_3$, —CH(CH$_3$)OCH$_3$, a phenyl group which may be substituted by 1-3 halogen atoms, 1-3 amino groups or 1-3 alkyl groups (which may optionally be halogenated), or represents -L-#1, $R^5$ represents —H, $R^6$ and $R^7$ independently of one another represent H, $C_{1-3}$-alkyl or halogen; in particular, $R^6$ and $R^7$ represent F;

$R^8$ represents $C_{1-4}$-alkyl (preferably tert-butyl) or cyclohexyl; and/or $R^9$ represents H.

Additionally, in accordance with the invention it is preferred when $R^1$ represents -L-#1, COOH or H, $R^2$ and $R^4$ represent H or $R^2$ and $R^4$ together (with formation of a pyrrolidine ring) represent —CH$_2$—CHR$^{11}$— or —CHR$^{11}$—CH$_2$—, where $R^{11}$ represents H, A represents CO, $R^3$ represents —(CH$_2$)OH, —CH(CH$_3$)OH, —CH$_2$SCH$_2$CH(COOH)NHCOCH$_3$, —CH(CH$_3$)OCH$_3$, a phenyl group which may be substituted by 1-3 halogen atoms, 1-3 amino groups or 1-3 alkyl groups (which may optionally be halogenated), or represents -L-#1, $R^5$ represents H, $R^6$ and $R^7$ independently of one another represent H, $C_{1-3}$-alkyl or halogen; in particular, $R^6$ and $R^7$ represent F;

$R^8$ represents $C_{1-4}$-alkyl (preferably tert-butyl); and $R^9$ represents H.

Other particularly preferred compounds have the formula (II) or (IIa) below:

Formula (II)

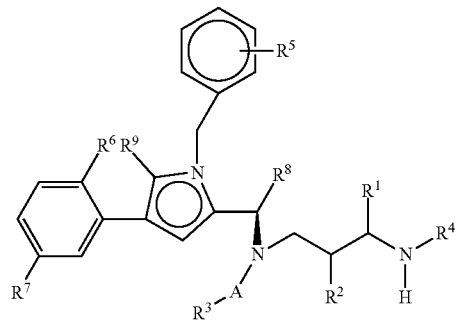

(II)

where
$R^1$ represents H, -L-BINDER, -MOD or —(CH$_2$)$_{0-3}$Z, where Z represents —H, —NHY$^3$, —OY$^3$, —SY$^3$, halogen, —CO—NY$^1$Y$^2$ or —CO—OY$^3$,
where Y$^1$ and Y$^2$ independently of one another represent H, NH$_2$, —(CH$_2$CH$_2$O)$_{0-3}$—(CH$_2$)$_{0-3}$Z' (e.g. —(CH$_2$)$_{0-3}$Z') or —CH(CH$_2$W)Z', and Y$^3$ represents H or —(CH$_2$)$_{0-3}$Z',
where Z' represents H, NH$_2$, SO$_3$H, —COOH, —NH—CO—CH$_2$—CH$_2$—CH(NH$_2$)COOH or —(CO—NH—CHY$^4$)$_{1-3}$COOH, where W represents H or OH,
where Y$^4$ represents straight-chain or branched $C_{1-6}$ alkyl which is optionally substituted by —NHCONH$_2$, or represents aryl or benzyl which are optionally substituted by —NH$_2$;
$R^2$ represents H, -MOD, —CO—CHY$^4$—NHY$^5$ or —(CH$_2$)$_{0-3}$Z, where Y$^4$ represents straight-chain or branched $C_{1-6}$ alkyl which is optionally substituted by —NHCONH$_2$, or represents aryl or benzyl which are optionally substituted by —NH$_2$, and Y$^5$ represents H or —CO—CHY$^6$—NH$_2$, where Y$^6$ represents straight-chain or branched $C_{1-6}$-alkyl,
where Z represents —H, halogen, —OY$^3$, —SY$^3$, NHY$^3$, —CO—NY$^1$Y$^2$ or —CO—OY$^3$,
where Y$^1$ and Y$^2$ independently of one another represent H, NH$_2$ or —(CH$_2$)$_{0-3}$Z', and Y$^3$ represents H or —(CH$_2$)$_{0-3}$Z', where Z' represents H, SO$_3$H, NH$_2$ or COOH;
$R^4$ represents H, -L-BINDER, -SG$_{lys}$-(CO)$_{0-1}$—R$^{4'}$, —CO—CHY$^4$—NHY$^5$ or —(CH$_2$)$_{0-3}$Z,
where SG$_{lys}$ represents a group which can be cleaved by a lysosomal enzyme, in particular a group consisting of a di- or tripeptide, $R^{4'}$ represents a $C_{1-10}$-alkyl, $C_{5-10}$-aryl or $C_{6-10}$-aralkyl, $C_{5-10}$-heteroalkyl, $C_{1-10}$-alkyl-O—$C_{6-10}$-aryl, $C_{5-10}$-heterocycloalkyl, heteroaryl, heteroarylalkyl, heteroarylalkoxy, $C_{1-10}$-alkoxy, $C_{6-10}$-aryloxy or $C_{6-10}$-aralkoxy, $C_{5-10}$-heteroaralkoxy, $C_{1-10}$-alkyl-O—$C_{6-10}$-aryloxy, $C_{5-10}$-heterocycloalkoxy group which may be mono- or polysubstituted by —NH$_2$, —NH-alkyl, —N(alkyl)$_2$, NH—CO-alkyl, N(alkyl)-COalkyl, —SO$_3$H, —SO$_2$NH$_2$, —SO$_2$—N(alkyl)$_2$, —COOH, —CONH$_2$, —CON(alkyl)$_2$ or —OH, —H or a group —O$_x$—(CH$_2$CH$_2$O)$_v$—R$^{4''}$ (where x represents 0 or 1 and v represents a number from 1 to 20 and R$^{4''}$ represents —H, -alkyl (preferably $C_{1-12}$-alkyl), —CH$_2$—COOH, —CH$_2$—CH$_2$—COOH or —CH$_2$—CH$_2$—NH$_2$);
where Z represents —H, halogen, —OY$^3$, —SY$^3$, NHY$^3$, —CO—NY$^1$Y$^2$ or —CO—OY$^3$,
where Y$^1$ and Y$^2$ independently of one another represent H, NH$_2$ or —(CH$_2$)$_{0-3}$Z', and Y$^3$ represents H or —(CH$_2$)$_{0-3}$Z', where Z' represents H, SO$_3$H, NH$_2$ or COOH;
where Y$^4$ represents straight-chain or branched $C_{1-6}$-alkyl which is optionally substituted by —NHCONH$_2$, or represents aryl or benzyl which are optionally substituted by —NH$_2$, and Y$^5$ represents H or —CO—CHY$^6$—NH$_2$, where Y$^6$ represents straight-chain or branched C$_{1-6}$-alkyl;

or R$^2$ and R$^4$ together (with formation of a pyrrolidine ring) represent —CH$_2$—CHR$^{11}$— or —CHR$^{11}$—CH$_2$—, where R$^{11}$ represents H, NH$_2$, SO$_3$H, COOH, SH or OH;

A represents CO, SO, SO$_2$, SO$_2$NH or CNNH$_2$;

R$^3$ represents -L-BINDER, -MOD or an optionally substituted alkyl, cycloalkyl, aryl, heteroaryl, heteroalkyl, heterocycloalkyl group, preferably -L-BINDER or a C$_{1-10}$-alkyl, C$_{6-10}$-aryl or C$_{6-10}$-aralkyl, C$_{5-10}$-heteroalkyl, C$_{1-10}$-alkyl-O—C$_{6-10}$-aryl or C$_{5-10}$-heterocycloalkyl group which may be substituted by 1-3-OH groups, 1-3 halogen atoms, 1-3 halogenated alkyl groups (each having 1-3 halogen atoms), 1-3 O-alkyl groups, 1-3-SH groups, 1-3-S-alkyl groups, 1-3-O—CO-alkyl groups, 1-3-O—CO—NH-alkyl groups, 1-3-NH—CO-alkyl groups, 1-3-NH—CO—NH-alkyl groups, 1-3-S(O)$_n$-alkyl groups, 1-3-SO$_2$—NH-alkyl groups, 1-3-NH-alkyl groups, 1-3-N(alkyl)$_2$ groups, 1-3-NH$_2$ groups or 1-3-(CH$_2$)$_{0-3}$Z groups, where Z represents —H, halogen, —OY$^3$, —SY$^3$, —NHY$^3$, —CO—NY$^1$Y$^2$ or —CO—OY$^3$, where Y$^1$ and Y$^2$ independently of one another represent H, NH$_2$ or —(CH$_2$)$_{0-3}$Z' and Y$^3$ represents H, —(CH$_2$)$_{0-3}$—CH(NHCOCH$_3$)Z', —(CH$_2$)$_{0-3}$—CH(NH$_2$)Z' or —(CH$_2$)$_{0-3}$Z', where Z' represents H, SO$_3$H, NH$_2$ or COOH (where "alkyl" preferably represents C$_{1-10}$-alkyl);

R$^5$ represents H, NH$_2$, NO$_2$, halogen (in particular F, Cl, Br), —CN, CF$_3$, —OCF$_3$, —CH$_2$F, —CH$_2$F, SH or —(CH$_2$)$_{0-3}$Z, where Z represents —H, —OY$^3$, —SY$^3$, halogen, NHY$^3$, —CO—NY$^1$Y$^2$ or —CO—OY$^3$, where Y$^1$ and Y$^2$ independently of one another represent H, NH$_2$ or —(CH$_2$)$_{0-3}$Z', and Y$^3$ represents H or —(CH$_2$)$_{0-3}$Z', where Z' represents H, SO$_3$H, NH$_2$ or COOH;

R$^6$ and R$^7$ independently of one another represent H, cyano, (optionally fluorinated) C$_{1-10}$-alkyl, (optionally fluorinated) C$_{2-10}$-alkenyl, (optionally fluorinated) C$_{2-10}$-alkynyl, hydroxy, NO$_2$, NH$_2$, COOH or halogen (in particular F, Cl, Br), R$^8$ represents (optionally fluorinated) C$_{1-10}$-alkyl, (optionally fluorinated) C$_{2-10}$-alkenyl, (optionally fluorinated) C$_{2-10}$-alkynyl, (optionally fluorinated) C$_{4-10}$-cycloalkyl or —(CH$_2$)$_{0-2}$—(HZ$^2$), where HZ$^2$ represents a 4- to 7-membered heterocycle having up to two heteroatoms selected from the group consisting of N, O and S, where each of these groups may be substituted by —OH, CO$_2$H or NH$_2$;

R$^9$ represents H, F, CH$_3$, CF$_3$, CH$_2$F or CHF$_2$;

where -MOD represents —(NR$^{10}$)$_n$-(G1)$_o$-G2-G3, where R$^{10}$ represents H or C$_1$-C$_3$-alkyl;

G1 represents —NHCO— or —CONH— (where, if G1 represents —NHCO—, R$^{10}$ does not represent NH$_2$);

n represents 0 or 1;

o represents 0 or 1; and

G2 represents a straight-chain and/or branched hydrocarbon group which has 1 to 10 carbon atoms and which may be interrupted once or more than once by one or more of the groups —O—, —S—, —SO—, SO$_2$, —NRy-, —NRyCO—, CONRy-, —NRyNRy-, —SO$_2$NRyNRy-, —CONRyNRy- (where R$^y$ represents H, phenyl, C$_1$-C$_{10}$-alkyl, C$_2$-C$_{10}$-alkenyl or C$_2$-C$_{10}$-alkynyl, each of which may be substituted by NHCONH$_2$, —COOH, —OH, —NH$_2$, NH—CNNH$_2$, sulphonamide, sulphone, sulphoxide or sulphonic acid), —CO—, —CR$^x$=N—O— (where Rx represents H, C$_1$-C$_3$-alkyl or phenyl), where the hydrocarbon chain including any side chains may be substituted by —NHCONH$_2$, —COOH, —OH, —NH$_2$, NH—CNNH$_2$, sulphonamide, sulphone, sulphoxide or sulphonic acid, G3 represents —H or —COOH, and where the group -MOD preferably has at least one group —COOH;

and the salts, solvates, salts of the solvates and epimers thereof.

In the case of binder conjugates of the KSP inhibitors of the formula (II), at most one representative of R$^1$, R$^3$ and R$^4$ (alternatively to one of the conditions given above) may represent -L-BINDER, where L represents a linker and BINDER represents an antibody, where the antibody may optionally be attached to a plurality of active compound molecules.

Formula (IIa)

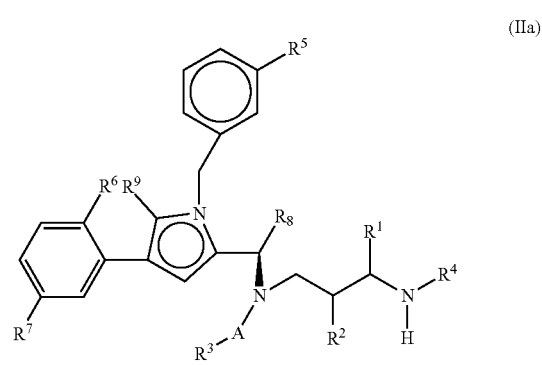

(IIa)

where

R$^1$ represents -L-BINDER, H or —(CH$_2$)$_{0-3}$Z, where Z represents —H, —NHY$^3$, —OY$^3$, —SY$^3$, halogen, —CO—NY$^1$Y$^2$ or —CO—OY$^3$, where Y$^1$ and Y$^2$ independently of one another represent H, NH$_2$, —(CH$_2$CH$_2$O)$_{0-3}$—(CH$_2$)$_{0-3}$Z' or —CH(CH$_2$W)Z', and Y$^3$ represents H or —(CH$_2$)$_{0-3}$Z', where Z' represents H, NH$_2$, SO$_3$H, COOH, —NH—CO—CH$_2$—CH$_2$—CH(NH$_2$)COOH or —(CO—NH—CHY$^4$)$_{1-3}$COOH; where W represents H or OH; where Y$^4$ represents straight-chain or branched C$_{1-6}$ alkyl which is optionally substituted by —NHCONH$_2$, or represents aryl or benzyl which are optionally substituted by —NH$_2$;

R$^2$ and R$^4$ independently of one another represent -SG$_{lys}$-(CO)$_{0-1}$—R$^{4'}$, H, —CO—CHY$^4$—NHY$^5$ or —(CH$_2$)$_{0-3}$Z, or R$^2$ and R$^4$ together (with formation of a pyrrolidine ring) represent —CH$_2$—CHR$^{11}$— or —CHR$^{11}$—CH$_2$—, or R$^2$ represents H, —CO—CHY$^4$—NHY$^5$ or —(CH$_2$)$_{0-3}$Z and R$^4$ represents -L-#1, where R$^{11}$ represents H, NH$_2$, SO$_3$H, COOH, SH, halogen (in particular F or Cl), C$_{1-4}$-alkyl, C$_{1-4}$-haloalkyl, C$_{1-4}$-alkoxy, hydroxyl-substituted C$_{1-4}$-alkyl, COO(C$_{1-4}$-alkyl) or OH;

where SG$_{lys}$ represents a group which can be cleaved by a lysosomal enzyme, in particular a group consisting of a di- or tripeptide, R$^{4'}$ represents a C$_{1-10}$-alkyl, C$_{5-10}$-aryl or C$_{6-10}$-aralkyl, C$_{5-10}$-heteroalkyl, C$_{1-10}$-alkyl-O—C$_{6-10}$-aryl, C$_{5-10}$-heterocycloalkyl, heteroaryl, heteroarylalkyl, heteroarylalkoxy, C$_{1-10}$-alkoxy, C$_{6-10}$-aryloxy or C$_{6-10}$-aralkoxy, C$_{5-10}$-heteroaralkoxy, C$_{1-10}$-alkyl-O—C$_{6-10}$-aryloxy, C$_{5-10}$-heterocycloalkoxy group which may be mono- or polysubstituted by —NH$_2$, —NH-alkyl, —N(alkyl)$_2$, NH—CO-alkyl, N(alkyl)-COalkyl, —SO$_3$H, —SO$_2$NH$_2$, —SO$_2$—N(alkyl)$_2$, —COOH, —CONH$_2$, —CON(alkyl)$_2$ or —OH, —H or a group —O$_x$—(CH$_2$CH$_2$O)$_v$—R$^{4''}$ (where x represents 0 or 1 and v represents a number from 1 to 20 and R$^{4''}$ represents —H, -alkyl (preferably C$_{1-12}$-alkyl), —CH$_2$—COOH, —CH$_2$—CH$_2$—COOH or —CH$_2$—CH$_2$—NH$_2$);

where Z represents —H, halogen, —OY$^3$, —SY$^3$, NHY$^3$, —CO—NY$^1$Y$^2$ or —CO—OY$^3$,
where Y$^1$ and Y$^2$ independently of one another represent H, NH$_2$ or —(CH$_2$)$_{0-3}$Z', and Y$^3$ represents H or —(CH$_2$)$_{0-3}$Z', where Z' represents H, SO$_3$H, NH$_2$ or COOH;
where Y$^4$ represents straight-chain or branched C$_{1-6}$-alkyl which is optionally substituted by —NHCONH$_2$, or represents aryl or benzyl which are optionally substituted by —NH$_2$, and Y$^5$ represents H or —CO—CHY$^6$—NH$_2$, where Y$^6$ represents straight-chain or branched C$_{1-6}$-alkyl;
A represents CO, SO, SO$_2$, SO$_2$NH or CNNH$_2$;
R$^3$ represents -L-BINDER or an optionally substituted alkyl, aryl, heteroaryl, heteroalkyl, heterocycloalkyl group, preferably -L-BINDER or a C$_{1-10}$-alkyl, C$_{6-10}$-aryl or C$_{6-10}$-aralkyl, C$_{5-10}$-heteroalkyl, C$_{1-10}$-alkyl-O—C$_{6-10}$-aryl or C$_{5-10}$-heterocycloalkyl group which may be substituted by 1-3-OH groups, 1-3 halogen atoms, 1-3 halogenated alkyl groups (each having 1-3 halogen atoms), 1-3 O-alkyl groups, 1-3-SH groups, 1-3-S-alkyl groups, 1-3-O—CO-alkyl groups, 1-3-O—CO—NH-alkyl groups, 1-3-NH—CO-alkyl groups, 1-3-NH—CO—NH-alkyl groups, 1-3-S(O)$_n$-alkyl groups, 1-3-SO$_2$—NH-alkyl groups, 1-3-NH-alkyl groups, 1-3-N(alkyl)$_2$ groups, 1-3-NH$_2$ groups or 1-3 —(CH$_2$)$_{0-3}$Z groups, where Z represents —H, halogen, —OY$^3$, —SY$^3$, —NHY$^3$, —CO—NY$^1$Y$^2$ or —CO—OY$^3$, where Y$^1$ and Y$^2$ independently of one another represent H, NH$_2$ or —(CH$_2$)$_{0-3}$Z' and Y$^3$ represents H, —(CH$_2$)$_{0-3}$—CH(NHCOCH$_3$)Z', —(CH$_2$)$_{0-3}$—CH(NH$_2$)Z' or —(CH$_2$)$_{0-3}$Z', where Z' represents H, SO$_3$H, NH$_2$ or COOH
(where "alkyl" preferably represents C$_{1-10}$-alkyl);
R$^5$ represents H, F, NH$_2$, NO$_2$, halogen, SH or —(CH$_2$)$_{0-3}$Z, where Z represents —H, halogen, —OY$^3$, —SY$^3$, —NHY$^3$, —CO—NY$^1$Y$^2$ or —CO—OY$^3$,
where Y$^1$ and Y$^2$ independently of one another represent H, NH$_2$ or —(CH$_2$)$_{0-3}$Z', and Y$^3$ represents H or —(CH$_2$)$_{0-3}$Z', where Z' represents H, SO$_3$H, NH$_2$ or COOH;
where L represents a linker and BINDER represents a binder or a derivative thereof, where the binder may optionally be attached to a plurality of active compound molecules,
R$^6$ and R$^7$ independently of one another represent H, cyano, (optionally fluorinated) C$_{1-10}$-alkyl, (optionally fluorinated) C$_{2-10}$-alkenyl, (optionally fluorinated) C$_{2-10}$-alkynyl, hydroxy or halogen,
R$^8$ represents (optionally fluorinated) C$_{1-10}$-alkyl, (optionally fluorinated) C$_{4-10}$-cycloalkyl or optionally substituted oxetane; and
R$^9$ represents H, F, CH$_3$, CF$_3$, CH$_2$F or CHF$_2$; and the salts, solvates, salts of the solvates and epimers thereof.

Preference according to the invention is furthermore given to the KSP inhibitor/antibody conjugates below:

Formula (IIb)

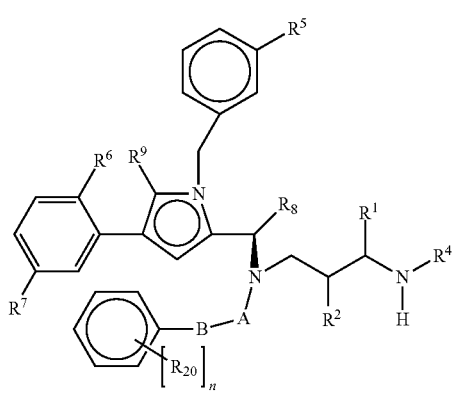

(IIb)

where R$^1$, R$^2$, R$^4$, R$^5$, R$^6$, R$^7$, R$^8$ and R$^9$ have the same meaning as in formula (II) or (IIa), A represents CO, B represents a single bond, —O—CH$_2$— or —CH$_2$—O— and R$^{20}$ represents NH$_2$, F, CF$_3$ or CH$_3$, and n represents 0, 1 or 2.

Formula (IIc)

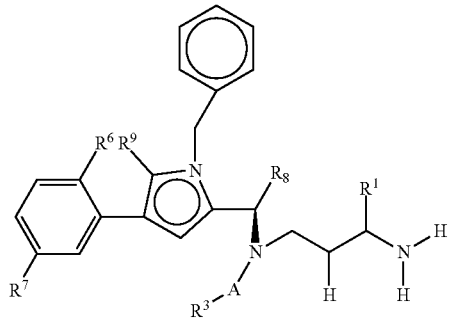

(IIc)

where A, R$^1$, R$^3$, R$^6$, R$^7$, R$^8$ and R$^9$ have the same meaning as in formula (II) or (IIa), where A preferably represents CO and R$^3$ represents —CH$_2$OH, —CH$_2$OCH$_3$, CH(CH$_3$)OH or CH(CH$_3$)OCH$_3$.

Formula (IId)

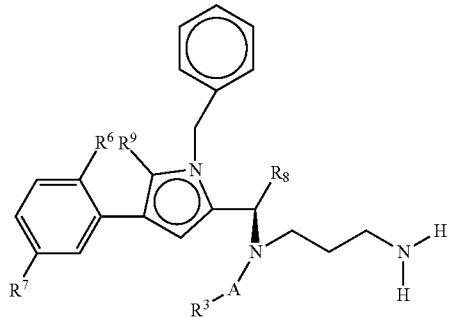

(IId)

where A, R$^3$, R$^6$, R$^7$, R$^8$ and R$^9$ have the same meaning as in formula (II) or (IIa), where A preferably represents CO and R$^3$ represents —CH$_2$—S$_x$—(CH$_2$)$_{0-4}$—CHY$^5$—COOH, where x represents 0 or 1 and Y$^5$ represents H or NHY$^6$, where Y$^6$ represents H or —COCH$_3$.

Formula (IIe)

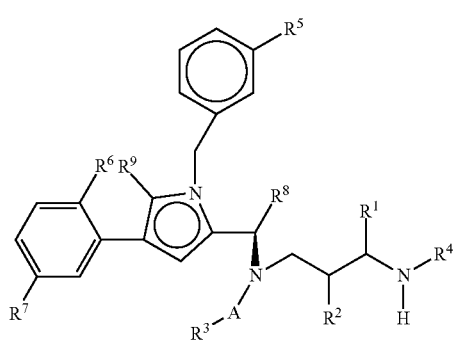

(IIe)

where A, $R^2$, $R^3$, $R^4$, $R^6$, $R^7$, $R^8$ and $R^9$ have the same meaning as in formula (II) or (IIa) and $R^1$ represents -L-BINDER.

Formula (IIi)

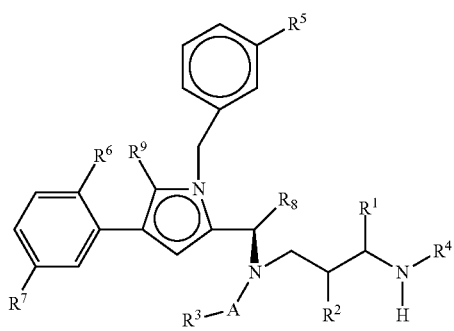

(IIi)

where A, $R^1$, $R^2$, $R^3$, $R^6$, $R^7$, $R^8$ and $R^9$ have the same meaning as in formula (II) or (IIa) and $R^4$ represents -L-BINDER, preferably an enzymatically cleavable binder, so that after cleavage $R^4$=H. $R^1$ or $R^3$ particularly preferably represent -MOD.

Formula (IIj)

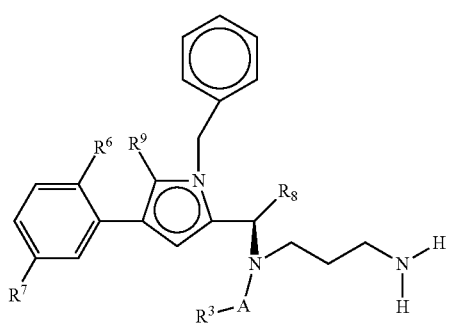

(IIj)

where
$R^3$ represents -L-#1;
A represents CO; and
$R^6$, $R^7$, $R^8$ and $R^9$ have the same meaning as in formula (I)

Formula (IIk)

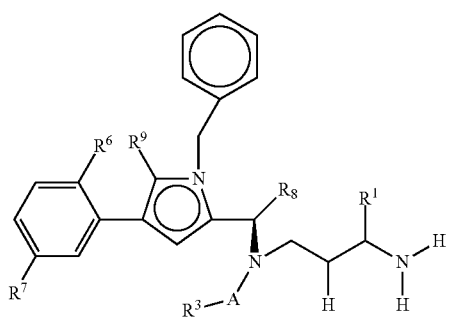

(IIk)

where
$R^1$ represents -L-#1;
A represents CO and $R^3$ represents —$CH_2OH$;
$R^3$, $R^6$, $R^7$, $R^8$ and $R^9$ have the same meaning as in formula (I).

Furthermore, it is preferred when in the compounds of the formulae (II), (IIa), (IIb), (IIc), (IId), (IIe), (IIi), (IIj) and (IIk) (alone or in combination):
Z represents Cl or Br;
$R^1$ represents —$(CH_2)_{0-3}Z$, where Z represents —COOH or —CO—$NY^1Y^2$, where $Y^2$ represents —$(CH_2CH_2O)_{0-3}$—$(CH_2)_{0-3}Z'$ and $Y^1$ represents H, $NH_2$ or —$(CH_2CH_2O)_{0-3}$—$(CH_2)_{0-3}Z'$;
$Y^1$ represents H, $Y^2$ represents —$(CH_2CH_2O)_3$—$CH_2CH_2Z'$ and $Z'$ represents —COOH;
$Y^1$ represents H, $Y^2$ represents —$CH_2CH_2Z'$ and $Z'$ represents —$(CONHCHY^4)_2COOH$;
$Y^1$ represents H, $Y^2$ represents —$CH_2CH_2Z'$, $Z'$ represents —$(CONHCHY^4)_2COOH$ and one of the $Y^4$ radicals represents i-propyl and the other —$(CH_2)_3$—$NHCONH_2$;
$Y^1$ represents H, $Y^2$ represents —$CH_2CH_2Z'$, $Z'$ represents —$(CONHCHY^4)_2COOH$ and one of the $Y^4$ radicals represents —$CH_3$ and the other —$(CH_2)_3$—$NHCONH_2$;
$Y^4$ represents straight-chain or branched $C_{1-6}$-alkyl which is optionally substituted by —$NHCONH_2$; at least one $Y^4$ representative is selected from the group consisting of i-propyl and —$CH_3$;
$Y^1$ represents H, $Y^2$ represents —$CH_2CH_2Z'$, $Z'$ represents —$CONHCHY^4COOH$ and $Y^4$ represents aryl or benzyl which are optionally substituted by —$NH_2$;
$Y^4$ represents aminobenzyl;
$R^2$ represents —$(CH_2)_{0-3}Z$ and Z represents —$SY^3$;
$R^4$ represents —CO—$CHY^4$—$NHY^5$ and $Y^5$ represents H;
$R^4$ represents —CO—$CHY^4$—$NHY^5$ and $Y^5$ represents —CO—$CHY^6$—$NH_2$;
$Y^4$ represents straight-chain or branched $C_{1-6}$-alkyl which is optionally substituted by —$NHCONH_2$.

Furthermore, it is preferred when in the formula (I) or (II) $R^1$, $R^2$ or $R^3$ represents -MOD.
Particularly preferably, $R^3$ represents -MOD and $R^1$ or $R^4$ represents -L-#1 or -L-BINDER,
where -MOD represents —$(NR^{10})_n$-$(G1)_o$-G2-G3, where $R^{10}$ represents H or $C_1$-$C_3$-alkyl;
G1 represents —NHCO— or —CONH— (where, if G1 represents —NHCO—, $R^{10}$ does not represent $NH_2$);
n represents 0 or 1;
o represents 0 or 1; and
G2 represents a straight-chain and/or branched hydrocarbon group which has 1 to 10 carbon atoms and which may be interrupted once or more than once by one or more of the groups —O—, —S—, —SO—, $SO_2$, —NRy-, —NRyCO—, CONRy-, —NRyNRy-, —$SO_2NRyNRy$-, —CONRyNRy- (where $R^y$ represents H, phenyl, $C_1$-$C_{10}$-alkyl, $C_2$-$C_{10}$-alkenyl or $C_2$-$C_{10}$-alkynyl, each of which may be substituted by $NHCONH_2$, —COOH, —OH, —$NH_2$, —NH—$CNNH_2$, sulphonamide, sulphone, sulphoxide or sulphonic acid), —CO—, or —$CR^x$=N—O— (where Rx represents H, $C_1$-$C_3$-alkyl or phenyl), where the hydrocarbon chain including any side chains may be substituted by $NHCONH_2$, —COOH, —OH, —$NH_2$, NH—$CNNH_2$, sulphonamide, sulphone, sulphoxide or sulphonic acid, where G3 represents —H or —COOH, where the group -MOD preferably has at least one group —COOH;
Particularly preferably, the group -MOD has a (preferably terminal) —COOH group, for example in a betaine group.
Preferably, the group -MOD has the formula —$CH_2$—$S_x$—$(CH_2)_{0-4}$—$CHY^5$—COOH where x is 0 or 1, and $Y^5$ represents H or $NHY^6$, where $Y^6$ represents H or —$COCH_3$.

Other particularly preferred compounds have the formula (III) below:

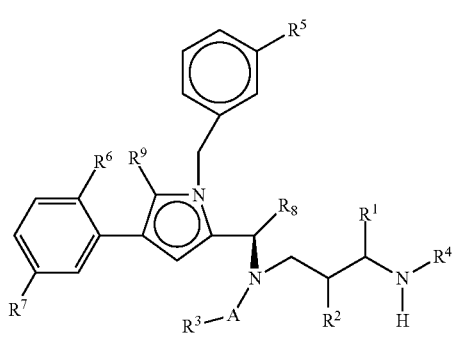

(III)

where
$R^1$ represents -L-BINDER, H or —$(CH_2)_{0-3}Z$, where Z represents —H, —$NHY^3$, —$OY^3$, —$SY^3$, halogen, —CO—$NY^1Y^2$ or —CO—$OY^3$,
where $Y^1$ and $Y^2$ independently of one another represent H, $NH_2$, —$(CH_2CH_2O)_{0-3}$—$(CH_2)_{0-3}Z'$ or —$CH(CH_2W)Z'$, and $Y^3$ represents H or —$(CH_2)_{0-3}Z'$, where Z' represents H, $NH_2$, $SO_3H$, COOH, —NH—CO—$CH_2$—$CH_2$—$CH(NH_2)$COOH or —$(CO-NH-CHY^4)_{1-3}$COOH;
where $Y^4$ represents straight-chain or branched $C_{1-6}$ alkyl which is optionally substituted by —$NHCONH_2$, or represents aryl or benzyl which are optionally substituted by —$NH_2$;
$R^2$ and $R^4$ independently of one another represent H, -$SG_{lys}$-$(CO)_{0-1}$—$R^{4'}$, —CO—$CHY^4$—$NHY^5$ or —$(CH_2)_{0-3}Z$, or $R^2$ and $R^4$ together (with formation of a pyrrolidine ring) represent —$CH_2$—$CHR^{11}$— or —$CHR^{11}$—$CH_2$—, where $R^{11}$ represents H, $NH_2$, $SO_3H$, COOH, SH, halogen (in particular F or Cl), $C_{1-4}$-alkyl, $C_{1-4}$-haloalkyl, $C_{1-4}$-alkoxy, hydroxyl-substituted $C_{1-4}$-alkyl, COO($C_{1-4}$-alkyl) or OH;
where $SG_{lys}$ represents a group which can be cleaved by a lysosomal enzyme, in particular a group consisting of a di- or tripeptide, $R^{4'}$ represents a $C_{1-10}$-alkyl, $C_{5-10}$-aryl or $C_{6-10}$-aralkyl, $C_{5-10}$-heteroalkyl, $C_{1-10}$-alkyl-O—$C_{6-10}$-aryl, $C_{5-10}$-heterocycloalkyl, heteroaryl, heteroarylalkyl, heteroarylalkoxy, $C_{1-10}$-alkoxy, $C_{6-10}$-aryloxy or $C_{6-10}$-aralkoxy, $C_{5-10}$-heteroaralkoxy, $C_{1-10}$-alkyl-O—$C_{6-10}$-aryloxy, $C_{5-10}$-heterocycloalkoxy group which may be mono- or polysubstituted by —$NH_2$, —NH-alkyl, —N(alkyl)$_2$, NH—CO-alkyl, N(alkyl)-COalkyl, —$SO_3H$, —$SO_2NH_2$, —$SO_2$—N(alkyl)$_2$, —COOH, —$CONH_2$, —CON(alkyl)$_2$ or —OH, —H or a group —$O_x$—$(CH_2CH_2O)_v$—$R^{4''}$ (where x represents 0 or 1 and v represents a number from 1 to 20 and $R^{4''}$ represents —H, -alkyl (preferably $C_{1-12}$-alkyl), —$CH_2$—COOH, —$CH_2$—$CH_2$—COOH or —$CH_2$—$CH_2$—$NH_2$);
where Z represents —H, halogen, —$OY^3$, —$SY^3$, $NHY^3$, —CO—$NY^1Y^2$ or —CO—$OY^3$,
where $Y^1$ and $Y^2$ independently of one another represent H, $NH_2$ or —$(CH_2)_{0-3}Z'$, and $Y^3$ represents H or —$(CH_2)_{0-3}Z'$, where Z' represents H, $SO_3H$, $NH_2$ or COOH;
where $Y^4$ represents straight-chain or branched $C_{1-6}$-alkyl which is optionally substituted by —$NHCONH_2$, or represents aryl or benzyl which are optionally substituted by —$NH_2$, and $Y^5$ represents H or —CO—$CHY^6$—$NH_2$, where $Y^6$ represents straight-chain or branched $C_{1-6}$-alkyl;
A represents CO, SO, $SO_2$, $SO_2NH$ or $CNNH_2$;

$R^3$ represents -L-BINDER or an optionally substituted alkyl, aryl, heteroaryl, heteroalkyl, heterocycloalkyl group, or —$CH_2$—$S_x$—$(CH_2)_{0-4}$—$CHY^5$—COOH, where x represents 0 or 1 and $Y^5$ represents H or $NHY^6$, where $Y^6$ represents H or —$COCH_3$, preferably -L-BINDER or a $C_{1-10}$-alkyl, $C_{6-10}$-aryl or $C_{6-10}$-aralkyl, $C_{5-10}$-heteroalkyl, $C_{1-10}$-alkyl-O—$C_{6-10}$-aryl or $C_{5-10}$-heterocycloalkyl group which may be substituted by 1-3-OH groups, 1-3 halogen atoms, 1-3 halogenated alkyl groups (each having 1-3 halogen atoms), 1-3 O-alkyl groups, 1-3-SH groups, 1-3-S-alkyl groups, 1-3-O—CO-alkyl groups, 1-3-O—CO—NH-alkyl groups, 1-3-NH—CO-alkyl groups, 1-3-NH—CO—NH-alkyl groups, 1-3-S(O)$_n$-alkyl groups, 1-3-$SO_2$—NH-alkyl groups, 1-3-NH-alkyl groups, 1-3-N(alkyl)$_2$ groups, 1-3-$NH_2$ groups or 1-3-$(CH_2)_{0-3}Z$ groups, where Z represents —H, halogen, —$OY^3$, —$SY^3$, —$NHY^3$, —CO—$NY^1Y^2$ or —CO—$OY^3$, where $Y^1$ and $Y^2$ independently of one another represent H, $NH_2$ or —$(CH_2)_{0-3}Z'$ and $Y^3$ represents H, —$(CH_2)_{0-3}$—$CH(NHCOCH_3)Z'$, —$(CH_2)_{0-3}$—$CH(NH_2)Z'$ or —$(CH_2)_{0-3}Z'$, where Z' represents H, $SO_3H$, $NH_2$ or COOH,
(where "alkyl" preferably represents $C_{1-10}$-alkyl);
$R^5$ represents H, F, $NH_2$, $NO_2$, halogen, SH or —$(CH_2)_{0-3}Z$, where Z represents —H, halogen, —$OY^3$, —$SY^3$, —$NHY^3$, —CO—$NY^1Y^2$ or —CO—$OY^3$,
where $Y^1$ and $Y^2$ independently of one another represent H, $NH_2$ or —$(CH_2)_{0-3}Z'$, and $Y^3$ represents H or —$(CH_2)_{0-3}Z'$, where Z' represents H, $SO_3H$, $NH_2$ or COOH;
where L represents a linker and BINDER represents the antibody, where the binder may optionally be attached to a plurality of active compound molecules,
$R^6$ and $R^7$ independently of one another represent H, cyano, (optionally fluorinated) $C_{1-10}$-alkyl, (optionally fluorinated) $C_{2-10}$-alkenyl, (optionally fluorinated) $C_{2-10}$-alkynyl, hydroxy or halogen,
$R^8$ represents (optionally fluorinated) $C_{1-10}$-alkyl, (optionally fluorinated) $C_{4-10}$-cycloalkyl or optionally substituted oxetane; and
$R^9$ represents H, F, $CH_3$, $CF_3$, $CH_2F$ or $CHF_2$;
and the salts, solvates, salts of the solvates and epimers thereof.

Furthermore, it is preferred when (alone or in combination) in the formula (I), (Ia), (II), (IIa), (IIb), (IIc), (IId), (IIe), (IIi), (IIj), (IIk) or (III):
Z represents Cl or Br;
$R^1$ represents —$(CH_2)_{0-3}Z$, where Z represents —CO—$NY^1Y^2$, where $Y^2$ represents —$(CH_2CH_2O)_{0-3}$—$(CH_2)O_3Z'$ and $Y^1$ represents H, $NH_2$ or —$(CH_2CH_2O)_{0-3}$—$(CH_2)_{0-3}Z'$;
$Y^1$ represents H, $Y^2$ represents —$(CH_2CH_2O)_3$—$CH_2CH_2Z'$ and Z' represents —COOH;
$Y^1$ represents H, $Y^2$ represents —$CH_2CH_2Z'$ and Z' represents —$(CONHCHY^4)_2$COOH;
$Y^1$ represents H, $Y^2$ represents —$CH_2CH_2Z'$, Z' represents —$(CONHCHY^4)_2$COOH and one $Y^4$ representative represents i-propyl and the other represents —$(CH_2)_3$—$NHCONH_2$;
$Y^1$ represents H, $Y^2$ represents —$CH_2CH_2Z'$, Z' represents —$(CONHCHY^4)_2$COOH and one $Y^4$ representative represents —$CH_3$ and the other represents —$(CH_2)_3$—$NHCONH_2$;
$Y^4$ represents straight-chain or branched $C_{1-6}$-alkyl which is optionally substituted by —$NHCONH_2$; at least one $Y^4$ representative is selected from the group consisting of i-propyl and —$CH_3$;
$Y^1$ represents H, $Y^2$ represents —$CH_2CH_2Z'$, Z' represents —$CONHCHY^4$COOH and $Y^4$ represents aryl or benzyl which are optionally substituted by —$NH_2$;

$Y^4$ represents aminobenzyl;

$R^2$ represents —$(CH_2)_{0-3}Z$ and Z represents —$SY^3$;

$R^4$ represents —CO—$CHY^4$—$NHY^5$ and $Y^5$ represents H;

$R^4$ represents —CO—$CHY^4$—$NHY^5$ and $Y^5$ represents —CO—$CHY^6$—$NH_2$; and/or $Y^4$ represents straight-chain or branched $C_{1-6}$-alkyl which is optionally substituted by —$NHCONH_2$.

Preference is furthermore given to compounds of the formula (I), (Ia), (II), (IIa) or (III) where $R^1$ represents H, -L-#1 or -L-BINDER, -MOD or —$(CH_2)_{0-3}Z$, where Z represents —H, —$NHY^3$, —$OY^3$, —$SY^3$, halogen, —CO—$NY^1Y^2$ or —CO—$OY^3$, where $Y^1$ and $Y^2$ independently of one another represent H, $NH_2$, —$(CH_2CH_2O)_{0-3}$—$(CH_2)_{0-3}Z'$ (e.g. —$(CH_2)_{0-3}Z'$) or —$CH(CH_2W)Z'$, and $Y^3$ represents H or —$(CH_2)_{0-3}Z'$, where Z' represents H, $NH_2$, $SO_3H$, COOH, —NH—CO—$CH_2$—$CH_2$—$CH(NH_2)COOH$ or —(CO—NH—$CHY^4)_{1-3}COOH$, where W represents H or OH, where $Y^4$ represents straight-chain or branched $C_{1-6}$ alkyl which is optionally substituted by —$NHCONH_2$, or represents aryl or benzyl which are optionally substituted by —$NH_2$;

$R^2$ represents H, —CO—$CHY^4$—$NHY^5$ or —$(CH_2)_{0-3}Z$, where Z represents —H, halogen, —$OY^3$, —$SY^3$, $NHY^3$, —CO—$NY^1Y^2$ or —CO—$OY^3$, where $Y^1$ and $Y^2$ independently of one another represent H, $NH_2$ or —$(CH_2)_{0-3}Z'$, and $Y^3$ represents H or —$(CH_2)_{0-3}Z'$, where Z' represents H, $SO_3H$, $NH_2$ or COOH;

where $Y^4$ independently of one another represents straight-chain or branched $C_{1-6}$-alkyl which is optionally substituted by —$NHCONH_2$, or represents aryl or benzyl which are optionally substituted by —$NH_2$, and $Y^5$ represents H or —CO—$CHY^6$—$NH_2$, where $Y^6$ represents straight-chain or branched $C_{1-6}$-alkyl;

$R^4$ represents H or -L-#1 or -L-BINDER (where -L-#1 or -L-BINDER is an enzymatically cleavable linker leading to the conversion of $R^4$ into H);

A represents CO, SO, $SO_2$, $SO_2NH$ or $CNNH_2$;

$R^3$ represents -L-#1 or -L-BINDER, -MOD or an optionally substituted alkyl, cycloalkyl, aryl, heteroaryl, heteroalkyl, heterocycloalkyl group, preferably a $C_{1-10}$-alkyl, $C_{6-10}$-aryl or $C_{6-10}$-aralkyl, $C_{5-10}$-heteroalkyl, $C_{1-10}$-alkyl-O—$C_{6-10}$-aryl or $C_{5-10}$-heterocycloalkyl group which may be substituted by 1-3 OH groups, 1-3 halogen atoms, 1-3 halogenated alkyl groups (each having 1-3 halogen atoms), 1-3 O-alkyl groups, 1-3 SH groups, 1-3 S-alkyl groups, 1-3 O—CO-alkyl groups, 1-3 O—CO—NH-alkyl groups, 1-3 NH—CO-alkyl groups, 1-3 NH—CO—NH-alkyl groups, 1-3 S(O)$_n$-alkyl groups, 1-3 $SO_2$—NH-alkyl groups, 1-3 NH-alkyl groups, 1-3 N(alkyl)$_2$ groups, 1-3 NH(($CH_2CH_2O$)1-20H) groups, 1-3 $NH_2$ groups or 1-3-$(CH_2)_{0-3}Z$ groups, where Z represents —H, halogen, —$OY^3$, —$SY^3$, —$NHY^3$, —CO—$NY^1Y^2$ or —CO—$OY^3$, where $Y^1$ and $Y^2$ independently of one another represent H, $NH_2$ or —$(CH_2)_{0-3}Z'$ and $Y^3$ represents H, —$(CH_2)_{0-3}$—$CH(NHCOCH_3)Z'$, —$(CH_2)_{0-3}$—$CH(NH_2)Z'$ or —$(CH_2)_{0-3}Z'$, where Z' represents H, $SO_3H$, $NH_2$ or COOH (where "alkyl" is preferably $C_{1-10}$-alkyl);

$R^5$ represents H, -MOD, $NH_2$, $NO_2$, halogen (in particular F, Cl, Br), —CN, $CF_3$, —$OCF_3$, —$CH_2F$, —$CH_2F$, SH or —$(CH_2)_{0-3}Z$, where Z represents —H, —$OY^3$, —$SY^3$, halogen, $NHY^3$, —CO—$NY^1Y^2$ or —CO—$OY^3$, where $Y^1$ and $Y^2$ independently of one another represent H, $NH_2$ or —$(CH_2)_{0-3}Z'$, and $Y^3$ represents H or —$(CH_2)_{0-3}Z'$, where Z' represents H, $SO_3H$, $NH_2$ or COOH;

$R^6$ and $R^7$ independently of one another represent H, cyano, (optionally fluorinated) $C_{1-10}$-alkyl, (optionally fluorinated) $C_{2-10}$-alkenyl, (optionally fluorinated) $C_{2-10}$-alkynyl, hydroxy, $NO_2$, $NH_2$, COOH or halogen (in particular F, Cl, Br);

$R^8$ represents (optionally fluorinated) $C_{1-10}$-alkyl, (optionally fluorinated) $C_{2-10}$-alkenyl, (optionally fluorinated) $C_{2-10}$-alkynyl or (optionally fluorinated) C4-10-cycloalkyl;

where one of the substituents $R^1$ and $R^3$ represents -L-#1 or -L-BINDER,

L represents the linker and #1 represents the bond to the antibody and BINDER represents the antibody, $R^9$ represents H, F, $CH_3$, $CF_3$, $CH_2F$ or $CHF_2$;

where -MOD represents —$(NR^{10})_n$-(G1)$_o$-G2-G3, where $R^{10}$ represents H or $C_1$-$C_3$-alkyl;

G1 represents —NHCO— or —CONH— (where, if G1 represents —NHCO—, $R^{10}$ does not represent $NH_2$);

n represents 0 or 1;

o represents 0 or 1; and

G2 represents a straight-chain and/or branched hydrocarbon group which has 1 to 10 carbon atoms and which may be interrupted once or more than once by one or more of the groups —O—, —S—, —SO—, $SO_2$, —NRy-, —NRyCO—, CONRy-, —NRyNRy-, —$SO_2$NRyNRy-, —CONRyNRy- (where $R^y$ represents H, phenyl, $C_1$-$C_{10}$-alkyl, $C_2$-$C_{10}$-alkenyl or $C_2$-$C_{10}$-alkynyl, each of which may be substituted by $NHCONH_2$, —COOH, —OH, —$NH_2$, NH—$CNNH_2$, sulphonamide, sulphone, sulphoxide or sulphonic acid), —CO—, —$CR^x$=N—O— (where Rx represents H, $C_1$-$C_3$-alkyl or phenyl), where the hydrocarbon chain including any side chains may be substituted by —$NHCONH_2$, —COOH, —OH, —$NH_2$, NH—$CNNH_2$, sulphonamide, sulphone, sulphoxide or sulphonic acid, where G3 represents —H or —COOH, and where the group -MOD preferably has at least one group —COOH;

and the salts, solvates, salts of the solvates and epimers thereof.

Preference is furthermore given to compounds of the formula (I), (Ia), (II), (IIa) or (III) in which $R^1$ represents H, -L-#1 or -L-BINDER, -MOD or —$(CH_2)_{0-3}Z$, where Z represents —H, —$NHY^3$, —$OY^3$, —$SY^3$, halogen, —CO—$NY^1Y^2$ or —CO—$OY^3$, where $Y^1$ and $Y^2$ independently of one another represent H, $NH_2$, —$(CH_2CH_2O)_{0-3}$—$(CH_2)_{0-3}Z'$ (e.g. —$(CH_2)_{0-3}Z'$) or —$CH(CH_2W)Z'$, and $Y^3$ represents H or —$(CH_2)_{0-3}Z'$, where Z' represents H, $NH_2$, $SO_3H$, COOH, —NH—CO—$CH_2$—$CH_2$—$CH(NH_2)COOH$ or —(CO—NH—$CHY^4)_{1-3}COOH$, where W represents H or OH, where $Y^4$ represents straight-chain or branched $C_{1-6}$ alkyl which is optionally substituted by —$NHCONH_2$, or represents aryl or benzyl which are optionally substituted by —$NH_2$;

$R^2$ represents H, —CO—$CHY^4$—$NHY^5$ or —$(CH_2)_{0-3}Z$, where Z represents —H, halogen, —$OY^3$, —$SY^3$, $NHY^3$, —CO—$NY^1Y^2$ or —CO—$OY^3$, where $Y^1$ and $Y^2$ independently of one another represent H, $NH_2$ or —$(CH_2)_{0-3}Z'$, and $Y^3$ represents H or —$(CH_2)_{0-3}Z'$, where Z' represents H, $SO_3H$, $NH_2$ or COOH;

where $Y^4$ represents straight-chain or branched $C_{1-6}$-alkyl which is optionally substituted by —$NHCONH_2$, or represents aryl or benzyl which are optionally substituted by —$NH_2$, and $Y^5$ represents H or —CO—$CHY^6$—$NH_2$, where $Y^6$ represents straight-chain or branched $C_{1-6}$-alkyl;

$R^4$ represents H,

A represents CO, SO, $SO_2$, $SO_2NH$ or $CNNH_2$;

$R^3$ represents -L-#1 or -L-BINDER, -MOD or an optionally substituted alkyl, cycloalkyl, aryl, heteroaryl, heteroalkyl, heterocycloalkyl group, preferably a $C_{1-10}$-alkyl, $C_{6-10}$-aryl or $C_{6-10}$-aralkyl, $C_{5-10}$-heteroalkyl, $C_{1-10}$-alkyl-O—$C_{6-10}$- aryl or $C_{5-10}$-heterocycloalkyl group which may be substituted by 1-3 -OH groups, 1-3 halogen atoms, 1-3 halogenated alkyl groups (each having 1-3 halogen atoms), 1-3 O-alkyl groups, 1-3 -SH groups, 1-3 S-alkyl groups, 1-3-O—CO-alkyl groups, 1-3-O—CO—NH-alkyl groups, 1-3-NH—CO-alkyl groups, 1-3-NH—CO—NH-alkyl groups, 1-3-S(O)$_n$-alkyl groups, 1-3-SO$_2$—NH-alkyl groups, 1-3-NH-alkyl groups, 1-3-N(alkyl)$_2$ groups, 1-3-NH((CH$_2$CH$_2$O)1-20H) groups, 1-3-NH$_2$ groups or 1-3-(CH$_2$)$_{0-3}$Z groups, where Z represents —H, halogen, —OY$^3$, —SY$^3$, —NHY$^3$, —CO—NY$^1$Y$^2$ or —CO—OY$^3$, where Y$^1$ and Y$^2$ independently of one another represent H, NH$_2$ or —(CH$_2$)$_{0-3}$Z' and Y$^3$ represents H, —(CH$_2$)$_{0-3}$—CH(NHCOCH$_3$)Z', —(CH$_2$)$_{0-3}$—CH(NH$_2$)Z' or —(CH$_2$)$_{0-3}$Z', where Z' represents H, SO$_3$H, NH$_2$ or COOH (where "alkyl" is preferably $C_{1-10}$-alkyl);

R$^5$ represents H, -MOD, NH$_2$, NO$_2$, halogen (in particular F, Cl, Br), —CN, CF$_3$, —OCF$_3$, —CH$_2$F, —CH$_2$F, SH or —(CH$_2$)$_{0-3}$Z, where Z represents —H, —OY$^3$, —SY$^3$, halogen, NHY$^3$, —CO—NY$^1$Y$^2$ or —CO—OY$^3$, where Y$^1$ and Y$^2$ independently of one another represent H, NH$_2$ or —(CH$_2$)$_{0-3}$Z', and Y$^3$ represents H or —(CH$_2$)$_{0-3}$Z', where Z' represents H, SO$_3$H, NH$_2$ or COOH;

R$^6$ and R$^7$ independently of one another represent H or halogen (in particular F, Cl, Br);

R$^8$ represents (optionally fluorinated) $C_{1-10}$-alkyl;

where one of the substituents R$^1$ and R$^3$ represents -L-#1 or -L-BINDER,

L represents the linker and #1 represents the bond to the antibody and BINDER represents the antibody, R$^9$ represents H, F, CH$_3$, CF$_3$, CH$_2$F or CHF$_2$;

where -MOD represents —CH$_2$—S$_x$—(CH$_2$)$_{0-4}$—CHY$^5$—COOH where x is 0 or 1, and Y$^5$ represents H or NHY$^6$, where Y$^6$ represents H or —COCH$_3$, and the salts, solvates and salts of the solvates thereof.

Preference is furthermore given to the following compounds which may optionally be present together with an acid such as, for example, trifluoroacetic acid. These compounds may be attached via the positions corresponding to the positions R$^1$, R$^3$ and R$^4$ via a linker to the antibody (where a hydrogen atom is substituted by the linker):

N-(3-Aminopropyl)-N-{(1R)-1-[1-benzyl-4-(2,5-difluorophenyl)-1H-pyrrol-2-yl]-2,2-dimethylpropyl}-2-hydroxyacetamide;

(2S)-2-amino-4-[{(1R)-1-[1-benzyl-4-(2,5-difluorophenyl)-1H-pyrrol-2-yl]-2,2-dimethylpropyl}(glycoloyl)amino]-N-methylbutanamide (1:1);

N-(3-aminopropyl)-N-{(1S)-1-[1-benzyl-4-(2,5-difluorophenyl)-1H-pyrrol-2yl]-2,2-dimethylpropyl}acetamide;

N-(3-aminopropyl)-N-{(1S)-1-[1-benzyl-4-(2,5-difluorophenyl)-1H-pyrrol-2-yl]-2,2-dimethylpropyl}-2-hydroxyacetamide;

S-(1-{2-[(N-{(2S)-2-amino-4-[{(1R)-1-[1-benzyl-4-(2,5-difluorophenyl)-1H-pyrrol-2-yl]-2,2-dimethylpropyl}(glycoloyl)amino]butanoyl}-beta-alanyl)amino]ethyl}-2,5-dioxopyrrolidin-3-yl)-L-cysteine;

S-(1-{2-[(N-{(2S)-2-amino-4-[{(1R)-1-[1-benzyl-4-(2,5-difluorophenyl)-1H-pyrrol-2-yl]-2,2-dimethylpropyl}(glycoloyl)amino]butanoyl}-beta-alanyl)amino]ethyl}-2,5-dioxopyrrolidin-3-yl)-L-cysteine;

S-[1-(2-{[2-({(2S)-2-amino-4-[{(1R)-1-[1-benzyl-4-(2,5-difluorophenyl)-1H-pyrrol-2-yl]-2,2-dimethylpropyl}(glycoloyl)amino]butanoyl}amino)ethyl]amino}-2-oxoethyl)-2,5-dioxopyrrolidin-3-yl]-L-cysteine;

N-[19-(3(R/S)-{[(2R)-2-amino-2-carboxyethyl]sulphanyl}-2,5-dioxopyrrolidin-1-yl)-17-oxo-4,7,10,13-tetraoxa-16-azanonadecan-1-oyl]-R/S-{2-[(3-aminopropyl){(1R)-1-[1-benzyl-4-(2,5-difluorophenyl)-1H-pyrrol-2-yl]-2,2-dimethylpropyl}amino]-2-oxoethyl}homocysteine;

S-{(3R/S)-1-[2-({(2S)-2-amino-4-[{(1R)-1-[1-benzyl-4-(2,5-difluorophenyl)-1H-pyrrol-2-yl]-2,2-dimethylpropyl}(glycoloyl)amino]butanoyl}amino)ethyl]-2,5-dioxopyrrolidin-3-yl}-L-cysteine;

S-[(3R/S)-1-(2-{[6-({2-[(3-aminopropyl){(1R)-1-[1-benzyl-4-(2,5-difluorophenyl)-1H-pyrrol-2-yl]-2,2-dimethylpropyl}amino]-2-oxoethyl}sulphanyl)hexanoyl]amino}ethyl)-2,5-dioxopyrrolidin-3-yl]-L-cysteine;

S-{1-[2-({[(1R,3S)-3-({(2S)-2-amino-4-[{(1R)-1-[1-benzyl-4-(2,5-difluorophenyl)-1H-pyrrol-2-yl]-2,2-dimethylpropyl}(glycoloyl)amino]butanoyl}amino)cyclopentyl]carbonyl}amino)ethyl]-2,5-dioxopyrrolidin-3-yl}-L-cysteine;

S-(2-{[2-({(2S)-2-amino-4-[{(1R)-1-[1-benzyl-4-(2,5-difluorophenyl)-1H-pyrrol-2-yl]-2,2-dimethylpropyl}(glycoloyl)amino]butanoyl}amino)ethyl]amino}-2-oxoethyl)-L-cysteine;

$N^6$—(N-{(2S)-2-amino-4-[{(1R)-1-[1-benzyl-4-(2,5-difluorophenyl)-1H-pyrrol-2-yl]-2,2-dimethylpropyl}(glycoloyl)amino]butanoyl}-beta-alanyl)-$N^2$-{N-[6-(3-{[(2R)-2-amino-2-carboxyethyl]sulphanyl}-2,5-dioxopyrrolidin-1-yl)hexanoyl]-L-valyl-L-alanyl}-L-lysine;

N-[2-({(2S)-2-amino-4-[{(1R)-1-[1-benzyl-4-(2,5-difluorophenyl)-1H-pyrrol-2-yl]-2,2-dimethylpropyl}(glycoloyl)amino]butanoyl}amino)ethyl]-L-glutamine;

$N^6$—(N-{(2S)-2-amino-4-[{(1R)-1-[1-benzyl-4-(2,5-difluorophenyl)-1H-pyrrol-2-yl]-2,2-dimethylpropyl}(glycoloyl)amino]butanoyl}-beta-alanyl)-L-lysine;

N-(3-aminopropyl)-N-{(1R)-1-[1-benzyl-4-(2,5-difluorophenyl)-1H-pyrrol-2-yl]-2,2-dimethylpropyl}-3,3,3-trifluoropropanamide;

N-(3-aminopropyl)-N-{(1R)-1-[1-benzyl-4-(2,5-difluorophenyl)-1H-pyrrol-2-yl]-2,2-dimethylpropyl}-4-fluorobenzamide;

N-(3-aminopropyl)-N-{(1R)-1-[1-benzyl-4-(2,5-difluorophenyl)-1H-pyrrol-2-yl]-2,2-dimethylpropyl}acetamide;

N-(3-aminopropyl)-N-{(1R)-1-[1-benzyl-4-(2,5-difluorophenyl)-1H-pyrrol-2-yl]-2,2-dimethylpropyl}-4-(trifluoromethyl)benzamide;

(2S)-2-amino-4-[{(1R)-1-[1-benzyl-4-(2,5-difluorophenyl)-1H-pyrrol-2-yl]-2,2-dimethylpropyl}(glycoloyl)amino]butanoic acid;

(2S)-2-amino-N-(2-aminoethyl)-4-[{(1R)-1-[1-benzyl-4-(2,5-difluorophenyl)-1H-pyrrol-2-yl]-2,2-dimethylpropyl}(glycoloyl)amino]butanamide;

4-[(2-{[2-({(2S)-2-amino-4-[{(1R)-1-[1-benzyl-4-(2,5-difluorophenyl)-1H-pyrrol-2-yl]-2,2-dimethylpropyl}(glycoloyl)amino]butanoyl}amino)ethyl]amino}-2-oxoethyl)amino]-3-{[(2R)-2-amino-2-carboxyethyl]sulphanyl}-4-oxobutanoic acid;

4-[(2-{[2-({(2S)-2-amino-4-[{(1R)-1-[1-benzyl-4-(2,5-difluorophenyl)-1H-pyrrol-2-yl]-2,2-dimethylpropyl}(glycoloyl)amino]butanoyl}amino)ethyl]amino}-2-oxoethyl)amino]-2-{[(2R)-2-amino-2-carboxyethyl]sulphanyl}-4-oxobutanoic acid;

N-({(2S)-2-amino-4-[{(1R)-1-[1-benzyl-4-(2,5-difluorophenyl)-1H-pyrrol-2-yl]-2,2-dimethylpropyl}(glycoloyl)amino]butanoyl}-beta-alanine;

N-({(2S)-2-amino-4-[{(1R)-1-[1-benzyl-4-(2,5-difluorophenyl)-1H-pyrrol-2-yl]-2,2-dimethylpropyl}(glycoloyl)amino]butanoyl}-L-serine;

N-({(2S)-2-amino-4-[{(1R)-1-[1-benzyl-4-(2,5-difluorophenyl)-1H-pyrrol-2-yl]-2,2-dimethylpropyl}(glycoloyl)amino]butanoyl}-L-alanine;

N-({(2S)-2-amino-4-[{(1R)-1-[1-benzyl-4-(2,5-difluoro-phenyl)-1H-pyrrol-2-yl]-2,2-dimethylpropyl}(glycoloyl) amino]butanoyl}glycine;
N-(3-aminopropyl)-N-{(1R)-1-[1-benzyl-4-(2,5-difluoro-phenyl)-1H-pyrrol-2-yl]-2,2-dimethylpropyl}-4-methyl-benzamide;
N-(3-aminopropyl)-N-{(1R)-1-[1-benzyl-4-(2,5-difluoro-phenyl)-1H-pyrrol-2-yl]-2,2-dimethylpropyl}-4-(methyl-sulphanyl)benzamide;
(2S)—N-(3-aminopropyl)-N-{(1R)-1-[1-benzyl-4-(2,5-dif-luorophenyl)-1H-pyrrol-2-yl]-2,2-dimethylpropyl}-2-hy-droxypropanamide;
N-(3-aminopropyl)-N-{(1R)-1-[1-benzyl-4-(2,5-difluoro-phenyl)-1H-pyrrol-2-yl]-2,2-dimethylpropyl}-2-(methyl-sulphanyl)acetamide;
(2S)—N-(3-aminopropyl)-N-{(1R)-1-[4-benzyl-1-(2,5-dif-luorophenyl)-1H-pyrazol-3-yl]-2,2-dimethylpropyl}-2-hydroxypropanamide;
methyl 4-[(3-aminopropyl){(1R)-1-[1-benzyl-4-(2,5-difluo-rophenyl)-1H-pyrrol-2-yl]-2,2-dimethylpropyl}amino]-4-oxobutanoate;
4-[(3-aminopropyl){(1R)-1-[1-benzyl-4-(2,5-difluorophe-nyl)-1H-pyrrol-2-yl]-2,2-dimethylpropyl}amino]-4-oxobutanoic acid;
(2R)-22-[(3R/S)-3-{[(2R)-2-amino-2-carboxyethyl]sulpha-nyl}-2,5-dioxopyrrolidin-1-yl]-2-[({2-[(3-aminopropyl) {(1R)-1-[1-benzyl-4-(2,5-difluorophenyl)-1H-pyrrol-2-yl]-2,2-dimethylpropyl}amino]-2-oxoethyl}sulphanyl) methyl]-4,20-dioxo-7,10,13,16-tetraoxa-3,19-diazado-cosan-1-oic acid;
N-acetyl-S-{2-[(3-aminopropyl){(1R)-1-[1-benzyl-4-(2,5-difluorophenyl)-1H-pyrrol-2-yl]-2,2-dimethylpropyl}amino]-2-oxoethyl}-L-cysteine;
N-acetyl-S-[2-([3-(L-alanylamino)propyl]{(1R)-1-[1-ben-zyl-4-(2,5-difluorophenyl)-1H-pyrrol-2-yl]-2,2-dimethylpropyl}amino)-2-oxoethyl]-L-cysteine;
(2S)—N-(3-aminopropyl)-N-{(1R)-1-[1-benzyl-4-(2,5-dif-luorophenyl)-1H-pyrrol-2-yl]-2,2-dimethylpropyl}tetrahydrofuran-2-carboxamide;
3-({2-[(3-aminopropyl){(1R)-1-[1-benzyl-4-(2,5-difluoro-phenyl)-1H-pyrrol-2-yl]-2,2-dimethylpropyl}amino]-2-oxoethyl}sulphanyl)propanoic acid;
S-{2-[(3-aminopropyl){(1R)-1-[1-benzyl-4-(2,5-difluoro-phenyl)-1H-pyrrol-2-yl]-2,2-dimethylpropyl}amino]-2-oxoethyl}homocysteine;
4-amino-N-(3-aminopropyl)-N-{(1R)-1-[1-benzyl-4-(2,5-difluorophenyl)-1H-pyrrol-2-yl]-2,2-dimethylpropyl}benzamide;
4-[(2-{[(2R)-2-({(2S)-2-amino-4-[{(1R)-1-[1-benzyl-4-(2,5-difluorophenyl)-1H-pyrrol-2-yl]-2,2-dimethylpropyl} (glycoloyl)amino]butanoyl}amino)-2-carboxyethyl] amino}-2-oxoethyl)amino]-3-{[(2R)-2-amino-2-carboxyethyl]sulphanyl}-4-oxobutanoic acid;
4-[(2-{[(2R)-2-({(2S)-2-amino-4-[{(1R)-1-[1-benzyl-4-(2,5-difluorophenyl)-1H-pyrrol-2-yl]-2,2-dimethylpropyl} (glycoloyl)amino]butanoyl}amino)-2-carboxyethyl] amino}-2-oxoethyl)amino]-2-{[(2R)-2-amino-2-carboxyethyl]sulphanyl}-4-oxobutanoic acid.

Particular preference according to the invention is given to the following compounds of the formula IV where $R^1$, $R^2$, $R^3$, $R^4$ and $R^5$ have the meanings mentioned above (as mentioned, for example for formula (I) or (II)):

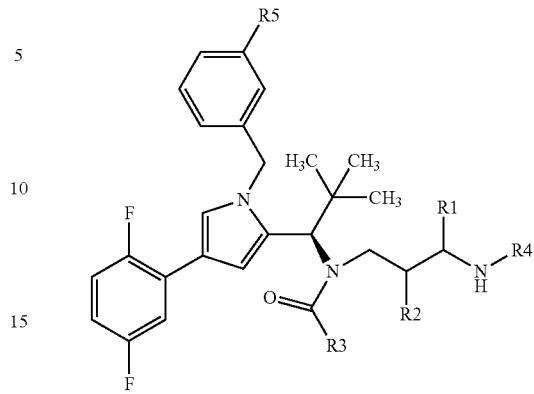

Formula IV

Particular preference is given to the compounds of the formula IV where $R^1$ and $R^5$ represent H or -L-#1; $R^2$ and $R^4$ represent H or $R^2$ and $R^4$ together (with formation of a pyrrolidine ring) represent —$CH_2$—$CHR^{11}$— or —$CHR^{11}$—$CH_2$—, where $R^{11}$ represents H; and $R^3$ represents $CH_2OH$, $CH(CH_3)OH$ or -L-#1, where one of the substituents $R^1$ and $R^3$ represents -L-#1. In addition, particular preference is given to the compounds of the formula IV where $R^1$ represents H or COOH; $R^2$ and $R^5$ represent H; $R^4$ represents -L-#1; and $R^3$ represents $CH_2OH$ or $CH(CH_3)$ OH, where -L-#1 is an enzymatically cleavable linker leading to the conversion of $R^4$ into H.

Linkers

The literature discloses various options for covalently coupling (conjugating) organic molecules to binders such as, for example antibodies (see, for example, K. Lang and J. W. Chin. Chem. Rev. 2014, 114, 4764-4806, M. Rashidian et al. *Bioconjugate Chem.* 2013, 24, 1277-1294). Preference according to the invention is given to conjugation of the KSP inhibitors to an antibody via one or more sulphur atoms of cysteine residues of the antibody which are either already present as free thiols or generated by reduction of disulphide bridges, and/or via one or more NH groups of lysine residues of the antibody. However, it is also possible to attach the KSP inhibitor to the antibody via tyrosine residues, via glutamine residues, via residues of unnatural amino acids, via free carboxyl groups or via sugar residues of the antibody. For coupling, use is made of linkers. Linkers can be categorized into the group of the linkers which can be cleaved in vivo and the group of the linkers which are stable in vivo (see L. Ducry and B. Stump, *Bioconjugate Chem.* 21, 5-13 (2010)). The linkers which can be cleaved in vivo have a group which can be cleaved in vivo, where, in turn, a distinction may be made between groups which are chemically cleavable in vivo and groups which are enzymatically cleavable in vivo. "Chemically cleavable in vivo" and "enzymatically cleavable in vivo" means that the linkers or groups are stable in circulation and are cleaved only at or in the target cell by the chemically or enzymatically different environment therein (lower pH; elevated glutathione concentration; presence of lysosomal enzymes such as proteases, or glyosidases such as, for example, 1-glucuronidases), thus releasing the low-molecular weight KSP inhibitor or a derivative thereof. Groups which can be cleaved chemically in vivo are in particular disulphide, hydrazone, acetal and aminal; groups which can be cleaved enzymatically in vivo, in particular those which are cleavable by lysosomal enzymes, are in particular the 2-8-oligopeptide group, especially a tri- or dipeptide group or glycoside. Peptide cleaving sites are disclosed in *Bioconjugate Chem.* 2002, 13, 855-869 and *Bioorganic & Medicinal Chemistry Letters* 8 (1998) 3341-3346 and also *Bioconjugate Chem.* 1998, 9, 618-626. These include, for example, valine-alanine, valine-lysine, valine-citrulline, alanine-lysine and phenylalanine-lysine (optionally with additional amide group).

Linkers which are stable in vivo are distinguished by a high stability (less than 5% metabolites after 24 hours in plasma) and do not have the chemically or enzymatically in vivo cleavable groups mentioned above.

The linker -L- preferably has one of the basic structures (i) to (iv) below:

$$-(CO)_m-SG1-L1-L2- \qquad (i)$$

$$-(CO)_m-L1-SG-L1-L2- \qquad (ii)$$

$$-(CO)_m-L1-L2- \qquad (iii)$$

$$-(CO)_m-L1-SG-L2 \qquad (iv)$$

where m is 0 or 1; SG is a (chemically or enzymatically) in vivo cleavable group (in particular disulphide, hydrazone, acetal and aminal; or a 2-8-oligopeptide group which can be cleaved by a protease), SG1 is an oligopeptide group or preferably a dipeptide group, L1 independently of one another represent in vivo stable organic groups, and L2 represents a coupling group to the binder or a single bond. Here, coupling is preferably to a cysteine residue or a lysine residue of the antibody. Alternatively, coupling can be to a tyrosine residue, glutamine residue or to an unnatural amino acid of the antibody. The unnatural amino acids may contain, for example, aldehyde or keto groups (such as, for example, formylglycine) or azide or alkyne groups (see Lan & Chin, Cellular Incorporation of Unnatural Amino Acids and Bioorthogonal Labeling of Proteins, Chem. Rev. 2014, 114, 4764-4806).

Particular preference according to the invention is given to the basic linker structure (iii). Via metabolization, the administration of a conjugate according to the invention having a basic linker structure (iii) and coupling of the linker to a cysteine or lysine residue of the antibody leads to cysteine or lysine derivatives of the formulae below:

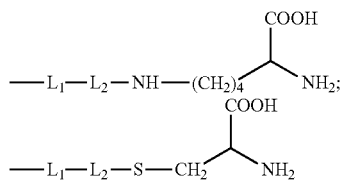

where L1 is in each case attached to the low-molecular weight KSP inhibitor, for example a compound of the formula (I), (Ia), (II), (IIa), (IIb), (IIca), (IId), (IIe), (IIf), (III) or (IV).

Preference according to the invention is also given to the basic linker structures (ii) and (iv), in particular when attachment is at position $R^1$, in particular when group L1 has one of the following structures:

(a) $-NH-(CH_2)_{0-4}-(CHCH_3)_{0-4}-CHY^5-CO-Y^7$, where $Y^5$ represents H or $NHY^6$, where $Y^6$ represents H or $-COCH_3$, and $Y^7$ represents a single bond or $-NH-(CH_2)_{0-4}-CHNH_2-CO-$, so that after cleavage the corresponding structure $-NH-(CH_2)_{0-4}-(CHCH_3)_{0-4}-CHY^5-COOH$ or $-NH-(CH_2)_{0-4}-(CHCH_3)_{0-4}-CHY^5-CO-NH-(CH_2)_{0-4}-CHNH_2-COOH$ is obtained.

(b) $-CH_2-S_x-(CH_2)_{0-4}-CHY^5-CO-$, where x is 0 or 1, and $Y^5$ represents H or $NHY^6$, where $Y^6$ represents H or $-COCH_3$, such that after cleavage the corresponding structure $-CH_2-S_x-(CH_2)_{0-4}-CHY^5-COOH$ is obtained.

Preference according to the invention is also given to the basic linker structure (i) when attached to position $R^4$, in particular if m=0.

If the linker is attached to a cysteine side chain or a cysteine residue, L2 is preferably derived from a group which reacts with the sulphhydryl group of the cysteine. These include haloacetyls, maleimides, aziridines, acryloyls, arylating compounds, vinylsulphones, pyridyl disulphides, TNB thiols and disulphide-reducing agents. These groups generally react in an electrophilic manner with the sulphhydryl bond, forming a sulphide (e.g. thioether) or disulphide bridge. Preference is given to stable sulphide bridges. L2 is preferably

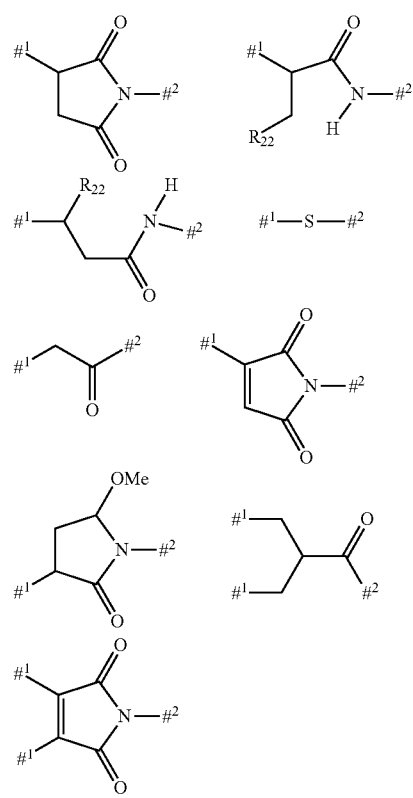

where $\#^1$ denotes the point of attachment to the sulphur atom of the antibody, $\#^2$ denotes the point of attachment to group $L^1$, and $R_{22}$ represents COOH, COOR, COR, CONHR, CONR$_2$ (where R in each case represents C1-3-alkyl), CONH$_2$, preferably COOH.

Particularly preferred for L2 is:

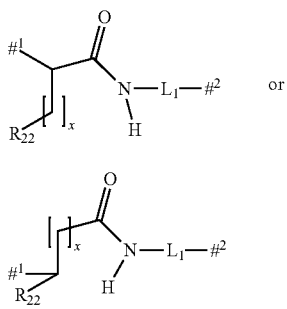

Formula A3 or

Formula A4 where #¹ denotes the point of attachment to the sulphur atom of the antibody, #² denotes the point of attachment to the active compound, x represents 1 or 2, and $R^{22}$ represents COOH, COOR, COR, CONR₂, CONHR (where R in each case represents C1-3-alkyl), CONH₂, preferably COOH. It is preferred when x=1 and $R^{22}$ represents COOH.

In a conjugate according to the invention or in a mixture of the conjugates according to the invention, the bonds to a cysteine residue of the antibody are present, to an extent of preferably more than 80%, particularly preferably more than 90% (in each case based on the total number of bonds of the linker to the antibody), particularly preferably as one of the two structures of the formula A3 or A4. Here, the structures of the formula A3 or A4 are generally present together, preferably in a ratio of from 60:40 to 40:60, based on the number of bonds to the antibody. The remaining bonds are then present as the structure

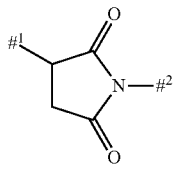

According to the invention, L1 is preferably represented by the formula $\#^1$—$(NR^{10})_n$-$(G1)_o$-G2-$\#^2$ where
$R^{10}$ represents H, NH₂ or $C_1$-$C_3$-alkyl;
G1 represents —NHCO—, —CONH— or

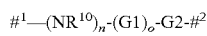

($R^{10}$ is preferably not NH₂, if G1 represents NHCO or

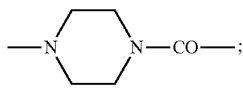

).

n represents 0 or 1;
o represents 0 or 1; and

G2 represents a straight-chain or branched hydrocarbon chain which has 1 to 100 carbon atoms from arylene groups and/or straight-chain and/or branched and/or cyclic alkylene groups and which may be interrupted once or more than once by one or more of the groups —O—, —S—, —SO—, SO₂, —NRy-, —NRyCO—, —C(NH)NRy-, CONRy-, —NRyNRy-, —SO₂NRyNRy-, —CONRyNRy- (where $R^y$ represents H, phenyl, $C_1$-$C_{10}$-alkyl, $C_2$-$C_{10}$-alkenyl or $C_2$-$C_{10}$-alkynyl, each of which may be substituted by NHCONH₂, —COOH, —OH, —NH₂, NH—CNNH₂, sulphonamide, sulphone, sulphoxide or sulphonic acid), —CO—, —$CR^x$=N—O— (where $R^x$ represents H, $C_1$-$C_3$-alkyl or phenyl) and/or a 3- to 10-membered aromatic or non-aromatic heterocycle having up to 4 heteroatoms selected from the group consisting of N, O and S, —SO— or —SO₂— (preferably

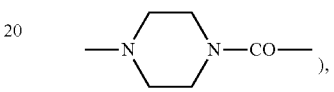

), where the hydrocarbon chain including any side chains may be substituted by —NHCONH₂, —COOH, —OH, —NH₂, NH—CNNH₂, sulphonamide, sulphone, sulphoxide or sulphonic acid.

G2 represents a straight-chain or branched hydrocarbon chain having 1 to 100 carbon atoms from arylene groups and/or straight-chain and/or branched and/or cyclic alkylene groups and which may be interrupted once or more than once by one or more of the groups —O—, —S—, —SO—, SO₂, —NH—, —CO—, —NHCO—, —CONH—, —NMe-, —NHNH—, —SO₂NHNH—, —CONHNH— and a 5- to 10-membered aromatic or non-aromatic heterocycle having up to 4 heteroatoms selected from the group consisting of N, O and S, or —SO— (preferably

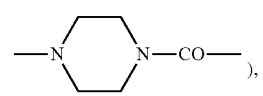

), where the side chains, if present, may be substituted by —NHCONH₂, —COOH, —OH, —NH₂, NH—CNNH₂, sulphonamide, sulphone, sulphoxide or sulphonic acid.

G2 preferably represents a straight-chain or branched hydrocarbon chain having 1 to 100 carbon atoms from arylene groups and/or straight-chain and/or branched and/or cyclic alkylene groups and which may be interrupted once or more than once by one or more of the groups —O—, —S—, —SO—, SO₂, —NH—, —CO—, —NHCO—, —CONH—, —NMe-, —NHNH—, —SO₂NHNH—, —CONHNH—, —$CR^x$=N—O— (where $R^x$ represents H, C1-C3-alkyl or phenyl) and a 3- to 10-membered, for example 5- to 10-membered, aromatic or non-aromatic heterocycle having up to 4 heteroatoms selected from the group consisting of N, O and S, —SO— or —SO₂— (preferably

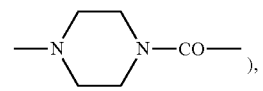

), where the hydrocarbon chain including the side chains, if present, may be substituted by —NHCONH$_2$, —COOH, —OH, —NH$_2$, NH—CNNH$_2$, sulphonamide, sulphone, sulphoxide or sulphonic acid.

Further interrupting groups in G2 are preferably

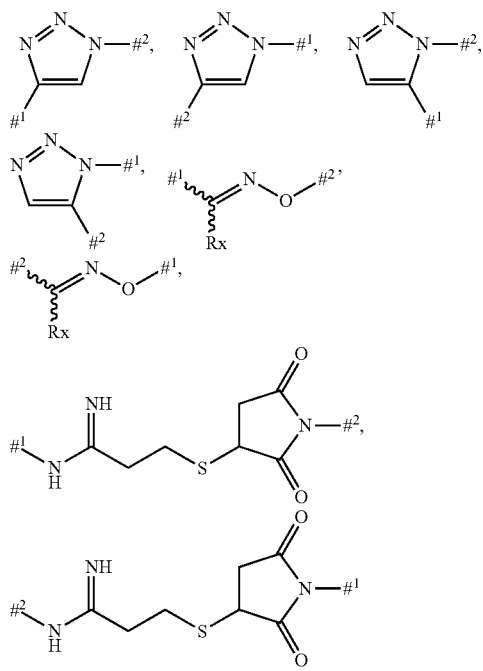

where R$^x$ represents H, C$_1$-C$_3$-alkyl or phenyl.

Here, #$^1$ is the bond to the KSP inhibitor and #$^2$ is the bond to the coupling group to the antibody (e.g. L2).

A straight-chain or branched hydrocarbon chain of arylene groups and/or straight-chain and/or branched and/or cyclic alkylene groups generally comprises a α,ω-divalent alkyl radical having the respective number of carbon atoms stated. The following may be mentioned by way of example and as preferred: methylene, ethane-1,2-diyl (1,2-ethylene), propane-1,3-diyl (1,3-propylene), butane-1,4-diyl (1,4-butylene), pentane-1,5-diyl (1,5-pentylene), hexane-1,6-diyl (1,6-hexylene), heptane-1,7-diyl (1,7-hexylene), octane-1,8-diyl (1,8-octylene), nonane-1,9-diyl (1,9-nonylene), decane-1,10-diyl (1,10-decylene). However, the alkylene groups in the hydrocarbon chain may also be branched, i.e. one or more hydrogen atoms of the straight-chain alkylene groups mentioned above may optionally be substituted by C1-10-alkyl groups, thus forming side chains. The hydrocarbon chain may furthermore contain cyclic alkylene groups (cycloalkanediyl), for example 1,4-cyclohexanediyl or 1,3-cyclopentanediyl. These cyclic groups may be unsaturated. In particular, aromatic groups (arylene groups), for example phenylene, may be present in the hydrocarbon group. In turn, in the cyclic alkylene groups and the arylene groups, too, one or more hydrogen atoms may optionally be substituted by C1-10-alkyl groups. In this way, an optionally branched hydrocarbon chain is formed. This hydrocarbon chain has a total of 0 to 100 carbon atoms, preferably 1 to 50, particularly preferably 2 to 25 carbon atoms.

The side chains, if present, may be mono- or polysubstituted, identically or differently, by —NHCONH$_2$, —COOH, —OH, —NH$_2$, NH—CNNH$_2$, sulphonamide, sulphone, sulphoxide or sulphonic acid.

The hydrocarbon chain may be interrupted once or more than once, identically or differently, by —O—, —S—, —SO—, SO$_2$, —NH—, —CO—, —NHCO—, —CONH—, —NMe-, —NHNH—, —SO$_2$NHNH—, —CONHNH— and a 5- to 10-membered aromatic or non-aromatic heterocycle having up to 4 heteroatoms selected from the group consisting of N, O and S, —SO— or —SO$_2$— (preferably

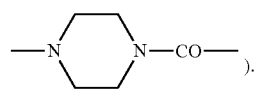

Further interrupting groups in G2 are preferably

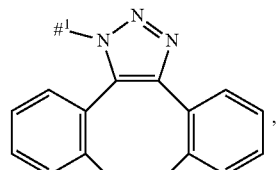

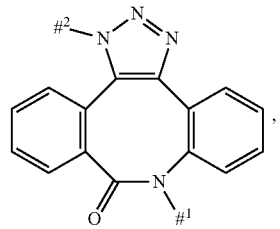

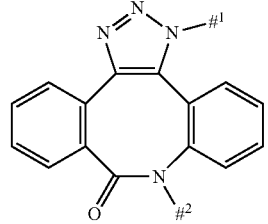

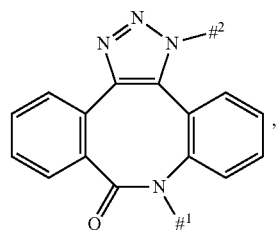

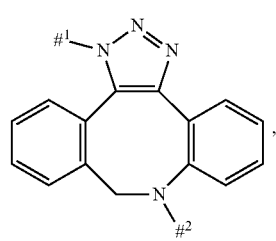

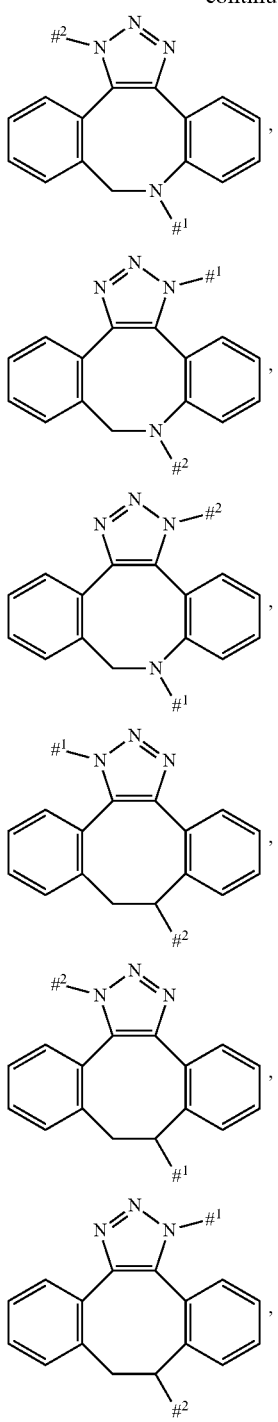
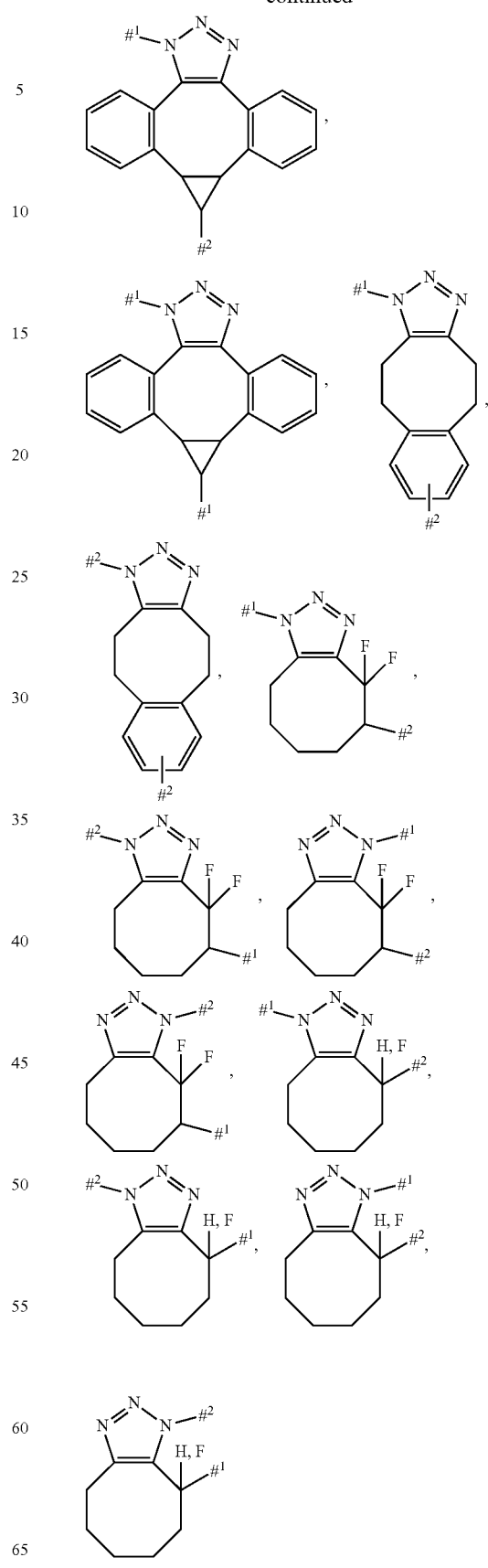

Preferably, the linker corresponds to the formula below:

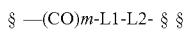

where
m represents 0 or 1;
§ represents the bond to the active compound molecule and
§ § represents the bond to the binder peptide or protein, and
L1 and L2 have the meaning given above.
Particularly preferably, L1 has the formula —NR$^{11}$B—, where
R$^{11}$ represents H or NH$_2$;
B represents —[(CH$_2$)$_x$—(X$^4$)$_y$]$_w$—(CH$_2$)$_z$—,
w=0 to 20;
x=0 to 5;
y=0 or 1;
z=0 to 5; and
X$^4$ represents —O—, —CONH—, —NHCO— or

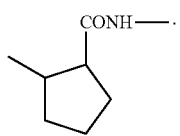

Linkers L which are preferred in accordance with the invention have the formula below:

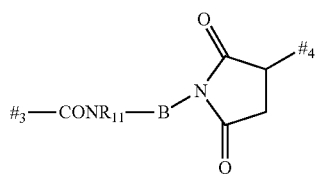

where
3 represents the bond to the active compound molecule,
4 represents the bond to the binder peptide or protein,
R11 represents H or NH$_2$;
B represents —[(CH$_2$)$_x$—(X$^4$)$_y$]w-(CH$_2$)$_z$—,
w=0 to 20;
x=0 to 5;
y=0 or 1;
z=1 to 5; and
X$^4$ represents —O—, —CONH—, —NHCO— or

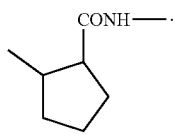

The linkers mentioned above are especially preferred in conjugates of the formula (I) or (II) in which the linker couples by substitution of a hydrogen atom at R1 or in combination with a cleavable linker SG1 at R4, i.e. R1 represents -L-#1 or R4 represents -SG1-L-#1, where #1 represents the bond to the antibody.
Preference in accordance with the invention is furthermore given to the linkers below: In a conjugate according to the invention or in a mixture of the conjugates according to the invention, the bonds to a cysteine residue of the antibody are present, to an extent of preferably more than 80%, particularly preferably more than 90% (in each case based on the total number of bonds of the linker to the antibody), particularly preferably as one of the two structures of the formula A5 or A6:

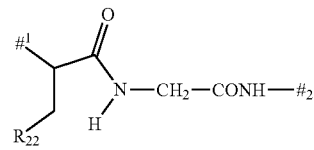

Formula A5

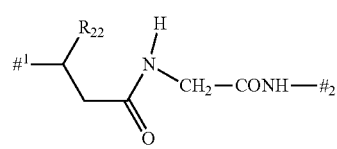

Formula A6 where
$^1$ denotes the point of attachment to the sulphur atom of the antibody,
$^2$ denotes the point of attachment to group L$^1$, and
R$^{22}$ represents COOH, COOR, COR, CONR$_2$, CONHR (where R in each case represents C1-3-alkyl), CONH$_2$, preferably COOH.
Here, the structures of the formula A5 or A6 are generally present together, preferably in a ratio of from 60:40 to 40:60, based on the number of bonds to the antibody. The remaining bonds are then present as the structure

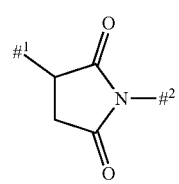

Other linkers -L- attached to a cysteine side chain or cysteine residue have the formula below:

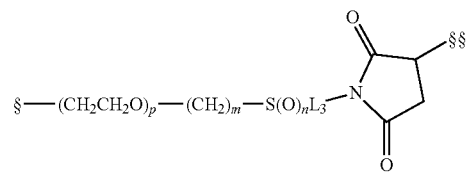

where
§ represents the bond to the active compound molecule and
§ § represents the bond to the binder peptide or protein,
m represents 0, 1, 2 or 3;
n represents 0, 1 or 2;
p represents 0 to 20; and
L3 represents

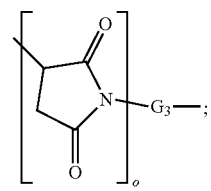

where
o represents 0 or 1;
and
G3 represents a straight-chain or branched hydrocarbon chain having 1 to 100 carbon atoms from arylene groups and/or straight-chain and/or cyclic alkylene groups and which may be interrupted once or more than once by one or more of the groups —O—, —S—, —SO—, $SO_2$, —NH—, —CO—, —NHCO—, —CONH—, —NMe-, —NHNH—, —$SO_2$NHNH—, —CONHNH— and a 3- to 10-membered (preferably 5- to 10-membered) aromatic or non-aromatic heterocycle having up to 4 heteroatoms selected from the group consisting of N, O and S, —SO— or $SO_2$ (preferably

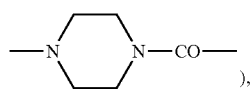

), where the side chains, if present, may be substituted by —NHCO$NH_2$, —COOH, —OH, —$NH_2$, NH—CN$NH_2$, sulphonamide, sulphone, sulphoxide or sulphonic acid.

In the formula above, preferably
m represents 1;
p represents 0;
n represents 0;
and L3 represents

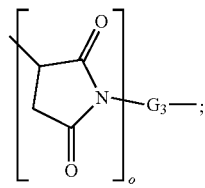

where
o represents 0 or 1; and
G3 represents —($CH_2CH_2O)_s(CH_2)_t(CONH)_uCH_2CH_2O)_v(CH_2)_w$—, where
s, t, v and w each independently of one another are from 0 to 20 and u is 0 or 1.

Preferred groups L1 in the formula § —(CO)m-L1-L2- § § above are those below, where r in each case independently of one another represents a number from 0 to 20, preferably from 0 to 15, particularly preferably from 1 to 20, especially preferably from 2 to 10:

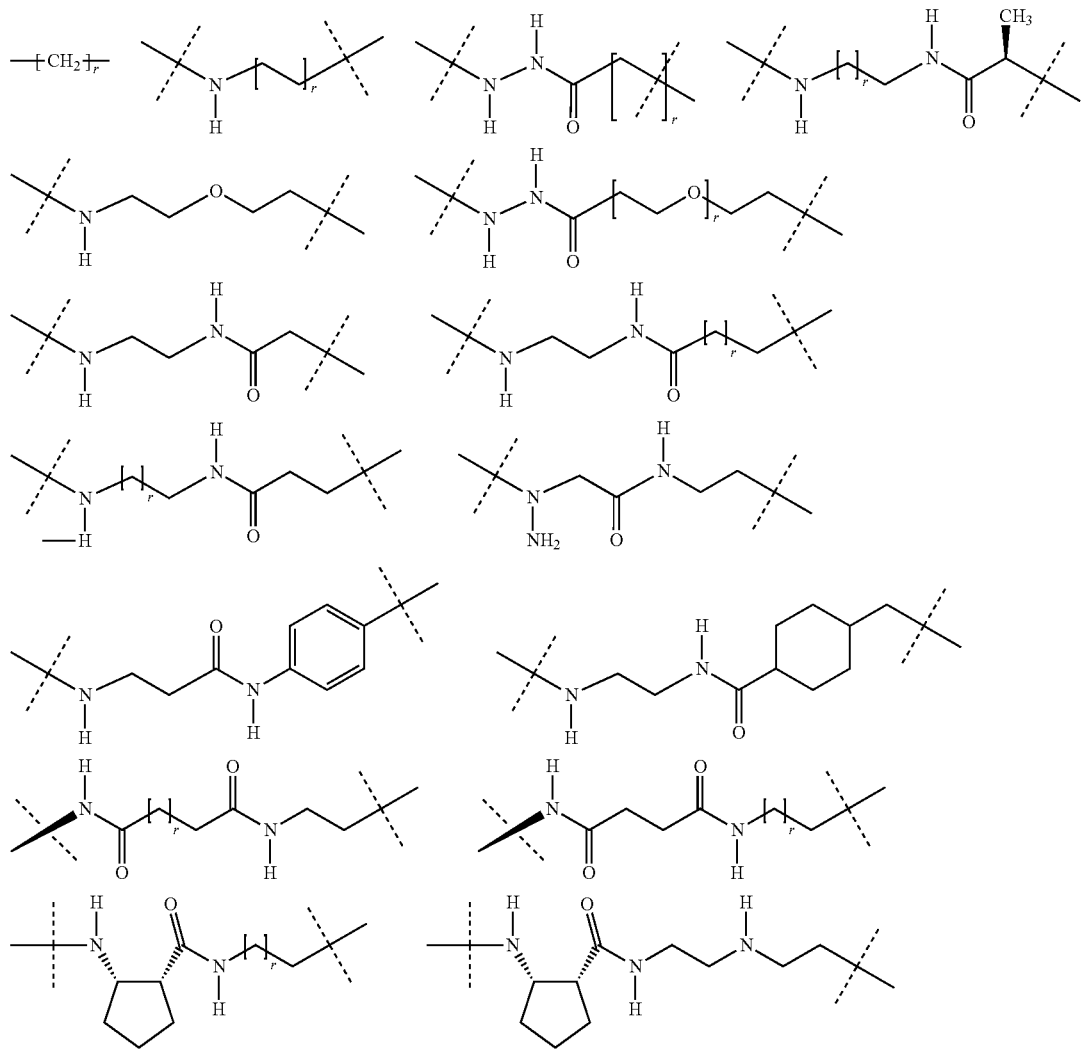

-continued
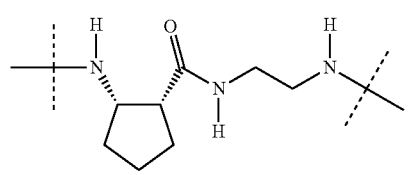
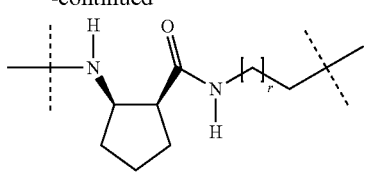
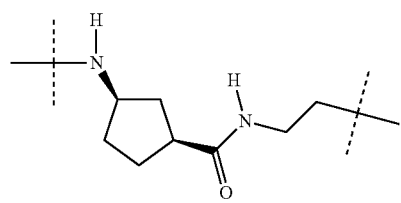
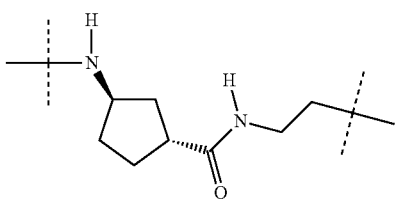
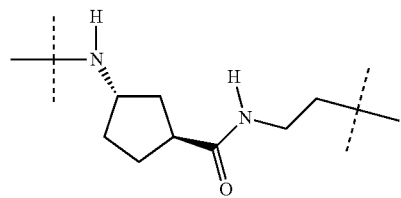
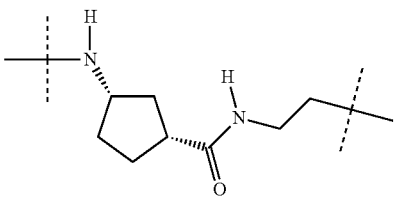
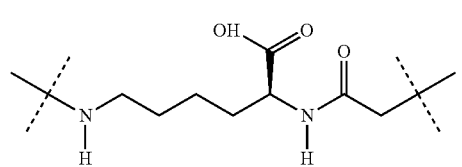
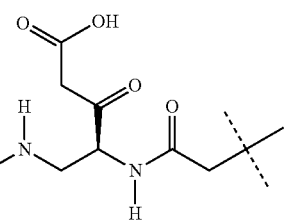
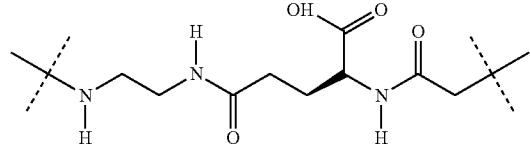
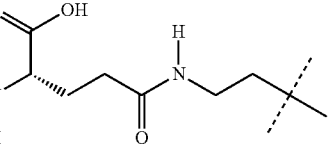
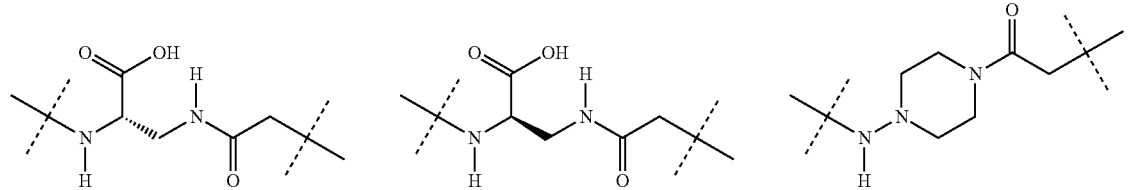
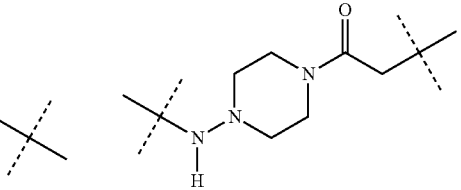
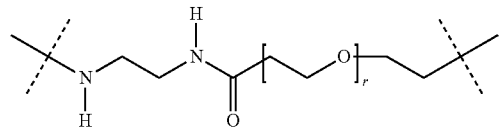
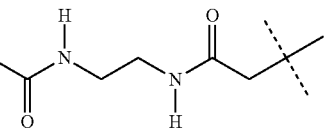
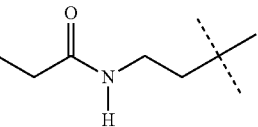

-continued
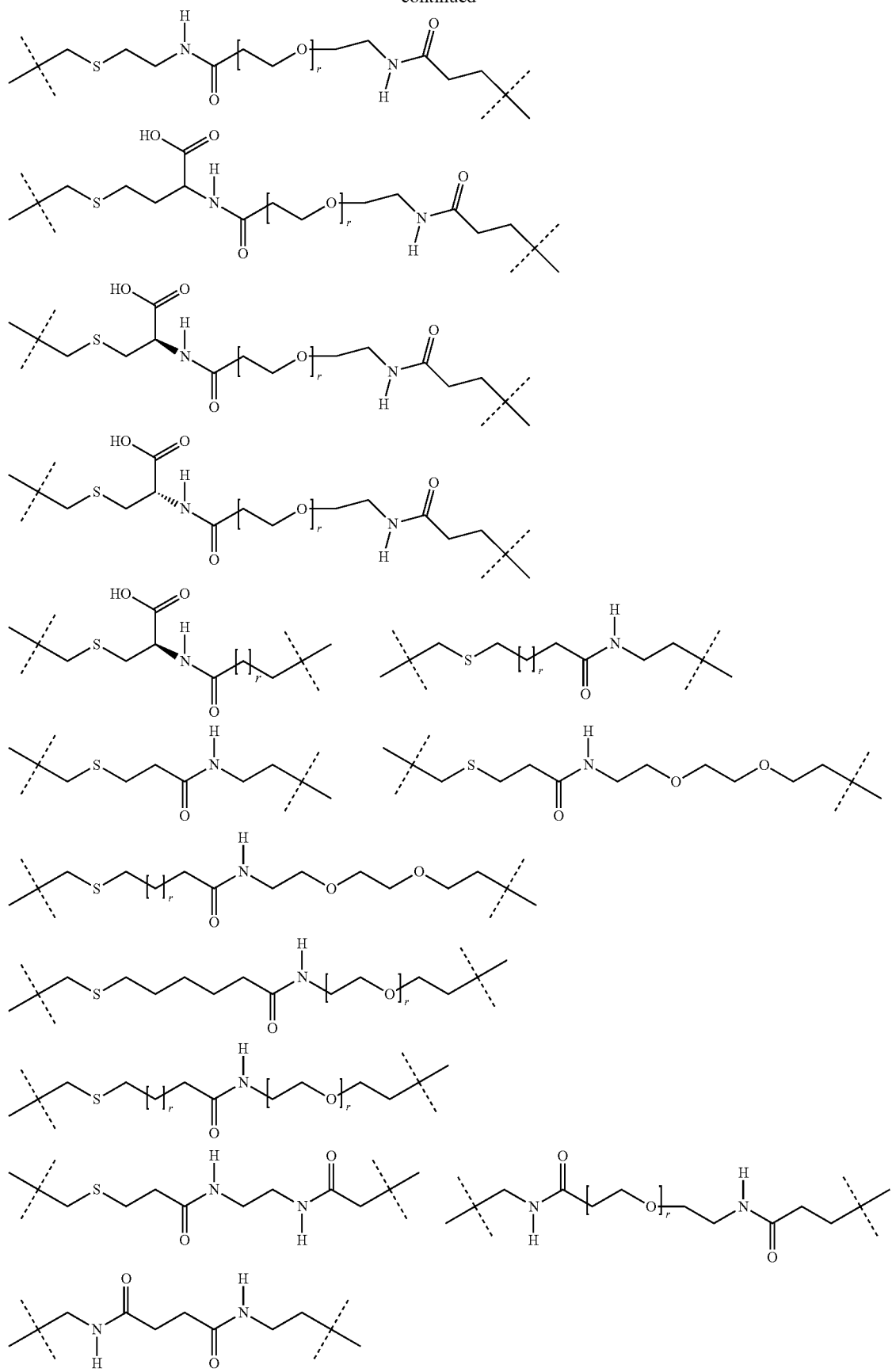

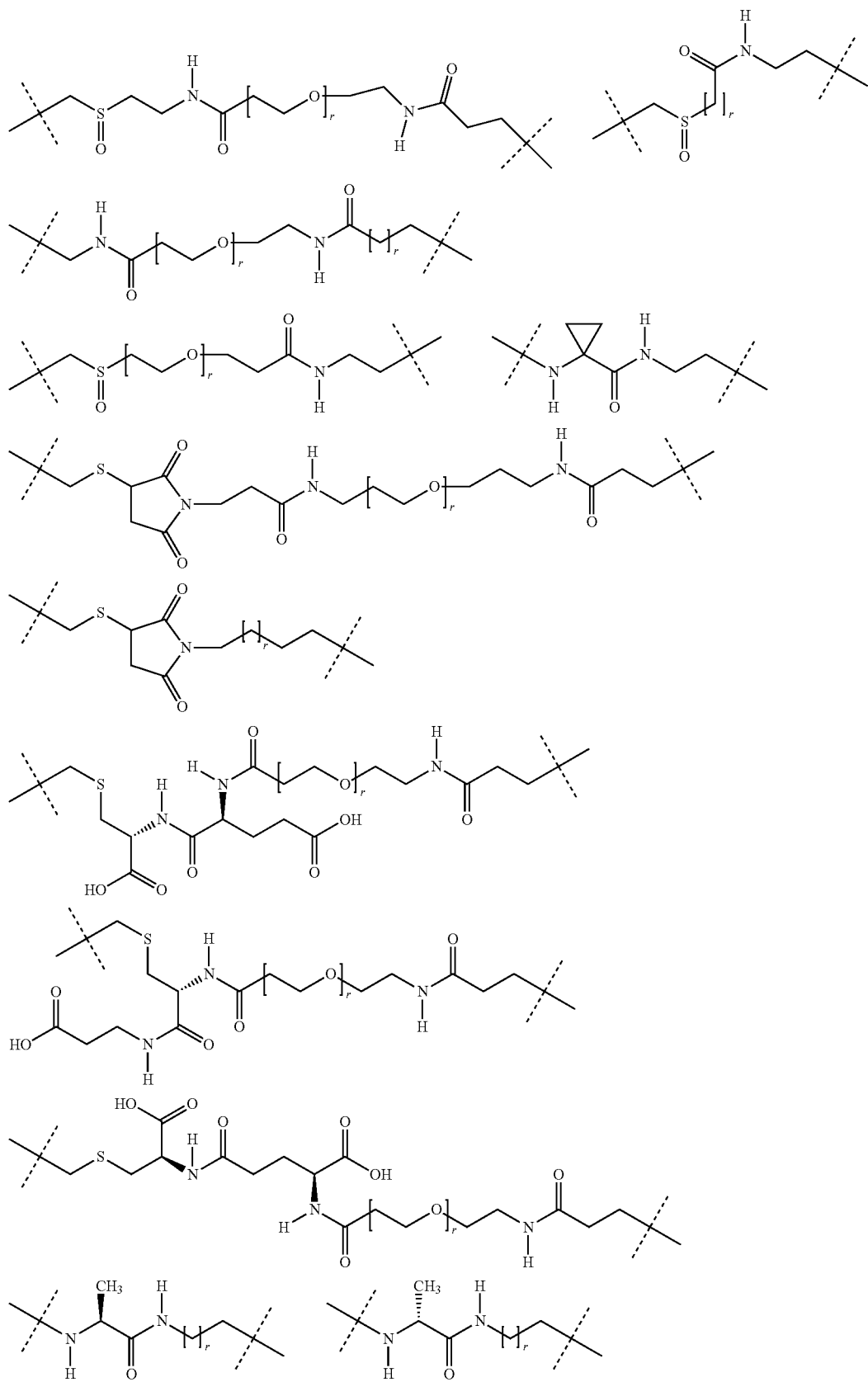

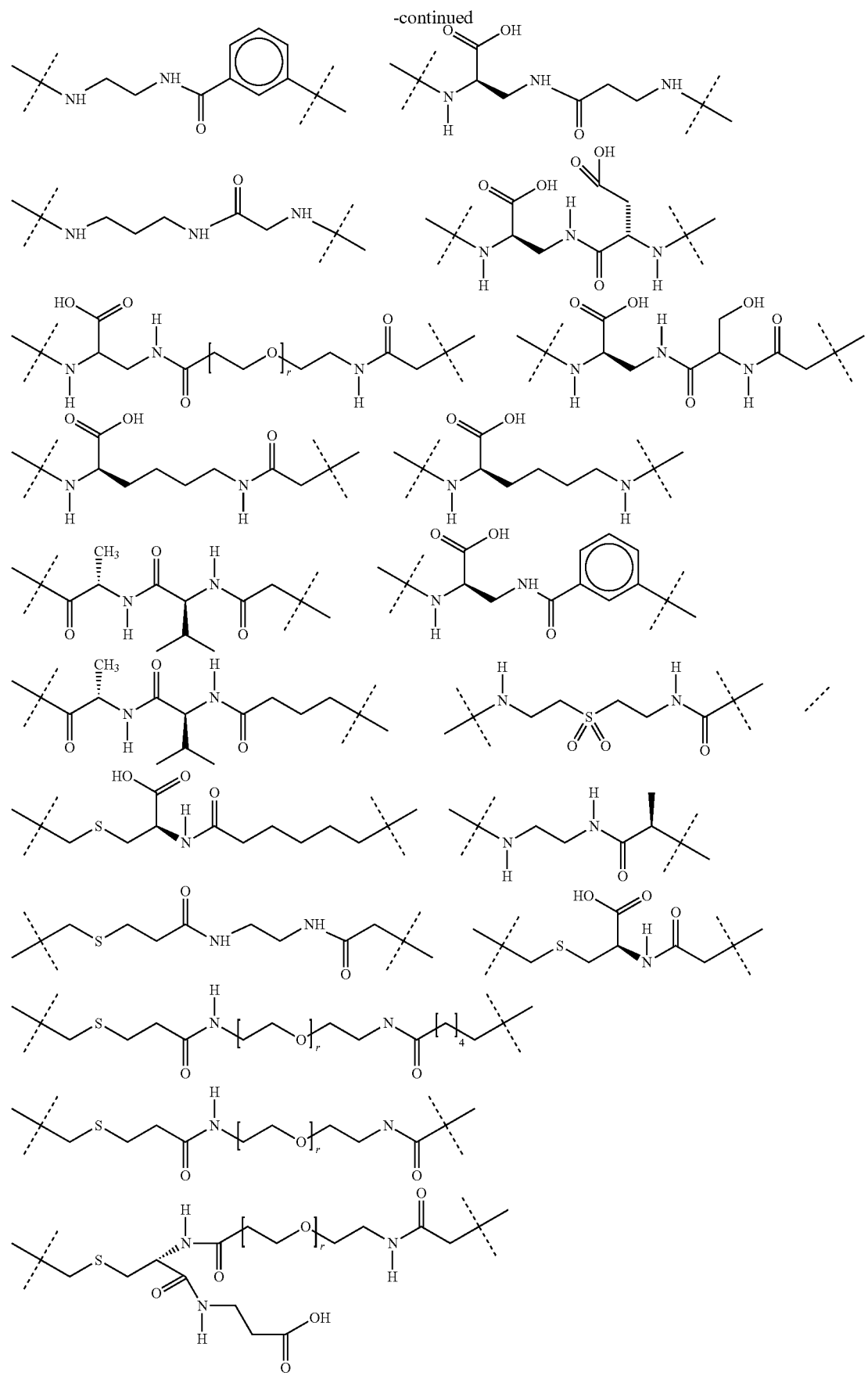

-continued
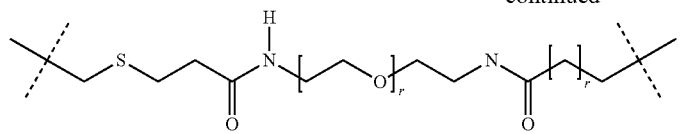
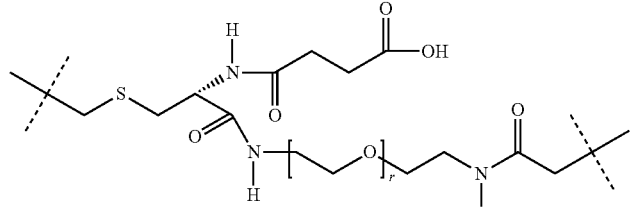
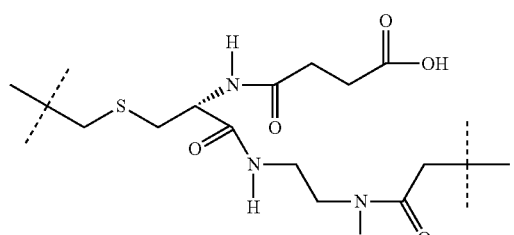
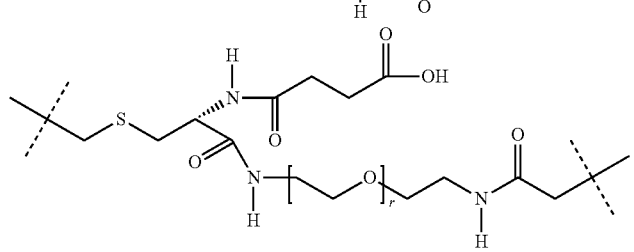
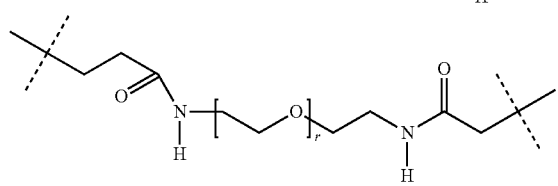
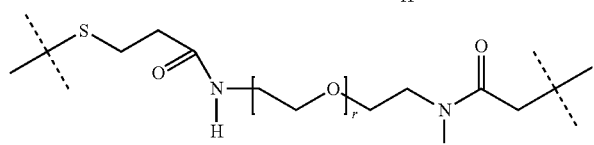
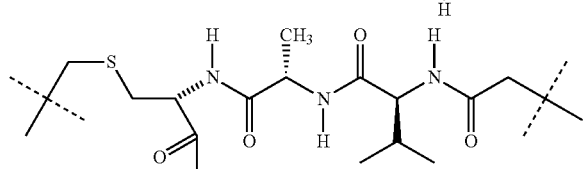
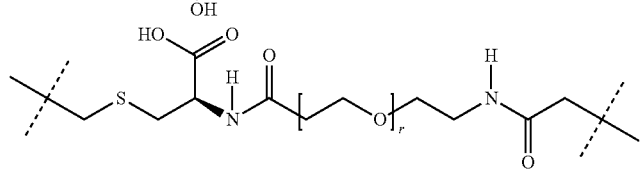
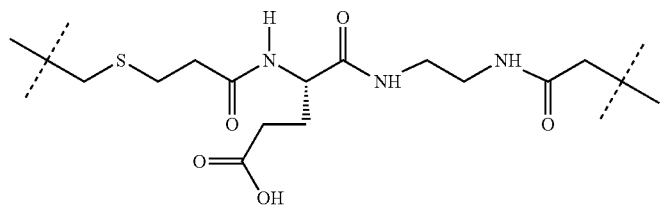

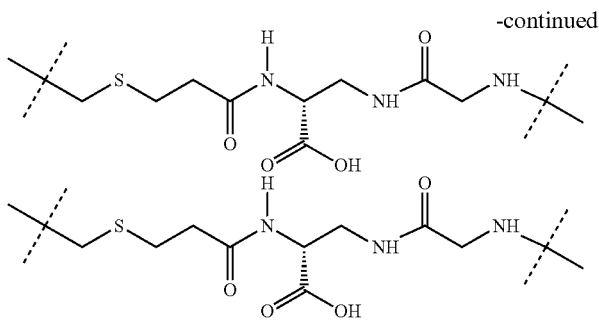

Further examples of L1 are given in Table C, in which this group is highlighted in a box.

Examples of a linker moiety L1 are given in Tables A and A' below. The table furthermore states with which group L2 these examples of L1 are preferably combined, and also the preferred coupling point ($R^1$ or $R^3$ or $R^4$) and the preferred value for m, this is whether there is a carbonyl group in front of L1 or not (cf. § —(CO)m-L1-L2- § §). These linkers are preferably coupled to a cysteine residue. If L2 is a succinimide or derived therefrom, this imide may also be fully or partially in the form of the hydrolysed open-chain succinamide, as described above. Depending on L1, this hydrolysis to open-chain succinamides may be more or less pronounced or not present at all.

TABLE A

| Subst. | m | L1 | L2 |
|---|---|---|---|
| $R^1$ | 1 | | |
| $R^1$ | 1 | | |
| $R^1$ | 1 | | |
| $R^1$ | 1 | | |
| $R^1$ | 1 | | |

TABLE A-continued

| Subst. | m | L1 | L2 |
|---|---|---|---|
| R¹ | 1 | (structure: -NH-CH₂CH₂-NH-C(O)-CH₂-) | (succinimide structure) See note** |
| R¹ | 1 | (structure: -N(NH₂)-CH₂-C(O)-NH-CH₂CH₂-) | (succinimide structure) |
| R¹ | 1 | (structure: -NH-CH₂CH₂-NH-C(O)-CH(CH₂CH₂COOH)-NH-C(O)-CH₂-) | (succinimide structure) See note** |
| R¹ | 1 | (structure: -NH-CH₂CH₂-C(O)-NH-C₆H₄-) | (succinimide structure) |
| R¹ | 1 | (structure: -NH-CH₂CH₂-NH-C(O)-cyclohexyl-CH₂-) | (succinimide structure) |
| R¹ | 1 | (structure: -NH-cyclopentyl-C(O)-NH-CH₂CH₂-) | (succinimide structure) |
| R¹ | 1 | (structure: -NH-cyclopentyl-C(O)-NH-CH₂CH₂-) | (succinimide structure) |
| R¹ | 1 | (structure: lysine-based -NH-(CH₂)₄-CH(COOH)-NH-C(O)-CH₂-) | (succinimide structure) See note** |

TABLE A-continued

| Subst. | m | L1 | L2 |
|---|---|---|---|
| R¹ | 1 | (structure) | (succinimide structure) See note** |
| R¹ | 1 | (structure) | (succinimide structure) |
| R¹ | 1 | (structure) | (succinimide structure) See note** |
| R¹ | 1 | (structure) | (succinimide structure) |
| R¹ | 1 | (structure) | (succinimide structure) |
| R¹ | 1 | (structure) | —C(O)—CH$_2$— |
| R¹ | 1 | (structure) | (succinimide structure) |
| R³ | 0 | (structure) | (succinimide structure) |

TABLE A-continued

| Subst. | m | L1 | L2 |
|---|---|---|---|
| R¹ | 1 | (structure) | (maleimide) |
| R³ | 0 | (structure) | (maleimide) |
| R¹ | 1 | (structure) | (maleimide) |
| R¹ | 0 | (structure) | (maleimide) |
| R³ | 0 | (structure) | (maleimide) |
| R³ | 0 | (structure) | (maleimide) |
| R¹ | 1 | (structure) | (maleimide) |
| R³ | 0 | (structure) | (maleimide) |

TABLE A-continued

| Subst. | m | L1 | L2 |
|---|---|---|---|
| $R^3$ | 0 | (structure: thioether–succinimide–CH2CH2C(O)NH–(CH2CH2O)3–CH2CH2CH2NHC(O)–) | succinimide |
| $R^3$ | 0 | (structure: thioether–succinimide–N–(CH2)4–) | succinimide |
| $R^3$ | 0 | (structure: thioether–succinimide–N–(CH2)5–) | succinimide |
| $R^1$ | 1 | (structure: –NH–CH(CH3)–C(O)–NH–CH2CH2–) | succinimide |
| $R^1$ | 1 | (structure: –NH–CH(CH3)–C(O)–NH–CH2CH2–) | succinimide |

**With particular preference, the linkers L1 given in these rows are attached to a linker L2 selected from:

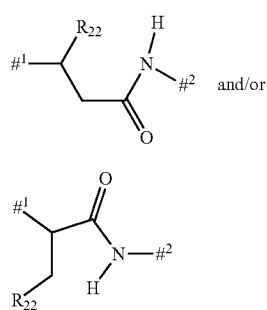 and/or

Formula A7

Formula A8 where $\#^1$ denotes the point of attachment to the sulphur atom of the binder, $\#^2$ denotes the point of attachment to group $L^1$, $R^{22}$ preferably represents COOH. In a conjugate according to the invention or in a mixture of the conjugates according to the invention, the bonds to a cysteine residue of the binder are present, to an extent of preferably more than 80%, particularly preferably more than 90% (in each case based on the total number of bonds of the linker to the binder), particularly preferably as one of the two structures of the formula A7 or A8. Here, the structures of the formula A7 or A8 are generally present together, preferably in a ratio of from 60:40 to 40:60, based on the number of bonds to the binder. The remaining bonds are then present as the structure

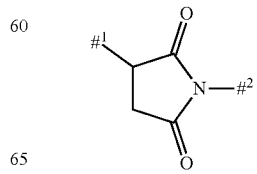

TABLE A'

| Subst. | m | L1 | L2 |
|---|---|---|---|
| R¹ | 1 | [structure] | [structure] |
| R¹ | 1 | [structure] | [structure] |
| R¹ | 1 | [structure] | [structure] |
| R¹ | 1 | [structure] | —C(O)—CH₂— |
| R¹ | 1 | [structure] | [structure] |
| R¹ | 1 | [structure] | [structure] |
| R³ | 0 | [structure] | [structure] |
| R³ | 0 | [structure] | [structure] |

TABLE A'-continued
| Subst. | m | L1 | L2 |
|---|---|---|---|
| R³ | 0 |  | 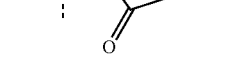 |
| R³ | 0 | 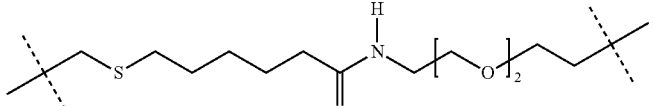 | 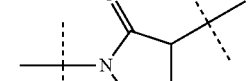 |
| R³ | 0 | 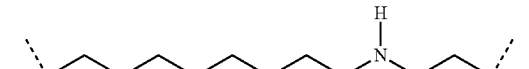 | 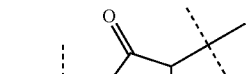 |
| R¹ | 1 |  | 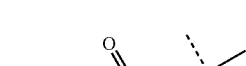 |
| R¹ | 1 | 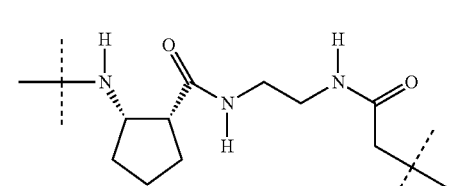 | 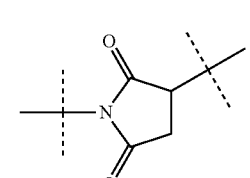<br>See note** |
| R¹ | 1 | 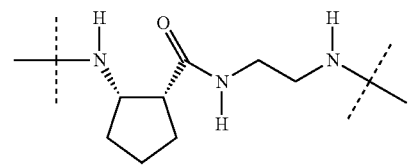 | 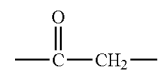 |
| R¹ | 1 | 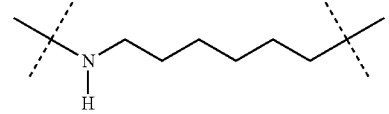 | 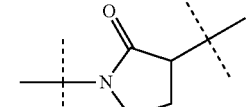 |
| R¹ | 1 | 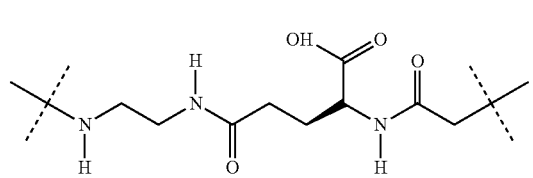 | 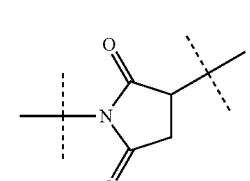<br>See note** |

TABLE A'-continued

| Subst. | m | L1 | L2 |
|---|---|---|---|
| R[1] | 1 | (structure) | (structure) See note** |
| R[1] | 1 | (structure) | (structure) See note** |
| R[1] | 0 | (structure) | (structure) |
| R[1] | 1 | (structure) | (structure) |
| R[1] | 1 | (structure) | (structure) and (structure) See note*** |
| R[1] | 1 | (structure) | (structure) |

TABLE A'-continued

| Subst. | m | L1 | L2 |
|---|---|---|---|
| R¹ | 1 | (structure) | (structure) Identical to the two above |
| R¹ | 1 | (structure) | (structure) |
| R³ | 0 | (structure) | (structure) |
| R³ | 0 | (structure) | (structure) |
| R³ | 0 | (structure) | (structure) |
| R³ | 0 | (structure) | (structure) |
| R³ | 0 | (structure) | (structure) See note** |
| R³ | 0 | (structure) | (structure) |

TABLE A'-continued

| Subst. | m | L1 | L2 |
|---|---|---|---|
| R³ | 0 | (structure) | (structure) |
| R³ | 0 | (structure) | (structure) See note** |
| R³ | 0 | (structure) | (structure) |
| R² | 0 | (structure) | (structure) |
| R¹ | 1 | (structure) | (structure) where $R_{22}$ = —OH or —NH$_2$ |
| R¹ | 1 | (structure) | (structure) where $R_{22}$ = —OH or —NH$_2$ |

TABLE A'-continued

| Subst. | m | L1 | L2 |
|---|---|---|---|
| R¹ | 1 | (structure: -N(H)-CH2-C(CH3)2-) | (structure: -N(H)-C(=O)-CH(-)-CH2-COOH) and (structure: -N(H)-C(=O)-CH2-CH(-)-COOH) See note*** |
| R¹ | 1 | (structure: -N(H)-CH2-C(CH3)2-) | (structure: -N(H)-C(=O)-CH(-)-CH2-COOH) |
| R¹ | 1 | (structure: -N(H)-CH2-C(CH3)2-) | (structure: -N(H)-C(=O)-CH2-CH(-)-COOH) |
| R¹ | 1 | (structure: -N(H)-CH(COOH)-CH2-CH2-N(H)-C(=O)-) | (structure: -N(H)-C(=O)-CH(-)-CH2-COOH) and (structure: -N(H)-C(=O)-CH2-CH(-)-COOH) See note*** |

TABLE A'-continued

| Subst. | m | L1 | L2 |
|---|---|---|---|
| R¹ | 1 | (structure) | (structure) |
| R¹ | 1 | (structure) | (structure) |
| R³ | 0 | (structure) | (structure) and (structure) See note*** |
| R³ | 0 | (structure) | (structure) |
| R³ | 0 | (structure) | (structure) |
| R³ | 0 | (structure) | (structure) and |

TABLE A'-continued

| Subst. | m | L1 | L2 |
|---|---|---|---|
| | | | (structure: -NH-CH2-CH(COOH)-) See note*** |
| R³ | 0 | Cys-based linker with S-CH2, CH(COOH)NH-C(=O)-C(CH3)2- | (structure: -NH-CH2-CH(COOH)-CH2-) |
| R³ | 0 | Cys-based linker with S-CH2, CH(COOH)NH-C(=O)-C(CH3)2- | (structure: -NH-CH2-CH(COOH)-CH2-) |
| R³ | 0 | -CH2-S-CH2CH2-C(=O)-NH-CH2CH2-NH-C(=O)-C(CH3)2- | (structure: -NH-CH2-CH(COOH)-CH2-) and (structure: -NH-CH2-CH(COOH)-) See note*** |
| R³ | 0 | -CH2-S-CH2CH2-C(=O)-NH-CH2CH2-NH-C(=O)-C(CH3)2- | (structure: -NH-CH2-CH(COOH)-CH2-) |
| R³ | 0 | -CH2-S-CH2CH2-C(=O)-NH-CH2CH2-NH-C(=O)-C(CH3)2- | (structure: -NH-CH2-CH(COOH)-) |

TABLE A'-continued

| Subst. | m | L1 | L2 |
|---|---|---|---|
| R¹ | 1 | —NH—CH₂CH₂—NH—C(O)—CH₂—NH— | —C(O)—CH₂— |
| R¹ | 1 | —NH—(CH₂)₃—NH—C(O)— | —C(O)—CH(CH₂COOH)—NH— and —NH—C(O)—CH₂—CH(COOH)— See note*** |
| R¹ | 1 | —NH—(CH₂)₃—NH—C(O)— | —C(O)—CH(CH₂COOH)—NH— |
| R¹ | 1 | —NH—(CH₂)₃—NH—C(O)— | —NH—C(O)—CH₂—CH(COOH)— |
| R¹ | 1 | —NH—CH₂CH₂—O—CH₂CH₂—NH—C(O)— | —C(O)—CH(CH₂COOH)—NH— and —NH—C(O)—CH₂—CH(COOH)— See note*** |

TABLE A'-continued

| Subst. | m | L1 | L2 |
|---|---|---|---|
| R¹ | 1 | –NH–CH₂CH₂–O–CH₂CH₂–NH–C(=O)–CH₂– | –NH(H)–C(=O)–CH(CH₂COOH)– |
| R¹ | 1 | –NH–CH₂CH₂–O–CH₂CH₂–NH–C(=O)–CH₂– | –NH(H)–C(=O)–CH₂–CH(COOH)– |
| R3 | 0 | –CH₂–S–CH₂–CH(NH₂)–C(=O)–NH–CH₂CH₂–NH–C(=O)–(CH₂)₅– | succinimide (N-substituted 2,5-dioxopyrrolidin-3-yl) |
| R1 | 0 | –NH–C(=O)–CH₂CH₂–C(=O)–NH–CH₂CH₂–NH–C(=O)– | –NH(H)–C(=O)–CH(CH₂COOH)– and –NH(H)–C(=O)–CH₂–CH(COOH)– See note*** |
| R1 | 0 | –NH–C(=O)–CH₂CH₂–C(=O)–NH–CH₂CH₂–NH–C(=O)– | –NH(H)–C(=O)–CH(CH₂COOH)– |
| R1 | 0 | –NH–C(=O)–CH₂CH₂–C(=O)–NH–CH₂CH₂–NH–C(=O)– | –NH(H)–C(=O)–CH₂–CH(COOH)– |

TABLE A'-continued

| Subst. | m | L1 | L2 |
|---|---|---|---|
| R1 | 1 | (structure: —NH—CH₂CH₂—NH—C(=O)—CH₂—) | (structure: —NH—C(=O)—CH(CH₂COOH)—) and (structure: —NH—C(=O)—CH₂—CH(COOH)—) |
| R1 | 1 | (structure: —NH—CH₂CH₂—O—CH₂CH₂—) | (structure: succinimide, N-linked, 2,5-dioxopyrrolidine) |
| R1 | 1 | (structure: —NH—CH₂CH₂—NH—C(=O)—(m-phenylene)—) | (structure: —NH—C(=O)—CH(CH₂COOH)—) and (structure: —NH—C(=O)—CH₂—CH(COOH)—) |
| R¹ | 1 | (structure: L-Dap-β-Ala type: —NH—CH(COOH)—CH₂—NH—C(=O)—CH₂CH₂—NH—) | —C(=O)—CH₂— |
| R¹ | 1 | (structure: —NH—CH₂CH₂CH₂—NH—C(=O)—CH₂—NH—) | —C(=O)—CH₂— |
| R¹ | 1 | (structure: Dap-Asp dipeptide: —NH—CH(COOH)—CH₂—NH—C(=O)—CH(COOH)—CH₂—NH—) | —C(=O)—CH₂— |

TABLE A'-continued
| Subst. | m | L1 | L2 |
|---|---|---|---|
| R¹ | 1 | 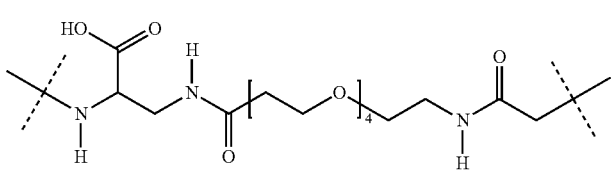 | 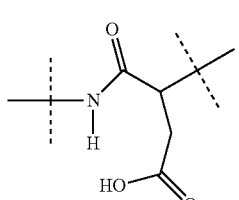<br>and<br>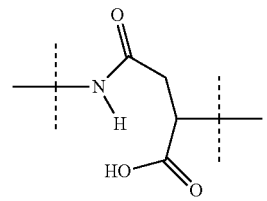<br>See note*** |
| R¹ | 1 | 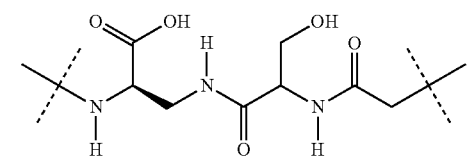 | 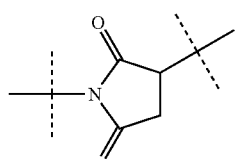<br>See note** |
| R¹ | 1 | 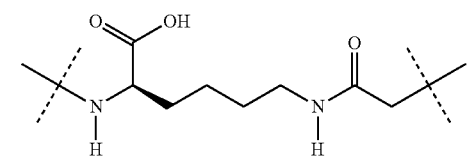 | 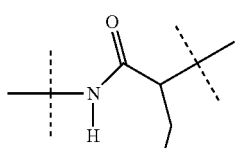<br>and<br><br>See note*** |
| R¹ | 1 | 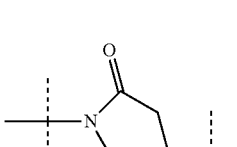 | 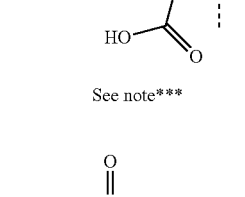 |

TABLE A'-continued
| Subst. | m | L1 | L2 |
|---|---|---|---|
| R⁴ | 0 | 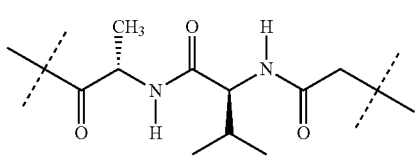 | 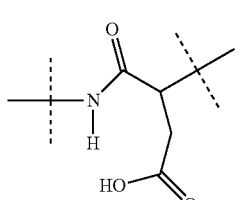<br>and<br>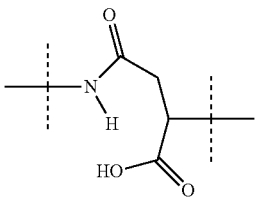<br>See note*** |
| R¹ | 1 | 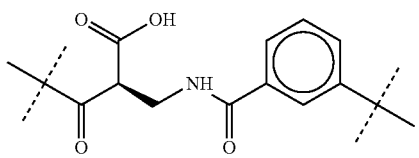 | 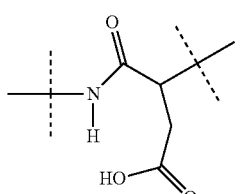<br>and<br>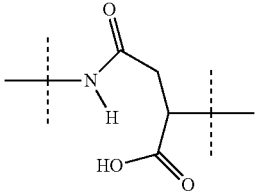<br>See note*** |
| R⁴ | 0 | 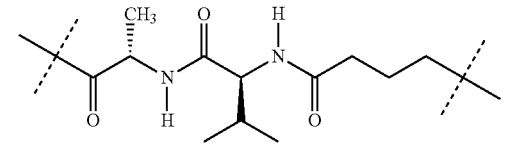 | 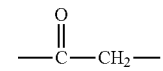 |
| R¹ | 1 | 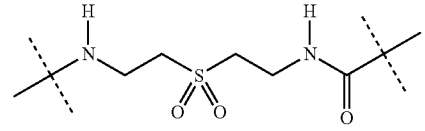 | — | 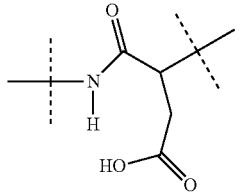<br>and |

TABLE A'-continued
| Subst. | m | L1 | L2 |
|---|---|---|---|
| | | | 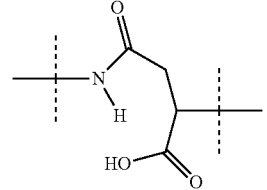<br>See note** |
| R³ | 0 | 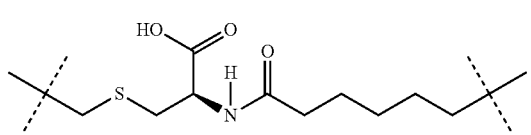 | 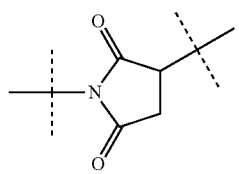<br>See note** |
| R¹ | 1 | 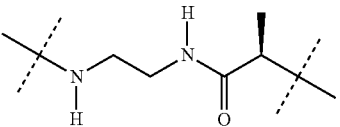 | 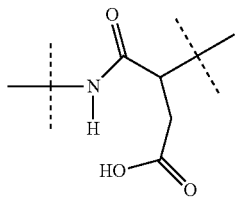<br>and<br>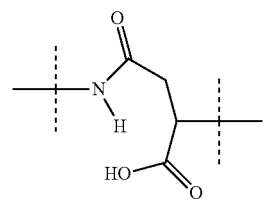<br>See note*** |
| R³ | 0 | 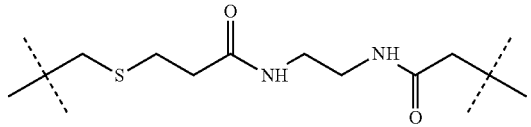 | 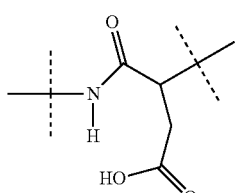<br>and<br>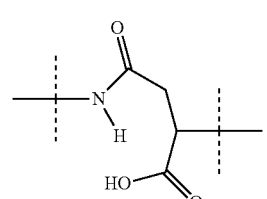<br>See note*** |

TABLE A'-continued
| Subst. | m | L1 | L2 |
|---|---|---|---|
| R³ | 0 | 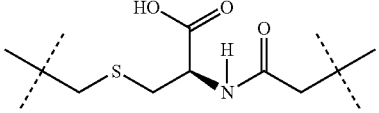 | 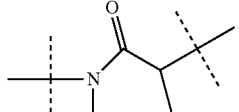<br>and<br>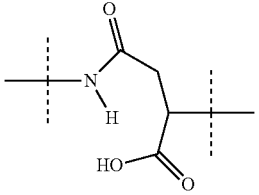<br>See note*** |
| R³ | 0 | 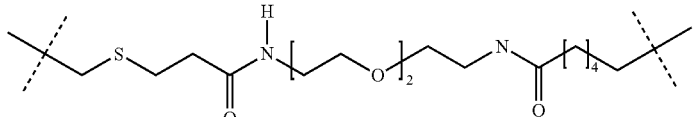 | 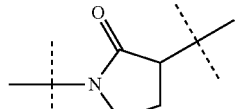<br>See note** |
| R³ | 0 | 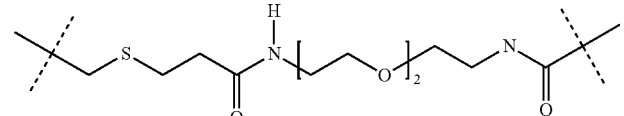 | 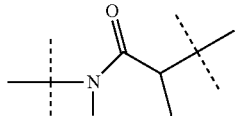<br>and<br><br>See note*** |
| R³ | 0 | 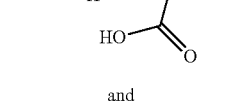 | 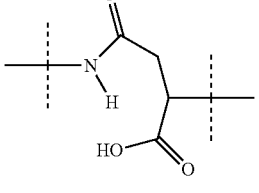<br>and |

TABLE A'-continued
| Subst. | m | L1 | L2 |
|---|---|---|---|
| | | | 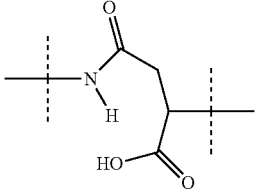<br>See note*** |
| R³ | 0 | 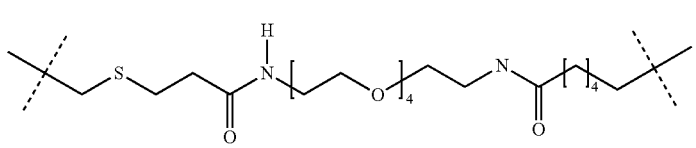 | 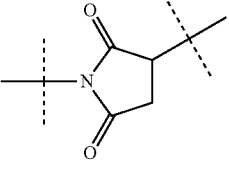<br>See note** |
| R³ | 0 | 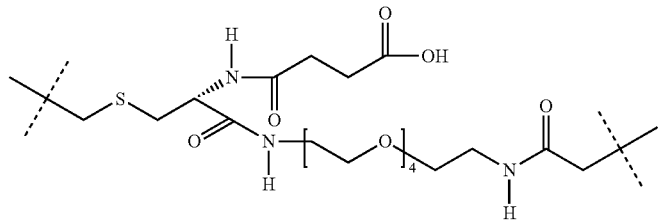 | 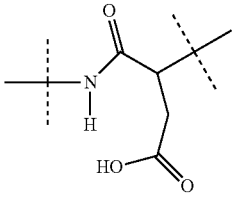<br>and<br>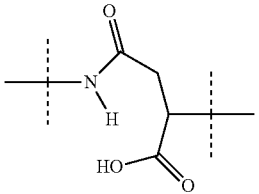<br>See note*** |
| R³ | 0 | 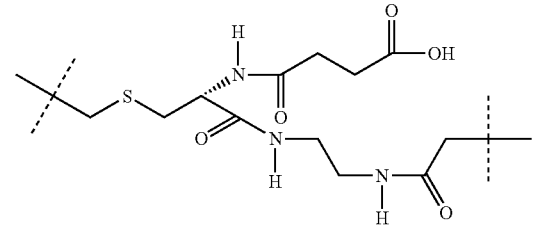 | 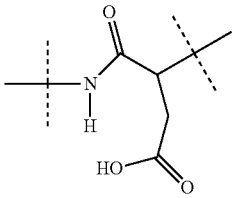<br>and<br>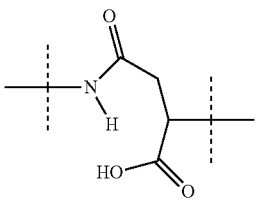<br>See note*** |

TABLE A'-continued
| Subst. | m | L1 | L2 |
|---|---|---|---|
| R³ | 0 | 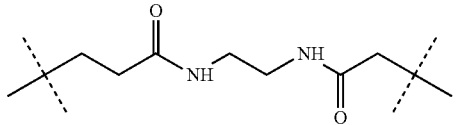 | 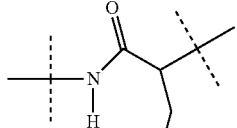<br>and<br>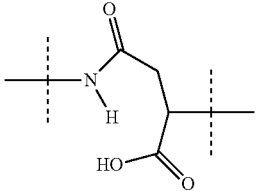<br>See note*** |
| R³ | 0 | 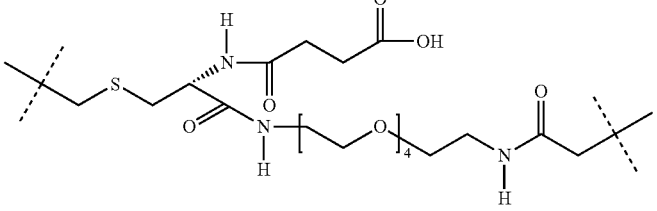 | 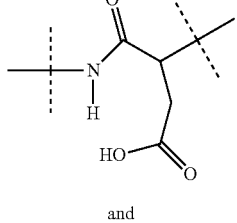<br>and<br>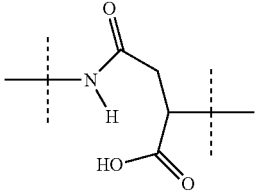<br>See note*** |
| R³ | 0 | 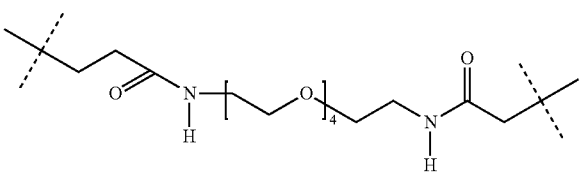 | 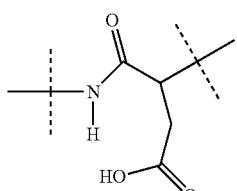<br>and<br>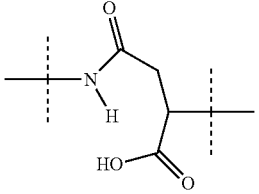<br>See note*** |

TABLE A'-continued

| Subst. | m | L1 | L2 |
|---|---|---|---|
| R³ | 0 | (structure: thioether-CH₂-C(O)-NH-[CH₂CH₂O]₄-CH₂CH₂-NH-C(O)-) | (structure with NH-C(O)-CH(CH₂COOH)-) and (structure with NH-C(O)-CH₂-CH(COOH)-) See note*** |
| R³ | 0 | (structure: S-Cys(COOH)-Ala-Val-C(O)-) | (structure with NH-C(O)-CH(CH₂COOH)-) and (structure with NH-C(O)-CH₂-CH(COOH)-) See note*** |
| R³ | 0 | (structure: S-Cys(COOH)-NH-C(O)-[CH₂CH₂O]₂-CH₂CH₂-NH-C(O)-) | (structure with NH-C(O)-CH(CH₂COOH)-) and (structure with NH-C(O)-CH₂-CH(COOH)-) See note*** |

TABLE A'-continued
| Subst. | m | L1 | L2 |
|---|---|---|---|
| R³ | 0 | (structure) | (structure) and (structure) See note*** |
| R³ | 0 | (structure) | (structure) and (structure) See note*** |
| R³ | 0 | (structure) | —C(=O)—CH₂— |
See note  for Table A.
***When this structure L2 is present, there may simultaneously be a structure L2 of the formula below:
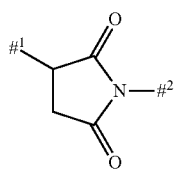

Examples of conjugates having corresponding linkers have the following structures, where X1 represents CH, X2 represents C and X3 represents N and L1 has the meaning given above, L2 and L3 have the same meaning as L1, AK1 represents an anti-CD123 antibody attached via a cysteine residue and n is a number from 1 to 10. With particular preference, AK1 is a human, humanized or chimeric monoclonal anti-CD123 antibody. Particular preference is given here to a chimeric or humanized anti-CD123 antibody derived from an antibody 7G3 or 12F1 originating from mice. Particular preference is given to the antibodies TPP-6013, TPP-5968, TPP-5969 and TPP-5971.

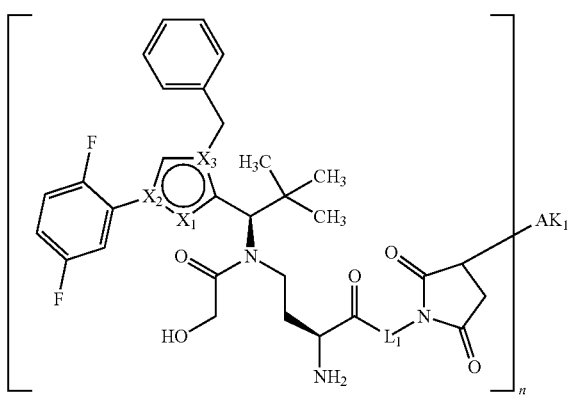

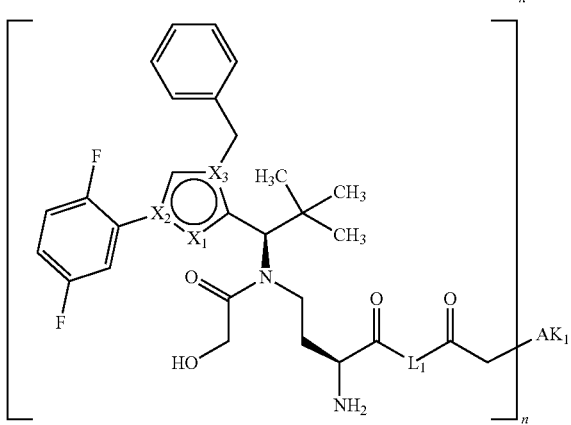

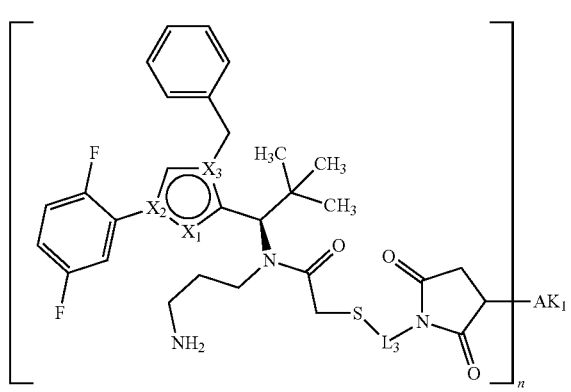

If the linker is attached to a lysine side chain or a lysine residue, it preferably has the formula below:

-§ —(SG)$_x$-L4-CO—§ § where

§ represents the bond to the active compound molecule and

§ § represents the bond to the binder peptide or protein, x represents 0 or 1,

SG represents a cleavable group, preferably a 2-8 oligopeptide, particularly preferably a dipeptide, and L4 represents a single bond or a group —(CO)$_y$-G4-, where y represents 0 or 1, and G4 represents a straight-chain or branched hydrocarbon chain having 1 to 100 carbon atoms from arylene groups and/or straight-chain and/or branched and/or cyclic alkylene groups and which may be interrupted once or more than once by one or more of the groups —O—, —S—, —SO—, SO$_2$, —NH—, —CO—, —NHCO—, —CONH—, —NMe-, —NHNH—, —SO$_2$NHNH—, —CONHNH— and a 5- to 10-membered aromatic or non-aromatic heterocycle having up to 4 heteroatoms selected from the group consisting of N, O and S, —SO— or —SO$_2$— (preferably

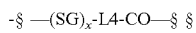
), where the side chains, if present, may be substituted by —NHCONH$_2$, —COOH, —OH, —NH$_2$, NH—CNNH$_2$, sulphonamide, sulphone, sulphoxide or sulphonic acid.

Table B below gives examples of linkers to a lysine residue. The table furthermore gives the preferred coupling point (R$^1$—R$^5$). The first column furthermore states the example numbers in which the corresponding linkers are used.

TABLE B

| lysine linker -§-(SG)$_x$—L4—CO-§§ | | |
|---|---|---|
| Ex. | Subst. | (SG)$_x$—L4 |
| 194, 294 | R$^4$ | 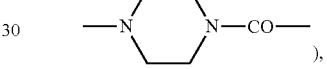 |

Examples of conjugates having corresponding linkers have the following structures, where X1 represents CH, X2 represents C and X3 represents N and L4 has the meaning given above, AK2 represents an antibody attached via a lysine residue and n is a number from 1 to 10. Particularly preferably, AK2 is a human, humanized or chimeric monoclonal anti-CD123 antibody or an antigen-binding fragment thereof. Particular preference is given here to a chimeric or humanized anti-CD123 antibody derived from an antibody 7G3 or 12F1 originating from mice. Particular preference is given to the antibodies TPP-6013, TPP-5968, TPP-5969 and TPP-5971.

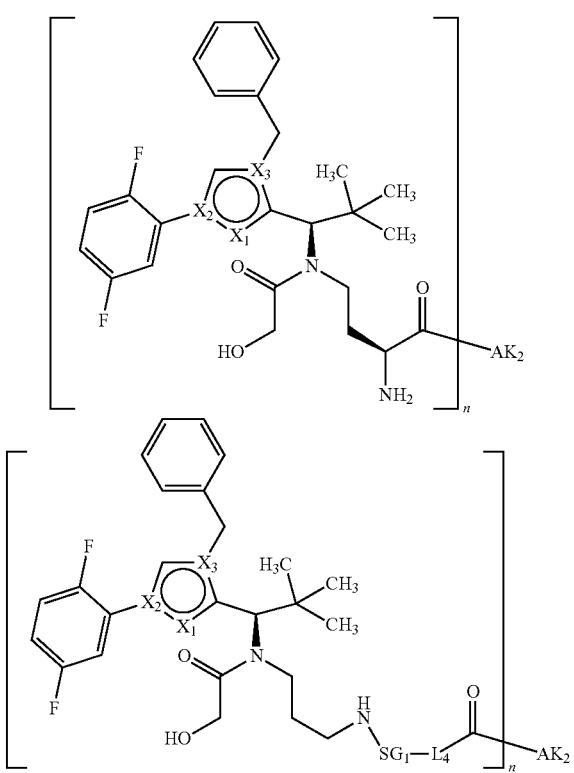

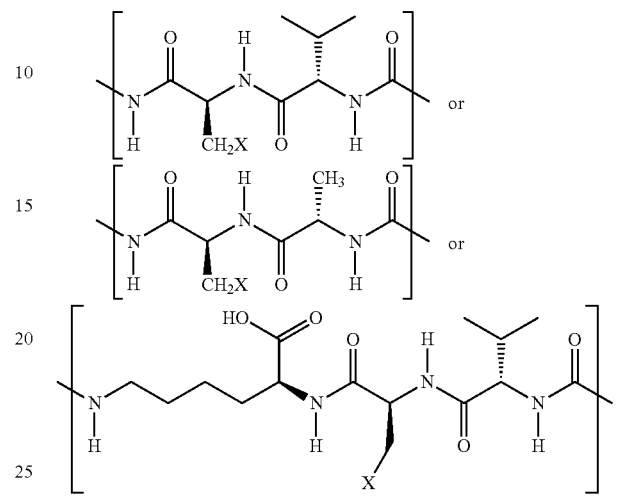

where X represents H or a $C_{1-10}$-alkyl group which may optionally be substituted by —$NHCONH_2$, —COOH, —OH, $NH_2$, —NH—$CNNH_2$ or sulphonic acid.

Preference according to the invention is furthermore given to the basic structure (i), (ii) or (iv), where SG1 or SG represents a group which can be cleaved by a protease and L1 and L2 have the meanings given above. Particular preference is given to the following groups:

-Val-Ala-CONH— (hereby cleavage of the amide bond at the C-terminal amide of alanine)
—NH-Val-Lys-CONH— (cleavage of the amide bond at the C-terminal amide of lysine)
—NH-Val-Cit-CONH— (cleavage of the amide bond at the C-terminal amide of citrulline)
—NH-Phe-Lys-CONH (cleavage of the amide bond at the C-terminal amide of lysine)
—NH-Ala-Lys-CONH— (cleavage of the amide bond at the C-terminal amide of lysine)
—NH-Ala-Cit-CONH— (cleavage of the amide bond at the C-terminal amide of citrulline)

SG1 or SG is particularly preferably

Table C below gives examples of a linker moiety -SG1-L1- or -L1-SG-L1-, where SG1 and SG are groups which can be cleaved by a protease. Table C furthermore states with which group L2 these examples of -SG1-L1- and -L1-SG-L1- are preferably combined, and also the preferred coupling point ($R^1$—$R^5$) and the preferred value for m, thus whether there is a carbonyl group in front of L1 or not (cf. § —(CO)m-L1-L2- § §). These linkers are preferably coupled to a cysteine residue. The L1 group is highlighted in a box. However, these groups L1 can be replaced by one of the groups L1 given for formula § —(CO)m-L1-L2- § § above. If L2 is a succinamide or derived therefrom, this amide may also be fully or partially in the form of the hydrolysed open-chain succinamide, as described above.

TABLE C

| Sub St. | m | —SG1—L1— or —L1—SG—L1— | L2 |
|---|---|---|---|
| $R^1$ | 1 | | |

TABLE C-continued
| Sub St. | m | —SG1—L1— or —L1—SG—L1— | L2 |
|---|---|---|---|
| R¹ | 1 | 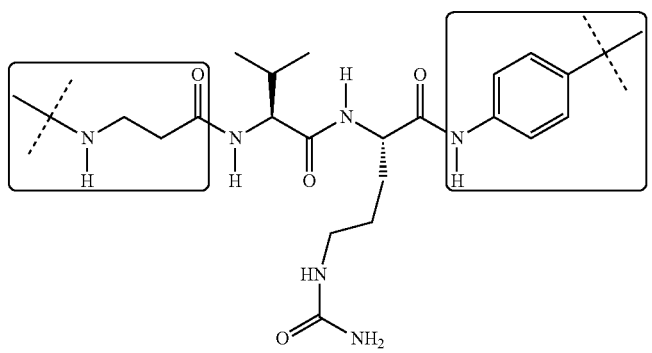 | 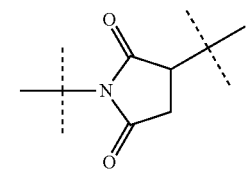 |
| R¹ | 1 | 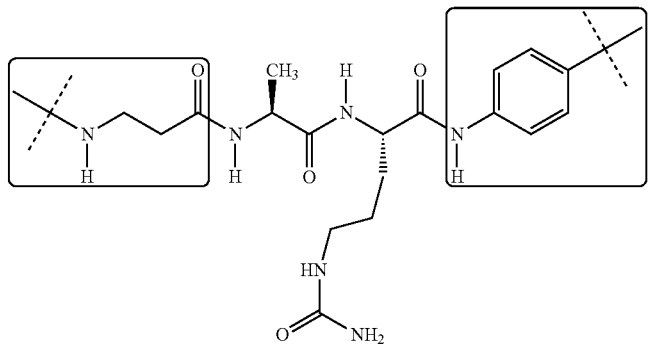 | 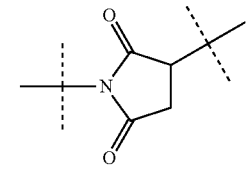 |
| R¹ | 1 | 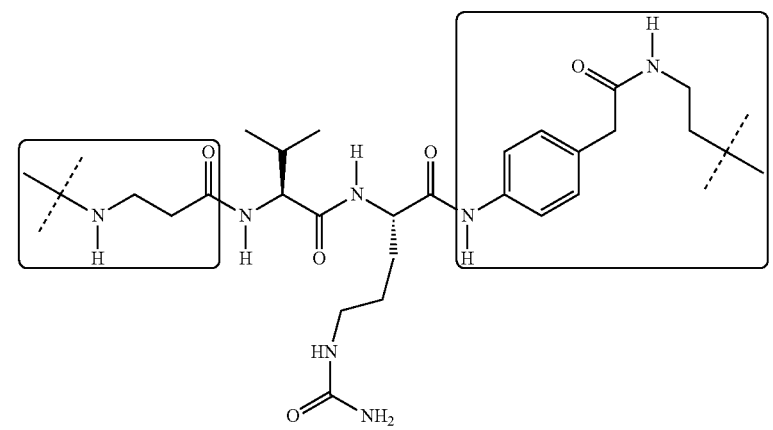 | 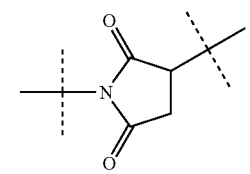 |

TABLE C-continued
| Sub St. | m | —SG1—L1— or —L1—SG—L1— | L2 |
|---|---|---|---|
| R¹ | 1 | 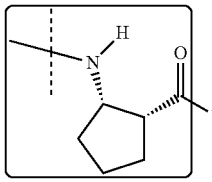 | 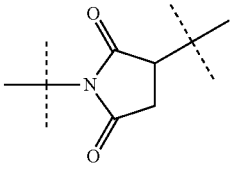 |
| R¹ | 1 | 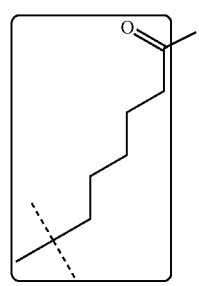 | 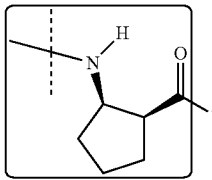 |
| R¹ | 1 | 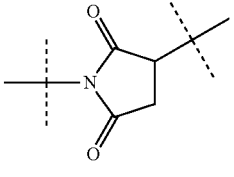 | 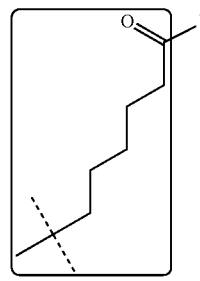 |

TABLE C-continued

| Sub St. | m | —SG1—L1— or —L1—SG—L1— | L2 |
|---|---|---|---|
| R¹ | 1 | (structure: β-Ala–Ala–Cit–PAB-type linker with 4-aminophenylacetamide) | maleimide |
| R¹ | 1 | (structure: β-Ala–Ala–Cit–aniline-CH2-C(O)NH- linker) | maleimide |
| R¹ | 1 | (structure: NH-PEG3-propanoyl–Val–Cit–PAB linker) | maleimide |
| R¹ | 1 | (structure: β-Ala–Val–Lys–PAB-type linker with 4-aminophenylacetamide) | maleimide |

TABLE C-continued
| Sub St. | m | —SG1—L1— or —L1—SG—L1— | L2 |
|---|---|---|---|
| R¹ | 1 | 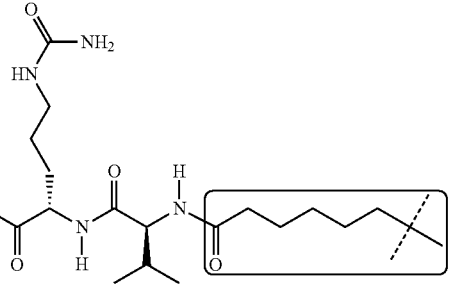 | 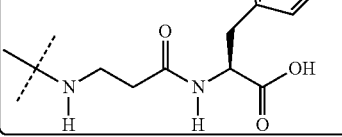 |
| R¹ | 1 | 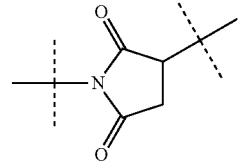 | 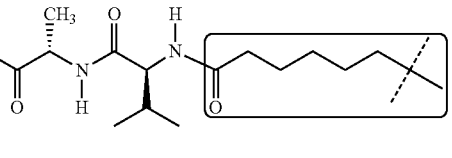 |
| R¹ | 0 | 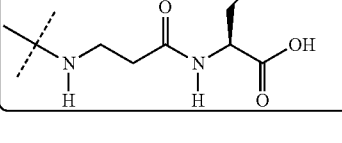 | 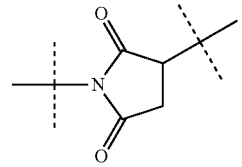 |
| R¹ | 1 | 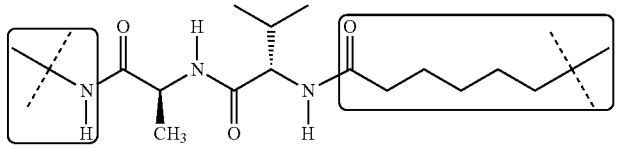 | 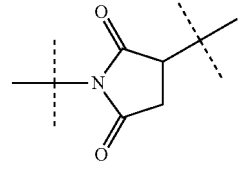 |
| R¹ | 0 | 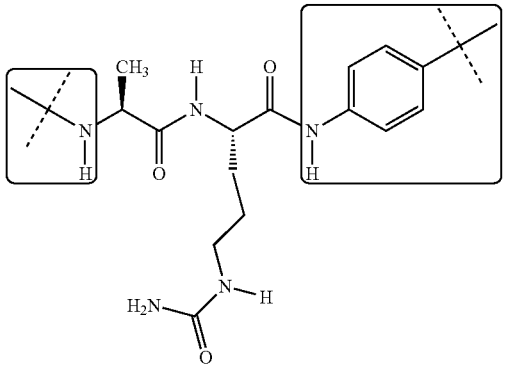 | 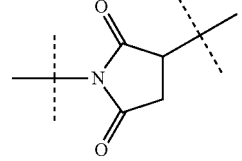 |

TABLE C-continued
| Sub St. | m | —SG1—L1— or —L1—SG—L1— | L2 |
|---|---|---|---|
| R¹ | 0 | 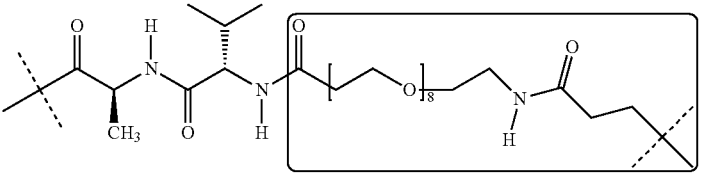 | 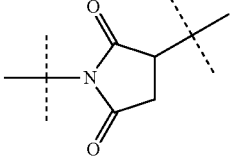 |
| R¹ | 0 | 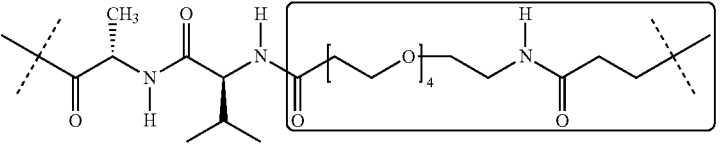 | 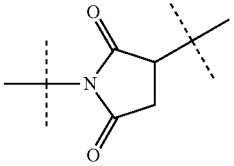 |
| R¹ | 0 |  | 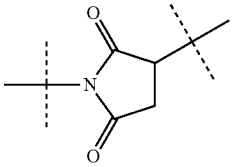 |
| R¹ | 0 | 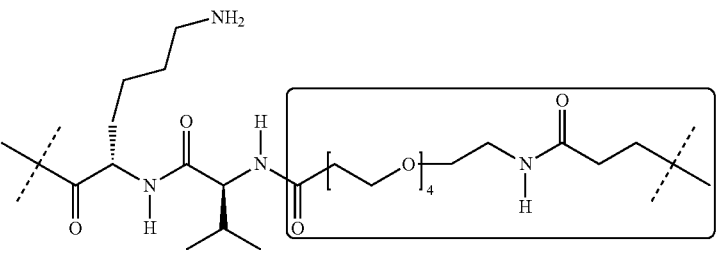 | 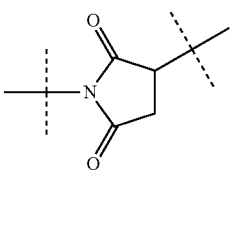 |
| R¹ | 0 | 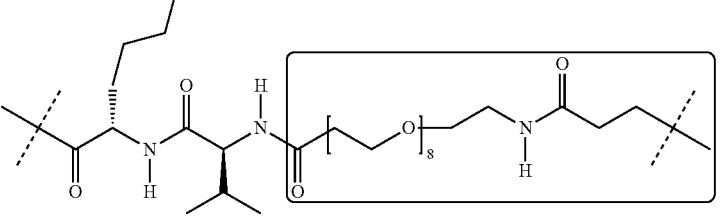 | 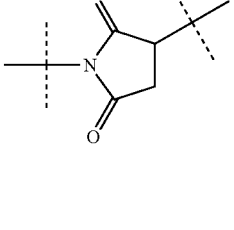 |
| R¹ | 0 | 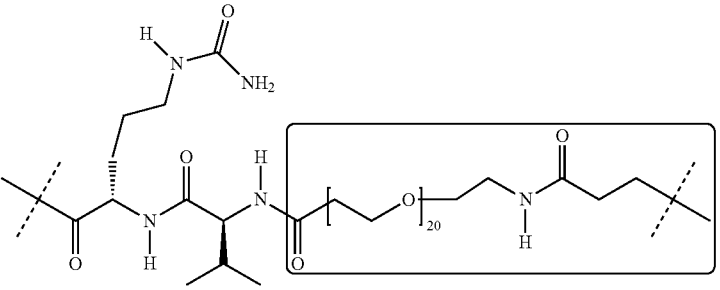 | 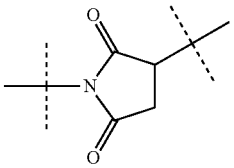 |

TABLE C-continued
| Sub St. | m | —SG1—L1— or —L1—SG—L1— | L2 |
|---|---|---|---|
| R³ | 0 | 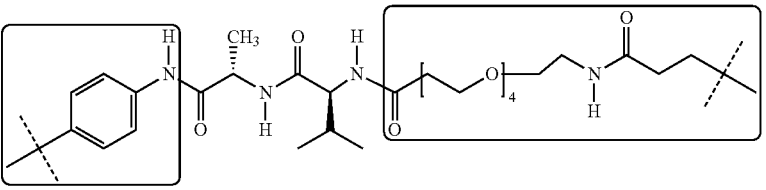 | 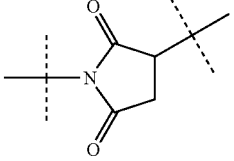 |
| R³ | 0 | 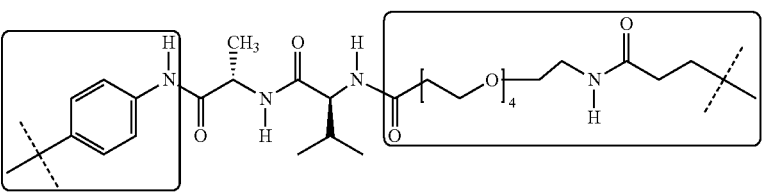 | 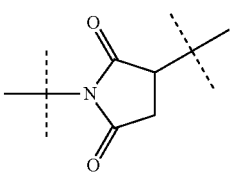 |
| R¹ | 1 | 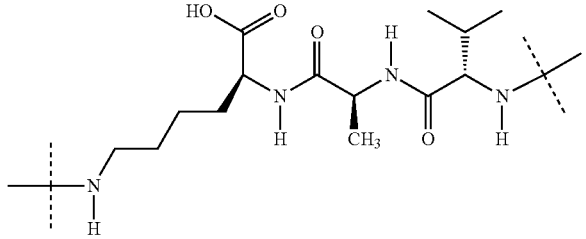 | 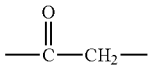 |
| R¹ | 1 | 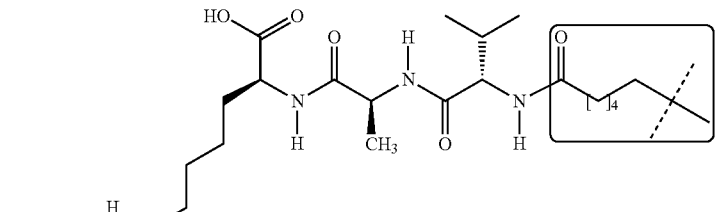 | 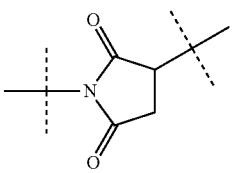 |
| R¹ | 1 | 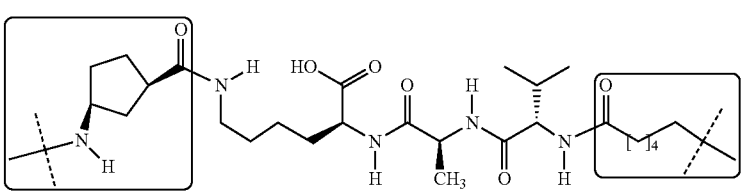 | 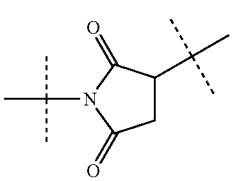 |
| R³ | 0 | 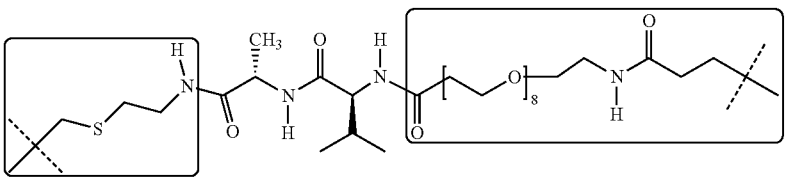 | 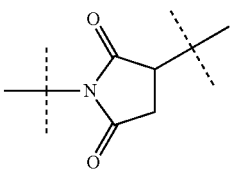 |

US 10,744,205 B2
TABLE C-continued
| Sub St. | m | —SG1—L1— or —L1—SG—L1— | L2 |
|---|---|---|---|
| R¹ | 1 | 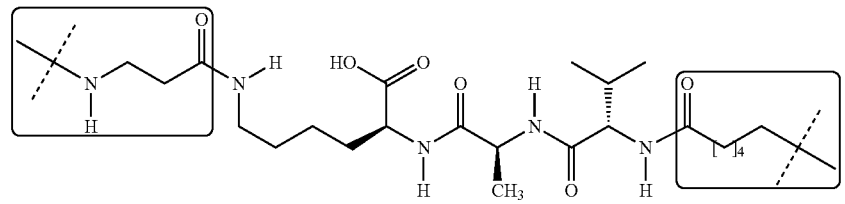 | 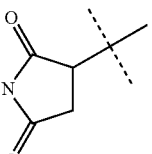 |
| R¹ | 1 | 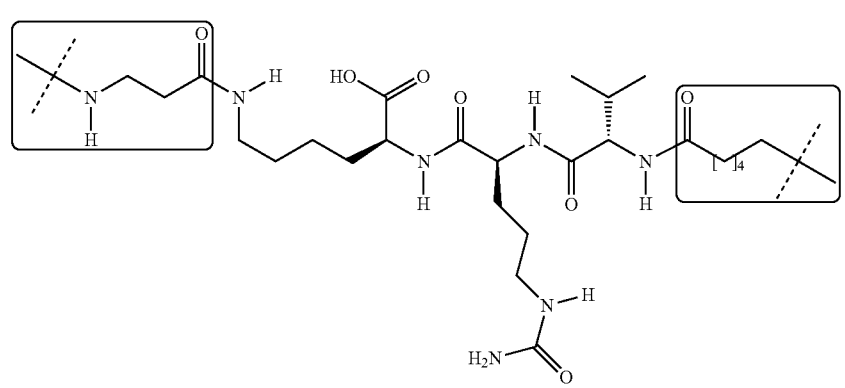 | 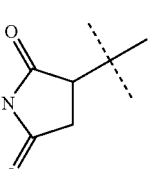 |
| R¹ | 1 | 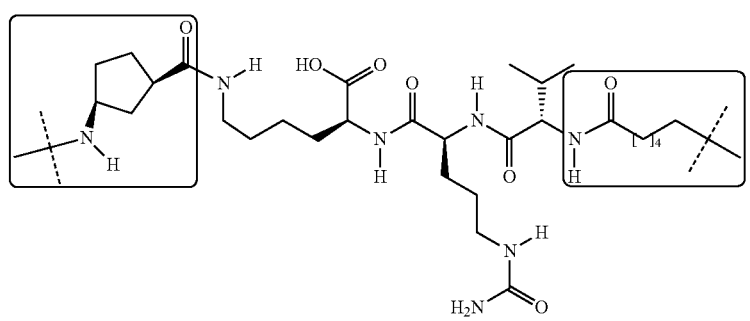 | 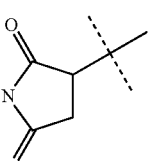 |
| R¹ | 1 | 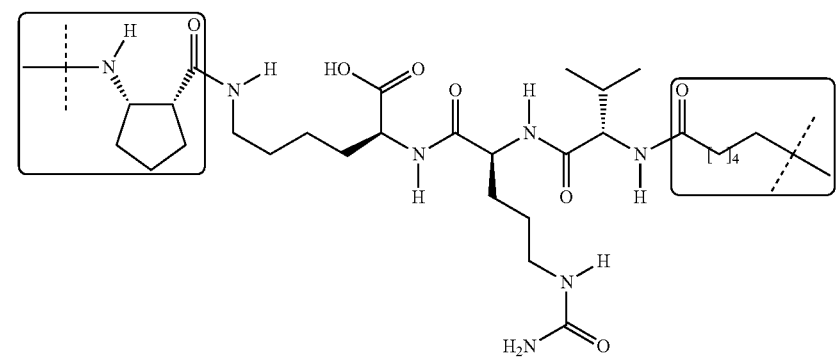 | 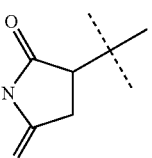 |
| R¹ | 1 | 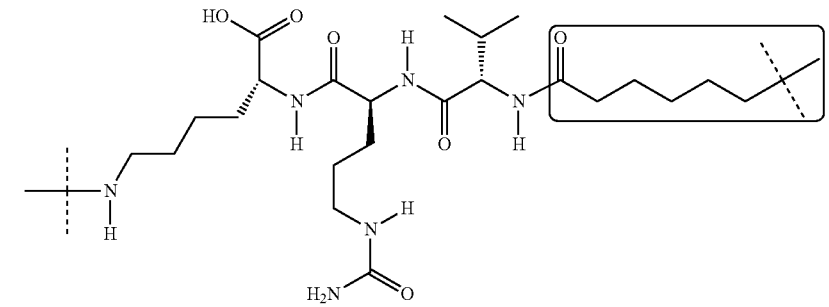 | 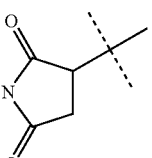 |

TABLE C-continued
| Sub St. | m | —SG1—L1— or —L1—SG—L1— | L2 |
|---|---|---|---|
| R[1] | 1 | 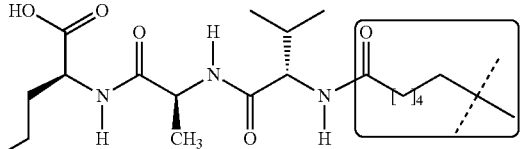 | 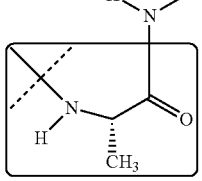 |
| R[1] | 1 | 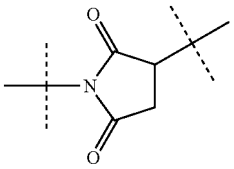 | 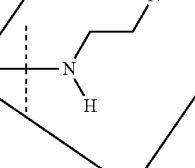 |
| R[1] | 1 | 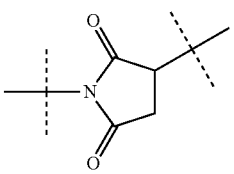 | 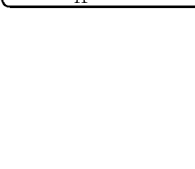 |
| R[1] | 1 | 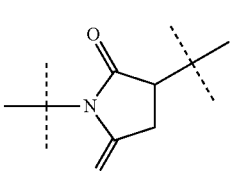 | 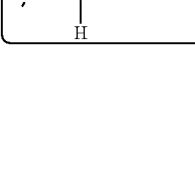 |

TABLE C-continued

| Sub St. | m | —SG1—L1— or —L1—SG—L1— | L2 |
|---|---|---|---|
| $R^1$ | 1 | 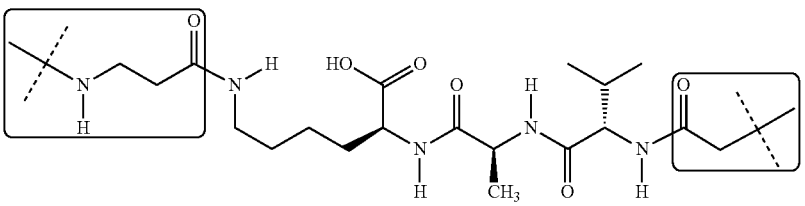 | 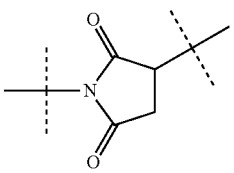 |
| $R^3$ | 0 | 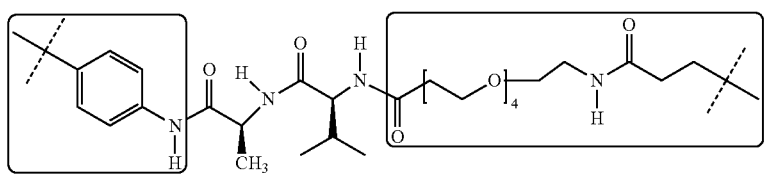 | 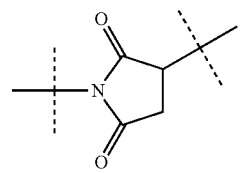 |

Examples of conjugates having basic structure (i) have the following structure, where X1 represents CH, X2 represents C and X3 represents N, L4 has the same meaning as L1, AK1 represents an anti CD-123 antibody attached via a cysteine residue and n is a number from 1 to 10. Particular preference is given here to a chimeric or humanized anti-CD123 antibody derived from an antibody 7G3 or 12F1 originating from mice. Particular preference is given to the antibodies TPP-6013, TPP-5968, TPP-5969 and TPP-5971.

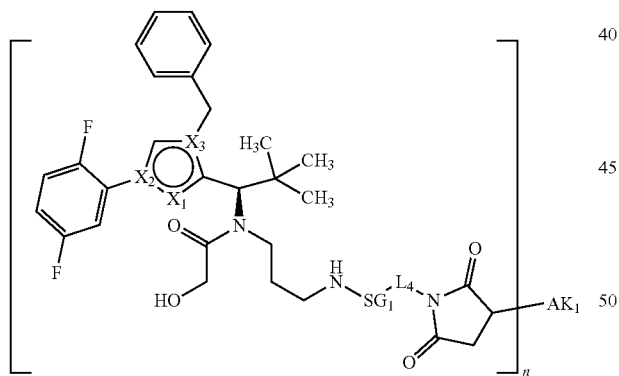

KSP Inhibitor—Linker-Intermediates and Preparation of the Conjugates

The conjugates according to the invention are prepared by initially providing the low-molecular weight KSP inhibitor with a linker. The intermediate obtained in this manner is then reacted with the binder (preferably antibody).

Preferably, for coupling to a cysteine residue, one of the compounds below is reacted with the cysteine-containing binder such as an antibody, which is optionally partially reduced for this purpose:

127
-continued
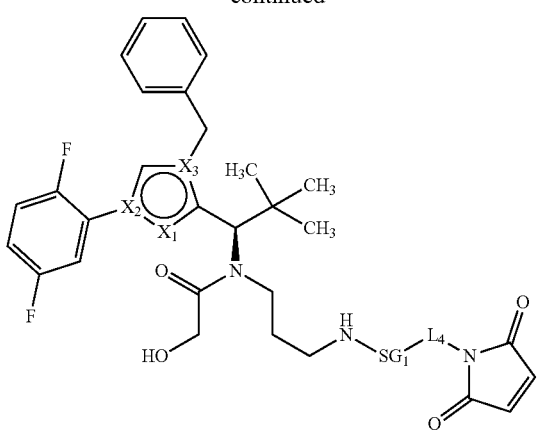
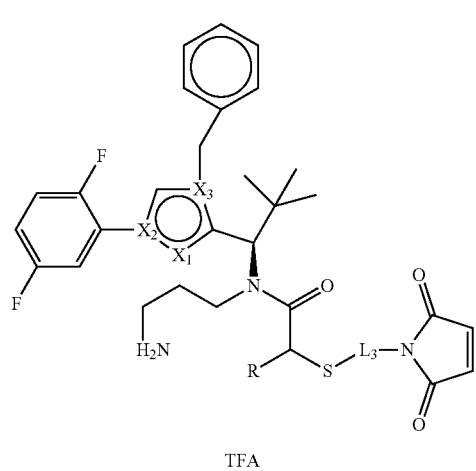
TFA
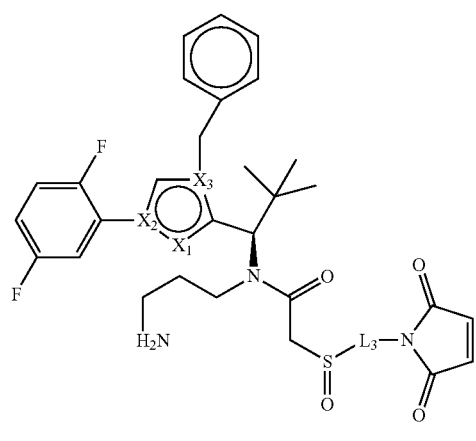
TFA
128
-continued
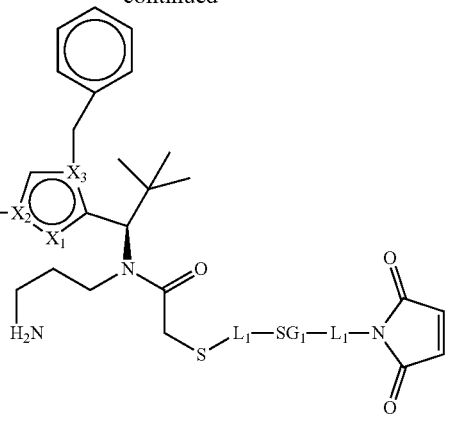
TFA
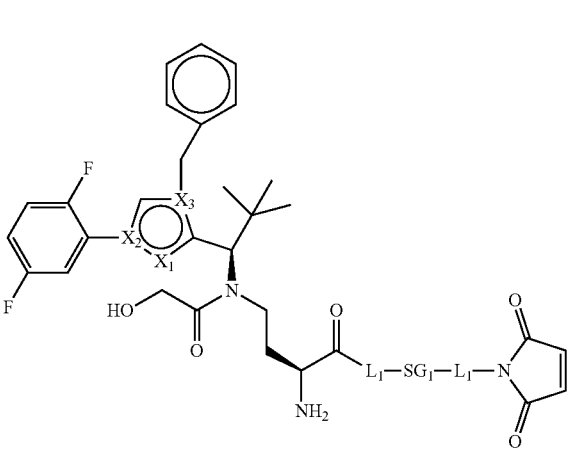
TFA -continued

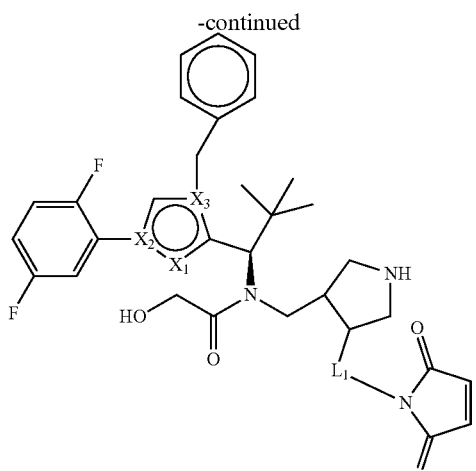

TFA

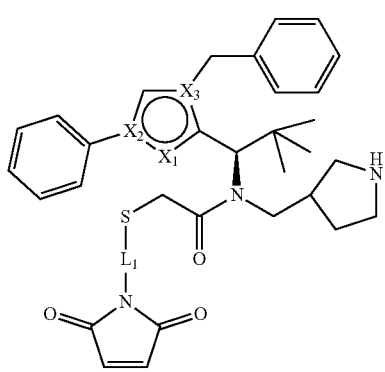

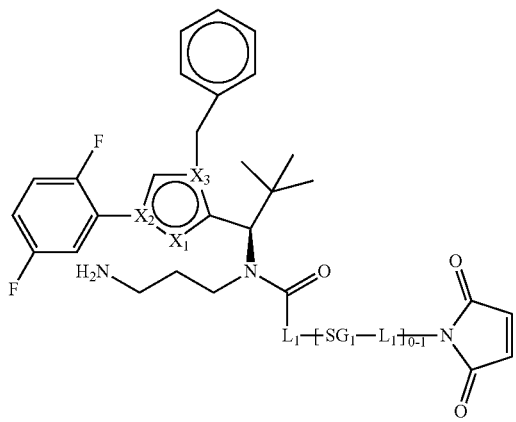

TFA where R represents —H or —COOH,
where K represents straight-chain or branched $C_1$-$C_6$ alkyl which is optionally substituted by $C_1$-$C_6$-alkoxy or —OH, and where X1 represents CH, X2 represents C and X3 represents N, SG1, L1, L2, L3 and L4 have the same meaning as described above.

In each of the above compounds and in the compounds below, the tert-butyl group may be replaced by cyclohexyl.

The compound may be employed, for example, in the form of its trifluoroacetic acid salt. For the reaction with the binder such as, for example, the antibody, the compound is preferably used in a 2- to 12-fold molar excess with respect to the binder.

Preferably, for coupling to a lysine residue, one of the compounds below is reacted with the lysine-containing binder such as an antibody:

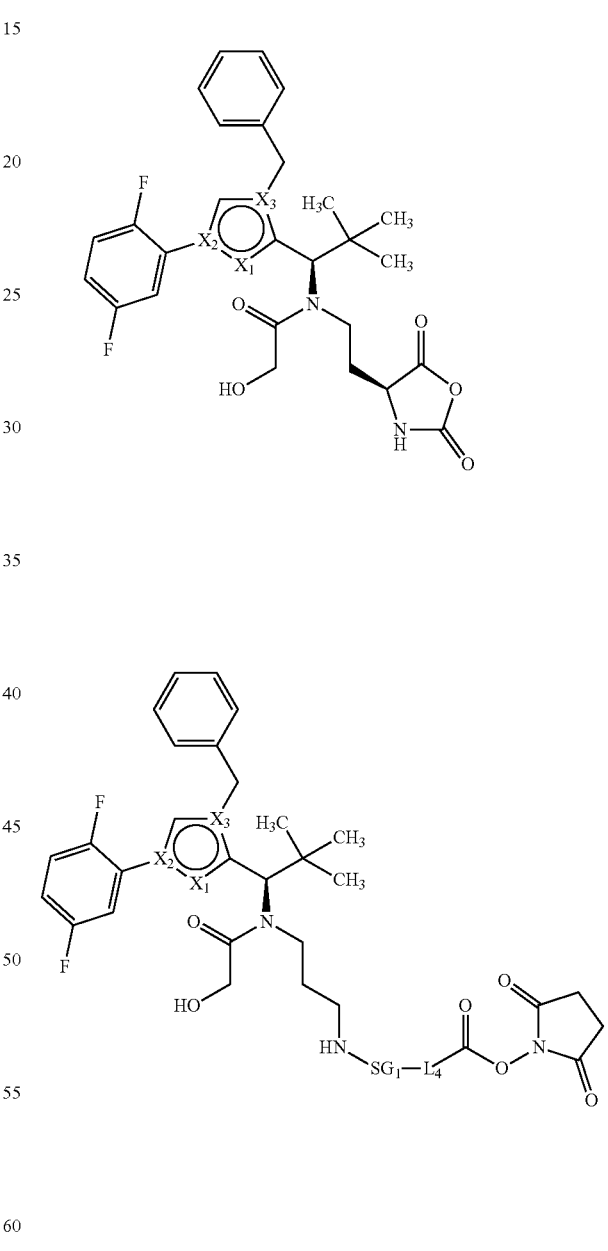

where X1 represents CH, X2 represents C and X3 represents N and L4 has the same meaning as L1 and L1 has the same meaning as described above.

For an intermediate coupling to a cysteine residue, the reactions can be illustrated as follows:

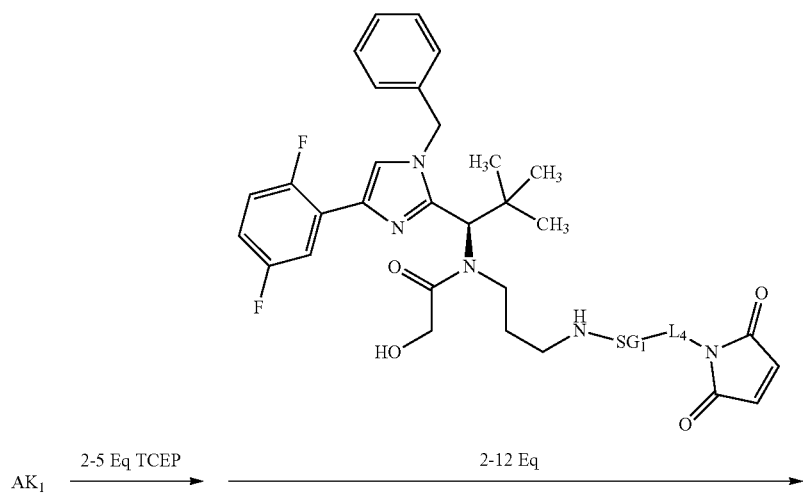
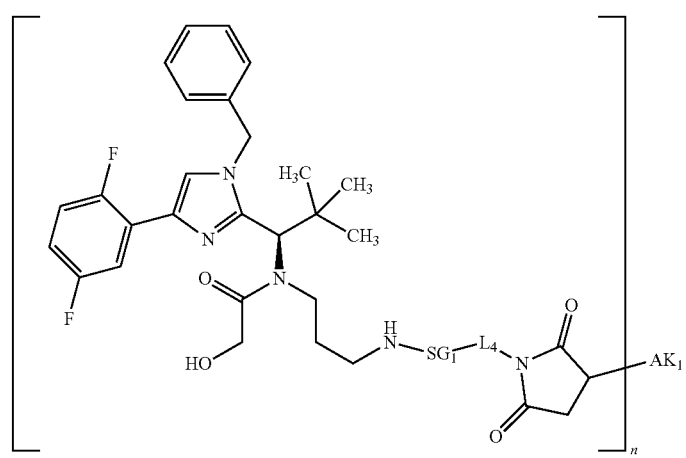
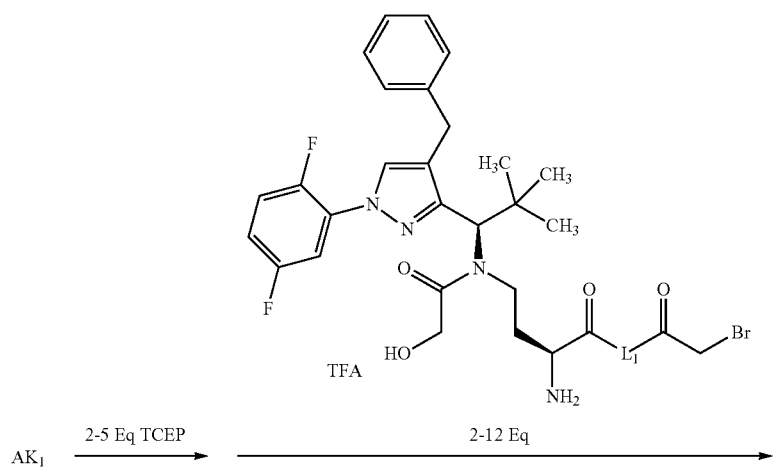

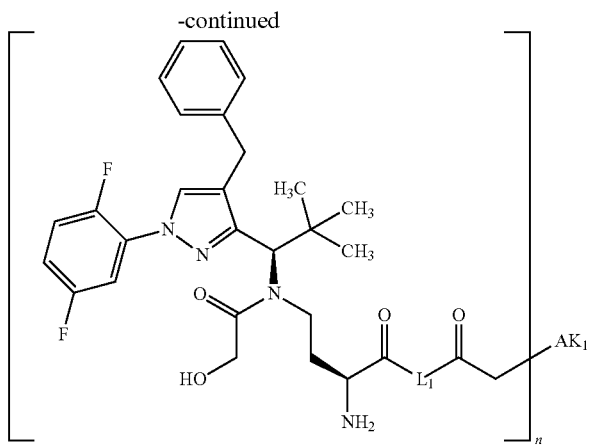
The other intermediates and other antibodies can be reacted correspondingly.
For an intermediate coupling to a lysine residue, the reaction can be illustrated as follows:
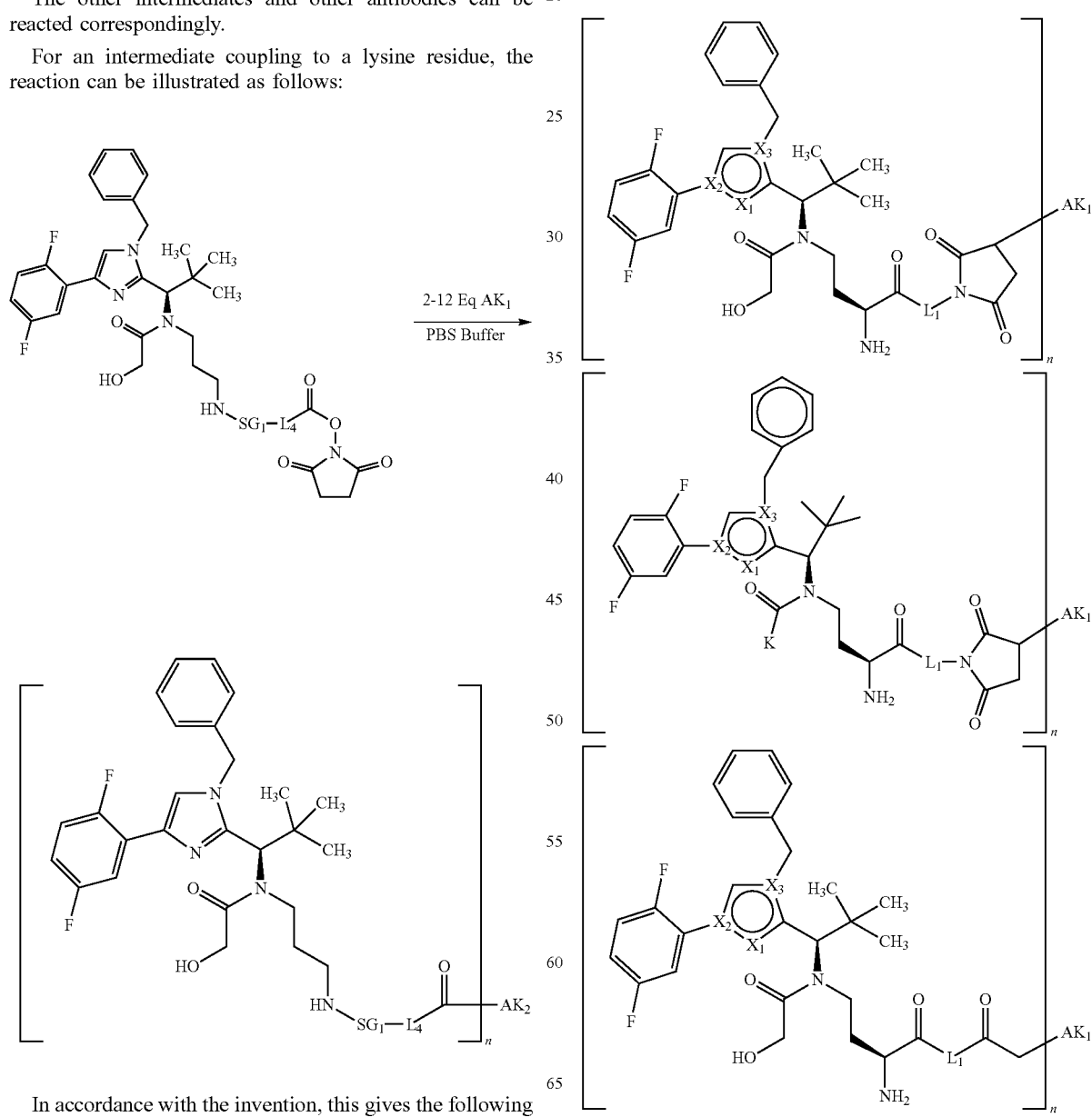
In accordance with the invention, this gives the following conjugates:

135
-continued
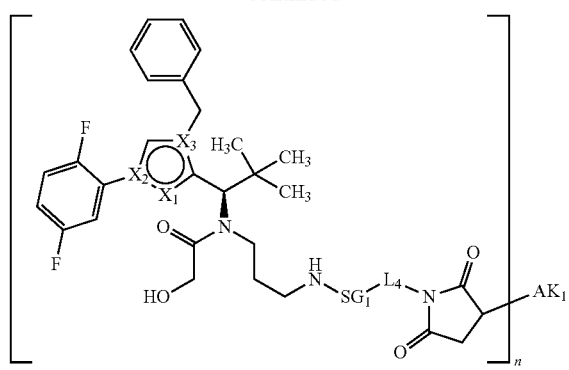
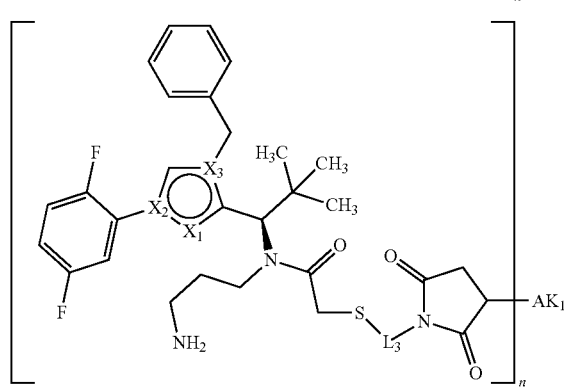
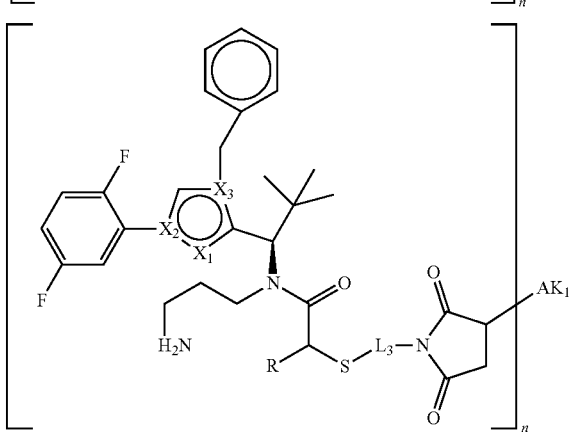
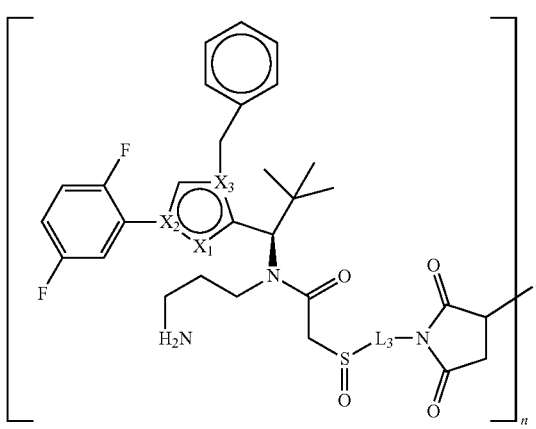
136
-continued
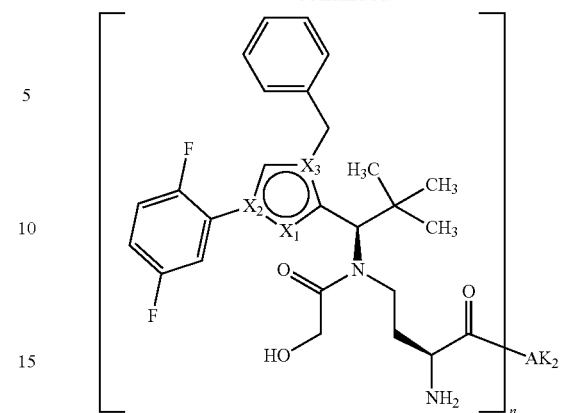
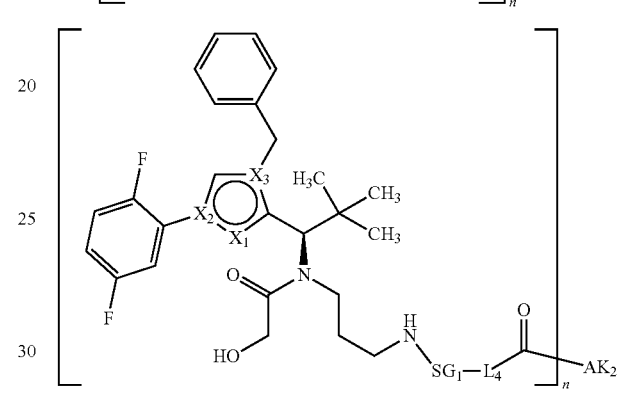
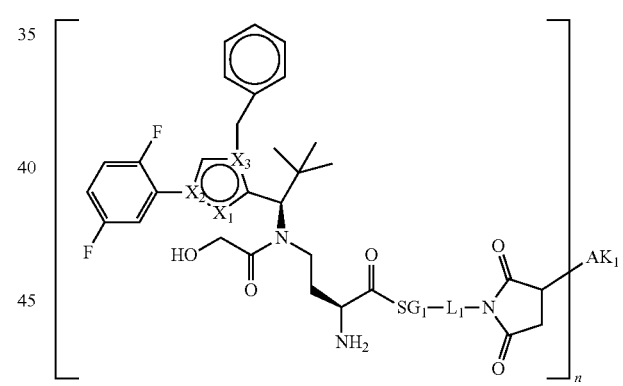
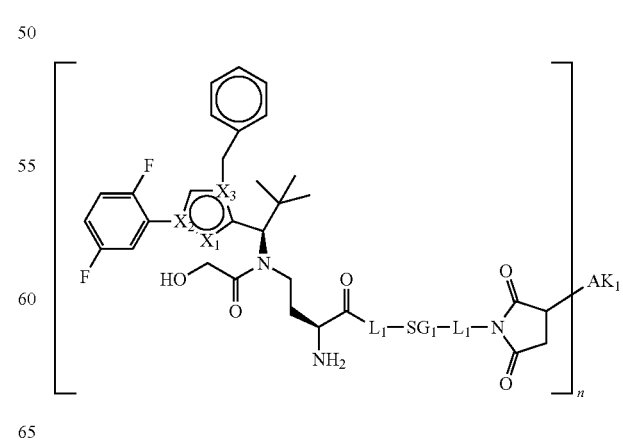

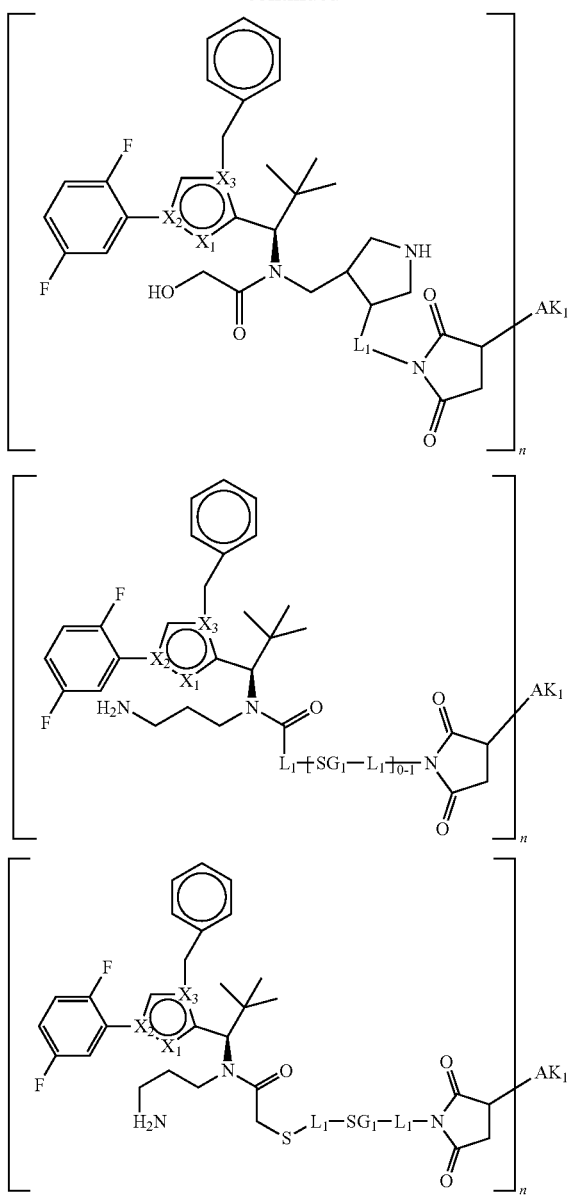

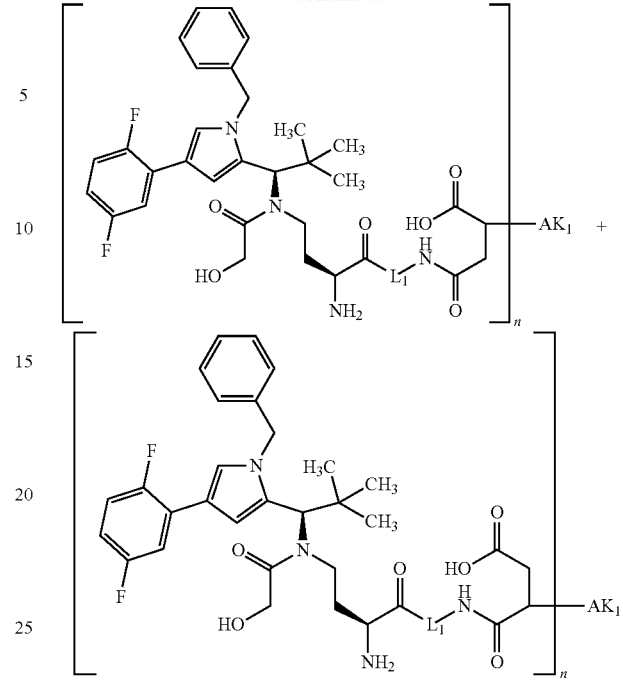

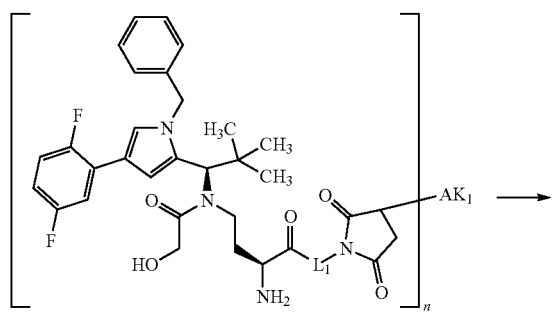

Depending on the linker, succinimide-linked ADCs may, after conjugation, be converted into the open-chain succinamides, which have an advantageous stability profile.

This reaction (ring opening) can be carried out at pH 7.5 to 9, preferably at pH 8, at a temperature of from 25° C. to 37° C., for example by stirring. The preferred stirring time is 8 to 30 hours.

In the above formulae, X1 represents CH, X2 represents C and X3 represents N, SG1 and L1 have the same meaning as described above and L2, L3 and L4 have the same meaning as L1; and R and K have the same meaning as described above. AK1 is an anti-CD123 antibody coupled via a cysteine residue, and AK2 is an anti-CD123 antibody coupled via a lysine residue. With particular preference, AK1 and AK2 are chimeric or humanized anti-CD123 antibodies derived from an antibody 7G3 or 12F1 originating from mice. Particular preference is given to the antibodies TPP-6013, TPP-5968, TPP-5969 and TPP-5971.

Anti-CD123 Antibodies

The literature also discloses various options of covalent coupling (conjugation) of organic molecules to antibodies. Preference according to the invention is given to the conjugation of the toxophores to the antibody via one or more sulphur atoms of cysteine residues of the antibody and/or via one or more NH groups of lysine residues of the antibody. However, it is also possible to bind the toxophor to the antibody via free carboxyl groups or via sugar residues of the antibody.

The antibody can be attached to the linker via a bond. Attachment of the antibody can be via a heteroatom of the binder. Heteroatoms according to the invention of the antibody which can be used for attachment are sulphur (in one embodiment via a sulphhydryl group of the antibody), oxygen (according to the invention by means of a carboxyl or hydroxyl group of the antibody) and nitrogen (in one embodiment via a primary or secondary amine group or amide group of the antibody). These heteroatoms may be present in the natural antibody or are introduced by chemical methods or methods of molecular biology. According to the invention, the attachment of the antibody to the toxophor has only a minor effect on the binding activity of the antibody with respect to the target molecule. In a preferred embodiment, the attachment has no effect on the binding activity of the antibody with respect to the target molecule.

In accordance with the present invention, the term "antibody" is to be understood in its broadest meaning and comprises immunoglobulin molecules, for example intact or modified monoclonal antibodies, polyclonal antibodies or multispecific antibodies (e.g. bispecific antibodies). An immunoglobulin molecule preferably comprises a molecule having four polypeptide chains, two heavy chains (H chains) and two light chains (L chains) which are typically linked by disulphide bridges. Each heavy chain comprises a variable domain of the heavy chain (abbreviated VH) and a constant domain of the heavy chain. The constant domain of the heavy chain may, for example, comprise three domains CH1, CH2 and CH3. Each light chain comprises a variable domain (abbreviated VL) and a constant domain. The constant domain of the light chain comprises a domain (abbreviated CL). The VH and VL domains may be subdivided further into regions having hypervariability, also referred to as complementarity determining regions (abbreviated CDR) and regions having low sequence variability (framework region, abbreviated FR). Typically, each VH and VL region is composed of three CDRs and up to four FRs. For example from the amino terminus to the carboxy terminus in the following order: FR1, CDR1, FR2, CDR2, FR3, CDR3, FR4. An antibody may be obtained from any suitable species, e.g. rabbit, llama, camel, mouse or rat. In one embodiment, the antibody is of human or murine origin. An antibody may, for example, be human, humanized or chimeric.

The term "monoclonal" antibody refers to antibodies obtained from a population of substantially homogeneous antibodies, i.e. individual antibodies of the population are identical except for naturally occurring mutations, of which there may be a small number. Monoclonal antibodies recognize a single antigenic binding site with high specificity. The term monoclonal antibody does not refer to a particular preparation process.

The term "intact" antibody refers to antibodies comprising both an antigen-binding domain and the constant domain of the light and heavy chain. The constant domain may be a naturally occurring domain or a variant thereof having a number of modified amino acid positions.

The term "modified intact" antibody refers to intact antibodies fused via their amino terminus or carboxy terminus by means of a covalent bond (e.g. a peptide bond) with a further polypeptide or protein not originating from an antibody. Furthermore, antibodies may be modified such that, at defined positions, reactive cysteines are introduced to facilitate coupling to a toxophor (see Junutula et al. Nat Biotechnol. 2008, 26(8):925-32).

The term "human" antibody refers to antibodies which can be obtained from a human or which are synthetic human antibodies. A "synthetic" human antibody is an antibody which is partially or entirely obtainable in silico from synthetic sequences based on the analysis of human antibody sequences. A human antibody can be encoded, for example, by a nucleic acid isolated from a library of antibody sequences of human origin. An example of such an antibody can be found in Siderlind et al., Nature Biotech. 2000, 18:853-856.

The term "humanized" or "chimeric" antibody describes antibodies consisting of a non-human and a human portion of the sequence. In these antibodies, part of the sequences of the human immunoglobulin (recipient) is replaced by sequence portions of a non-human immunoglobulin (donor). In many cases, the donor is a murine immunoglobulin. In the case of humanized antibodies, amino acids of the CDR of the recipient are replaced by amino acids of the donor. Sometimes, amino acids of the framework, too, are replaced by corresponding amino acids of the donor. In some cases the humanized antibody contains amino acids present neither in the recipient nor in the donor, which were introduced during the optimization of the antibody. In the case of chimeric antibodies, the variable domains of the donor immunoglobulin are fused with the constant regions of a human antibody.

The term complementarity determining region (CDR) as used herein refers to those amino acids of a variable antibody domain which are required for binding to the antigen. Typically, each variable region has three CDR regions referred to as CDR1, CDR2 and CDR3. Each CDR region may embrace amino acids according to the definition of Kabat and/or amino acids of a hypervariable loop defined according to Chotia. The definition according to Kabat comprises, for example, the region from about amino acid position 24-34 (CDR1), 50-56 (CDR2) and 89-97 (CDR3) of the variable light chain and 31-35 (CDR1), 50-65 (CDR2) and 95-102 (CDR3) of the variable heavy chain (Kabat et al., Sequences of Proteins of Immunological Interest, 5th Ed. Public Health Service, National Institutes of Health, Bethesda, Md. (1991)). The definition according to Chotia comprises, for example, the region from about amino acid position 26-32 (CDR1), 50-52 (CDR2) and 91-96 (CDR3) of the variable light chain and 26-32 (CDR1), 53-55 (CDR2) and 96-101 (CDR3) of the variable heavy chain (Chothia and Lesk; J Mol Biol 196: 901-917 (1987)). In some cases, a CDR may comprise amino acids from a CDR region defined according to Kabat and Chotia.

Depending on the amino acid sequence of the constant domain of the heavy chain, antibodies may be categorized into different classes. There are five main classes of intact antibodies: IgA, IgD, IgE, IgG and IgM, and several of these can be divided into further subclasses. (Isotypes), e.g. IgG1, IgG2, IgG3, IgG4, IgA1 and IgA2. The constant domains of the heavy chain, which correspond to the different classes, are referred to as [alpha/α], [delta/δ], [epsilon/ε], [gamma/γ] and [my/μ]. Both the three-dimensional structure and the subunit structure of antibodies are known.

The term "functional fragment" or "antigen-binding antibody fragment" of an antibody/immunoglobulin is defined as a fragment of an antibody/immunoglobulin (e.g. the variable domains of an IgG) which still comprise the antigen binding domains of the antibody/immunoglobulin. The "antigen binding domain" of an antibody typically comprises one or more hypervariable regions of an antibody, for example the CDR, CDR2 and/or CDR3 region. However, the "framework" or "skeleton" region of an antibody may also play a role during binding of the antibody to the antigen. The framework region forms the skeleton of the CDRs. Preferably, the antigen binding domain comprises at least amino acids 4 to 103 of the variable light chain and amino acids 5 to 109 of the variable heavy chain, more preferably amino acids 3 to 107 of the variable light chain and 4 to 111 of the variable heavy chain, particularly preferably the complete variable light and heavy chains, i.e. amino acids 1-109 of the VL and 1 to 113 of the VH (numbering according to WO97/08320).

"Functional fragments" or "antigen-binding antibody fragments" of the invention encompass, non-conclusively, Fab, Fab', F(ab')$_2$ and Fv fragments, diabodies, Single Domain Antibodies (DAbs), linear antibodies, individual chains of antibodies (single-chain Fv, abbreviated to scFv);

and multispecific antibodies, such as bi and tri-specific antibodies, for example, formed from antibody fragments C. A. K Borrebaeck, editor (1995) Antibody Engineering (Breakthroughs in Molecular Biology), Oxford University Press; R. Kontermann & S. Duebel, editors (2001) Antibody Engineering (Springer Laboratory Manual), Springer Verlag. Antibodies other than "multispecific" or "multifunctional" antibodies are those having identical binding sites. Multispecific antibodies may be specific for different epitopes of an antigen or may be specific for epitopes of more than one antigen (see, for example, WO 93/17715; WO 92/08802; WO 91/00360; WO 92/05793; Tutt, et al., 1991, J. Immunol. 147:60 69; U.S. Pat. Nos. 4,474,893; 4,714,681; 4,925,648; 5,573,920; 5,601,819; or Kostelny et al., 1992, J. Immunol. 148: 1547 1553). An F(ab')$_2$ or Fab molecule may be constructed such that the number of intermolecular disulphide interactions occurring between the Ch1 and the CL domains can be reduced or else completely prevented.

"Epitopes" refer to protein determinants capable of binding specifically to an immunoglobulin or T cell receptors. Epitopic determinants usually consist of chemically active surface groups of molecules such as amino acids or sugar side chains or combinations thereof, and usually have specific 3-dimensional structural properties and also specific charge properties.

"Functional fragments" or "antigen-binding antibody fragments" may be fused with another polypeptide or protein, not originating from an antibody, via the amino terminus or carboxyl terminus thereof, by means of a covalent bond (e.g. a peptide linkage). Furthermore, antibodies and antigen-binding fragments may be modified by introducing reactive cysteines at defined locations, in order to facilitate coupling to a toxophore (see Junutula et al. Nat Biotechnol. 2008 August; 26(8):925-32).

Polyclonal antibodies can be prepared by methods known to a person of ordinary skill in the art. Monoclonal antibodies may be prepared by methods known to a person of ordinary skill in the art (Köhler and Milstein, Nature, 256, 495-497, 1975). Human and humanized monoclonal antibodies may be prepared by methods known to a person of ordinary skill in the art (Olsson et al., Meth Enzymol. 92, 3-16 or Cabilly et al U.S. Pat. No. 4,816,567 or Boss et al U.S. Pat. No. 4,816,397).

A person of ordinary skill in the art is aware of diverse methods for preparing human antibodies and fragments thereof, such as, for example, by means of transgenic mice (N Lonberg and D Huszar, Int Rev Immunol. 1995; 13(1): 65-93) or phage display technologies (Clackson et al., Nature. 1991 Aug. 15; 352(6336):624-8). Antibodies of the invention may be obtained from recombinant antibody libraries consisting for example of the amino acid sequences of a multiplicity of antibodies compiled from a large number of healthy volunteers. Antibodies may also be produced by means of known recombinant DNA technologies. The nucleic acid sequence of an antibody can be obtained by routine sequencing or is available from publically accessible databases.

An "isolated" antibody or binder has been purified to remove other constituents of the cell. Contaminating constituents of a cell which may interfere with a diagnostic or therapeutic use are, for example, enzymes, hormones, or other peptidic or non-peptidic constituents of a cell. A preferred antibody or binder is one which has been purified to an extent of more than 95% by weight, relative to the antibody or binder (determined for example by Lowry method, UV-Vis spectroscopy or by SDS capillary gel electrophoresis). Moreover an antibody which has been purified to such an extent that it is possible to determine at least 15 amino acids of the amino terminus or of an internal amino acid sequence, or which has been purified to homogeneity, the homogeneity being determined by SDS-PAGE under reducing or non-reducing conditions (detection may be determined by means of Coomassie Blau staining or preferably by silver coloration). However, an antibody is normally prepared by one or more purification steps.

The term "specific binding" or "binds specifically" refers to an antibody or binder which binds to a predetermined antigen/target molecule. Specific binding of an antibody or binder typically describes an antibody or binder having an affinity of at least $10^{-7}$ M (as Kd value; i.e. preferably those with Kd values smaller than $10^{-7}$ M), with the antibody or binder having an at least two times higher affinity for the predetermined antigen/target molecule than for a non-specific antigen/target molecule (e.g. bovine serum albumin, or casein) which is not the predetermined antigen/target molecule or a closely related antigen/target molecule. The antibodies preferably have an affinity of at least $10^{-7}$ M (as Kd value; in other words preferably those with smaller Kd values than $10^{-7}$ M), preferably of at least $10^{-8}$ M, more preferably in the range from $10^{-9}$ M to $10^{-11}$ M. The Kd values may be determined, for example, by means of surface plasmon resonance spectroscopy.

The antibody-drug conjugates of the invention likewise exhibit affinities in these ranges. The affinity is preferably not substantially affected by the conjugation of the drugs (in general, the affinity is reduced by less than one order of magnitude, in other words, for example, at most from $10^{-8}$ M to $10^{-7}$ M).

The antibodies used in accordance with the invention are also notable preferably for a high selectivity. A high selectivity exists when the antibody of the invention exhibits an affinity for the target protein which is better by a factor of at least 2, preferably by a factor of 5 or more preferably by a factor of 10, than for an independent other antigen, e.g. human serum albumin (the affinity may be determined, for example, by means of surface plasmon resonance spectroscopy).

Furthermore, the antibodies of the invention that are used are preferably cross-reactive. In order to be able to facilitate and better interpret preclinical studies, for example toxicological or activity studies (e.g. in xenograft mice), it is advantageous if the antibody used in accordance with the invention not only binds the human target protein but also binds the species target protein in the species used for the studies. In one embodiment the antibody used in accordance with the invention, in addition to the human target protein, is cross-reactive to the target protein of at least one further species. For toxicological and activity studies it is preferred to use species of the families of rodents, dogs and non-human primates. Preferred rodent species are mouse and rat. Preferred non-human primates are rhesus monkeys, chimpanzees and long-tailed macaques.

In one embodiment the antibody used in accordance with the invention, in addition to the human target protein, is cross-reactive to the target protein of at least one further species selected from the group of species consisting of mouse, rat and long-tailed macaque (*Macaca fascicularis*). Especially preferred are antibodies used in accordance with the invention which in addition to the human target protein are at least cross-reactive to the mouse target protein. Preference is given to cross-reactive antibodies whose affinity for the target protein of the further non-human species differs by a factor of not more than 50, more particularly by a factor of not more than ten, from the affinity for the human target protein.

Antibodies Directed Against a Cancer Target Molecule

The target molecule towards which the binder, for example an antibody or an antigen-binding fragment thereof, is directed is preferably a cancer target molecule. The term "cancer target molecule" describes a target molecule which is more abundantly present on one or more cancer cell species than on non-cancer cells of the same tissue type. Preferably, the cancer target molecule is selectively present on one or more cancer cell species compared with non-cancer cells of the same tissue type, where selectively describes an at least two-fold enrichment on cancer cells compared to non-cancer cells of the same tissue type (a "selective cancer target molecule"). The use of cancer target molecules allows the selective therapy of cancer cells using the conjugates according to the invention.

Particular preference is given here to the extracellular cancer target molecule IL-3Rα, CD123 (SEQ ID NO: 41)

The functional interleukin 3 receptor is a heterodimer which comprises the specific alpha chain (IL-3Rα, CD123) and a "general" IL-3 receptor beta chain (BC, CD131) which is shared with the receptors for the granolocyte macrophage colony stimulating factor (GM-CSF) and interleukin 5 (IL-5). IL-3Rα, CD123, is a transmembrane protein of type 1 having a calculated molecular weight of about 41 kDa. CD123 comprises an extracellular domain involved in IL-3 binding, a transmembrane domain and a short cytoplasmic end of about 50 amino acids. The extracellular domain consists of two regions: an N-terminal region of about 100 amino acids having sequence similarity to the equivalent regions of the GM-CSF and the IL-5 receptor alpha chain, and a region proximal to the transmembrane domain which region comprises four conserved cysteine residues and a WSXWS motif (SEQ ID NO: 43) common in the cytokin receptor family.

The IL-3 binding domain comprises a cytokin receptor motif (CRM) of about 200 amino acid residues which is constructed of two domains which are folded Ig-like. The extracellular domain of IL-3Rα, CD123, is highly glycosylated, the N-glycosylation being required for ligand binding and receptor signal transduction.

IL-3Rα, CD123, is expressed extensively throughout the haematopoietic system, for example on haematopoietic precursor cells, mast cells, erythroid cells, megakaryocytes, neutrophil, basophil and eosinophil granulocytes, monocytes/macrophages, and CD5+B lymphocytes; CD123 is also expressed on non-haematopoietic cells such as dendritic cells, Leydig cells, endothelial cells and stromal cells.

IL-3Rα, CD123, is also expressed by cells involved in certain diseases; these diseases comprise: myelodysplastic syndrome, leukaemia (such as acute myeloid leukaemia (AML)), lymphoma, allergies and autoimmune disorders such as lupus or scleroderma.

Owing to these relationships, anti-IL-3Rα, anti-CD123, antibodies can be employed in therapy as naked antibodies or coupled antibodies (such as ADCs).

The present invention relates to conjugates comprising antibodies specifically binding to IL-3Rα, CD123 (SEQ ID NO: 41).

The term "anti-CD123 antibody" or "an antibody which specifically binds to CD123" relates to an antibody which binds the cancer target molecule CD123 (IL-3Rα, SEQ ID NO: 41) with an affinity which is sufficient for a diagnostic and/or therapeutic application. In one embodiment, binding of an anti-CD123 antibody to a protein not related to CD123 is less than 10% of the binding of the antibody to CD123, determined, for example, by surface plasmon resonance spectroscopy. In certain embodiments, the antibody binds CD123 (IL-3Rα, SEQ ID NO: 41) with a dissociation constant (KD) of ≤1M, ≤100 nM, ≤10 nM, ≤1 nM, ≤0.1 nM, ≤0.01 nM, or ≤0.001 nM. In certain embodiments, the anti-CD123 antibody binds to an epitope which is conserved between different species.

Antibodies which bind cancer target molecules may be prepared by a person of ordinary skill in the art using known processes, such as, for example, chemical synthesis or recombinant expression. Binders for cancer target molecules may be acquired commercially or may be prepared by a person of ordinary skill in the art using known processes, such as, for example, chemical synthesis or recombinant expression. Further processes for preparing antibodies or antigen-binding antibody fragments are described in WO 2007/070538 (see page 22 "Antibodies"). The person skilled in the art knows how processes such as phage display libraries (e.g. Morphosys HuCAL Gold) can be compiled and used for discovering antibodies or antigen-binding antibody fragments (see WO 2007/070538, page 24 ff and AK Example 1 on page 70, AK Example 2 on page 72). Further processes for preparing antibodies that use DNA libraries from B cells are described for example on page 26 (WO 2007/070538). Processes for humanizing antibodies are described on page 30-32 of WO2007070538 and in detail in Queen, et al., Pros. Natl. Acad. Sci. USA 86:10029-10033, 1989 or in WO 90/0786. Furthermore, processes for the recombinant expression of proteins in general and of antibodies in particular are known to the person skilled in the art (see, for example, in Berger and Kimrnel (Guide to Molecular Cloning Techniques, Methods in Enzymology, Vol. 152, Academic Press, Inc.); Sambrook, et al., (Molecular Cloning: A Laboratory Manual, (Second Edition, Cold Spring Harbor Laboratory Press; Cold Spring Harbor, N.Y.; 1989) Vol. 1-3); Current Protocols in Molecular Biology, (F. M. Ausabel et al. [Eds.], Current Protocols, Green Publishing Associates, Inc./John Wiley & Sons, Inc.); Harlow et al., (Monoclonal Antibodies: A Laboratory Manual, Cold Spring Harbor Laboratory Press (19881, Paul [Ed.]); Fundamental Immunology, (Lippincott Williams & Wilkins (1998)); and Harlow, et al., (Using Antibodies: A Laboratory Manual, Cold Spring Harbor Laboratory Press (1998)). The person skilled in the art knows the corresponding vectors, promoters and signal peptides which are necessary for the expression of a protein/antibody. Commonplace processes are also described in WO 2007/070538 on pages 41-45.

Processes for preparing an IgG1 antibody are described for example in WO 2007/070538 in Example 6 on page 74 ff. Processes which allow the determination of the internalization of an antibody after binding to its antigen are known to the skilled person and are described for example in WO 2007/070538 on page 80. The person skilled in the art is able to use the processes described in WO 2007/070538 that have been used for preparing carboanhydrase IX (Mn) antibodies in analogy for the preparation of antibodies with different target molecule specificity.

Anti-CD123 Antibodies

According to the invention, use is made of an anti-CD123 antibody or an antigen-binding fragment thereof, preferably one selected from those described below or modified by suitable mutation. In addition, the person skilled in the art is familiar with antibodies binding to CD123.

Sun et al. (Sun et al., 1996, Blood 87(1):83-92) describe the generation and properties of the monoclonal antibody 7G3, which binds to the N-terminal domain of IL-3Rα, CD123. U.S. Pat. No. 6,177,078 (Lopez) relates to the anti-CD123 antibody 7G3. A chimeric variant of this antibody (CSL360) is described in WO 2009/070844, and a humanized version (CSL362) in WO 2012/021934. The sequence of the 7G3 antibody is disclosed in EP2426148. This sequence represents the starting point of the humanized antibodies TPP-5968, TPP-5969 and TPP-5971 obtained by CDR grafting.

An antibody which, after cell surface antigen binding, is internalized particularly well is the anti-CD123 antibody 12F1 disclosed by Kuo et al. (Kuo et al., 2009, Bioconjug Chem. 20(10):1975-82). The antibody 12F1 binds with higher affinity to CD123 than the antibody 7G3 and, after cell surface antigen binding, is internalized markedly faster than 7G3. Bispecific scFv immunofusion proteins based on 12F1 are disclosed in WO 2013/173820. Antibody TPP-6013 is a chimeric variant of 12F1.

The invention relates in particular to conjugates with antibodies or antigen-binding antibody fragments thereof or variants thereof derived from the antibodies 7G3 (Sun et al., 1996, Blood 87(1):83-92) and 12F1 (Kuo et al., 2009, Bioconjug Chem. 20(10):1975-82) originated from the mouse, or to conjugates with antibodies or antigen-binding antibody fragments thereof or variants thereof derived from the antibody 12F1 (Kuo et al., 2009, Bioconjug Chem. 20(10):1975-82) originating from the mouse.

Generation of the Anti-CD123 Antibodies

Based on the publication of the sequences of the variable regions (VH and VL) of 7G3 (EP2426148), the following antibody sequences were obtained by CDR grafting in human framework regions: TPP-5968, TPP-5969 and TPP-5971.

Based on the publication of the sequences of the variable regions (VH and VL) of 12F1 (WO 2013/173820), the following antibody sequences were obtained by fusion of the variable domains of the donor immunoglobulin (VH and VL) with the constant regions of a human antibody: TPP-6013.

Further humanized variants of the anti-CD123 antibodies can be generated by humanization processes known in the art.

Reviews of methods for their generation can be found in Almagro and Fransson, Front. Biosci. 13:1619-1633 (2008), and further in Riechmann et al., Nature 332:323-329 (1988); Queen et al., Proc. Natl Acad. Sci. USA 86:10029-10033 (1989); U.S. Pat. Nos. 5,821,337, 7,527,791, 6,982,321, and 7,087,409; Kashmiri et al., Methods 36:25-34 (2005) (describing specificity determining region (SDR) grafting); Padlan, Mol. Immunol. 28:489-498 (1991) (describing resurfacing); Dall' Acqua et al., Methods 36:43-60 (2005) (describing FR shuffling); and Osbourn et al., Methods 36:61-68 (2005) and Klimka et al., Br. J. Cancer, 83:252-260 (2000) (describing the guided selection approach for FR shuffling).

Particular Embodiments of Anti-CD123 Antibodies

In the present application, reference is made to the following preferred anti-CD123 antibodies of the invention, as shown in the table below: "TPP-6013", "TPP-5968", "TPP-5969" and "TPP-5971".

TPP-6013 is a chimeric variant of 12F1 where the variable regions VH and VL are linked to the constant regions (CL, $CH_1$, $CH_2$, $CH_3$) of a human IgG1 of the kappa subtype.

The antibodies TPP-5968, TPP-5969 and TPP-5971 are humanized variants of 7G3 as a subtype of human IgG1 kappa.

TABLE

Protein sequences of the antibodies:

| Antibody | VH | H-CDR1 | H-CDR2 | H-CDR3 | VL | L-CDR1 | L-CDR2 | L-CDR3 | Heavy Chain (IgG) | Light Chain (IgG) |
|---|---|---|---|---|---|---|---|---|---|---|
| TPP-5968 | 1 | 2 | 3 | 4 | 5 | 6 | 7 | 8 | 9 | 10 |
| TPP-5969 | 11 | 12 | 13 | 14 | 15 | 16 | 17 | 18 | 19 | 20 |
| TPP-5971 | 21 | 22 | 23 | 24 | 25 | 26 | 27 | 28 | 29 | 30 |
| TPP-6013 | 31 | 32 | 33 | 34 | 35 | 36 | 37 | 38 | 39 | 40 |

TPP-5968 is an antibody comprising a region of the heavy chain corresponding to SEQ ID NO: 9 and a region of the light chain corresponding to SEQ ID NO: 10.

TPP-5969 is an antibody comprising a region of the heavy chain corresponding to SEQ ID NO: 19 and a region of the light chain corresponding to SEQ ID NO: 20.

TPP-5971 is an antibody comprising a region of the heavy chain corresponding to SEQ ID NO: 29 and a region of the light chain corresponding to SEQ ID NO: 30.

TPP-6013 is an antibody comprising a region of the heavy chain corresponding to SEQ ID NO: 39 and a region of the light chain corresponding to SEQ ID NO: 40.

TPP-5968 is: an antibody comprising a variable region of the heavy chain corresponding to SEQ ID NO: 1 and a variable region of the light chain corresponding to SEQ ID NO: 5.

TPP-5969 is: an antibody comprising a variable region of the heavy chain corresponding to SEQ ID NO: 11 and a variable region of the light chain corresponding to SEQ ID NO: 15.

TPP-5971 is: an antibody comprising a variable region of the heavy chain corresponding to SEQ ID NO: 21 and a variable region of the light chain corresponding to SEQ ID NO: 25.

TPP-6013 is: an antibody comprising a variable region of the heavy chain corresponding to SEQ ID NO: 31 and a variable region of the light chain corresponding to SEQ ID NO: 35.

Preferred embodiments of the anti-CD123 antibody for coupling with linkers and/or toxophores according to the invention are those below:

1. An antibody or an antigen-binding fragment which binds to CD123 and is a chimeric or humanized variant of the antibody 7G3 or 12F1.
2. An antibody or an antigen-binding fragment binding to CD123, comprising:
    a variable heavy chain comprising the variable CDR1 sequence of the heavy chain, as shown in SEQ ID NO: 2, the variable CDR2 sequence of the heavy chain, as shown in SEQ ID NO: 3, and the variable CDR3 sequence of the heavy chain, as shown in SEQ ID NO: 4, and a variable light chain comprising the variable CDR1 sequence of the light chain, as shown in SEQ ID NO: 6, the variable CDR2 sequence of the light chain, as shown in SEQ ID NO: 7, and the variable CDR3 sequence of the light chain, as shown in SEQ ID NO: 8, or a variable heavy chain comprising the variable CDR1 sequence of the heavy chain, as shown in SEQ ID NO: 12, the variable CDR2 sequence of the heavy chain, as shown in SEQ ID NO: 13, and the variable CDR3 sequence of the heavy chain, as shown in SEQ ID NO: 14, and a variable light chain comprising the variable CDR1 sequence of the light chain, as shown in SEQ ID NO: 16, the variable CDR2 sequence of the light chain, as shown in SEQ ID NO: 17, and the variable CDR3 sequence of the light chain, as shown in SEQ ID NO: 18, or a variable heavy chain comprising the variable CDR1 sequence of the heavy chain, as shown in SEQ ID NO: 22, the variable CDR2 sequence of the heavy chain, as shown in SEQ ID NO: 23, and the variable CDR3 sequence of the heavy chain, as shown in SEQ ID NO: 24, and a variable light chain comprising the variable CDR1 sequence of the light chain, as shown in SEQ ID NO: 26, the variable CDR2 sequence of the light chain, as shown in SEQ ID NO: 27, and the variable CDR3 sequence of the light chain, as shown in SEQ ID NO: 28, or a variable heavy chain comprising the variable CDR1 sequence of the heavy chain, as shown in SEQ ID NO: 32, the variable CDR2 sequence of the heavy chain, as shown in SEQ ID NO: 33, and the variable CDR3 sequence of the heavy chain, as shown in SEQ ID NO: 34, and a variable light chain comprising the variable CDR1 sequence of the light chain, as shown in SEQ ID NO: 36, the variable CDR2 sequence of the light chain, as shown in SEQ ID NO: 37, and the variable CDR3 sequence of the light chain, as shown in SEQ ID NO: 38.

3. The antibody or an antigen-binding fragment thereof according to embodiment 2, comprising:

a variable sequence of the heavy chain, as shown in SEQ ID NO:1, and also a variable sequence of the light chain, as shown in SEQ ID NO:5, or a variable sequence of the heavy chain, as shown in SEQ ID NO: 11, and also a variable sequence of the light chain, as shown in SEQ ID NO: 15, or a variable sequence of the heavy chain, as shown in SEQ ID NO:21, and also a variable sequence of the light chain, as shown in SEQ ID NO:25, or a variable sequence of the heavy chain, as shown in SEQ ID NO:31, and also a variable sequence of the light chain, as shown in SEQ ID NO:35.

4. The antibody according to any of the preceding embodiments which is an IgG antibody.

5. The antibody according to any of the preceding embodiments, comprising:

a sequence of the heavy chain, as shown in SEQ ID NO:9, and also a sequence of the light chain, as shown in SEQ ID NO: 10, or a sequence of the heavy chain, as shown in SEQ ID NO: 19, and also a sequence of the light chain, as shown in SEQ ID NO:20, or a sequence of the heavy chain, as shown in SEQ ID NO:29, and also a sequence of the light chain, as shown in SEQ ID NO:30, or a sequence of the heavy chain, as shown in SEQ ID NO:39, and also a sequence of the light chain, as shown in SEQ ID NO:40.

6. The antibody according to any of the preceding embodiments, comprising: The antigen-binding fragment according to any of the preceding embodiments or an antigen-binding fragment of an antibody according to any of the preceding embodiments which is an scFv, Fab, Fab fragment or a F(ab)$_2$ fragment.

7. The antibody or the antigen-binding fragment according to any of the preceding embodiments which is a monoclonal antibody or an antigen-binding fragment thereof.

8. The antibody or the antigen-binding fragment according to any of the preceding embodiments which is a human, humanized or chimeric antibody or an antigen-binding fragment.

Particular preference is given to the anti-CD123 antibodies "TPP-6013", "TPP-5968", "TPP-5969" and "TPP-5971".

Isotopes, Salts, Solvates, Isotopic Variants

The present invention also encompasses all suitable isotopic variants of the compounds of the invention. An isotopic variant of a compound of the invention is understood here to mean a compound in which at least one atom within the compound of the invention has been exchanged for another atom of the same atomic number, but with a different atomic mass from the atomic mass which usually or predominantly occurs in nature. Examples of isotopes which can be incorporated into a compound of the invention are those of hydrogen, carbon, nitrogen, oxygen, phosphorus, sulphur, fluorine, chlorine, bromine and iodine, such as $^2$H (deuterium), $^3$H (tritium), $^{13}$C, $^{14}$C, $^{15}$N, $^{17}$O, $^{18}$O, $^{32}$P, $^{33}$P, $^{33}$S, $^{34}$S, $^{35}$S, $^{36}$S, $^{18}$F, $^{36}$Cl, $^{82}$Br, $^{123}$I, $^{124}$I, $^{129}$I and $^{131}$I. Particular isotopic variants of a compound of the invention, especially those in which one or more radioactive isotopes have been incorporated, may be beneficial, for example, for the examination of the mechanism of action or of the active ingredient distribution in the body; due to comparatively easy preparability and detectability, especially compounds labelled with $^3$H or $^{14}$C isotopes are suitable for this purpose. In addition, the incorporation of isotopes, for example of deuterium, may lead to particular therapeutic benefits as a consequence of greater metabolic stability of the compound, for example an extension of the half-life in the body or a reduction in the active dose required; such modifications of the compounds of the invention may therefore in some cases also constitute a preferred embodiment of the present invention. Isotopic variants of the compounds of the invention can be prepared by the processes known to those skilled in the art, for example by the methods described further down and the procedures described in the working examples, by using corresponding isotopic modifications of the respective reagents and/or starting compounds.

Preferred salts in the context of the present invention are physiologically acceptable salts of the compounds according to the invention. Also encompassed are salts which are not themselves suitable for pharmaceutical applications but can be used, for example, for isolation or purification of the compounds of the invention.

Physiologically acceptable salts of the compounds according to the invention include acid addition salts of mineral acids, carboxylic acids and sulphonic acids, for example salts of hydrochloric acid, hydrobromic acid, sulphuric acid, phosphoric acid, methanesulphonic acid, ethanesulphonic acid, benzenesulphonic acid, toluenesulphonic acid, naphthalenedisulphonic acid, acetic acid, trifluoroacetic acid, propionic acid, lactic acid, tartaric acid, malic acid, citric acid, fumaric acid, maleic acid and benzoic acid.

Physiologically acceptable salts of the inventive compounds also include salts of conventional bases, by way of example and with preference alkali metal salts (e.g. sodium and potassium salts), alkaline earth metal salts (e.g. calcium and magnesium salts) and ammonium salts derived from ammonia or organic amines having 1 to 16 carbon atoms, by way of example and with preference ethylamine, diethylamine, triethylamine, ethyldiisopropylamine, monoethanolamine, diethanolamine, triethanolamine, dicyclohexylamine, dimethylaminoethanol, procaine, dibenzylamine, N-methylpiperidine, N-methylmorpholine, arginine, lysine and 1,2-ethylenediamine.

Designated as solvates in the context of the invention are those forms of the compounds according to the invention which form a complex in the solid or liquid state by coordination with solvent molecules. Hydrates are a specific form of the solvates in which the coordination is with water. Solvates preferred in the context of the present invention are hydrates.

The present invention additionally also encompasses prodrugs of the compounds of the invention. The term "prodrugs" in this context refers to compounds which may themselves be biologically active or inactive but are converted (for example metabolically or hydrolytically) to compounds of the invention during their residence time in the body.

PARTICULAR EMBODIMENTS

The following embodiments are particularly preferred:

Embodiment A

An ADC of the formula

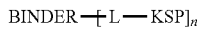

where KSP-L- represents a compound of the formula (I), (Ia), (II), (IIa), (IIb), (IIc), (IId), (IIe), (IIi), (IIj), (IIk) below or of the formula (IIf) below, the binder is an anti-CD123 antibody (particularly preferably a chimeric or humanized anti-CD123 antibody derived from an antibody 7G3 or 12F1 originating from mice, in particular the antibodies TPP-6013, TPP-5968, TPP-5969 and TPP-5971), and n represents a number from 1 to 10:

Formula (IIf):

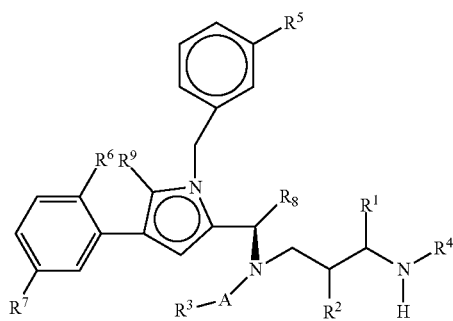

where
A represents CO (carbonyl);
$R^1$ represents -L-#1, H, —COOH, —CONHNH$_2$, —(CH$_2$)$_{1-3}$NH$_2$, —CONZ"(CH$_2$)$_{1-3}$NH$_2$ and —CONZ"CH$_2$COOH, where Z" represents H or NH$_2$;
$R^2$ and $R^4$ represent H, or $R^2$ and $R^4$ together (with formation of a pyrrolidine ring) represent —CH$_2$—CHR$^{11}$— or —CHR$^{11}$—CH$_2$—, where R$^{11}$ represents H;
$R^3$ represents -L-#1 or a C1-10-alkyl-, which may optionally be substituted by —OH, O-alkyl, SH, S-alkyl, O—CO-alkyl, O—CO—NH-alkyl, NH—CO-alkyl, NH—CO—NH-alkyl, S(O)$_n$-alkyl, SO$_2$—NH— alkyl, NH-alkyl, N(alkyl)$_2$ or NH$_2$ (where alkyl is preferably C$_{1-3}$-alkyl);
$R^5$ represents H or F;
$R^6$ and $R^7$ independently of one another represent H, (optionally fluorinated) C$_{1-3}$-alkyl, (optionally fluorinated) C$_{2-4}$-alkenyl, (optionally fluorinated) C$_{2-4}$-alkynyl, hydroxy or halogen;
$R^8$ represents a branched C$_{1-5}$-alkyl group; and
$R^9$ represents H or F,
where one of the substituents $R^1$ and $R^3$ represents -L-#1, and
-L- represents the linker and #1 represents the bond to the antibody,
and salts, solvates and salts of the solvates of the ADC.
The linker is preferably a linker § —(CO)m-L1-L2- § § where
m represents 0 or 1;
§ represents the bond to KSP and
§ § represents the bond to the antibody, and
L2 represents

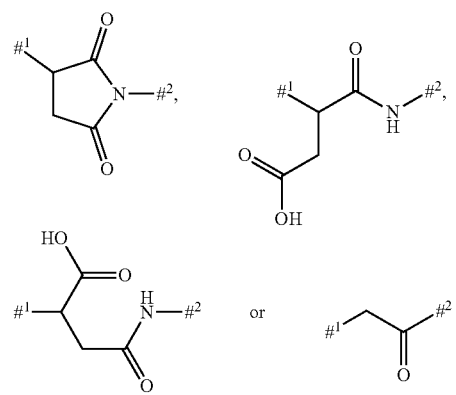

where
¹ denotes the point of attachment to the sulphur atom of the antibody,
² denotes the point of attachment to group L¹,
and L1 is represented by formula

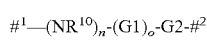

where
$R^{10}$ represents H, $NH_2$ or C1-C3-alkyl;
G1 represents —NHCO— or

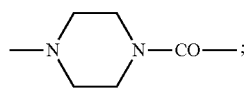

n represents 0 or 1;
o represents 0 or 1; and
G2 represents a straight-chain or branched hydrocarbon chain having 1 to 100 carbon atoms from arylene groups and/or straight-chain and/or branched and/or cyclic alkylene groups and which may be interrupted once or more than once by one or more of the groups —O—, —S—, —SO—, $SO_2$, —NH—, —CO—, —NHCO—, —CONH—, —NMe-, —NHNH—, —$SO_2$NHNH—, —CONHNH— and a 3- to 10-membered aromatic or non-aromatic heterocycle having up to 4 heteroatoms selected from the group consisting of N, O and S, or —SO— (preferably

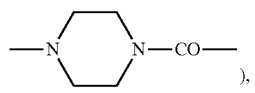

where the side chains, if present, may be substituted by —NHCONH₂, —COOH, —OH, —NH₂, NH—CNNH₂, sulphonamide, sulphone, sulphoxide or sulphonic acid.

Here, #¹ is the bond to the KSP inhibitor and #² is the bond to the coupling group to the antibody (e.g. L2).

Embodiment B

An ADC of the formula

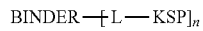

where KSP-L- represents a compound of the formula (I), (Ia), (II), (IIa), (IIb), (IIc), (IId), (IIe), (IIf), (IIi), (IIj), (IIk) below or of the formula (IIg) below, the binder is an anti-CD123 antibody (particularly preferably a chimeric or humanized anti-CD123 antibody derived from an antibody 7G3 or 12F1 originating from mice, in particular the antibodies TPP-6013, TPP-5968, TPP-5969 and TPP-5971), and n represents a number from 1 to 10:

Formula (IIg):

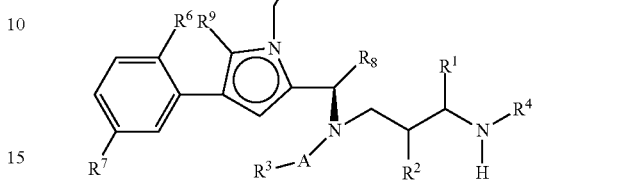

where
A represents CO (carbonyl);
$R^1$ represents -L-#1, H, —COOH, —CONHNH₂, —(CH₂)₁₋₃NH₂, —CONZ"(CH₂)₁₋₃ NH₂ and —CONZ"CH₂COOH, where Z" represents H or NH₂;
$R^2$ and $R^4$ represent H, or $R^2$ and $R^4$ together (with formation of a pyrrolidine ring) represent —CH₂—CHR¹¹— or —CHR¹¹—CH₂—, where $R^{11}$ represents H;
$R^3$ represents -L-#1 or a $C_{1-10}$-alkyl-, which may optionally be substituted by —OH, O-alkyl, SH, S-alkyl, O—CO-alkyl, O—CO—NH-alkyl, NH—CO-alkyl, NH—CO—NH-alkyl, S(O)ₙ-alkyl, SO₂—NH-alkyl, NH-alkyl, N(alkyl)₂ or NH₂ (where alkyl is preferably $C_{1-3}$-alkyl);
$R^5$ represents H or F;
$R^6$ and $R^7$ independently of one another represent H, (optionally fluorinated) $C_{1-3}$-alkyl, (optionally fluorinated) $C_{2-4}$-alkenyl, (optionally fluorinated) $C_{2-4}$-alkynyl, hydroxy or halogen;
$R^8$ represents a branched $C_{1-5}$-alkyl group; and
$R^9$ represents H or F,
where one of the substituents $R^1$ and $R^3$ represents -L-#1, and
-L- represents the linker and #1 represents the bond to the antibody,
where -L- is represented by

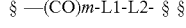

where
m represents 0 or 1;
§ represents the bond to KSP and
§ § represents the bond to the antibody, and
L2 represents

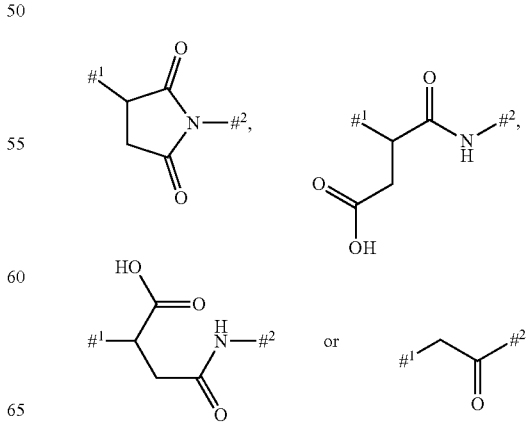

where

¹ denotes the point of attachment to the sulphur atom of the antibody,

² denotes the point of attachment to group L¹, and L1 is represented by formula

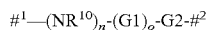

where $R^{10}$ represents H, $NH_2$ or C1-C3-alkyl;

G1 represents —NHCO— or

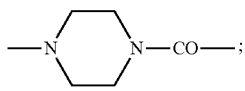

n represents 0 or 1;

o represents 0 or 1; and

G2 represents a straight-chain or branched hydrocarbon chain having 1 to 100 carbon atoms from arylene groups and/or straight-chain and/or branched and/or cyclic alkylene groups and which may be interrupted once or more than once by one or more of the groups —O—, —S—, —SO—, $SO_2$, —NH—, —CO—, —NHCO—, —CONH—, —NMe-, —NHNH—, —SO₂NHNH—, —CONHNH— and a 3- to 10-membered aromatic or non-aromatic heterocycle having up to 4 heteroatoms selected from the group consisting of N, O and S, or —SO— (preferably

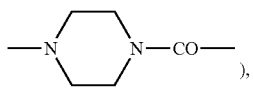

where the side chains, if present, may be substituted by —NHCONH₂, —COOH, —OH, —NH₂, NH—CNNH₂, sulphonamide, sulphone, sulphoxide or sulphonic acid,

¹ is the bond to the KSP inhibitor and #² is the bond to the coupling group to the antibody (e.g. L2), and salts, solvates and salts of the solvates of the ADC.

Embodiment C

An ADC of the formula

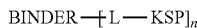

where KSP-L- represents a compound of the formula (II), (IIa), (IIb), (IIc), (IId), (IIe), (IIf), (IIg); (IIi), (IIj), (IIk) below or of the formula (IIh) below, the binder is an anti-CD123 antibody (particularly preferably a chimeric or humanized anti-CD123 antibody derived from an antibody 7G3 or 12F1 originating from mice, in particular the antibodies TPP-6013, TPP-5968, TPP-5969 and TPP-5971), and n represents a number from 1 to 10:

Formula (IIh):

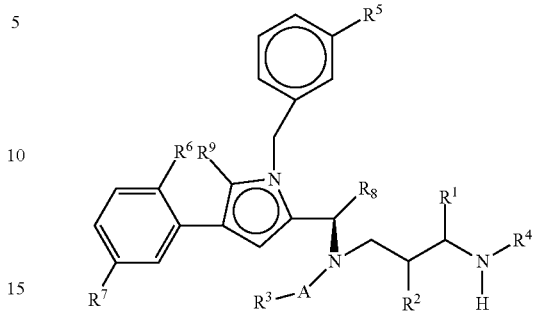

(IIh)

where

A represents CO (carbonyl);

$R^1$ represents -L-#1;

$R^2$ and $R^4$ represent H, or $R^2$ and $R^4$ together (with formation of a pyrrolidine ring) represent —CH₂—CHR¹¹— or —CHR¹¹—CH₂—, where $R^{11}$ represents H;

$R^3$ represents $C_{1-10}$-alkyl-, which may optionally be substituted by —OH, O-alkyl, SH, S-alkyl, O—CO-alkyl, O—CO—NH-alkyl, NH—CO-alkyl, NH—CO—NH-alkyl, S(O)ₙ-alkyl, SO₂—NH-alkyl, NH-alkyl, N(alkyl)₂ or NH₂ (where alkyl is preferably $C_{1-3}$-alkyl), or -MOD;

where -MOD represents —(NR¹⁰)ₙ-(G1)ₒ-G2-G3, where $R^{10}$ represents H or $C_1$-$C_3$-alkyl;

G1 represents —NHCO— or —CONH— (where, if G1 represents —NHCO—, $R^{10}$ does not represent NH₂);

n represents 0 or 1;

o represents 0 or 1; and

G2 represents a straight-chain or branched hydrocarbon group which has 1 to 10 carbon atoms and which may be interrupted once or more than once by one or more of the groups —O—, —S—, —SO—, SO₂, —NRy-, —NRyCO—, CONRy-, —NRyNRy-, —SO₂NRyNRy-, —CONRyNRy- (where Rʸ represents H, phenyl, C1-C10-alkyl, C2-C10-alkenyl or C2-C10-alkynyl, each of which may be substituted by NHCONH₂, —COOH, —OH, —NH₂, NH—CNNH₂, sulphonamide, sulphone, sulphoxide or sulphonic acid), —CO—, —CRˣ=N—O— (where Rx represents H, C1-C3-alkyl or phenyl), where the hydrocarbon chain including any side chains may be substituted by —NHCONH₂, —COOH, —OH, —NH₂, NH—CNNH₂, sulphonamide, sulphone, sulphoxide or sulphonic acid, G3 represents —H or —COOH, where the group -MOD preferably has at least one group —COOH;

$R^5$ represents H or F;

$R^6$ and $R^7$ independently of one another represent H, (optionally fluorinated) $C_{1-3}$-alkyl, (optionally fluorinated) $C_{2-4}$-alkenyl, (optionally fluorinated) $C_{2-4}$-alkynyl, hydroxy or halogen;

$R^8$ represents a branched $C_{1-5}$-alkyl group; and $R^9$ represents H or F, where -L- represents the linker and #1 represents the bond to the antibody, where -L- is represented by § —(CO)m-L1-L2- § § where m represents 0 or 1;

§ represents the bond to KSP and

§ § represents the bond to the antibody, and

L2 represents

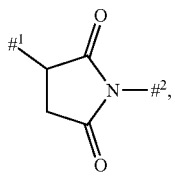 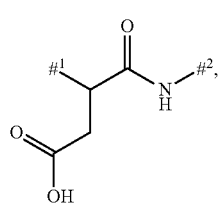

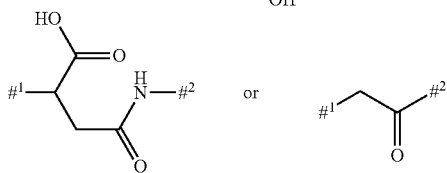

where
¹ denotes the point of attachment to the sulphur atom of the antibody,
² denotes the point of attachment to group L¹,
and L1 is represented by formula

¹—(NR¹⁰)$_n$-(G1)$_o$-G2-#² where
R¹⁰ represents H, NH$_2$ or C1-C3-alkyl;
G1 represents —NHCO— or;

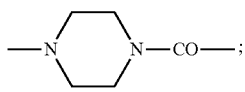

n represents 0 or 1;
o represents 0 or 1; and
G2 represents a straight-chain or branched hydrocarbon chain having 1 to 100 carbon atoms from arylene groups and/or straight-chain and/or branched and/or cyclic alkylene groups and which may be interrupted once or more than once by one or more of the groups —O—, —S—, —SO—, SO$_2$, —NH—, —CO—, —NHCO—, —CONH—, —NMe-, —NHNH—, —SO$_2$NHNH—, —CONHNH—, —CR$^x$=N—O— (where Rx represents H, C$_1$-C$_3$-alkyl or phenyl) and a 3- to 10-membered aromatic or non-aromatic heterocycle having up to 4 heteroatoms selected from the group consisting of N, O and S, —SO— or -SO$_2$-(preferably

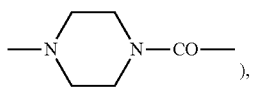

where the hydrocarbon chain including the side chains, if present, may be substituted by —NHCONH$_2$, —COOH, —OH, —NH$_2$, NH—CNNH$_2$, sulphonamide, sulphone, sulphoxide or sulphonic acid,
¹ is the bond to the KSP inhibitor and #² is the bond to the coupling group to the antibody (e.g. L2),
and salts, solvates and salts of the solvates of the ADC.

Embodiment D

The invention also provides binder/active compound conjugates of the general formula below:

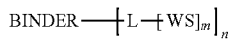

where BINDER represents the anti-CD123 antibody (particularly preferably a chimeric or humanized anti-CD123 antibody derived from an antibody 7G3 or 12F1 originating from mice, in particular the antibodies TPP-6013, TPP-5968, TPP-5969 and TPP-5971), L represents the linker, WS represents the active compound, preferably a KSP inhibitor such as, for example, a KSP inhibitor according to the invention of one of the formulae (I), (Ia), (II), (IIa), (IIb), (IIc), (IId), (IIe), (IIf), (IIg), (IIh) (IIi), m represents a number from 1 to 2, preferably 1, and n represents a number from 1 to 50, preferably from 1.2 to 20 and particularly preferably from 2 to 8, where L has one of the structures below. Here, m represents the number of active compound molecules per linker and n a mean of the number of active compound/linker conjugates per BINDER. The sum of all WS present in a conjugate molecule is therefore the product of m and n.

WS is an active compound which has local or systemic therapeutic action in animals, preferably in humans. These active compounds generally have a molecular weight below 5 kDa, preferably below 1.5 kDa. Preferred active compounds are vinca alkaloids, auristatins, tubulysins, duocarmycins, kinase inhibitors, MEK inhibitors and KSP inhibitors.

Here, L represents one of the formulae A3 and A4 below

Formula A3

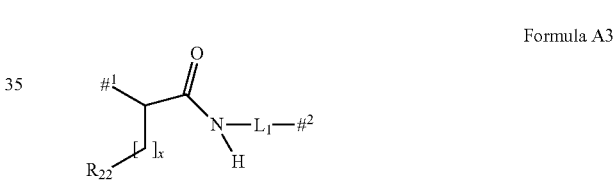

Formula A4

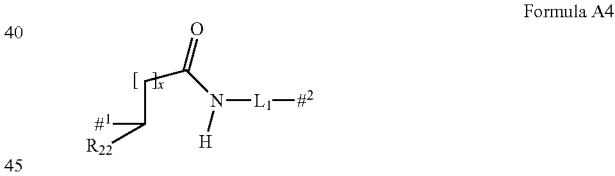

where #¹ denotes the point of attachment to the sulphur atom of the binder, #² denotes the point of attachment to the active compound, x represents 1 or 2, and R22 represents COOH, COOR, COR (where R in each case represents C1-3-alkyl), CONH$_2$, Br, preferably COOH.

L1 has the same meaning as above. Preferably, -L1-#² is represented by the formula below:

³—(NR¹⁰)$_n$-(G1)$_o$-G2-#² where
3 denotes the point of attachment to the nitrogen atom,
R¹⁰ represents H, NH$_2$ or C$_1$-C$_3$-alkyl;
G1 represents —NHCO—, —CONH— or

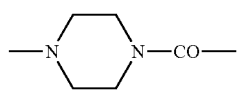

(where, if G1 represents NHCO or

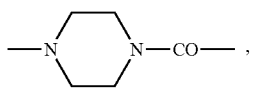

$R^{10}$ does not represent $NH_2$), n represents 0 or 1;

o represents 0 or 1; and

G2 represents a straight-chain or branched hydrocarbon chain which has 1 to 100 carbon atoms from arylene groups and/or straight-chain and/or branched and/or cyclic alkylene groups and which may be interrupted once or more than once by one or more of the groups —O—, —S—, —SO—, $SO_2$, —NRy-, —NRyCO—, —C(NH)NRy-, CONRy-, —NRyNRy-, —$SO_2$NRyNRy-, —CONRyNRy- (where $R^y$ represents H, phenyl, $C_1$-$C_{10}$-alkyl, $C_2$-$C_{10}$-alkenyl or $C_2$-$C_{10}$-alkynyl, each of which may be substituted by NHCONH2, —COOH, —OH, —$NH_2$, NH—$CNNH_2$, sulphonamide, sulphone, sulphoxide or sulphonic acid), —CO—, —$CR^x$=N—O— (where $R^x$ represents H, $C_1$-$C_3$-alkyl or phenyl) and/or a 3- to 10-membered aromatic or non-aromatic heterocycle having up to 4 heteroatoms selected from the group consisting of N, O and S, —SO— or —$SO_2$— (preferably

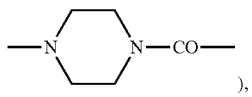

where the hydrocarbon chain including any side chains may be substituted by —$NHCONH_2$, —COOH, —OH, —$NH_2$, NH—$CNNH_2$, sulphonamide, sulphone, sulphoxide or sulphonic acid.

Further interrupting groups in G2 are preferably

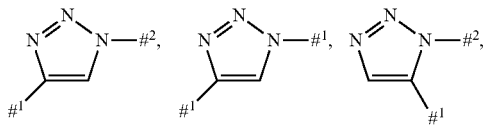

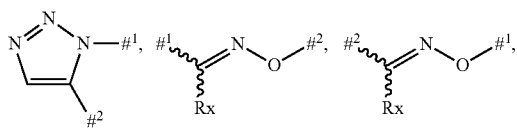

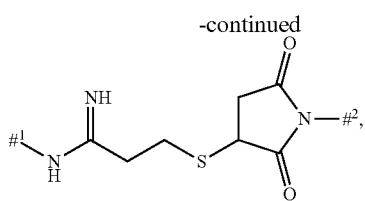

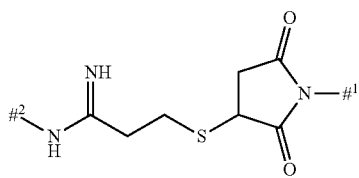

where $R^x$ represents H, $C_1$-$C_3$-alkyl or phenyl.

In the conjugate according to the invention or in a mixture of the conjugates according to the invention, the bonds to a cysteine residue of the antibody are present, to an extent of preferably more than 80%, particularly preferably more than 90% (in each case based on the total number of bonds of the linker to the antibody) as one of the two structures of the formula A3 or A4.

The conjugates with the linkers of formula A3 or A4 can be obtained by coupling the antibodies to the appropriate bromine derivatives of the formulae A3' and A4', respectively, below:

Formula A3'

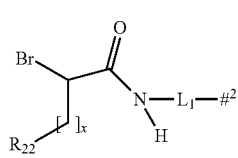

Formula A4'

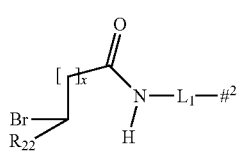

These bromine derivatives of the formula A3' or A4' can be obtained by reacting $R_{22}CH_2CHBrCOOH$ or $R_{22}CHBrCH_2COOH$ with an amine group of the binder, as illustrated in an exemplary manner in Schemes 30 to 32 below.

Scheme 30
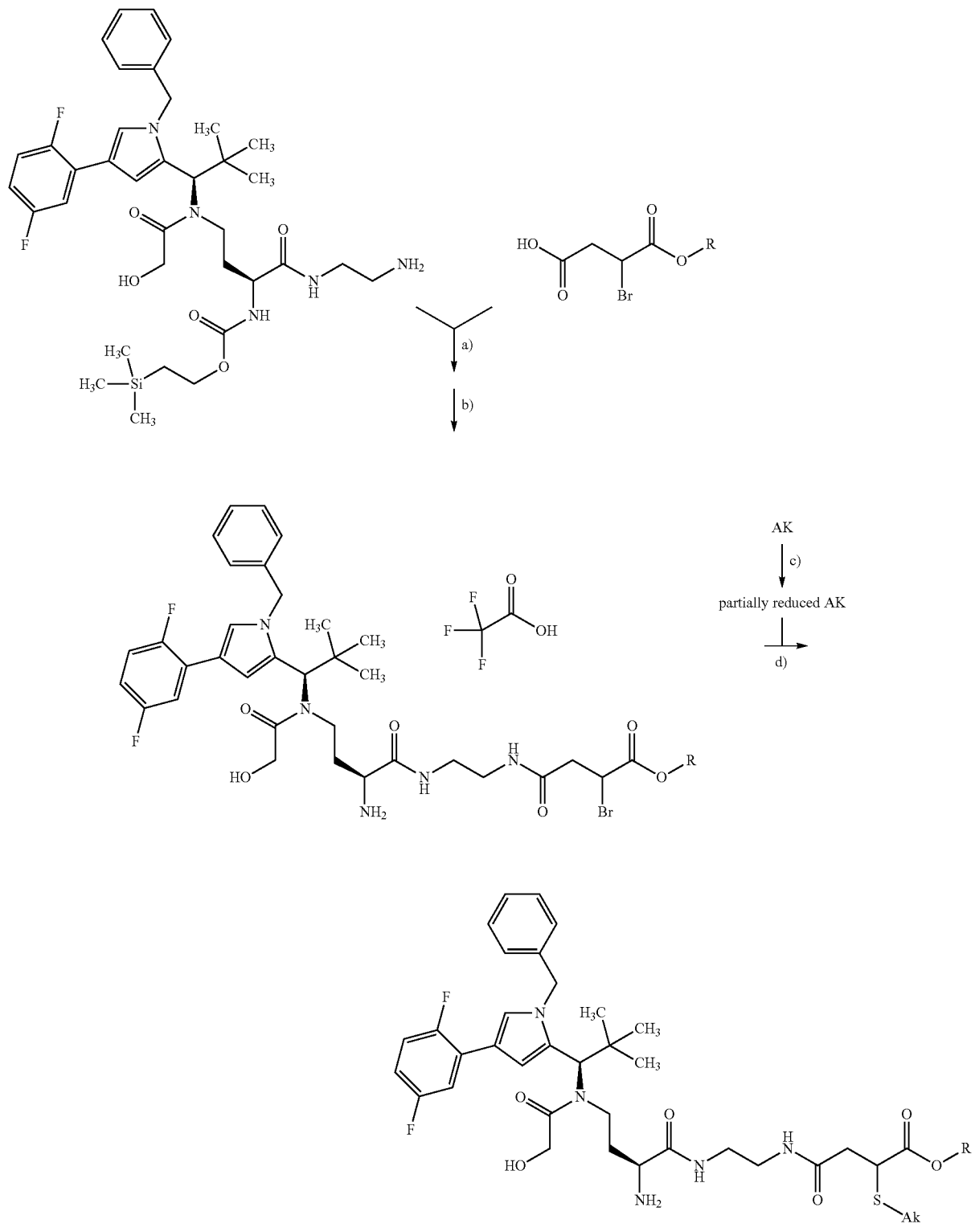
[a]: 2-bromo-1-ethylpyridinium tetrafluoroborate (BEP), DCM, pyridine, RT; b) zinc chloride, trifluoroethanol, 50° C., EDTA; c) 3-4 equivalents of TCEP, PBS buffer; d) PBS buffer, 20 h RT.]

Scheme 31
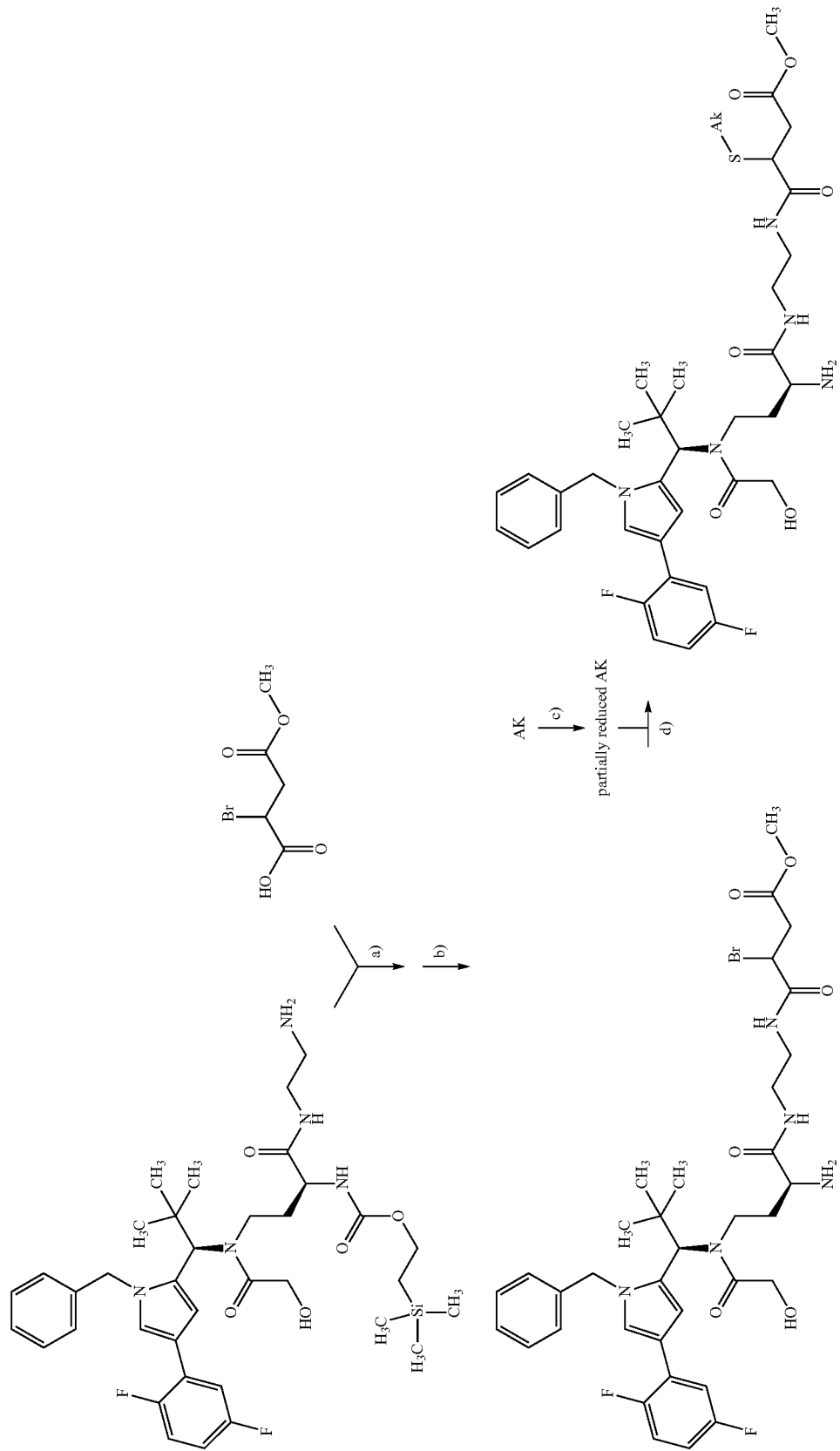
[a): 2-bromo-1-ethylpyridinium tetrafluoroborate (BEP), DCM, pyridine, RT; b) zinc chloride, trifluoroethanol, 50° C., EDTA; c) 3-4 equivalents of TCEP, PBS buffer; d) PBS buffer, 20 h RT.]

Embodiment E

The invention also provides binder/active compound conjugates of the general formula below:

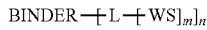

where BINDER represents the anti-CD123 antibody (particularly preferably a chimeric or humanized anti-CD123 antibody derived from an antibody 7G3 or 12F1 originating from mice, in particulate the antibodies TPP-6013, TPP-5968, TPP-5969 and TPP-5971), L represents the linker, WS represents the binder/active compound referably a KSP inhibitor such as, for example, a KSP inhibitor according to the invention of one of the formulae (I), (Ia), (II), or (IIa), m represents a number from 1 to 2, preferably 1, and n represents a number from 1 to 50, preferably from 1.2 to 20 and particularly preferably from 2 to 8, where L has one of the structures below. Here, m represents the number of active compound molecules per linker and n a mean of the number of active compound/linker conjugates per BINDER. The sum of all WS present in a conjugate molecule is therefore the product of m and n.

Here, L represents:

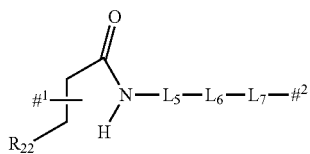

Formula A where #¹ denotes the point of attachment to the sulphur atom of the antibody, #² denotes the point of attachment to the active compound and $R^{22}$ represents COOH, COOR, COR (where R in each case represents C1-3-alkyl), $CONH_2$, Br, preferably COOH; The link to the sulphur atom of the binder may thus have one of the structures below:

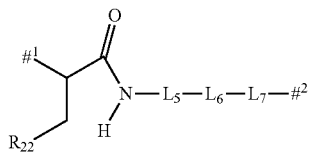

Formula A1

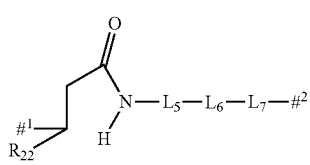

Formula A2

In the case of antibody drug conjugates containing more than one active compound molecule WS per antibody drug conjugate, both structures according to the formulae A1 and/or A2 may be present in an antibody drug conjugate. Since the antibody drug conjugates according to the invention may be mixtures of different antibody drug conjugates, it is also possible for this mixture to comprise both antibody drug conjugates of formula A1 or formula A2 and those of formula A1 and A2.

$L_5$ is a group selected from $-(CH_2)_m-(CHRS)_n-(OCH_2CH_2)_o-(X)_p-(CH_2)_q-$, where m, n, o, p and q independently of one another have the following values: m=0-10; n=0 or 1; o=0-10; p=0 or 1; and q=0-10, where m+n+o=1-15, preferably 1-6. X represents a 5- or 6-membered aromatic or nonaromatic hetero- or homocycle, preferably $-C_6H_4-$ or $-C_6H_{10}-$. RS represents an acid group, preferably $-COOH$ or $SO_3H$.

$L_6$ is a group selected from $-CONH-$, $-OCONH-$, $-NHCO-$, $-NHCOO-$,

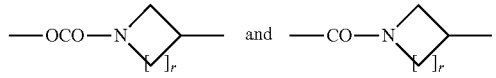

r and r where r is 1, 2 or 3.

$L_7$ is a single bond or a group selected from a straight-chain or branched hydrocarbon chain which has 1 to 100 (preferably 1 to 10) carbon atoms from arylene groups and/or straight-chain and/or branched and/or cyclic alkylene groups and which may be interrupted once or more than once by one or more of the groups $-O-$, $-S-$, $-SO-$, $SO_2$, $-NRy-$, $-NRyCO-$, $-C(NH)NRy-$, $CONRy-$, $-NRyNRy-$, $-SO_2NRyNRy-$, $-CONRyNRy-$ (where $R^y$ represents H, phenyl, $C_1-C_{10}$-alkyl, $C_2-C_{10}$-alkenyl or $C_2-C_{10}$-alkynyl, each of which may be substituted by $NHCONH_2$, $-COOH$, $-OH$, $-NH_2$, $NH-CNNH_2$, sulphonamide, sulphone, sulphoxide or sulphonic acid), $-CO-$, $-CR^x=N-O-$ (where Rx represents H, $C_1-C_3$-alkyl or phenyl) and/or a 3- to 10-membered, preferably 5- to 10-membered aromatic or non-aromatic heterocycle having up to 4 heteroatoms selected from the group consisting of N, O and S, $-SO-$ or $-SO_2-$ (preferably

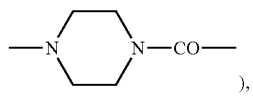

), where the hydrocarbon chain including any side chains may be substituted by $-NHCONH_2$, $-COOH$, $-OH$, $-NH_2$, $NH-CNNH_2$, sulphonamide, sulphone, sulphoxide or sulphonic acid.

$L_5$ is preferably a group $-(CH_2)_m-(CHRS)_n-(OCH_2CH_2)_o-(X)_p-(CH_2)_q-$ where m=1-3, n=0, o=0-7, p=0 and q=0 or 1. Particular preference is given to a group $-(CH_2)_m-(CHRS)_n-(OCH_2CH_2)_o-(X)_p-(CH_2)_q-$ where m=1 or 2, n=0, o=0 or 1, p=0 and q=0 or 1.

$L_6$ is preferably a group selected from $-CONH-$ and $-NHCO-$.

$L_7$ is preferably a single bond or $-[(CH_2)_x-(X^4)_y]w-(CH_2)_z-$,
where
w=0 to 20;
x=0 to 5;
y=0 or 1;
$X^4$ represents $-O-$, $-CONH-$, $-NHCO-$ or

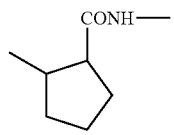

Particularly preferably, $L_7$ is a single bond or a group —[(CH$_2$)$_x$—NHCO—)], where x=1 to 5.

Particularly preferably, -L$_5$-L$_6$-L$_7$-represents —(CH$_2$)$_m$—(CHRS)$_n$—(OCH$_2$CH$_2$)$_o$—(X)$_p$—(CH$_2$)$_q$—NHCO—[(CH$_2$)$_x$—NHCO—)], where m=1 or 2, n=0, o=0 or 1, p=0, and q=0 or 1, and x=1-5.

However, it is also possible that these two structures are jointly present in the conjugate according to the invention.

According to the invention, these antibody drug conjugates can be prepared from the compounds of the formula

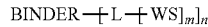

BINDER─┤L─┤WS]$_m$]$_n$ where L has the formula A' below:

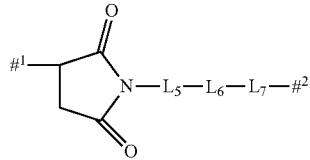

Formula A'

Preferably, the conversion of A' into A is carried out by stirring in a pH buffer having a pH of from 7.5 to 8.5, preferably 8, at a temperature below 37° C., preferably from 10 to 25° C., over a period of up to 40 hours, preferably 1 to 15 hours.

Embodiment I

An antibody drug conjugate of the formula

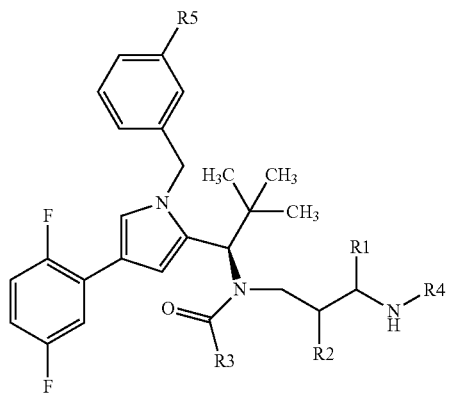

where
R2, R4 and R5 represent H;
R3 represents —CH$_2$OH;
R1 represents -L1-L2-BINDER, where
L1 represents

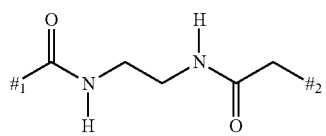

where #2 represents the attachment to L2 and #1 represents the attachment to the other attachment;

and L2 represents one or both of the structures of the formulae A5 and A6 below:

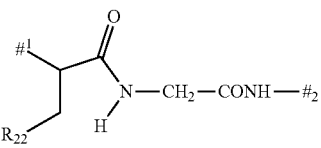

Formula A5

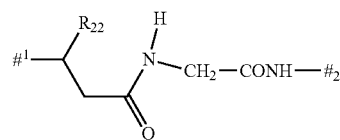

Formula A6 where
$\#^1$ denotes the point of attachment to the sulphur atom of the antibody, $\#^2$ denotes the point of attachment to group $L^1$, and
$R^{22}$ represents COOH, COOR, COR, CONHR (where R in each case represents C1-3-alkyl), CONH$_2$, preferably COOH.

In a conjugate according to the invention or in a mixture of the conjugates according to the invention, the bonds to a cysteine residue of the antibody are present, to an extent of preferably more than 80%, particularly preferably more than 90% (in each case based on the total number of bonds of the linker to the antibody), particularly preferably as one of the two structures of the formula A5 or A6:

Here, the structures of the formula A5 or A6 are generally present together, preferably in a ratio of from 60:40 to 40:60, based on the number of bonds to the antibody. The remaining bonds are then present as the structure

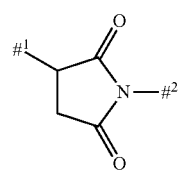

The antibody is preferably a chimeric or humanized anti-CD123 antibody derived from an antibody 7G3 or 12F1 originating from mice. Particular preference is given to the antibodies TPP-6013, TPP-5968, TPP-5969 and TPP-5971.

Specific Embodiments

The following particularly preferred antibody conjugates according to one of the formulae below are provided, where n is a number from 1 to 20 and AK1 (as well as AK1a, AK1b, etc.) and AK2 (as well as AK2a, AK2b, etc.) are antibodies. AK1 is an antibody attached via cysteine, AK2 is an antibody attached via lysine. The antibody (AK1 or AK2) in one of the following formulae is preferably a chimeric or humanized anti-CD123 antibody derived from an antibody 7G3 or 12F1 originating from mice. Particular preference is given to the antibodies TPP-6013, TPP-5968, TPP-5969 and TPP-5971.

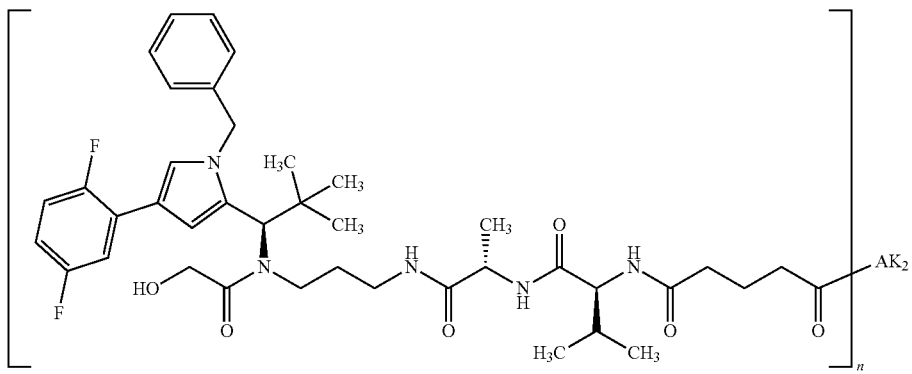
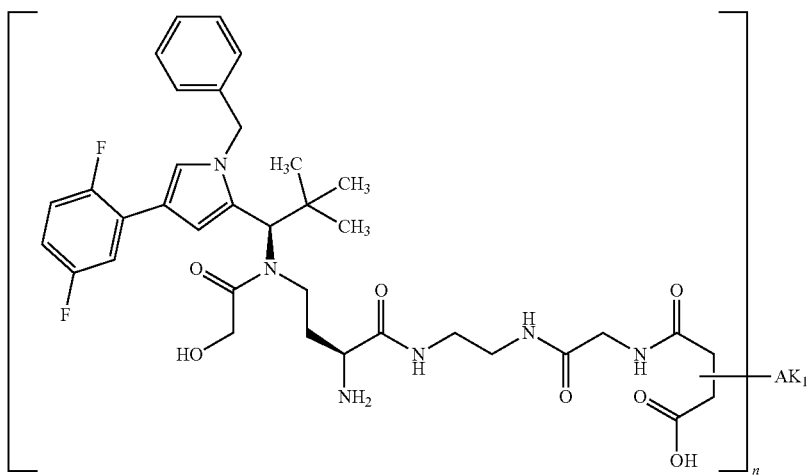
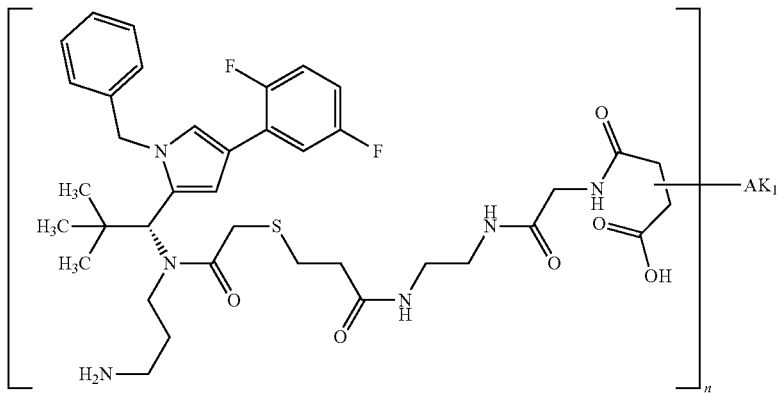

-continued
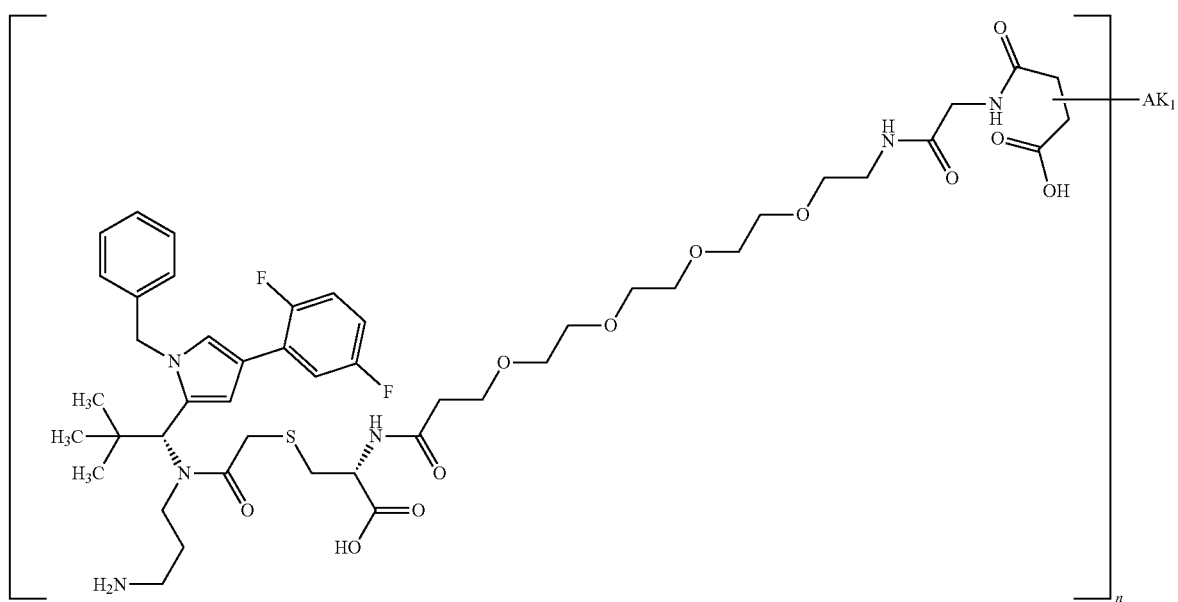
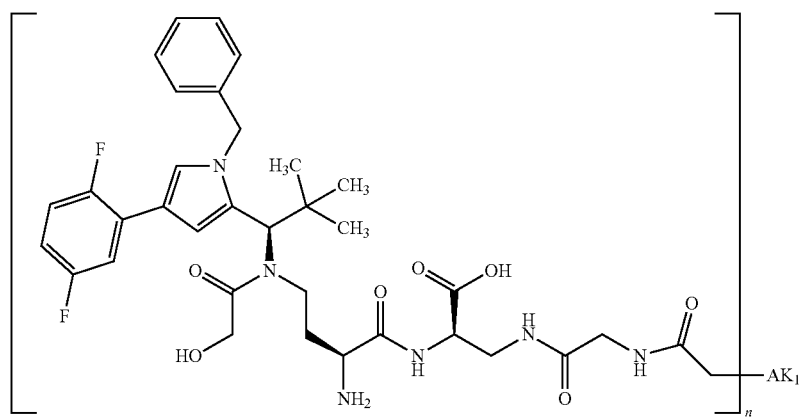
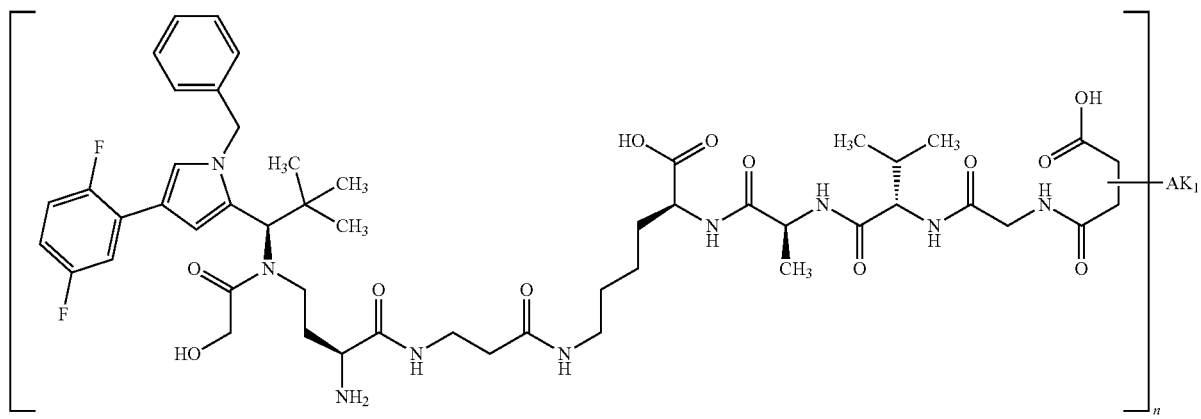

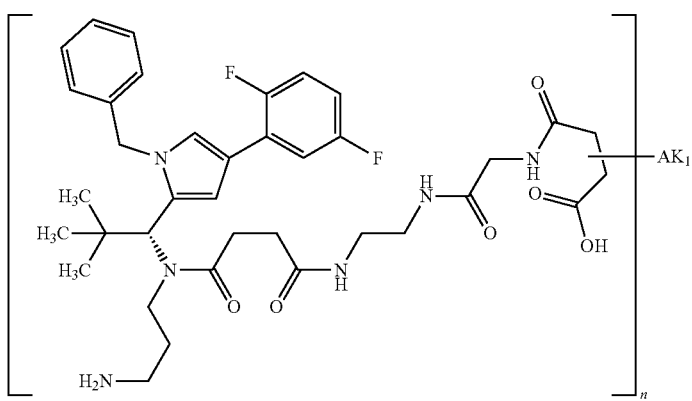
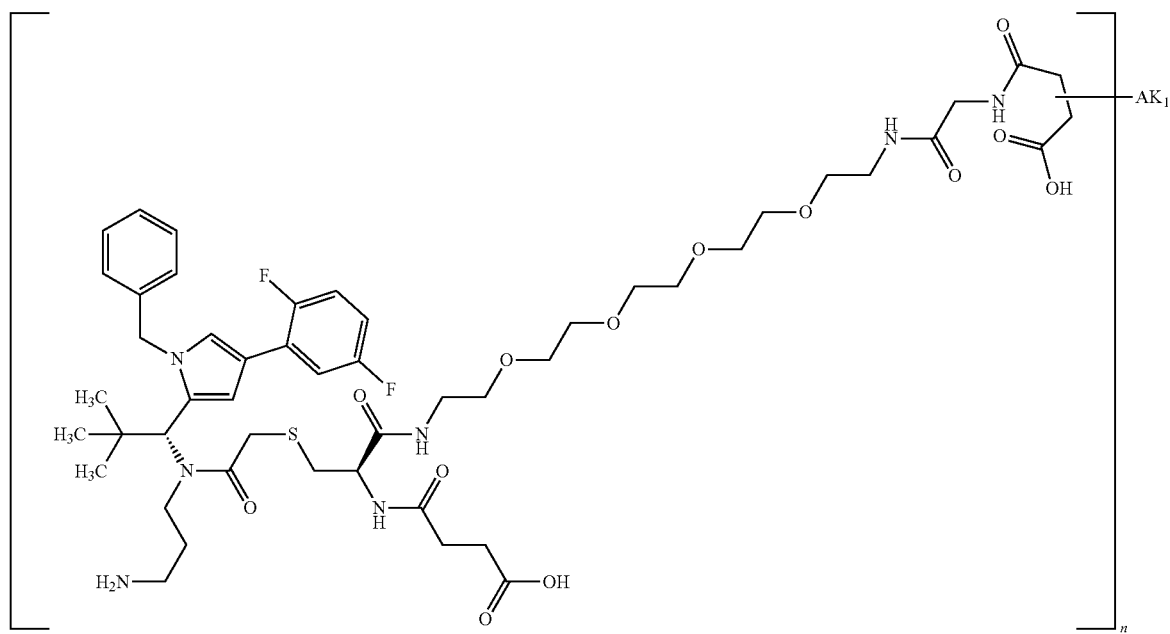
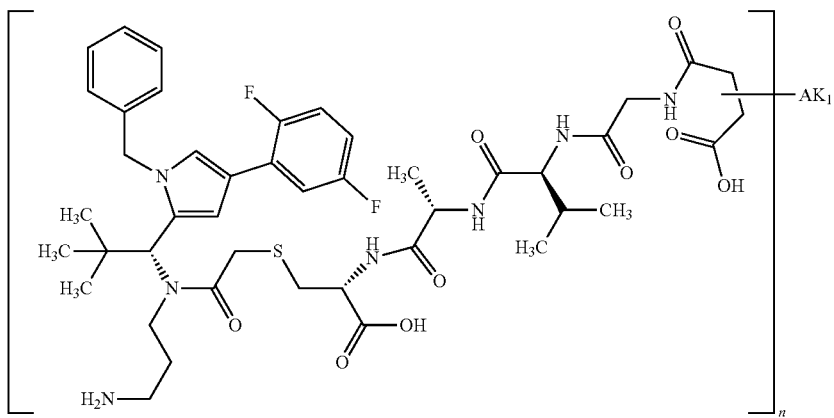

173 174
-continued
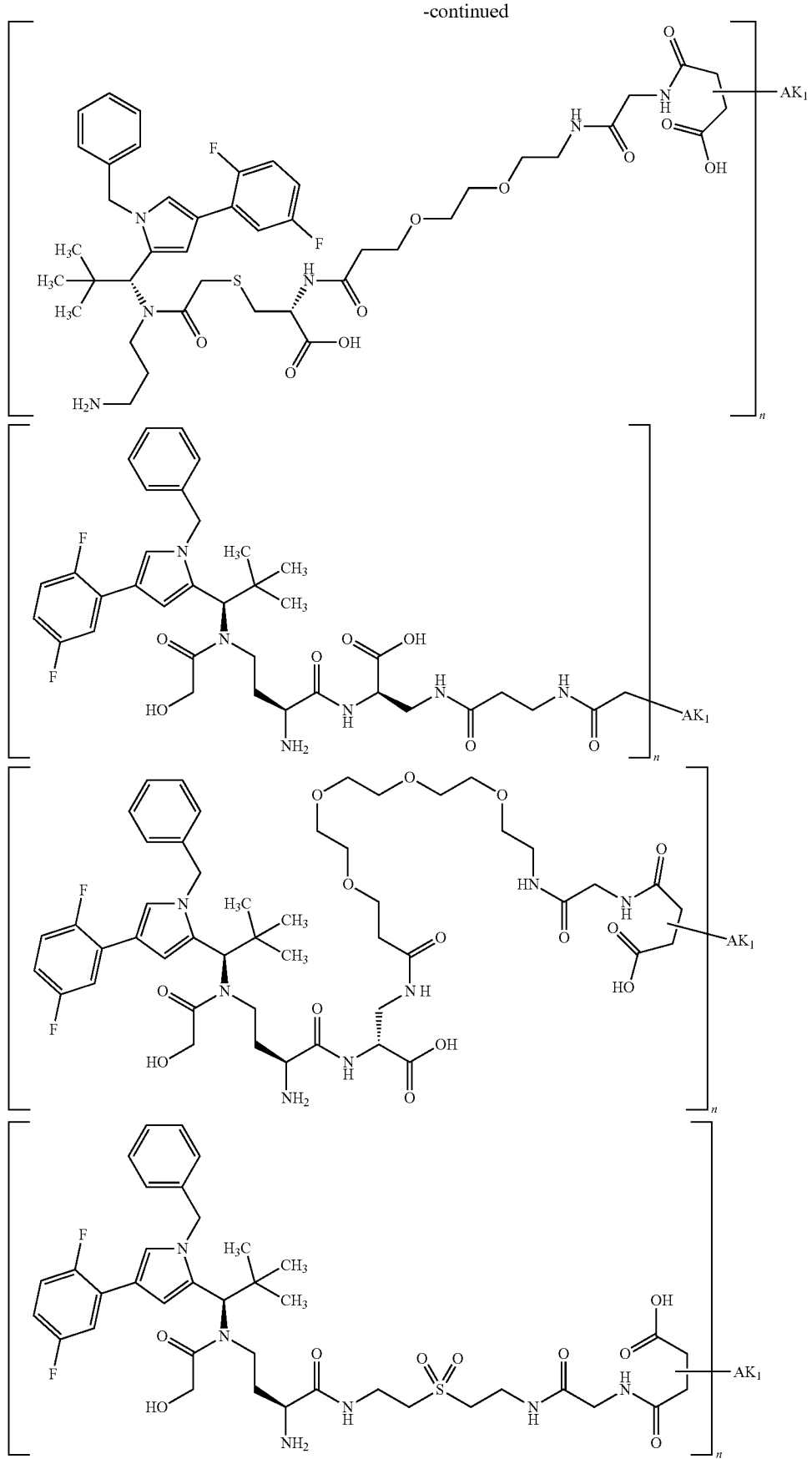

-continued
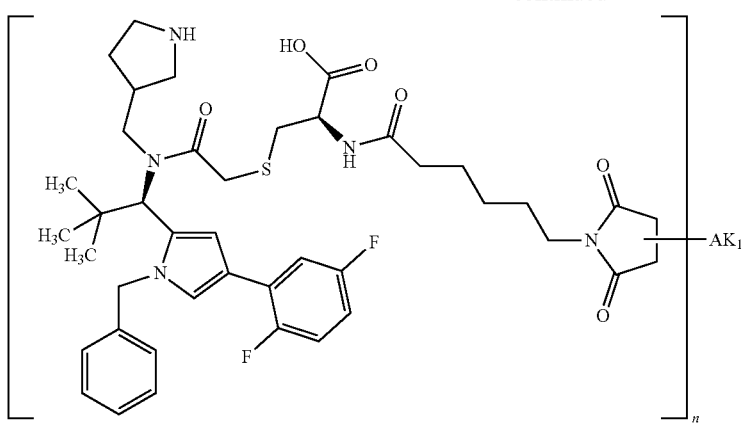
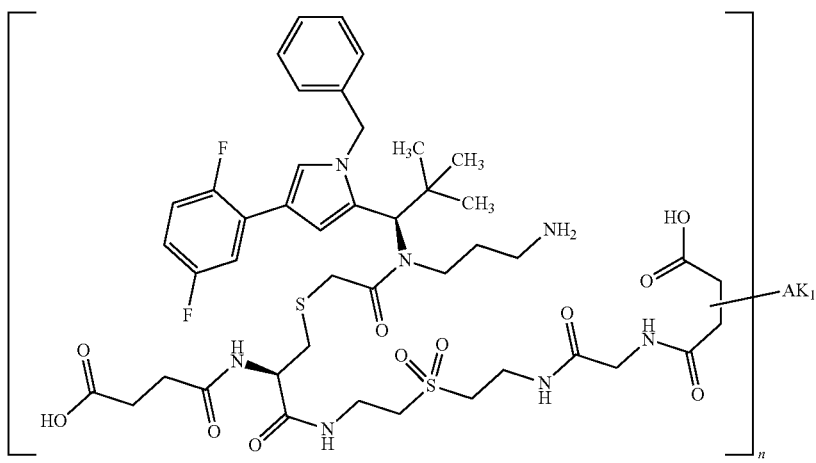
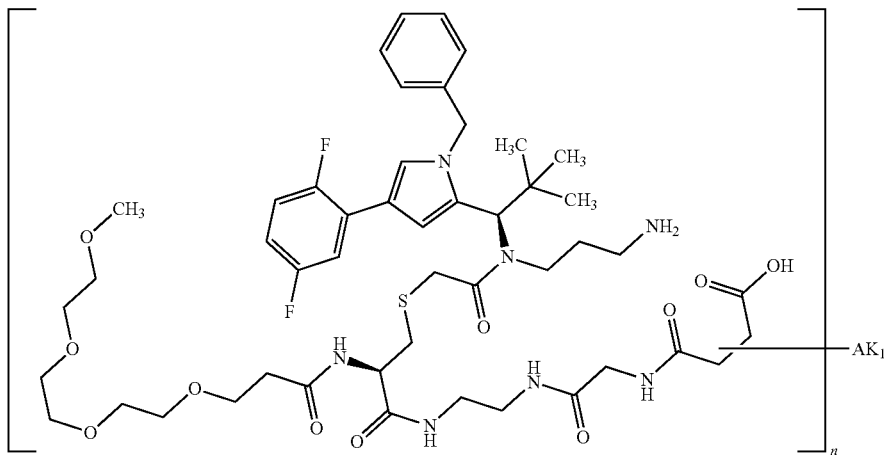

-continued
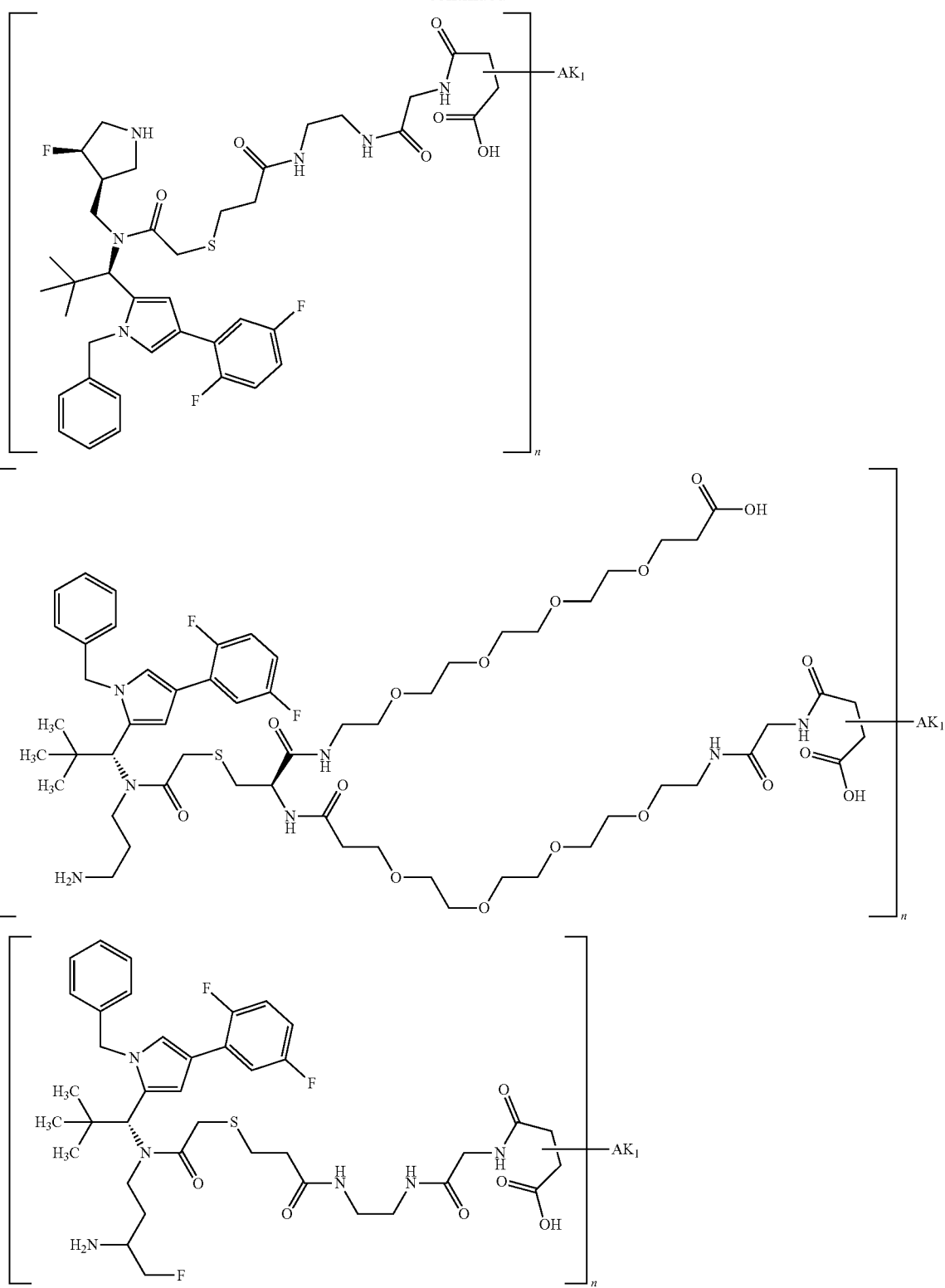

-continued
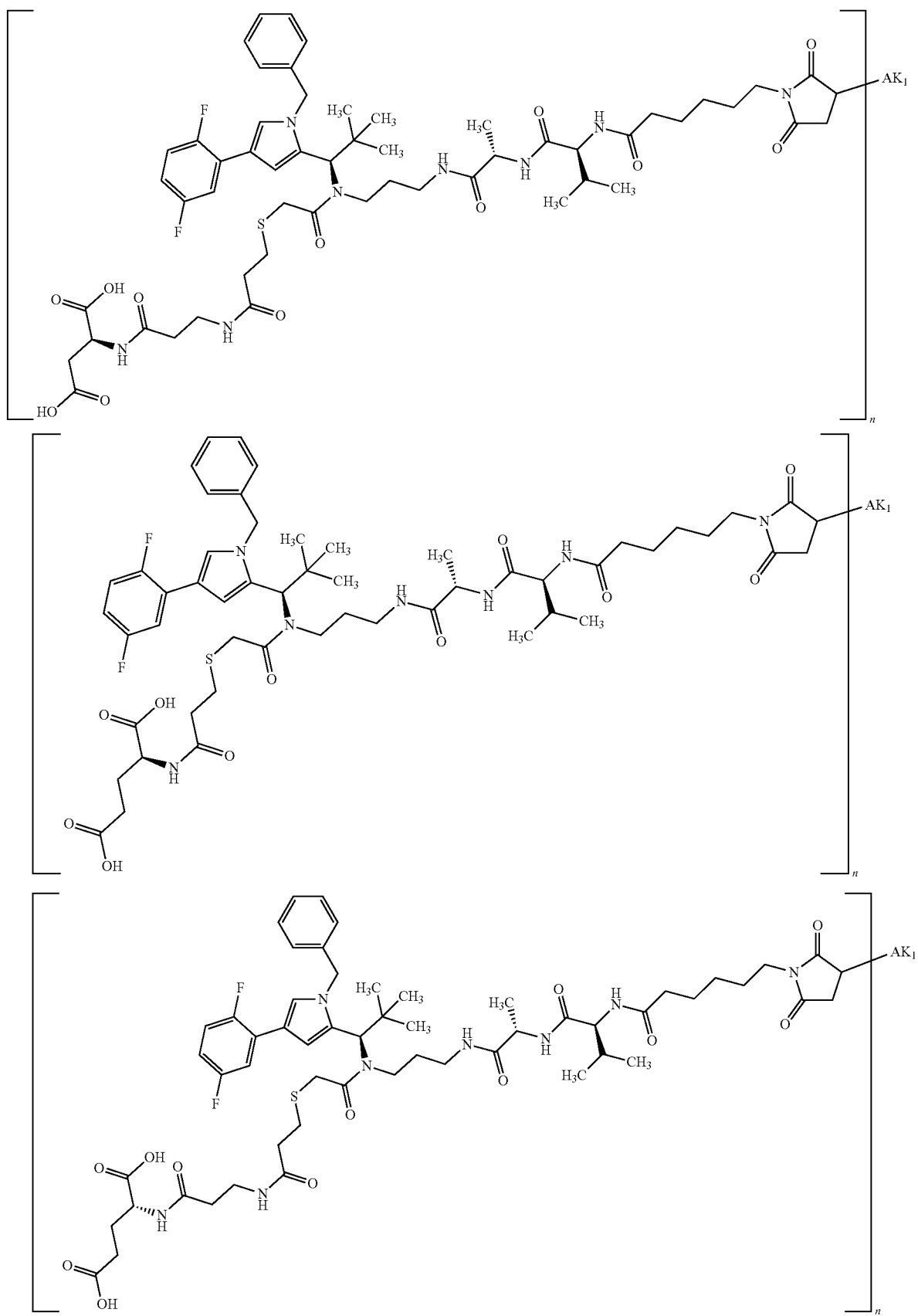

181 182
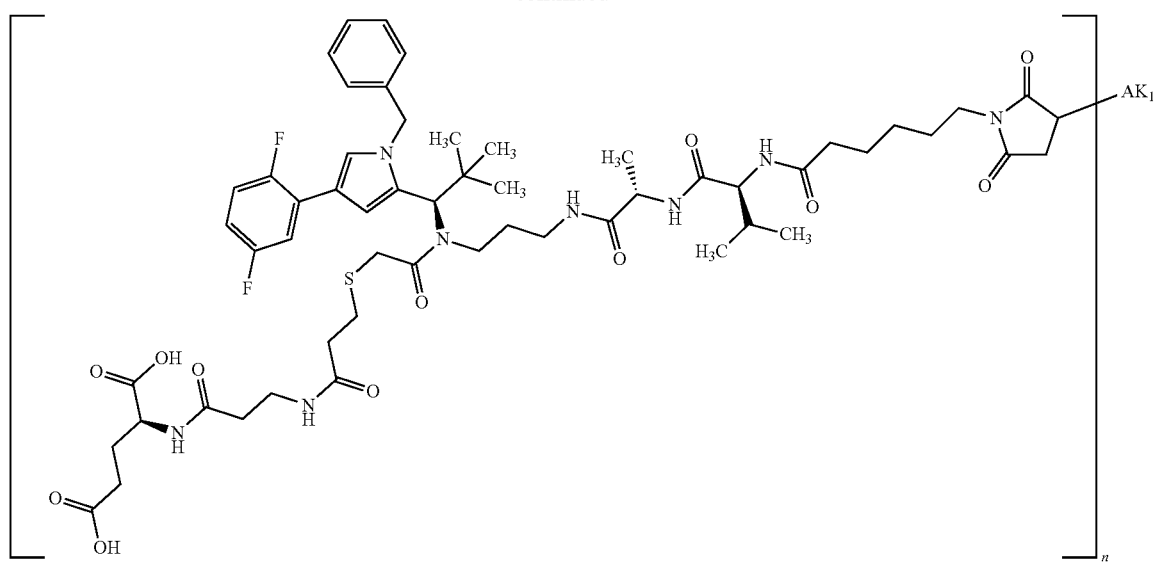
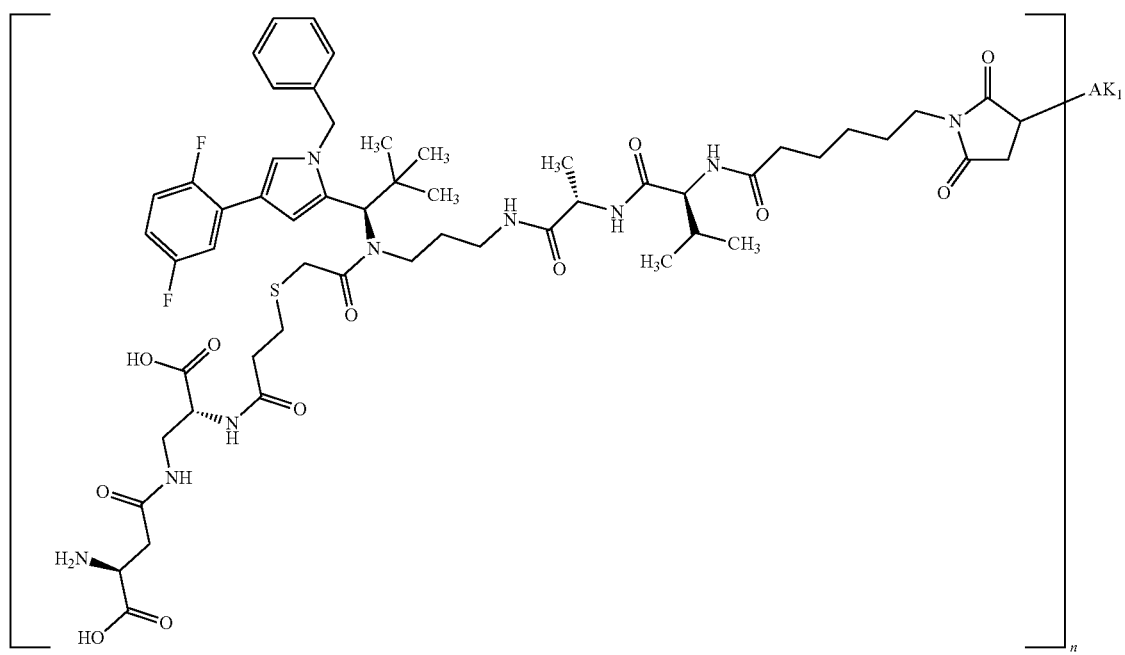

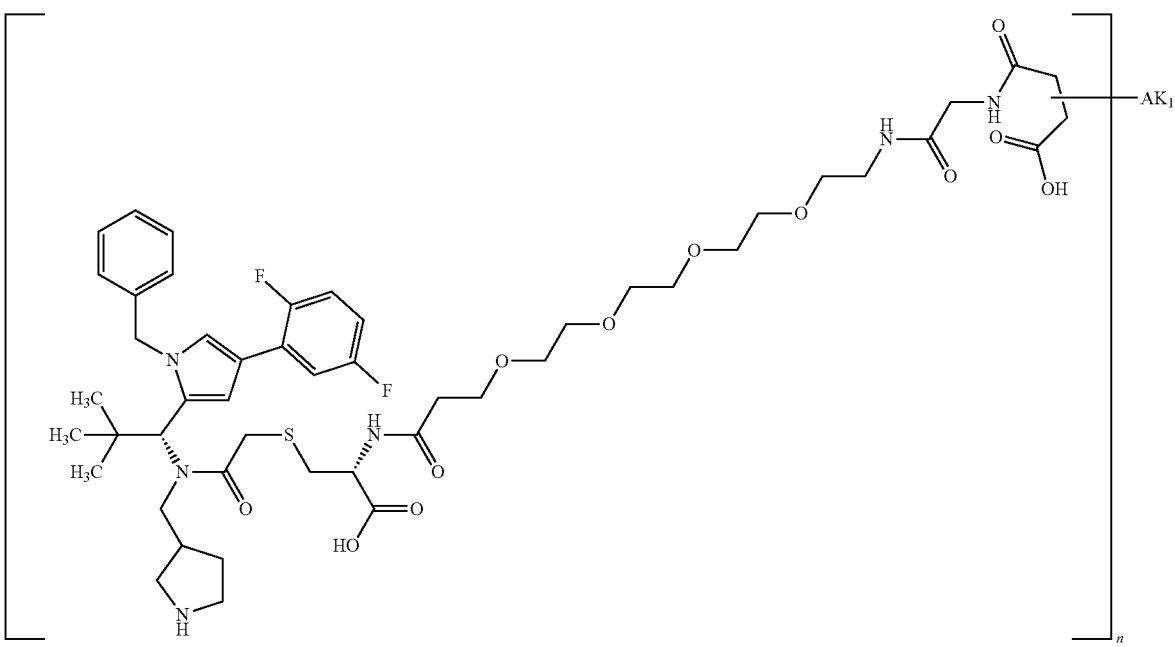
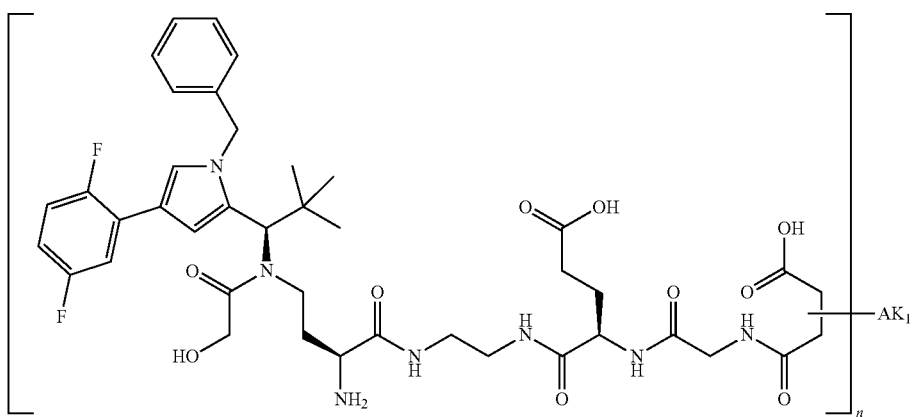
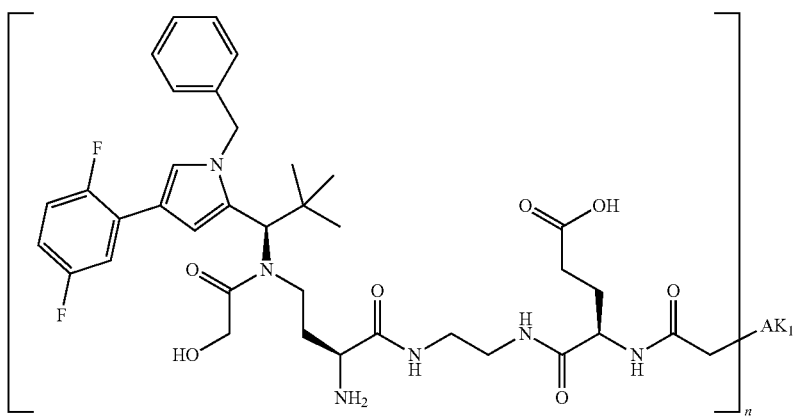

Further Conjugates
Further conjugates may have one of the following formulae:
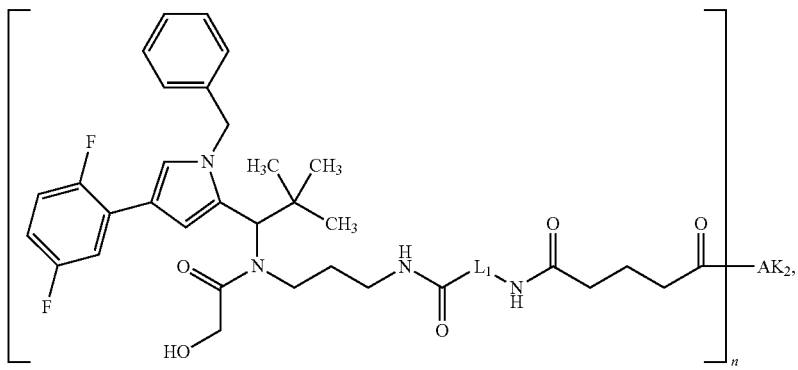
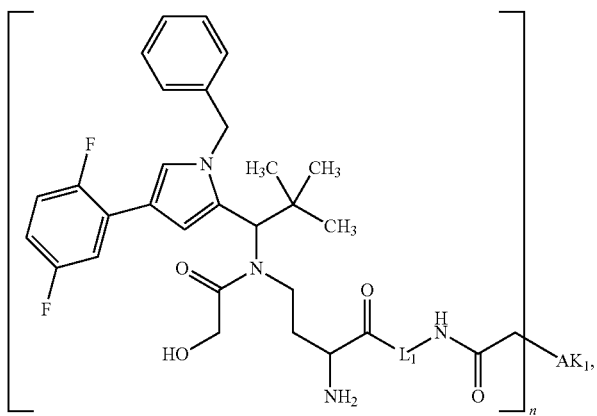
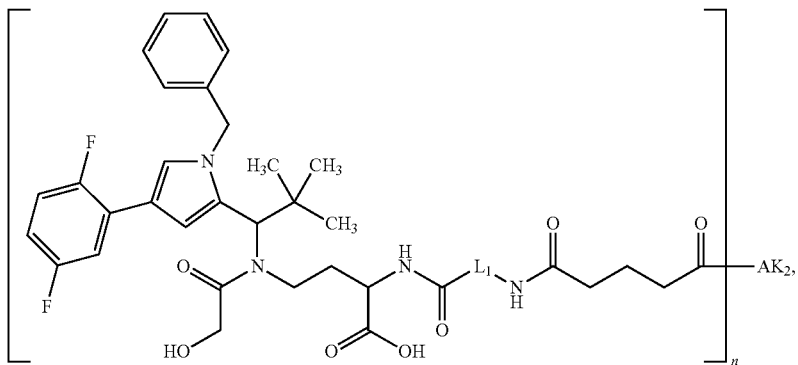
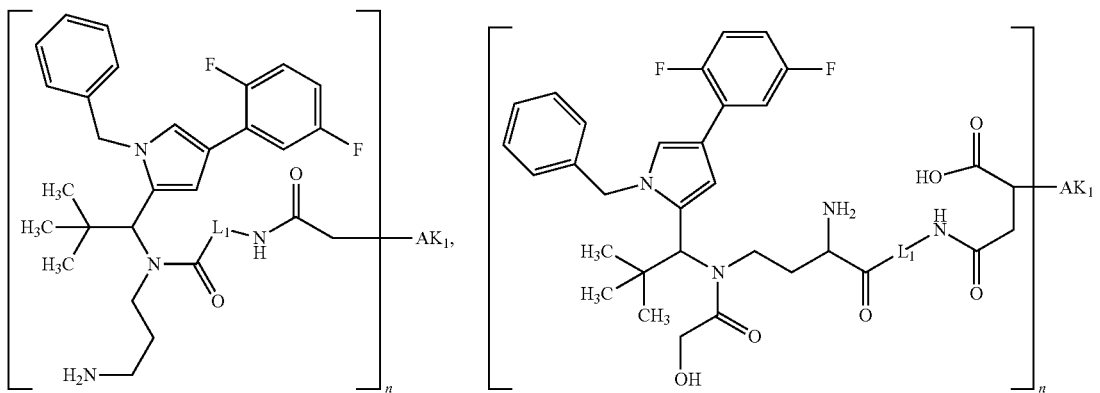

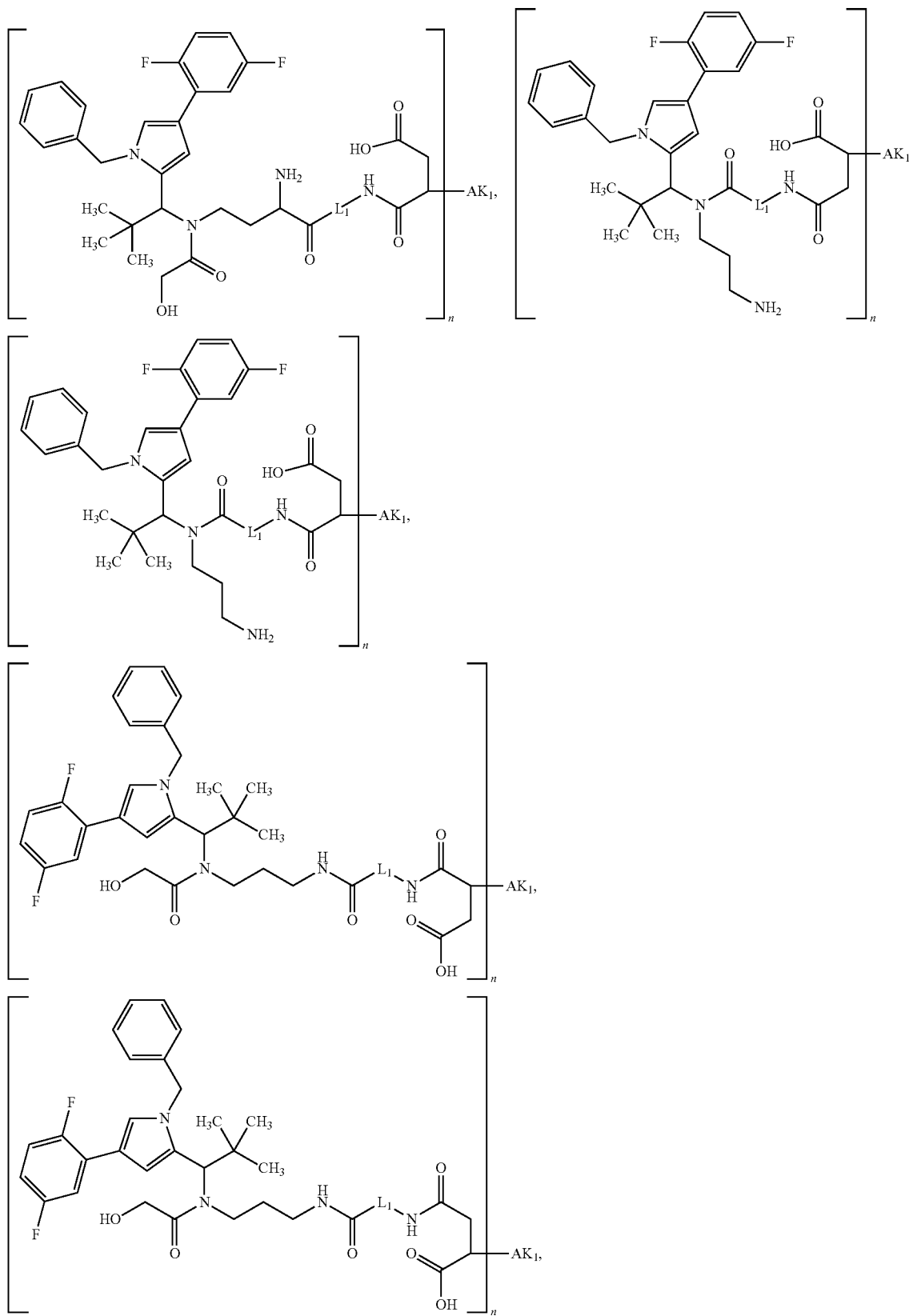

189 190
-continued
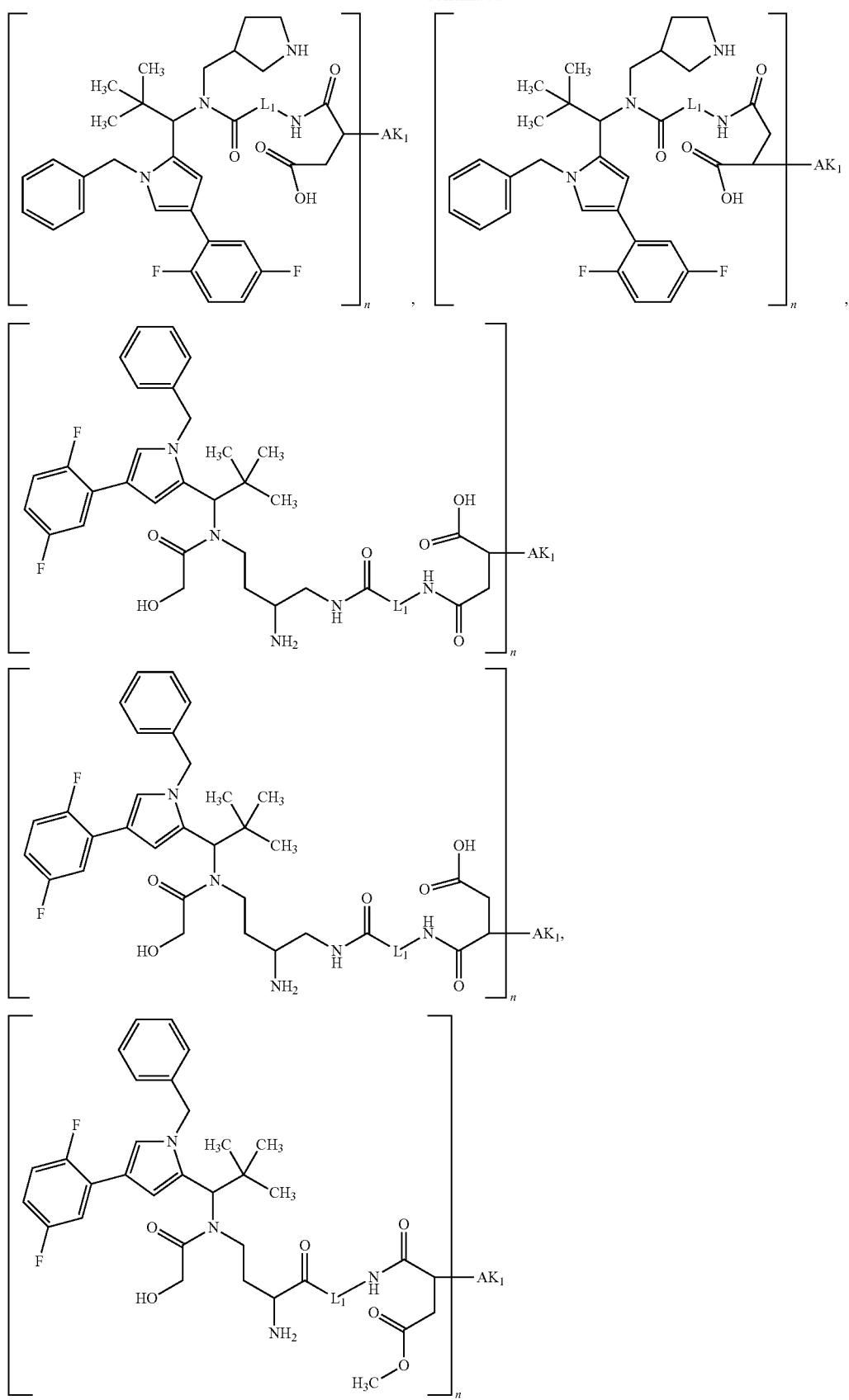

-continued
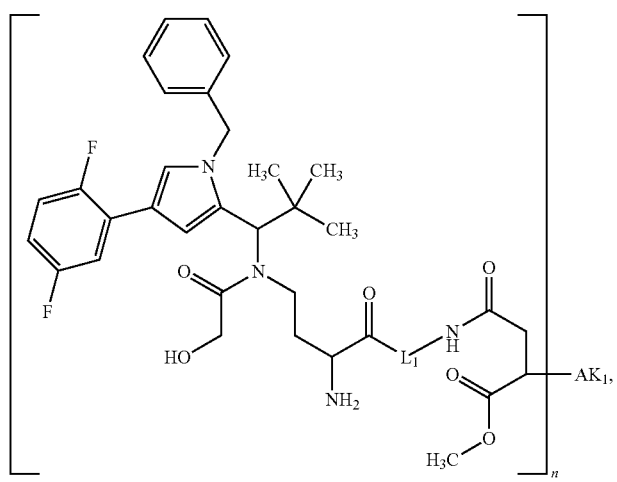
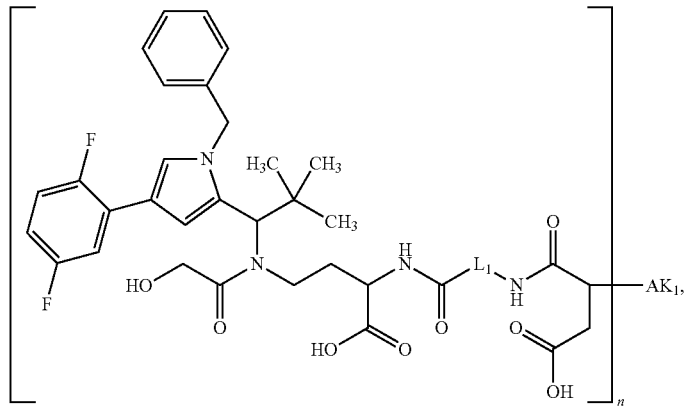
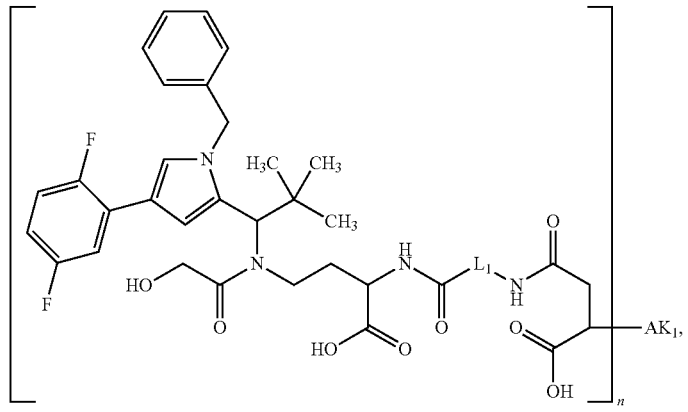
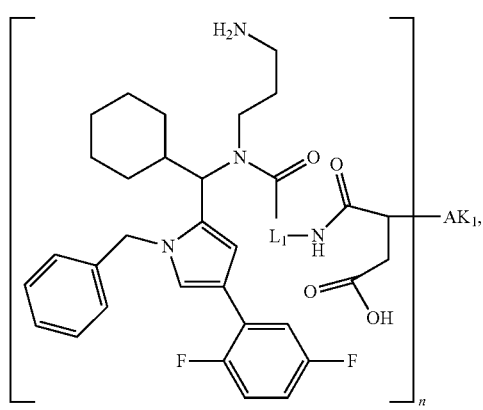
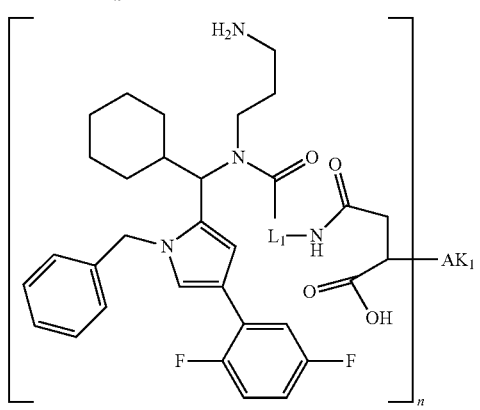

-continued
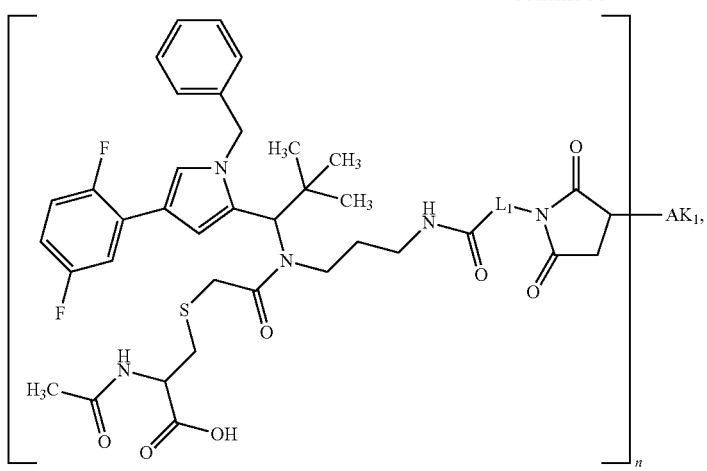
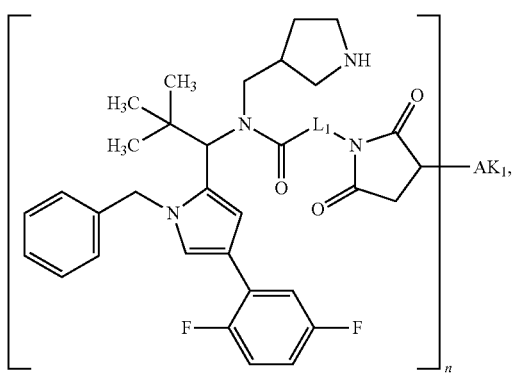
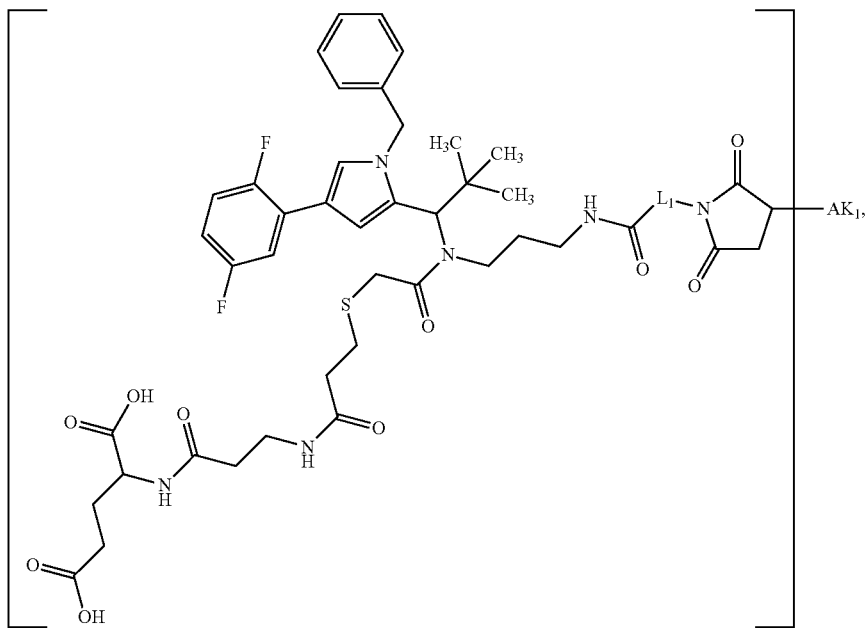

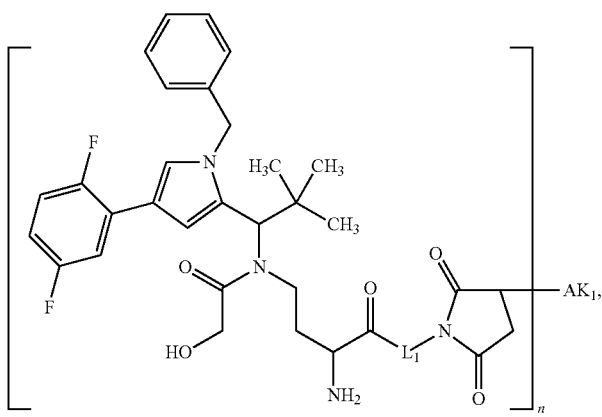
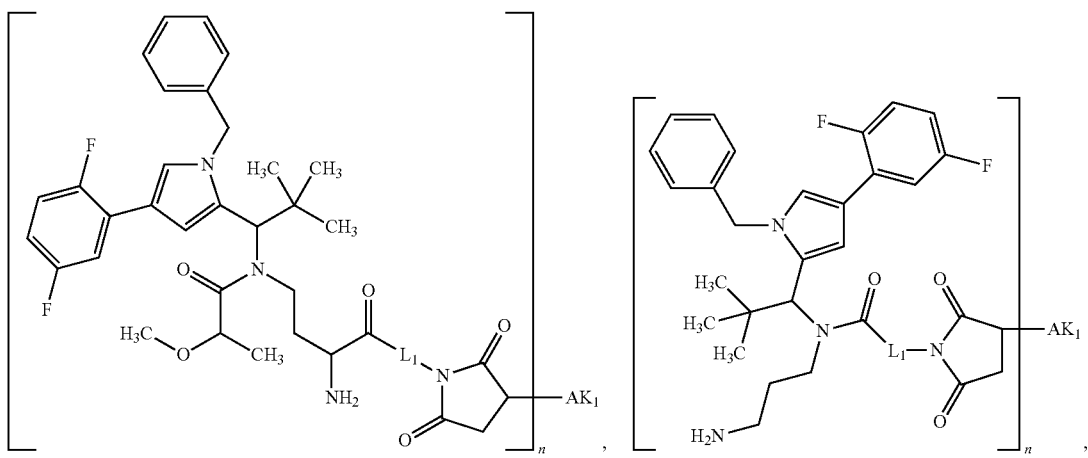
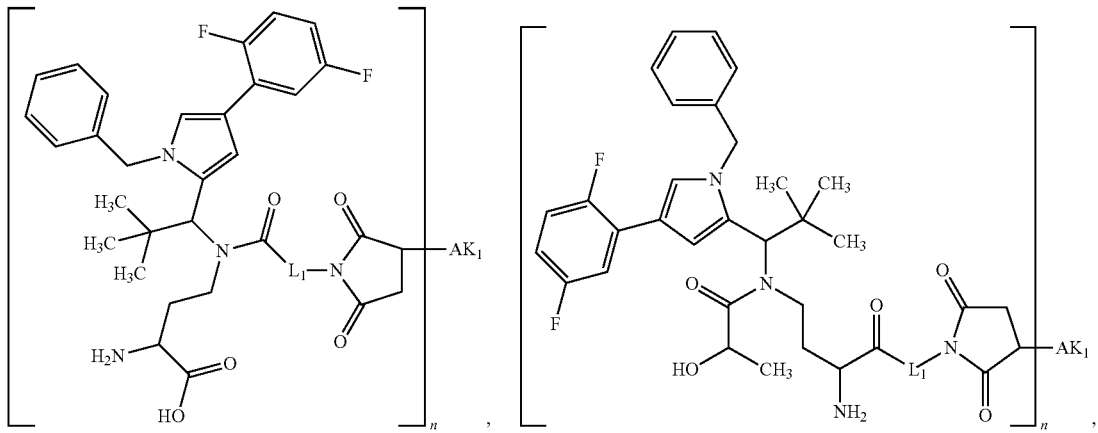

197
198
-continued
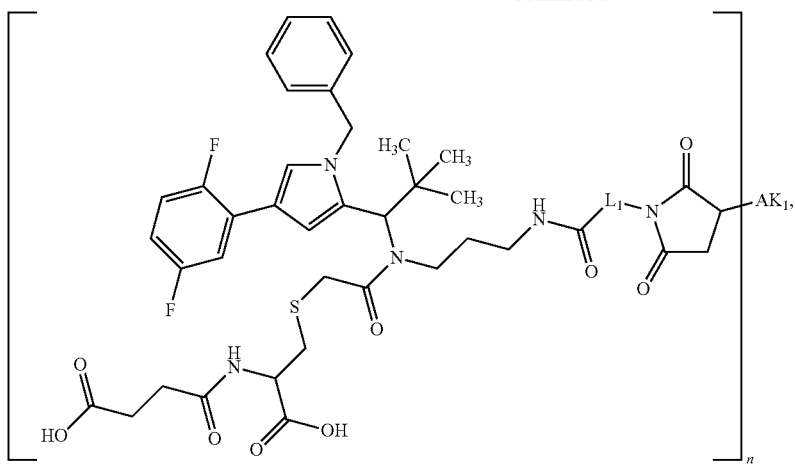
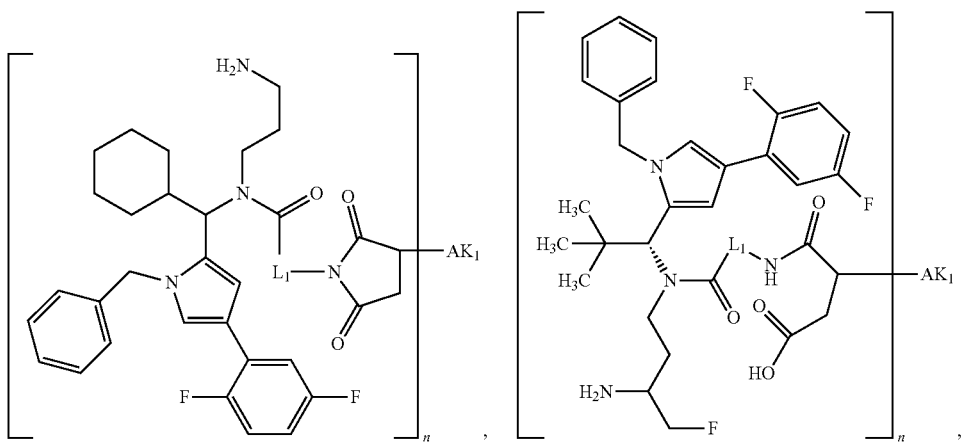
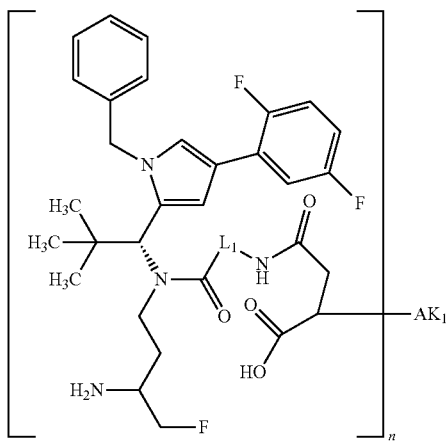

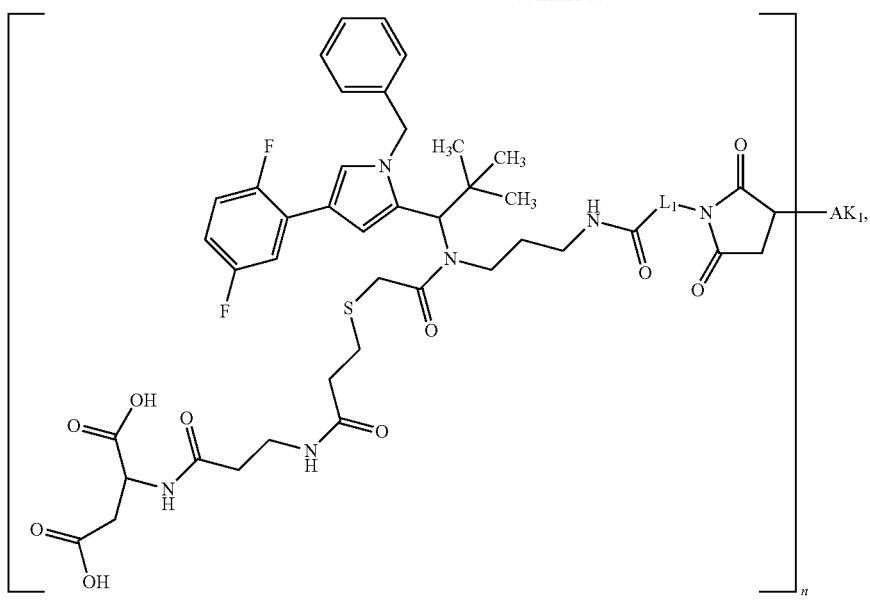
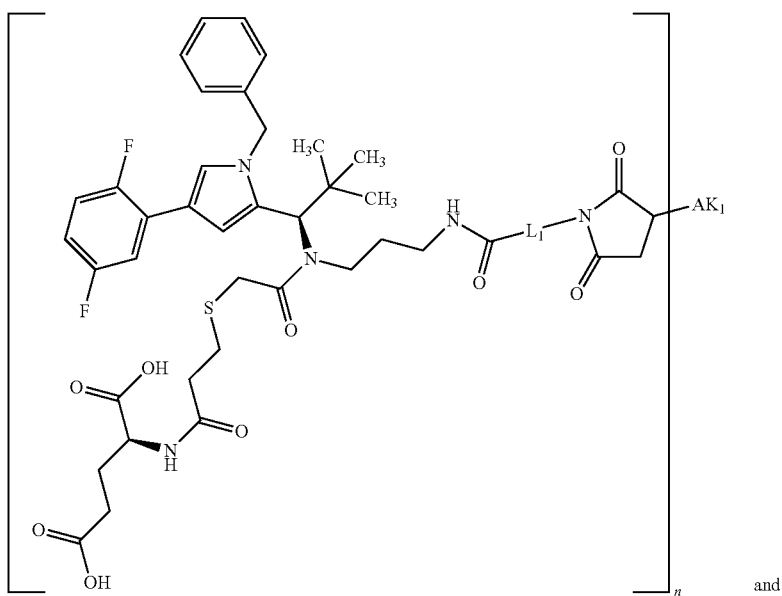
and

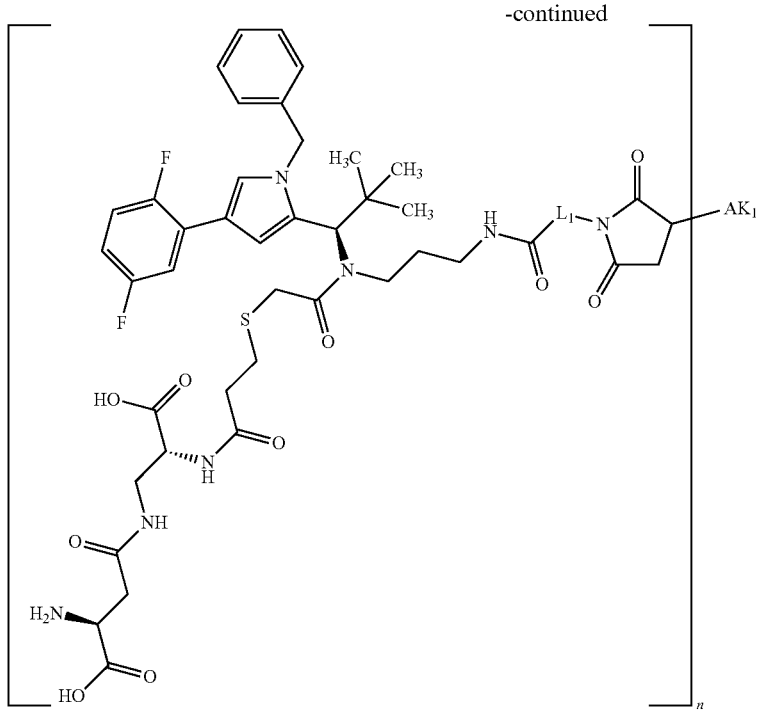

where
AK1 represents an antibody attached via cysteine and AK2 represents an antibody attached via lysine, which antibody binds to CD123 and represents a chimeric or humanized variant of the antibody 7G3 or 12F1 or is an antibody fragment thereof, n represents a number from 1 to 20; and $L_1$ represents a straight-chain or branched hydrocarbon chain having 1 to 30 carbon atoms which may be interrupted once or more than once, identically or differently, by —O—, —S—, —C(=O)—, —S(=O)$_2$—, —NH—, cyclopentyl, piperidinyl, phenyl, where the straight-chain or branched hydrocarbon chain may be substituted by —COOH or —NH$_2$, and their salts, solvates, salts of the solvates and epimers thereof.

Here, the linker $L_1$ preferably represents the group

§ —NH—(CH$_2$)$_2$—§ §;
§ —NH—(CH$_2$)$_6$—§ §;
§ —NH—(CH$_2$)$_2$—O—(CH$_2$)$_2$—§ §;
§ —NH—CH(COOH)—(CH$_2$)$_4$—§ §
§ —NH—NH—C(=O)—(CH$_2$)$_5$—§ §;
§ —NH—(CH$_2$)$_2$—C(=O)—O—(CH$_2$)$_2$—§ §;
§ —NH—(CH$_2$)$_2$—C(=O)—NH—(CH$_2$)$_2$—§ §;
§ —NH—(CH$_2$)$_2$—NH—C(=O)—CH$_2$—§ §;
§ —NH—(CH$_2$)$_3$—NH—C(=O)—CH$_2$—§ §;
§ —NH—(CH$_2$)$_2$—NH—C(=O)—(CH$_2$)$_2$—§ §;
§ —NH—(CH$_2$)$_2$—NH—C(=O)—(CH$_2$)$_5$—§ §;
§ —NH—(CH$_2$)$_2$—NH—C(=O)—CH(CH$_3$)— § §;
§ —NH—(CH$_2$)$_2$—O—(CH$_2$)$_2$—NH—C(=O)—CH$_2$—§ §;
§ —NH—CH(COOH)—CH$_2$—NH—C(=O)—CH$_2$—§ §;
§ —NH—CH(COOH)—(CH$_2$)$_2$—NH—C(=O)—CH$_2$—§ §;
§ —NH—CH(COOH)—(CH$_2$)$_4$—NH—C(=O)—CH$_2$—§ §;
§ —NH—CH(COOH)—CH$_2$—NH—C(=O)—(CH$_2$)$_2$—§ §;
§ —NH—(CH$_2$)$_2$—NH—C(=O)—CH(C$_2$H$_4$COOH)—§ §;
§ —NH—(CH$_2$)$_2$—NH—C(=O)—((CH$_2$)$_2$—O)$_3$—(CH$_2$)$_2$—§ §;
§ —NH—(CH$_2$)$_2$—S(=O)$_2$—(CH$_2$)$_2$—NH—C(=O)—CH$_2$—§ §;
§ —NH—(CH$_2$)$_2$—NH—C(=O)—CH$_2$—NH—C(=O)—CH$_2$—§ §;
§ —NH—(CH$_2$)$_3$—NH—C(=O)—CH$_2$—NH—C(=O)—CH$_2$—§ §;
§ —NH—CH(COOH)—CH$_2$—NH—C(=O)—CH(CH$_2$COOH)—§ §;
§ —NH—(CH$_2$)$_2$—NH—C(=O)—CH(C$_2$H$_4$COOH)—NH—C(=O)—CH$_2$—§ §;
§ —NH—CH(COOH)—CH$_2$—NH—C(=O)—(CH$_2$)$_2$—NH—C(=O)—CH$_2$—§ §;
§ —NH—(CH$_2$)$_2$—NH—C(=O)—(CH$_2$)$_2$—CH(COOH)—NH—C(=O)—CH$_2$—§ §;
§ —NH—CH(COOH)—CH$_2$—NH—C(=O)—CH(CH$_2$OH)—NH—C(=O)—CH$_2$—§ §;
§ —NH—CH[C(=O)—NH—(CH$_2$)$_2$—O)$_4$—(CH$_2$)$_2$COOH]—CH$_2$—NH—C(=O)—CH$_2$—§ §;
§ —NH—CH(COOH)—CH$_2$—NH—C(=O)—((CH$_2$)$_2$—O)$_4$—(CH$_2$)$_2$—NH—C(=O)—CH$_2$—§ §;
§ —NH—(CH$_2$)$_4$—CH(COOH)—NH—C(=O)—CH(CH$_3$)—NH—C(=O)—CH(isoC$_3$H$_7$)—§ §;
§ —NH—(CH$_2$)$_4$—CH(COOH)—NH—C(=O)—CH(CH$_3$)—NH—C(=O)—CH(isoC$_3$H$_7$)—NH—C(=O)—(CH$_2$)$_5$—§ §;
§ —NH—(CH$_2$)$_2$—C(=O)—NH—(CH$_2$)$_4$—CH(COOH)—NH—C(=O)—CH(CH$_3$)—NH—C(=O)—CH(isoC$_3$H$_7$)—NH—C(=O)—CH$_2$—§ §;
§ —NH—(CH$_2$)$_2$—C(=O)—NH—(CH$_2$)$_4$—CH(COOH)—NH—C(=O)—CH(CH$_3$)—NH—C(=O)—CH(isoC$_3$H$_7$)—NH—C(=O)—(CH$_2$)$_5$—§ §;

203

§—NH—(CH₂)₄—CH(COOH)—NH—C(=O)—CH[(CH₂)₃—NH—C(=O)—NH₂]—NH—C(=O)—CH(isoC₃H₇)—NH—C(=O)—(CH₂)₅—§ §;

§—NH—(CH₂)₂—NH—C(=O)—(CH₂)₂—CH(COOH)—NH—C(=O)—CH(CH₃)—NH—C(=O)—CH(isoC₃H₇)—NH—C(=O)—(CH₂)₅—§ §;

204

§—NH—CH(CH₃)—C(=O)—NH—(CH₂)₄—CH(COOH)—NH—C(=O)—CH(CH₃)—NH—C(=O)—CH(isoC₃H₇)—NH—C(=O)—(CH₂)₅—§ §;

§—NH—(CH₂)₂—C(=O)—NH—(CH₂)₄—CH(COOH)—NH—C(=O)—CH[(CH₂)₃—NH—C(=O)—NH₂]—NH—C(=O)—CH(isoC₃H₇)—NH—C(=O)—(CH₂)₅—§ §;

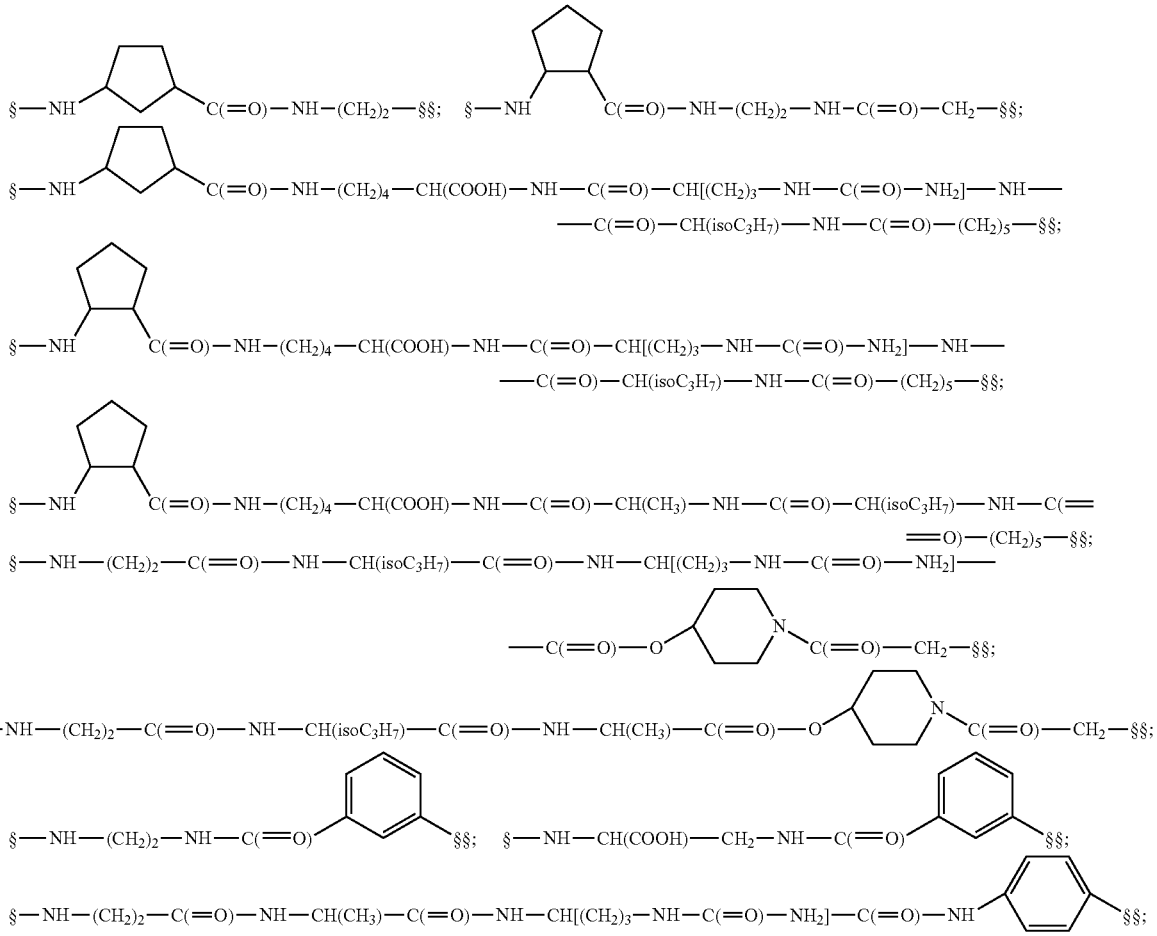

§—(CH₂)₂—C(=O)—NH—(CH₂)₂—§ §;
§—(CH₂)₂—C(=O)—NH—(CH₂)₂—NH—C(=O)—CH₂—§ §;
§—CH(CH₃)—NH—C(=O)—CH(isoC₃H₇)—§ §;
§—CH(CH₃)—NH—C(=O)—CH(isoC₃H₇)—NH—C(=O)—CH₂—§ §;
§—CH(CH₃)—NH—C(=O)—CH(isoC₃H₇)—NH—C(=O)—(CH₂)₅—§ §;
§—(CH₂)₂—C(=O)—NH—((CH₂)₂—O)₄—(CH₂)₂—NH—C(=O)—CH₂—§ §;
§—CH(CH₃)—NH—C(=O)—CH(isoC₃H₇)—NH—C(=O)—((CH₂)₂—O)₄—(CH₂)₂—NH—C(=O)—(CH₂)₂—§ §;

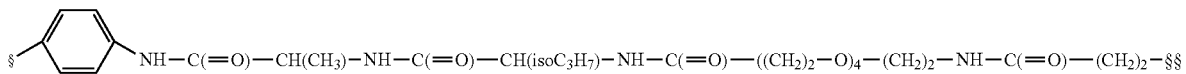

§—CH₂—S—(CH₂)₂—C(=O)—NH—(CH₂)₂—§ §;
§—CH₂—S—(CH₂)₅—C(=O)—NH—(CH₂)₂—§ §;
§ —CH₂—S—CH₂CH(COOH)—NH—C(=O)—CH₂—§ §;
§ —CH₂—S—CH₂CH(COOH)—NH—C(=O)—(CH₂)₅—§ §;
§ —CH₂—S—(CH₂)₂—C(=O)—NH—((CH₂)₂—O)₂—(CH₂)₂—§ §;
§ —CH₂—S—(CH₂)₂—C(=O)—NH—((CH₂)₂—O)₂—(CH₂)₅—§ §;
§ —CH₂—S—(CH₂)₂—C(=O)—NH—(CH₂)₂—NH—C(=O)—CH₂—§ §;
§ —CH₂—S—(CH₂)₂—C(=O)—NH—(CH₂)₂—NH—C(=O)—CH₅— § §;
§ —CH₂—S—(CH₂)₂—C(=O)—NH—CH(COOH)—CH₂—NH—C(=O)—CH₂—§ §;
§ —CH₂—S—CH₂CH(NH₂)—C(=O)—NH—(CH₂)₂—NH—C(=O)—(CH₂)₅—§ §;
§ —CH₂—S—(CH₂)₂—C(=O)—NH—((CH₂)₂—O)₂—(CH₂)₂—NH—C(=O)—CH₂—§ §;
§ —CH₂—S—(CH₂)₂—C(=O)—NH—((CH₂)₂—O)₄—(CH₂)₂—NH—C(=O)—CH₂—§ §;
§ —CH₂—S—(CH₂)₂—C(=O)—NH—((CH₂)₂—O)₂—(CH₂)₂—NH—C(=O)—(CH₂)₅—§ §;
§ —CH₂—S—(CH₂)₂—C(=O)—NH—((CH₂)₂—O)₄—(CH₂)₂—NH—C(=O)—(CH₂)₅—§ §;
§ —CH₂—S—CH₂CH(COOH)—NH—C(=O)—((CH₂)₂—O)₂—(CH₂)₂—NH—C(=O)—CH₂—§ §;
§ —CH₂—S—CH₂CH(COOH)—NH—C(=O)—((CH₂)₂—O)₄—(CH₂)₂—NH—C(=O)—CH₂—§ §;
§ —CH₂—S—CH₂CH(COOH)—NH—C(=O)—((CH₂)₂—O)₄—(CH₂)₂—NH—C(=O)—(CH₂)₂—§ §;
§ —CH₂—S—(CH₂)₂—CH(COOH)—NH—C(=O)—((CH₂)₂—O)₄—(CH₂)₂—NH—C(=O)—(CH₂)₂—§§;
§ —CH₂—S—(CH₂)₂—C(=O)—NH—CH(C₂H₄COOH)—C(=O)—NH—(CH₂)₂—NH—C(=O)—CH₂—§§;
§ —CH₂—S—CH₂CH[NH—C(=O)—(CH₂)₂—COOH]—C(=O)—NH—(CH₂)₂—NH—C(=O)—CH₂—§§;
§ —CH₂—S—CH₂CH[NH—C(=O)—((CH₂)₂—O)₄—CH₃]—C(=O)—NH—(CH₂)₂—NH—C(=O)—CH₂— § §;
§ —CH₂—S—CH₂CH(COOH)—NH—C(=O)—CH(CH₃)—NH—C(=O)—CH(isoC₃H₇)—NH—C(=O)—CH₂—§ §;
§ —CH₂—S—CH₂CH[NH—C(=O)—(CH₂)₂—COOH]—C(=O)—NH—(CH₂)₂—S(=O)₂—(CH₂)₂—NH—C(=O)—CH₂—§ §;
§ —CH₂—S—CH₂CH[NH—C(=O)—(CH₂)₂—COOH]—C(=O)—NH—((CH₂)₂—O)₄—(CH₂)₂—NH—C(=O)—CH₂—§ §;
§ —CH₂—S—CH₂CH[C(=O)—NH—(CH₂)₂—COOH]—NH—C(=O)—((CH₂)₂—O)₄—(CH₂)₂—NH—C(=O)—CH₂—§ §;
§ —CH₂—S—CH₂CH[C(=O)—NH—(CH₂)₂—COOH]—NH—C(=O)—((CH₂)₂—O)₄—(CH₂)₂—NH—C(=O)—(CH₂)₂—§ §;
§ —CH₂—S—CH₂CH(COOH)—NH—C(=O)—(CH₂)₂CH(COOH)—NH—C(=O)—((CH₂)₂—O)₄—(CH₂)₂—NH—C(=O)—CH₂—§ §;
§ —CH₂—S—CH₂CH[C(=O)—NH—((CH₂)₂—O)₄—(CH₂)₂—COOH]—NH—C(=O)—((CH₂)₂—O)₄—(CH₂)₂—NH—C(=O)—CH₂—§ §;

or
§ —CH₂—S—CH₂CH(COOH)—NH—C(=O)—CH[(CH₂)₂—COOH]—NH—C(=O)—((CH₂)₂—O)₄—(CH₂)₂—NH—C(=O)—(CH₂)₂—§ §,
where
§ represents the bond to the active compound molecule and
§ § represents the bond to the antibody and
isoC₃H₇ represents an isopropyl radical.

These conjugates also include their salts, solvates, salts of the solvates and epimers.

Therapeutic Use

The hyper-proliferative diseases, for the treatment of which the compounds according to the invention may be employed, include in particular the group of cancer and tumour diseases. In the context of the present invention, these are understood to mean especially the following diseases, but without any limitation thereto: mammary carcinomas and mammary tumours (mammary carcinomas including ductal and lobular forms, also in situ), tumours of the respiratory tract (small-cell and non-small-cell pulmonary carcinoma, bronchial carcinoma), cerebral tumours (e.g. of the brain stem and of the hypothalamus, astrocytoma, ependymoma, glioblastoma, glioma, medulloblastoma, meningioma and neuro-ectodermal and pineal tumours), tumours of the digestive organs (carcinomas of the oesophagus, stomach, gall bladder, small intestine, large intestine, rectum and anal carcinomas), liver tumours (inter alia hepatocellular carcinoma, cholangiocarcinoma and mixed hepatocellular cholangiocarcinoma), tumours of the head and neck region (larynx, hypopharynx, nasopharynx, oropharynx, lips and oral cavity carcinomas, oral melanomas), skin tumours (basaliomas, spinaliomas, squamous cell carcinomas, Kaposi's sarcoma, malignant melanoma, non-melanomatous skin cancer, Merkel cell skin cancer, mast cell tumours), tumours of the stroma and connective tissue (inter alia soft tissue sarcomas, osteosarcomas, malignant fibrous histiocytomas, chondrosarcomas, fibrosarcomas, haemangiosarcomas, leiomyosarcomas, liposarcomas, lymphosarcoma and rhabdomyosarcomas), tumours of the eyes (inter alia intraocular melanoma and retinoblastoma), tumours of the endocrine and exocrine glands (e.g. of the thyroid and parathyroid glands, pancreas and salivary gland carcinomas, adenocarcinomas), tumours of the urinary tract (tumours of the bladder, penis, kidney, renal pelvis and ureter) and tumours of the reproductive organs (carcinomas of the endometrium, cervix, ovary, vagina, vulva and uterus in women and carcinomas of the prostate and testes in men). These also include proliferative diseases of the blood, the lymph system and the spinal cord, in solid form and as circulating cells, such as leukaemias, lymphomas and myeloproliferative diseases, for example acute myeloid, acute lymphoblastic, chronic lymphocytic, chronic myelogenous and hairy cell leukaemia, and AIDS-correlated lymphomas, Hodgkin's lymphomas, non-Hodgkin's lymphomas, cutaneous T cell lymphomas, Burkitt's lymphomas and lymphomas in the central nervous system.

These well-characterized diseases in humans can also occur with a comparable aetiology in other mammals and can likewise be treated there with the compounds of the present invention.

The treatment of the cancer diseases mentioned above with the compounds according to the invention comprises both a treatment of the solid tumors and a treatment of metastasizing or circulating forms thereof.

In the context of this invention, the term "treatment" or "treat" is used in the conventional sense and means attending to, caring for and nursing a patient with the aim of combating, reducing, attenuating or alleviating a disease or health abnormality, and improving the living conditions impaired by this disease, as, for example, in the event of a cancer.

The present invention thus further provides for the use of the compounds of the invention for treatment and/or prevention of disorders, especially of the aforementioned disorders.

The present invention further provides for the use of the compounds according to the invention for producing a medicament for the treatment and/or prevention of disorders, especially of the aforementioned disorders.

The present invention further provides for the use of the compounds of the invention in a method for treatment and/or prevention of disorders, especially of the aforementioned disorders.

The present invention further provides a process for treatment and/or prevention of disorders, especially of the aforementioned disorders, using an effective amount of at least one of the compounds according to the invention.

The compounds of the invention can be used alone or, if required, in combination with one or more other pharmacologically active substances, provided that this combination does not lead to undesirable and unacceptable side effects. Accordingly, the present invention further provides medicaments comprising at least one of the compounds of the invention and one or more further active ingredients, especially for treatment and/or prevention of the aforementioned disorders.

For example, the compounds of the present invention can be combined with known anti-hyper-proliferative, cytostatic or cytotoxic substances for the treatment of cancer diseases. Examples of suitable combination active compounds include:

131I-chTNT, abarelix, abiraterone, aclarubicin, afatinib, aflibercept, aldesleukin, alemtuzumab, alisertib, alitretinoin, alpharadin (radium-223 chloride), altretamine, aminoglutethimide, AMP-514, amrubicin, amsacrine, anastrozole, arglabin, arsenic trioxide, asparaginase, AT9283, axitinib, azacitidine, basiliximab, belotecan, bendamustine, bevacizumab, bexarotene, bicalutamide, bisantrene, bleomycin, BMS-936559, bosutinib, bortezomib, brentuximab vedotin, buserelin, busulfan, cabazitaxel, cabozantinib, calcium folinate, calcium levofolinate, capecitabine, carboplatin, carfilzomib (proteasome inhibitor), carmofur, carmustine, catumaxomab, celecoxib, celmoleukin, cetuximab, chlorambucil, chlormadinone, chlormethine, cisplatin, cladribine, clodronic acid, clofarabine, copanlisib, crisantaspase, crizotinib, cyclophosphamide, CYC116, cyproterone, cytarabine, dacarbazine, dactinomycin, darbepoetin alfa, dabrafenib, danusertib, dasatinib, daunorubicin, decitabine, degarelix, denileukin diftitox, denosumab, deslorelin, dibrospidium chloride, docetaxel, doxifluridine, doxorubicin, doxorubicin+estrone, eculizumab, edrecolomab, elliptinium acetate, eltrombopag, endostatin, ENMD-2076, enocitabine, epirubicin, epitiostanol, epoetin alfa, epoetin beta, eptaplatin, eribulin, erlotinib, estradiol, estramustine, etoposide, everolimus, exemestane, fadrozole, filgrastim, fludarabine, fluorouracil, flutamide, formestane, fotemustine, fulvestrant, gallium nitrate, ganirelix, gefitinib, gemcitabine, gemtuzumab, glutoxim, goserelin, histamine dihydrochloride, histrelin, hydroxycarbamide, 1-125 seeds, ibandronic acid, ibritumomab tiuxetan, ibrutinib, idarubicin, ifosfamide, imatinib, imiquimod, INCB24360, improsulfan, interferon alpha, interferon beta, interferon gamma, ipilimumab, irinotecan, ixabepilone, lambrolizumab, lanreotide, lapatinib, lenalidomide, lenograstim, lentinan, letrozole, leuprorelin, levamisole, lisuride, lobaplatin, lomustine, lonidamine, masoprocol, medroxyprogesterone, megestrol, melphalan, mepitiostane, mercaptopurine, methotrexate, methoxsalen, methyl aminolevulinate, methyltestosterone, mifamurtide, miltefosine, miriplatin, mitobronitol, mitoguazone, mitolactol, mitomycin, mitotane, mitoxantrone, MLN-8054, Mpsl inhibitors (disclosed in WO2013/087579, in particular Example 01.01, WO2014/131739, in particular Example 2), nedaplatin, nelarabine, nemorubicin, nilotinib, nilutamide, nimotuzumab, nimustine, nitracrine, nivolumab, NMS-P715, NMS-P937, ofatumumab, omeprazole, oprelvekin, oxaliplatin, p53 gene therapy, paclitaxel, palbociclib, palifermin, palladium-103 seed, pamidronic acid, panitumumab, pazopanib, pegaspargase, PEG-epoetin beta (methoxy-PEG-epoetin beta), pegfilgrastim, peginterferon alfa 2b, pemetrexed, pentazocine, pentostatin, peplomycin, perfosfamide, picibanil, pirarubicin, plerixafor, plicamycin, poliglusam, polyestradiol phosphate, polysaccharide-K, ponatinib, porfimer sodium, pralatrexate, prednimustine, procarbazine, quinagolide, R763, raloxifene, raltitrexed, ranimustine, razoxane, refametinib, regorafenib, risedronic acid, rituximab, romidepsin, romiplostim, roninciclib, ruxolitinib, sargramostim, sipuleucel-T, sizofiran, sobuzoxane, sodium glycididazole, SNS-314, sorafenib, streptozocin, sunitinib, talaporfin, tamibarotene, tamoxifen, tasonermin, teceleukin, tegafur, tegafur+gimeracil+oteracil, temoporfin, temozolomide, temsirolimus, teniposide, testosterone, tetrofosmin, thalidomide, thiotepa, thymalfasin, TKM-PLK1, tioguanine, tocilizumab, topotecan, toremifene, tositumomab, tozasertib, trabectedin, trametinib, trastuzumab, trastuzumab emtansine, treosulfan, tretinoin, trilostane, triptorelin, trofosfamide, tryptophan, ubenimex, valrubicin, vandetanib, vapreotide, vemurafenib, vinblastine, vincristine, vindesine, vinflunine, vinorelbine, volasertib, vorinostat, vorozole, XL228, yttrium-90 glass microspheres, zinostatin, zinostatin stimalamer, zoledronic acid, zorubicin.

In addition, the compounds of the present invention can be combined, for example, with binders which, by way of example, can bind to the following targets: OX-40, CD137/4-1BB, DR3, IDO1/IDO2, LAG-3, CD40.

In addition, the compounds according to the invention can also be used in combination with radiotherapy and/or surgical intervention.

Generally, the following aims can be pursued with the combination of compounds of the present invention with other cytostatically or cytotoxically active agents:

improved efficacy in slowing the growth of a tumour, in reducing its size or even in completely eliminating it, compared with treatment with an individual active compound;

the possibility of using the chemotherapeutics used in a lower dosage than in the case of monotherapy;

the possibility of a more tolerable therapy with fewer side effects compared with individual administration;

the possibility of treatment of a broader spectrum of neoplastic disorders;

the achievement of a higher rate of response to the therapy;

a longer survival time of the patient compared with present-day standard therapy.

In addition, the compounds according to the invention can also be used in combination with radiotherapy and/or surgical intervention.

The present invention further provides medicaments which comprise at least one compound of the invention, typically together with one or more inert, nontoxic, pharmaceutically suitable excipients, and for the use thereof for the aforementioned purposes.

The compounds of the invention can act systemically and/or locally. For this purpose, they can be administered in a suitable manner, for example parenterally, possibly inhalatively or as implants or stents.

The compounds of the invention can be administered in administration forms suitable for these administration routes.

Parenteral administration can bypass an absorption step (for example intravenously, intraarterially, intracardially, intraspinally or intralumbally) or include an absorption (for example intramuscularly, subcutaneously, intracutaneously, percutaneously or intraperitoneally). Administration forms suitable for parenteral administration include preparations for injection and infusion in the form of solutions, suspensions, emulsions or lyophilizates. Preference is given to parenteral administration, especially intravenous administration.

In general, it has been found to be advantageous in the case of parenteral administration to administer amounts of about 0.001 to 1 mg/kg, preferably about 0.01 to 0.5 mg/kg, of body weight to achieve effective results.

It may nevertheless be necessary in some cases to deviate from the stated amounts, specifically as a function of body weight, route of administration, individual response to the active ingredient, nature of the preparation and time or interval over which administration takes place. Thus, in some cases less than the abovementioned minimum amount may be sufficient, while in other cases the upper limit mentioned must be exceeded. In the case of administration of greater amounts, it may be advisable to divide them into several individual doses over the day.

EXAMPLES

The examples which follow illustrate the invention. The invention is not restricted to the examples.

Unless stated otherwise, the percentages in the tests and examples which follow are percentages by weight; parts are parts by weight. Solvent ratios, dilution ratios and concentration data for the liquid/liquid solutions are based in each case on volume.

If, in the description of experiments, the temperature at which the reaction is carried out is not stated, room temperature can be assumed.

Synthesis Routes:

Exemplary for the working examples, the schemes below show exemplary synthesis routes leading to the working examples:

Scheme 20: Synthesis of cysteine-linked ADCs

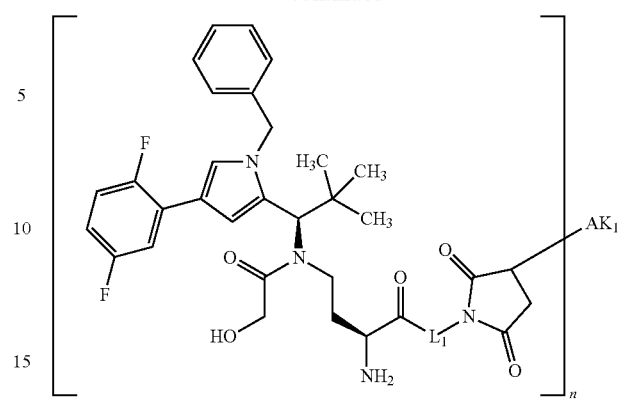

Scheme 21: Synthesis of cysteine-linked ADCs

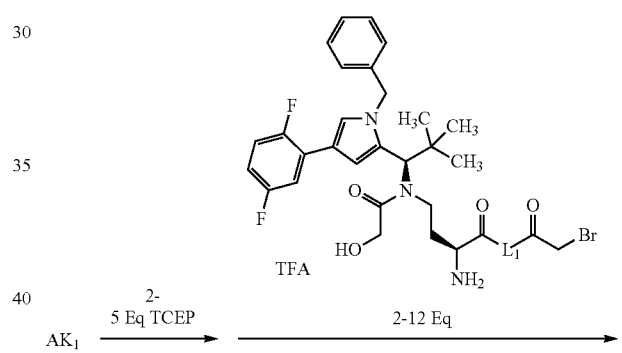

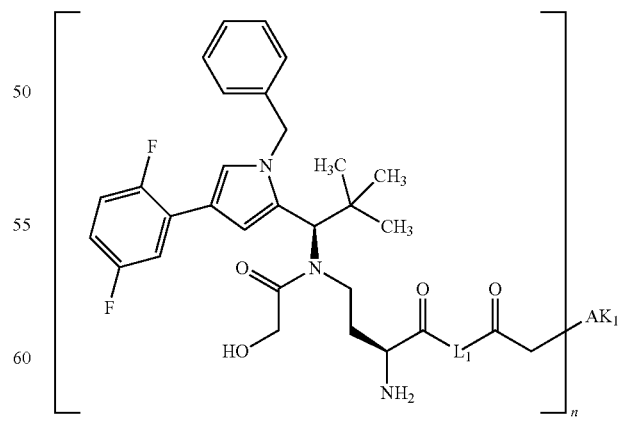

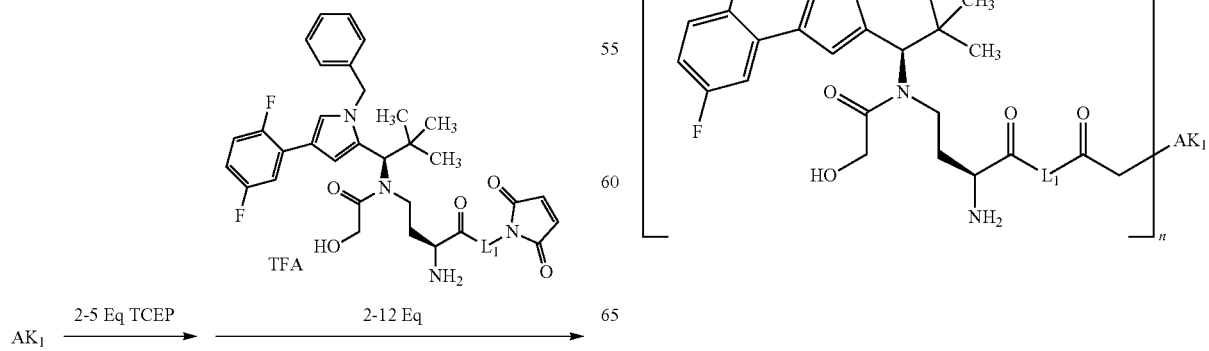

Scheme 22: Synthesis of intermediates
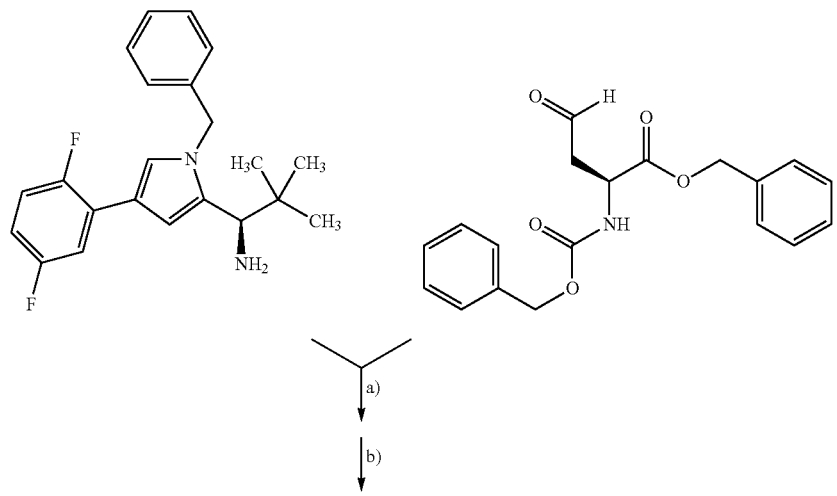
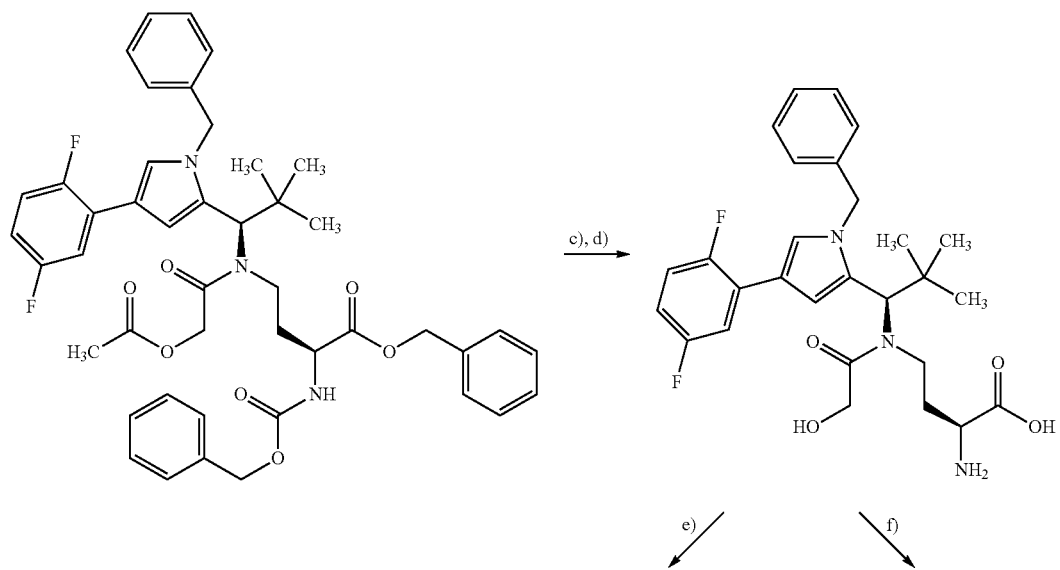

213
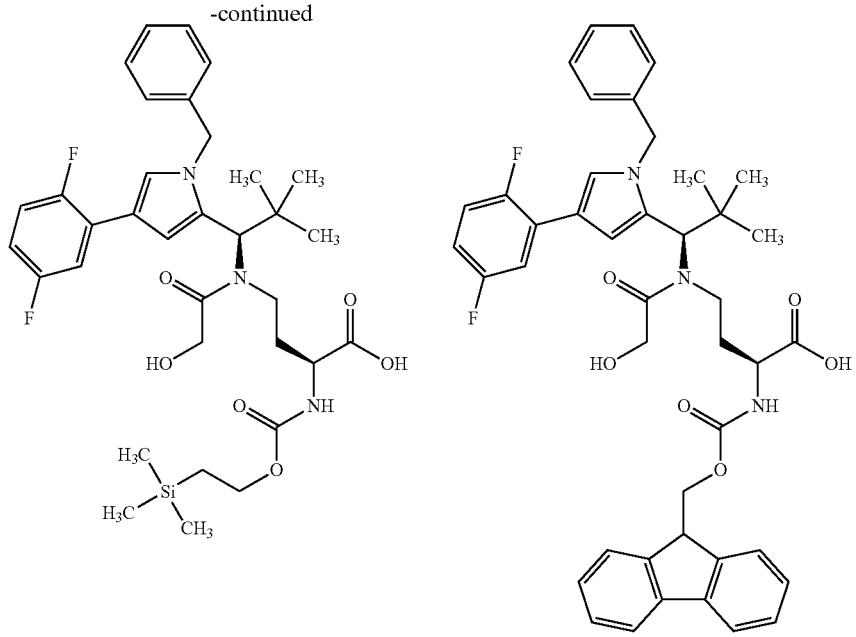
[a): for example sodium triacetoxyborohydride, acetic acid, DCM, RT, RT; b) for example acetoxyacetyl chloride, NEt3, DCM, RT; c) for example LiOH, THF/water, RT; d) for example H₂, Pd-C, EtOH, RT; e) for example Teoc-OSu, NEt3, dioxane, RT; f) for example Fmoc-Cl, diisopropylethylamine, dioxane/water 2:1, RT]
Scheme 24: Synthesis of intermediates
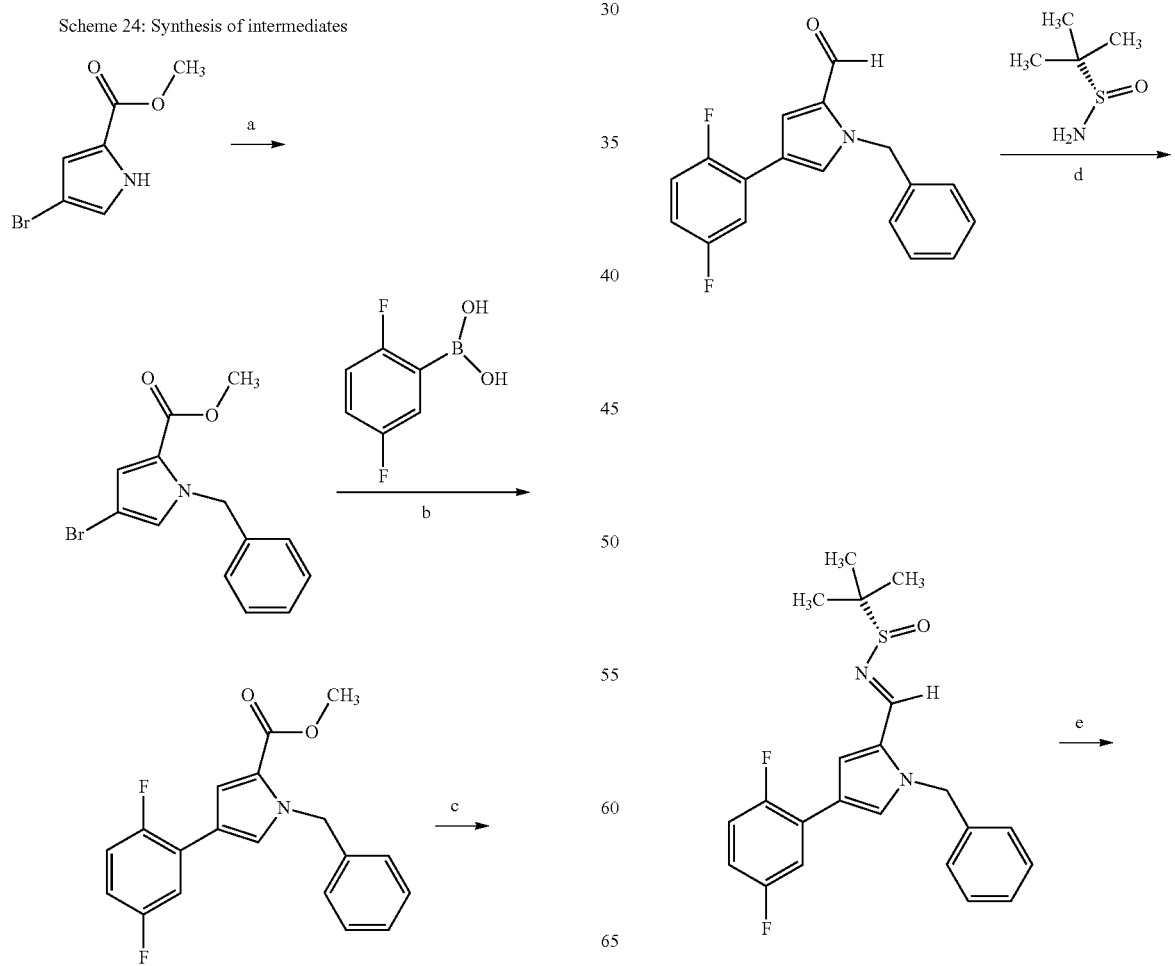

215
-continued

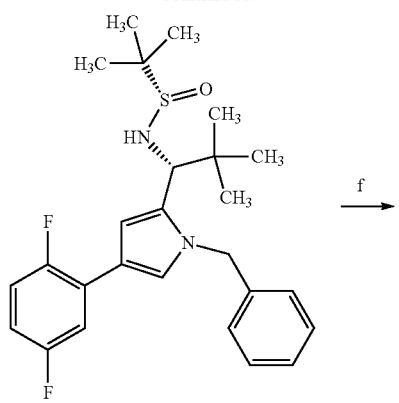

216
-continued

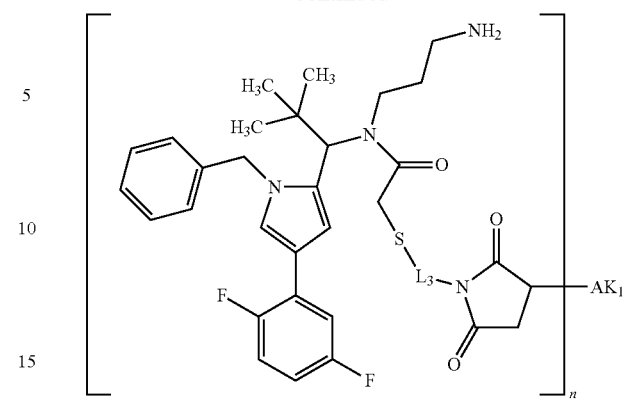

Scheme 26: Synthesis of cysteine-linked ADCs via hydrolyzed succinamides

This process was used in particular for ADCs where L1 = $CH_2$ or where L1 = CH—$CH_3$ or where L1 = phenyl to convert these ADCs into the open-chain linking forms.

[a]: for example benzyl bromide, $Cs_2CO_3$, DMF, RT; b) for example $Pd(dppf)_2Cl_2$, DMF, $Na_2CO_3$, 85° C.; c) for example $LiAlH_4$, THF, 0° C.; $MnO_2$, DCM, RT; d) for example Ti(iOPr)$_4$, THF, RT; e) for example tBuLi, THF, -78° C.; MeOH, $NH_4Cl$; f) for example HCl/1,4-dioxane]

Scheme 25: Synthesis of cysteine-linked ADCs

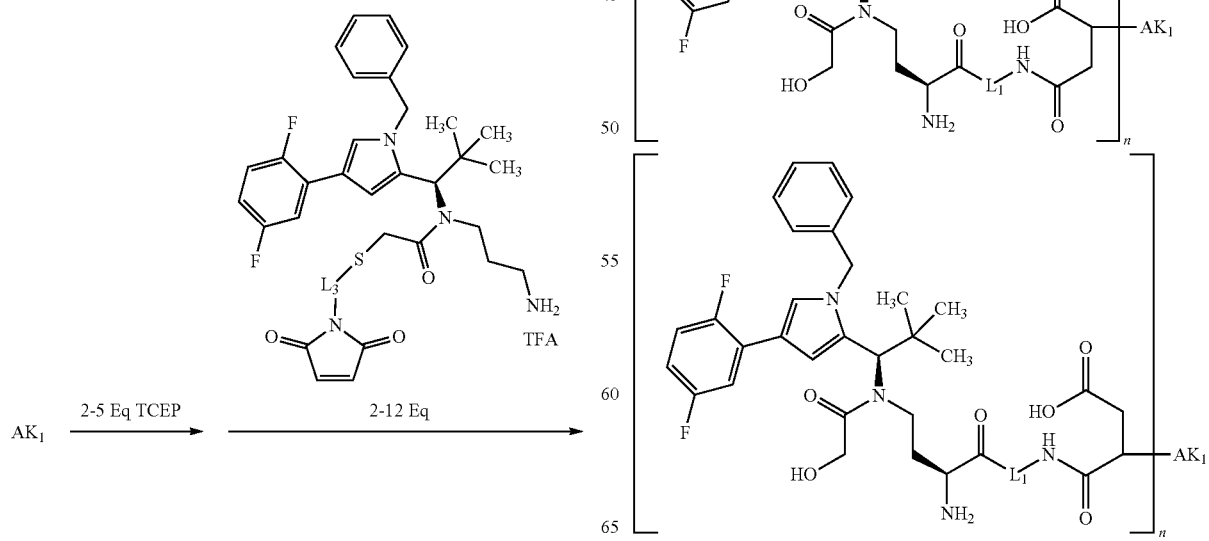

Scheme 27: Synthesis of ADC precursor molecules
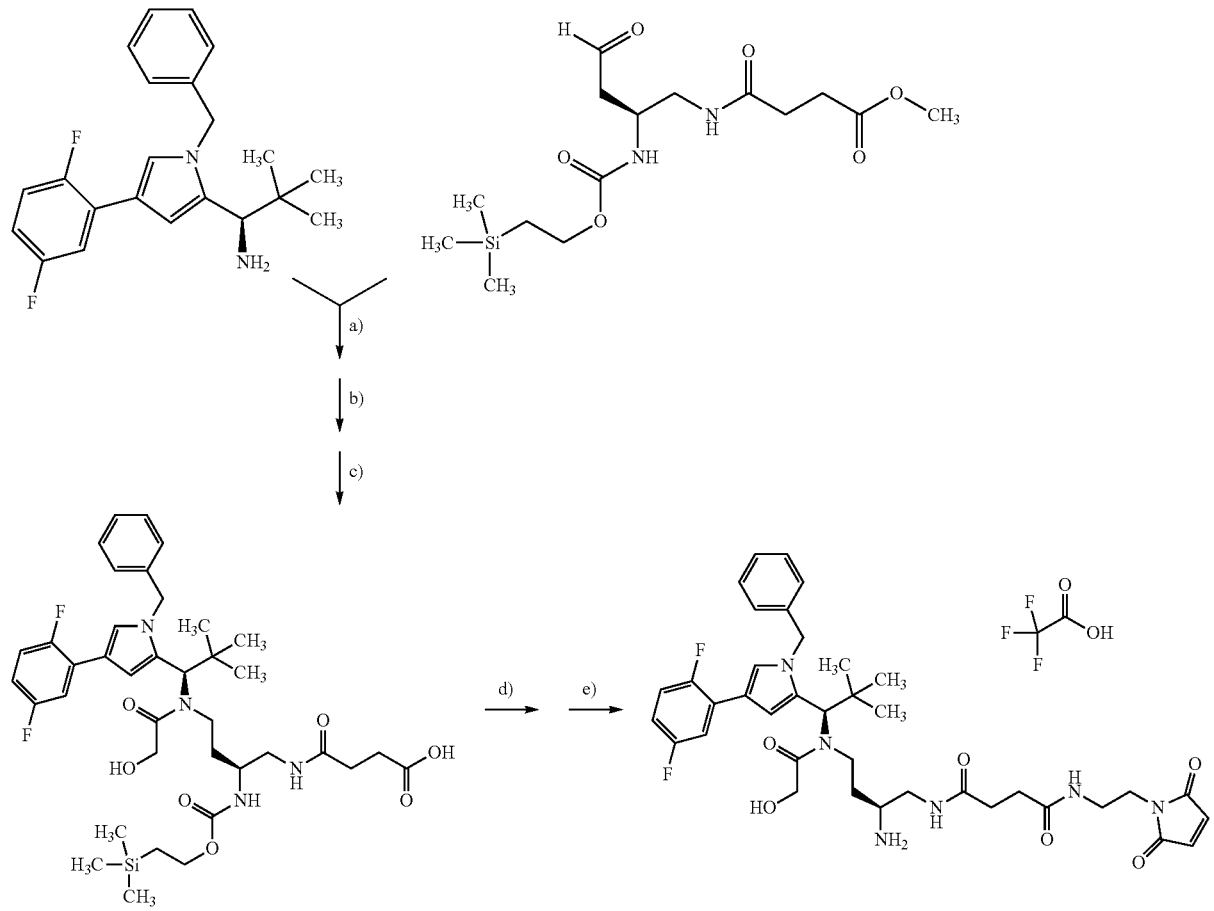
[a]: sodium triacetoxyborohydride, acetic acid, DCM, RT; b) acetoxyacetyl chloride, diisopropylethylamine, DCM, RT; c) LiOH, MeOH, RT; d) trifluoroacetic acid/1-(2-aminoethyl)-1H-pyrrole-2,5-dione, (1:1) HATU, DMF, diisopropylethylamine, RT; e) zinc chloride, trifluoroethanol, 50° C., EDTA.]
Scheme 28: Synthesis of ADC precursor molecules
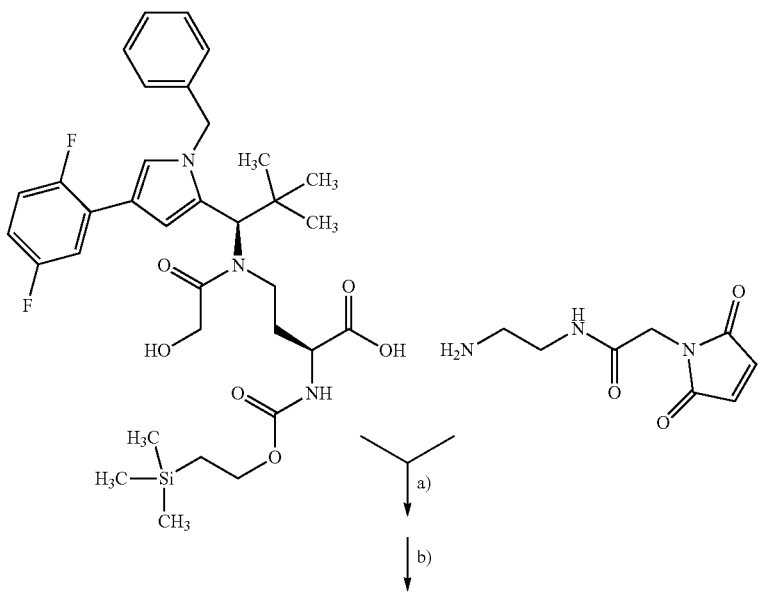

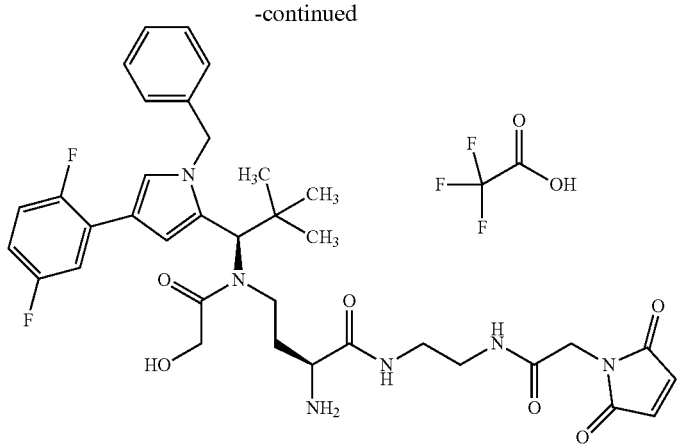

[a]: HATU, DMF, diisopropylethylamine, RT; b) zinc chloride, trifluoroethanol, 50° C., EDTA.]

Scheme 29: Synthesis of ADC precursor molecules

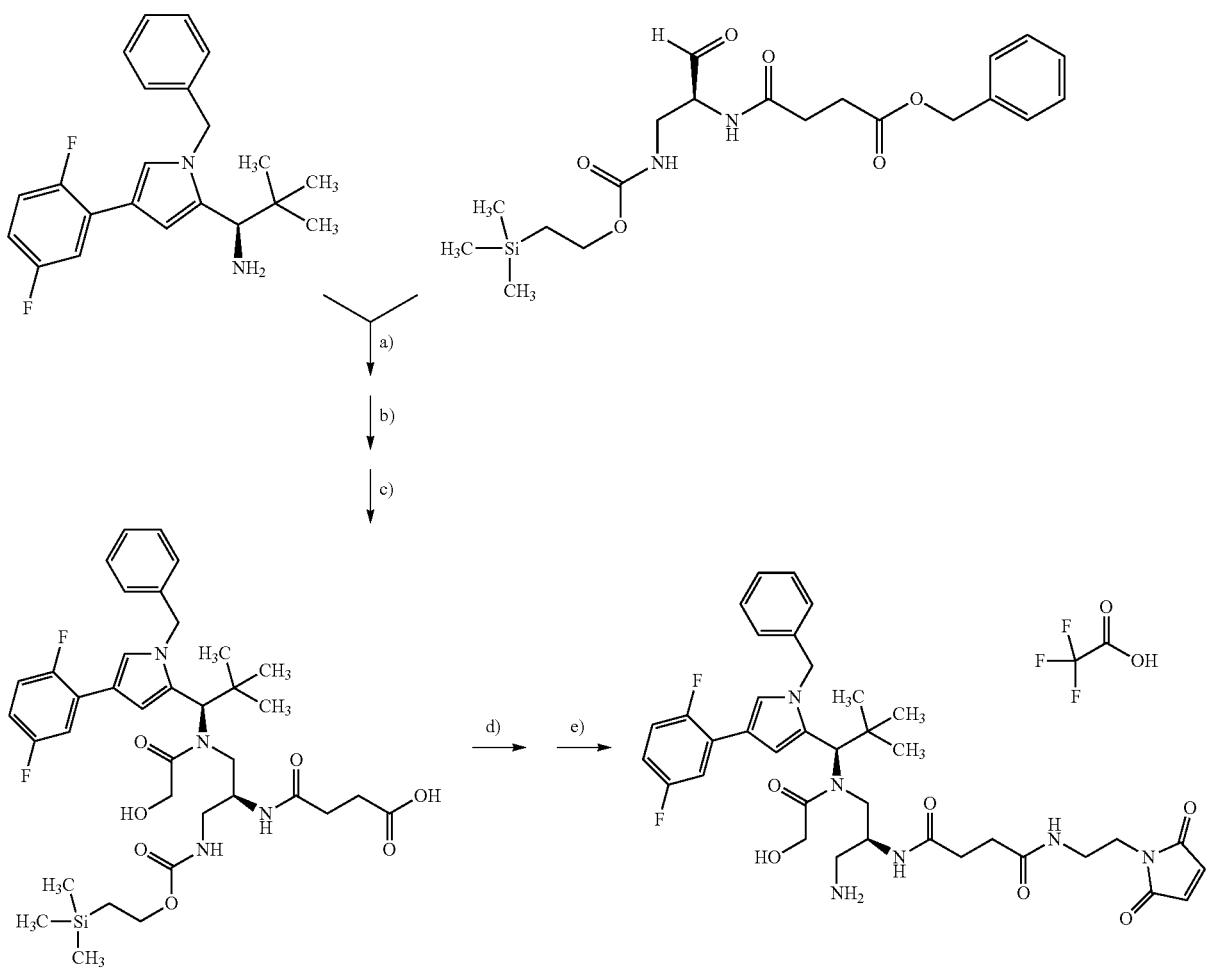

[a]: sodium triacetoxyborohydride, acetic acid, DCM, RT; b) acetoxyacetyl chloride, triethylamine, DCM, RT; c) LiOH, MeOH, RT; d) trifluoroacetic acid/1-(2-aminoethyl)-1H-pyrrole-2,5-dione (1:1) HATU, DMF, diisopropylethylamine, RT; e) zinc chloride, trifluoroethanol, 50° C., EDTA.]

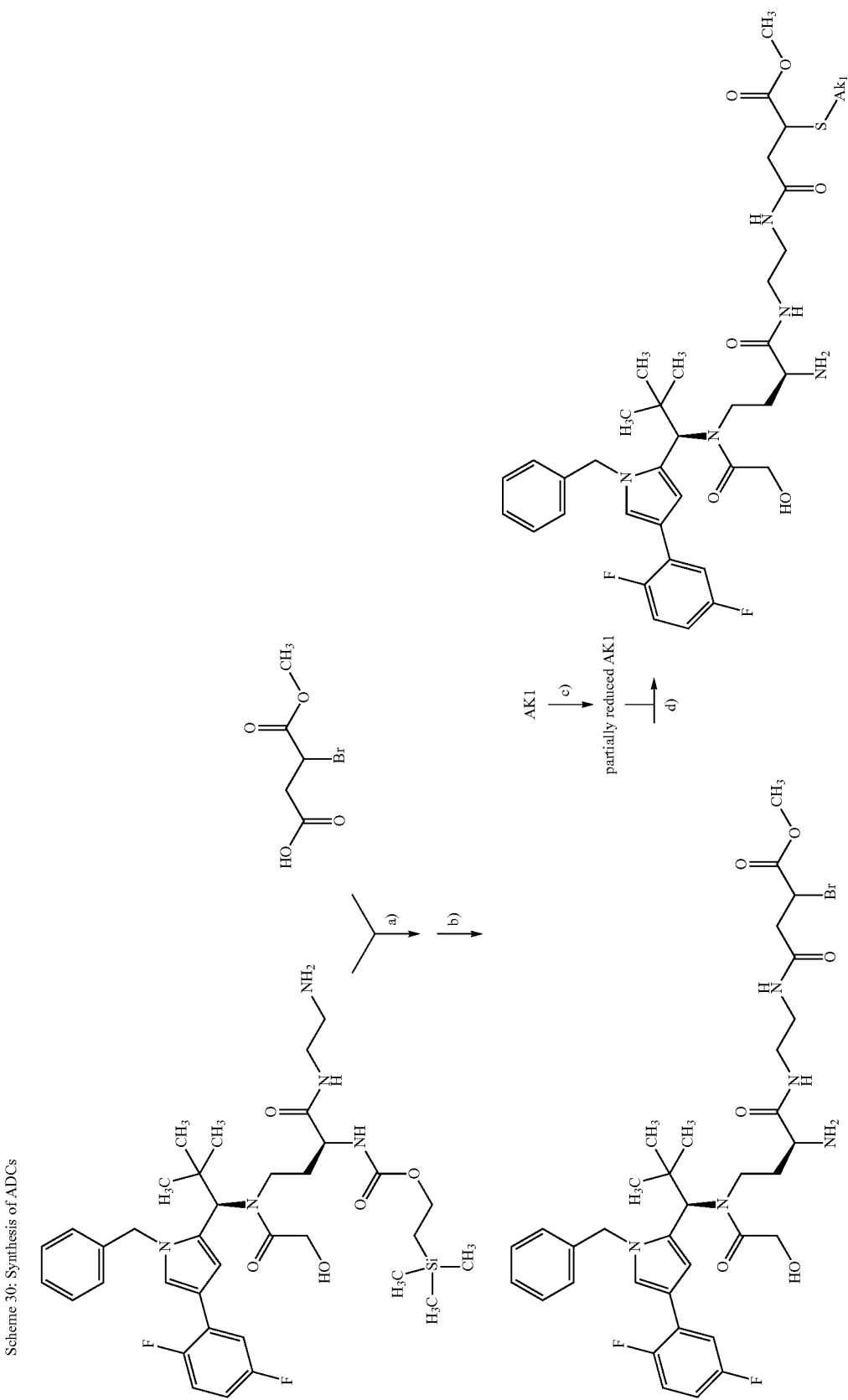

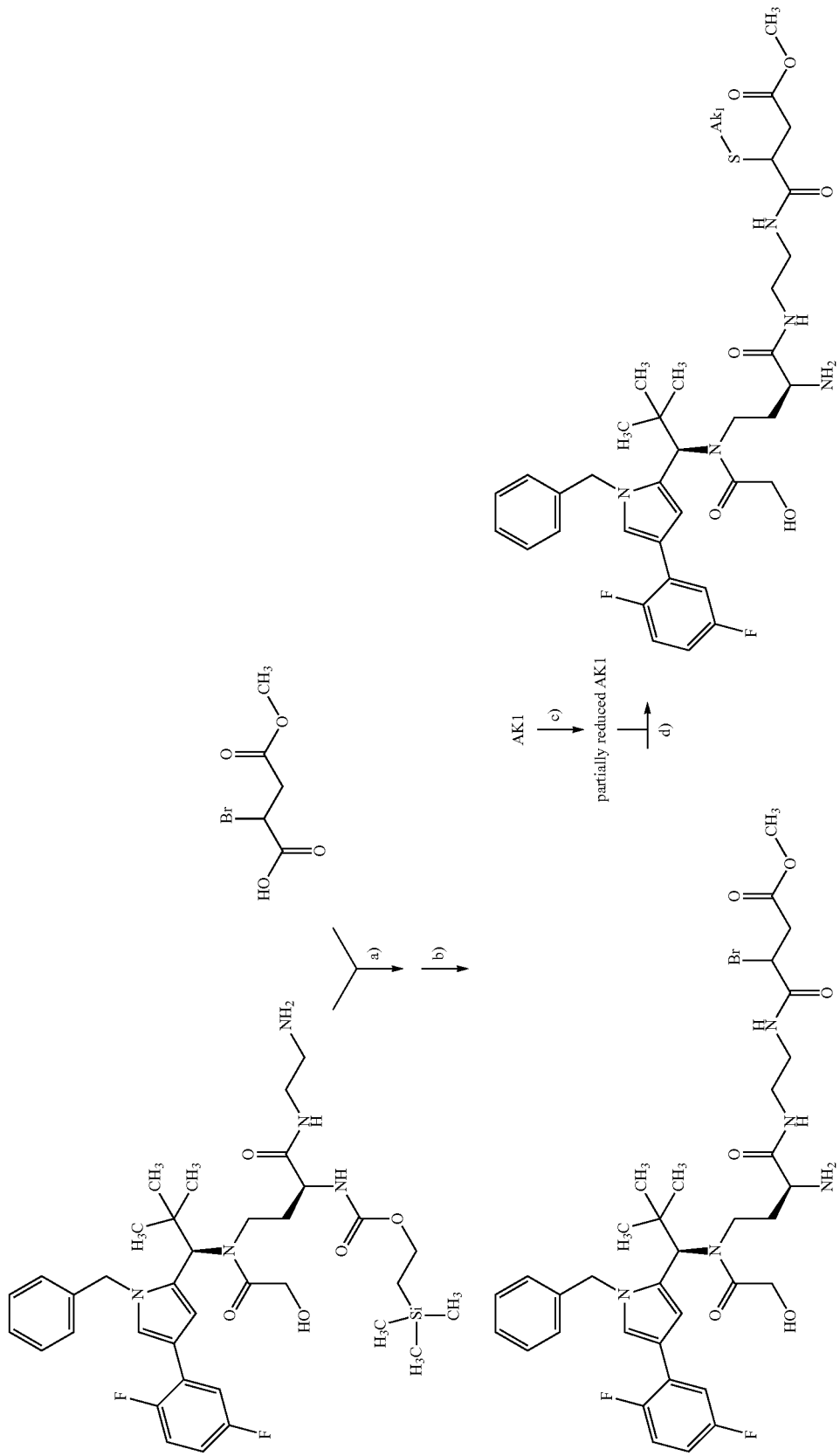
Scheme 31: Synthesis of ADCs
[a]: 2-bromo-1-ethylpyridinium tetrafluoroborate (BEP), DCM, pyridine, RT; b) zinc chloride, trifluoroethanol, 50° C., EDTA; c) 3-4 equivalents of TCEP, PBS buffer; d) PBS buffer, 20 h RT.]

Scheme 32: Synthesis of intermediates
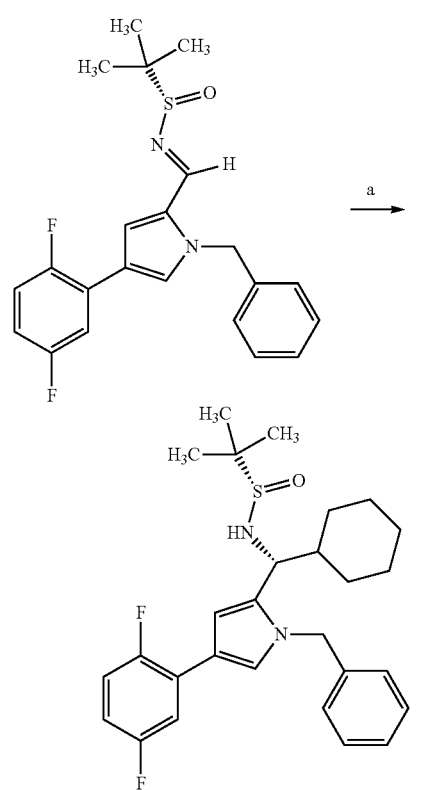
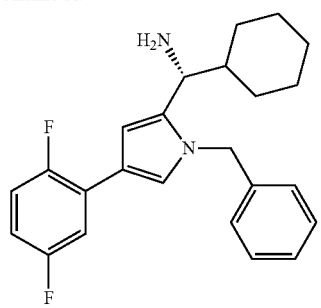
[a) for example dimethylzinc, cyhexylMgCl, THF, -78° C.; NH₄Cl; b) for example HCl/1,4-dioxane]

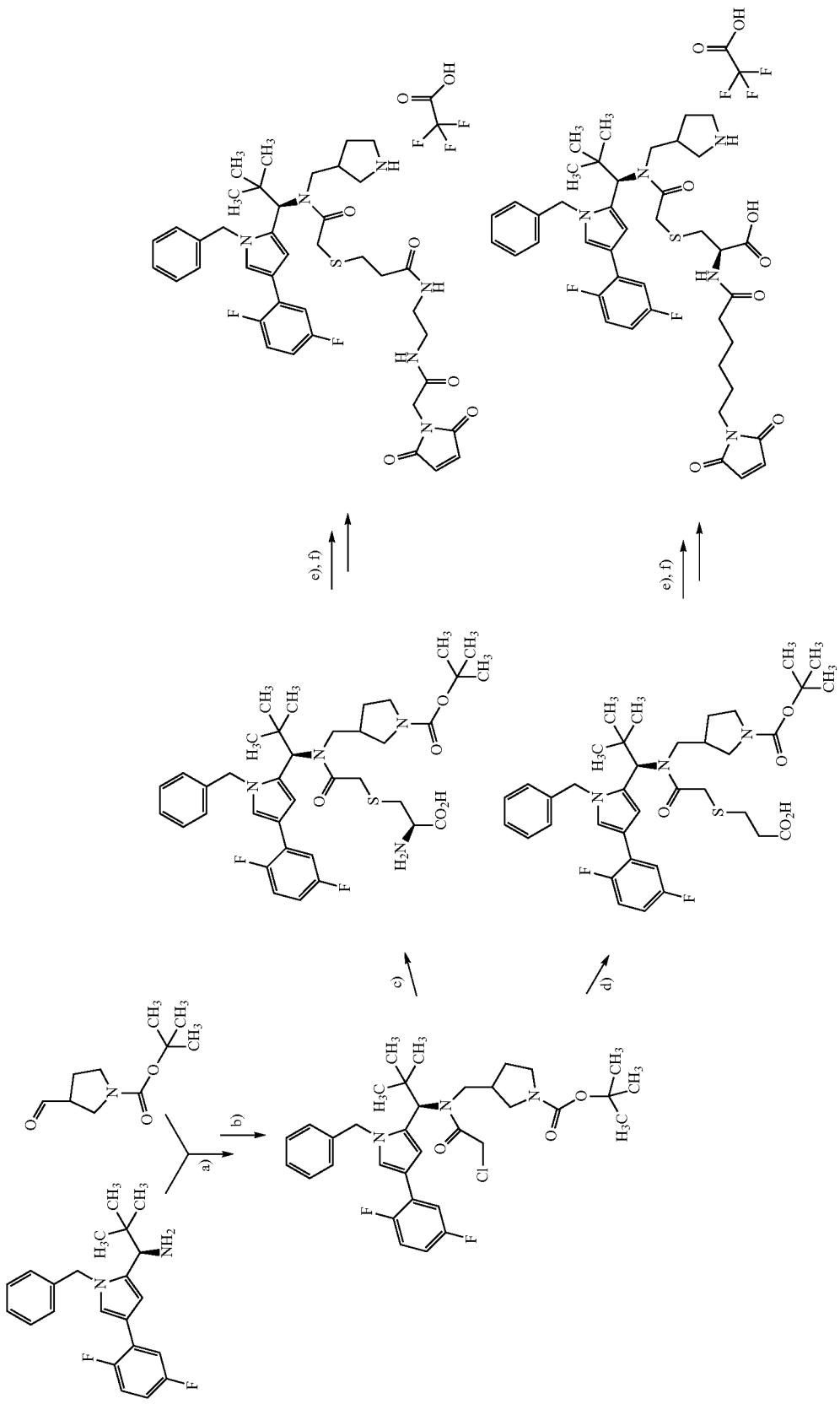
Scheme 33: Synthesis of ADCs precursor molecules
[a): sodium triacetoxyborohydride, acetic acid, DCM, RT; b) acetoxyacetyl chloride, triethylamine, DCM, RT; c) L-cysteine, NaHCO₃, DBU, isopropanol/water, RT; d) 3-sulphanylpropanoic acid, K₂CO₃, RT; e) linker, HATU, DMF, diisopropylethylamine, RT; e) zinc chloride, trifluoroethanol, 50° C., EDTA.]

Scheme 34: Synthesis of lysine-linked ADCs

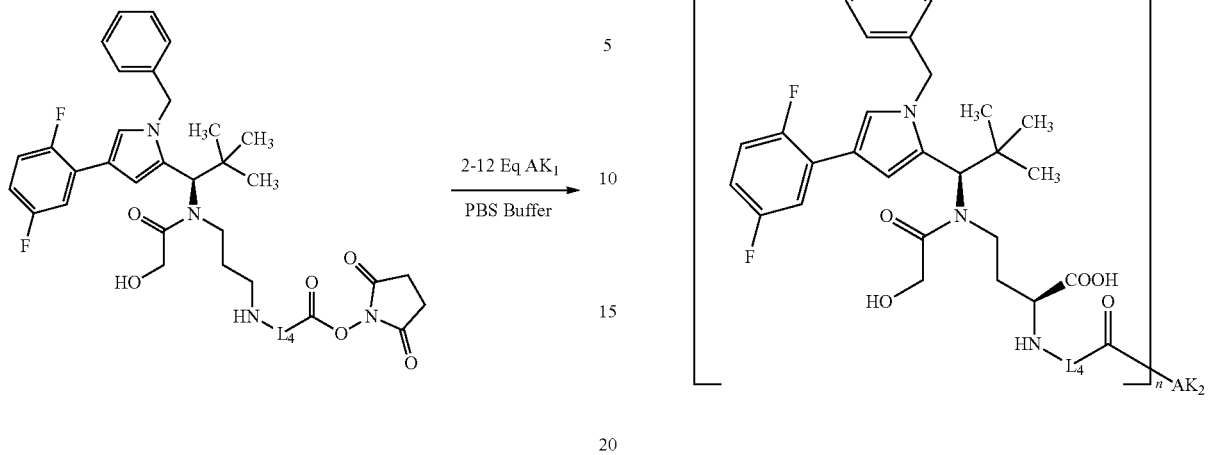

Scheme 35: Synthesis of lysine-linked ADCs

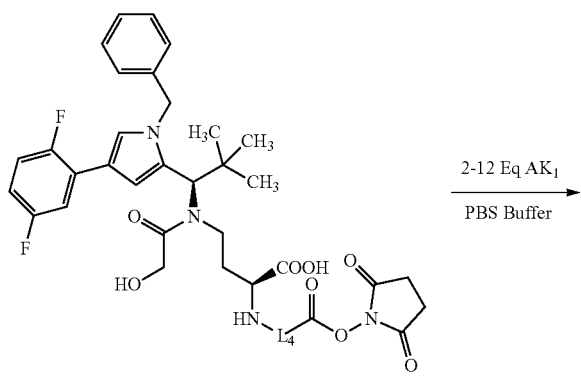

A. EXAMPLES

Abbreviations and Acronyms

ABCB1 ATP-binding cassette sub-family B member 1 (synonym for P-gp and MDR1)
abs. absolute
Ac acetyl
ACN acetonitrile
aq. aqueous, aqueous solution
ATP adenosine triphosphate
BCRP breast cancer resistance protein, an efflux transporter
BEP 2-bromo-1-ethylpyridinium tetrafluoroborate
Boc tert-butoxycarbonyl
br. broad (in NMR)
Ex. Example
CI chemical ionization (in MS)
D doublet (in NMR)
D day(s)
TLC thin-layer chromatography
DCI direct chemical ionization (in MS)
DCM dichloromethane
Dd doublet of doublets (in NMR)
DMAP 4-N,N-dimethylaminopyridine
DME 1,2-dimethoxyethane
DMEM Dulbecco's Modified Eagle Medium (standardized nutrient medium for cell culture)
DMF N,N-dimethylformamide
DMSO dimethyl sulphoxide
DPBS, D-PBS, PBS Dulbecco's phosphate-buffered salt solution
  PBS=DPBS=D-PBS, pH 7.4, from Sigma, No D8537
  Composition:
  0.2 g KCl
  0.2 g $KH_2PO_4$ (anhyd)
  8.0 g NaCl
  1.15 g $Na_2HPO_4$ (anhyd)
  made up ad 1 l with $H_2O$
Dt doublet of triplets (in NMR)
DTT DL-dithiothreitol
EDC N'-(3-dimethylaminopropyl)-N-ethylcarbodiimide hydrochloride
EGFR epidermal growth factor receptor
EI electron impact ionization (in MS)
ELISA enzyme-linked immunosorbent assay
eq. equivalent(s)

ESI electrospray ionization (in MS)
ESI-MicroTofq ESI-MicroTofq (name of the mass spectrometer with Tof=time of flight and q=quadrupol)
FCS foetal calf serum
Fmoc (9H-fluoren-9-ylmethoxy)carbonyl
sat. saturated
GTP guanosine-5'-triphosphate
H hour(s)
HATU O-(7-azabenzotriazol-1-yl)-N,N,N',N'-tetramethyluronium hexafluorophosphate
HEPES 4-(2-hydroxyethyl)piperazine-1-ethanesulphonic acid
HOAc acetic acid
HOAt 1-hydroxy-7-azabenzotriazole
HOBt 1-hydroxy-1H-benzotriazole hydrate
HOSu N-hydroxysuccinimide
HPLC high-pressure, high-performance liquid chromatography
$IC_{50}$ half-maximal inhibitory concentration
i.m. intramuscularly, administration into the muscle
i.v. intravenously, administration into the vein
KG-1 human tumour cell line
conc. concentrated
LC-MS liquid chromatography-coupled mass spectrometry
LLC-PK1 cells Lewis lung carcinoma pork kidney cell line
L-MDR human MDR1 transfected LLC-PK1 cells
LoVo human tumour cell line
L428 human tumour cell line
m multiplet (in NMR)
MDR1 Multidrug resistance protein 1
MeCN acetonitrile
Me methyl
min minute(s)
MOLM-13 human tumour cell line
MS mass spectrometry
MTT 3-(4,5-dimethylthiazol-2-yl)-2,5-diphenyl-2H-tetrazolium bromide 3
MV-4-11 human tumour cell line
NCI-H292 human tumour cell line
NMM N-methylmorpholine
NMP N-methyl-2-pyrrolidinone
NMR nuclear magnetic resonance spectrometry
NMRI mouse strain originating from the Naval Medical Research Institute (NMRI)
Nude mice Nude mice (test animal)
NSCLC non small cell lung cancer
PBS phosphate-buffered salt solution
Pd/C palladium on activated carbon
P-gp P-gycoprotein, a transporter protein
PNGaseF enzyme for cleaving sugar
quant. quantitative (in yield)
quart quartet (in NMR)
quint quintet (in NMR)
$R_f$ retention index (in TLC)
RT room temperature
$R_t$ retention time (in HPLC)
s singlet (in NMR)
s.c. subcutaneously, administration under the skin
SCID mice test mice with severe combined immunodeficiency
t triplet (in NMR)
TBAF tetra-n-butylammonium fluoride
TEMPO (2,2,6,6-tetramethylpiperidin-1-yl)oxyl
tert tertiary
TFA trifluoroacetic acid
THF tetrahydrofuran
THP-1 human tumour cell line
T3P® 2,4,6-tripropyl-1,3,5,2,4,6-trioxatriphosphinane 2,4,6-trioxide
UV ultraviolet spectrometry
v/v volume to volume ratio (of a solution)
Z benzyloxycarbonyl
HPLC and LC-MS Methods:
Method 1 (LC-MS):
Instrument: Waters ACQUITY SQD UPLC System; column: Waters Acquity UPLC HSS T3 1.8µ 50×1 mm; mobile phase A: 1 l of water+0.25 ml of 99% strength formic acid, mobile phase B: 1 l of acetonitrile+0.25 ml of 99% strength formic acid; gradient: 0.0 min 90% A→1.2 min 5% A→2.0 min 5% A oven: 50° C.; flow rate: 0.40 ml/min; UV detection: 208-400 nm.
Method 2 (LC-MS):
MS instrument type: Waters Synapt G2S; UPLC instrument type: Waters Acquity I-CLASS; column: Waters, BEH300, 2.1×150 mm, C18 1.7 µm; mobile phase A: 1 l of water+0.01% formic acid; mobile phase B: 1 l of acetonitrile+0.01% formic acid; gradient: 0.0 min 2% B→1.5 min 2% B→8.5 min 95% B→10.0 min 95% B; oven: 50° C.; flow rate: 0.50 ml/min; UV detection: 220 nm
Method 3 (LC-MS):
MS instrument type: Waters (Micromass) QM; HPLC instrument: Agilent 1100 Series; column: Agilent ZORBAX Extend-C18 3.0×50 mm 3.5-micron; mobile phase A: 1 l of water+0.01 mol of ammonium carbonate, mobile phase B: 1 l of acetonitrile; gradient: 0.0 min 98% A→0.2 min 98% A→3.0 min 5% A→4.5 min 5% A; oven: 40° C.; flow rate: 1.75 ml/min; UV detection: 210 nm
Method 4 (LC-MS):
MS instrument type: Waters Synapt G2S; UPLC instrument type: Waters Acquity I-CLASS; column: Waters, HSST3, 2.1×50 mm, C18 1.8 µm; mobile phase A: 1 l of water+0.01% formic acid; mobile phase B: 1 l of acetonitrile+0.01% formic acid; gradient: 0.0 min 10% B→0.3 min 10% B→1.7 min 95% B→2.5 min 95% B; oven: 50° C.; flow rate: 1.20 ml/min; UV detection: 210 nm
Method 5 (LC-MS):
Instrument: Waters ACQUITY SQD UPLC System; column: Waters Acquity UPLC HSS T3 1.8µ 50×1 mm; mobile phase A: 1 l of water+0.25 ml of 99% strength formic acid, mobile phase B: 1 l of acetonitrile+0.25 ml of 99% strength formic acid; gradient: 0.0 min 95% A→6.0 min 5% A→7.5 min 5% A oven: 50° C.; flow rate: 0.35 ml/min; UV detection: 210-400 nm.
Method 6 (LC-MS):
Instrument: Micromass Quattro Premier with Waters UPLC Acquity; column: Thermo Hypersil GOLD 1.9µ 50×1 mm; mobile phase A: 1 l of water+0.5 ml of 50% strength formic acid, mobile phase B: 1 l of acetonitrile+0.5 ml of 50% strength formic acid; gradient: 0.0 min 97% A→0.5 min 97% A→3.2 min 5% A→4.0 min 5% A oven: 50° C.; flow rate: 0.3 ml/min; UV detection: 210 nm.
Method 7 (LC-MS):
Instrument: Agilent MS Quad 6150; HPLC: Agilent 1290; column: Waters Acquity UPLC HSS T3 1.8µ 50×2.1 mm; mobile phase A: 1 l of water+0.25 ml of 99% strength formic acid, mobile phase B: 1 l of acetonitrile+0.25 ml of 99% strength formic acid; gradient: 0.0 min 90% A→0.3 min 90% A→1.7 min 5% A→3.0 min 5% A oven: 50° C.; flow rate: 1.20 ml/min; UV detection: 205-305 nm.
Method 8 (LC-MS):
MS instrument type: Waters Synapt G2S; UPLC instrument type: Waters Acquity I-CLASS; column: Waters, HSST3, 2.1×50 mm, C18 1.8 µm; mobile phase A: 1 l of water+0.01% formic acid; mobile phase B: 1 l of acetonitrile+0.01% formic acid; gradient: 0.0 min 2% B→2.0 min 2% B→13.0 min 90% B→15.0 min 90% B; oven: 50° C.; flow rate: 1.20 ml/min; UV detection: 210 nm Method 9: LC-MS-Prep Purification Method for Examples 181-191 (Method LIND-LC-MS-Prep)

MS instrument: Waters, HPLC instrument: Waters (column Waters X-Bridge C18, 19 mm×50 mm, 5 µm, mobile phase A: water+0.05% ammonia, mobile phase B: acetonitrile (ULC) with gradient; flow rate: 40 ml/min; UV detection: DAD; 210-400 nm).

or

MS instrument: Waters, HPLC instrument: Waters (column Phenomenex Luna 5µ C18(2) 100 A, AXIA Tech. 50×21.2 mm, mobile phase A: water+0.05% formic acid, mobile phase B: acetonitrile (ULC) with gradient; flow rate: 40 ml/min; UV detection: DAD; 210-400 nm).

Method 10: LC-MS Analysis Method for Examples 181-191 (LIND_SQD_SB_AQ)

MS instrument: Waters SQD; Instrument HPLC: Waters UPLC; column: Zorbax SB-Aq (Agilent), 50 mm×2.1 mm, 1.8 µm; mobile phase A: water+0.025% formic acid, mobile phase B: acetonitrile (ULC)+0.025% formic acid; gradient: 0.0 min 98% A-0.9 min 25% A-1.0 min 5% A-1.4 min 5% A-1.41 min 98% A-1.5 min 98% A; oven: 40° C.; flow rate: 0.600 ml/min; UV detection: DAD; 210 nm.

Method 11 (HPLC):
Instrument: HP1100 Series
column: Merck Chromolith SpeedROD RP-18e, 50-4.6 mm, Cat. No. 1.51450.0001, precolumn Chromolith Guard Cartridge Kit, RP-18e, 5-4.6 mm, Cat. No. 1.51470.0001
gradient: flow rate 5 ml/min
   injection volume 5 µl
solvent A: HClO4 (70% strength) in water (4 ml/l)
solvent B: acetonitrile
start 20% B
0.50 min 20% B
3.00 min 90% B
3.50 min 90% B
3.51 min 20% B
4.00 min 20% B
column temperature: 40° C.
wavelength: 210 nm Method 12 (LC-MS):
MS instrument type: Thermo Scientific FT-MS; UHPLC+ instrument type: Thermo Scientific UltiMate 3000; column: Waters, HSST3, 2.1×75 mm, C18 1.8 µm; mobile phase A: 1 l of water+0.01% formic acid; mobile phase B: 1 l of acetonitrile+0.01% formic acid; gradient: 0.0 min 10% B→2.5 min 95% B→3.5 min 95% B; oven: 50° C.; flow rate: 0.90 ml/min; UV detection: 210 nm/optimum integration path 210-300 nm Method 13: (LC-MS):
MS instrument: Waters (Micromass) Quattro Micro; Instrument Waters UPLC Acquity; column: Waters BEH C18 1.7µ 50×2.1 mm; mobile phase A: 1 l of water+0.01 mol ammonium formate, mobile phase B: 1 l of acetonitrile; gradient: 0.0 min 95% A→0.1 min 95% A→2.0 min 15% A→2.5 min 15% A→2.51 min 10% A→3.0 min 10% A; oven: 40° C.; flow rate: 0.5 ml/min; UV detection: 210 nm Method 14: (LC-MS):
MS instrument type: ThermoFisherScientific LTQ-Orbitrap-XL; HPLC instrument type: Agilent 1200SL; column: Agilent, POROSHELL 120, 3×150 mm, SB-C18 2.7 µm; mobile phase A: 1 l of water+0.1% trifluoroacetic acid; mobile phase B: 1 l of acetonitrile+0.1% trifluoroacetic acid; gradient: 0.0 min 2% B→0.3 min 2% B→5.0 min 95% B→10.0 min 95% B; oven: 40° C.; flow rate: 0.75 ml/min; UV detection: 210 nm All reactants or reagents whose preparation is not described explicitly hereinafter were purchased commercially from generally accessible sources. For all other reactants or reagents whose preparation likewise is not described hereinafter and which were not commercially obtainable or were obtained from sources which are not generally accessible, a reference is given to the published literature in which their preparation is described.

Starting Materials and Intermediates:

Intermediate C11

R/S-(11-{(1R)-1-[1-Benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-homocysteine/trifluoroacetate (1:1)

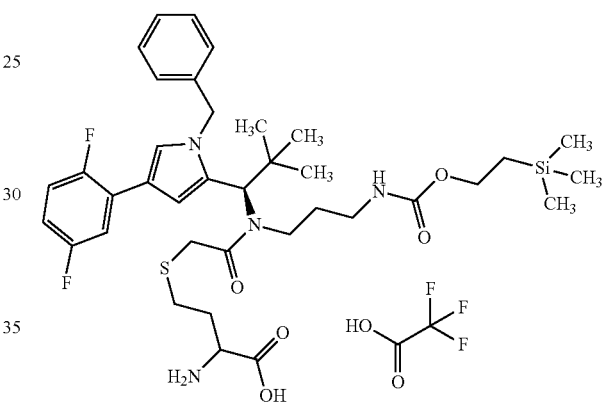

990.0 mg (2.79 mmol) of (1R)-1-[1-benzyl-4-(2,5-difluorophenyl)-1H-pyrrol-2-yl]-2,2-dimethylpropan-1-amine were initially charged in 15.0 ml of dichloromethane, and 828.8 mg (3.91 mmol) of sodium triacetoxyborohydride and 129.9 mg (3.21 mmol) of acetic acid were added, and the mixture was stirred at RT for 5 min. 698.1 mg (3.21 mmol) of 2-(trimethylsilyl)ethyl (3-oxopropyl)carbamate (Intermediate L58) dissolved in 15.0 ml of dichloromethane were added, and the reaction mixture was stirred at RT overnight. The reaction mixture was diluted with ethyl acetate and the organic phase was washed in each case twice with saturated sodium carbonate solution and saturated NaCl solution. The organic phase was dried over magnesium sulphate and the solvent was evaporated under reduced pressure. The residue was purified on silica gel (mobile phase: dichloromethane/methanol=100:2). The solvents were evaporated under reduced pressure and the residue was dried under high vacuum. This gave 1.25 g (73% of theory) of the compound 2-(trimethylsilyl)ethyl [3-({(1R)-1-[1-benzyl-4-(2,5-difluorophenyl)-1H-pyrrol-2-yl]-2,2-dimethylpropyl}amino)propyl]carbamate.

LC-MS (Method 1): $R_t$=1.09 min; MS (ESIpos): m/z=556 (M+H)$^+$.

151.4 mg (1.5 mmol) of triethylamine and 161.6 mg (1.43 mmol) of chloroacetyl chloride were added to 400.0 mg (0.65 mmol) of 2-(trimethylsilyl)ethyl [3-({(1R)-1-[1-benzyl-4-(2,5-difluorophenyl)-1H-pyrrol-2-yl]-2,2-dimethylpropyl}amino)propyl]carbamate. The reaction mixture was stirred at RT overnight. Ethyl acetate was added to the reaction mixture and the organic phase was washed three times with water and once with saturated NaCl solution. The organic phase was dried over magnesium sulphate and the solvent was evaporated under reduced pressure. The residue was purified by silica gel chromatography (mobile phase: cyclohexane/ethyl acetate=3:1). The solvents were evaporated under reduced pressure and the residue was dried under high vacuum. This gave 254.4 mg (57% of theory) of the compound 2-(trimethylsilyl)ethyl {3-[{(1R)-1-[1-benzyl-4-(2,5-difluorophenyl)-1H-pyrrol-2-yl]-2,2-dimethylpropyl}(chloroacetyl)amino]propyl}carbamate.

LC-MS (Method 1): $R_t$=1.49 min; MS (ESIneg): m/z=676 (M+HCOO$^-$)$^-$.

117.4 mg (0.19 mmol) of 2-(trimethylsilyl)ethyl {3-[{(1R)-1-[1-benzyl-4-(2,5-difluorophenyl)-1H-pyrrol-2-yl]-2,2-dimethylpropyl}(chloroacetyl)amino]propyl}carbamate were dissolved in 10.0 ml of isopropanol, and 928.4 µl of 1M NaOH and 50.2 mg (0.37 mmol) of DL-homocysteine were added. The reaction mixture was stirred at 50° C. for 4.5 h. Ethyl acetate was added to the reaction mixture and the organic phase was washed with saturated sodium bicarbonate solution and saturated NaCl solution. The organic phase was dried over magnesium sulphate and the solvent was evaporated under reduced pressure. The residue was purified by preparative RP-HPLC (column: Reprosil 250×40; 10µ, flow rate: 50 ml/min, MeCN/water, 0.1% TFA). The solvents were evaporated under reduced pressure and the residue was dried under high vacuum. This gave 75.3 mg (48% of theory) of the title compound.

LC-MS (Method 1): $R_t$=1.24 min; MS (ESIpos): m/z=731 (M+H)$^+$.

$^1$H-NMR (400 MHz, DMSO-d$_6$): δ[ppm]=0.03 (s, 9H), 0.40 (m, 1H), 0.75-0.91 (m, 11H), 1.30 (m, 1H), 1.99-2.23 (m, 2H), 2.63-2.88 (m, 4H), 3.18-3.61 (m, 5H), 3.79-4.10 (m, 3H), 4.89 (d, 1H), 4.89 (d, 1H), 5.16 (d, 1H), 5.56 (s, 1H), 6.82 (m, 1H), 6.91 (s, 1H), 6.97 (m, 1H), 7.13-7.38 (m, 6H), 7.49 (s, 1H), 7.63 (m, 1H), 8.26 (s, 3H).

Intermediate C12

R/S-[(8 S)-11-{(1R)-1-[1-Benzyl-4-(2,5-difluorophenyl)-1H-pyrrol-2-yl]-2,2-dimethylpropyl}-8-carboxy-2,2-dimethyl-6,12-dioxo-5-oxa-7,11-diaza-2-silatridecan-13-yl]homocysteine

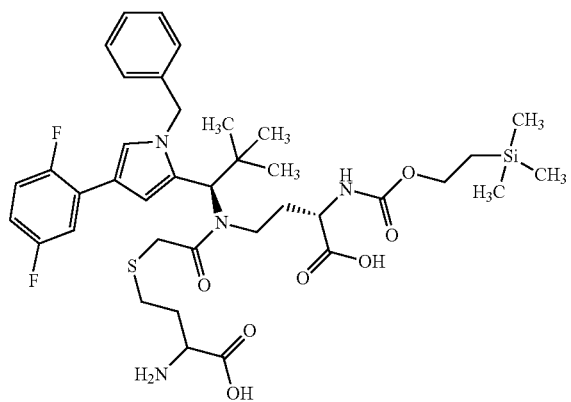 [SMILES: CC(C)(C)[C@H](c1cc(-c2cc(F)ccc2F)cn1Cc1ccccc1)N(CC[C@H](NC(=O)OCC[Si](C)(C)C)C(=O)O)C(=O)CSCCC(N)C(=O)O]

The synthesis was carried out analogously to the synthesis of Intermediate C11 using methyl (2S)-4-oxo-2-({[2-(trimethylsilyl)ethoxy]carbonyl}amino)butanoate (Intermediate L57) and Intermediate C52 as starting materials.

LC-MS (Method 1): $R_t$=1.18 min; MS (ESIpos): m/z=775 (M+H)$^+$.

Intermediate C52

(1R)-1-[1-Benzyl-4-(2,5-difluorophenyl)-1H-pyrrol-2-yl]-2,2-dimethylpropan-1-amine

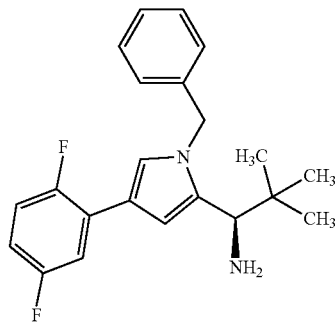 [SMILES: CC(C)(C)[C@@H](N)c1cc(-c2cc(F)ccc2F)cn1Cc1ccccc1]

10.00 g (49.01 mmol) of methyl 4-bromo-1H-pyrrole-2-carboxylate were initially charged in 100.0 ml of DMF, and 20.76 g (63.72 mmol) of caesium carbonate and 9.22 g (53.91 mmol) of benzyl bromide were added. The reaction mixture was stirred at RT overnight. The reaction mixture was partitioned between water and ethyl acetate and the aqueous phase was extracted with ethyl acetate. The combined organic phases were dried over magnesium sulphate and the solvent was evaporated under reduced pressure. The reaction was repeated with 90.0 g of methyl 4-bromo-1H-pyrrole-2-carboxylate.

The two combined reactions were purified by preparative RP-HPLC (column: Daiso 300×100; 10µ, flow rate: 250 ml/min, MeCN/water). The solvents were evaporated under reduced pressure and the residue was dried under high vacuum. This gave 125.15 g (87% of theory) of the compound methyl 1-benzyl-4-bromo-1H-pyrrole-2-carboxylate.

LC-MS (Method 1): $R_t$=1.18 min; MS (ESIpos): m/z=295 [M+H]$^+$.

Under argon, 4.80 g (16.32 mmol) of methyl 1-benzyl-4-bromo-1H-pyrrole-2-carboxylate were initially charged in DMF, and 3.61 g (22.85 mmol) of (2,5-difluorophenyl)boronic acid, 19.20 ml of saturated sodium carbonate solution and 1.33 g (1.63 mmol) of [1,1'-bis(diphenylphosphino)ferrocene]-dichloropalladium(II):dichloromethane were added. The reaction mixture was stirred at 85° C. overnight. The reaction mixture was filtered through Celite and the filter cake was washed with ethyl acetate. The organic phase was extracted with water and then washed with saturated NaCl solution. The organic phase was dried over magnesium sulphate and the solvent was evaporated under reduced pressure. The residue was purified by silica gel chromatography (mobile phase: cyclohexane/ethyl acetate 100:3). The solvents were evaporated under reduced pressure and the residue was dried under high vacuum. This gave 3.60 g (67% of theory) of the compound methyl 1-benzyl-4-(2,5-difluorophenyl)-1H-pyrrole-2-carboxylate.

LC-MS (Method 7): $R_t$=1.59 min; MS (ESIpos): m/z=328 [M+H]$^+$.

3.60 g (11.00 mmol) of methyl 1-benzyl-4-(2,5-difluorophenyl)-1H-pyrrole-2-carboxylate were initially charged in 90.0 ml of THF, and 1.04 g (27.50 mmol) of lithium aluminium hydride (2.4 M in THF) were added at 0° C. The reaction mixture was stirred at 0° C. for 30 minutes. At 0° C., saturated potassium sodium tartrate solution was added, and ethyl acetate was added to the reaction mixture. The organic phase was extracted three times with saturated potassium sodium tartrate solution. The organic phase was washed once with saturated NaCl solution and dried over magnesium sulphate. The solvent was evaporated under reduced pressure and the residue was dissolved in 30.0 ml of dichloromethane. 3.38 g (32.99 mmol) of manganese(IV) oxide were added, and the mixture was stirred at RT for 48 h. Another 2.20 g (21.47 mmol) of manganese(IV) oxide were added, and the mixture was stirred at RT overnight. The reaction mixture was filtered through Celite and the filter cake was washed with dichloromethane. The solvent was evaporated under reduced pressure and the residue 2.80 g of (1-benzyl-4-(2,5-difluorophenyl)-1H-pyrrole-2-carbaldehyde) was used without further purification in the next step of the synthesis.

LC-MS (Method 7): $R_t$=1.48 min; MS (ESIpos): m/z=298 [M+H]$^+$.

28.21 g (94.88 mmol) of 1-benzyl-4-(2,5-difluorophenyl)-1H-pyrrole-2-carbaldehyde together with 23.00 g (189.77 mmol) of (R)-2-methylpropane-2-sulphinamide were initially charged in 403.0 ml of absolute THF, and 67.42 g (237.21 mmol) of titanium(IV) isopropoxide were added and the mixture was stirred at RT overnight. 500.0 ml of saturated NaCl solution and 1000.0 ml of ethyl acetate were added, and the mixture was stirred at RT for 1 h. The mixture was filtered through kieselguhr and the filtrate was washed twice with saturated NaCl solution. The organic phase was dried over magnesium sulphate, the solvent was evaporated under reduced pressure and the residue was purified using Biotage Isolera (silica gel, column 1500+340 g SNAP, flow rate 200 ml/min, ethyl acetate/cyclohexane 1:10).

LC-MS (Method 7): $R_t$=1.63 min; MS (ESIpos): m/z=401 [M+H]$^+$.

25.00 g (62.42 mmol) of (R)—N-{(E/Z)-[1-benzyl-4-(2,5-difluorophenyl)-1H-pyrrol-2-yl]methylene}-2-methylpropane-2-sulphinamide were initially charged in absolute THF under argon and cooled to −78° C. 12.00 g (187.27 mmol) of tert-butyllithium (1.7 M solution in pentane) were then added at −78° C. and the mixture was stirred at this temperature for 3 h. At −78° C., 71.4 ml of methanol and 214.3 ml of saturated ammonium chloride solution were then added in succession, and the reaction mixture was allowed to warm to RT and stirred at RT for 1 h. The mixture was diluted with ethyl acetate and washed with water. The organic phase was dried over magnesium sulphate and the solvent was evaporated under reduced pressure. The residue (R)—N-{(1R)-1-[1-benzyl-4-(2,5-difluorophenyl)-1H-pyrrol-2-yl]-2,2-dimethylpropyl}-2-methylpropane-2-sulphinamide was used without further purification in the next step of the synthesis.

LC-MS (Method 6): $R_t$=2.97 min; MS (ESIpos): m/z=459 [M+H]$^+$.

28.00 g (61.05 mmol) of (R)—N-{(1R)-1-[1-benzyl-4-(2,5-difluorophenyl)-1H-pyrrol-2-yl]-2,2-dimethylpropyl}-2-methylpropane-2-sulphinamide were initially charged in 186.7 ml of 1,4-dioxane, and 45.8 ml of HCl in 1,4-dioxane solution (4.0 M) were then added. The reaction mixture was stirred at RT for 2 h and the solvent was evaporated under reduced pressure. The residue was purified by preparative RP-HPLC (column: Kinetix 100×30; flow rate: 60 ml/min, MeCN/water). The acetonitrile was evaporated under reduced pressure and dichloromethane was added to the aqueous residue. The organic phase was washed with sodium bicarbonate solution and dried over magnesium sulphate. The solvent was evaporated under reduced pressure and the residue was dried under high vacuum. This gave 16.2 g (75% of theory) of the title compound.

LC-MS (Method 6): $R_t$=2.10 min; MS (ESIpos): m/z=338 [M-NH$_2$]$^+$, 709 [2M+H]$^+$.

$^1$H-NMR (400 MHz, DMSO-d$_6$): δ[ppm]=0.87 (s, 9H), 1.53 (s, 2H), 3.59 (s, 1H), 5.24 (d, 2H), 6.56 (s, 1H), 6.94 (m, 1H), 7.10 (d, 2H), 7.20 (m, 1H), 7.26 (m, 2H), 7.34 (m, 2H), 7.46 (m, 1H).

Intermediate C53

(2S)-4-[{(1R)-1-[1-Benzyl-4-(2,5-difluorophenyl)-1H-pyrrol-2-yl]-2,2-dimethylpropyl}(glycoloyl)amino]-2-{[(9H-fluoren-9-ylmethoxy)carbonyl]amino}butanoic acid

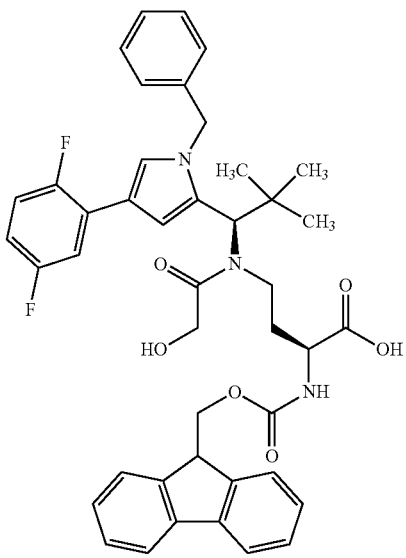 [SMILES: CC(C)(C)[C@H](c1cc(-c2cc(F)ccc2F)cn1Cc1ccccc1)N(CC[C@H](NC(=O)OCC1c2ccccc2-c2ccccc21)C(=O)O)C(=O)CO]

First, intermediate C52 was reductively alkylated with benzyl (2S)-2-{[(benzyloxy)carbonyl]amino}-4-oxobutanoate analogously to intermediate C58. The secondary amino group was then acylated with 2-chloro-2-oxoethyl acetate as described for Intermediate C58, and the two ester groups were then hydrolysed with 2M lithium hydroxide solution in methanol. The intermediate obtained in this manner was dissolved in ethanol, palladium on carbon (10%) was added and the mixture was hydrogenated at RT with hydrogen under standard pressure for 1 h. The deprotected compound was taken up in dioxane/water 2:1 and in the last step the Fmoc protective group was introduced using 9H-fluoren-9-ylmethyl chlorocarbonate in the presence of N,N-diisopropylethylamine.

LC-MS (Method 1): $R_t$=1.37 min; MS (ESIpos): m/z=734 (M−H)$^-$.

Intermediate C54

N-[(2S)-4-[{(1R)-1-[1-Benzyl-4-(2,5-difluorophenyl)-1H-pyrrol-2-yl]-2,2-dimethylpropyl}(glycoloyl)amino]-2-{[(9H-fluoren-9-ylmethoxy)carbonyl]amino}butanoyl]-beta-alanine

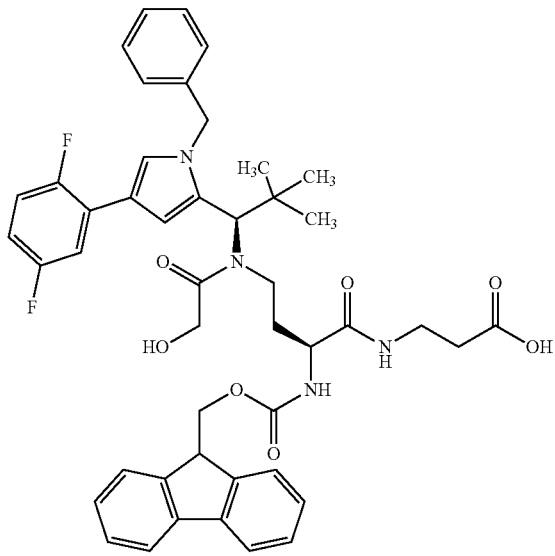 [SMILES: CC(C)(C)[C@H](c1cc(-c2cc(F)ccc2F)cn1Cc1ccccc1)N(CC[C@H](NC(=O)OCC1c2ccccc2-c2ccccc21)C(=O)NCCC(=O)O)C(=O)CO]

First, Intermediate C52 was reductively alkylated with benzyl N-[(2S)-2-{[(benzyloxy)carbonyl]amino}-4-oxobutanoyl]-beta-alaninate analogously to Intermediate C2. The secondary amino group was then acylated with 2-chloro-2-oxoethyl acetate as described for Intermediate C58. The intermediate obtained in this manner was dissolved in methanol, palladium on carbon (10%) was added and the mixture was hydrogenated at RT with hydrogen under standard pressure for 1 h. The ester group was then hydrolyzed with 2M lithium hydroxide solution in methanol. The deprotected compound was taken up in dioxane/water 2:1 and in the last step the Fmoc protective group was introduced using 9H-fluoren-9-ylmethyl chlorocarbonate in the presence of N,N-diisopropylethylamine. 48 mg of the title compound were obtained.

LC-MS (Method 1): $R_t$=1.38 min; MS (ESIpos): m/z=807 (M+H)$^+$.

Intermediate C58

(2S)-4-[{(1R)-1-[1-Benzyl-4-(2,5-difluorophenyl)-1H-pyrrol-2-yl]-2,2-dimethylpropyl}(glycoloyl)amino]-2-({[2-(trimethylsilyl)ethoxy]carbonyl}amino)butanoic acid

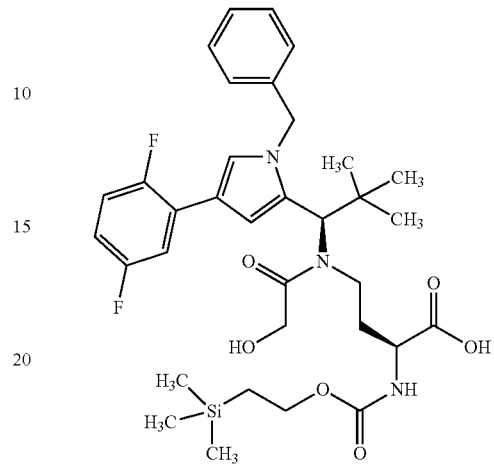

First, Intermediate C52 was reductively alkylated with benzyl (2S)-2-{[(benzyloxy)carbonyl]amino}-4-oxobutanoate analogously to Intermediate C2. The secondary amino group was then acylated with 2-chloro-2-oxoethyl acetate as described for Intermediate C27, and the two ester groups were then hydrolysed with 2M lithium hydroxide solution in methanol. The intermediate obtained in this manner was dissolved in ethanol, palladium on carbon (10%) was added and the mixture was hydrogenated at RT with hydrogen under standard pressure for 1 h.

500 mg (0.886 mmol) of this fully deprotected intermediate were taken up in 60 ml of dioxane, and 253 mg (0.975 mmol) of 1-({[2-(trimethylsilyl)ethoxy]carbonyl}oxy)pyrrolidine-2,5-dione and 198 μl of triethylamine were added. After 24 h of stirring at RT, the reaction was concentrated and the residue was purified by preparative HPLC. Combination of the appropriate fractions, concentration under reduced pressure and drying under high vacuum gave 312 mg (50% of theory) of the title compound.

LC-MS (Method 5): $R_t$=4.61 min; MS (ESIpos): m/z=658 (M+H)$^+$.

Alternatively, Intermediate C58 was prepared by the following route:

4.3 g (12.2 mmol) of Intermediate C52 were dissolved in 525 ml of DCM, and 3.63 g (17.12 mmol) of sodium triacetoxyborohydride and 8.4 ml of acetic acid were added. After 5 min of stirring at RT, 8.99 g (24.5 mmol) of Intermediate L57 dissolved in 175 ml of DCM were added and the reaction was stirred at RT for a further 45 min. The reaction was then diluted with 300 ml of DCM and washed twice with 100 ml of sodium bicarbonate solution and once with saturated NaCl solution. The organic phase was dried over magnesium sulphate, the solvent was evaporated under reduced pressure and the residue was dried under high vacuum. The residue was then purified by preparative RP-HPLC (column: Chromatorex C18). After combination of the appropriate fractions, the solvent was evaporated under reduced pressure and the residue was dried under high vacuum. This gave 4.6 g (61% of theory) of methyl (2S)-4-({(1R)-1-[1-benzyl-4-(2,5-difluorophenyl)-1H-pyrrol-2-yl]-2,2-dimethylpropyl}amino)-2-({[2-(trimethylsilyl)ethoxy]carbonyl}amino)butanoate.

LC-MS (Method 12): $R_t$=1.97 min; MS (ESIpos): m/z=614 (M+H)$^+$.

2.06 g (3.36 mmol) of this intermediate were initially charged in 76 ml of DCM and acylated with 0.81 ml (7.17 mmol) of 2-chloro-2-oxoethyl acetate in the presence of 2.1 ml of triethylamine. After 20 h of stirring at RT, 0.36 ml of 2-chlor-2-oxoethyl acetate and 0.94 ml of triethylamine were added and the reaction was stirred at RT for a further 15 min. The mixture was then diluted with 500 ml of ethyl acetate and extracted successively twice with 300 ml of 5% strength citric acid, twice with 300 ml of saturated sodium bicarbonate solution and once with 100 ml of saturated sodium chloride solution and then dried over magnesium sulphate and concentrated. Drying under high vacuum gave 2.17 g (79% of theory) of the protected intermediate.

LC-MS (Method 1): $R_t$=1.48 min; MS (ESIpos): m/z=714 (M+H)$^+$.

2.17 mg (2.64 mmol) of this intermediate were dissolved in 54 ml of THF and 27 ml of water, and 26 ml of a 2-molar lithium hydroxide solution were added. The mixture was stirred at RT for 30 min and then adjusted to a pH between 3 and 4 using 1.4 ml of TFA. The mixture was concentrated under reduced pressure. Once most of the THF had been distilled off, the aqueous solution was extracted twice with DCM and then concentrated to dryness under reduced pressure. The residue was purified by preparative HPLC (column: Chromatorex C18). After combination of the appropriate fractions, the solvent was evaporated under reduced pressure and the residue was lyophilized from acetonitrile/water. This gave 1.1 g (63% of theory) of the title compound.

LC-MS (Method 1): $R_t$=1.34 min; MS (ESIpos): m/z=656 (M−H)$^−$.

$^1$H-NMR (400 MHz, DMSO-d$_6$): δ[ppm]=0.03 (s, 9H), 0.58 (m, 1H), 0.74-0.92 (m, 11H), 1.40 (m, 1H), 3.3 (m, 2H), 3.7 (m, 1H), 3.8-4.0 (m, 2H), 4.15 (q, 2H), 4.9 and 5.2 (2d, 2H), 5.61 (s, 1H), 6.94 (m, 2H), 7.13-7.38 (m, 7H), 7.48 (s, 1H), 7.60 (m, 1H), 12.35 (s, 1H).

Intermediate C59

(2S)-4-({(1R)-1-[1-Benzyl-4-(2,5-difluorophenyl)-1H-pyrrol-2-yl]-2,2-dimethylpropyl}[(2S)-2-methoxypropanoyl]amino)-2-{[(9H-fluoren-9-ylmethoxy)carbonyl]amino}butanoic acid

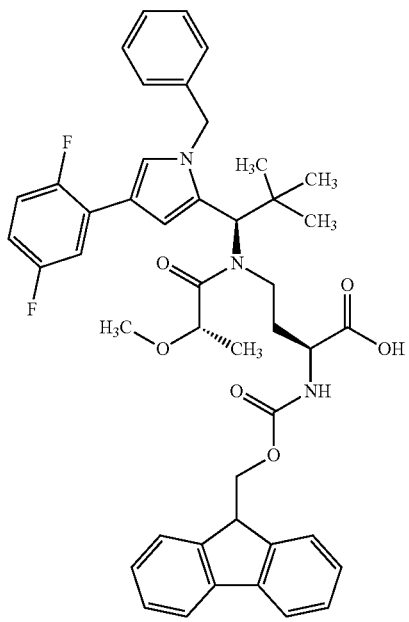 [SMILES: CO[C@@H](C)C(=O)N(CC[C@H](NC(=O)OCC1c2ccccc2-c2ccccc21)C(=O)O)[C@@H](c1cc(-c2cc(F)ccc2F)cn1Cc1ccccc1)C(C)(C)C]

Initially, the secondary amino group of benzyl (2S)-4-({(1R)-1-[1-benzyl-4-(2,5-difluorophenyl)-1H-pyrrol-2-yl]-2,2-dimethylpropyl}amino)-2-{[(benzyloxy)carbonyl]amino}butanoate was acylated with (2S)-2-methoxypropanoyl chloride (intermediate of Intermediate C53) in the presence of triethylamine as described for Intermediate C53. The intermediate obtained was taken up in ethanol, palladium on carbon (10%) was added and the mixture was hydrogenated at RT with hydrogen under standard pressure for 1 h. The deprotected compound was taken up in dioxane/water 2:1 and in the last step the Fmoc protective group was introduced using 9H-fluoren-9-ylmethyl chlorocarbonate in the presence of N,N-diisopropylethylamine.

LC-MS (Method 1): $R_t$=1.39 min; MS (ESIpos): m/z=764 (M−H)$^−$.

Intermediate C60

(2S)-4-({(1R)-1-[1-Benzyl-4-(2,5-difluorophenyl)-1H-pyrrol-2-yl]-2,2-dimethylpropyl}[(2S)-2-methoxypropanoyl]amino)-2-{[(9H-fluoren-9-ylmethoxy)carbonyl]amino}butanoic acid

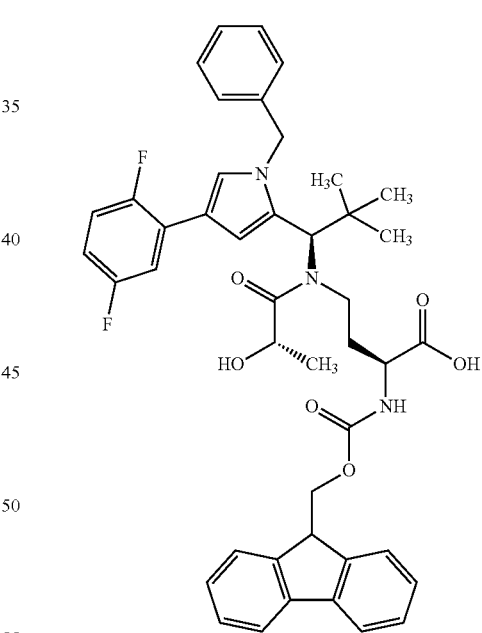

The synthesis was carried out analogously to Intermediate C53.

LC-MS (Method 1): $R_t$=1.41 min; MS (ESIpos): m/z=750 (M+H)$^+$.

Intermediate C61

N-[(2S)-4-[{(1R)-1-[1-Benzyl-4-(2,5-difluorophenyl)-1H-pyrrol-2-yl]-2,2-dimethylpropyl}(glycoloyl)amino]-2-({[2-(trimethylsilyl)ethoxy]carbonyl}amino)butanoyl]-beta-alanine

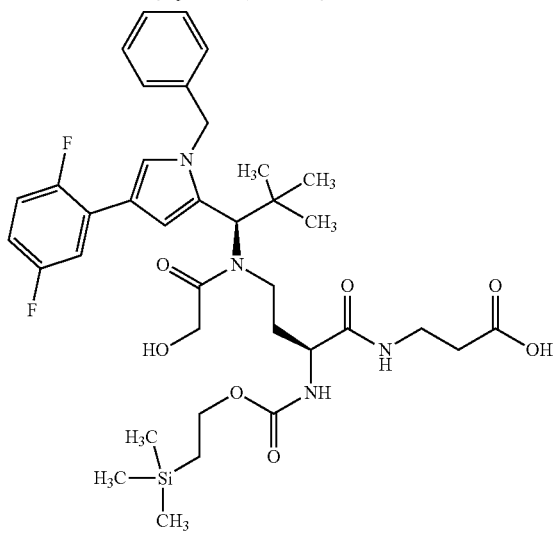

The title compound was prepared by coupling 60 mg (0.091 mmol) of Intermediate C58 with methyl 1-alaninate, followed by ester cleavage with 2M lithium hydroxide solution. This gave 67 mg (61% of theory) of the title compound over 2 steps.

LC-MS (Method 1): $R_t$=1.29 min; MS (ESIpos): m/z=729 (M+H)$^+$.

Intermediate C62

N-[(2S)-4-[{(1R)-1-[1-Benzyl-4-(2,5-difluorophenyl)-1H-pyrrol-2-yl]-2,2-dimethylpropyl}(glycoloyl)amino]-2-({[2-(trimethylsilyl)ethoxy]carbonyl}amino)butanoyl]-D-alanine

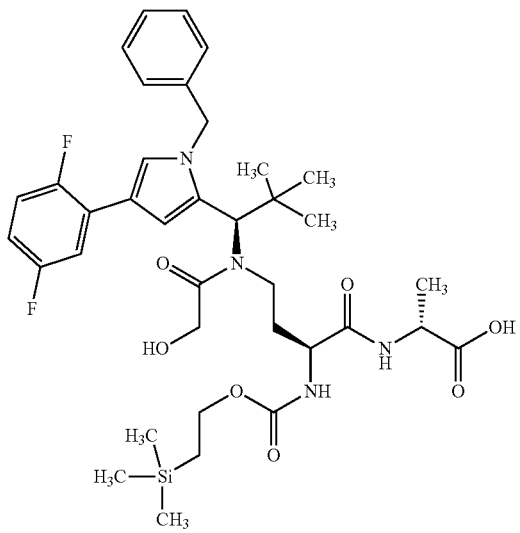 [SMILES: C[C@@H](NC(=O)[C@H](CCN(C(=O)CO)[C@@H](c1cc(-c2cc(F)ccc2F)cn1Cc1ccccc1)C(C)(C)C)NC(=O)OCC[Si](C)(C)C)C(=O)O]

The title compound was prepared analogously to Intermediate C61 from Intermediate C58 and methyl D-alaninate.

LC-MS (Method 1): $R_t$=1.32 min; MS (ESIpos): m/z=729 (M+H)$^+$.

Intermediate C64

Trifluoroacetic acid/2-(trimethylsilyl)ethyl {(2S)-1-[(2-aminoethyl)amino]-4-[{(1R)-1-[1-benzyl-4-(2,5-difluorophenyl)-1H-pyrrol-2-yl]-2,2-dimethylpropyl}(glycoloyl)amino]-1-oxobutan-2-yl}carbamate (1:1)

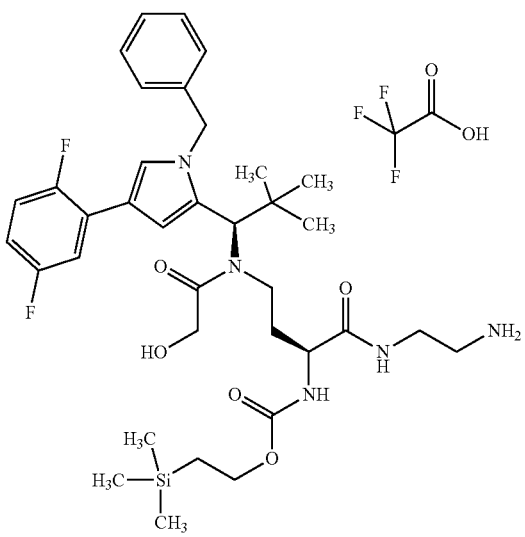 [SMILES: CC(C)(C)[C@H](c1cc(-c2cc(F)ccc2F)cn1Cc1ccccc1)N(CC[C@H](NC(=O)OCC[Si](C)(C)C)C(=O)NCCN)C(=O)CO ; O=C(O)C(F)(F)F]

The title compound was prepared from Intermediate C58 analogously to Intermediate C63.

HPLC (Method 11): $R_t$=2.4 min;
LC-MS (Method 1): $R_t$=1.01 min; MS (ESIpos): m/z=700 (M+H)$^+$.

Intermediate C65

(8S)-8-{2-[{(1R)-1-[1-Benzyl-4-(2,5-difluorophenyl)-1H-pyrrol-2-yl]-2,2-dimethylpropyl}-(glycoloyl)amino]ethyl}-2,2-dimethyl-6,11-dioxo-5-oxa-7,10-diaza-2-silatetradecan-14-oic acid

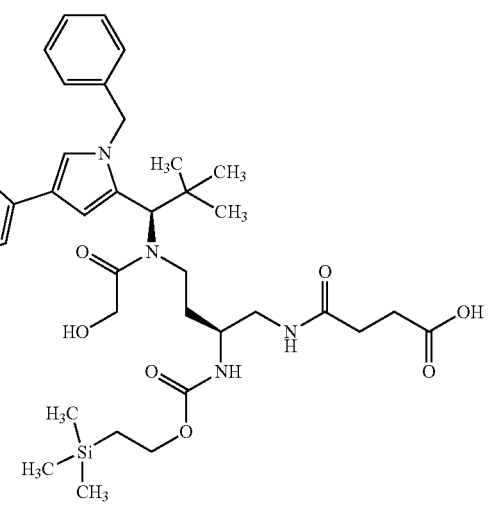

215 mg (0.59 mmol) of Intermediate L66 were initially charged in 25 ml of dichloromethane, and 377 mg (0.89 mmol) of Dess-Martin periodinane and 144 µl (1.78 mmol) of pyridine were added. The mixture was stirred at RT for 30 min. The reaction was then diluted with 300 ml of dichloromethane and the organic phase was washed in each case twice with 10% strength $Na_2S_2O_3$ solution, 10% strength citric acid solution and saturated sodium bicarbonate solution. The organic phase was dried over magnesium sulphate and the solvent was evaporated under reduced pressure. This gave 305 mg of the aldehyde which was reacted without further purification.

175 mg (0.49 mmol) of Intermediate C52 were dissolved in 50 ml of dichloromethane, and 147 mg (0.69 mmol) of sodium triacetoxyborohydride and 32.5 µl of acetic acid were added. After 5 min of stirring at RT, 214 mg (0.593 mmol) of the aldehyde described above were added, and the reaction was stirred at RT overnight. Here, instead of the expected product, 2-(trimethylsilyl)ethyl [(2S)-4-({(1R)-1-[1-benzyl-4-(2,5-difluorophenyl)-1H-pyrrol-2-yl]-2,2-dimethylpropyl}amino)-1-(2,5-dioxopyrrolidin-1-yl)butan-2-yl]carbamate was formed. Since this imide can also be converted into the title compound, the reaction was concentrated and the residue was purified by preparative HPLC. After combination of the appropriate imide-containing fractions, the solvent was evaporated under reduced pressure and the residue was dried under high vacuum. This gave 195 mg (58%) of the imide named above.

LC-MS (Method 5): $R_t$=3.32 min; MS (ESIpos): m/z=667 $(M+H)^+$.

65 mg (97.5 µmol) of this imide were taken up in 15 ml of dichloromethane, and 367 µl (3.4 mmol) of acetoxyacetyl chloride and 595 µl of N,N-diisopropylethylamine were added. After 30 min of stirring at RT, the reaction was concentrated without heating under reduced pressure and the residue was purified by preparative HPLC. The appropriate fractions were combined giving, after evaporation of the solvents and drying under high vacuum, 28 mg (37% of theory) of (8S)-11-{(1R)-1-[1-benzyl-4-(2,5-difluorophenyl)-1H-pyrrol-2-yl]-2,2-dimethylpropyl}-8-[(2,5-dioxopyrrolidin-1-yl)methyl]-2,2-dimethyl-6,12-dioxo-5-oxa-7,11-diaza-2-silatridecan-13-yl acetate.

LC-MS (Method 1): $R_t$=1.44 min; MS (ESIpos): m/z=767 $(M+H)^+$.

28 mg (37 µmol) of this intermediate were dissolved in 3 ml of methanol, and 548 µl of a 2M lithium hydroxide solution were added. After 10 min of stirring at RT, the reaction was adjusted to pH 4 with trifluoroacetic acid and then concentrated. The residue was purified by preparative HPLC. The appropriate fractions were combined, the solvent was evaporated and the residue was dried under high vacuum, giving 26 mg (96% of theory) of the title compound as a white solid.

LC-MS (Method 1): $R_t$=1.33 min; MS (ESIpos): m/z=743 $(M+H)^+$.

Intermediate C66

2-(Trimethylsilyl)ethyl [(2S)-4-[{(1R)-1-[1-benzyl-4-(2,5-difluorophenyl)-1H-pyrrol-2-yl]-2,2-dimethylpropyl}(glycoloyl)amino]-1-({[2-(glycylamino)ethyl]amino}-1-oxobutan-2-yl]carbamate

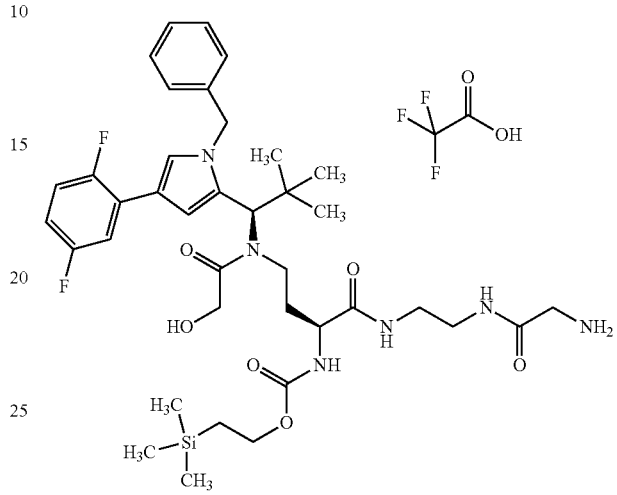

First, trifluoroacetic acid/benzyl {2-[(2-aminoethyl)amino]-2-oxoethyl}carbamate (1:1) was prepared from N-[(benzyloxy)carbonyl]glycine and tert-butyl (2-aminoethyl)carbamate according to classical methods of peptide chemistry (HATU coupling and Boc removal).

13 mg (0.036 mmol) of this intermediate and 25 mg (0.033 mmol) of Intermediate C58 were taken up in 3 ml of DMF, and 19 mg (0.05 mmol) of HATU and 17 µl of N,N-diisopropylethylamine were added. After 10 min of stirring at RT, the mixture was concentrated and the residue was purified by preparative HPLC. This gave 17.8 mg (60% of theory) of the intermediate.

LC-MS (Method 1): $R_t$=1.36 min; MS (ESIpos): m/z=891 $(M+H)^+$.

17 mg (0.019 mmol) of this intermediate were dissolved in 10 ml of ethanol, palladium on carbon (10%) was added and the mixture was hydrogenated at RT with hydrogen at standard pressure for 2 h. The catalyst was filtered off, the solvents were evaporated under reduced pressure and the residue was dried under high vacuum. This gave 9 mg (62% of theory) of the title compound.

LC-MS (Method 1): $R_t$=1.03 min; MS (ESIpos): m/z=757 $(M+H)^+$.

Intermediate C67

9H-Fluoren-9-ylmethyl [3-({(1R)-1-[1-benzyl-4-(2,5-difluorophenyl)-1H-pyrrol-2-yl]-2,2-dimethylpropyl}amino)propyl]carbamate

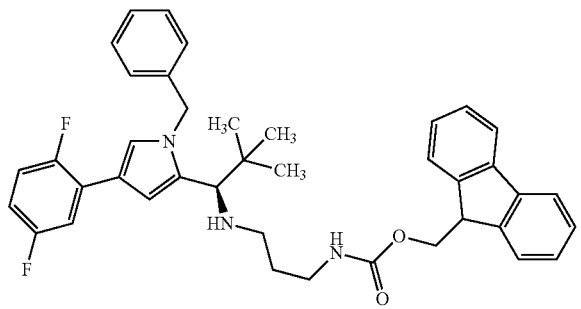 [SMILES: CC(C)(C)[C@@H](NCCCNC(=O)OCC1c2ccccc2-c2ccccc21)c1cc(-c2cc(F)ccc2F)cn1Cc1ccccc1]

605.3 mg (1.71 mmol) of (1R)-1-[1-benzyl-4-(2,5-difluorophenyl)-1H-pyrrol-2-yl]-2,2-dimethylpropan-1-amine (Intermediate C52) were initially charged in 10.0 ml of dichloromethane, and 506.7 mg (2.39 mmol) of sodium triacetoxyborohydride and 117.9 mg (1.96 mmol) of acetic acid were added and the mixture was stirred at RT for 5 min. 580.0 mg (1.96 mmol) of 9H-fluoren-9-ylmethyl (3-oxopropyl)carbamate (Intermediate L70) dissolved in 10.0 ml of dichloromethane were added and the reaction mixture stirred at RT overnight. The reaction mixture was diluted with ethyl acetate and the organic phase was washed in each case twice with saturated sodium carbonate solution and saturated NaCl solution. The organic phase was dried over magnesium sulphate and the solvent was evaporated under reduced pressure. The residue was purified by silica gel chromatography (mobile phase: cyclohexane/ethyl acetate 3:1). The solvents were evaporated under reduced pressure and the residue was dried under high vacuum. This gave 514.7 mg (46% of theory) of the title compound.

LC-MS (Method 1): $R_t$=1.10 min; MS (ESIpos): m/z=634 (M+H)$^+$.

Intermediate C69

11-{(1R)-1-[1-Benzyl-4-(2,5-difluorophenyl)-1H-pyrrol-2-yl]-2,2-dimethylpropyl}-2,2-dimethyl-6,12-dioxo-5-oxa-14-thia-7,11-diaza-2-silaheptadecan-17-oic acid

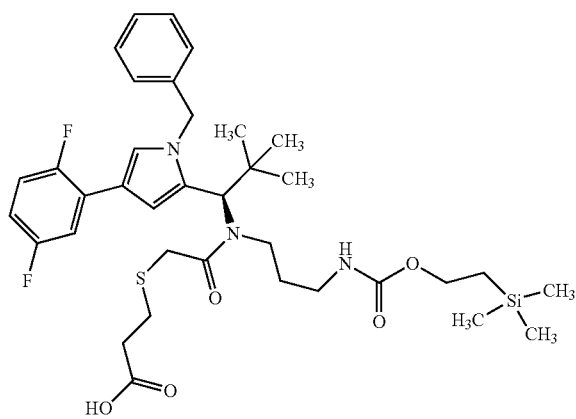 [SMILES: CC(C)(C)[C@H](c1cc(-c2cc(F)ccc2F)cn1Cc1ccccc1)N(CCCNC(=O)OCC[Si](C)(C)C)C(=O)CSCCC(=O)O]

117.0 mg (0.19 mmol) of (2-(trimethylsilyl)ethyl {3-[{(1R)-1-[1-benzyl-4-(2,5-difluorophenyl)-1H-pyrrol-2-yl]-2,2-dimethylpropyl}(chloroacetyl)amino]propyl}carbamate (Intermediate C70) and 21.6 mg (0.20 mmol) of 3-sulphanylpropanoic acid were initially charged in 3.0 ml of methanol, 89.5 mg (0.65 mmol) of potassium carbonate were added and the mixture was stirred at 50° C. for 4 h. The reaction mixture was diluted with ethyl acetate and the organic phase was washed with water and saturated NaCl solution. The organic phase was dried over magnesium sulphate, the solvent was evaporated under reduced pressure and the residue was dried under high vacuum. The residue was used without further purification in the next step of the synthesis. This gave 106.1 mg (73% of theory) of the title compound.

LC-MS (Method 1): $R_t$=1.42 min; MS (ESIneg): m/z=700 (M−H)$^−$.

Intermediate C70

(2-(Trimethylsilyl)ethyl {3-[{(1R)-1-[1-benzyl-4-(2,5-difluorophenyl)-1H-pyrrol-2-yl]-2,2-dimethylpropyl}(chloroacetyl)amino]propyl}carbamate

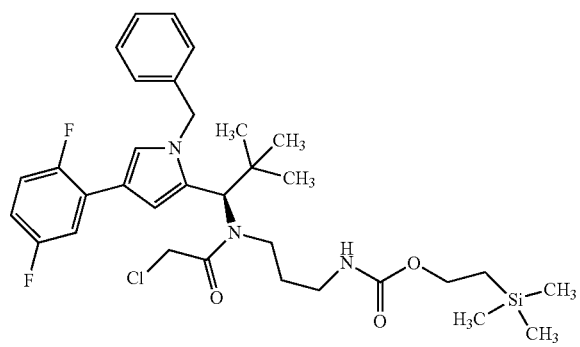 [SMILES: CC(C)(C)[C@H](c1cc(-c2cc(F)ccc2F)cn1Cc1ccccc1)N(CCCNC(=O)OCC[Si](C)(C)C)C(=O)CCl]

908.1 mg (1.63 mmol) of 2-(trimethylsilyl)ethyl [3-({(1R)-1-[1-benzyl-4-(2,5-difluorophenyl)-1H-pyrrol-2-yl]-2,2-dimethylpropyl}amino)propyl]carbamate (see synthesis of Intermediate C11) and 545.6 mg (5.39 mmol) of triethylamine were initially charged in 10.0 ml of dichloromethane, and the mixture was cooled to 0° C. At this temperature, 590.5 mg (5.23 mmol) of chloroacetyl chloride were added and the mixture was stirred at RT overnight. The reaction mixture was diluted with ethyl acetate and the organic phase was washed in each case three times with saturated sodium bicarbonate solution and saturated ammonium chloride solution. The organic phase was washed with saturated NaCl solution and dried over magnesium sulphate. The residue was purified by preparative RP-HPLC (column: Reprosil 250×30; 10μ, flow rate: 50 ml/min, MeCN/water, 0.1% TFA). The solvents were evaporated under reduced pressure and the residue was dried under high vacuum. This gave 673.8 mg (65% of theory) of the title compound.

LC-MS (Method 1): $R_t$=1.53 min; MS (ESIneg): m/z=676 (M+HCOO$^−$)$^−$.

Intermediate C71

S-(11-{(1R)-1-[1-Benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-L-cysteine/trifluoroacetic acid (1:1)

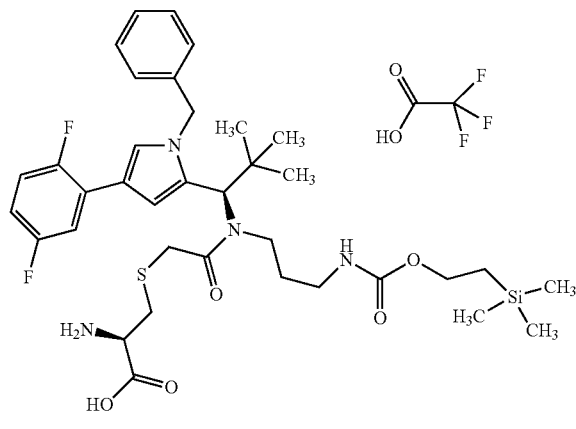 [SMILES: CC(C)(C)[C@H](c1cc(-c2cc(F)ccc2F)cn1Cc1ccccc1)N(CCCNC(=O)OCC[Si](C)(C)C)C(=O)CSC[C@H](N)C(=O)O ; O=C(O)C(F)(F)F]

536.6 mg (4.43 mmol) of L-cysteine were suspended in 2.5 ml of water together with 531.5 mg (6.33 mmol) of sodium bicarbonate. 400.0 mg (0.63 mmol) of 2-(trimethylsilyl)ethyl {3-[{(1R)-1-[1-benzyl-4-(2,5-difluorophenyl)-1H-pyrrol-2-yl]-2,2-dimethylpropyl}(chloroacetyl)amino]propyl}carbamate (Intermediate C70) dissolved in 25.0 ml of isopropanol and 1.16 g (7.59 mmol) of 1,8-diazabicyclo[5.4.0]undec-7-ene were added. The reaction mixture was stirred at 50° C. for 1.5 h. Ethyl acetate was added to the reaction mixture and the organic phase was washed repeatedly with saturated sodium bicarbonate solution and once with sat. NaCl solution. The organic phase was dried over magnesium sulphate, the solvent was evaporated under reduced pressure and the residue was dried under high vacuum. The residue was purified by preparative RP-HPLC (column: Reprosil 250×30; 10μ, flow rate: 50 ml/min, MeCN/water, 0.1% TFA). The solvents were evaporated under reduced pressure and the residue was dried under high vacuum. This gave 449.5 mg (86% of theory) of the title compound.

LC-MS (Method 1): $R_t$=1.20 min; MS (ESIpos): m/z=717 $(M+H)^+$.

Intermediate C72

(9S)-9-{[{(1R)-1-[1-Benzyl-4-(2,5-difluorophenyl)-1H-pyrrol-2-yl]-2,2-dimethylpropyl}(glycoloyl)amino]methyl}-2,2-dimethyl-6,11-dioxo-5-oxa-7,10-diaza-2-silatetradecan-14-oic acid

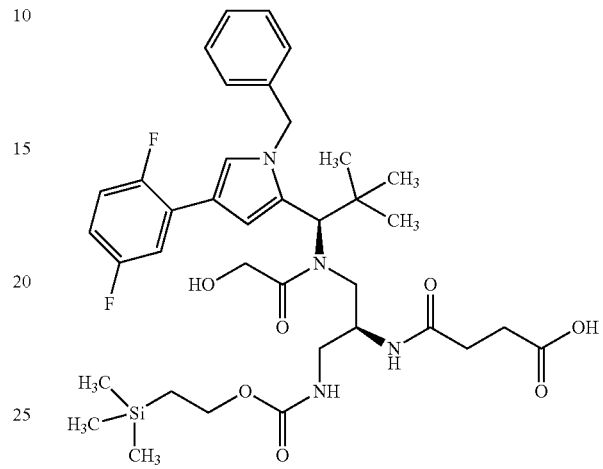

90 mg (0.212 mmol) of Intermediate L72 were initially charged in 6 ml of dichloromethane, and 86 μl (1.06 mmol) of pyridine and 135 mg (0.318 mmol) of Dess-Martin periodinane were added. The mixture was stirred at RT for 30 min. The reaction was then diluted with 30 ml of dichloromethane and the organic phase was washed twice with 10% strength $Na_2S_2O_3$ solution and once with 5% strength citric acid solution. The organic phase was dried over magnesium sulphate and the solvent was evaporated under reduced pressure. The aldehyde obtained in this manner was reacted without further purification.

63 mg (0.177 mmol) of Intermediate C52 were dissolved in 15 ml of dichloromethane, and 52.4 mg (0.247 mmol) of sodium triacetoxyborohydride and 20.2 μl of acetic acid were added. After 5 min of stirring at RT, 89.6 mg (0.212 mmol) of the aldehyde described above were added, and the reaction was stirred at RT for 20 min. The reaction was concentrated under reduced pressure and the residue was purified by preparative HPLC. After combination of the appropriate fractions, the solvent was evaporated under reduced pressure and the residue was lyophilized from acetonitrile/water. This gave 71 mg (53% of theory over 2 steps) of benzyl (9R)-9-[({(1R)-1-[1-benzyl-4-(2,5-difluorophenyl)-1H-pyrrol-2-yl]-2,2-dimethylpropyl}amino)methyl]-2,2-dimethyl-6,11-dioxo-5-oxa-7,10-diaza-2-silatetradecan-14-oate.

LC-MS (Method 1): $R_t$=1.21 min; MS (ESIpos): m/z=761 $(M+H)^+$.

70 mg (92 μmol) of this intermediate were taken up in 15 ml of dichloromethane, the mixture was cooled to 10° C. and 54 μl of triethylamine and 25.5 μl (0.23 mmol) of acetoxyacetyl chloride were added. After 1 h of stirring at RT, the same amounts of acid chloride and triethylamine were added, and once more after a further hour of stirring at RT. The reaction was then stirred at RT for a further 30 min and then concentrated under reduced pressure, and the residue was purified by preparative HPLC. The appropriate fractions were combined giving, after evaporation of the solvents and lyophilization of the residue from acetonitrile/water, 46.5 mg (59% of theory) of the acylated intermediate.

LC-MS (Method 1): $R_t$=1.53 min; MS (ESIpos): m/z=861 (M+H)$^+$.

46 mg (53 μmol) of this intermediate were dissolved in 5 ml of methanol, and 2.7 ml of a 2M lithium hydroxide solution were added. After 10 min of stirring at RT, the reaction was adjusted to pH 3-4 with acetic acid and then diluted with 15 ml of water. The aqueous phase was extracted with ethyl acetate and the organic phase was dried over magnesium sulphate and concentrated. The residue was lyophilized from acetonitrile/water giving, after drying of the residue under high vacuum, 37 mg (90% of theory) of the title compound as a white solid.

LC-MS (Method 1): $R_t$=1.32 min; MS (ESIpos): m/z=729 (M+H)$^+$.

Intermediate C73

S-(11-{(1R)-1-[1-Benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-N-[3-(trimethylsilyl)propanoyl]-L-cysteine

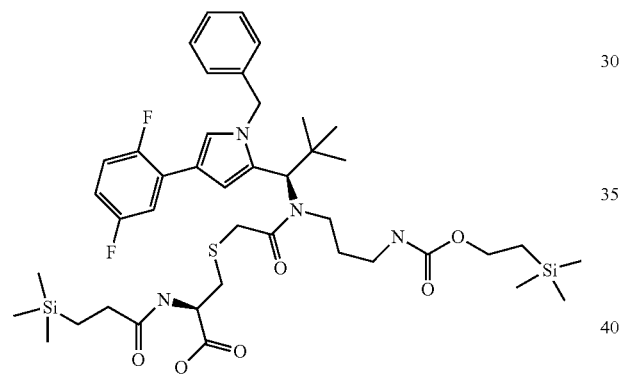

619 mg (0.86 mmol) of S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-L-cysteine/trifluoroacetic acid (1:1) (Intermediate C71) were initially charged in 8.8 ml of dichloromethane, and 87 mg (0.86 mmol) of triethylamine and 224 mg (0.86 mmol) of N-[2-(trimethylsilyl)ethoxycarbonyloxy]pyrrolidine-2,5-dione were added. After 1 h, 45 mg (0.17 mmol) of N-[2-(trimethylsilyl)ethoxycarbonyloxy]pyrrolidine-2,5-dione were added. The reaction mixture was stirred at RT for 1 h. The mixture was concentrated under reduced pressure, the residue was taken up in dichloromethane and the organic phase was then washed twice with water and a saturated sodium bicarbonate solution. The organic phase was dried over magnesium sulphate, concentrated on a rotary evaporator and dried under high vacuum. The residue was used further without further purification. This gave 602 mg (71%, purity 87%) of the title compound.

LC-MS (Method 1): $R_t$=1.58 min; MS (ESIpos): m/z=861 (M+H)$^+$.

Intermediate C74

Trifluoroacetic acid 2-(trimethylsilyl)ethyl 3-amino-N-[(2S)-4-[{(1R)-1-[1-benzyl-4-(2,5-difluorophenyl)-1H-pyrrol-2-yl]-2,2-dimethylpropyl}(glycoloyl)amino]-2-({[2-(trimethylsilyl)ethoxy]carbonyl}amino)butanoyl]-D-alaninate (1:1)

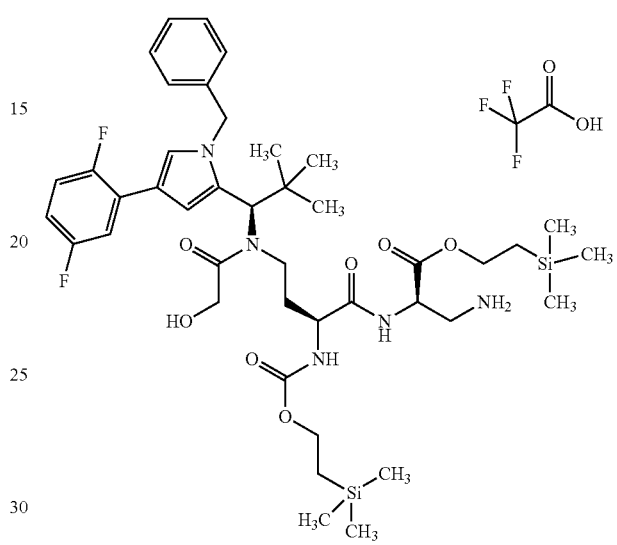

75 mg (0.114 mmol) of Intermediate C58 were taken up in 12.5 ml of DMF and coupled with 78 mg (0.171 mmol) of Intermediate L75 in the presence of 65 mg (0.11 mmol) of HATU and 79 μl of N,N-diisopropylethylamine. After purification by preparative HPLC, the intermediate was taken up in 20 ml of ethanol and hydrogenated over 10% palladium on activated carbon at RT under hydrogen standard pressure for 1 h. The catalyst was then filtered off, the solvent was removed under reduced pressure and the product was purified by preparative HPLC. Lyophilization from acetonitrile/water 1:1 gave 63 mg (64% of theory over 2 steps) of the title compound.

LC-MS (Method 1): $R_t$=1.16 min; MS (EIpos): m/z=844 [M+H]$^+$.

Intermediate C75

Methyl (2S)-4-[(acetoxyacetyl){(1R)-1-[1-benzyl-4-(2,5-difluorophenyl)-1H-pyrrol-2-yl]-2,2-dimethylpropyl}amino]-2-({[2-(trimethylsilyl)ethoxy]carbonyl}amino)butanoate

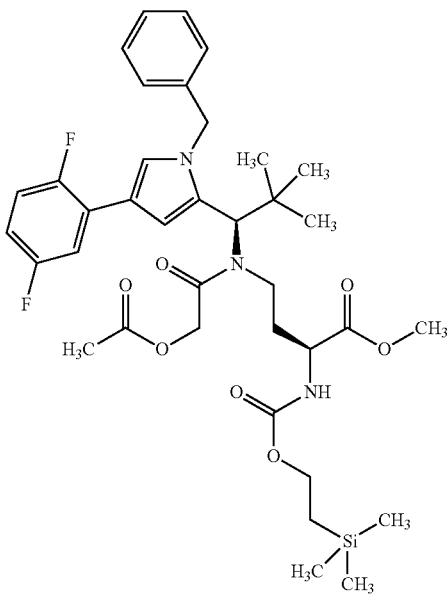 [SMILES: COC(=O)[C@H](CCN(C(=O)COC(C)=O)[C@@H](c1cc(-c2cc(F)ccc2F)cn1Cc1ccccc1)C(C)(C)C)NC(=O)OCC[Si](C)(C)C]

4.3 g (12.2 mmol) of Intermediate C52 were dissolved in 525 ml of DCM, and 3.63 g (17.12 mmol) of sodium triacetoxyborohydride and 8.4 ml of acetic acid were added. After 5 min of stirring at RT, 3.23 g (11.85 mmol) of methyl (2S)-4-oxo-2-({[2-(trimethylsilyl)ethoxy]carbonyl}amino)butanoate (prepared from (3S)-3-amino-4-methoxy-4-oxobutanoic acid by classical methods) dissolved in 175 ml of DCM were added, and the mixture was stirred at RT for a further 45 min. The mixture was then diluted with DCM and extracted twice with 100 ml of saturated sodium bicarbonate solution and then with saturated sodium chloride solution. The organic phase was dried over magnesium sulphate, filtered and concentrated. The residue was purified by preparative HPLC. Combination of the appropriate fractions, concentration and drying of the residue under high vacuum gave 4.6 g (61% of theory) of the intermediate.

LC-MS (Method 12): $R_t$=1.97 min; MS (ESIpos): m/z=614.32 (M+H)$^+$.

200 mg (0.33 mmol) of this intermediate were dissolved in 10 ml of DCM, and 105 µl of triethylamine and 77 µl (0.717 mmol) of acetoxyacetyl chloride were then added. The mixture was stirred at RT overnight and then concentrated under reduced pressure. The residue was taken up in ethyl acetate and extracted twice with saturated sodium bicarbonate solution and then with saturated sodium chloride solution. The organic phase was dried over magnesium sulphate and then concentrated. This gave 213 mg (75%) of the title compound as a beige foam.

LC-MS (Method 1): $R_t$=1.46 min; MS (ESIpos): m/z=714 (M+H)$^+$.

Intermediate C76

N-[(Benzyloxy)carbonyl]-L-valyl-N-{(1S)-3-[{(1R)-1-[1-benzyl-4-(2,5-difluorophenyl)-1H-pyrrol-2-yl]-2,2-dimethylpropyl}(glycoloyl)amino]-1-carboxypropyl}-L-alaninamide

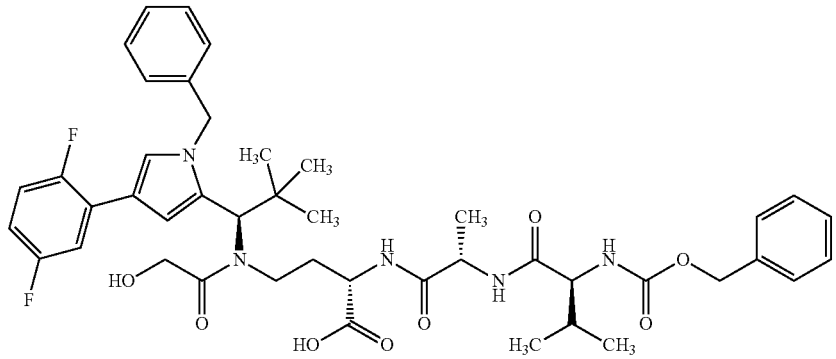 [SMILES: CC(C)[C@H](NC(=O)OCc1ccccc1)C(=O)N[C@@H](C)C(=O)N[C@@H](CCN(C(=O)CO)[C@@H](c1cc(-c2cc(F)ccc2F)cn1Cc1ccccc1)C(C)(C)C)C(=O)O]

The title compound was prepared from Intermediate C75 according to classical methods of peptide chemistry (removal of the Teoc protective group with zinc chloride, acylation with N-[(benzyloxy)carbonyl]-L-valyl-L-alanine in the presence of HATU and ester cleavage with lithium hydroxide in THF/water).

LC-MS (Method 1): $R_t$=1.23 min; MS (ESIpos): m/z=818 (M+H)$^+$.

Intermediate C77

S-(11-{(1R)-1-[1-Benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-N-(4-tert-butoxy-4-oxobutanoyl)-L-cysteine

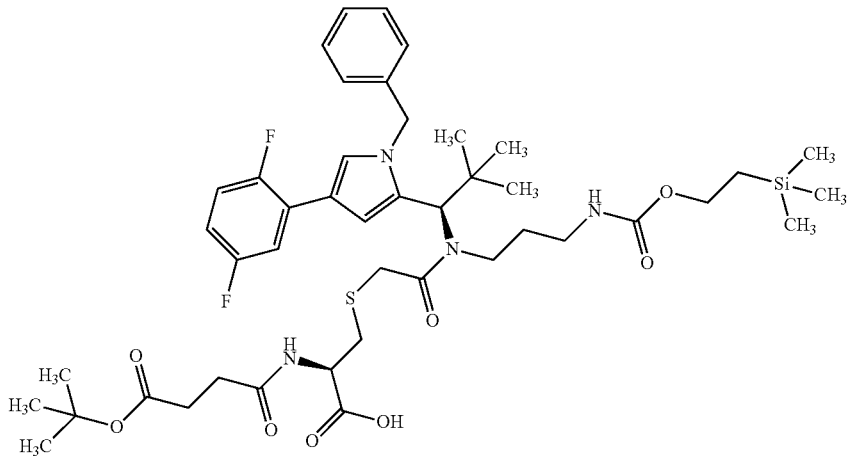 [SMILES: CC(C)(C)OC(=O)CCC(=O)N[C@@H](CSCC(=O)N(CCCNC(=O)OCC[Si](C)(C)C)[C@@H](c1cc(-c2cc(F)ccc2F)cn1Cc1ccccc1)C(C)(C)C)C(=O)O]

4-tert-Butoxy-4-oxobutanoic acid (8.39 mg, 48.1 µmol) was initially charged in 1.0 ml of DMF, 7.37 mg (48.1 µmol) of 1-hydroxy-1H-benzotriazole hydrate, 15.5 mg ((48.1 µmol) of (benzotriazol-1-yloxy)bisdimethylaminomethylium fluoroborat and 8.60 µl (48.1 µmol) of N,N-diisopropylethylamine were added and the mixture was stirred at RT for 10 minutes. 40.0 mg (0.048 mmol) S-(11-{(1R)-1-[1-Benzyl-4-(2,5-difluorphenyl)-1H-pyrrol-2-yl]-2,2-dimethylpropyl}-2,2-dimethyl-6,12-dioxo-5-oxa-7,11-diaza-2-silatridecan-13-yl)-L-cysteine trifluoroacetic acid (1:1) (Intermediate C71) were initially charged in 1.0 ml of DMF, 25.4 µl (141.9 µmol) of N,N-diisopropylethylamine were added, the mixture was added to the reaction and the reaction mixture was stirred at RT for 4 h. The reaction mixture was purified directly by preparative RP-HPLC (column: Reprosil 125×30; 10µ, flow rate: 50 ml/min, MeCN/water, 0.1% TFA). The solvents were evaporated under reduced pressure and the residue was dried under high vacuum. This gave 35.0 mg (83% of theory) of the title compound.

LC-MS (Method 12): $R_t$=2.76 min; MS (ESIpos): m/z=873 [M+H]$^+$

Intermediate C78

11-{(1R)-1-[1-Benzyl-4-(2,5-difluorophenyl)-1H-pyrrol-2-yl]-2,2-dimethylpropyl}-2,2-dimethyl-6,12-dioxo-5-oxa-7,11-diaza-2-silapentadecane-15-acid

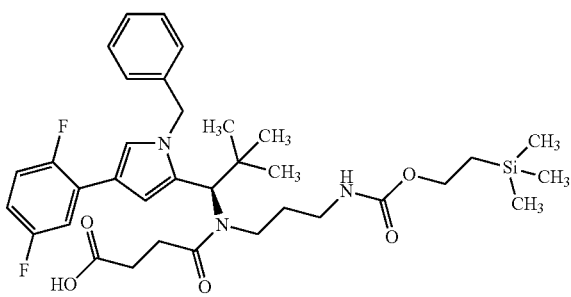 [SMILES: CC(C)(C)[C@H](c1cc(-c2cc(F)ccc2F)cn1Cc1ccccc1)N(CCCNC(=O)OCC[Si](C)(C)C)C(=O)CCC(=O)O]

197 mg (0.354 mmol) of 2-(trimethylsilyl)ethyl [3-({(1R)-1-[1-benzyl-4-(2,5-difluorophenyl)-1H-pyrrol-2-yl]-2,2-dimethylpropyl}amino)propyl]carbamate (see synthesis of Intermediate C11) were initially charged in 5.0 ml of dichloromethane, and the mixture was heated to 40° C. At this temperature, 240 µl (3.0 mmol) of pyridine and 220 µl (1.8 mmol) of methyl 4-chloro-4-oxobutanoate were added, and the mixture was stirred at RT for 1 h. 240 µl (3.0 mmol) of pyridine and 220 µl (1.8 mmol) of methyl 4-chloro-4-oxobutanoate were then added, and the mixture was stirred at RT for 1 h. 240 µl (3.0 mmol) of pyridine and 220 µl (1.8 mmol) of methyl 4-chloro-4-oxobutanoate were then added, and the mixture was stirred at RT for 1 h. The reaction mixture was diluted with ethyl acetate and the organic phase was extracted in each case three times with 5% strength KHSO$_4$ solution. The organic phase was washed with saturated NaCl solution and dried over magnesium sulphate. The solvents were evaporated under reduced pressure. The residue was purified by preparative RP-HPLC (column: Reprosil 250×30; 10µ, flow rate: 50 ml/min, MeCN/water, 0.1% TFA). The solvents were evaporated under reduced pressure and the residue was dried under high vacuum. This gave 74.1 mg (31% of theory) of methyl 11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silapentadecan-15-oate.

LC-MS (Method 1): $R_t$=1.49 min; MS (ESIpos): m/z=670 [M+H]$^+$ 78.3 mg (117 µmol) of methyl 11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silapentadecan-15-oate were initially charged in 4.0 ml of THF, and 800 µl of methanol, 160 µl of water and 230 µl (230 µmol) of aqueous LiOH solution (1M) were added. The reaction mixture was stirred at RT for 3 h, quenched with acetic acid and purified directly by preparative RP-HPLC (column: Reprosil 250×30; 10µ, flow rate: 50 ml/min, MeCN/water, 0.1% TFA). The solvents were evaporated under reduced pressure and the residue was dried under high vacuum. This gave 64.8 mg (85% of theory) of the title compound.

LC-MS (Method 12): $R_t$=2.61 min; MS (ESIneg): m/z=654 [M−H]−

Intermediate C79

Trifluoroacetic acid 2-(trimethylsilyl)ethyl 3-amino-N-(11-{(1R)-1-[1-benzyl-4-(2,5-difluorophenyl)-1H-pyrrol-2-yl]-2,2-dimethylpropyl}-2,2-dimethyl-6,12,17-trioxo-5-oxa-14-thia-7,11-diaza-2-silaheptadecan-17-yl)-D-alaninate (1:1)

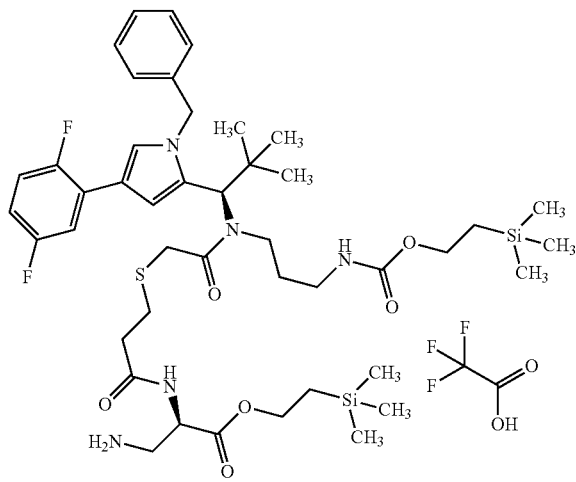

57.4 mg (81.8 μmol) of 11-{(1R)-1-[1-benzyl-4-(2,5-difluorophenyl)-1H-pyrrol-2-yl]-2,2-dimethylpropyl}-2,2-dimethyl-6,12-dioxo-5-oxa-14-thia-7,11-diaza-2-silaheptadecan-17-oic acid (Intermediate C69) were initially charged in 5.7 ml of DMF, 74.0 mg (164 μmol) of trifluoroacetic acid 2-(trimethylsilyl)ethyl 3-{[(benzyloxy)carbonyl]amino}-D-alaninate (1:1) (Intermediate L75), 43 μl (250 μmol) of N,N-diisopropylethylamine and 62.2 mg (164 μmol) of HATU were added and the mixture was stirred at RT for 1 h. The reaction mixture was stirred at RT for 1 h, quenched with acetic acid and purified directly by preparative RP-HPLC (column: Reprosil 125×30; 10μ, flow rate: 50 ml/min, MeCN/water, 0.1% TFA). The solvents were evaporated under reduced pressure and the residue was dried under high vacuum. This gave 52.4 mg (63% of theory) of the compound 2-(trimethylsilyl)ethyl N-(11-{(1R)-1-[1-benzyl-4-(2,5-difluorophenyl)-1H-pyrrol-2-yl]-2,2-dimethylpropyl}-2,2-dimethyl-6,12,17-trioxo-5-oxa-14-thia-7,11-diaza-2-silaheptadecan-17-yl)-3-{[(benzyloxy)carbonyl]amino}-D-alaninate.

LC-MS (Method 1): $R_t$=1.64 min; MS (ESIpos): m/z=1022 [M]+

Under argon, 6.23 mg (27.7 μmol) of palladium(II) acetate: were initially charged in 3.0 ml of dichloromethane, 12 μl (83 μmol) of triethylamine and 89 μl (550 μmol) of triethylsilane were added and the mixture was stirred for 5 minutes. 56.7 mg (55.5 μmol) of 2-(trimethylsilyl)ethyl N-(11-{(1R)-1-[1-benzyl-4-(2,5-difluorophenyl)-1H-pyrrol-2-yl]-2,2-dimethylpropyl}-2,2-dimethyl-6,12,17-trioxo-5-oxa-14-thia-7,11-diaza-2-silaheptadecan-17-yl)-3-{[(benzyloxy)carbonyl]amino}-D-alaninate in 3.0 ml of dichloromethane were then added, and the mixture was stirred at RT overnight. The mixture was concentrated almost to dryness, acetonitrile/water was added, and the mixture was filtered and purified by preparative RP-HPLC (column: Reprosil 125×30; 10μ, flow rate: 50 ml/min, MeCN/water, 0.1% TFA). The solvents were evaporated under reduced pressure and the residue was dried under high vacuum. This gave 37.4 mg (67% of theory) of the title compound.

LC-MS (Method 12): $R_t$=2.15 min; MS (ESIpos): m/z=888 [M+H]+

Intermediate C80

S-(11-{(1R)-1-[1-Benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-N-[15-(glycylamino)-4,7,10,13-tetraoxapentadecan-1-oyl]-L-cysteine trifluoroacetic acid (1:1)

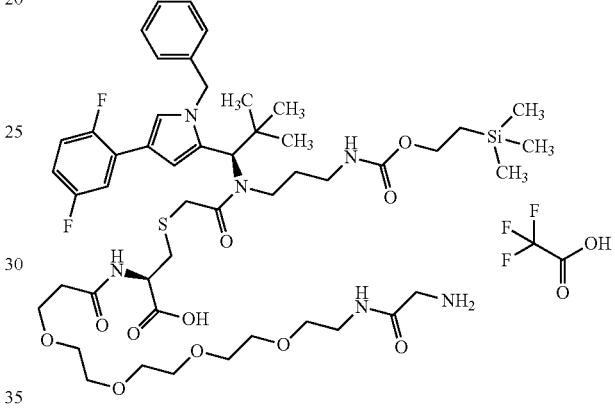

Under argon, 43.4 mg (95.1 μmol) of 1-({N-[(benzyloxy)carbonyl]glycyl}amino)-3,6,9,12-tetraoxapentadecan-15-oic acid (Intermediate L90) were initially charged in 2.5 ml of DMF, 14.6 mg (95.1 μmol) of 1-hydroxy-1H-benzotriazole hydrate, 30.5 mg (95.1 μmol) of (benzotriazol-1-yloxy) bisdimethylaminomethylium fluoroborate and 16.5 μl (95.1 μmol) of N,N-diisopropylethylamine were added and the mixture was stirred for 10 min. 79.0 mg (95.1 μmol) of S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-L-cysteine trifluoroacetic acid (1:1) (Intermediate C71) were dissolved in 2.5 ml of DMF, 49.5 μl (285.3 μmol) of N,N-diisopropylethylamine were added and the mixture was added to the reaction. The reaction mixture was stirred at RT for 2 h and purified directly by preparative RP-HPLC (column: Reprosil 125×30; 10μ, flow rate: 50 ml/min, MeCN/water, 0.1% TFA). The solvents were evaporated under reduced pressure and the residue was dried under high vacuum. This gave 44.2 mg (40% of theory) of the compound S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-N-[15-({N-[(benzyloxy)carbonyl]glycyl}amino)-4,7,10,13-tetraoxapentadecan-1-oyl]-L-cysteine.

LC-MS (Method 12): $R_t$=2.57 min; MS (ESIpos): m/z=1156 [M+H]+

60.2 mg (52.1 μmol) of S-(1-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-N-[15-({N-[(benzyloxy)carbonyl]glycyl}amino)-4,7,10, 13-tetraoxapentadecan-1-oyl]-L-cysteine were suspended in 3.0 ml of ethanol, 6.0 mg of palladium on activated carbon (10%) were added and the mixture was hydrogenated with hydrogen at RT and standard pressure for 1 h. Twice, 6.0 mg of palladium on activated carbon (10%) were added and the mixture was hydrogenated with hydrogen at RT and standard pressure for 1 h. The catalyst was filtered off and the reaction mixture was freed from the solvent under reduced pressure and dried under high vacuum. The residue was purified by preparative RP-HPLC (column: Reprosil 125× 30; 10μ, flow rate: 50 ml/min, MeCN/water, 0.1% TFA). The solvents were evaporated under reduced pressure and the residue was dried under high vacuum. This gave 29.4 mg (50% of theory) of the title compound.

LC-MS (Method 5): $R_t$=3.77 min; MS (ESIpos): m/z=1021 [M+H]$^+$

Intermediate C81

(R)-1-[1-Benzyl-4-(2,5-difluorophenyl)-1H-pyrrol-2-yl]-1-cyclohexylmethanamine

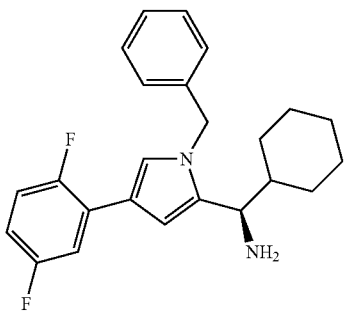 [SMILES: N[C@@H](c1cc(-c2cc(F)ccc2F)cn1Cc1ccccc1)C1CCCCC1]

Under argon and at −78° C., 18.7 ml (37.45 mmol) of cyclohexylmagnesium chloride in diethyl ether (2M) were added to a solution of 3.12 ml (6.24 mmol) of dimethylzinc in toluene (2.0 M), and the mixture was stirred at −78° C. for 30 minutes. A solution of 5.0 g (12.48 mmol) of (R)—N-{(E/Z)-[1-benzyl-4-(2,5-difluorophenyl)-1H-pyrrol-2-yl]methylene}-2-methylpropane-2-sulphinamide in THF was then added at −78° C., and the reaction mixture was stirred at this temperature for 1 h and then at RT for 4 h. At −78° C., saturated ammonium chloride solution was then added and the reaction mixture was allowed to warm to RT. The mixture was diluted with ethyl acetate and washed with water. The organic phase was dried over magnesium sulphate and the solvent was evaporated under reduced pressure. The residue was purified using Biotage Isolera (silica gel, ethyl acetate/cyclohexane 25:75). This gave 1.59 g (26% of theory) of the intermediate.

LC-MS (Method 12): $R_t$=2.76 min; MS (ESIneg): m/z=483 [M−H]$^−$

Under argon, 264.0 mg (0.54 mmol) of this intermediate were initially charged in 0.5 ml of 1,4-dioxane, and 1.36 ml of HCl in 1,4-dioxane solution (4.0 M) were then added. The reaction mixture was stirred at RT for 1 h. Dichloromethane was added, and the reaction mixture was washed with an aqueous 1M sodium hydroxide solution. The organic phase was dried with magnesium sulphate and the solvent was evaporated under reduced pressure. The residue was purified using Biotage Isolera (silica gel, methanol/dichloromethane 98:2). The solvent was evaporated under reduced pressure and the residue was dissolved in dichloromethane, washed with a sodium bicarbonate solution and dried over sodium sulphate. The solvent was evaporated under reduced pressure and the residue was dried under high vacuum. This gave 148 mg (72% of theory) of the title compound.

LC-MS (Method 13): $R_t$=2.07 min; MS (ESIpos): m/z=364 [M−NH$_2$]$^+$

Intermediate C82

2-(Trimethylsilyl)ethyl (3-{[(R)-[1-benzyl-4-(2,5-difluorophenyl)-1H-pyrrol-2-yl](cyclohexyl)methyl]amino}propyl)carbamate

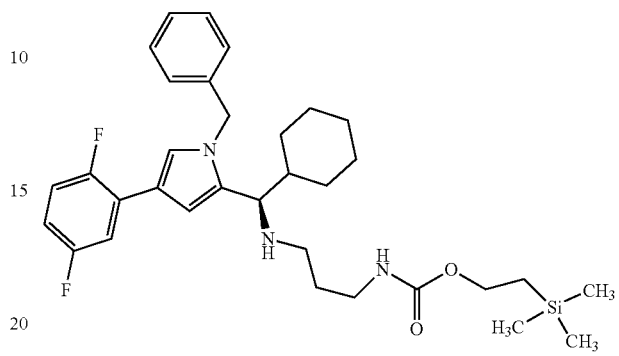

Under argon, 392.2 mg (1.85 mmol) of sodium triacetoxyborohydride and 91.29 mg (1.52 mmol) of acetic acid were added to a solution of 503.0 mg (1.32 mmol) of 1-[1-benzyl-4-(2,5-difluorophenyl)-1H-pyrrol-2-yl]-1-cyclohexylmethanamine (Intermediate C81) in 1.4 ml of dichloromethane, and the reaction mixture was stirred at RT for 10 minutes. A solution of 574.6 (2.38 mmol) of 2-(trimethylsilyl)ethyl (3-oxopropyl)carbamate in dichloromethane was then added, and the mixture was stirred at RT overnight. After addition of 143 mg (0.66 mmol) of 2-(trimethylsilyl)ethyl (3-oxopropyl)carbamate, the mixture was stirred for a further 2 h. The reaction mixture was diluted with dichloromethane and the organic phase was washed in each case twice with saturated sodium carbonate solution and with saturated NaCl solution, dried over sodium sulphate and concentrated. The residue was purified by preparative HPLC. The solvents were evaporated under reduced pressure and the residue was dried under high vacuum. This gave 488 g (63% of theory) of the title compound.

LC-MS (Method 12): $R_t$=1.89 min; MS (ESIpos): m/z=582 (M+H)$^+$.

Intermediate C83

2-(Trimethylsilyl)ethyl (3-{[(R)-[1-benzyl-4-(2,5-difluorophenyl)-1H-pyrrol-2-yl](cyclohexyl)methyl](chloroacetyl)amino}propyl)carbamate

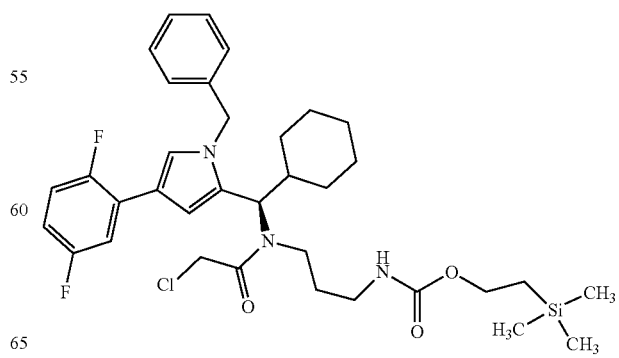

280.0 mg (2.77 mmol) of triethylamine and 397.8 mg (3.52 mmol) of chloroacetyl chloride were added to a solution of 487.9 mg (0.84 mmol) 2-(trimethylsilyl)ethyl (3-{[(R)-[1-benzyl-4-(2,5-difluorophenyl)-1H-pyrrol-2-yl](cyclohexyl)methyl]amino}propyl)carbamate (Intermediate C82) in 8.40 ml of dichloromethane with 4 Å molecular sieve, and the reaction mixture was stirred at RT for 6 h. The reaction mixture was diluted with dichloromethane and the organic phase was washed with saturated sodium bicarbonate solution and saturated ammonium chloride solution. The organic phase was dried over sodium sulphate and concentrated. The residue was used further without purification. This gave 470 mg (85% of theory) of the title compound.

LC-MS (Method 12): $R_t$=2.88 min; MS (ESIpos): m/z=680 (M+Na)$^+$.

Intermediate C84

S-{11-[(R)-[1-Benzyl-4-(2,5-difluorophenyl)-1H-pyrrol-2-yl](cyclohexyl)methyl]-2,2-dimethyl-6,12-dioxo-5-oxa-7,11-diaza-2-silatridecan-13-yl}-L-cysteine

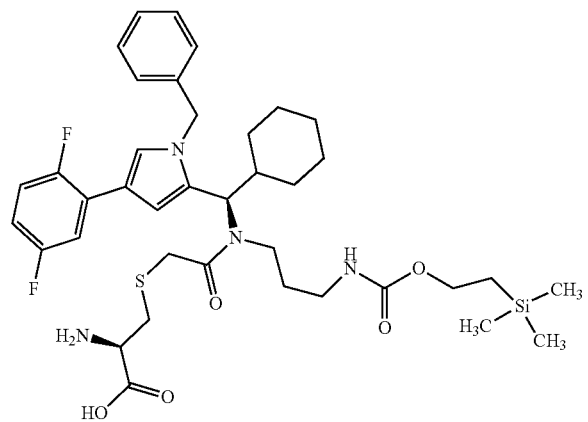 [SMILES: C[Si](C)(C)CCOC(=O)NCCCN(C(=O)CSC[C@H](N)C(=O)O)[C@@H](c1cc(-c2cc(F)ccc2F)cn1Cc1ccccc1)C1CCCCC1]

322.1 mg (2.66 mmol) of L-cysteine were suspended in 0.19 ml of water together with 319.0 mg (3.80 mmol) of sodium bicarbonate. 250.0 mg (0.38 mmol) of 2-(trimethylsilyl)ethyl (3-{[(R)-[1-benzyl-4-(2,5-difluorophenyl)-1H-pyrrol-2-yl](cyclohexyl)methyl](chloroacetyl)amino}propyl)carbamate (Intermediate C83) dissolved in 1.90 ml of isopropanol and 693.8 g (4.56 mmol) of 1,8-diazabicyclo[5.4.0]undec-7-ene were added. The reaction mixture was stirred at 50° C. for 3.5 h. Ethyl acetate was added to the reaction mixture and the organic phase was washed repeatedly with saturated sodium bicarbonate solution and once with saturated NaCl solution. The organic phase was dried over sodium sulphate and the solvent was evaporated under reduced pressure. The residue was used further without further purification. This gave 276 mg (97% of theory) of the title compound.

LC-MS (Method 12): $R_t$=2.34 min; MS (ESIpos): m/z=744 (M+H)$^+$.

Intermediate C85

S-{11-[(R)-[1-Benzyl-4-(2,5-difluorophenyl)-1H-pyrrol-2-yl](cyclohexyl)methyl]-2,2-dimethyl-6,12-dioxo-5-oxa-7,11-diaza-2-silatridecan-13-yl}-N-[6-(2,5-dioxo-2,5-dihydro-1H-pyrrol-1-yl)hexanoyl]-L-cysteine

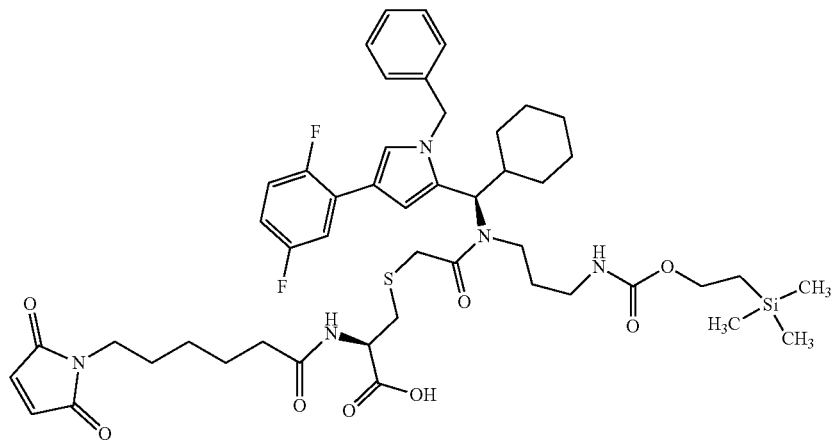 [SMILES: C[Si](C)(C)CCOC(=O)NCCCN(C(=O)CSC[C@H](NC(=O)CCCCCN1C(=O)C=CC1=O)C(=O)O)[C@@H](c1cc(-c2cc(F)ccc2F)cn1Cc1ccccc1)C1CCCCC1]

34.8 mg (0.27 mmol) of N,N-diisopropylethylamine were added to a mixture of 100 mg (0.13 mmol) of S-{11-[(R)-[1-benzyl-4-(2,5-difluorophenyl)-1H-pyrrol-2-yl](cyclohexyl)methyl]-2,2-dimethyl-6,12-dioxo-5-oxa-7,11-diaza-2-silatridecan-13-yl}-L-cysteine (1:1) (Intermediate C84) and 41.5 mg (0.13 mmol) of 1-{6-[(2,5-dioxopyrrolidin-1-yl)oxy]-6-oxohexyl}-1H-pyrrole-2,5-dione in 4.0 ml of DMF, and the reaction mixture was stirred at RT for 3 h. Without work-up, the mixture was purified by preparative HPLC. This gave 88 mg (70% of theory) of the title compound.

LC-MS (Method 12): $R_t$=2.71 min; MS (ESIpos): m/z=936 (M+H)$^+$.

Intermediate C86

11-[(R)-[1-Benzyl-4-(2,5-difluorophenyl)-1H-pyrrol-2-yl](cyclohexyl)methyl]-2,2-dimethyl-6,12-dioxo-5-oxa-14-thia-7,11-diaza-2-silaheptadecan-17-oic acid

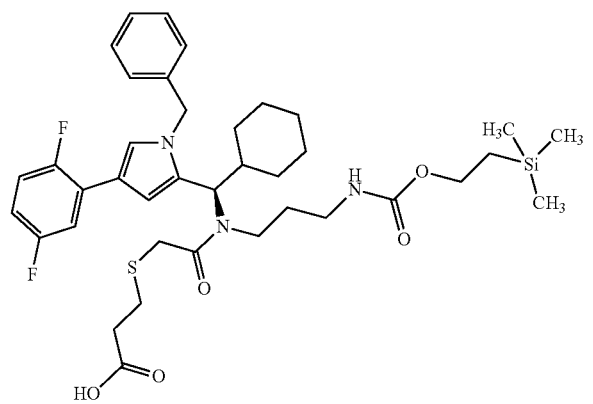 [SMILES: C[Si](C)(C)CCOC(=O)NCCCN(C(=O)CSCCC(=O)O)[C@@H](c1cc(-c2cc(F)ccc2F)cn1Cc1ccccc1)C1CCCCC1]

161.65 mg (1.17 mmol) of potassium carbonate were added to a mixture of 220.0 mg (0.33 mmol) of 2-(trimethylsilyl)ethyl (3-{[(R)-[1-benzyl-4-(2,5-difluorophenyl)-1H-pyrrol-2-yl](cyclohexyl)methyl](chloroacetyl)amino}propyl)carbamate (Intermediate C83) and 39.02 mg (0.37 mmol) of 3-sulphanylpropanoic acid in 7.45 ml of methanol and a few drops of water. The reaction mixture was stirred at 50° C. for 4 h. Ethyl acetate was added to the reaction mixture and the organic phase was washed repeatedly with water and with saturated NaCl solution. The organic phase was dried over sodium sulphate and the solvent was evaporated under reduced pressure. The residue was used further without work-up. This gave 201 mg (83% of theory) of the title compound.

LC-MS (Method 12): $R_t$=2.72 min; MS (ESIneg): m/z=726 (M−H)$^-$.

Intermediate C87

2-(Trimethylsilyl)ethyl {13-[(R)-[1-benzyl-4-(2,5-difluorophenyl)-1H-pyrrol-2-yl](cyclohexyl)methyl]-1-(2,5-dioxo-2,5-dihydro-1H-pyrrol-1-yl)-2,7,12-trioxo-10-thia-3,6,13-triazahexadecan-16-yl}carbamate

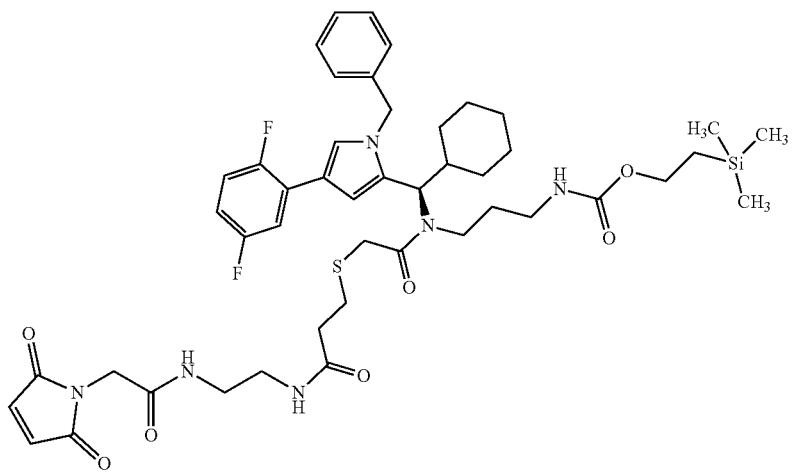 [SMILES: C[Si](C)(C)CCOC(=O)NCCCN(C(=O)CSCCC(=O)NCCNC(=O)CN1C(=O)C=CC1=O)[C@@H](c1cc(-c2cc(F)ccc2F)cn1Cc1ccccc1)C1CCCCC1]

54.18 mg (0.28 mmol) of N-(2-aminoethyl)-2-(2,5-dioxo-2,5-dihydro-1H-pyrrol-1-yl)acetamide (Intermediate L1), 71.01 mg (0.50 mmol) of N,N-diisopropylethylamine, 104.46 mg (0.27 mmol) of HATU and 0.23 ml (0.14 mmol) of 1-hydroxy-7-azabenzotriazole 0.5 M in DMF were added to a solution of 100 mg (0.14 mmol) of 11-[(R)-[1-benzyl-4-(2,5-difluorophenyl)-1H-pyrrol-2-yl](cyclohexyl)methyl]-2,2-dimethyl-6,12-dioxo-5-oxa-14-thia-7,11-diaza-2-silaheptadecan-17-oic acid (Intermediate C86) in 1.37 ml of DMF. The reaction mixture was stirred at RT for 5 h. Without further work-up, the mixture was purified by preparative HPLC. This gave 41 mg (33% of theory) of the title compound.

LC-MS (Method 12): $R_t$=2.61 min; MS (ESIpos): m/z=907 (M+H)$^+$.

Intermediate C88 tert-Butyl 3-[({(1R)-1-[1-benzyl-4-(2,5-difluorophenyl)-1H-pyrrol-2-yl]-2,2-dimethylpropyl}amino)methyl]pyrrolidine-1-carboxylate trifluoroacetic acid (1:1)

Mixture of Stereoisomers

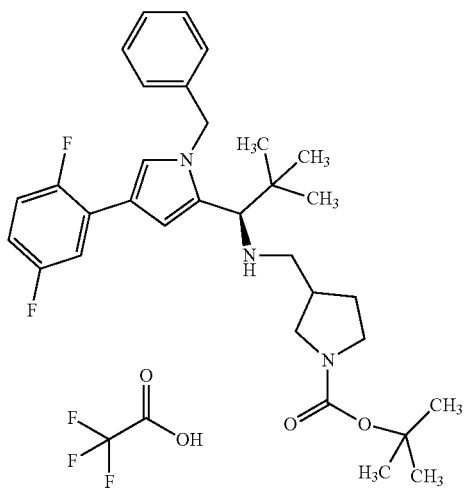 [SMILES: CC(C)(C)OC(=O)N1CCC(CN[C@@H](c2cc(-c3cc(F)ccc3F)cn2Cc2ccccc2)C(C)(C)C)C1 ; O=C(O)C(F)(F)F]

1.71 g (8.05 mmol) of sodium triacetoxyborohydride and 0.40 g (6.61 mmol) of acetic acid were added to a solution of 2.04 mg (5.75 mmol) of (1R)-1-[1-benzyl-4-(2,5-difluorophenyl)-1H-pyrrol-2-yl]-2,2-dimethylpropane-1-amine (Intermediate C52) in 51 ml of dichloromethane, and the reaction mixture was stirred at RT for 5 minutes. A solution of 1.32 g (6.61 mmol) of tert-butyl 3-formylpyrrolidine-1-carboxylate in 20 ml of dichloromethane was then added, and the mixture was stirred at RT overnight. The reaction mixture was diluted with ethyl acetate and the organic phase was washed in each case twice with saturated sodium carbonate solution and with saturated NaCl solution, dried over magnesium sulphate and concentrated. The residue was purified by preparative HPLC. The solvents were evaporated under reduced pressure and the residue was dried under high vacuum. This gave 1.86 g (50% of theory) of the title compound.

LC-MS (Method 1): $R_t$=0.99 min; MS (ESIpos): m/z=538 (M+H-CF$_3$CO$_2$H)$^+$.

Intermediate C89 tert-Butyl 3-{[{(1R)-1-[1-benzyl-4-(2,5-difluorophenyl)-1H-pyrrol-2-yl]-2,2-dimethylpropyl}(chloroacetyl)amino]methyl}pyrrolidine-1-carboxylate

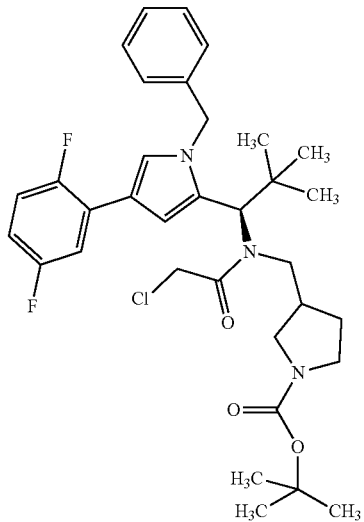 [SMILES: CC(C)(C)OC(=O)N1CCC(CN(C(=O)CCl)[C@@H](c2cc(-c3cc(F)ccc3F)cn2Cc2ccccc2)C(C)(C)C)C1]

1.36 g (13.42 mmol) of triethylamine and 2.13 g (18.87 mmol) of chloracetyl chloride were added to a solution of 2.89 g (4.19 mmol, 80% pure) of tert-butyl 3-[({(1R)-1-[1-benzyl-4-(2,5-difluorophenyl)-1H-pyrrol-2-yl]-2,2-dimethylpropyl}amino)methyl]pyrrolidine-1-carboxylate (Intermediate C88) in 42 ml of dichloromethane with 4 Å molecular sieve. The reaction mixture was stirred at RT for 5 h. The mixture was concentrated on a rotary evaporator and the residue was purified by preparative HPLC. This gave 449 mg (17% of theory) of Isomer 1 and 442 mg (17% of theory) of Isomer 2 of the title compound.

Isomer 1 LC-MS (Method 1): $R_t$=2.74 min; MS (ESIpos): m/z=614 (M+H)$^+$.
Isomer 2 LC-MS (Method 1): $R_t$=2.78 min; MS (ESIpos): m/z=614 (M+H)$^+$.

Intermediate C90

S-[2-({(1R)-1-[1-Benzyl-4-(2,5-difluorophenyl)-1H-pyrrol-2-yl]-2,2-dimethylpropyl}{[1-(tert-butoxycarbonyl)pyrrolidin-3-yl]methyl}amino)-2-oxoethyl]-L-cysteine (Isomer 1)

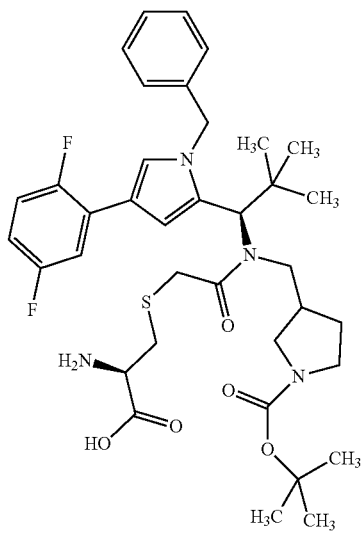 [SMILES: CC(C)(C)OC(=O)N1CCC(CN(C(=O)CSC[C@H](N)C(=O)O)[C@@H](c2cc(-c3cc(F)ccc3F)cn2Cc2ccccc2)C(C)(C)C)C1]

357.3 mg (0.58 mmol) of L-cysteine were suspended in 2.3 ml of water together with 488.7 mg (4.07 mmol) of sodium bicarbonate. 357.0 mg (0.58 mmol) of tert-butyl 3-{[{(1R)-1-[1-benzyl-4-(2,5-difluorophenyl)-1H-pyrrol-2-yl]-2,2-dimethylpropyl}(chloroacetyl)amino]methyl}pyrrolidine-1-carboxylate (Isomer 1) (Intermediate C89, Isomer 1) dissolved in 23.0 ml of isopropanol and 1.06 g (6.98 mmol) of 1,8-diazabicyclo[5.4.0]undec-7-ene were added. The reaction mixture was stirred at 50° C. for 3 h. Ethyl acetate was added to the reaction mixture and the organic phase was washed repeatedly with saturated sodium bicarbonate solution and once with sat. NaCl solution. The organic phase was dried over magnesium sulphate and the solvent was evaporated under reduced pressure. The residue was used further without purification. This gave 255.0 mg (62% of theory) of the title compound.

LC-MS (Method 1): $R_t$=1.09 min; MS (ESIpos): m/z=699 (M+H)$^+$.

Intermediate C91

S-[2-({(1R)-1-[1-Benzyl-4-(2,5-difluorophenyl)-1H-pyrrol-2-yl]-2,2-dimethylpropyl}{[1-(tert-butoxycarbonyl)pyrrolidin-3-yl]methyl}amino)-2-oxoethyl]-L-cysteine (Isomer 2)

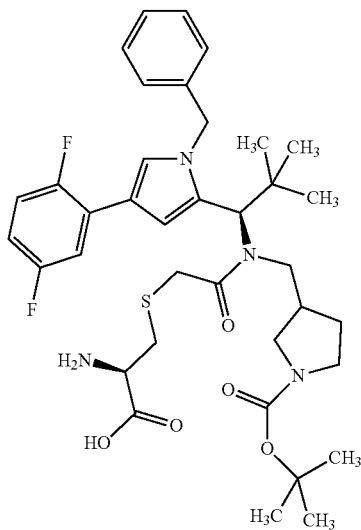 [SMILES: CC(C)(C)OC(=O)N1CCC(CN(C(=O)CSC[C@H](N)C(=O)O)[C@@H](c2cc(-c3cc(F)ccc3F)cn2Cc2ccccc2)C(C)(C)C)C1]

453.5 mg (3.74 mmol) of L-cysteine were suspended in 2.1 ml of water together with 449.2 mg (5.35 mmol) of sodium bicarbonate. 3287.4 mg (0.54 mmol) of tert-butyl 3-{[{(1R)-1-[1-benzyl-4-(2,5-difluorophenyl)-1H-pyrrol-2-yl]-2,2-dimethylpropyl}(chloroacetyl)amino]methyl}pyrrolidine-1-carboxylate (Intermediate C89, Isomer 2) dissolved in 21.1 ml of isopropanol and 0.98 g (6.42 mmol) of 1,8-diazabicyclo[5.4.0]undec-7-ene were added. The reaction mixture was stirred at 50° C. for 3 h. Ethyl acetate was added to the reaction mixture and the organic phase was washed repeatedly with saturated sodium bicarbonate solution and once with sat. NaCl solution. The organic phase was dried over magnesium sulphate and the solvent was evaporated under reduced pressure. The residue was used further without purification. This gave 221.0 mg (59% of theory) of the title compound.

LC-MS (Method 1): $R_t$=1.12 min; MS (ESIpos): m/z=699 (M+H)$^+$.

Intermediate C92

S-[2-({(1R)-1-[1-Benzyl-4-(2,5-difluorophenyl)-1H-pyrrol-2-yl]-2,2-dimethylpropyl}{[1-(tert-butoxycarbonyl)pyrrolidin-3-yl]methyl}amino)-2-oxoethyl]-N-[6-(2,5-dioxo-2,5-dihydro-1H-pyrrol-1-yl)hexanoyl]-L-cysteine (Isomer 1)

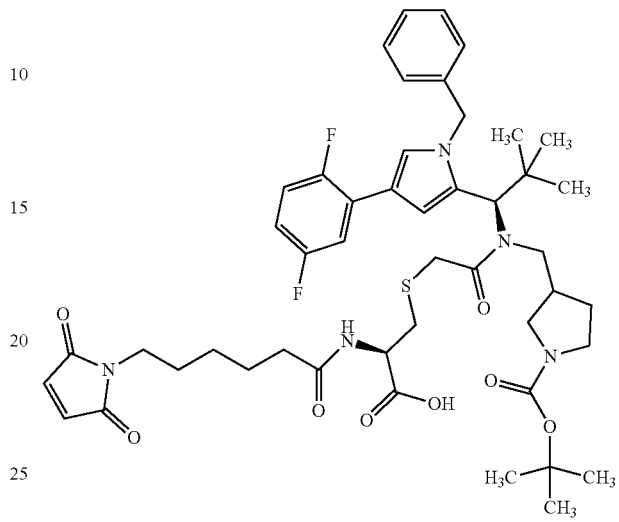

18.49 mg (0.14 mmol) of N,N-diisopropylethylamine were added to a mixture of 50 mg (0.07 mmol) of S-[2-({(1R)-1-[1-benzyl-4-(2,5-difluorophenyl)-1H-pyrrol-2-yl]-2,2-dimethylpropyl}{[1-(tert-butoxycarbonyl)pyrrolidin-3-yl]methyl}amino)-2-oxoethyl]-L-cysteine (Intermediate C90) and 22.06 mg (0.07 mmol) of 1-{6-[(2,5-dioxopyrrolidin-1-yl)oxy]-6-oxohexyl}-1H-pyrrole-2,5-dione in 3.3 ml of DMF, and the reaction mixture was stirred at RT for 45 minutes. Without work-up, the mixture was purified by preparative HPLC. This gave 65 mg (100% of theory, 71% pure) of the title compound.

LC-MS (Method 1): $R_t$=1.31 min; MS (ESIpos): m/z=892 (M+H)$^+$.

Intermediate C93

S-[2-({(1R)-1-[1-Benzyl-4-(2,5-difluorophenyl)-1H-pyrrol-2-yl]-2,2-dimethylpropyl}{[1-(tert-butoxycarbonyl)pyrrolidin-3-yl]methyl}amino)-2-oxoethyl]-N-[6-(2,5-dioxo-2,5-dihydro-1H-pyrrol-1-yl)hexanoyl]-L-cysteine (Isomer 2)

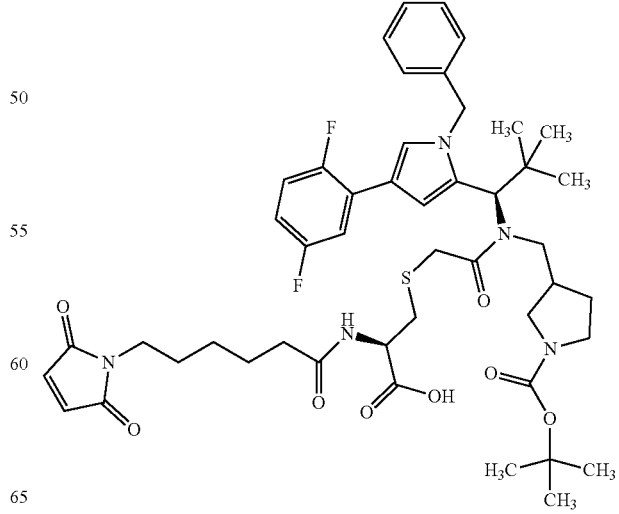

18.49 mg (0.14 mmol) of N,N-diisopropylethylamine were added to a mixture of 50.0 mg (0.07 mmol) of S-[2-({(1R)-1-[1-benzyl-4-(2,5-difluorophenyl)-1H-pyrrol-2-yl]-2,2-dimethylpropyl}{[1-(tert-butoxycarbonyl)pyrrolidin-3-yl]methyl}amino)-2-oxoethyl]-L-cysteine (Intermediate C91) and 22.06 mg (0.07 mmol) of 1-{6-[(2,5-dioxopyrrolidin-1-yl)oxy]-6-oxohexyl}-1H-pyrrole-2,5-dione in 3.0 ml of DMF, and the reaction mixture was stirred at RT for 90 minutes. Without work-up, the mixture was purified by preparative HPLC. This gave 63 mg (98% of theory, 73% pure) of the title compound.

LC-MS (Method 1): $R_t$=1.34 min; MS (ESIpos): m/z=892 (M+H)⁺.

Intermediate C94

S-[2-({(1R)-1-[1-Benzyl-4-(2,5-difluorophenyl)-1H-pyrrol-2-yl]-2,2-dimethylpropyl}{[1-(tert-butoxycarbonyl)pyrrolidin-3-yl]methyl}amino)-2-oxoethyl]-N-[(2,5-dioxo-2,5-dihydro-1H-pyrrol-1-yl)acetyl]-L-cysteine (Isomer 1)

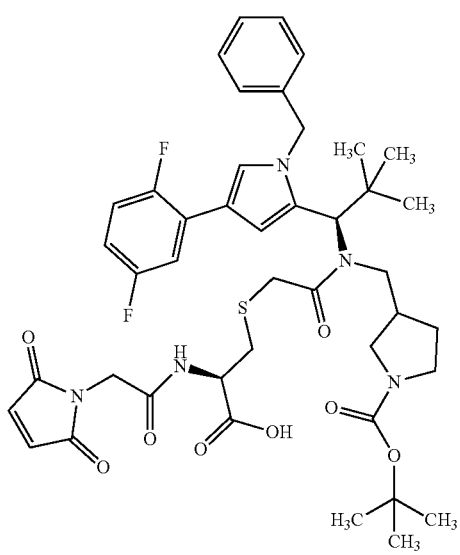 [SMILES: CC(C)(C)OC(=O)N1CCC(CN(C(=O)CSC[C@H](NC(=O)CN2C(=O)C=CC2=O)C(=O)O)[C@@H](c2cc(-c3cc(F)ccc3F)cn2Cc2ccccc2)C(C)(C)C)C1]

18.5 mg (0.14 mmol) of N,N-diisopropylethylamine were added to a mixture of 50.0 mg (0.07 mmol) of S-[2-({(1R)-1-[1-benzyl-4-(2,5-difluorophenyl)-1H-pyrrol-2-yl]-2,2-dimethylpropyl}{[-1-(tert-butoxycarbonyl)pyrrolidin-3-yl]methyl}amino)-2-oxoethyl]-L-cysteine (Intermediate C90) and 18.0 mg (0.07 mmol) of 1-{2-[(2,5-dioxopyrrolidin-1-yl)oxy]-2-oxoethyl}-1H-pyrrole-2,5-dione in 3.3 ml of DMF, and the reaction mixture was stirred at RT for 30 minutes. Ethyl acetate was added to the reaction mixture and the organic phase was washed repeatedly with saturated NH₄Cl solution and once with saturated NaCl solution. The organic phase was dried over magnesium sulphate and the solvent was evaporated under reduced pressure. The residue was employed without further purification. This gave 57 mg (81% of theory, 85% pure) of the title compound.

LC-MS (Method 1): $R_t$=0.96 min; MS (ESIpos): m/z=836 (M+H)⁺.

Intermediate C95

3-{[2-({(1R)-1-[1-Benzyl-4-(2,5-difluorophenyl)-1H-pyrrol-2-yl]-2,2-dimethylpropyl}{[1-(tert-butoxycarbonyl)pyrrolidin-3-yl]methyl}amino)-2-oxoethyl]sulphanyl}propanoic acid (Isomer 1)

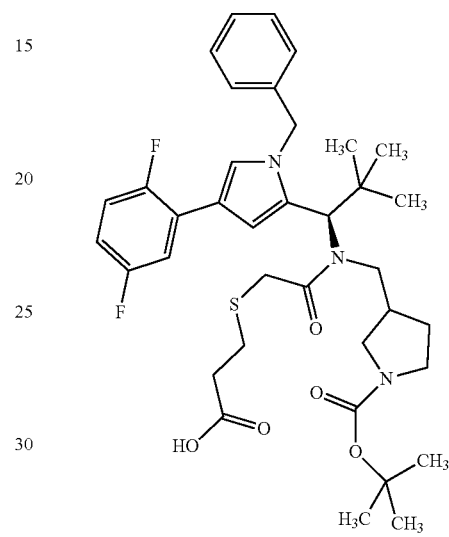

302.5 mg (2.19 mmol) of potassium carbonate were added to a mixture of 384.0 mg (0.62 mmol) of tert-butyl 3-{[{(1R)-1-[1-benzyl-4-(2,5-difluorophenyl)-1H-pyrrol-2-yl]-2,2-dimethylpropyl}(chloroacetyl)amino]methyl}pyrrolidine-1-carboxylate (Intermediate C89, Isomer 1) and 73.0 mg (0.69 mmol) of 3-sulphanylpropanoic acid in 14 ml of methanol and a few drops of water. The reaction mixture was stirred at 50° C. for 2.5 h. Ethyl acetate was added to the reaction mixture and the organic phase was washed repeatedly with water and with saturated NaCl solution. The organic phase was dried over magnesium sulphate, the solvent was evaporated under reduced pressure and the residue was dried under high vacuum. The residue was used further without work-up. This gave 358.0 mg (84% of theory) of the title compound.

LC-MS (Method 1): $R_t$=1.33 min; MS (ESIpos): m/z=684 (M+H)⁺.

Intermediate C96

3-{[2-({(1R)-1-[1-Benzyl-4-(2,5-difluorophenyl)-1H-pyrrol-2-yl]-2,2-dimethylpropyl}{[1-(tert-butoxycarbonyl)pyrrolidin-3-yl]methyl}amino)-2-oxoethyl]sulphanyl}propanoic acid (Isomer 2)

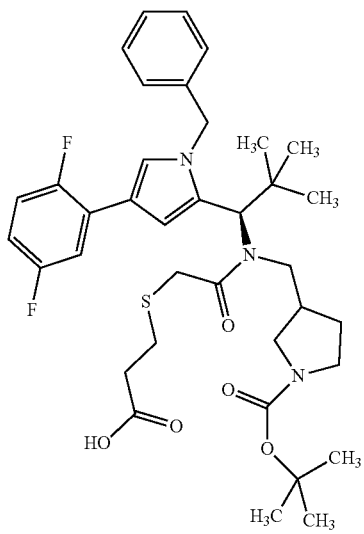 [SMILES: CC(C)(C)OC(=O)N1CCC(CN(C(=O)CSCCC(=O)O)[C@@H](c2cc(-c3cc(F)ccc3F)cn2Cc2ccccc2)C(C)(C)C)C1]

226.0 mg (1.64 mmol) of potassium carbonate were added to a mixture of 287.0 mg (0.45 mmol) of tert-butyl 3-{[{(1R)-1-[1-benzyl-4-(2,5-difluorophenyl)-1H-pyrrol-2-yl]-2,2-dimethylpropyl}(chloroacetyl)amino]methyl}pyrrolidine-1-carboxylate (Intermediate C89, Isomer 2) and 54.6 mg (0.51 mmol) of 3-sulphanylpropanoic acid in 14 ml of methanol and a few drops of water. The reaction mixture was stirred at 50° C. for 2.5 h. Ethyl acetate was added to the reaction mixture and the organic phase was washed repeatedly with water and with saturated NaCl solution. The organic phase was dried over magnesium sulphate, the solvent was evaporated under reduced pressure and the residue was dried under high vacuum. The residue was used further without work-up. This gave 318.7 mg (88% of theory, 88% pure) of the title compound.

LC-MS (Method 1): $R_t$=1.36 min; MS (ESIpos): m/z=684 (M+H)$^+$.

Intermediate C97 tert-Butyl 3-[2-{(1R)-1-[1-benzyl-4-(2,5-difluorophenyl)-1H-pyrrol-2-yl]-2,2-dimethylpropyl}-14-(2,5-dioxo-2,5-dihydro-1H-pyrrol-1-yl)-3,8,13-trioxo-5-thia-2,9,12-triazatetradec-1-yl]pyrrolidine-1-carboxylate (Isomer 2)

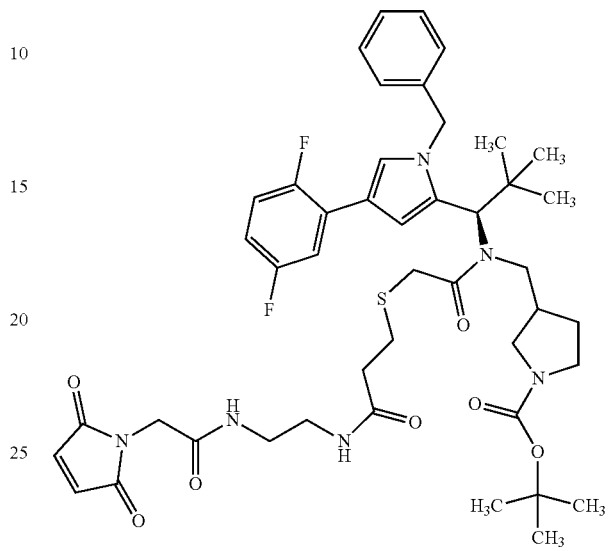

Under argon, 14.17 mg (0.11 mmol) of N,N-diisopropylethylamine and 27.80 mg (0.07 mmol) of HATU were added to a solution of 25.0 mg (0.04 mmol) of 3-{[2-({(1R)-1-[1-benzyl-4-(2,5-difluorophenyl)-1H-pyrrol-2-yl]-2,2-dimethylpropyl}{[1-(tert-butoxycarbonyl)pyrrolidin-3-yl]methyl}amino)-2-oxoethyl]sulphanyl}propanoic acid (Intermediate C96) in 2.81 ml of DMF. The reaction mixture was stirred at RT for 10 minutes. A solution of 22.75 mg (0.07 mmol) of N-(2-aminoethyl)-2-(2,5-dioxo-2,5-dihydro-1H-pyrrol-1-yl)acetamide-ethane (1:1) trifluoroacetic acid (Intermediate L1) in 1.4 ml of DMF and 5 mg (0.04 mmol) of N,N-diisopropylethylamine was then added, and the mixture was stirred at RT overnight. Water was added and the mixture was extracted with dichloromethane. The organic phase was dried over magnesium sulphate and the solvent was evaporated under reduced pressure. The residue was used further without work-up. This gave 26 mg (84% of theory) of the title compound.

LC-MS (Method 5): $R_t$=4.39 min; MS (ESIpos): m/z=86

Intermediate C98 tert-Butyl 3-[2-{(1R)-1-[1-benzyl-4-(2,5-difluorophenyl)-1H-pyrrol-2-yl]-2,2-dimethylpropyl}-18-(2,5-dioxo-2,5-dihydro-1H-pyrrol-1-yl)-3,8,13-trioxo-5-thia-2,9,12-triazaoctadec-1-yl]pyrrolidine-1-carboxylate (Isomer 2)

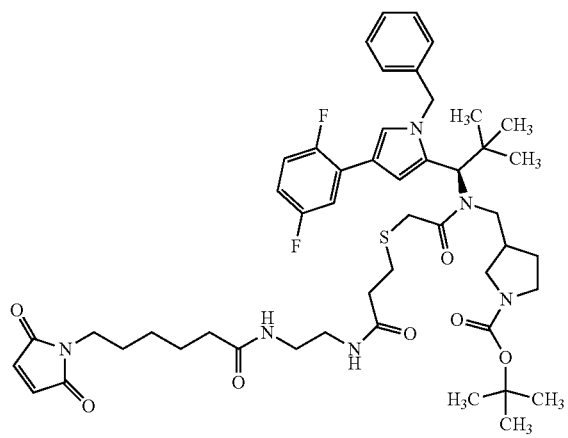 [SMILES: CC(C)(C)OC(=O)N1CCC(CN(C(=O)CSCCC(=O)NCCNC(=O)CCCCCN2C(=O)C=CC2=O)[C@@H](c2cc(-c3cc(F)ccc3F)cn2Cc2ccccc2)C(C)(C)C)C1]

Under argon, 14.17 mg (0.11 mmol) of N,N-diisopropylethylamine and 27.80 mg (0.07 mmol) of HATU were added to a solution of 25.0 mg (0.04 mmol) of 3-{[2-({(1R)-1-[1-benzyl-4-(2,5-difluorophenyl)-1H-pyrrol-2-yl]-2,2-dimethylpropyl}{[1-(tert-butoxycarbonyl)pyrrolidin-3-yl]methyl}amino)-2-oxoethyl]sulphanyl}propanoic acid (Intermediate C96) in 2.81 ml of DMF. The reaction mixture was stirred at RT for 10 minutes. A solution of 37.30 mg (0.07 mmol) of N-(2-aminoethyl)-6-(2,5-dioxo-2,5-dihydro-1H-pyrrol-1-yl)hexanamide-ethane (1:1) trifluoroacetic acid in 1.4 ml of DMF and 5 mg (0.04 mmol) of N,N-diisopropylethylamine was then added, and the mixture was stirred at RT overnight. Water was added and the mixture was extracted with dichloromethane. The organic phase was dried over magnesium sulphate and the solvent was evaporated under reduced pressure. The residue was employed without further purification. This gave 22 mg (63% of theory) of the title compound.

LC-MS (Method 5): $R_t$=4.54 min; MS (ESIpos): m/z=919 (M+H)$^+$.

Intermediate C99 tert-Butyl 3-[2-{(1R)-1-[1-benzyl-4-(2,5-difluorophenyl)-1H-pyrrol-2-yl]-2,2-dimethylpropyl}-24-(2,5-dioxo-2,5-dihydro-1H-pyrrol-1-yl)-3,8,19-trioxo-12,15-dioxa-5-thia-2,9,18-triazatetracos-1-yl]pyrrolidine-1-carboxylate (Isomer 2)

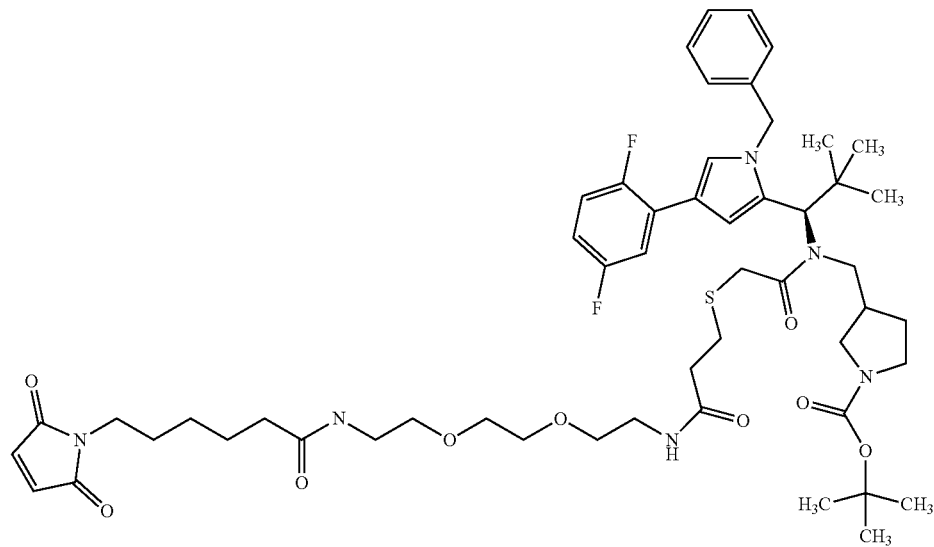 [SMILES: CC(C)(C)OC(=O)N1CCC(CN(C(=O)CSCCC(=O)NCCOCCOCCNC(=O)CCCCCN2C(=O)C=CC2=O)[C@@H](c2cc(-c3cc(F)ccc3F)cn2Cc2ccccc2)C(C)(C)C)C1]

Under argon, 14.17 mg (0.11 mmol) of N,N-diisopropylethylamine and 27.80 mg (0.07 mmol) of HATU were added to a solution of 25.0 mg (0.04 mmol) of 3-{[2-({(1R)-1-[1-benzyl-4-(2,5-difluorophenyl)-1H-pyrrol-2-yl]-2,2-dimethylpropyl}{[1-(tert-butoxycarbonyl)pyrrolidin-3-yl]methyl}amino)-2-oxoethyl]sulphanyl}propanoic acid (Intermediate C96) in 2.81 ml of DMF. The reaction mixture was stirred at RT for 10 minutes. A solution of 35.05 mg (0.07 mmol) of N-{2-[2-(2-Aminoethoxy)ethoxy]ethyl}-6-(2,5-dioxo-2,5-dihydro-1H-pyrrol-1-yl)hexanamide-ethane (1:1) trifluoroacetic acid (Intermediate L82) in 1.4 ml of DMF and 5 mg (0.04 mmol) of N,N-diisopropylethylamine was then added, and the mixture was stirred at RT overnight. Water was added and the mixture was extracted with dichloromethane. The organic phase was dried over magnesium sulphate, the solvent was evaporated under reduced pressure and the residue was dried under high vacuum. The residue was purified by prep. HPLC. This gave 25 mg (60% of theory) of the title compound.

LC-MS (Method 1): $R_t$=4.52 min; MS (ESIpos): m/z=1007 (M+H)$^+$.

Intermediate C100

2-(Trimethylsilyl)ethyl {(2S)-4-[{(1R)-1-[1-benzyl-4-(2,5-difluorophenyl)-1H-pyrrol-2-yl]-2,2-dimethylpropyl}(glycoloyl)amino]-1-[(2-{[(2R)-2-(2,5-dioxo-2,5-dihydro-1H-pyrrol-1-yl)propanoyl]amino}ethyl)amino]-1-oxobutan-2-yl}carbamate

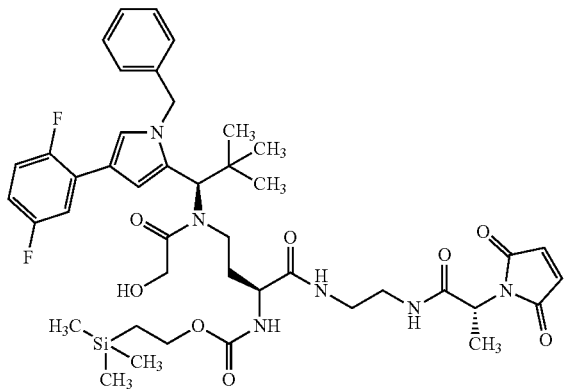 [SMILES: C[C@H](C(=O)NCCNC(=O)[C@H](CCN(C(=O)CO)[C@@H](c1cc(-c2cc(F)ccc2F)cn1Cc1ccccc1)C(C)(C)C)NC(=O)OCC[Si](C)(C)C)N1C(=O)C=CC1=O]

22.2 mg (0.068 mmol) of (2R)—N-(2-aminoethyl)-2-(2,5-dioxo-2,5-dihydro-1H-pyrrol-1-yl)propanamide (1:1) trifluoroacetic acid were added to a solution of 45 mg (0.068 mmol) of (2S)-4-[{(1R)-1-[1-benzyl-4-(2,5-difluorophenyl)-1H-pyrrol-2-yl]-2,2-dimethylpropyl}(glycoloyl)amino]-2-({[2-(trimethylsilyl)ethoxy]carbonyl}amino)butanoic acid (Intermediate C58) in 5.8 ml of DMF. After 30 minutes of stirring at RT, 39 mg (0.10 mmol) of HATU and 36 mg (0.27 mmol) of N,N-diisopropylethylamine were added to the mixture. The reaction mixture was stirred at RT for 1 h. Without work-up, the mixture was purified by preparative HPLC. This gave 7 mg (12% of theory) of the title compound.

LC-MS (Method 1): $R_t$=1.41 min; MS (ESIpos): m/z 851 (M+H)$^+$.

Intermediate C101

Trifluoroacetic acid/methyl (2S)-4-[(acetoxyacetyl){(1R)-1-[1-benzyl-4-(2,5-difluorophenyl)-1H-pyrrol-2-yl]-2,2-dimethylpropyl}amino]-2-aminobutanoate (1:1)

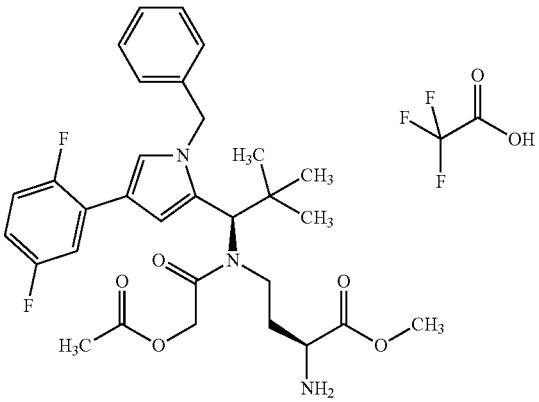 [SMILES: COC(=O)[C@@H](N)CCN(C(=O)COC(C)=O)[C@@H](c1cc(-c2cc(F)ccc2F)cn1Cc1ccccc1)C(C)(C)C ; O=C(O)C(F)(F)F]

4.3 g (12.2 mmol) of intermediate C52 were dissolved in 525 ml of DCM, and 3.63 g (17.12 mmol) of sodium triacetoxyborohydride and 8.4 ml of acetic acid were added. After 5 min of stirring at RT, 3.23 g (11.85 mmol) of methyl (2S)-4-oxo-2-({[2-(trimethylsilyl)ethoxy]carbonyl}amino)butanoate (prepared from (3S)-3-amino-4-methoxy-4-oxobutanoic acid using classical methods), dissolved in 175 ml of DCM, were added and the mixture was stirred at RT for a further 45 min. The mixture was then diluted with DCM and extracted twice with 100 ml of saturated sodium bicarbonate solution and then with saturated sodium chloride solution. The organic phase was dried over magnesium sulphate, filtered and then concentrated. The residue was purified by preparative HPLC. Combining the appropriate fractions, concentration and drying of the residue under high vacuum gave 4.6 g (61% of theory) of the intermediate.

LC-MS (Method 12): $R_t$=1.97 min; MS (ESIpos): m/z=614.32 (M+H)$^+$.

2.06 g (3.36 mmol) of this intermediate were initially charged in 76 ml of DCM and acylated using 0.81 ml (7.17 mmol) of 2-chloro-2-oxoethyl acetate in the presence of 2.1 ml of triethylamine. After 20 h of stirring at RT, a further 0.36 ml of 2-chloro-2-oxoethyl acetate and 0.94 ml of triethylamine were added, and the mixture was stirred at RT for a further 15 min. The mixture was then diluted with 500 ml of ethyl acetate and extracted successively twice with 300 ml of 5% strength citric acid, twice with 300 ml of saturated sodium bicarbonate solution and once with 100 ml of saturated sodium chloride solution and then dried over magnesium sulphate and concentrated. Drying under high vacuum gave 2.17 g (79% of theory) of the protected intermediate.

LC-MS (Method 1): $R_t$=1.48 min; MS (ESIpos): m/z=714 (M+H)$^+$.

321 mg (0.342 mmol) of this intermediate were dissolved in 7 ml of 2,2,2-trifluoroethanol. 279.5 mg (2.05 mmol) of zinc chloride were added, and the mixture was stirred at 50° C. for 2 h. 599 mg (2.05 mmol) of ethylenediamine-N,N,N',N'-tetraacetic acid and 2 ml of a 0.1% strength solution of trifluoroacetic acid in water were then added, and the mixture was subsequently concentrated under reduced pressure. The residue was purified by preparative HPLC. Concentration of the appropriate fractions and lyophilization of the residue from acetonitrile/water gave 60 mg (26% of theory) of the title compound which still contains some of the deacetylated compound.

LC-MS (Method 1): $R_t$=0.91 min and 0.95 min; MS (ESIpos): m/z=528 and 570 (M+H)$^+$.

Intermediate C102

(2S)-4-[{(1R)-1-[1-Benzyl-4-(2,5-difluorophenyl)-1H-pyrrol-2-yl]-2,2-dimethylpropyl}(glycoloyl)amino]-2-{[(benzyloxy)carbonyl]amino]}butanoic acid

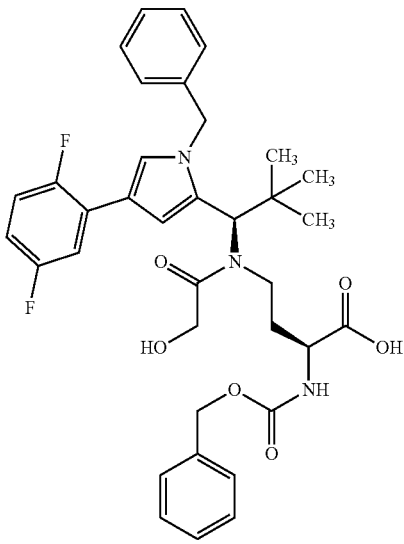 [SMILES: CC(C)(C)[C@H](c1cc(-c2cc(F)ccc2F)cn1Cc1ccccc1)N(CC[C@H](NC(=O)OCc1ccccc1)C(=O)O)C(=O)CO]

First, intermediate C52 was subjected to a reductive alkylation with benzyl (2S)-2-{[(benzyloxy)carbonyl]amino}-4-oxobutanoate analogously to intermediate C2. Subsequently, the secondary amino group was acylated with 2-chloro-2-oxoethyl acetate, and finally the two ester groups were hydrolyzed using a 2M solution of lithium hydroxide in methanol.

LC-MS (Method 1): $R_t$=1.31 min; MS (ESIpos): m/z=646 (M−H)−.

Intermediate C103

2-(Trimethylsilyl)ethyl N-[2-({(2S)-2-amino-4-[{(1R)-1-[1-benzyl-4-(2,5-difluorophenyl)-1H-pyrrol-2-yl]-2,2-dimethylpropyl}(glycoloyl)amino]butanoyl}amino)ethyl]-N2-{[2-(trimethylsilyl)ethoxy]carbonyl}-L-glutaminate

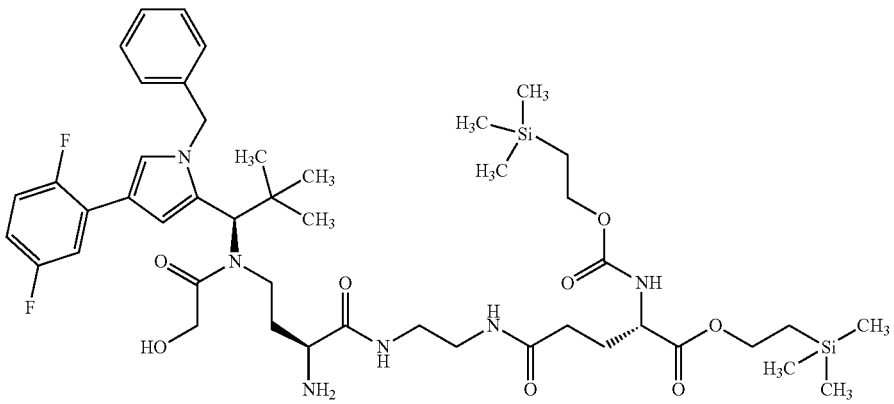 [SMILES: CC(C)(C)[C@H](c1cc(-c2cc(F)ccc2F)cn1Cc1ccccc1)N(CC[C@H](N)C(=O)NCCNC(=O)CC[C@H](NC(=O)OCC[Si](C)(C)C)C(=O)OCC[Si](C)(C)C)C(=O)CO]

The title compound was prepared by initially coupling 151 mg (0.23 mmol) of intermediate C102 with 128 mg (0.234 mmol) of intermediate L98 in DMF in the presence of HATU and N,N-diisopropylethylamine. The Z protective group was then removed by hydrogenating over 10% palladium on activated carbon at RT at standard hydrogen pressure for 30 minutes, giving the title compound.

Yield: 30% of theory over 2 steps

LC-MS (Method 1): $R_t$=1.14 min; MS (ESIpos): m/z=929 (M+H)+.

Intermediate C104

2-(Trimethylsilyl)ethyl (3R,4R)-3-[({(1R)-1-[1-benzyl-4-(2,5-difluorophenyl)-1H-pyrrol-2-yl]-2,2-dimethylpropyl}amino)methyl]-4-fluoropyrrolidine-1-carboxylate

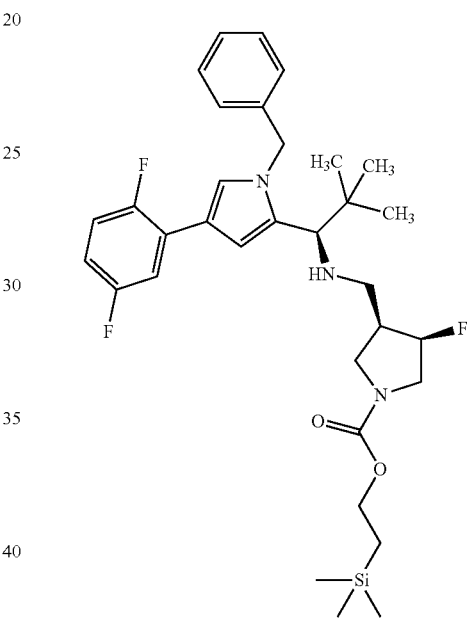

1.87 g (8.84 mmol) of sodium triacetoxyborohydride were added to a solution of 2.24 g (6.31 mmol) of (1R)-1-[1-benzyl-4-(2,5-difluorophenyl)-1H-pyrrol-2-yl]-2,2-dimethylpropane-1-amine in 56.0 ml of dichloromethane with molecular sieve 4 Å, and the mixture was stirred at room temperature for 15 minutes. 2.20 g (7.58 mmol) of 2-(trimethylsilyl)ethyl (3R,4S)-3-fluoro-4-formylpyrrolidine-1-carboxylate (lit: WO 2014/151030A1) were then added, and the reaction mixture was stirred at room temperature for 3.5 h. The mixture was diluted with dichloromethane and the organic phase was washed with sat. sodium bicarbonate solution and water. The organic phase was dried over sodium sulphate and concentrated. The residue was purified by prep. HPLC. This gave 1.39 g (24% of theory) of the title compound.

LC-MS (Method 1): $R_t$=1.15 min; MS (ESIpos): m/z=600 (M+H)$^+$.

Intermediate C105

2-(Trimethylsilyl)ethyl (3R,4R)-3-{[{(1R)-1-[1-benzyl-4-(2,5-difluorophenyl)-1H-pyrrol-2-yl]-2,2-dimethylpropyl}(chloroacetyl)amino]methyl}-4-fluoropyrrolidine-1-carboxylate

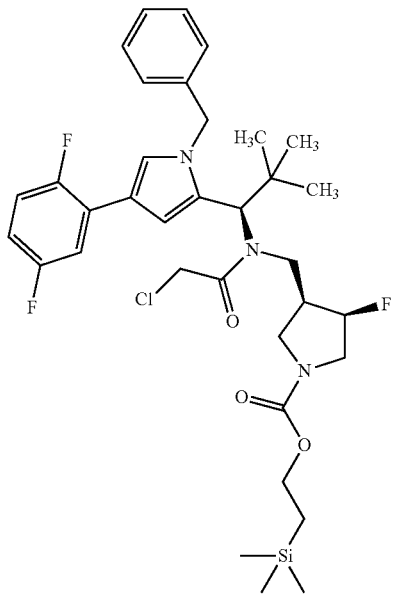 [SMILES: CC(C)(C)[C@H](c1cc(-c2cc(F)ccc2F)cn1Cc1ccccc1)N(C[C@@H]1CN(C(=O)OCC[Si](C)(C)C)C[C@@H]1F)C(=O)CCl]

295.0 mg (2.91 mmol) of triethylamine and 418.9 mg (3.71 mmol) of chloroacetyl chloride were added to a solution of 692.8 mg (0.88 mmol) of 2-(trimethylsilyl)ethyl (3R,4R)-3-[({(1R)-1-[1-benzyl-4-(2,5-difluorophenyl)-1H-pyrrol-2-yl]-2,2-dimethylpropyl}amino)methyl]-4-fluoropyrrolidine-1-carboxylate (Intermediate C104) in 8.7 ml of dichloromethane with molecular sieve 4 Å, and the reaction mixture was stirred at RT for 2.5 h. The reaction mixture was diluted with dichloromethane and the organic phase was washed with sat. sodium bicarbonate solution and sat. ammonium chloride solution. The organic phase was dried over sodium sulphate and concentrated. Once more, 295.0 mg (2.91 mmol) of triethylamine and 418.9 mg (3.71 mmol) of chloroacetyl chloride were added to the residue in 8.7 ml of dichloromethane with molecular sieve 4 Å, and the reaction mixture was stirred at RT for 3 h. The reaction mixture was diluted with dichloromethane and the organic phase was washed with sat. sodium bicarbonate solution and sat. ammonium chloride solution. The organic phase was dried over sodium sulphate and concentrated. The organic phase was dried over sodium sulphate, concentrated and used further without purification. This gave 691 mg (74% of theory, 64% pure) of the title compound.

LC-MS (Method 1): $R_t$=1.78 min; MS (ESIpos): m/z=676 (M+H)$^+$.

Intermediate C106

3-{[2-({(1R)-1-[1-Benzyl-4-(2,5-difluorophenyl)-1H-pyrrol-2-yl]-2,2-dimethylpropyl}{[(3R,4R)-4-fluoro-1-{[2-(trimethylsilyl)ethoxy]carbonyl}pyrrolidin-3-yl]methyl}amino)-2-oxoethyl]sulphanyl}propanoic acid

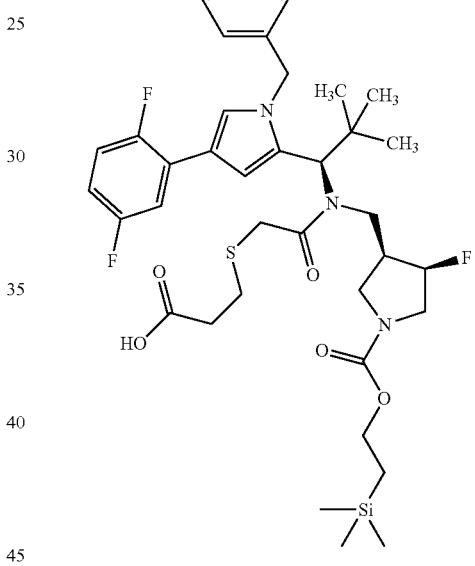

316 mg (2.29 mmol) of potassium carbonate were added to a mixture of 691.0 mg (0.65 mmol) of 2-(trimethylsilyl)ethyl (3R,4R)-3-{[{(1R)-1-[1-benzyl-4-(2,5-difluorophenyl)-1H-pyrrol-2-yl]-2,2-dimethylpropyl}(chloroacetyl)amino]methyl}-4-fluoropyrrolidine-1-carboxylate (intermediate C105) and 76.3 mg (0.72 mmol) of 3-sulphanylpropanoic acid in 15 ml of methanol and a few drops of water. The reaction mixture was stirred at 50° C. for 1.5 h. Ethyl acetate was added to the reaction mixture, and the org. phase was washed repeatedly with water and with sat. NaCl solution. The organic phase was dried over magnesium sulphate and the solvent was evaporated under reduced pressure and the residue was dried under high vacuum. The residue was used further without work-up. This gave 502 mg (67% of theory, 65% pure) of the title compound.

LC-MS (Method 1): $R_t$=1.48 min; MS (ESIneg): m/z=744 (M−H)$^-$.

Intermediate C107

S-[2-({(1R)-1-[1-Benzyl-4-(2,5-difluorophenyl)-1H-pyrrol-2-yl]-2,2-dimethylpropyl}{[(3R,4R)-4-fluoro-1-{[2-(trimethylsilyl)ethoxy]carbonyl}pyrrolidin-3-yl]methyl}amino)-2-oxoethyl]-L-cysteine

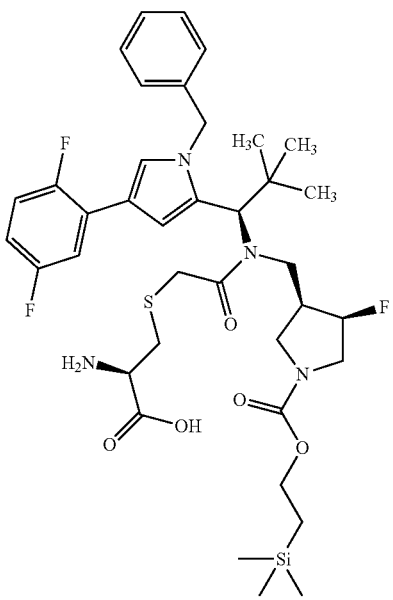 [SMILES: CC(C)(C)[C@H](c1cc(-c2cc(F)ccc2F)cn1Cc1ccccc1)N(C[C@@H]1CN(C(=O)OCC[Si](C)(C)C)C[C@@H]1F)C(=O)CSC[C@H](N)C(=O)O]

203.6 mg (1.68 mmol) of L-cysteine together with 201.7 mg (2.40 mmol) of sodium bicarbonate were suspended in 0.95 ml of water. 170.0 mg (0.24 mmol) of 2-(trimethylsilyl)ethyl (3R,4R)-3-{[{(1R)-1-[1-benzyl-4-(2,5-difluorophenyl)-1H-pyrrol-2-yl]-2,2-dimethylpropyl}(chloroacetyl)amino]methyl}-4-fluoropyrrolidine-1-carboxylate (intermediate 105), dissolved in 9.5 ml of isopropanol, and 438.5 mg (2.40 mmol) and 1,8-diazabicyclo[5.4.0]undec-7-ene were added. The reaction mixture was stirred at 50° C. for 3 h. Ethyl acetate was added to the mixture and the org. phase was washed repeatedly with sat. sodium bicarbonate solution and with sat. NaCl solution. The organic phase was dried over sodium sulphate and the solvent was evaporated under reduced pressure. The residue was used further without further purification. This gave 152 mg (83% of theory) of the title compound.

LC-MS (Method 1): $R_t$=1.26 min; MS (ESIpos): m/z=762 (M+H)$^+$.

Intermediate C115

N-[6-(2,5-Dioxo-2,5-dihydro-1H-pyrrol-1-yl)hexanoyl]-L-valyl-N-[3-({(1R)-1-[1-benzyl-4-(2,5-difluorophenyl)-1H-pyrrol-2-yl]-2,2-dimethylpropyl}{[(2-carboxyethyl)sulphanyl]acetyl}amino)propyl]-L-alaninamide

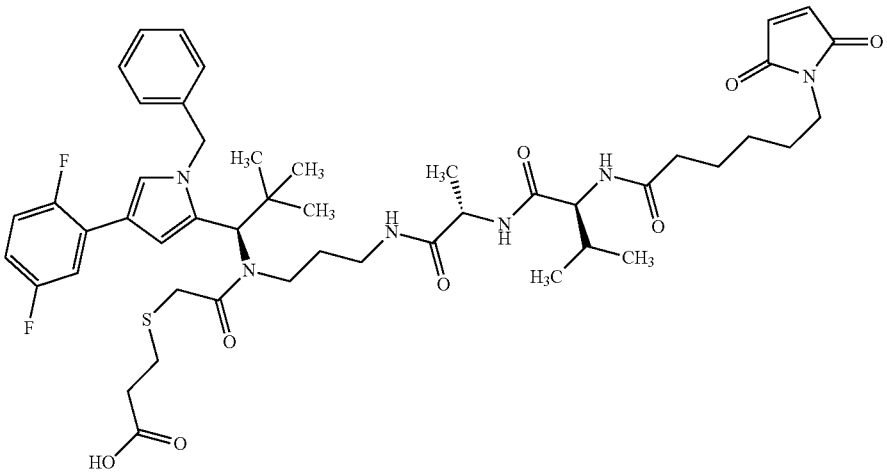 [SMILES: CC(C)[C@H](NC(=O)CCCCCN1C(=O)C=CC1=O)C(=O)N[C@@H](C)C(=O)NCCCN(C(=O)CSCCC(=O)O)[C@@H](c1cc(-c2cc(F)ccc2F)cn1Cc1ccccc1)C(C)(C)C]

11-{(1R)-1-[1-Benzyl-4-(2,5-difluorophenyl)-1H-pyrrol-2-yl]-2,2-dimethylpropyl}-2,2-dimethyl-6,12-dioxo-5-oxa-14-thia-7,11-diaza-2-silaheptadecan-17-oic acid (200 mg, 285 µmol) (intermediate C69) was dissolved in 10 ml of trifluoroethanol. Zinc chloride (233 mg, 1.71 mmol) was added and the reaction mixture was stirred at 50° C. for 1 hour. Two more times, zinc chloride (233 mg, 1.71 mmol) was added and the reaction mixture was stirred at 50° C. for 1 hour. Ethylenediamine-N,N,N',N'-tetraacetic acid (1.50 g, 5.13 mmol) was added, followed by water (0.1% TFA), and the mixture was then concentrated under reduced pressure.

The residue was purified by prep. RP-HPLC (column: Reprosil 250×30; 10μ, flow rate: 50 ml/min, MeCN/water, 0.1% TFA). The solvents were evaporated under reduced pressure and the residue was dried under high vacuum. This gives 162 mg (85% of theory) of the compound 3-({2-[(3-aminopropyl){(1R)-1-[1-benzyl-4-(2,5-difluorophenyl)-1H-pyrrol-2-yl]-2,2-dimethylpropyl}amino]-2-oxoethyl}sulphanyl)propanoic acid/trifluoroacetic acid (1:1).

LC-MS (Method 1): $R_t$=0.94 min; MS (ESIneg): m/z=556 [M−H]⁻

3-({2-[(3-Aminopropyl){(1R)-1-[1-benzyl-4-(2,5-difluorophenyl)-1H-pyrrol-2-yl]-2,2-dimethylpropyl}amino]-2-oxoethyl}sulphanyl)propanoic acid/trifluoroacetic acid (1:1) (80.0 mg, 119 μmol) was dissolved in 5.0 ml of DMF, and 2,5-dioxopyrrolidin-1-yl N-[6-(2,5-dioxo-2,5-dihydro-1H-pyrrol-1-yl)hexanoyl]-L-valyl-L-alaninate (69.4 mg, 82% pure, 119 μmol) (intermediate L88) and N,N-diisopropylethylamine (41 μl, 240 μmol) were added. The reaction mixture was stirred at RT for 2 h30, and water (0.1% TFA) was added. The mixture was concentrated and purified directly by prep. RP-HPLC (column: Reprosil 250×30; 10μ, flow rate: 50 ml/min, MeCN/water, 0.1% TFA). The solvent was evaporated under reduced pressure and the residue was dried under high vacuum. This gave 82.2 mg (75% of theory) of the title compound.

LC-MS (Method 1): $R_t$=1.17 min; MS (ESIpos): m/z=921 [M+H]⁺

Intermediate C116

N-[6-(2,5-Dioxo-2,5-dihydro-1H-pyrrol-1-yl)hexanoyl]-L-valyl-N-[3-({(1R)-1-[1-benzyl-4-(2,5-difluorophenyl)-1H-pyrrol-2-yl]-2,2-dimethylpropyl}[({3-[(2-carboxyethyl)amino]-3-oxopropyl}sulphanyl) acetyl]amino)propyl]-L-alaninamide Under argon, N-[6-(2,5-dioxo-2,5-dihydro-1H-pyrrol-1-yl)hexanoyl]-L-valyl-N-[3-({(1R)-1-[1-benzyl-4-(2,5-difluorophenyl)-1H-pyrrol-2-yl]-2,2-dimethylpropyl}{[(2-carboxyethyl)sulphanyl]acetyl}amino)propyl]-L-alaninamide (56.7 mg, 61.6 μmol) (intermediate C115) and tert-butyl beta-alaninate hydrochloride (1:1) (13.4 mg, 73.9 μmol) were initially charged in 3.0 ml of DMF, and HATU (28.1 mg, 73.9 μmol) and N,N-diisopropylethylamine (32 μl, 180 μmol) were added. The reaction mixture was stirred at RT for 10 min and then purified directly by prep. RP-HPLC (column: Reprosil 250×30; 10μ, flow rate: 50 ml/min, MeCN/water). The solvents were evaporated under reduced pressure and the residue was dried under high vacuum. This gave 41.4 mg (64% of theory) of the compound N-[6-(2,5-dioxo-2,5-dihydro-1H-pyrrol-1-yl)hexanoyl]-L-valyl-N-(14-{(1R)-1-[1-benzyl-4-(2,5-difluorophenyl)-1H-pyrrol-2-yl]-2,2-dimethylpropyl}-2,2-dimethyl-4,8,13-trioxo-3-oxa-11-thia-7,14-diazaheptadecan-17-yl)-L-alaninamide.

LC-MS (Method 1): $R_t$=1.28 min; MS (ESIpos): m/z=1048 [M+H]⁺

N-[6-(2,5-Dioxo-2,5-dihydro-1H-pyrrol-1-yl)hexanoyl]-L-valyl-N-(14-{(1R)-1-[1-benzyl-4-(2,5-difluorophenyl)-1H-pyrrol-2-yl]-2,2-dimethylpropyl}-2,2-dimethyl-4,8,13-trioxo-3-oxa-11-thia-7,14-diazaheptadecan-17-yl)-L-alaninamide (39.3 mg, 37.5 μmol) was dissolved in 2.5 ml of trifluoroethanol. Zinc chloride (30.7 mg, 225 μmol) was added and the reaction mixture was stirred at 50° C. for 1 hour. Once more, zinc chloride (30.7 mg, 225 μmol) was added and the reaction mixture was stirred at 50° C. for 1 hour. Ethylenediamine-N,N,N',N'-tetraacetic acid (131 mg, 450 μmol) was added, followed by water (0.1% TFA), and the mixture was then concentrated under reduced pressure. The residue was purified by prep. RP-HPLC (column: Reprosil 250×30; 10μ, flow rate: 50 ml/min, MeCN/water, 0.1% TFA). The solvents were evaporated under reduced pressure and the residue was taken up in a little water and lyophilized. This gave 30 mg (81% of theory) of the title compound.

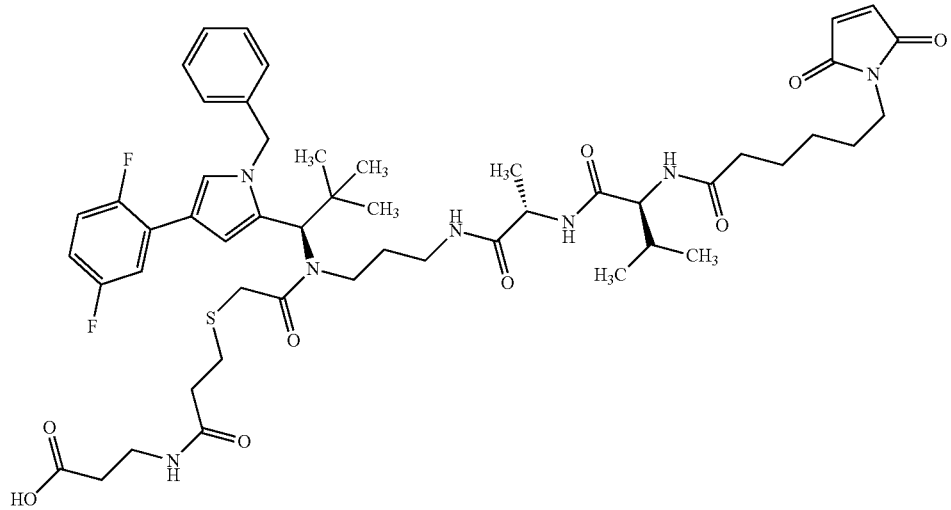 [SMILES: CC(C)[C@H](NC(=O)CCCCCN1C(=O)C=CC1=O)C(=O)N[C@@H](C)C(=O)NCCCN(C(=O)CSCCC(=O)NCCC(=O)O)[C@@H](c1cc(-c2cc(F)ccc2F)cn1Cc1ccccc1)C(C)(C)C]

LC-MS (Method 1): R$_t$=1.12 min; MS (ESIpos): m/z=992 [M+H]$^+$

Intermediate L1

Trifluoroacetic acid/N-(2-aminoethyl)-2-(2,5-dioxo-2,5-dihydro-1H-pyrrol-1-yl)acetamide (1:1)

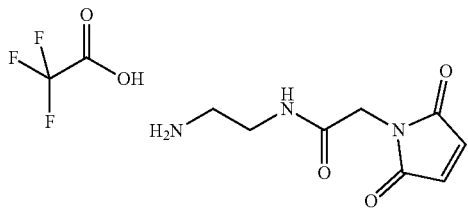 [SMILES: O=C(O)C(F)(F)F ; NCCNC(=O)CN1C(=O)C=CC1=O]

The title compound was prepared by classical methods of peptide chemistry from commercially available (2,5-dioxo-2,5-dihydro-1H-pyrrol-1-yl)acetic acid and tert-butyl (2-aminoethyl)carbamate.

HPLC (Method 11): R$_t$=0.19 min;

LC-MS (Method 1): R$_t$=0.17 min; MS (ESIpos): m/z=198 (M+H)$^+$.

Intermediate L2

Trifluoroacetic acid/rel-(1R,2S)-2-amino-N-[2-(2,5-dioxo-2,5-dihydro-1H-pyrrol-1-yl)ethyl]cyclopentanecarboxamide (1:1)

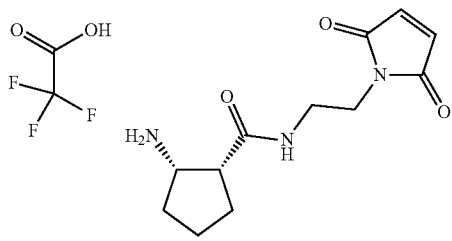 [SMILES: O=C(O)C(F)(F)F ; N[C@H]1CCC[C@H]1C(=O)NCCN1C(=O)C=CC1=O]

The title compound was prepared from 50 mg (0.214 mmol) of commercially available cis-2-[(tert-butoxycarbonyl)amino]-1-cyclopentanecarboxylic acid and 60 mg (0.235 mmol) of likewise commercially available trifluoroacetic acid/1-(2-aminoethyl)-1H-pyrrole-2,5-dione (1:1) by coupling with EDC/HOBT and subsequent deprotection with TFA. This gave 36 mg (38% of theory over 2 steps) of the title compound.

HPLC (Method 11): R$_t$=0.2 min;

LC-MS (Method 1): R$_t$=0.17 min; MS (ESIpos): m/z=252 (M+H)$^+$.

Intermediate L3

Trifluoroacetic acid/(1S,2R)-2-amino-N-[2-(2,5-dioxo-2,5-dihydro-1H-pyrrol-1-yl)ethyl]cyclopentanecarboxamide (1:1)

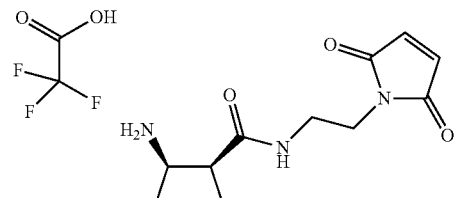

The title compound was prepared from 50 mg (0.214 mmol) of commercially available (1S,2R)-2-[(tert-butoxycarbonyl)amino]cyclopentanecarboxylic acid with 72 mg (0.283 mmol) of likewise commercially available trifluoroacetic acid/1-(2-aminoethyl)-1H-pyrrole-2,5-dione (1:1) by coupling with EDC/HOBT and subsequent deprotection with TFA. This gave 13 mg (16% of theory over 2 steps) of the title compound.

HPLC (Method 11): R$_t$=0.2 min;

LC-MS (Method 1): R$_t$=0.2 min; MS (ESIpos): m/z=252 (M+H)$^+$.

Intermediate L4

Trifluoroacetic acid/N-(2-aminoethyl)-4-(2,5-dioxo-2,5-dihydro-1H-pyrrol-1-yl)cyclohexanecarboxamide (1:1)

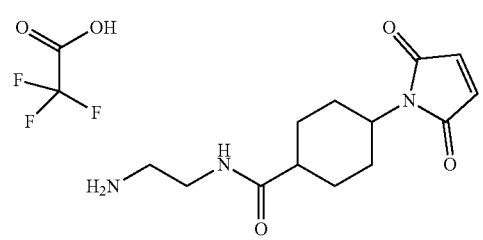 [SMILES: O=C(O)C(F)(F)F ; NCCNC(=O)C1CCC(N2C(=O)C=CC2=O)CC1]

The title compound was prepared by classical methods of peptide chemistry from commercially available 1-[(4-{[(2,5-dioxopyrrolidin-1-yl)oxy]carbonyl}cyclohexyl)methyl]-1H-pyrrole-2,5-dione and tert-butyl (2-aminoethyl)carbamate.

HPLC (Method 11): R$_t$=0.26 min;

LC-MS (Method 1): R$_t$=0.25 min; MS (ESIpos): m/z=280 (M+H)$^+$.

Intermediate L5

Trifluoroacetic acid/N-[4-(2,5-dioxo-2,5-dihydro-1H-pyrrol-1-yl)phenyl]-beta-alaninamide (1:1)

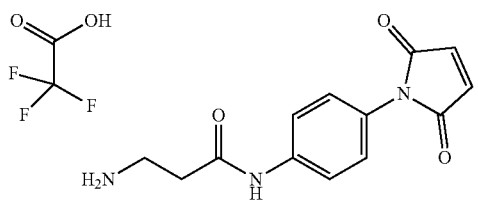 [SMILES: O=C(O)C(F)(F)F ; NCCC(=O)Nc1ccc(N2C(=O)C=CC2=O)cc1]

The title compound was prepared by classical methods of peptide chemistry from commercially available 1-(4-aminophenyl)-1H-pyrrole-2,5-dione and N-(tert-butoxycarbonyl)-beta-alanine.

HPLC (Method 11): $R_t$=0.22 min;

LC-MS (Method 1): $R_t$=0.22 min; MS (ESIpos): m/z=260 (M+H)$^+$.

Intermediate L6

Trifluoroacetic acid/tert-butyl-N-[6-(2,5-dioxo-2,5-dihydro-1H-pyrrol-1-yl)hexanoyl]-L-valyl-L-alanyl-L-lysinate (1:1)

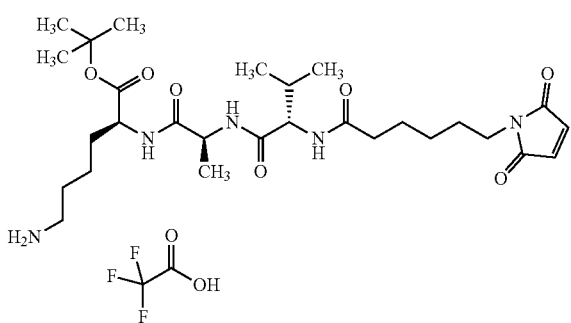 [SMILES: CC(C)[C@H](NC(=O)CCCCCN1C(=O)C=CC1=O)C(=O)N[C@@H](C)C(=O)N[C@@H](CCCCN)C(=O)OC(C)(C)C ; O=C(O)C(F)(F)F]

The title compound was prepared by initially coupling, in the presence of EDC/HOBT, commercially available 6-(2,5-dioxo-2,5-dihydro-1H-pyrrol-1-yl)hexanoic acid with the partially protected peptide tert-butyl L-valyl-L-alanyl-N$^6$-(tert-butoxycarbonyl)-L-lysinate, prepared by classical methods of peptide chemistry. This was followed by deprotection at the amino group under gentle conditions by stirring in 5% strength trifluoroacetic acid in DCM at RT, which gave the title compound in a yield of 37%.

HPLC (Method 11): $R_t$=1.29 min;

LC-MS (Method 1): $R_t$=0.62 min; MS (ESIpos): m/z=566 (M+H)$^+$.

Intermediate L7

Trifluoroacetic acid/beta-alanyl-L-valyl-N$^5$-carbamoyl-N-[4-(2,5-dioxo-2,5-dihydro-1H-pyrrol-1-yl)phenyl]-L-ornithinamide (1:1)

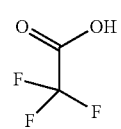

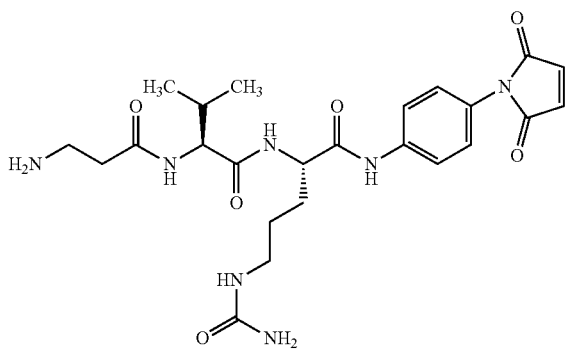

The title compound was prepared according to classical methods of peptide chemistry from commercially available 1-(4-aminophenyl)-1H-pyrrole-2,5-dione by sequential coupling with N$^2$-(tert-butoxycarbonyl)-N$^5$-carbamoyl-L-ornithine in the presence of HATU, deprotection with TFA, coupling with 2,5-dioxopyrrolidin-1-yl N-(tert-butoxycarbonyl)-L-valinate, deprotection with TFA, coupling with 2,5-dioxopyrrolidin-1-yl N-(tert-butoxycarbonyl)-beta-alaninate and another deprotection with TFA. 32 mg of the title compound were obtained.

HPLC (Method 11): $R_t$=0.31 min;

LC-MS (Method 1): $R_t$=0.47 min; MS (ESIpos): m/z=516 (M+H)$^+$.

Intermediate L8

Trifluoroacetic acid/L-alanyl-N5-carbamoyl-N-[4-(2,5-dioxo-2,5-dihydro-1H-pyrrol-1-yl)phenyl]-L-ornithinamide (1:1)

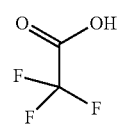

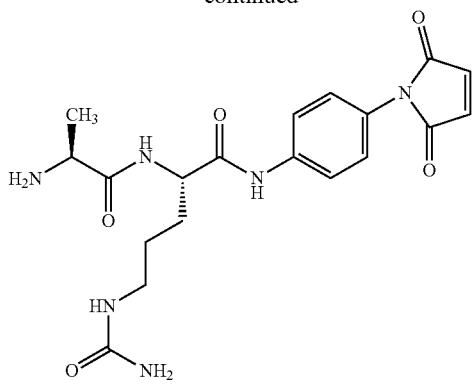

The title compound was prepared according to classical methods of peptide chemistry from commercially available 1-(4-aminophenyl)-1H-pyrrole-2,5-dione by sequential coupling with $N^{2}$-(tert-butoxycarbonyl)-$N^{5}$-carbamoyl-L-ornithine in the presence of HATU, deprotection with TFA, coupling with 2,5-dioxopyrrolidin-1-yl N-(tert-butoxycarbonyl)-L-alaninate and another deprotection with TFA. 171 mg of the title compound were obtained.

HPLC (Method 11): $R_t$=0.23 min;

LC-MS (Method 7): $R_t$=0.3 min; MS (ESIpos): m/z=417 (M+H)$^+$.

Intermediate L9

Trifluoroacetic acid/beta-alanyl-L-valyl-$N^{5}$-carbamoyl-N-[4-(2-methoxy-2-oxoethyl)phenyl]-L-ornithinamide (1:1)

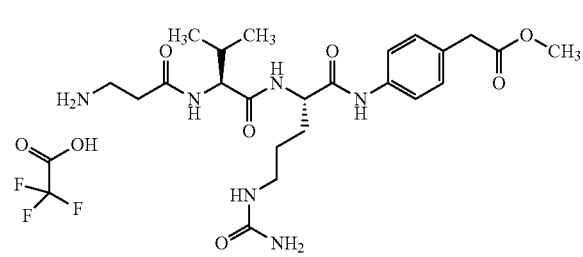 [SMILES: O=C(O)C(F)(F)F ; COC(=O)Cc1ccc(NC(=O)[C@H](CCCNC(N)=O)NC(=O)[C@@H](NC(=O)CCN)C(C)C)cc1]

The title compound was prepared analogously to Intermediate L7 from commercially available methyl (4-aminophenyl)acetate. 320 mg of the title compound were obtained.

HPLC (Method 11): $R_t$=0.45 min;

LC-MS (Method 1): $R_t$=0.48 min; MS (ESIpos): m/z=493 (M+H)$^+$.

Intermediate L10

N-[6-(2,5-Dioxo-2,5-dihydro-1H-pyrrol-1-yl)hexanoyl]-L-valyl-L-alanyl-rel-$N^{6}$-{[(1R,2S)-2-aminocyclopentyl]carbonyl}-L-lysine/trifluoroacetic acid (1:2)

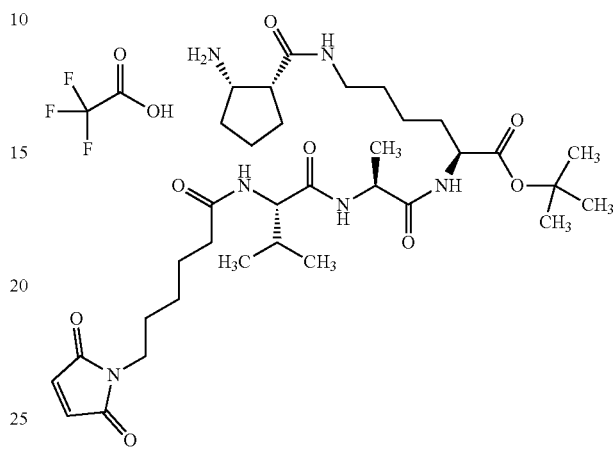

The title compound was prepared from Intermediate L6 by coupling with cis-2-[(tert-butoxycarbonyl)amino]-1-cyclopentanecarboxylic acid with EDC/HOBT and subsequent deprotection with TFA. This gave 12 mg (52% of theory over 2 steps) of the title compound.

HPLC (Method 11): $R_t$=1.45 min;

LC-MS (Method 1): $R_t$=0.73 min; MS (ESIpos): m/z=677 (M+H)$^+$.

Intermediate L11

N-[6-(2,5-Dioxo-2,5-dihydro-1H-pyrrol-1-yl)hexanoyl]-L-valyl-L-alanyl-$N^{6}$-{[(1S,2R)-2-aminocyclopentyl]carbonyl}-L-lysine/trifluoroacetic acid (1:2)

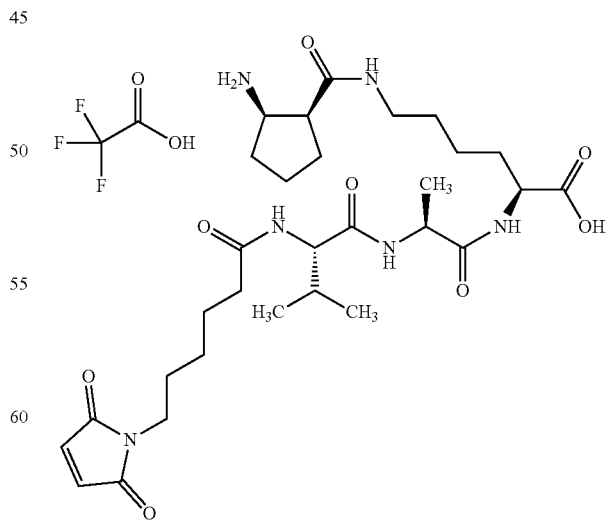

The title compound was prepared from Intermediate L6 by coupling with (1S,2R)-2-[(tert-butoxycarbonyl)amino]

291 cyclopentanecarboxylic acid with EDC/HOBT and subsequent deprotection with TFA. This gave 11 mg (39% of theory over 2 steps) of the title compound.

HPLC (Method 11): R$_t$=1.45 min;
LC-MS (Method 1): R$_t$=0.74 min; MS (ESIpos): m/z=677 (M+H)$^+$.

Intermediate L12

Trifluoroacetic acid/1-[2-(2-aminoethoxy)ethyl]-1H-pyrrole-2,5-dione (1:1)

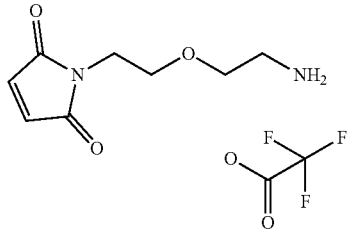 [SMILES: NCCOCCN1C(=O)C=CC1=O ; O=C(O)C(F)(F)F]

381 mg (2.46 mmol) of methyl 2,5-dioxo-2,5-dihydro-1H-pyrrole-1-carboxylate were added to 228 mg (1.12 mmol) of tert-butyl [2-(2-aminoethoxy)ethyl]carbamate dissolved in 7 ml of dioxane/water 1:1. 1.2 ml of a saturated sodium bicarbonate solution were then added and the reaction was stirred at RT. After a total of 5 days of stirring and 2 further additions of the same amounts of the sodium bicarbonate solution, the reaction was worked up by acidification with trifluoroacetic acid, concentration on a rotary evaporator and purification of the residue by preparative HPLC. The appropriate fractions were combined, the solvent was removed under reduced pressure and the residue was lyophilized from acetonitrile/water 1:1.

The residue was taken up in 3 ml of dichloromethane, and 1 ml of trifluoroacetic acid was added. After 15 min of stirring at RT, the solvent was removed under reduced pressure and the residue was lyophilized from acetonitrile/water 1:1. This gave 70 mg (67% of theory over 2 steps) of the title compound as a resinous residue.

HPLC (Method 11): R$_t$=0.2 min;
LC-MS (Method 1): R$_t$=0.18 min; MS (ESIpos): m/z=185 (M+H)$^+$.

Intermediate L13

Trifluoroacetic acid/tert-butyl N$^2$-[(2,5-dioxo-2,5-dihydro-1H-pyrrol-1-yl)acetyl]-L-lysinate (1:1)

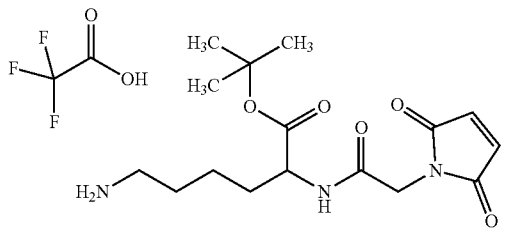 [SMILES: O=C(O)C(F)(F)F ; CC(C)(C)OC(=O)C(CCCCN)NC(=O)CN1C(=O)C=CC1=O]

The title compound was prepared by coupling of (2,5-dioxo-2,5-dihydro-1H-pyrrol-1-yl)acetic acid with tert-butyl N$^6$-(tert-butoxycarbonyl)-L-lysinate hydrochloride (1:1) in the presence of EDC/HOBT and subsequent gentle removal of the tert-butoxycarbonyl protective group analogously to Intermediate L6.

HPLC (Method 11): R$_t$=0.42 min;
LC-MS (Method 1): R$_t$=0.43 min; MS (ESIpos): m/z=340 (M+H)$^+$.

Intermediate L14

Trifluoroacetic acid/1-[2-(4-aminopiperazin-1-yl)-2-oxoethyl]-1H-pyrrole-2,5-dione (1:1)

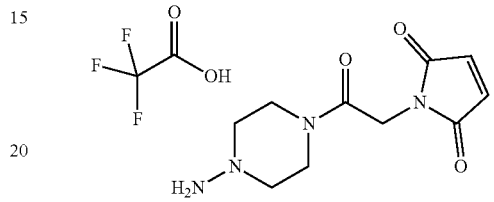

The title compound was prepared analogously to Intermediate L2 over 2 steps from tert-butyl piperazin-1-ylcarbamate and (2,5-dioxo-2,5-dihydro-1H-pyrrol-1-yl)acetic acid.

HPLC (Method 11): R$_t$=0.2 min;
LC-MS (Method 3): R$_t$=0.25 min; MS (ESIpos): m/z=239 (M+H)$^+$.

Intermediate L15

Trifluoroacetic acid/N-(2-aminoethyl)-3-(2-{2-[2-(2,5-dioxo-2,5-dihydro-1H-pyrrol-1-yl)ethoxy]ethoxy}ethoxy)propanamide (1:1)

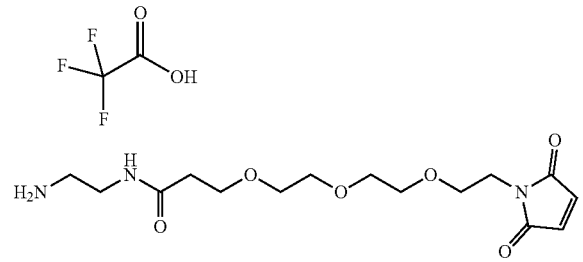

2.93 g (10.58 mmol) of tert-butyl 3-{2-[2-(2-aminoethoxy)ethoxy]ethoxy}propanoate were dissolved in 100 ml of dioxane/water 1:1, and 3.28 g (21.15 mmol) of methyl 2,5-dioxo-2,5-dihydro-1H-pyrrole-1-carboxylate and a saturated sodium bicarbonate solution were added until a pH of 6-7 had been reached. The solution was stirred at RT for 30 min and the 1,4-dioxane was then evaporated under reduced pressure. 200 ml of water were then added, and the mixture was extracted three times with in each case 300 ml of ethyl acetate. The organic extracts were combined, dried over magnesium sulphate and filtered. Concentration gave tert-butyl 3-(2-{2-[2-(2,5-dioxo-2,5-dihydro-1H-pyrrol-1-yl)ethoxy]ethoxy}ethoxy)propanoate as a brown oil which was then dried under high vacuum.

HPLC (Method 11): R$_t$=1.5 min;
LC-MS (Method 3): R$_t$=0.88 min; MS (ESIpos): m/z=375 (M+NH$_4$)+.

This intermediate was converted by standard methods (deprotection with TFA, coupling with tert-butyl (2-aminoethyl)carbamate and another deprotection with TFA) into the title compound.

HPLC (Method 11): $R_t$=0.2 min;
LC-MS (Method 3): $R_t$=0.25 min; MS (ESIpos): m/z=344 (M+H)$^+$.

Intermediate L16

N-[6-(2,5-Dioxo-2,5-dihydro-1H-pyrrol-1-yl)hexanoyl]-L-valyl-N$^5$-carbamoyl-L-ornithine

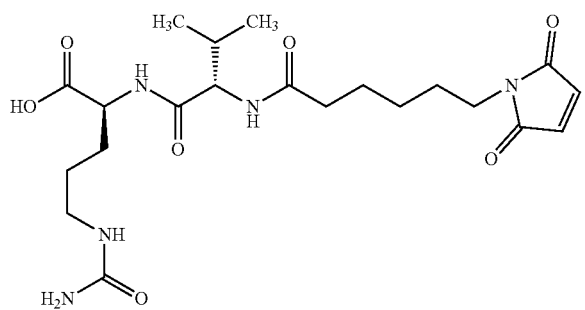 [SMILES: CC(C)[C@H](NC(=O)CCCCCN1C(=O)C=CC1=O)C(=O)N[C@@H](CCCNC(N)=O)C(=O)O]

535 mg (1.73 mmol) of commercially available 1-{6-[(2,5-dioxopyrrolidin-1-yl)oxy]-6-oxohexyl}-1H-pyrrole-2,5-dione and 930 ml of N,N-diisopropylethylamine were added to a solution of 266 mg (1.33 mmol) of L-valyl-N5-carbamoyl-L-ornithine in 24 ml of DMF. The reaction was treated in an ultrasonic bath for 24 h and then concentrated to dryness under reduced pressure. The residue that remained was purified by preparative HPCL and gave, after concentration of the appropriate fractions and drying of the residue under high vacuum, 337 mg (50% of theory) of the title compound.

HPLC (Method 11): $R_t$=0.4 min;
LC-MS (Method 3): $R_t$=0.58 min; MS (ESIpos): m/z=468 (M+H)$^+$.

Intermediate L17

Trifluoroacetic acid/tert-butyl N-[6-(2,5-dioxo-2,5-dihydro-1H-pyrrol-1-yl)hexanoyl]-L-valyl-N$^5$-carbamoyl-L-ornithyl-L-lysinate (1:1)

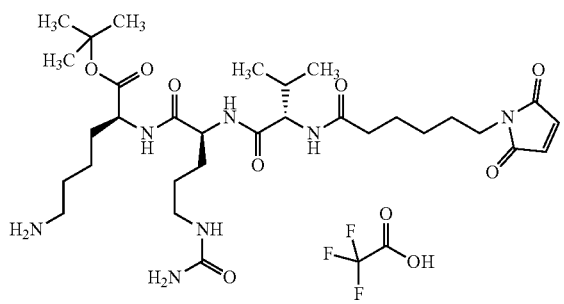 [SMILES: CC(C)[C@H](NC(=O)CCCCCN1C(=O)C=CC1=O)C(=O)N[C@@H](CCCNC(N)=O)C(=O)N[C@@H](CCCCN)C(=O)OC(C)(C)C ; O=C(O)C(F)(F)F]

The title compound was prepared by initially coupling 172 mg (0.37 mmol) of Intermediate L16 and 125 mg (0.37 mmol) of tert-butyl N6-(tert-butoxycarbonyl)-L-lysinate hydrochloride (1:1) in the presence of EDC/HOBT and N,N-diisopropylethylamine and then deprotecting the amino group under gentle conditions by stirring for 2 h in 10% strength trifluoroacetic acid in DCM at RT.

Freeze-drying from acetonitrile/water gave 194 mg (49% of theory) of the title compound over 2 steps.

HPLC (Method 11): $R_t$=1.1 min;
LC-MS (Method 1): $R_t$=0.58 min; MS (ESIpos): m/z=652 (M+H)$^+$.

Intermediate L18

Trifluoroacetic acid/beta-alanyl-L-alanyl-N$^5$-carbamoyl-N-[4-(2-methoxy-2-oxoethyl)phenyl]-L-ornithinamide (1:1)

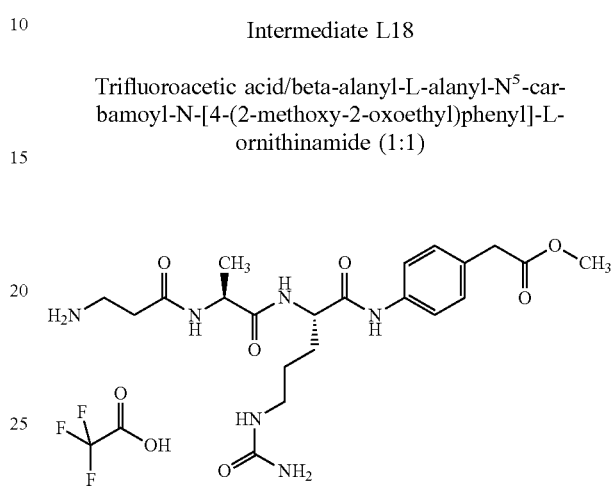

The title compound was prepared from methyl (4-aminophenyl)acetate analogously to Intermediate L7 sequentially according to classical methods of peptide chemistry by linking N$^2$-(tert-butoxycarbonyl)-N$^5$-carbamoyl-L-ornithine in the presence of HATU, deprotection with TFA, coupling with 2,5-dioxopyrrolidin-1-yl N-(tert-butoxycarbonyl)-L-alaninate, deprotection with TFA, coupling with 2,5-dioxopyrrolidin-1-yl N-(tert-butoxycarbonyl)-beta-alaninate and another deprotection with TFA. 330 mg of the title compound were obtained.

HPLC (Method 11): $R_t$=0.29 min;
LC-MS (Method 1): $R_t$=0.41 min; MS (ESIpos): m/z=465 (M+H)$^+$.

Intermediate L19

Trifluoroacetic acid/L-alanyl-N5-carbamoyl-N-(4-{[(2,5-dioxo-2,5-dihydro-1H-pyrrol-1-yl)acetyl]amino}phenyl)-L-ornithinamide (1:1)

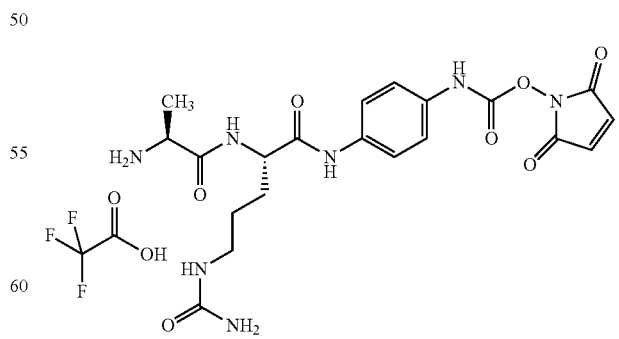

The title compound was prepared from 1,4-phenylenediamine sequentially according to classical methods of peptide chemistry. In the first step, 942 mg (8.72 mmol) of 1,4-phenylenediamine were monoacylated with 0.8 g (2.9 mmol) of N²-(tert-butoxycarbonyl)-N⁵-carbamoyl-L-ornithine in the presence of HATU and N,N-diisopropylethylamine. In the second step, in an analogous manner, the second anilinic amino group was acylated with (2,5-dioxo-2,5-dihydro-1H-pyrrol-1-yl)acetic acid in the presence of HATU and N,N-diisopropylethylamine. Deprotection with TFA, coupling with 2,5-dioxopyrrolidin-1-yl N-(tert-butoxycarbonyl)-L-alaninate and another deprotection with TFA then gave, in 3 further synthesis steps, the title compound, 148 mg of which were obtained by this route.

LC-MS (Method 1): $R_t$=0.21 min; MS (ESIpos): m/z=474 (M+H)⁺.

LC-MS (Method 4): $R_t$=0.2 min; MS (ESIpos): m/z=474 (M+H)⁺.

Intermediate L20

Trifluoroacetic acid/L-valyl-N⁵-carbamoyl-N-[4-(2,5-dioxo-2,5-dihydro-1H-pyrrol-1-yl)phenyl]-L-ornithinamide (1:1)

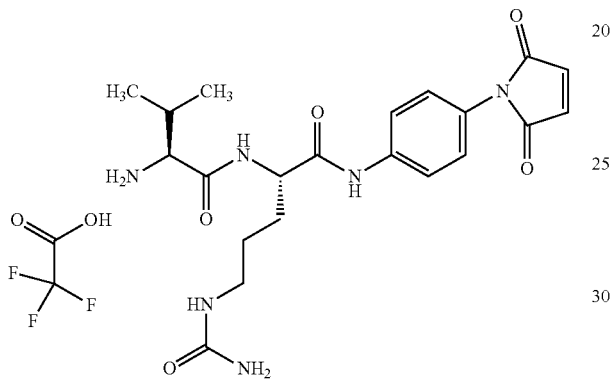

The title compound was prepared according to classical methods of peptide chemistry analogously to Intermediate L8 from commercially available 1-(4-aminophenyl)-1H-pyrrole-2,5-dione by sequential coupling with N²-(tert-butoxycarbonyl)-N⁵-carbamoyl-L-ornithine in the presence of HATU, deprotection with TFA, coupling with 2,5-dioxopyrrolidin-1-yl N-(tert-butoxycarbonyl)-L-valinate and another deprotection with TFA. 171 mg of the title compound were obtained.

HPLC (Method 11): $R_t$=0.28 min;

LC-MS (Method 1): $R_t$=0.39 min; MS (ESIpos): m/z=445 (M+H)⁺.

Intermediate L21

L-Valyl-N⁶-(tert-butoxycarbonyl)-N-[4-(2-methoxy-2-oxoethyl)phenyl]-L-lysinamide

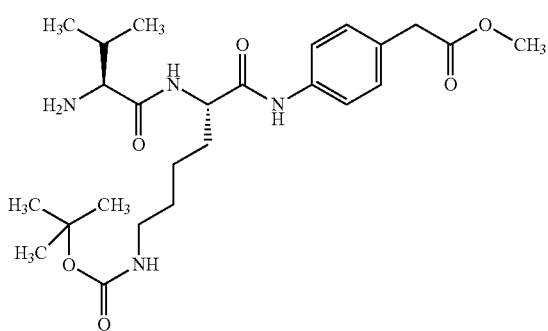 [SMILES: COC(=O)Cc1ccc(NC(=O)[C@H](CCCCNC(=O)OC(C)(C)C)NC(=O)[C@@H](N)C(C)C)cc1]

The title compound was prepared according to classical methods of peptide chemistry from commercially available 0.42 g (2.56 mmol) of methyl (4-aminophenyl)acetate by sequential coupling with N6-(tert-butoxycarbonyl)-N2-[(9H-fluoren-9-ylmethoxy)carbonyl]-L-lysine in the presence of HATU and N,N-diisopropylethylamine, deprotection with piperidine, coupling with 2,5-dioxopyrrolidin-1-yl N-[(benzyloxy)carbonyl]-L-valinate in the presence of N,N-diisopropylethylamine and subsequent hydrogenolytic removal of the benzyloxycarbonyl protective group over 10% palladium on activated carbon. This gave 360 mg (32% of theory over 4 steps) of the title compound.

HPLC (Method 11): $R_t$=1.5 min;

LC-MS (Method 1): $R_t$=0.73 min; MS (ESIpos): m/z=493 (M+H)⁺.

Intermediate L22

Trifluoroacetic acid/N-[(9H-fluoren-9-ylmethoxy)carbonyl]-L-valyl-N-{4-[(2S)-2-amino-3-methoxy-3-oxopropyl]phenyl}-N-carbamoyl-L-ornithinamide (1:1)

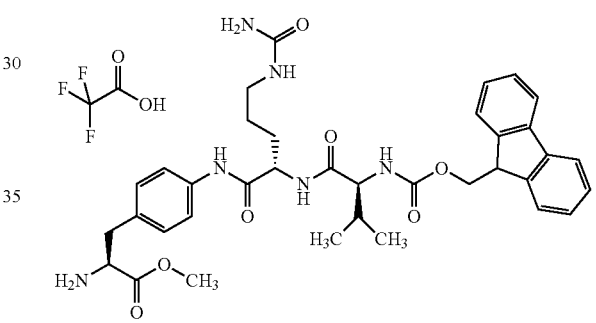

The title compound was prepared from N-(tert-butoxycarbonyl)-4-nitro-L-phenylalanine sequentially according to classical methods of peptide chemistry. 2.5 g (8.06 mmol) of this starting material were in the first step initially converted into the caesium salt and then with iodomethane in DMF into the methyl ester.

Hydrogenolytically in methanol over 10% palladium on activated carbon, the nitro group was then converted into an amino group.

The amino group generated in this manner was then acylated with N5-carbamoyl-N2-[(9H-fluoren-9-ylmethoxy)carbonyl]-L-ornithine in DMF in the presence of HATU and N,N-diisopropylethylamine. In the next step, the Fmoc group was removed with piperidine in DMF. Coupling was then carried out in DMF with N-[(9H-fluoren-9-ylmethoxy)carbonyl]-L-valine in the presence of 1-(3-dimethylaminopropyl)-3-ethylcarbodiimide hydrochloride, 1-hydroxy-1H-benzotriazole hydrate and N,N-diisopropylethylamine and finally removal of the tert-butoxycarbonyl group with trifluoroacetic acid.

HPLC (Method 11): $R_t$=1.6 min;

LC-MS (Method 1): $R_t$=0.77 min; MS (ESIpos): m/z=673 (M+H)⁺.

Intermediate L23

Trifluoroacetic acid/N-[2-(2,5-dioxo-2,5-dihydro-1H-pyrrol-1-yl)ethyl]-beta-alaninamide (1:1)

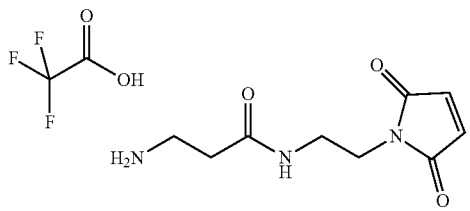 [SMILES: O=C(O)C(F)(F)F ; NCCC(=O)NCCN1C(=O)C=CC1=O]

The title compound was prepared from commercially available trifluoroacetic acid/1-(2-aminoethyl)-1H-pyrrole-2,5-dione (1:1) by coupling with N-(tert-butoxycarbonyl)-beta-alanine in the presence of EDCI/HOBT and N,N-diisopropylethylamine and subsequent deprotection with trifluoroacetic acid.

HPLC (Method 11): $R_t$=0.19 min.

Intermediate L24

Trifluoroacetic acid/1-amino-N-[2-(2,5-dioxo-2,5-dihydro-1H-pyrrol-1-yl)ethyl]cyclopropanecarboxamide (1:1)

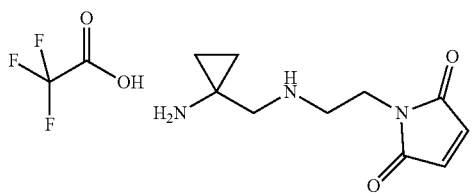 [SMILES: O=C(O)C(F)(F)F ; NC1(CNCCN2C(=O)C=CC2=O)CC1]

114 mg (0.67 mmol) of commercially available 1-[(tert-butoxycarbonyl)amino]cyclopropane-carboxylic acid were dissolved in 25 ml of DCM, 110 mg (0.623 mmol) of commercially available trifluoroacetic acid/1-(2-aminoethyl)-1H-pyrrole-2,5-dione (1:1) and 395 μl of N,N-diisopropylethylamine were added and the mixture was cooled to −10° C. 217 mg (0.793 mmol) of 2-bromo-1-ethylpyridinium tetrafluoroborate were then added, and the mixture was stirred at RT for 2 h. The mixture was then diluted with ethyl acetate and extracted successively with 10% strength citric acid, saturated sodium bicarbonate solution and saturated sodium chloride solution, then dried over magnesium sulphate and concentrated. Drying under high vacuum gave 152 mg of the protected intermediate.

These were then taken up in 10 ml of DCM and deprotected with 1 ml of trifluoroacetic acid. Lyophilization from acetonitrile/water gave 158 mg (71% of theory over 2 steps) of the title compound.

HPLC (Method 11): $R_t$=0.19 min.
LC-MS (Method 3): $R_t$=0.98 min; MS (ESIpos): m/z=224 (M+H)⁺.

Intermediate L25

N-[31-(2,5-Dioxo-2,5-dihydro-1H-pyrrol-1-yl)-29-oxo-4,7,10,13,16,19,22,25-octaoxa-28-azahentriacontan-1-oyl]-L-valyl-L-alanine

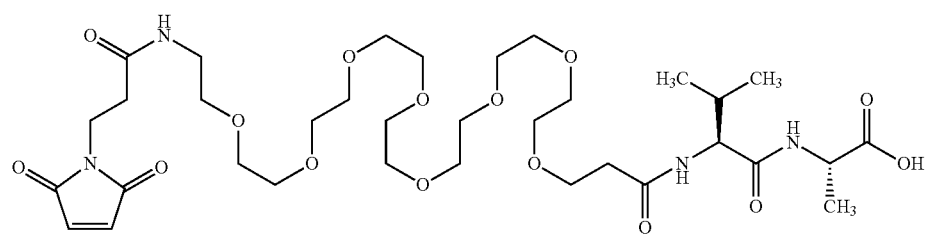 [SMILES: CC(C)[C@H](NC(=O)CCOCCOCCOCCOCCOCCOCCOCCOCCNC(=O)CCN1C(=O)C=CC1=O)C(=O)N[C@@H](C)C(=O)O]

31.4 mg (0.17 mmol) of valyl-L-alanine were dissolved in 3.0 ml of DMF, and 115.0 mg (0.17 mmol) of 3-(2,5-dioxo-2,5-dihydro-1H-pyrrol-1-yl)-N-{27-[(2,5-dioxopyrrolidin-1-yl)oxy]-27-oxo-3,6,9,12,15,18,21,24-octaoxaheptacos-1-yl}propanamide and 33.7 mg (0.33 mmol) of triethylamine were added. The mixture was stirred at RT overnight. The reaction mixture was purified directly by preparative RP-HPLC (column: Reprosil 250×30; 10μ, flow rate: 50 ml/min, MeCN/water). The solvents were evaporated under reduced pressure and the residue was dried under high vacuum. This gave 74.1 mg (58% of theory) of the title compound.

LC-MS (Method 1): $R_t$=0.61 min; MS (ESIpos): m/z=763 [M+H]⁺.

Intermediate L26

L-Valyl-N6-(tert-butoxycarbonyl)-L-lysine

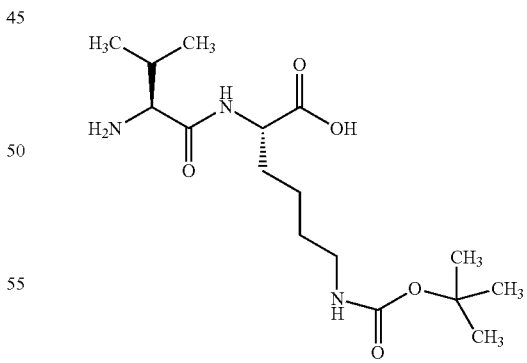

600.0 mg (1.58 mmol) of N2-[(benzyloxy)carbonyl]-N6-(tert-butoxycarbonyl)-L-lysine were suspended in 25.0 ml of water/ethanol/THF (1:1:0.5), palladium on carbon (10%) was added and the mixture was hydrogenated at RT with hydrogen under standard pressure for 5 h. The catalyst was filtered off and the solvents were evaporated under reduced pressure. The compound obtained was used in the next step without further purification.

LC-MS (Method 1): $R_t$=0.42 min; MS (ESIpos): m/z=247 [M+H]$^+$. 180 mg (0.73 mmol) of N6-(tert-butoxycarbonyl)-L-lysine were dissolved in 5.0 ml of DMF, and 74.0 mg (0.73 mmol) of triethylamine were added. 254.6 mg (0.73 mmol) of 2,5-dioxopyrrolidin-1-yl N-[(benzyloxy)carbonyl]-L-valinate and 74.0 mg (0.73 mmol) of triethylamine were then added. The reaction mixture was stirred at RT for 3.5 h. The reaction solution was purified directly by preparative RP-HPLC (column: Reprosil 250×30; 10μ, flow rate: 50 ml/min, MeCN/water, 0.1% TFA). The solvents were evaporated under reduced pressure and the residue was dried under high vacuum. This gave 294.1 mg (76% of theory) of N-[(benzyloxy)carbonyl]-L-valyl-N6-(tert-butoxycarbonyl)-L-lysine.

LC-MS (Method 1): $R_t$=0.97 min; MS (ESIpos): m/z=480 [M+H]$^+$.

272.2 mg (0.57 mmol) of N-[(benzyloxy)carbonyl]-L-valyl-N6-(tert-butoxycarbonyl)-L-lysine were initially charged in 20.0 ml of ethyl acetate/ethanol/THF (1:1:1), and 27.2 mg of palladium on activated carbon were added. The mixture was hydrogenated with hydrogen at RT under standard pressure for 5 h. The mixture was filtered off with the aid of Celite® and the filter cake was washed with ethyl acetate/ethanol/THF (1:1:1). The solvents were evaporated under reduced pressure and the residue was dried under high vacuum. The title compound (182 mg, 72% of theory) was used in the next reaction step without further purification.

LC-MS (Method 1): $R_t$=0.53 min; MS (ESIpos): m/z=346 [M+H]$^+$.

Intermediate L27

N-[31-(2,5-Dioxo-2,5-dihydro-1H-pyrrol-1-yl)-29-oxo-4,7,10,13,16,19,22,25-octaoxa-28-azahentriacontan-1-oyl]-L-valyl-N6-(tert-butoxycarbonyl)-L-lysine

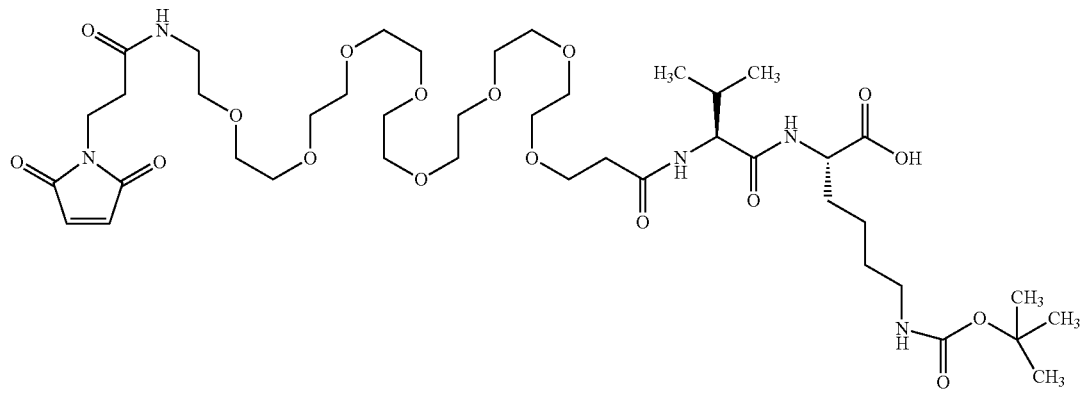 [SMILES: CC(C)[C@H](NC(=O)CCOCCOCCOCCOCCOCCOCCOCCOCCNC(=O)CCN1C(=O)C=CC1=O)C(=O)N[C@@H](CCCCNC(=O)OC(C)(C)C)C(=O)O]

30 mg (0.07 mmol) of L-valyl-N6-(tert-butoxycarbonyl)-L-lysine (Intermediate L26) and 46.1 mg (0.07 mmol) of 3-(2,5-dioxo-2,5-dihydro-H-pyrrol-1-yl)-N-{27-[(2,5-dioxopyrrolidin-1-yl)oxy]-27-oxo-3,6,9,12,15,18,21,24-octaoxaheptacos-1-yl}propanamide were initially charged in 1.5 ml of DMF, and 6.8 mg (0.07 mmol) of 4-methylmorpholine were added. The reaction solution was stirred at RT overnight. The reaction mixture was purified directly by preparative RP-HPLC (column: Reprosil 250×30; 10μ, flow rate: 50 ml/min, MeCN/water). The solvents were evaporated under reduced pressure and the residue was dried under high vacuum. This gave 55.6 mg (90% of theory) of the title compound.

LC-MS (Method 1): $R_t$=0.77 min; MS (ESIpos): m/z=920 [M+H]$^+$.

Intermediate L28 tert-Butyl 3-formyl-4-({[2-(trimethylsilyl)ethoxy]carbonyl}amino)pyrrolidine-1-carboxylate

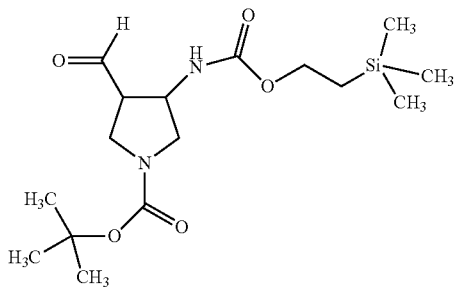 [SMILES: CC(C)(C)OC(=O)N1CC(C=O)C(NC(=O)OCC[Si](C)(C)C)C1]

461.7 mg (1.15 mmol) of 1-tert-butyl 3-ethyl-4-({[2-(trimethylsilyl)ethoxy]carbonyl}amino)pyrrolidine-1,3-dicarboxylate (this compound was prepared according to the literature procedure of WO 2006/066896) were initially charged in 5.0 ml of absolute dichloromethane and the mixture was cooled to −78° C. 326.2 mg (2.29 mmol) of diisobutylaluminum hydride solution (1 M in THF) were then slowly added dropwise and the mixture was stirred at −78° C. for 2 h (monitored by thin-layer chromatography (petroleum ether/ethyl acetate=3:1). 1.3 g (4.59 mmol) of potassium sodium tartrate dissolved in 60 ml of water were added dropwise and the reaction mixture was allowed to warm to RT. Ethyl acetate was added to the reaction mixture and the aqueous phase was extracted three times with ethyl acetate. The combined organic phases were washed once with sat. NaCl solution and dried over magnesium sulphate. The solvent was evaporated under reduced pressure and the residue was dried under high vacuum. This gave 629.0 mg of the title compound as a crude product which was used immediately without further purification in the next reaction step.

Intermediate L29 tert-Butyl 3-formyl-4-[({[2-(trimethylsilyl)ethoxy]carbonyl}amino)methyl]pyrrolidine-1-carboxylate Mixture of Diastereomers.

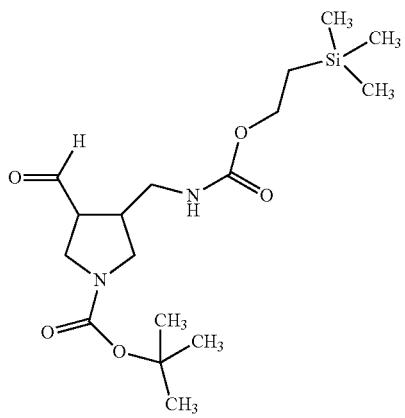 [SMILES: CC(C)(C)OC(=O)N1CC(C=O)C(CNC(=O)OCC[Si](C)(C)C)C1]

807.1 mg (2.34 mmol) of tert-butyl 3-({[tert-butyl(dimethyl)silyl]oxy}methyl)-4-(hydroxymethyl)pyrrolidine-1-carboxylate (prepared according to the literature procedure of WO 2006/100036) were initially charged in 8.0 ml of dichloromethane, and 236.4 mg (2.34 mmol) of triethylamine were added. At 0° C., 267.6 mg (2.34 mmol) of methanesulphonyl chloride were added dropwise, and the reaction mixture stirred at RT overnight. A further 133.8 mg (1.17 mmol) of methanesulphonyl chloride and 118.2 mg (1.17 mmol) of triethylamine were added. The reaction mixture was stirred at RT overnight. The mixture was diluted with dichloromethane and the organic phase was washed in each case once with saturated sodium bicarbonate solution, 5% strength potassium hydrogen sulphate solution and saturated NaCl solution. After drying over magnesium sulphate, the solvent was evaporated under reduced pressure and the residue was purified on Biotage Isolera (silica gel, column 50 g SNAP, flow rate 66 ml/min, cyclohexane/ethyl acetate). The solvents were evaporated under reduced pressure and the residue was dried under high vacuum. This gave 402.0 mg (41% of theory) of the compound tert-butyl 3-({[tert-butyl(dimethyl) silyl]oxy}methyl)-4-{[(methylsulphonyl)oxy]methyl}pyrrolidine-1-carboxylate.

LC-MS (Method 1): $R_t$=1.38 min; MS (ESIpos): m/z=424 [M+H]$^+$.

400.0 mg (0.94 mmol) of tert-butyl 3-({[tert-butyl(dimethyl)silyl]oxy}methyl)-4-{[(methylsulphonyl)oxy]methyl}pyrrolidine-1-carboxylate were initially charged in 5.0 ml of DMF, and 98.2 mg (1.51 mmol) of sodium azide were added. The reaction mixture was stirred at 40° C. for 10 h. Another 30.7 mg (0.47 mmol) of sodium azide were then added, and the mixture was stirred at 40° C. for a further 10 h. Ethyl acetate was added and the organic phase was washed repeatedly with water. After drying of the organic phase over magnesium sulphate, the solvent was evaporated under reduced pressure and the residue was dried under high vacuum. This gave 309.5 mg (89% of theory) of the compound tert-butyl 3-(azidomethyl)-4-({[tert-butyl(dimethyl)silyl]oxy}methyl)pyrrolidine-1-carboxylate. The compound was used without further purification in the next step of the synthesis.

LC-MS (Method 1): $R_t$=1.50 min; MS (ESIpos): m/z=371 [M+H]$^+$.

250 mg (0.68 mmol) of tert-butyl 3-(azidomethyl)-4-({[tert-butyl(dimethyl)silyl]oxy}methyl)pyrrolidine-1-carboxylate were dissolved in 10.0 ml of ethyl acetate/ethanol (1:1), and 25.0 mg of palladium on activated carbon (10%) were added. The mixture was hydrogenated with hydrogen at RT under standard pressure for 8 h. The reaction was filtered through Celite® and the filter cake was washed thoroughly with ethyl acetate. The solvent was evaporated under reduced pressure and the residue was dried under high vacuum. This gave 226.2 mg (82% of theory) of the compound tert-butyl 3-(aminomethyl)-4-({[tert-butyl(dimethyl)silyl]oxy}methyl)pyrrolidine-1-carboxylate. The compound was used without further purification in the next step of the synthesis.

LC-MS (Method 1): $R_t$=0.89 min; MS (ESIpos): m/z=345 [M+H]$^+$.

715.0 mg (2.08 mmol) of tert-butyl 3-(aminomethyl)-4-({[tert-butyl(dimethyl)silyl]oxy}methyl)pyrrolidine-1-carboxylate were dissolved in 15.0 ml of THF, and 2.28 ml (2.28 mmol) of TBAF solution (1M in THF) were added. The reaction mixture was stirred at RT overnight. The solvent was evaporated under reduced pressure and the residue (1.54 g) used without further purification in the next step of the synthesis.

LC-MS (Method 1): $R_t$=0.41 min; MS (ESIpos): m/z=231 [M+H]$^+$.

1.54 g (4.88 mmol) of tert-butyl 3-(aminomethyl)-4-(hydroxymethyl)pyrrolidine-1-carboxylate were initially charged in 1,4-dioxane, and 541.8 mg (4.88 mmol) of calcium chloride (anhydrous) and 488.6 mg (4.88 mmol) of calcium carbonate were added and the mixture was stirred vigorously. 592.8 mg (5.86 mmol) of triethylamine and 1.52 g (5.86 mmol) of 1-({[2-(trimethylsilyl)ethoxy]carbonyl}oxy)pyrrolidine-2,5-dione were then added and the reaction mixture stirred at RT overnight. 644.9 mg (10.7 mmol) of HOAc and ethyl acetate were added. The organic phase was washed twice with water and once with saturated NaCl solution. After drying over magnesium sulphate, the solvent was evaporated under reduced pressure and the residue was purified on silica gel (mobile phase: dichloromethane/methanol=100:1). The solvents were evaporated under reduced pressure and the residue was dried under high vacuum. This gave 346.9 mg (19% of theory) of the compound tert-butyl 3-(hydroxymethyl)-4-[({[2-(trimethylsilyl)ethoxy]carbonyl}amino)methyl]pyrrolidine-1-carboxylate.

LC-MS (Method 1): $R_t$=1.08 min; MS (ESIpos): m/z=375 [M+H]$^+$.

804.0 mg (2.15 mmol) of tert-butyl 3-(hydroxymethyl)-4-[({[2-(trimethylsilyl)ethoxy]carbonyl}amino)methyl]pyrrolidine-1-carboxylate were initially charged in 20.0 ml of chloroform and 20.0 ml of 0.05 N potassium carbonate/0.05 N sodium bicarbonate solution (1:1). 59.7 mg (0.22 mmol) of tetra-n-butylammonium chloride, 429.9 mg (3.22 mmol) of N-chlorosuccinimide and 33.5 mg (0.22 mmol) of TEMPO were then added and the reaction mixture was stirred vigorously at RT overnight. The organic phase was separated off and freed from the solvent under reduced pressure. The residue was purified by silica gel chromatography (mobile phase: cyclohexane/ethyl acetate=3:1). This gave 517.0 mg (46% of theory) of the title compound.

LC-MS (Method 1): $R_t$=1.13 min; MS (ESIpos): m/z=373 [M+H]$^+$.

Intermediate L30 tert-Butyl 3-({[tert-butyl(dimethyl)silyl]oxy}methyl)-4-formylpyrrolidine-1-carboxylate Mixture of Stereoisomers

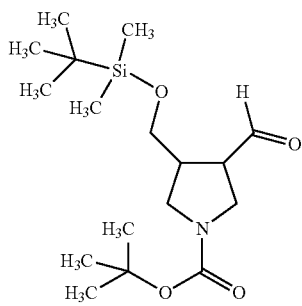

250.0 mg (0.72 mmol) of tert-butyl 3-({[tert-butyl(dimethyl)silyl]oxy}methyl)-4-(hydroxymethyl)pyrrolidine-1-carboxylate (the compound was prepared according to the literature procedure of WO2006/100036) were initially charged in 12.5 ml of dichloromethane/DMSO (4:1), and 219.6 mg (2.17 mmol) of triethylamine were added. At 2° C., 345.5 mg (2.17 mmol) of sulphur trioxide-pyridine complex were added a little at a time and the mixture was stirred at 2° C. for 3 h. Another 345.5 mg (2.17 mmol) of sulphur trioxide-pyridine complex were added a little at a time and the mixture was stirred at RT for 17 h. The reaction mixture was partitioned between dichloromethane and water. The aqueous phase was extracted three times with dichloromethane and the combined organic phases were washed once with water and dried over magnesium sulphate. The solvent was evaporated under reduced pressure and the residue was dried under high vacuum. The residue was used without further purification in the next step of the synthesis (thin-layer chromatography: petroleum ether/ethyl acetate 7:3).

Intermediate L31

Di-tert-butyl {[(tert-butoxycarbonyl)amino]methyl}malonate

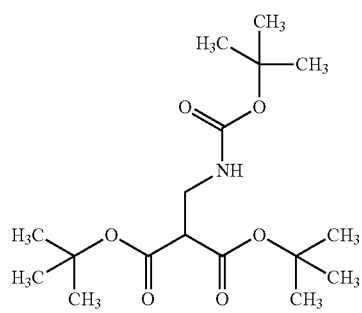 [SMILES: CC(C)(C)OC(=O)NCC(C(=O)OC(C)(C)C)C(=O)OC(C)(C)C]

57.2 g (488.27 mmol) of tert-butyl carbamate, 51.2 ml (683.57 mmol) of a 37% strength solution of formaldehyde in water and 25.9 g (244.13 mmol) of sodium carbonate were added to 600 ml of water. The mixture was warmed until a solution was formed and then stirred at RT for 16 h. The suspension formed was extracted with 500 ml of dichloromethane and the organic phase was separated off, washed with saturated sodium chloride solution and dried over sodium sulphate. The mixture was concentrated on a rotary evaporator and the residue was dried under high vacuum, giving a crystalline solid. The residue was taken up in 1000 ml of absolute THF, and a mixture of 322 ml (3.414 mol) of acetic anhydride and 138 ml (1.707 mol) of pyridine was added dropwise at RT. The reaction mixture was stirred at RT for 16 h and then concentrated on a rotary evaporator, with the water bath at room temperature. The residue was taken up in diethyl ether and washed three times with a saturated sodium bicarbonate solution and once with a saturated sodium chloride solution. The organic phase was dried over sodium sulphate and concentrated on a rotary evaporator and the residue was dried under high vacuum for 2 d. The residue was taken up in 2000 ml of absolute THF, and 456 ml (456.52 mmol) of a 1 M solution of potassium tert-butoxide in THF were added with ice cooling. The mixture was stirred at 0° C. for 20 min, and 100.8 g (456.52 mmol) of di-tert-butyl malonate dissolved in 200 ml of absolute THF were then added dropwise. The mixture was stirred at RT for 48 h, and water was then added. The reaction mixture was concentrated on a rotary evaporator and taken up in 500 ml of ethyl acetate. The mixture was washed with 500 ml of water and 100 ml of a saturated sodium chloride solution and the organic phase was dried over sodium sulphate. The organic phase was concentrated on a rotary evaporator and the residue was dried under high vacuum. The residue was purified by filtration on silica gel (mobile phase: cyclohexane/ethyl acetate, gradient=30:1→5:1). This gave 37.07 g (22% of theory) of the target compound.

LC-MS (Method 6): $R_t$=2.87 min; MS (ESIpos): m/z=346 [M+H]$^+$.

Intermediate L32 tert-Butyl [3-hydroxy-2-(hydroxymethyl)propyl]carbamate

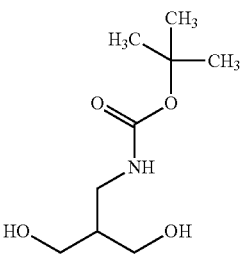

37.0 g (107.11 mmol) of di-tert-butyl (acetoxymethyl)malonate were dissolved in 1000 ml of absolute THF, and 535.5 ml (1071.10 mmol) of a 2 M solution of lithium borohydride in THF were added dropwise with ice cooling. 19.3 ml (1071.10 mmol) of water were added dropwise and the mixture was stirred at RT for 4.5 h. The reaction mixture was concentrated on a rotary evaporator and dried under high vacuum. The residue was taken up in 1500 ml of ethyl acetate, 100 ml of water were added and the mixture was stirred with water cooling (slightly exothermic) for 30 min.

The organic phase was separated off and the aqueous phase was extracted twice with 500 ml of ethyl acetate. The organic phase was concentrated on a rotary evaporator and the residue was dried under high vacuum. This gave 20.7 g (94% of theory) of the target compound.

LC-MS (Method 6): $R_t$=1.49 min; MS (EIpos): m/z=106 [M-C$_5$H$_8$O$_2$]$^+$.

Intermediate L33 tert-Butyl [3-{[tert-butyl(dimethyl)silyl]oxy}-2-(hydroxymethyl)propyl]carbamate

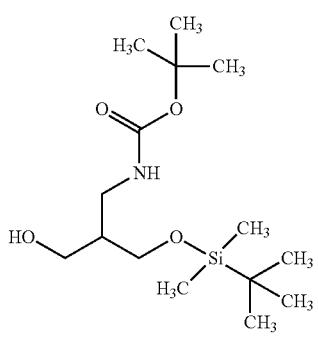 [SMILES: CC(C)(C)OC(=O)NCC(CO)CO[Si](C)(C)C(C)(C)C]

20.00 g (97.44 mmol) of tert-butyl [3-hydroxy-2-(hydroxymethyl)propyl]carbamate were dissolved in 1000 ml of absolute dichloromethane, and 6.63 g (97.44 mmol) of imidazole and 16.16 g (107.18 mmol) of tert-butyl(chloro)dimethylsilane were added at RT. The reaction mixture was stirred at RT for 16 h and washed with semiconcentrated sodium chloride solution. The aqueous phase was extracted with ethyl acetate and the combined organic phases were dried over sodium sulphate, concentrated on a rotary evaporator and dried under high vacuum. This gave 28.50 g (92% of theory) of the target compound.

$^1$H-NMR (400 MHz, DMSO-d$_6$): δ[ppm]=0.02 (s, 6H), 0.86 (s, 9H), 1.37 (s, 9H), 1.58-1.73 (m, 1H), 2.91 (q, 2H), 3.33-3.36 [m, (2H, hidden)], 3.53-3.58 (m, 2H), 6.65-6.72 (m, 1H).

Intermediate L34 tert-Butyl (3-{[tert-butyl(dimethyl)silyl]oxy}-2-formylpropyl)carbamate

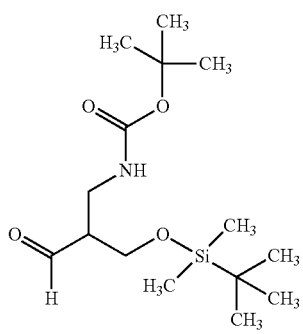 [SMILES: CC(C)(C)OC(=O)NCC(C=O)CO[Si](C)(C)C(C)(C)C]

12.65 g (39.591 mmol) of tert-butyl [3-{[tert-butyl(dimethyl)silyl]oxy}-2-(hydroxy-methyl)propyl]carbamate were dissolved in 200 ml of dichloromethane, and 19.31 g (45.53 mmol) of Dess-Martin periodinane dissolved in 150 ml of dichloromethane were added dropwise at RT. The mixture was stirred at room temperature for 2 h, 250 ml of a semiconcentrated sodium bicarbonate solution and 250 ml of a 10% strength sodium thiosulphate solution were then added and the mixture was stirred for 20 min. The organic phase was separated off and the aqueous phase was extracted with ethyl acetate. The combined organic phases were washed with 300 ml of water, dried over sodium sulphate, concentrated on a rotary evaporator and dried under high vacuum. This gave 11.35 g (90% of theory) of the target compound.

$^1$H-NMR (400 MHz, DMSO-d$_6$): δ[ppm]=0.02 (s, 6H), 0.84 (s, 9H), 1.36 (s, 9H), 1.48-1.51 (m, 1H), 3.08-3.32 [m, (1H, hidden)], 3.50-3.58 (m, 2H), 3.81-3.91 (m, 1H), 6.71 (t, 1H), 9.60 (d, 1H).

Intermediate L35 tert-Butyl (3-oxopropyl)carbamate

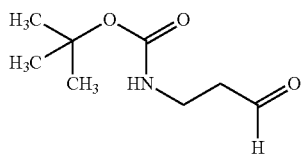

The title compound was prepared according to a method known from the literature (e.g. Jean Bastide et al. *J. Med. Chem.* 2003, 46(16), 3536-3545).

Intermediate L36

N-[(Benzyloxy)carbonyl]-L-valyl-N5-carbamoyl-L-ornithine

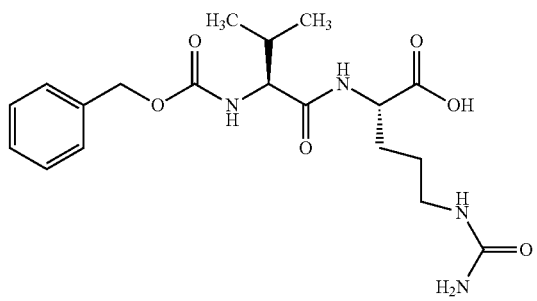 [SMILES: CC(C)[C@H](NC(=O)OCc1ccccc1)C(=O)N[C@@H](CCCNC(N)=O)C(=O)O]

100 mg (0.57 mmol) of N5-carbamoyl-L-ornithine were taken up in 4.0 ml of DMF, and 0.08 ml (0.57 mmol) of triethylamine was added. 199.0 mg (0.57 mmol) of 2,5-dioxopyrrolidin-1-yl-N-[(benzyloxy)carbonyl]-L-valine and 0.08 ml (0.57 mmol) of triethylamine were then added. The mixture was stirred at RT for 48 h. The reaction mixture was purified directly by preparative RP-HPLC (column: Reprosil 250×30; 10µ, flow rate: 50 ml/min, MeCN/water with 0.1% TFA). The solvents were evaporated under reduced pressure and the residue was dried under high vacuum. This gave 75.7 mg (33% of theory) of the title compound.

LC-MS (Method 1): $R_t$=0.69 min; MS (ESIpos): m/z=409 [M+H]$^+$.

Intermediate L37

L-Valyl-N5-carbamoyl-L-ornithine

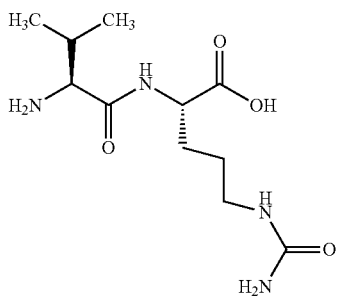 [SMILES: CC(C)[C@H](N)C(=O)N[C@@H](CCCNC(N)=O)C(=O)O]

75.7 mg (0.19 mmol) of Intermediate L36 were suspended in 25 ml of water/ethanol/THF, and 7.5 mg of palladium on activated carbon (10%) were added and the mixture was hydrogenated at RT with hydrogen under standard pressure for 4.5 h. The catalyst was filtered off and the reaction mixture was freed from the solvent under reduced pressure and dried under high vacuum. The residue was used for the next step without further purification. This gave 64.9 mg (93% of theory) of the title compound.

LC-MS (Method 6): $R_t$=0.25 min; MS (ESIpos): m/z=275 [M+H]$^+$.

Intermediate L38

N-[31-(2,5-Dioxo-2,5-dihydro-1H-pyrrol-1-yl)-29-oxo-4,7,10,13,16,19,22,25-octaoxa-28-azahentriacontan-1-oyl]-L-valyl-N5-carbamoyl-L-ornithine

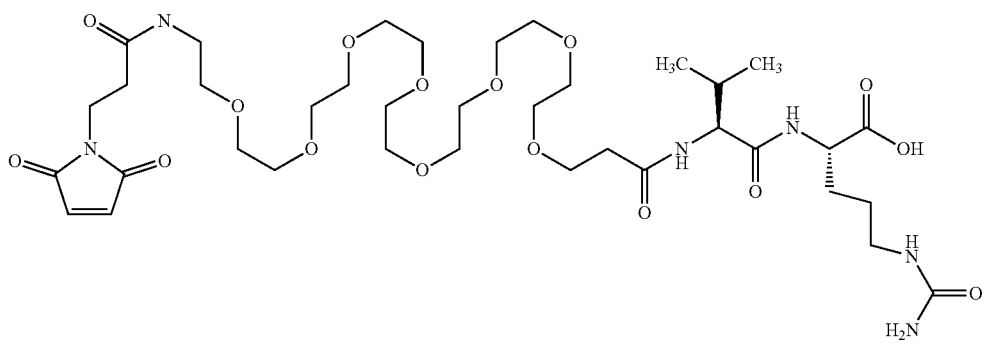 [SMILES: CC(C)[C@H](NC(=O)CCOCCOCCOCCOCCOCCOCCOCCOCCNC(=O)CCN1C(=O)C=CC1=O)C(=O)N[C@@H](CCCNC(N)=O)C(=O)O]

38.3 mg (0.14 mmol) of Intermediate L37 were initially charged in 3.0 ml of DMF, and 96.4 mg (0.14 mmol) of 3-(2,5-dioxo-2,5-dihydro-1H-pyrrol-1-yl)-N-{27-[(2,5-dioxopyrrolidin-1-yl)oxy]-27-oxo-3,6,9,12,15,18,21,24-octaoxaheptacos-1-yl}propanamide and 39.0 μl (0.28 mmol) of triethylamine were added. The mixture was stirred at RT overnight. 16.0 μl (0.28 mmol) of HOAc were then added, and the reaction mixture was purified directly by preparative RP-HPLC (column: Reprosil 250×30; 10μ, flow rate: 50 ml/min, MeCN/water). The solvents were evaporated under reduced pressure and the residue was dried under high vacuum. This gave 58.9 mg (45% of theory) of the title compound.

LC-MS (Method 1): $R_t$=0.61 min; MS (ESIpos): m/z=849 [M+H]$^+$.

Intermediate L39

2-(Trimethylsilyl)ethyl (2-sulphanylethyl)carbamate

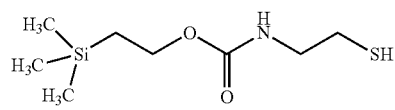

300 mg (2.64 mmol) of 2-aminoethanethiol hydrochloride (1:1) were initially charged in 3.0 ml of dichloromethane, and 668.0 mg (6.60 mmol) of triethylamine and 719.1 mg (2.77 mmol) of 1-({[2-(trimethylsilyl)ethoxy]carbonyl}oxy)pyrrolidine-2,5-dione were added. The mixture was stirred at RT for 2 days (monitored by thin-layer chromatography: dichloromethane/methanol=100:1.5). Ethyl acetate was added and the reaction mixture was washed three times with water. The organic phase was washed twice with saturated NaCl solution and dried over magnesium sulphate. The solvent was evaporated under reduced pressure and the residue was dried under high vacuum. The compound was used without further purification in the next step of the synthesis.

Intermediate L40

N-[31-(2,5-Dioxo-2,5-dihydro-1H-pyrrol-1-yl)-29-oxo-4,7,10,13,16,19,22,25-octaoxa-28-azahentria-contan-1-oyl]-L-valyl-N6-(tert-butoxycarbonyl)-L-lysine

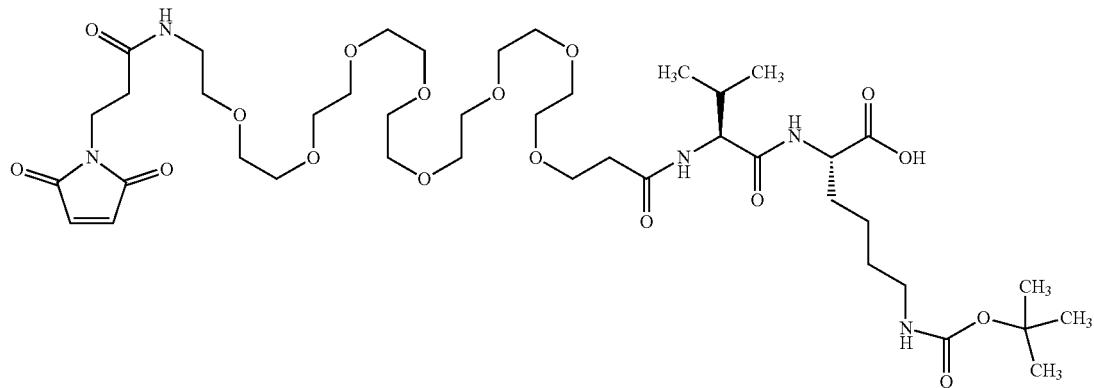 [SMILES: CC(C)[C@H](NC(=O)CCOCCOCCOCCOCCOCCOCCOCCOCCNC(=O)CCN1C(=O)C=CC1=O)C(=O)N[C@@H](CCCCNC(=O)OC(C)(C)C)C(=O)O]

600 mg (1.58 mmol) of N2-[(benzyloxy)carbonyl]-N6-(tert-butoxycarbonyl)-L-lysine were hydrogenated in 25.0 ml of water/ethanol/THF (1:1:0.5) using palladium on carbon (10%) at RT under standard pressure with hydrogen. The compound N6-(tert-butoxycarbonyl)-L-lysine is used without further purification in the next step of the synthesis.

LC-MS (Method 1): $R_t$=0.99 min; MS (ESIpos): m/z=247 [M+H]$^+$.

180.0 mg (0.73 mmol) of N6-(tert-butoxycarbonyl)-L-lysine were dissolved in 5.0 ml of DMF, and 74.0 mg (0.73 mmol) of triethylamine were added. 254.6 mg (0.73 mmol) of 2,5-dioxopyrrolidin-1-yl N-[(benzyloxy)carbonyl]-L-valinate and 74.0 mg (0.73 mmol) of triethylamine were added. The reaction mixture was stirred at RT for 3.5 h. The reaction mixture was purified directly by preparative RP-HPLC (column: Reprosil 250×30; 10µ, flow rate: 50 ml/min, MeCN/water, 0.1% TFA). The solvents were evaporated under reduced pressure and the residue was dried under high vacuum. This gave 294.1 mg (76% of theory) of the compound N-[(benzyloxy)carbonyl]-L-valyl-N6-(tert-butoxycarbonyl)-L-lysine.

LC-MS (Method 1): $R_t$=0.97 min; MS (ESIpos): m/z=480 [M+H]$^+$.

272.2 mg (0.57 mmol) of N-[(benzyloxy)carbonyl]-L-valyl-N6-(tert-butoxycarbonyl)-L-lysine were dissolved in 20 ml of ethyl acetate/ethanol/THF (1:1:1), 27.2 mg of palladium on activated carbon were added and the mixture was hydrogenated under standard pressure and at RT with hydrogen. The mixture was filtered through Celite® and the filter cake was washed thoroughly with ethyl acetate/ethanol/THF (1:1:1). The solvents were evaporated under reduced pressure and the residue was dried under high vacuum. This gave 182.0 mg (72% of theory) of the compound L-valyl-N6-(tert-butoxycarbonyl)-L-lysine.

LC-MS (Method 1): $R_t$=0.53 min; MS (ESIpos): m/z=346 [M+H]$^+$.

30.0 mg (0.07 mmol) of L-valyl-N6-(tert-butoxycarbonyl)-L-lysine and 46.1 mg (0.07 mmol) of 3-(2,5-dioxo-2,5-dihydro-1H-pyrrol-1-yl)-N-{27-[(2,5-dioxopyrrolidin-1-yl)oxy]-27-oxo-3,6,9,12,15,18,21,24-octaoxaheptacos-1-yl}propanamide were dissolved in 1.5 ml of DMF, and 6.8 mg (0.07 mmol) of 4-methylmorpholine were added. The reaction mixture was stirred at RT overnight. The reaction mixture was purified directly by preparative RP-HPLC (column: Reprosil 250×30; 10µ, flow rate: 50 ml/min, MeCN/water). The solvents were evaporated under reduced pressure and the residue was dried under high vacuum. This gave 55.6 mg (90% of theory) of the title compound.

LC-MS (Method 1): $R_t$=0.77 min; MS (ESIpos): m/z=920 [M+H]$^+$.

Intermediate L41

N-[19-(2,5-Dioxo-2,5-dihydro-1H-pyrrol-1-yl)-17-oxo-4,7,10,13-tetraoxa-16-azanonadecan-1-oyl]-L-valyl-N6-(tert-butoxycarbonyl)-L-lysine

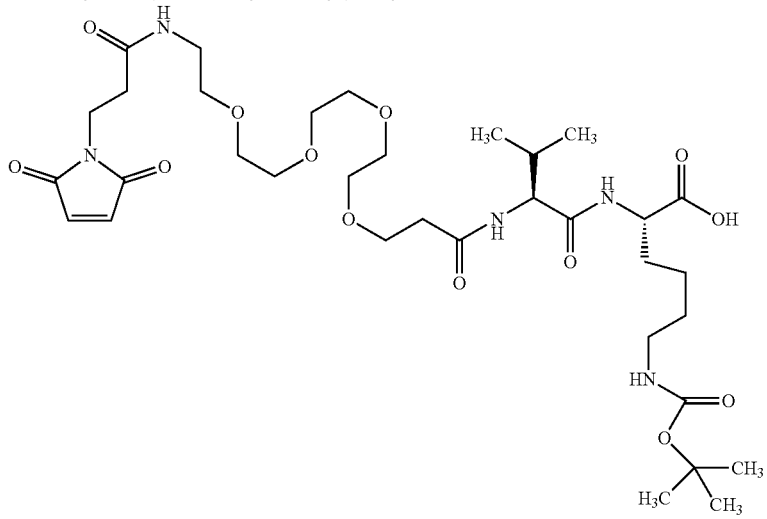 [SMILES: CC(C)[C@H](NC(=O)CCOCCOCCOCCOCCNC(=O)CCN1C(=O)C=CC1=O)C(=O)N[C@@H](CCCCNC(=O)OC(C)(C)C)C(=O)O]

600 mg (1.58 mmol) of N2-[(benzyloxy)carbonyl]-N6-(tert-butoxycarbonyl)-L-lysine were hydrogenated in 25.0 ml of water/ethanol/THF (1:1:0.5) using palladium on carbon (10%) at RT under standard pressure with hydrogen. The compound N6-(tert-butoxycarbonyl)-L-lysine is used without further purification in the next step of the synthesis.

LC-MS (Method 1): $R_t$=0.99 min; MS (ESIpos): m/z=247 [M+H]$^+$.

180.0 mg (0.73 mmol) of N6-(tert-butoxycarbonyl)-L-lysine were dissolved in 5.0 ml of DMF, and 74.0 mg (0.73 mmol) of triethylamine were added. 254.6 mg (0.73 mmol) of 2,5-dioxopyrrolidin-1-yl N-[(benzyloxy)carbonyl]-L-valinate and 74.0 mg (0.73 mmol) of triethylamine were added. The reaction mixture was stirred at RT for 3.5 h. The reaction mixture was purified directly by preparative RP-HPLC (column: Reprosil 250×30; 10μ, flow rate: 50 ml/min, MeCN/water, 0.1% TFA). The solvents were then evaporated under reduced pressure and the residue was dried under high vacuum. This gave 294.1 mg (76% of theory) of the compound N-[(benzyloxy)carbonyl]-L-valyl-N6-(tert-butoxycarbonyl)-L-lysine.

LC-MS (Method 1): $R_t$=0.97 min; MS (ESIpos): m/z=480 [M+H]$^+$.

272.2 mg (0.57 mmol) of N-[(benzyloxy)carbonyl]-L-valyl-N6-(tert-butoxycarbonyl)-L-lysine were dissolved in 20.0 ml of ethyl acetate/ethanol/THF (1:1:1), 27.2 mg of palladium on activated carbon were added and the mixture was hydrogenated under standard pressure and at RT with hydrogen. The mixture was filtered through Celite® and the filter cake was washed thoroughly with ethyl acetate/ethanol/THF (1:1:1). The solvents were evaporated under reduced pressure and the residue was dried under high vacuum. This gave 182.0 mg (72% of theory) of the compound L-valyl-N6-(tert-butoxycarbonyl)-L-lysine.

LC-MS (Method 1): $R_t$=0.53 min; MS (ESIpos): m/z=346 [M+H]$^+$.

30.0 mg (0.07 mmol) of L-valyl-N6-(tert-butoxycarbonyl)-L-lysine and 34.3 mg (0.07 mmol) of 3-(2,5-dioxo-2,5-dihydro-1H-pyrrol-1-yl)-N-{15-[(2,5-dioxopyrrolidin-1-yl)oxy]-15-oxo-3,6,9,12-tetraoxapentadec-1-yl}propanamide were dissolved in 1.5 ml of DMF, and 6.8 mg (0.07 mmol) of 4-methylmorpholine were added. The reaction mixture was stirred at RT overnight. The reaction mixture was purified directly by preparative RP-HPLC (column: Reprosil 250×30; 10μ, flow rate: 50 ml/min, MeCN/water). The solvents were evaporated under reduced pressure and the residue was dried under high vacuum. This gave 40.6 mg (82% of theory) of the title compound. LC-MS (Method 1): $R_t$=0.73 min; MS (ESIpos): m/z=744 [M+H]$^+$.

Intermediate L42

N-[19-(2,5-Dioxo-2,5-dihydro-1H-pyrrol-1-yl)-17-oxo-4,7,10,13-tetraoxa-16-azanonadecan-1-oyl]-L-valyl-N5-carbamoyl-L-ornithine

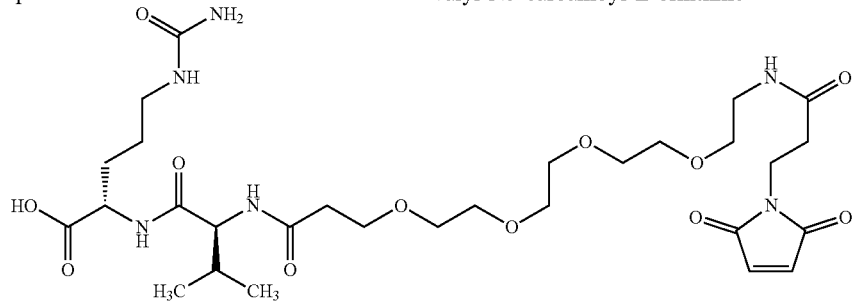

50.0 mg (0.18 mmol) of L-valyl-N5-carbamoyl-L-ornithine (Intermediate L37) were initially charged in DMF, and 93.6 mg (0.18 mmol) of 3-(2,5-dioxo-2,5-dihydro-1H-pyrrol-1-yl)-N-{15-[(2,5-dioxopyrrolidin-1-yl)oxy]-15-oxo-3,6,9,12-tetraoxapentadec-1-yl}propanamide and 36.9 mg (0.37 mmol) of triethylamine were added. The reaction mixture was stirred at RT overnight. 21.9 mg (0.37 mmol) of HOAc were added and the reaction mixture was purified directly by preparative RP-HPLC (column: Reprosil 250× 30; 10μ, flow rate: 50 ml/min, MeCN/water). The solvents were evaporated under reduced pressure and the residue was dried under high vacuum. This gave 20.6 mg (14% of theory) of the title compound.

LC-MS (Method 1): $R_t$=0.55 min; MS (ESIpos): m/z=673 [M+H]$^+$.

Intermediate L43

N-[67-(2,5-Dioxo-2,5-dihydro-1H-pyrrol-1-yl)-65-oxo-4,7,10,13,16,19,22,25,28,31,34,37,40,43,46,49,52,55,58,61-icosaoxa-64-azaheptahexacontan-1-oyl]-L-valyl-N5-carbamoyl-L-ornithine Intermediate L44

N-[19-(2,5-Dioxo-2,5-dihydro-1H-pyrrol-1-yl)-7-oxo-4,7,10,13-tetraoxa-16-azanonadecan-1-oyl]-L-valyl-L-alanine

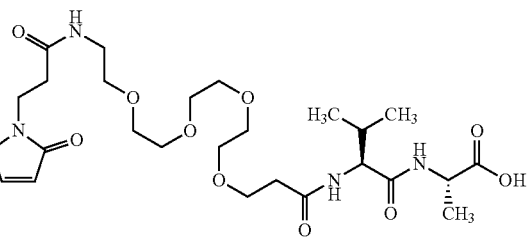

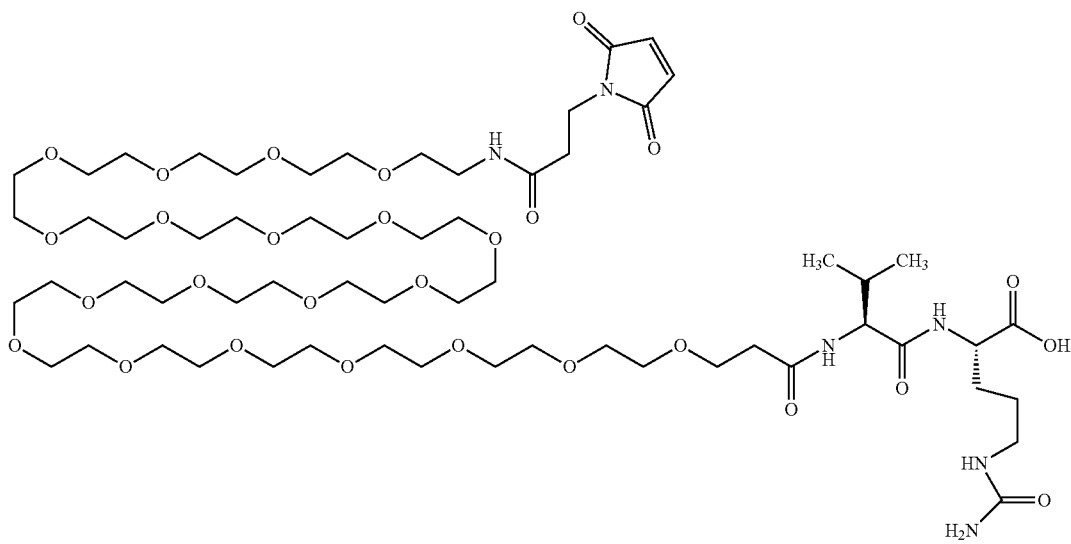 [SMILES: CC(C)[C@H](NC(=O)CCOCCOCCOCCOCCOCCOCCOCCOCCOCCOCCOCCOCCOCCOCCOCCOCCOCCOCCOCCOCCNC(=O)CCN1C(=O)C=CC1=O)C(=O)N[C@@H](CCCNC(N)=O)C(=O)O]

11.3 mg (0.04 mmol) of L-valyl-N5-carbamoyl-L-ornithine (Intermediate L37) were initially charged in DMF, and 50.0 mg (0.04 mmol) of 3-(2,5-dioxo-2,5-dihydro-1H-pyrrol-1-yl)-N-{63-[(2,5-dioxopyrrolidin-1-yl)oxy]-63-oxo-3,6,9,12,15,18,21,24,27,30,33,36,39,42,45,48,51,54,57,60-icosaoxatrihexacont-1-yl}propanamide and 8.3 mg (0.08 mmol) of triethylamine were added. The reaction mixture was stirred at RT overnight. 4.9 mg (0.08 mmol) of HOAc were added and the reaction mixture was purified directly by preparative RP-HPLC (column: Reprosil 250×30; 10μ, flow rate: 50 ml/min, MeCN/water). The solvents were evaporated under reduced pressure and the residue was dried under high vacuum. This gave 15.8 mg (20% of theory) of the title compound.

LC-MS (Method 4): $R_t$=0.94 min; MS (ESIpos): m/z=1377 [M+H]$^+$.

73.3 mg (0.39 mmol) of L-valyl-L-alanine were dissolved in 7.0 ml of DMF, and 200.0 mg (0.39 mmol) of 3-(2,5-dioxo-2,5-dihydro-1H-pyrrol-1-yl)-N-{15-[(2,5-dioxopyrrolidin-1-yl)oxy]-15-oxo-3,6,9,12-tetraoxapentadec-1-yl}propanamide and 78.8 mg (0.78 mmol) of triethylamine were added. The reaction mixture was stirred at RT overnight. The reaction mixture was purified directly by preparative RP-HPLC (column: Reprosil 250×30; 10μ, flow rate: 50 ml/min, MeCN/water). The solvents were evaporated under reduced pressure and the residue was dried under high vacuum. This gave 103.3 mg (45% of theory) of the title compound.

LC-MS (Method 1): $R_t$=0.58 min; MS (ESIpos): m/z=587 [M+H]$^+$.

Intermediate L45 tert-Butyl (2S)-2-[(tert-butoxycarbonyl)amino]-4-oxobutanoate

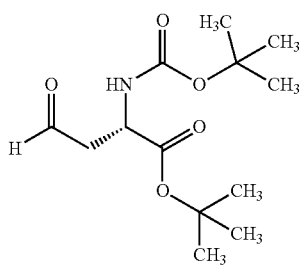 [SMILES: CC(C)(C)OC(=O)N[C@@H](CC=O)C(=O)OC(C)(C)C]

2.00 g (7.26 mmol) of tert-butyl N-(tert-butoxycarbonyl)-L-homoserinate were dissolved in 90 ml of dichloromethane, and 1.76 ml of pyridine and 4.62 g (10.90 mmol) of 1,1,1-triacetoxy-llambda5,2-benziodoxol-3(1H)-on (Dess-Martin periodinane) were then added. The reaction was stirred at RT for 2 h and then diluted with 200 ml of dichloromethane and extracted twice with 10% strength sodium thiosulphate solution and then successively twice with 5% strength citric acid and twice with saturated sodium bicarbonate solution. The organic phase was separated off, dried over sodium sulphate and then concentrated under reduced pressure. 100 ml of diethyl ether and cyclohexane (v/v=1:1) were added to the residue and the mixture was somewhat concentrated, resulting in the formation of a white precipitate. This was filtered off with suction. The filtrate was concentrated on a rotary evaporator and dried under high vacuum, giving 1.74 g (88% of theory) of the target compound as a light-yellow oil.

LC-MS (Method 1): $R_t$=0.85 min; MS (ESIpos): m/z=274 [M+H]$^+$.

$^1$H-NMR (400 MHz, DMSO-$d_6$): δ[ppm]=1.38 (s, 18H), 2.64-2.81 (m, 2H), 4.31-4.36 (m, 1H), 7.23 (d, 1H), 9.59 (s, 1H).

Intermediate L46

Trifluoroacetic acid/tert-butyl N-[2-(2,5-dioxo-2,5-dihydro-1H-pyrrol-1-yl)ethyl]-L-glutaminate (1:1)

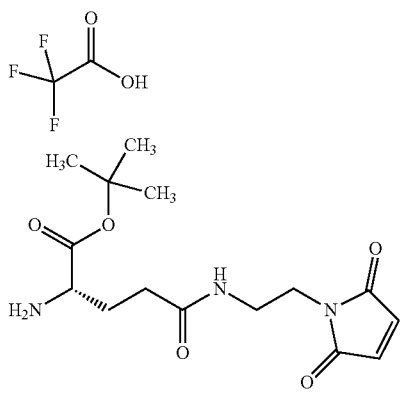

The title compound was prepared by first coupling 200 mg (0.79 mmol) of trifluoroacetic acid/1-(2-aminoethyl)-1H-pyrrole-2,5-dione (1:1) with 263 mg (0.87 mmol) of (4S)-5-tert-butoxy-4-[(tert-butoxycarbonyl)amino]-5-oxopentanoic acid/trifluoroacetic acid (1:1) in the presence of EDC/HOBT and N,N-diisopropylethylamine and then deprotecting the amino group under gentle conditions by stirring for 1 h in 10% strength trifluoroacetic acid in DCM at RT. Freeze-drying from acetonitrile/water gave 85 mg (20% of theory) of the title compound over 2 steps.

LC-MS (Method 1): $R_t$=0.37 min; MS (ESIpos): m/z=326 [M+H]$^+$.

Intermediate L47

Trifluoroacetic acid/beta-alanyl-L-alanyl-N5-carbamoyl-N-[4-(2,5-dioxo-2,5-dihydro-1H-pyrrol-1-yl)phenyl]-L-ornithinamide (1:1)

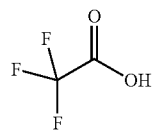

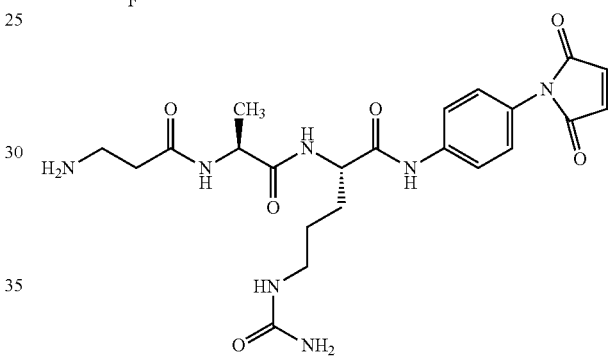

The title compound was prepared by coupling Intermediate L8 with 2,5-dioxopyrrolidin-1-yl N-(tert-butoxycarbonyl)-beta-alaninate and subsequent deprotection with TFA.

LC-MS (Method 3): $R_t$=1.36 min; MS (ESIpos): m/z=488 (M+H)$^+$.

Intermediate L48

Trifluoroacetic acid/(1R,2S)-2-amino-N-[2-(2,5-dioxo-2,5-dihydro-1H-pyrrol-1-yl)ethyl]cyclopentanecarboxamide (1:1)

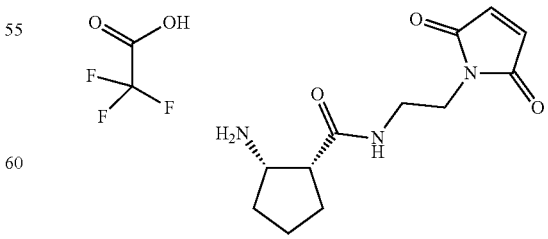

The title compound was prepared from commercially available (1R,2S)-2-[(tert-butoxycarbonyl)amino]cyclopentanecarboxylic acid analogously to Intermediate L2.

LC-MS (Method 3): $R_t$=1.22 min; MS (ESIpos): m/z=252 (M+H)$^+$.

Intermediate L49

Trifluoroacetic acid/tert-butyl N-(bromoacetyl)-L-valyl-L-alanyl-L-lysinate (1:1)

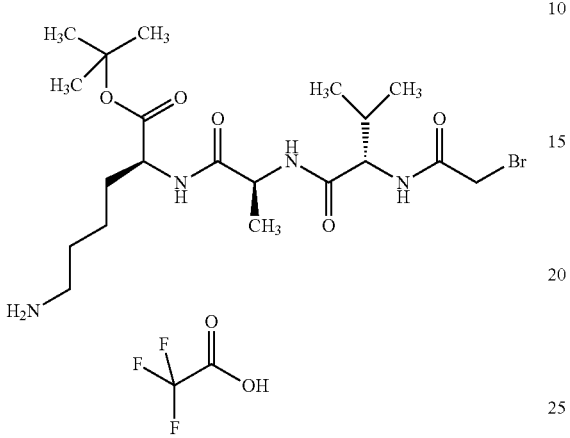

The title compound was prepared by first coupling commercially available bromoacetic anhydride with the partially protected peptide tert-butyl L-valyl-L-alanyl-N$^6$-(tert-butoxycarbonyl)-L-lysinate, prepared according to classical methods of peptide chemistry, in the presence of N,N-diisopropylethylamine in dichloromethane. This was followed by deprotection at the amino group under gentle conditions by stirring in 10% strength trifluoroacetic acid in DCM at RT, giving the title compound in 49% yield over 2 steps.

LC-MS (Method 1): $R_t$=1.09 min; MS (ESIpos): m/z=593 and 595 (M+H)$^+$.

Intermediate L50

Trifluoroacetic acid/(1S,3R)-3-amino-N-[2-(2,5-dioxo-2,5-dihydro-1H-pyrrol-1-yl)ethyl]cyclopentanecarboxamide (1:1)

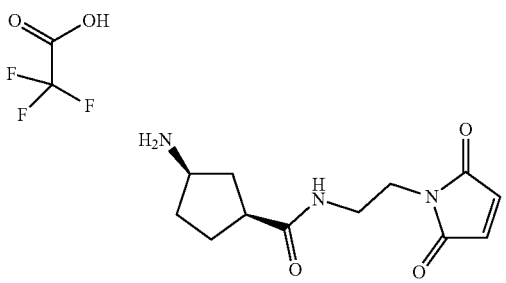 [SMILES: O=C(O)C(F)(F)F ; N[C@@H]1CC[C@H](C(=O)NCCN2C(=O)C=CC2=O)C1]

The title compound was prepared from commercially available (1S,3R)-3-[(tert-butoxycarbonyl)amino]cyclopentanecarboxylic acid and likewise commercially available trifluoroacetic acid/1-(2-aminoethyl)-1H-pyrrole-2,5-dione (1:1) by coupling with HATU in the presence of N,N-diisopropylethylamine and subsequent deprotection with TFA.

HPLC (Method 11): $R_t$=0.2 min;

LC-MS (Method 3): $R_t$=0.88 min; MS (ESIpos): m/z=252 (M+H)$^+$.

Intermediate L51

Trifluoroacetic acid/(1R,3R)-3-amino-N-[2-(2,5-dioxo-2,5-dihydro-1H-pyrrol-1-yl)ethyl]cyclopentanecarboxamide (1:1)

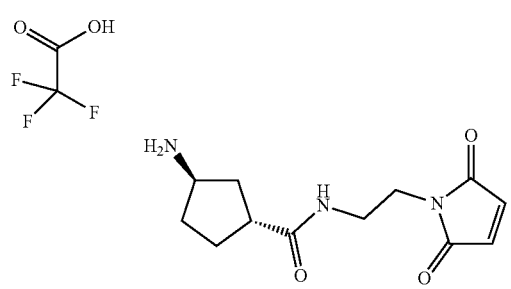 [SMILES: O=C(O)C(F)(F)F ; N[C@@H]1CC[C@@H](C(=O)NCCN2C(=O)C=CC2=O)C1]

The title compound was prepared from commercially available (1R,3R)-3-[(tert-butoxycarbonyl)amino]cyclopentanecarboxylic acid and likewise commercially available trifluoroacetic acid/1-(2-aminoethyl)-1H-pyrrole-2,5-dione (1:1) by coupling with HATU in the presence of N,N-diisopropylethylamine and subsequent deprotection with TFA.

LC-MS (Method 3): $R_t$=0.98 min; MS (ESIpos): m/z=250 (M−H)$^-$.

Intermediate L52

Trifluoroacetic acid/N-(2-aminoethyl)-2-bromoacetamide (1:1)

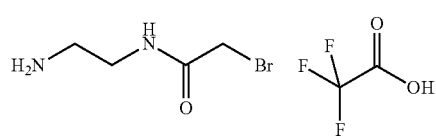

420 mg (2.62 mmol) of tert-butyl (2-aminoethyl)carbamate were taken up in 50 ml of dichloromethane, and 817 mg (3.15 mmol) of bromoacetic anhydride and 913 µl (5.24 mmol) of N,N-diisopropylethylamine were added. The reaction was stirred at RT for 1 h and then concentrated under reduced pressure. The residue was purified by preparative HPLC.

This gave 577 mg of the protected intermediate which were then taken up in 50 ml of dichloromethane, and 10 ml of trifluoroacetic acid were added. After 1 h of stirring at RT, the reaction was concentrated under reduced pressure and the residue was lyophilized from acetonitrile/water. This gave 705 mg (65% of theory) of the title compound.

LC-MS (Method 3): $R_t$=0.34 min; MS (ESIpos): m/z=181 and 183 (M+H)$^+$.

319

Intermediate L53

Trifluoroacetic acid/(1S,3S)-3-amino-N-[2-(2,5-dioxo-2,5-dihydro-1H-pyrrol-1-yl)ethyl]cyclopentanecarboxamide (1:1)

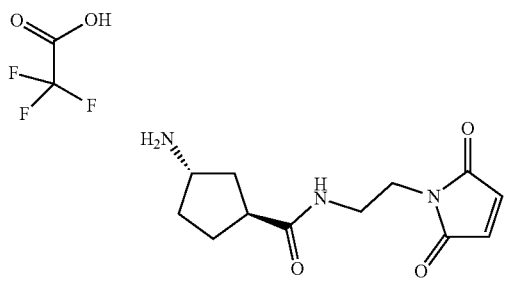 [SMILES: O=C(O)C(F)(F)F ; N[C@H]1CC[C@H](C(=O)NCCN2C(=O)C=CC2=O)C1]

The title compound was prepared from commercially available (1S,3S)-3-[(tert-butoxycarbonyl)amino]cyclopentanecarboxylic acid and likewise commercially available trifluoroacetic acid/1-(2-aminoethyl)-1H-pyrrole-2,5-dione (1:1) by coupling with HATU in the presence of N,N-diisopropylethylamine and subsequent deprotection with TFA.

HPLC (Method 11): $R_t$=0.19 min;

LC-MS (Method 3): $R_t$=0.88 min; MS (ESIpos): m/z=250 (M−H)⁻.

320

Intermediate L54

Trifluoroacetic acid/(1R,3S)-3-amino-N-[2-(2,5-dioxo-2,5-dihydro-1H-pyrrol-1-yl)ethyl]cyclopentanecarboxamide (1:1)

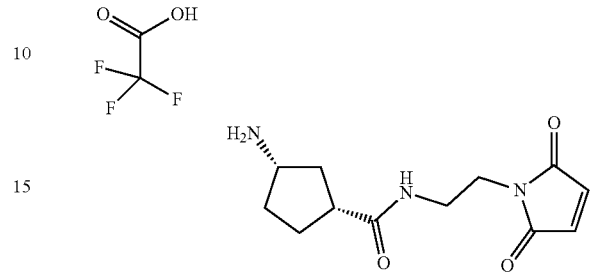

The title compound was prepared from commercially available (1R,3S)-3-[(tert-butoxycarbonyl)amino]cyclopentanecarboxylic acid and likewise commercially available trifluoroacetic acid/1-(2-aminoethyl)-1H-pyrrole-2,5-dione (1:1) by coupling with HATU in the presence of N,N-diisopropylethylamine and subsequent deprotection with TFA.

LC-MS (Method 3): $R_t$=0.89 min; MS (ESIpos): m/z=252 (M+H)⁺.

Intermediate L55

Trifluoroacetic acid/tert-butyl-N6-D-alanyl-N2-{N-[6-(2,5-dioxo-2,5-dihydro-1H-pyrrol-1-yl)-hexanoyl]-L-valyl-L-alanyl}-L-lysinate (1:1)

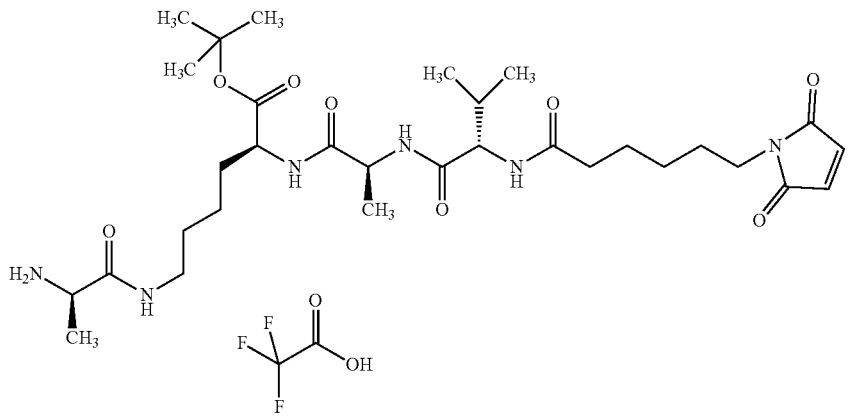 [SMILES: CC(C)[C@H](NC(=O)CCCCCN1C(=O)C=CC1=O)C(=O)N[C@@H](C)C(=O)N[C@@H](CCCCNC(=O)[C@@H](C)N)C(=O)OC(C)(C)C ; O=C(O)C(F)(F)F]

The title compound was prepared by first coupling Intermediate L6 with N-(tert-butoxycarbonyl)-D-alanine in the presence of HATU, followed by deprotection at the amino group under gentle conditions by stirring for 90 minutes in 5% strength trifluoroacetic acid in DCM at RT.

HPLC (Method 11): $R_t$=1.35 min;

LC-MS (Method 1): $R_t$=0.67 min; MS (ESIpos): m/z=637 (M+H)⁺.

Intermediate L56

Trifluoroacetic acid/tert-butyl-N-[6-(2,5-dioxo-2,5-dihydro-1H-pyrrol-1-yl)hexanoyl]-L-valyl-L-alanyl-N6-{[(1R,3S)-3-aminocyclopentyl]carbonyl}-L-lysinate (1:1)

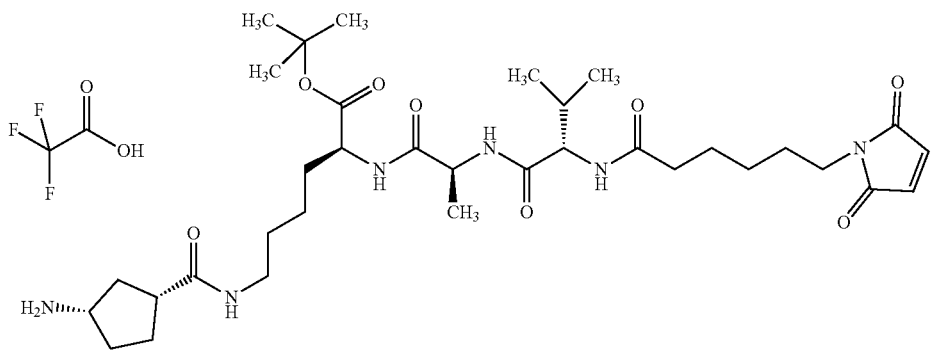 [SMILES: O=C(O)C(F)(F)F ; CC(C)[C@H](NC(=O)CCCCCN1C(=O)C=CC1=O)C(=O)N[C@@H](C)C(=O)N[C@@H](CCCCNC(=O)[C@@H]1CC[C@H](N)C1)C(=O)OC(C)(C)C]

The title compound was prepared by first coupling Intermediate L6 with (1R,3S)-3-[(tert-butoxycarbonyl)amino]cyclopentanecarboxylic acid in the presence of HATU, followed by deprotection at the amino group under gentle conditions by stirring for 15 minutes in 25% strength trifluoroacetic acid in DCM at RT.

HPLC (Method 11): $R_t$=1.4 min;

LC-MS (Method 1): $R_t$=0.7 min; MS (ESIpos): m/z=677 (M+H)$^+$.

Intermediate L57

Methyl (2S)-4-oxo-2-({[2-(trimethylsilyl)ethoxy]carbonyl}amino)butanoate

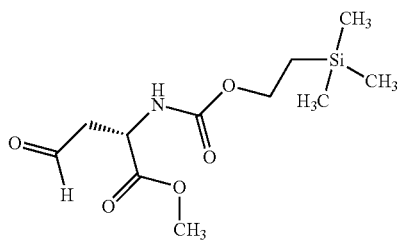 [SMILES: COC(=O)[C@H](CC=O)NC(=O)OCC[Si](C)(C)C]

500.0 mg (2.72 mmol) of methyl L-asparaginate hydrochloride and 706.3 mg (2.72 mmol) of 2-(trimethylsilyl)ethyl 2,5-dioxopyrrolidine-1-carboxylate were initially charged in 5.0 ml of 1,4-dioxane, and 826.8 mg (8.17 mmol) of triethylamine were added. The reaction mixture was stirred at RT overnight. The reaction mixture was purified directly by preparative RP-HPLC (column: Reprosil 250× 40; 10μ, flow rate: 50 ml/min, MeCN/water, 0.1% TFA). The solvents were then evaporated under reduced pressure and the residue was dried under high vacuum. This gave 583.9 mg (74% of theory) of the compound (3S)-4-methoxy-4-oxo-3-({[2-(trimethylsilyl)ethoxy]carbonyl}amino)butanoic acid.

LC-MS (Method 1): $R_t$=0.89 min; MS (ESIneg): m/z=290 (M−H)$^−$.

592.9 mg of (3S)-4-methoxy-4-oxo-3-({[2-(trimethylsilyl)ethoxy]carbonyl}amino)butanoic acid were initially charged in 10.0 ml of 1,2-dimethoxyethane, the mixture was cooled to −15° C. and 205.8 mg (2.04 mmol) of 4-methylmorpholine and 277.9 mg (2.04 mmol) of isobutyl chloroformate were added. The precipitate was filtered off with suction after 15 min and twice with in each case 10.0 ml of 1,2-dimethoxyethane. The filtrate was cooled to −10° C., and 115.5 mg (3.05 mmol) of sodium borohydride dissolved in 10 ml of water were added with vigorous stirring. The phases were separated and the organic phase was washed in each case once with saturated sodium bicarbonate solution and saturated NaCl solution. The organic phase was dried over magnesium sulphate, the solvent was evaporated under reduced pressure and the residue was dried under high vacuum. This gave 515.9 mg (91% of theory) of the compound methyl N-{[2-(trimethylsilyl)ethoxy]carbonyl}-L-homoserinate.

LC-MS (Method 1): $R_t$=0.87 min; MS (ESIpos): m/z=278 (M+H)$^+$.

554.9 mg (2.00 mmol) of methyl N-{[2-(trimethylsilyl)ethoxy]carbonyl}-L-homoserinate were initially charged in 30.0 ml of dichloromethane, and 1.27 g (3.0 mmol) of Dess-Martin periodinane and 474.7 mg (6.00 mmol) of pyridine were added. The mixture was stirred at RT overnight. After 4 h, the reaction was diluted with dichloromethane and the organic phase was washed in each case three times with 10% strength Na$_2$S$_2$O$_3$ solution, 10% strength citric acid solution and saturated sodium bicarbonate solution. The organic phase was dried over magnesium sulphate and the solvent was evaporated under reduced pressure. This gave 565.7 mg (97% of theory) of the title compound.

$^1$H-NMR (400 MHz, DMSO-d$_6$): δ[ppm]=0.03 (s, 9H), 0.91 (m, 2H), 2.70-2.79 (m, 1H), 2.88 (dd, 1H), 3.63 (s, 3H), 4.04 (m, 2H), 4.55 (m, 1H), 7.54 (d, 1H), 9.60 (t, 1H).

Intermediate L58

2-(Trimethylsilyl)ethyl (3-oxopropyl)carbamate

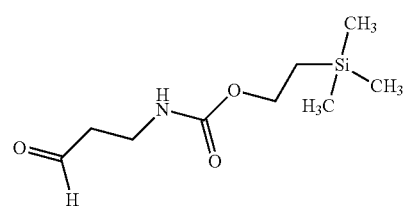

434.4 mg (5.78 mmol) of 3-amino-1-propanol and 1.50 g (5.78 mmol) of 2-(trimethylsilyl)ethyl 2,5-dioxopyrrolidine-1-carboxylate were dissolved in 10.0 ml of dichloromethane, 585.3 mg (5.78 mmol) of triethylamine were added and the mixture was stirred at RT overnight. The reaction mixture was diluted with dichloromethane and the organic phase was washed with water and saturated sodium bicarbonate solution and then dried over magnesium sulphate. The solvent was evaporated under reduced pressure. The residue 2-(trimethylsilyl)ethyl (3-hydroxypropyl)carbamate (996.4 mg, 79% of theory) was dried under high vacuum and used without further purification in the next step of the synthesis. 807.0 mg (3.68 mmol) of 2-(trimethylsilyl)ethyl (3-hydroxypropyl)carbamate were initially charged in 15.0 ml of chloroform and 15.0 ml of 0.05 N potassium carbonate/0.05 N sodium bicarbonate solution (1:1). 102.2 mg (0.37 mmol) of tetra-n-butylammonium chloride, 736.9 mg (5.52 mmol) of N-chlorosuccinimide and 57.5 mg (0.37 mmol) of TEMPO were then added and the reaction mixture was stirred vigorously at RT overnight. The reaction mixture was diluted with dichloromethane and the organic phase was washed with water and saturated NaCl solution. The organic phase was dried over magnesium sulphate and the solvent was evaporated under reduced pressure. The residue was dried under high vacuum and used without further purification in the next step of the synthesis (890.3 mg).

Intermediate L59

Trifluoroacetic acid/1-{2-[2-(2-aminoethoxy)ethoxy]ethyl}-1H-pyrrole-2,5-dione (1:1)

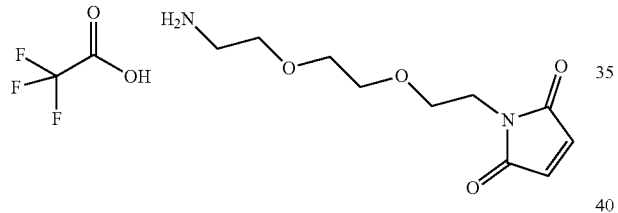

300.0 mg (0.91 mmol) of tert-butyl (2-{2-[2-(2,5-dioxo-2,5-dihydro-1H-pyrrol-1-yl)ethoxy]ethoxy}ethyl)carbamate were initially charged in dichloromethane, 4.2 g (36.54 mmol) of TFA were added and the mixture was stirred at RT for 1 h (monitored by TLC: dichloromethane/methanol 10:1). The volatile components were evaporated under reduced pressure and the residue was co-distilled four times with dichloromethane. The residue was dried under high vacuum and used without further purification in the next step of the synthesis.

LC-MS (Method 1): $R_t$=0.19 min; MS (ESIpos): m/z=229 (M+H)$^+$.

Intermediate L60

6-(2,5-Dioxo-2,5-dihydro-1H-pyrrol-1-yl)hexanoyl chloride

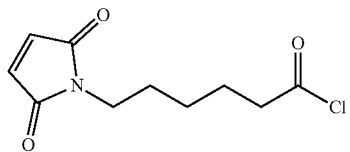 [SMILES: O=C(Cl)CCCCCN1C(=O)C=CC1=O]

200.0 mg (0.95 mmol) of 6-(2,5-dioxo-2,5-dihydro-1H-pyrrol-1-yl)hexanoic acid were dissolved in 4.0 ml of dichloromethane, and 338.0 mg (2.84 mmol) of thionyl chloride were added. The reaction mixture was stirred at RT for 3 h, and 1 drop of DMF was then added. The mixture was stirred for another 1 h. The solvent was evaporated under reduced pressure and the residue was co-distilled three times with dichloromethane. The crude product was used without further purification in the next step of the synthesis.

Intermediate L61

Trifluoroacetic acid/2-(trimethylsilyl)ethyl N-[6-(2,5-dioxo-2,5-dihydro-1H-pyrrol-1-yl)hexanoyl]-L-valyl-L-alanyl-L-lysinate (1:1)

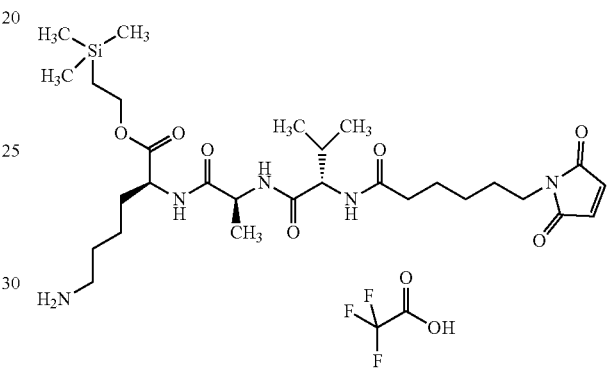

First, the tripeptide derivative 2-(trimethylsilyl)ethyl L-valyl-L-alanyl-N6-(tert-butoxycarbonyl)-L-lysinate was prepared from N2-[(benzyloxy)carbonyl]-N6-(tert-butoxycarbonyl)-L-lysine according to classical methods of peptide chemistry (esterification with 2-(trimethylsilylethanol using EDCI/DMAP, hydrogenolysis, coupling with N-[(benzyloxy)carbonyl]-L-valyl-L-alanine in the presence of HATU and another hydrogenolysis). The title compound was prepared by coupling this partially protected peptide derivative with commercially available 6-(2,5-dioxo-2,5-dihydro-1H-pyrrol-1-yl)hexanoic acid in the presence of HATU and N,N-diisopropylethylamine. This was followed by deprotection at the amino group under gentle conditions by stirring for 2.5 hours in 5% strength trifluoroacetic acid in DCM at RT with retention of the ester protective group. Work-up and purification by preparative HPLC gave 438 mg of the title compound.

HPLC (Method 11): $R_t$=1.69 min;

LC-MS (Method 1): $R_t$=0.78 min; MS (ESIpos): m/z=610 (M+H)$^+$.

Intermediate L62

Trifluoroacetic acid/2-(trimethylsilyl)ethyl N-[6-(2,5-dioxo-2,5-dihydro-1H-pyrrol-1-yl)hexanoyl]-L-valyl-N5-carbamoyl-L-ornithyl-L-lysinate (1:1)

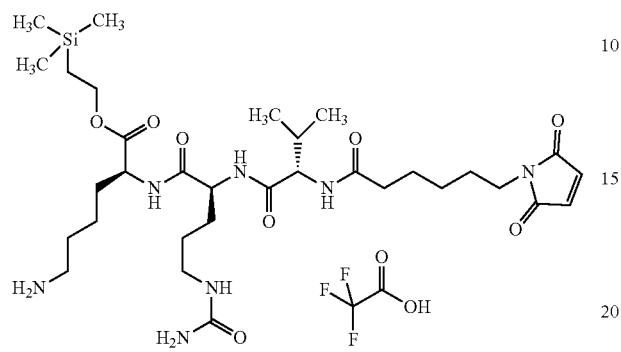

First, 2-(trimethylsilyl)ethyl N6-(tert-butoxycarbonyl)-L-lysinate was prepared from N2-[(benzyloxy)carbonyl]-N6-(tert-butoxycarbonyl)-L-lysine according to classical methods of peptide chemistry. 148 mg (0.43 mmol) of this intermediate were then coupled in the presence of 195 mg (0.51 mmol) of HATU and 149 µl of N,N-diisopropylethylamine with 200 mg (0.43 mmol) of Intermediate L16. After concentration and purification of the residue by preparative HPLC, the protected intermediate was taken up in 20 ml of DCM and the tert-butoxycarbonyl protective group was removed by addition of 2 ml of trifluoroacetic acid and 1 h of stirring at RT. Concentration and lyophilization of the residue from acetonitrile/water gave 254 mg (63% of theory over 2 steps).

HPLC (Method 11): $R_t$=1.51 min;

LC-MS (Method 1): $R_t$=0.68 min; MS (ESIpos): m/z=696 (M+H)$^+$.

Intermediate L63

(4S)-4-{[(2S)-2-{[(2S)-2-{[6-(2,5-Dioxo-2,5-dihydro-1H-pyrrol-1-yl)hexanoyl]amino}-3-methylbutanoyl]amino}propanoyl]amino}-5-oxo-5-[2-(trimethylsilyl)ethoxy]pentanoic acid

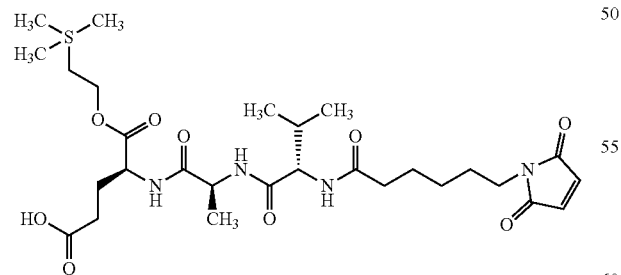

First, the tripeptide derivative (4S)-4-{[(2S)-2-{[(2S)-2-amino-3-methylbutanoyl]amino}propanoyl]amino}-5-oxo-5-[2-(trimethylsilyl)ethoxy]pentanoic acid was prepared from (2S)-5-(benzyloxy)-2-[(tert-butoxycarbonyl)amino]-5-oxopentanoic acid according to classical methods of peptide chemistry (esterification with 2-(trimethylsilylethanol using EDCI/DMAP, removal of the Boc protective group with trifluoroacetic acid, coupling with N-[(benzyloxy)carbonyl]-L-valyl-L-alanine in the presence of HATU and hydrogenolysis in methanol over 10% palladium on activated carbon). The title compound was prepared by coupling of this partially protected peptide derivative with commercially available 1-{6-[(2,5-dioxopyrrolidin-1-yl)oxy]-6-oxohexyl}-1H-pyrrole-2,5-dione. Work-up and purification by preparative HPLC gave 601 mg of the title compound.

LC-MS (Method 1): $R_t$=0.96 min; MS (ESIpos): m/z=611 (M+H)$^+$.

Intermediate L64

(4S)-4-{[(2,5-Dioxo-2,5-dihydro-1H-pyrrol-1-yl)acetyl]amino}-5-oxo-5-[2-(trimethylsilyl)ethoxy]pentanoic acid

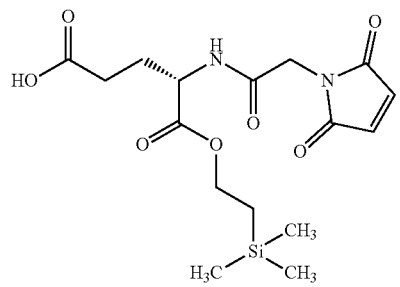 [SMILES: C[Si](C)(C)CCOC(=O)[C@H](CCC(=O)O)NC(=O)CN1C(=O)C=CC1=O]

The title compound was prepared from (2S)-5-(benzyloxy)-2-[(tert-butoxycarbonyl)amino]-5-oxopentanoic acid according to classical methods of peptide chemistry (esterification with 2-(trimethylsilylethanol using EDCI/DMAP, removal of the Boc protective group with trifluoroacetic acid, hydrogenolytic cleavage of the benzyl ester in methanol over 10% palladium on activated carbon and coupling with 1-{2-[(2,5-dioxopyrrolidin-1-yl)oxy]-2-oxoethyl}-1H-pyrrole-2,5-dione in the presence of N,N-diisopropylethylamine).

LC-MS (Method 1): $R_t$=0.84 min; MS (ESIpos): m/z=385 (M+H)$^+$.

Intermediate L65

Trifluoroacetic acid/2-(trimethylsilyl)ethyl 3-{[(benzyloxy)carbonyl]amino}-L-alaninate (1:1)

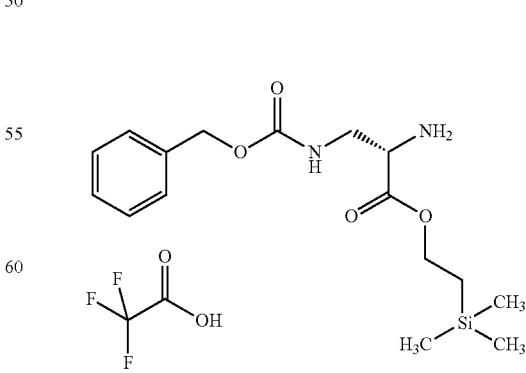

The title compound was prepared from 3-{[(benzyloxy)carbonyl]amino}-N-(tert-butoxycarbonyl)-L-alanine according to classical methods of peptide chemistry (esterification with 2-(trimethylsilylethanol using EDCI/DMAP and removal of the Boc protective group with trifluoroacetic acid. This gave 373 mg (79% of theory over 2 steps) of the title compound.

LC-MS (Method 1): $R_t$=0.72 min; MS (ESIpos): m/z=339 (M+H)$^+$.

Intermediate L66

Methyl (8S)-8-(2-hydroxyethyl)-2,2-dimethyl-6,11-dioxo-5-oxa-7,10-diaza-2-silatetradecan-14-oate

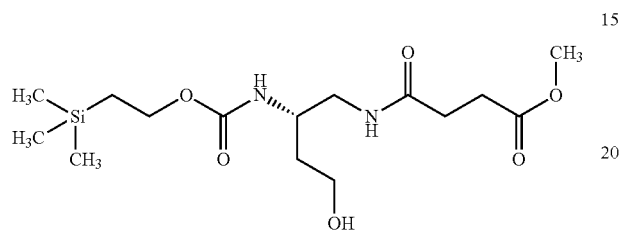

1000 mg (2.84 mmol) of (3S)-3-{[(benzyloxy)carbonyl]amino}-4-[(tert-butoxycarbonyl)amino]butanoic acid were initially charged in 10.0 ml of 1,2-dimethoxyethane, and 344.4 mg (3.4 mmol) of 4-methylmorpholine and 504 mg (3.69 mmol) of isobutyl chloroformate were added. After 10 min of stirring at RT, the reaction was cooled to 5° C. and 161 mg (4.26 mmol) of sodium borohydride dissolved in 3 ml of water were added a little at a time with vigorous stirring. After 1 h, the same amount of sodium borohydride was added again and the reaction was then slowly warmed to RT. 170 ml of water were added and the reaction was then extracted four times with in each case 200 ml of ethyl acetate. The phases were separated and the organic phase was washed once with citric acid and then with saturated sodium bicarbonate solution. The organic phase was dried over magnesium sulphate, the solvent was evaporated under reduced pressure and the residue was dried under high vacuum. This gave 760 mg (78% of theory) of the compound benzyl tert-butyl [(2S)-4-hydroxybutane-1,2-diyl]biscarbamate.

LC-MS (Method 1): $R_t$=0.84 min; MS (ESIpos): m/z=339 (M+H)$^+$.

760 mg (2.16 mmol) of this intermediate dissolved in 13 ml of hydrogen chloride/dioxane were stirred at RT for 20 min. The reaction was then concentrated to 5 ml, and diethyl ether was added. The precipitate was filtered off and lyophilized from acetonitrile/water 1:1.

The product obtained in this manner was dissolved in 132 ml of DMF, and 345.5 mg (2.35 mmol) of 4-methoxy-4-oxobutanoic acid, 970 mg (2.55 mmol) of HATU and 1025 µl of N,N-diisopropylethylamine were added. The mixture was stirred at RT for 5 min. The solvent was removed under reduced pressure and the residue that remained was purified by preparative HPLC. The appropriate fractions were combined and the acetonitrile was evaporated under reduced pressure. The aqueous phase that remained was extracted twice with ethyl acetate and the organic phase was then concentrated and dried under high vacuum.

The intermediate obtained in this manner was taken up in methanol and hydrogenated over 10% palladium on activated carbon at RT under hydrogen standard pressure for 1 h. The catalyst was then filtered off and the solvent was removed under reduced pressure.

247 mg of this deprotected compound were taken up in 20 ml of DMF, and 352 mg (1.36 mmol) of 1-({[2-(trimethylsilyl)ethoxy]carbonyl}oxy)pyrrolidine-2,5-dione and 592 µl of N,N-diisopropylethylamine were added. The reaction mixture was stirred at RT for 1 h and then concentrated, and the residue was purified by preparative HPLC. The solvents were then evaporated under reduced pressure and the residue was dried under high vacuum. This gave, over these 5 reaction steps, 218 mg of the title compound in a total yield of 21%.

LC-MS (Method 1): $R_t$=0.74 min; MS (ESIpos): m/z=363 (M+H)$^+$.

Intermediate L67

Trifluoroacetic acid/2-(2,5-dioxo-2,5-dihydro-1H-pyrrol-1-yl)ethyl-beta-alaninate (1:1)

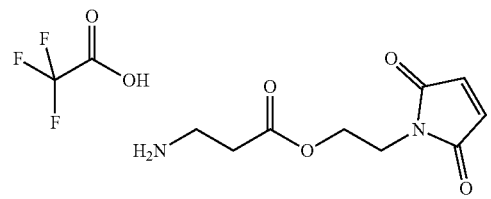 [SMILES: O=C(O)C(F)(F)F ; NCCC(=O)OCCN1C(=O)C=CC1=O]

The title compound was prepared from 50 mg (0.354 mmol) of commercially available 1-(2-hydroxyethyl)-1H-pyrrole-2,5-dione by coupling with 134 mg (0.71 mmol) of N-(tert-butoxycarbonyl)-beta-alanine in 10 ml of dichloromethane in the presence of 1.5 equivalents of EDCI and 0.1 equivalent of 4-N,N-dimethylaminopyridine and subsequent deprotection with trifluoroacetic acid.

Yield: 56 mg (48% of theory over 2 steps)

LC-MS (Method 3): $R_t$=1.15 min; MS (ESIpos): m/z=213 (M+H)$^+$.

Intermediate L68

Trifluoroacetic acid/N-(2-aminoethyl)-2-(2,5-dioxo-2,5-dihydro-1H-pyrrol-1-yl)propanamide (1:1)

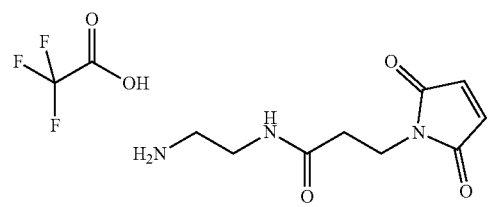 [SMILES: O=C(O)C(F)(F)F ; NCCNC(=O)CCN1C(=O)C=CC1=O]

The title compound was prepared analogously to Intermediate L1 according to classical methods of peptide chemistry from commercially available (2,5-dioxo-2,5-dihydro-1H-pyrrol-1-yl)propanoic acid and tert-butyl (2-aminoethyl)carbamate.

LC-MS (Method 1): $R_t$=0.17 min; MS (ESIpos): m/z=212 (M+H)$^+$.

Intermediate L69

Trifluoroacetic acid/1-[(benzyloxy)carbonyl]piperidin-4-yl-L-valyl-N5-carbamoyl-L-ornithinate (1:1)

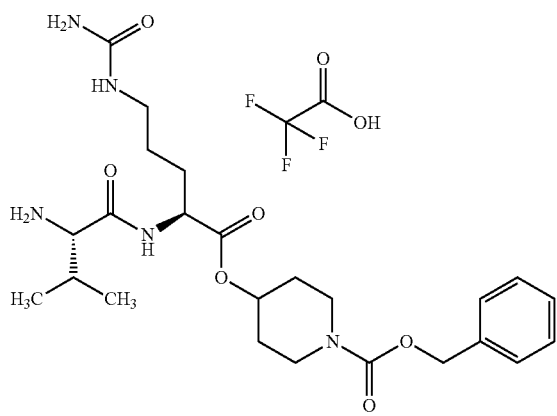

The title compound was prepared by classical methods of peptide chemistry from commercially available benzyl 4-hydroxypiperidine-1-carboxylate by esterification with N2-(tert-butoxycarbonyl)-N5-carbamoyl-L-ornithine using EDCI/DMAP, subsequent Boc removal with TFA, followed by coupling with N-[(tert-butoxy)carbonyl]-L-valine in the presence of HATU and N,N-diisopropylethylamine and finally another Boc removal with TFA.

LC-MS (Method 1): $R_t$=0.62 min; MS (ESIpos): m/z=492 (M+H)$^+$.

Intermediate L70

9H-Fluoren-9-ylmethyl (3-oxopropyl)carbamate

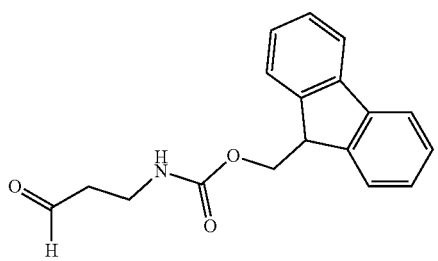 [SMILES: O=CCCNC(=O)OCC1c2ccccc2-c2ccccc21]

1000.0 mg (3.36 mmol) of 9H-fluoren-9-ylmethyl (3-hydroxypropyl)carbamate were initially charged in 15.0 ml of chloroform and 15.0 ml of 0.05 N potassium carbonate/0.05 N sodium bicarbonate solution (1:1). 93.5 mg (0.34 mmol) of tetra-n-butylammonium chloride, 673.6 mg (5.04 mmol) of N-chlorosuccinimide and 52.5 mg (0.34 mmol) of TEMPO were then added and the reaction mixture was stirred vigorously at RT overnight. The reaction mixture was diluted with dichloromethane and the organic phase was washed with water and saturated NaCl solution. The organic phase was dried over magnesium sulphate and the solvent was evaporated under reduced pressure. The residue was dried under high vacuum and purified by silica gel chromatography (mobile phase: cyclohexane/ethyl acetate 3:1-1:1). The solvents were evaporated under reduced pressure and the residue was dried under high vacuum. This gave 589.4 mg (58% of theory) of the title compound.

LC-MS (Method 6): $R_t$=2.15 min; MS (ESIpos): m/z=296 (M–H)$^+$.

Intermediate L71 tert-Butyl [4-(chlorocarbonyl)phenyl]carbamate

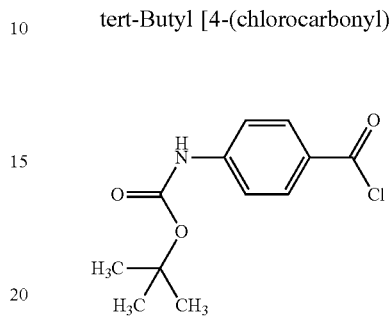

100.0 mg (0.42 mmol) of 4-[(tert-butoxycarbonyl)amino]benzoic acid were initially charged in 2.0 ml of dichloromethane, and 64.2 mg (0.51 mmol) of oxalyl dichloride were added. The reaction mixture was stirred at RT for 30 min (monitored by TLC: dichloromethane/methanol). Another 192.6 mg (1.53 mmol) of oxalyl dichloride and 1 drop of DMF were then added and the mixture was stirred at RT for 1 h. The solvent was evaporated under reduced pressure and the residue was co-distilled repeatedly with dichloromethane. The residue was used without further purification in the next step of the synthesis.

Intermediate L72

Benzyl (9S)-9-(hydroxymethyl)-2,2-dimethyl-6,11-dioxo-5-oxa-7,10-diaza-2-silatetradecan-14-oate

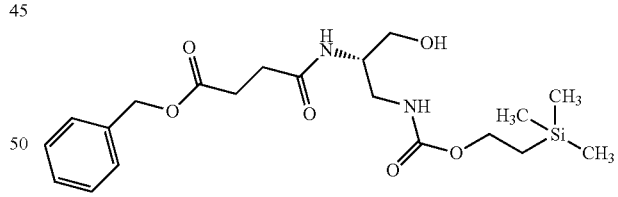

The title compound was prepared from commercially available benzyl tert-butyl [(2S)-3-hydroxypropan-1,2-diyl] biscarbamate according to classical methods of peptide chemistry by hydrogenolytic removal of the Z protective group, subsequent coupling with 4-(benzyloxy)-4-oxobutanoic acid in the presence of EDCI/HOBT, followed by removal of the Boc protective group with TFA and finally by reaction with 1-({[2-(trimethylsilyl)ethoxy]carbonyl}oxy)pyrrolidine-2,5-dione in the presence of triethylamine.

LC-MS (Method 1): $R_t$=0.94 min; MS (ESIpos): m/z=425 [M+H]$^+$.

Intermediate L73

N-(2-Aminoethyl)-6-(2,5-dioxo-2,5-dihydro-1H-pyrrol-1-yl)hexanamide

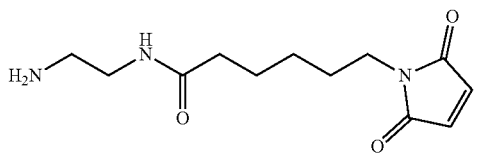 [SMILES: NCCNC(=O)CCCCCN1C(=O)C=CC1=O]

395.5 mg (1.87 mmol) of 6-(2,5-dioxo-2,5-dihydro-1H-pyrrol-1-yl)hexanoic acid, 1.21 g (9.36 mmol) of N,N-diisopropylethylamine and 854.3 mg (2.25 mmol) of HATU were added to a solution of 300 mg (1.87 mmol) of tert-butyl (2-aminoethyl)carbamate in 20 ml of dimethylformamide. The reaction mixture was stirred at RT for 5 minutes. After concentration of the mixture, the residue was taken up in DCM and washed with water. The organic phase was washed with brine, dried over magnesium sulphate, filtered off and concentrated. This gave 408 mg (33%, purity 53%) of the title compound which were used without further purification.

LC-MS (Method 1): $R_t$=0.75 min; MS (ESIpos): m/z=354 (M+H)$^+$.

1 ml of TFA was added to a solution of tert-butyl (2-{[6-(2,5-dioxo-2,5-dihydro-1H-pyrrol-1-yl)hexanoyl]amino}ethyl)carbamate (408 mg, 0.365 mmol) in 7 ml of dichloromethane. The reaction mixture was stirred at RT for 0.5 h. The reaction mixture was concentrated under reduced pressure and the residue was co-distilled twice with dichloromethane. The residue was used further without further purification. This gave 384 mg (94%, purity 57%) of the title compound.

LC-MS (Method 1): $R_t$=0.26 min; MS (ESIpos): m/z=254 (M+H)$^+$.

Intermediate L74

3-[2-[2-[2-[2-[[2-(2,5-Dioxopyrrol-1-yl)acetyl]amino]ethoxy]ethoxy]ethoxy]ethoxy]propanoic acid

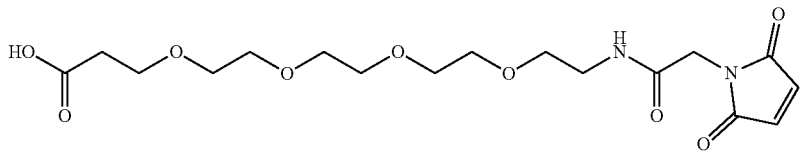 [SMILES: O=C(O)CCOCCOCCOCCOCCNC(=O)CN1C(=O)C=CC1=O]

107 mg (0.335 mmol) of tert-butyl 3-[2-[2-[2-(2-aminoethoxy)ethoxy]ethoxy]ethoxy]propanoate and 93 mg (0.369 mmol) of (2,5-dioxopyrrolidin-1-yl) 2-(2,5-dioxopyrrol-1-yl)acetate were dissolved in 5 ml of dimethylformamide, and 0.074 ml (0.671 mmol) of N-methylmorpholine were added. The reaction mixture was stirred at RT overnight. 0.048 ml (0.838 mmol) of acetic acid were added and the reaction mixture was purified directly by preparative RP-HPLC (column: Reprosil 125×30; 10µ, flow rate: 50 ml/min, MeCN/water/0.1% TFA). The solvents were evaporated under reduced pressure and the residue was dried under high vacuum. This gave 133 mg (86%, purity 100%) of tert-butyl 3-[2-[2-[2-[2-[[2-(2,5-dioxopyrrol-1-yl) acetyl]amino]ethoxy]ethoxy]ethoxy]ethoxy]propanoate.

LC-MS (Method 1): $R_t$=0.82 min; MS (ESIpos): m/z=459 (M+H)$^+$.

0.5 ml of TFA was added to a solution of tert-butyl 3-[2-[2-[2-[2-[[2-(2,5-dioxopyrrol-1-yl)acetyl]amino]ethoxy]ethoxy]ethoxy]ethoxy]propanoate (130 mg, 0.284 mmol) in 5 ml of dichloromethane. The reaction mixture was stirred at RT overnight. The reaction mixture was concentrated under reduced pressure and the residue was taken up in water and lyophilized. The residue was used further without further purification. This gave 102 mg (90%, purity 100%) of the title compound.

LC-MS (Method 1): $R_t$=0.52 min; MS (ESIpos): m/z=402 (M+H)$^+$.

Intermediate L75

Trifluoroacetic acid/2-(trimethylsilyl)ethyl 3-{[(benzyloxy)carbonyl]amino}-D-alaninate (1:1)

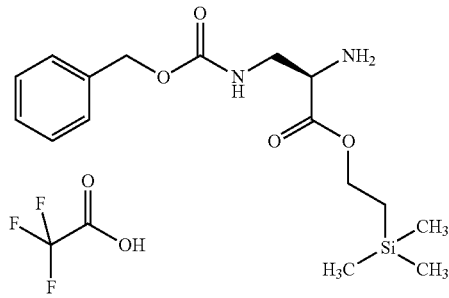

The title compound was prepared from 3-{[(benzyloxy)carbonyl]amino}-N-(tert-butoxycarbonyl)-D-alanine according to classical methods of peptide chemistry (esterification with 2-trimethylsilylethanol using EDCI/DMAP and removal of the Boc protective group with trifluoroacetic acid). This gave 405 mg (58% of theory over 2 steps) of the title compound.

LC-MS (Method 1): $R_t$=0.75 min; MS (ESIpos): m/z=339 (M+H)$^+$.

Intermediate L76

(2S)-2-Bromo-4-oxo-4-[2-(trimethylsilyl)ethoxy]butanoic acid

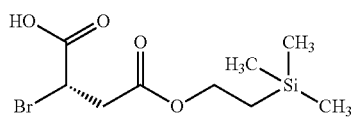

First, a suitably protected aspartic acid derivative was prepared from (3S)-4-(benzyloxy)-3-{[(benzyloxy)carbonyl]amino}-4-oxobutanoic acid according to classical methods of peptide chemistry (esterification with 2-trimethylsilylethanol using EDCI/DMAP and hydrogenolytic removal of the Z protective group and the benzyl ester). 470 mg (1.8 mmol) of the (2S)-2-amino-4-oxo-4-[2-(trimethylsilyl)ethoxy]butanoic acid obtained in this manner were suspended in 10 ml of water, and 1.8 ml of a 1 molar hydrochloric acid and 0.5 ml of concentrated sulphuric acid were added, followed by 863 mg (7.25 mmol) of potassium bromide. At 10° C., a solution of 150 mg (2.175 mmol) of sodium nitrite in 1 ml of water was then added dropwise over a period of 30 min, and the mixture was stirred at 10-15° C. for 2 h. The mixture was then extracted with 50 ml of ethyl acetate. The organic phase was washed with saturated sodium chloride solution and dried over magnesium sulphate. Evaporation of the solvent and purification of the product by preparative HPLC gave 260 mg (48% of theory) of the title compound.

LC-MS (Method 1): $R_t$=1.03 min; MS (ESIneg): m/z=295 and 297 (M−H)⁻.

¹H-NMR (400 MHz, CDCl₃): δ [ppm]=0.03 (s, 9H), 0.95 (t, 2H), 2.94 and 3.2 (2dd, 2H), 4.18 (t, 2H), 4.57 (t, 1H).

Intermediate L77

Trifluoroacetic acid/N-[2-(2-Aminoethoxy)ethyl]-2-bromoacetamide (1:1)

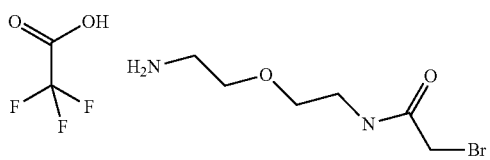 [SMILES: O=C(O)C(F)(F)F ; NCCOCCNC(=O)CBr]

418 mg (2.05 mmol) of tert-butyl [2-(2-aminoethoxy)ethyl]carbamate were initially reacted with 638 mg (2.46 mmol) of bromoacetic anhydride, and the Boc protective group was then removed with trifluoroacetic acid. This gave 551 mg (63% of theory over 2 steps) of the title compound.

LC-MS (Method): $R_t$=0.32 min; MS (ESIpos): m/z=227 and 225 (M+H)⁺.

Intermediate L78

N-[(2,5-Dioxo-2,5-dihydro-1H-pyrrol-1-yl)acetyl]-beta-alanine

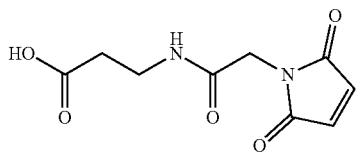 [SMILES: O=C(O)CCNC(=O)CN1C(=O)C=CC1=O]

The title compound was prepared from commercially available (2,5-dioxo-2,5-dihydro-1H-pyrrol-1-yl)acetic acid by coupling with tert-butyl beta-alaninate hydrochloride (1:1) in the presence of EDCI/HOBt and N,N-diisopropylethylamine and subsequent deprotection with trifluoroacetic acid.

LC-MS (Method 1): $R_t$=0.32 min; MS (ESIpos): m/z=227 (M+H)⁺.

Intermediate L79

N-[(2,5-Dioxo-2,5-dihydro-1H-pyrrol-1-yl)hexanoyl]-beta-alanine

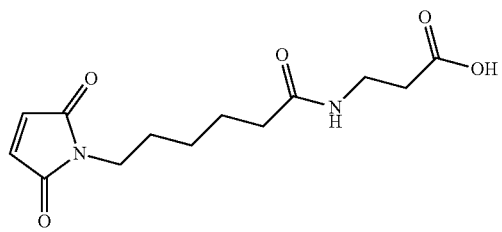 [SMILES: O=C(O)CCNC(=O)CCCCCN1C(=O)C=CC1=O]

64.8 mg (0.357 mmol) of tert-butyl beta-alaninate hydrochloride (1:1) and 100 mg (0.324 mmol) of 1-{6-[(2,5-dioxopyrrolidin-1-yl)oxy]-6-oxohexyl}-1H-pyrrole-2,5-dione were dissolved in 4 ml of dimethylformamide, and 65.6 mg (0.649 mmol) of N-methylmorpholine were added. The reaction mixture was stirred at RT overnight. 0.048 ml (0.838 mmol) of acetic acid were added and the reaction mixture was purified directly by preparative RP-HPLC (column: Reprosil 250×30; 10μ, flow rate: 50 ml/min, MeCN/water/0.1% TFA). The solvents were evaporated under reduced pressure and the residue was dried under high vacuum. This gave 84.5 mg (77%, purity 100%) of tert-butyl N-[6-(2,5-dioxo-2,5-dihydro-1H-pyrrol-1-yl)hexanoyl]-beta-alaninate.

LC-MS (Method 1): $R_t$=0.78 min; MS (ESIpos): m/z=339 (M+H)⁺.

1.62 ml of TFA were added to a solution of tert-butyl N-[6-(2,5-dioxo-2,5-dihydro-1H-pyrrol-1-yl)hexanoyl]-beta-alaninate (82.8 mg, 0.244 mmol) in 8 ml of dichloromethane. The reaction mixture was stirred at RT for 2 hours. The reaction mixture was concentrated under reduced pressure and the residue was taken up in water and lyophilized. The residue was used further without further purification. This gave 62.7 mg (87%, purity 95%) of the title compound.

LC-MS (Method 1): $R_t$=0.75 min; MS (ESIpos): m/z=283 (M+H)⁺.

Intermediate L80

2-(Trimethylsilyl)ethyl 3-[(15-amino-4,7,10,13-tetraoxapentadecan-1-oyl)amino]-N-(tert-butoxycarbonyl)-D-alaninate

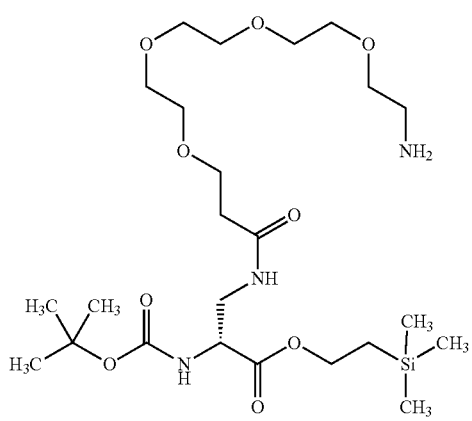 [SMILES: CC(C)(C)OC(=O)N[C@H](CNC(=O)CCOCCOCCOCCOCCN)C(=O)OCC[Si](C)(C)C]

The title compound was prepared from commercially available 3-{[(benzyloxy)carbonyl]amino}-N-(tert-butoxy-carbonyl)-D-alanine/N-cyclohexylcyclohexanamine (1:1) according to classical methods of peptide chemistry (release from the salt and esterification with 2-(trimethylsilyl)ethanol using EDCI/DMAP, hydrogenolytic removal of the Z protective group, coupling with commercially available 3-oxo-1-phenyl-2,7,10,13,16-pentaoxa-4-azanonadecan-19-oic acid in the presence of HATU and N,N-diisopropylethylamine and another hydrogenolytic removal of the Z protective group).

LC-MS (Method 1): $R_t$=0.70 min; MS (ESIpos): m/z=552 (M+H)$^+$.

Intermediate L81

Trifluoroacetic acid/benzyl {2-[(2-aminoethyl)sulphonyl]ethyl}carbamate (1:1

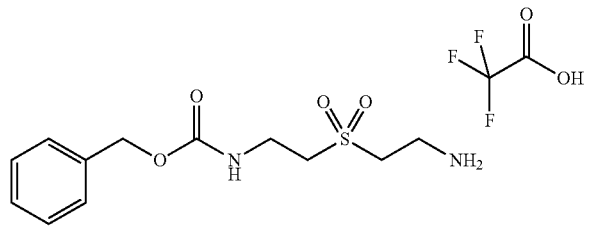

250 mg (1.11 mmol) of 2,2'-sulphonyldiethanamine were coupled with 92.3 mg (0.37 mmol) of 1-{[(benzyloxy)carbonyl]oxy}pyrrolidine-2,5-dione in the presence of N,N-diisopropylethylamine in DMF. Subsequent purification by HPLC gave 70 mg (47% of theory) of the title compound.
LC-MS (Method 12): $R_t$=0.64 min; MS (ESIpos): m/z=257.11 (M+H)$^+$.

Intermediate L82

Trifluoroacetic acid/N-{2-[2-(2-aminoethoxy)ethoxy]ethyl}-6-(2,5-dioxo-2,5-dihydro-1H-pyrrol-1-yl)hexanamide (1:1)

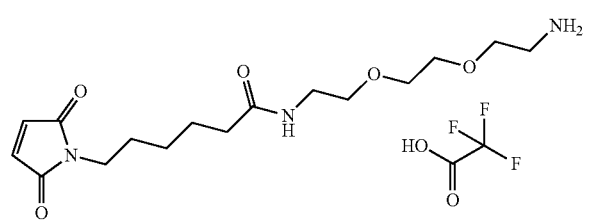

88.6 mg (0.357 mmol) of N-Boc-2,2'-(ethylenedioxy)diethylamine and 100 mg (0.324 mmol) of N-succinimidyl 6-maleimidohexanoate were dissolved in 4.0 ml of dimethylformamide, and 0.071 ml (0.650 mmol) of N-methylmorpholine were added. The reaction mixture was stirred at RT overnight. 0.048 ml (0.838 mmol) of acetic acid were added and the reaction mixture was purified directly by preparative RP-HPLC (column: Reprosil 125×30; 10μ, flow rate: 75 ml/min, MeCN/water/0.1% TFA). The solvents were evaporated under reduced pressure and the residue was dried under high vacuum. This gave 127 mg (81% of theory) of tert-butyl {2-[2-(2-{[6-(2,5-dioxo-2,5-dihydro-1H-pyrrol-1-yl)hexanoyl]amino}ethoxy)ethoxy]ethyl}carbamate.

LC-MS (Method 1): $R_t$=0.78 min; MS (ESIpos): m/z=442 (M+H)$^+$.

2.0 ml of TFA were added to a solution of 123 mg (225 μmol) tert-butyl {2-[2-(2-{[6-(2,5-dioxo-2,5-dihydro-1H-pyrrol-1-yl)hexanoyl]amino}ethoxy)ethoxy]ethyl}carbamate in 7.5 ml of dichloromethane. The reaction mixture was stirred at RT for 2 h. The reaction mixture was concentrated under reduced pressure and the residue was taken up in water and lyophilized. The residue was used further without further purification. This gave 111 mg (100% of theory) of the title compound.

LC-MS (Method 1): $R_t$=0.31 min; MS (ESIpos): m/z=342 (M+H)$^+$.

$^1$H-NMR (400 MHz, DMSO-d$_6$): δ[ppm]=1.17 (m, 2H), 1.47 (m, 4H), 2.04 (m, 2H), 2.98 (m, 2H), 3.19 (m, 2H), 3.39 (m, 4H), 3.56 (m, 6H), 7.01 (s, 2H), 7.72 (bs, 3H), 7.80 (m, 1H).

Intermediate L83

Trifluoroacetic acid/N-{2-[2-(2-aminoethoxy)ethoxy]ethyl}-2-(2,5-dioxo-2,5-dihydro-1H-pyrrol-1-yl)acetamide (1:1)

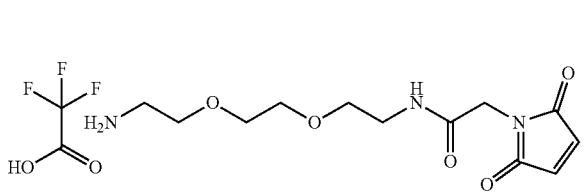

200 mg (0.805 mmol) of tert-butyl {2-[2-(2-aminoethoxy)ethoxy]ethyl}carbamate, 150 mg (0.966 mmol) of (2,5-dioxo-2,5-dihydro-1H-pyrrol-1-yl)acetic acid and 560 μl (3.2 mmol) of N,N-diisopropylethylamine were dissolved in 10 ml of dimethylformamide, and 459 mg (1.21 mmol) of HATU were added. The reaction mixture was stirred at RT for 30 minutes. The solvents were evaporated under reduced pressure and the residue was dissolved in dichloromethane. The organic phase was washed twice with 5% strength citric acid solution and dried over magnesium sulphate, and the solvent was evaporated under reduced pressure. The residue was purified using Biotage Isolera (silica gel, column 25 g SNAP, dichloromethane:methanol 98:2). This gave 276 mg (89% of theory) of tert-butyl {2-[2-(2-{[(2,5-dioxo-2,5-dihydro-1H-pyrrol-1-yl)acetyl]amino}ethoxy)ethoxy]ethyl}carbamate.

LC-MS (Method 1): $R_t$=0.67 min; MS (ESIpos): m/z=386 (M+H)$^+$.

4 ml of TFA were added to a solution of tert-butyl {2-[2-(2-{[(2,5-dioxo-2,5-dihydro-1H-pyrrol-1-yl)acetyl]amino}ethoxy)ethoxy]ethyl}carbamate (275 mg, 714 μmol) in 15 ml of dichloromethane. The reaction mixture was stirred at RT for 30 minutes. The reaction mixture was concentrated under reduced pressure and the residue was taken up in water and lyophilized. This gave 281 mg (99% of theory) of the title compound.

LC-MS (Method 1): $R_t$=0.17 min; MS (ESIpos): m/z=286 (M+H)$^+$.

Intermediate L84

Trifluoroacetic acid/N-(14-amino-3,6,9,12-tetraoxa-tetradec-1-yl)-6-(2,5-dioxo-2,5-dihydro-1H-pyrrol-1-yl)hexanamide (1:1)

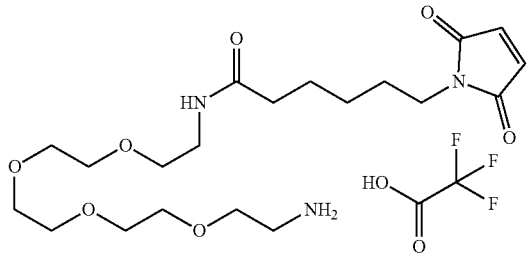

200 mg (0.594 mmol) of tert-butyl (14-amino-3,6,9,12-tetraoxatetradec-1-yl)carbamate and 202 mg (0.654 mmol) of 1-{6-[(2,5-dioxopyrrolidin-1-yl)oxy]-6-oxohexyl}-1H-pyrrole-2,5-dione were dissolved in 4.0 ml of dimethylformamide, and 0.130 ml (1.2 mmol) of N-methylmorpholine were added. The reaction mixture was stirred at RT overnight. 0.085 ml (1.5 mmol) of acetic acid were added and the reaction mixture was purified directly by preparative RP-HPLC (column: Reprosil 125×30; 10μ, flow rate: 50 ml/min, MeCN/water/0.1% TFA). The solvents were evaporated under reduced pressure and the residue was dried under high vacuum. This gave 275 mg (73% of theory) of tert-butyl [21-(2,5-dioxo-2,5-dihydro-1H-pyrrol-1-yl)-16-oxo-3,6,9,12-tetraoxa-15-azahenicos-1-yl]carbamate.

LC-MS (Method 1): $R_t$=0.81 min; MS (ESIpos): m/z=530 (M+H)$^+$.

780 μl (10 mmol) of TFA were added to a solution of tert-butyl [21-(2,5-dioxo-2,5-dihydro-1H-pyrrol-1-yl)-16-oxo-3,6,9,12-tetraoxa-15-azahenicos-1-yl]carbamate (268 mg, 505 μmol) in 5.0 ml of dichloromethane. The reaction mixture was stirred at RT overnight. The reaction mixture was concentrated under reduced pressure and the residue was taken up in water and lyophilized. The residue was used further without further purification. This gave 266 mg (97% of theory) of the title compound.

LC-MS (Method 1): $R_t$=0.46 min; MS (ESIpos): m/z=430 (M+H)$^+$.

$^1$H-NMR (400 MHz, DMSO-d$_6$): δ[ppm]=1.17 (m, 2H), 1.47 (m, 4H), 2.03 (m, 2H), 2.99 (m, 2H), 3.18 (m, 2H), 3.38 (m, 4H), 3.52 (m, 8H), 3.58 (m, 6H), 7.01 (s, 2H), 7.73 (bs, 3H), 7.80 (m, 1H).

Intermediate L85

Trifluoroacetic acid/N-(14-amino-3,6,9,12-tetraoxa-tetradec-1-yl)-2-(2,5-dioxo-2,5-dihydro-1H-pyrrol-1-yl)acetamide (1:1)

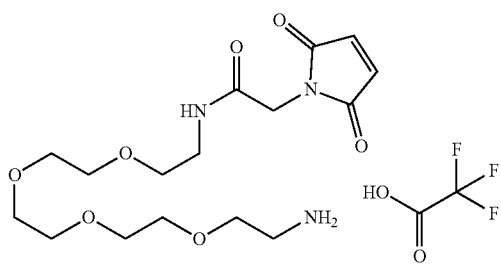

200 mg (0.594 mmol) of tert-butyl (14-amino-3,6,9,12-tetraoxatetradec-1-yl)carbamate, 111 mg (0.713 mmol) of (2,5-dioxo-2,5-dihydro-1H-pyrrol-1-yl)acetic acid and 410 μl (2.4 mmol) of N,N-diisopropylethylamine were dissolved in 6 ml of dimethylformamide, and 339 mg (0.892 mmol) of HATU were added. The reaction mixture was stirred at RT for 1 h and purified directly by preparative RP-HPLC (column: Reprosil 250×30; 10μ, flow rate: 50 ml/min, MeCN/water/0.1% TFA). The solvents were evaporated under reduced pressure and the residue was dried under high vacuum. This gave 130 mg (43% of theory) of tert-butyl [17-(2,5-dioxo-2,5-dihydro-1H-pyrrol-1-yl)-16-oxo-3,6,9,12-tetraoxa-15-azaheptadec-1-yl]carbamate.

LC-MS (Method 1): $R_t$=0.71 min; MS (ESIpos): m/z=474 (M+H)$^+$.

410 μl (5.3 mmol) of TFA were added to a solution of tert-butyl [17-(2,5-dioxo-2,5-dihydro-1H-pyrrol-1-yl)-16-oxo-3,6,9,12-tetraoxa-15-azaheptadec-1-yl]carbamate (126 mg, 267 μmol) in 4.0 ml of dichloromethane. The reaction mixture was stirred at RT overnight. The reaction mixture was concentrated under reduced pressure and the residue was dried under high vacuum. This gave 124 mg (95% of theory) of the title compound.

LC-MS (Method 13): $R_t$=0.74 min; MS (ESIpos): m/z=374 (M+H)$^+$.

$^1$H-NMR (400 MHz, DMSO-d$_6$): δ[ppm]=2.99 (m, 2H), 3.22 (m, 2H), 3.41 (m, 2H), 3.53 (m, 8H), 3.58 (m, 6H), 4.02 (s, 2H), 7.09 (s, 2H), 7.73 (bs, 3H), 8.21 (m, 1H).

Intermediate L86

N-[(2,5-Dioxo-2,5-dihydro-1H-pyrrol-1-yl)acetyl]-L-valyl-L-alanine

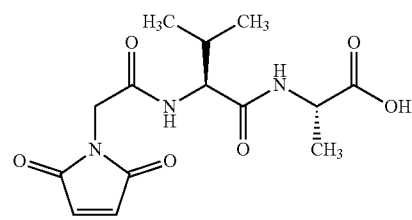 [SMILES: CC(C)[C@H](NC(=O)CN1C(=O)C=CC1=O)C(=O)N[C@@H](C)C(=O)O]

100 mg (0.531 mmol) of L-valyl-L-alanine and 134 mg (0.531 mmol) of 1-{2-[(2,5-dioxopyrrolidin-1-yl)oxy]-2-oxoethyl}-1H-pyrrole-2,5-dione were dissolved in 3 ml of dimethylformamide, and 0.150 ml (1.1 mmol) of triethylamine were added. The reaction mixture was stirred at RT for 8 h. The reaction mixture was purified directly by preparative RP-HPLC (column: Reprosil 250×30; 10μ, flow rate: 50 ml/min, MeCN/water). The solvents were evaporated under reduced pressure and the residue was dried under high vacuum. This gave 71.5 mg (41% of theory) of the title compound.

LC-MS (Method 1): $R_t$=0.42 min; MS (ESIpos): m/z=326 (M+H)$^+$.

Intermediate L87

3-[2-(2-{[(2,5-Dioxo-2,5-dihydro-1H-pyrrol-1-yl)acetyl]amino}ethoxy)ethoxy]propanoic acid

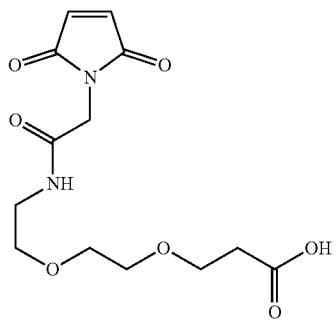 [SMILES: O=C(O)CCOCCOCCNC(=O)CN1C(=O)C=CC1=O]

250 mg (1.07 mmol) of tert-butyl 3-[2-(2-aminoethoxy)ethoxy]propanoate, 151 mg (0.974 mmol) of 2-(2,5-dioxo-2,5-dihydro-1H-pyrrol-1-yl)acetic acid, 224 mg (1.46 mmol) of 1-hydroxy-1H-benzotriazole hydrate and 224 mg (1.17 mmol) of 1-(3-dimethylaminopropyl)-3-ethylcarbodiimide hydrochloride were dissolved in 5.0 ml of dimethylformamide. The reaction mixture was stirred at RT for 1 h. Ethyl acetate was added and the mixture was extracted twice with 5% strength citric acid solution and with saturated sodium bicarbonate solution. The organic phase was washed twice with saturated sodium chloride solution and dried over magnesium sulphate, and the solvent was evaporated under reduced pressure. The residue was purified by preparative RP-HPLC (column: Reprosil 250×40; 10μ, flow rate: 50 ml/min, MeCN/water/0.1% TFA). The solvents were evaporated under reduced pressure and the residue was dried under high vacuum. This gave 267 mg (64% of theory) of tert-butyl 3-[2-(2-{[(2,5-dioxo-2,5-dihydro-1H-pyrrol-1-yl)acetyl]amino}ethoxy)ethoxy]propanoate.

LC-MS (Method 1): $R_t$=0.73 min; MS (ESIpos): m/z=371 (M+H)$^+$.

1.1 ml (14 mmol) of TFA were added to a solution of tert-butyl 3-[2-(2-{[(2,5-dioxo-2,5-dihydro-1H-pyrrol-1-yl)acetyl]amino}ethoxy)ethoxy]propanoate (263 mg, 710 μmol) in 10 ml of dichloromethane. The reaction mixture was stirred at RT overnight. The reaction mixture was concentrated under reduced pressure and the residue was dried under high vacuum. This gave 240 mg (94% of theory) of the title compound.

LC-MS (Method 12): $R_t$=0.57 min; MS (ESIpos): m/z=315 (M+H)$^+$.

Intermediate L88

2,5-Dioxopyrrolidin-1-yl N-[6-(2,5-dioxo-2,5-dihydro-1H-pyrrol-1-yl)hexanoyl]-L-valyl-L-alaninate

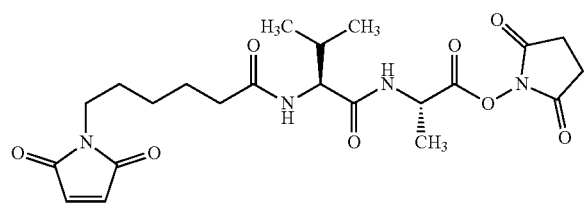 [SMILES: CC(C)[C@H](NC(=O)CCCCCN1C(=O)C=CC1=O)C(=O)N[C@@H](C)C(=O)ON1C(=O)CCC1=O]

150 mg (0.797 mmol) of L-valyl-L-alanine and 246 mg (0.797 mmol) of 1-{6-[(2,5-dioxopyrrolidin-1-yl)oxy]-6-oxohexyl}-1H-pyrrole-2,5-dione were dissolved in 4.0 ml of dimethylformamide, and 0.220 ml (1.6 mmol) of triethylamine were added. The reaction mixture was stirred at RT overnight. The reaction mixture was purified directly by preparative RP-HPLC (column: Reprosil 250×30; 10μ, flow rate: 50 ml/min, MeCN/water). The solvents were evaporated under reduced pressure and the residue was dried under high vacuum. This gave 302 mg (97% of theory) of N-[6-(2,5-dioxo-2,5-dihydro-1H-pyrrol-1-yl)hexanoyl]-L-valyl-L-alanine.

LC-MS (Method 12): $R_t$=1.02 min; MS (ESIpos): m/z=382 (M+H)$^+$.

$^1$H-NMR (400 MHz, DMSO-$d_6$): δ[ppm]=0.82 (dd, 6H), 1.17 (m, 2H), 1.27 (d, 3H), 1.48 (m, 4H), 1.94 (m, 1H), 2.13 (m, 2H), 3.38 (t, 2H), 4.17 (m, 2H), 7.00 (s, 2H), 7.75 (d, 1H), 8.19 (d, 1H).

130 mg (0.531 mmol) of N-[6-(2,5-dioxo-2,5-dihydro-1H-pyrrol-1-yl)hexanoyl]-L-valyl-L-alanine were dissolved in 6.5 ml of dichloromethane, and 58.8 mg (0.511 mmol) of 1-hydroxypyrrolidine-2,5-dione and 78.4 mg (0.409 mmol) of 1-(3-dimethylaminopropyl)-3-ethylcarbodiimide hydrochloride were added. Another 58.8 mg (0.511 mmol) of 1-hydroxypyrrolidine-2,5-dione and 78.4 mg (0.409 mmol) of 1-(3-dimethylaminopropyl)-3-ethylcarbodiimide hydrochloride were added. Dichloromethane was added and the mixture was washed three times with water. The organic phase was dried over magnesium sulphate, the solvent was evaporated under reduced pressure and the residue was dried under high vacuum. This gave 172 mg (87% of theory) of the title compound.

LC-MS (Method 12): $R_t$=1.28 min; MS (ESIpos): m/z=479 (M+H)$^+$.

Intermediate L89

1-Benzyl-5-[2-(trimethylsilyl)ethyl]-L-glutamate hydrochloride (1:1)

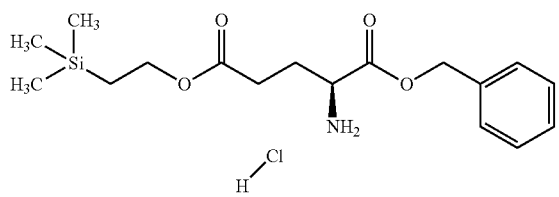 [SMILES: C[Si](C)(C)CCOC(=O)CC[C@H](N)C(=O)OCc1ccccc1 ; Cl]

1.00 g (2.96 mmol) of (4S)-5-(benzyloxy)-4-[(tert-butoxycarbonyl)amino]-5-oxopentanoic acid was initially charged in 13.0 ml of THF, and 510 μl (3.6 mmol) of 2-(trimethylsilyl)ethanol and 109 mg (889 μmol) of 4-dimethylaminopyridine were added. The reaction mixture was cooled to 0° C., and 682 mg (3.56 mmol) of N-ethyl-N'-3-(dimethylaminopropyl)carbodiimide hydrochloride were added. The reaction mixture was stirred at RT overnight. The solvents were evaporated under reduced pressure and the residue was dissolved in ethyl acetate. The organic phase was washed twice with 0.1 N HCl solution and saturated sodium chloride solution and dried over magnesium sulphate, and the solvent was evaporated under reduced pressure. The residue was purified using Biotage Isolera (silica gel, column 25 g SNAP, cyclohexane:ethyl acetate 80:20). This gave 649 mg (50% of theory) of the compound 1-benzyl-5-[2-(trimethylsilyl)ethyl]-N-(tert-butoxycarbonyl)-L-glutamate.

LC-MS (Method 1): $R_t$=4.6 min; MS (ESIpos): m/z=438 (M+H)$^+$.

649 mg (1.48 mmol) of 1-benzyl-5-[2-(trimethylsilyl)ethyl]-N-(tert-butoxycarbonyl)-L-glutamate were dissolved in 7.0 ml of dioxane and, with ice bath cooling, 14 ml (59 mmol) of 4N HCl in dioxane were added. The reaction mixture was stirred at RT overnight. The reaction mixture was concentrated under reduced pressure and the residue was dried under high vacuum and purified by Biotage Isolera (silica gel, column 25 g SNAP, dichloromethane:methanol 90:10). This gave 320 mg (57% of theory) of the title compound.

LC-MS (Method 1): $R_t$=0.79 min; MS (ESIpos): m/z=338 (M+H)$^+$.

Intermediate L90

1-({N-[(Benzyloxy)carbonyl]glycyl}amino)-3,6,9,12-tetraoxapentadecan-15-oic acid

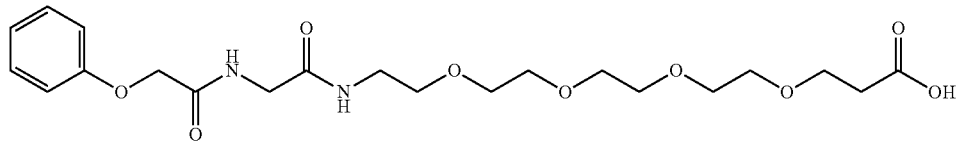 [SMILES: O=C(O)CCOCCOCCOCCOCCNC(=O)CNC(=O)COc1ccccc1]

118 mg (566 µmol) of N-[(benzyloxy)carbonyl]glycine were initially charged in 5.0 ml of DMF, 200 mg (622 µmol) of tert-butyl 1-amino-3,6,9,12-tetraoxapentadecan-15-oate, 130 mg (849 µmol) of 1-hydroxy-1H-benzotriazole hydrate and 130 mg (679 µmol) of 1-(3-dimethylaminopropyl)-3-ethylcarbodiimide hydrochloride were added and the mixture was stirred at RT for 1 h. Ethyl acetate was added and the mixture was extracted twice with 5% strength citric acid solution and with saturated sodium bicarbonate solution. The organic phase was washed twice with saturated sodium chloride solution and dried over magnesium sulphate. The solvents were evaporated under reduced pressure and the residue was dried under high vacuum. This gave 274 mg (95% of theory) of tert-butyl 1-({N-[(benzyloxy)carbonyl]glycyl}amino)-3,6,9,12-tetraoxapentadecan-15-oate.

LC-MS (Method 12): $R_t$=1.69 min; MS (ESIpos): m/z=513 (M+H)$^+$.

820 µl (11 mmol) of TFA were added to a solution of 274 mg (535 µmol) of tert-butyl 1-({N-[(benzyloxy)carbonyl]glycyl}amino)-3,6,9,12-tetraoxapentadecan-15-oate in 5.0 ml of dichloromethane. The reaction mixture was stirred at RT for 3 h. The reaction mixture was concentrated under reduced pressure and the residue was taken up in water and lyophilized. This gave 262 mg (100% of theory) of the title compound.

LC-MS (Method 12): $R_t$=1.12 min; MS (ESIpos): m/z=457 (M+H)$^+$.

Intermediate L91

Trifluoroacetic acid/2-(trimethylsilyl)ethyl 1-{[3-amino-N-(tert-butoxycarbonyl)-D-alanyl]amino}-3,6,9,12-tetraoxapentadecan-15-oate (1:1)

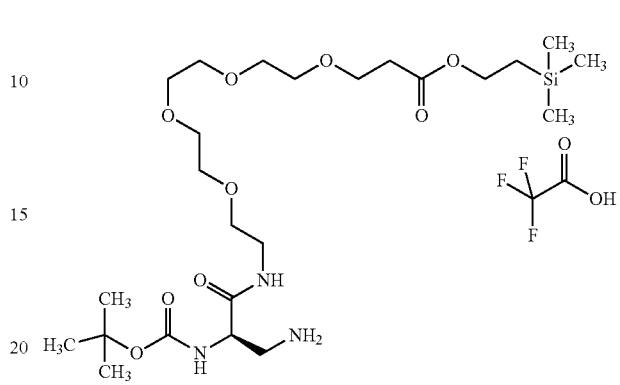

The title compound was prepared from commercially available 3-oxo-1-phenyl-2,7,10,13,16-pentaoxa-4-azanonadecan-19-oic acid by classical methods of peptide chemistry (esterification with 2-trimethylsilylethanol using EDCI/DMAP, hydrogenolytic removal of the Z protective group, coupling with commercially available N-(tert-butoxycarbonyl)-3-{[(9H-fluoren-9-ylmethoxy)carbonyl]amino}-D-alanine and removal of the Fmoc protective group).

LC-MS (Method 1): $R_t$=0.74 min; MS (ESIpos): m/z=552 (M+H)$^+$.

Intermediate L95

N-[(Benzyloxy)carbonyl]-L-valyl-L-alanine

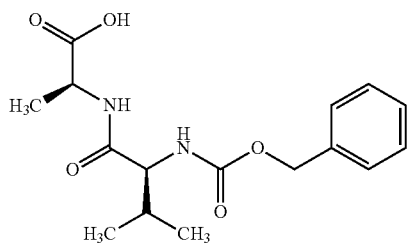 [SMILES: CC(C)[C@H](NC(=O)OCc1ccccc1)C(=O)N[C@@H](C)C(=O)O]

This intermediate was prepared from N-[(benzyloxy)carbonyl]-L-valine and tert-butyl L-alaninate hydrochloride (1:1) using classical methods of peptide chemistry.

LC-MS (Method 12): $R_t$=1.34 min; MS (ESIpos): m/z=323.16 (M+H)$^+$.

Intermediate L96

N-Acetyl-L-valyl-$N^5$-carbamoyl-L-ornithinamide

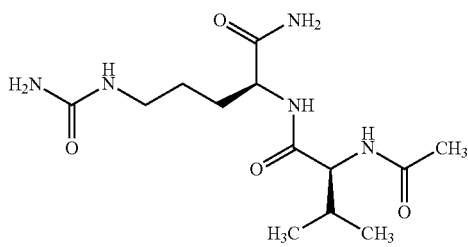 [SMILES: CC(=O)N[C@H](C(=O)N[C@@H](CCCNC(N)=O)C(N)=O)C(C)C]

This intermediate was prepared by classical methods of peptide chemistry starting with the coupling of 2,5-dioxopyrrolidin-1-yl N-[(benzyloxy)carbonyl]-L-valinate with $N^5$-carbamoyl-L-ornithine, followed by hydrogenolytic removal of the Z protective group over 10% palladium/activated carbon in ethanol and finally by reaction of the resulting dipeptide with 1-acetoxypyrrolidine-2,5-dione.

LC-MS (Method 1): $R_t$=0.25 min; MS (ESIpos): m/z=317 (M+H)$^+$.

Intermediate L97

1-(2,5-Dioxo-2,5-dihydro-1H-pyrrol-1-yl)-2-oxo-6, 9,12,15,18,21,24,27-octaoxa-3-azatriacontan-30-oic acid

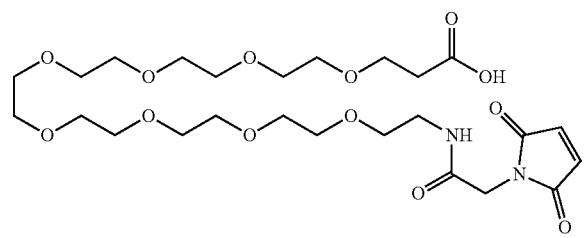 [SMILES: O=C(O)CCOCCOCCOCCOCCOCCOCCOCCOCCNC(=O)CN1C(=O)C=CC1=O]

Tert-Butyl 1-amino-3,6,9,12,15,18,21,24-octaoxaheptacosan-27-oate (100 mg, 201 µmol) was initially charged in 1.0 ml of DMF, and (2,5-dioxo-2,5-dihydro-1H-pyrrol-1-yl) acetic acid (46.8 mg, 301 µmol), 1-hydroxy-1H-benzotriazole hydrate (76.9 mg, 502 µmol) and 1-(3-dimethylaminopropyl)-3-ethylcarbodiimide hydrochloride (77.0 mg, 402 µmol) were added. The reaction mixture was stirred at RT overnight, and ethyl acetate was then added. The organic phase was washed twice with 5% strength citric acid solution, with sat. sodium bicarbonate solution and then with sat. sodium chloride solution. The organic phase was dried over magnesium sulphate. The solvents were evaporated under reduced pressure and the residue was purified by prep. RP-HPLC (column: Reprosil 125×30; 10µ, flow rate: 50 ml/min, MeCN/water/0.1% TFA). The solvents were evaporated under reduced pressure and the residue was dried under high vacuum. This gave 19.1 mg (13% of theory) of the compound tert-butyl 1-(2,5-dioxo-2,5-dihydro-1H-pyrrol-1-yl)-2-oxo-6,9,12,15,18,21,24,27-octaoxa-3-azatriacontan-30-oate.

LC-MS (Method 1): $R_t$=0.87 min; MS (ESIpos): m/z=635 [M+H]$^+$

TFA (62 µl, 600 µmol) was added to a solution of tert-butyl 1-(2,5-dioxo-2,5-dihydro-1H-pyrrol-1-yl)-2-oxo-6,9,12,15,18,21,24,27-octaoxa-3-azatriacontan-30-oate (19.1 mg, 30.1 µmol) in 1.0 ml of DCM. The reaction mixture was stirred at RT for 3 h. The reaction mixture was concentrated under reduced pressure and the residue was taken up in water and lyophilized. The residue was used further without further purification. This gave 10.8 mg (46% of theory) of the title compound.

LC-MS (Method 1): $R_t$=0.55 min; MS (ESIneg): m/z=577 [M−H]$^-$.

Intermediate L98

2,2-Dimethylpropanoic acid/2-(trimethylsilyl)ethyl N-(2-aminoethyl)-$N^2$-{[2-(trimethylsilyl)ethoxy]carbonyl}-L-glutaminate (1:1)

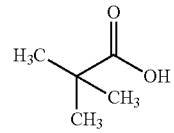

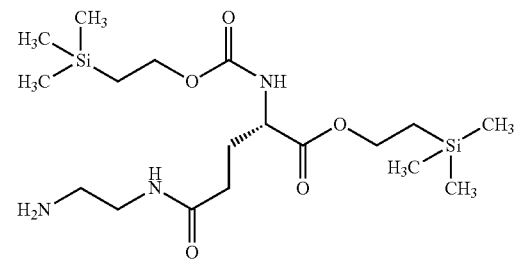

First, (4S)-5-tert-butoxy-4-[(tert-butoxycarbonyl)amino]-5-oxopentanoic acid was coupled in the presence of HATU and N,N-diisopropylethylamine with benzyl (2-aminoethyl) carbamate. Then, the Boc protective group and the tert-butyl ester were cleaved using trifluoroacetic acid in DCM. Subsequently, first the amino group was protected again by reaction with 1-({[2-(trimethylsilyl)ethoxy]carbonyl}oxy) pyrrolidine-2,5-dione in DMF/water in the presence of N,N-diisopropylethylamine, and then the carboxyl group by reaction with 2-(trimethylsilyl)ethanol in DCM in the presence of EDCI/DMAP. In the last step, the terminal amino group was deprotected by hydrogenolysis over 10% palladium on activated carbon in ethanol under standard pressure. Removal of the catalyst by filtration, concentration, purification by preparative HPLC and freeze-drying of the residue from acetonitrile/water gave the title compound.

LC-MS (Method 1): $R_t$=0.82 min; MS (ESIpos): m/z=434 (M+H)$^+$.

Intermediate L99

Trifluoroacetic acid/2-(trimethylsilyl)ethyl N-[(2,5-dioxo-2,5-dihydro-1H-pyrrol-1-yl)acetyl]-L-valyl-L-alanyl-beta-alanyl-L-lysinate (1:1)

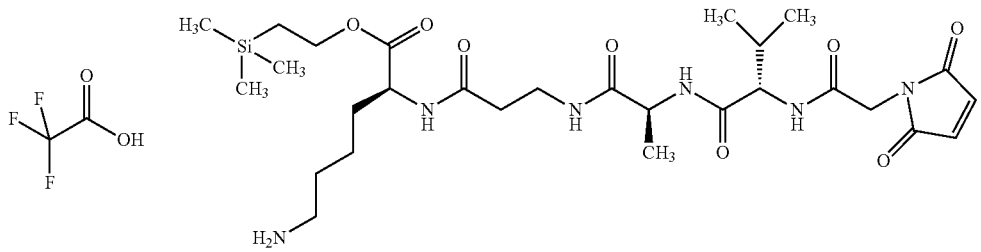 [SMILES: O=C(O)C(F)(F)F ; CC(C)[C@H](NC(=O)CN1C(=O)C=CC1=O)C(=O)N[C@@H](C)C(=O)NCCC(=O)N[C@@H](CCCCN)C(=O)OCC[Si](C)(C)C]

First, starting from N2-[(benzyloxy)carbonyl]-N6-(tert-butoxycarbonyl)-L-lysine, 2-(trimethylsilyl)ethyl N6-(tert-butoxycarbonyl)-L-lysinate was prepared by classical methods of peptide chemistry. This intermediate was then coupled in the presence of HATU and N,N-diisopropylethylamine using the tripeptide building block N-[(benzyloxy)carbonyl]-L-valyl-L-alanyl-beta-alanine, which had been prepared by standard methods. The Z protective group was subsequently removed by hydrogenolysis and methanol and the resulting intermediate was coupled with (2,5-dioxo-2,5-dihydro-1H-pyrrol-1-yl)acetic acid in the presence of HATU and N,N-diisopropylethylamine. In the last step, the side chain amino group was deprotected under mild conditions by stirring in 10% strength trifluoroacetic acid in DCM at RT for 1 h. Concentration and freeze-drying from acetonitrile/water gave the title compound.

LC-MS (Method 1): $R_t$=0.64 min; MS (ESIpos): m/z=625 (M+H)$^+$.

Intermediate L100

3-[5-(2-{[(2,5-Dioxo-2,5-dihydro-1H-pyrrol-1-yl)acetyl]amino}ethyl)-1,2,4-oxadiazol-3-yl]propanoic acid

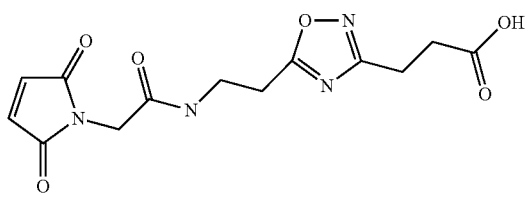 [SMILES: O=C(O)CCc1noc(CCNC(=O)CN2C(=O)C=CC2=O)n1]

461 mg (6.60 mmol) of hydroxylamine hydrochloride and 1341.86 mg (13.26 mmol) of triethylamine were added to a solution of methyl 3-cyanopropanoate (500 mg, 4.42 mmol) in 40 ml of ethanol. The reaction mixture was stirred at 50° C. for 3 h. The mixture was concentrated and the residue was dissolved in ethyl acetate and then washed with water and brine. The organic phase was dried over magnesium sulphate and concentrated. The residue was used without further purification. This gave 400 mg (62% of theory) of the title compound. 6.91 g (36.50 mmol) of N-(tert-butoxycarbonyl)-beta-alanine and 8.22 g (39.82 mmol) of 1,3-dicyclohexylcarbodiimide were added to a solution of methyl (4E)-4-{[N-(tert-butoxycarbonyl)-beta-alanyl]amino}-4-(hydroxyimino)butanoate (4.85 g, 33.19 mmol) in 120.0 ml of dioxane. The reaction mixture was stirred at room temperature for 3 h. The mixture was concentrated and the residue was dissolved in water and extracted with ethyl acetate. The organic phase was dried over sodium sulphate and concentrated. The residue was purified by flash chromatography. This gave 6.0 g (57% of theory) of the title compound.

A solution of methyl (4E)-4-{[N-(tert-butoxycarbonyl)-beta-alanyl]amino}-4-(hydroxyimino)butanoate (6.0 g, 18.91 mmol) in 100 ml of DMF was stirred at 120° C. for 5 h. Water was added and the mixture was extracted with ethyl acetate. The organic phase was dried over sodium sulphate and concentrated. The residue was purified by prep. HPLC. This gave 4 g (71% of theory) of the title compound.

2.96 g (25.96 mmol) of trifluoroacetic acid were added to a solution of 3-(5-{2-[(tert-butoxycarbonyl)amino]ethyl}-1,2,4-oxadiazol-3-yl)propanoic acid (2.0 g, 7.01 mmol) in 30 ml of dichloromethane. The reaction mixture was stirred at room temperature for 1 h. Water was added and the mixture was extracted with dichloromethane. The organic phase was dried over sodium sulphate and concentrated. The residue was used without further purification. This gave 1.50 g (72% of theory) of the title compound.

1.30 g (5.52 mmol) of 1-[2-(2,5-dioxopyrrolidin-1-yl)-2-oxoethyl]-1-pyrrole-2,5-dione and 1.52 g (15.04 mmol) of triethylamine were added to a solution of 3-[5-(2-aminoethyl)-1,2,4-oxadiazol-3-yl]propanoic acid (1.5 g, 5.01 mmol) in 25 ml of DMF. The reaction mixture was stirred at RT for 1 h. Water was added and the mixture was extracted with dichloromethane. The organic phase was dried over sodium sulphate and concentrated. The residue was purified by prep. HPLC. This gave 774 mg (47% of theory) of the title compound.

$^1$H-NMR (300 MHz, DMSO-d$_6$): δ [ppm]=2.67 (t, 2H), 2.91 (t, 2H), 3.03 (t, 2H), 3.46 (q, 2H), 4.28 (s, 2H), 7.01 (s, 2H), 8.37 (t, 1H), 12.28 (bs, 1H).

Intermediate L123 tert-Butyl [1-fluoro-4-oxobutan-2-yl]carbamate

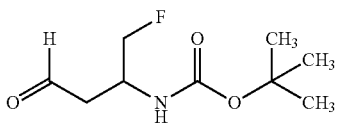

Under argon, ethyl 3-[(tert-butoxycarbonyl)amino]-4-fluorobutanoate (150 mg, 602 µmol) (Synth. Com., 1985, 15(5), 377) was initially charged in 12.0 ml of DCM. The reaction mixture was cooled to −78° C., diisobutylaluminum hydride 1M in toluene (1.2 ml, 1.0 M, 1.2 mmol) was added and the mixture was stirred for 2 hours. The mixture was carefully quenched with methanol, stirred for another 10 min and diluted with ethyl acetate. The organic phase was extracted three times with sat. potassium sodium tartrate solution. The organic phase was washed once with sat. NaCl solution and dried over magnesium sulphate. The solvent was evaporated under reduced pressure and the residue was dried under high vacuum. This gave 86.1 mg (67% of theory) of the title compound.

$^1$H-NMR (400 MHz, DMSO-d6) δ[ppm]: 1.37 (s, 9H), 2.58 (m, 2H), 4.18 (m, 1H), 4.31 (dd, 2H), 7.05 (d, 1H), 9.60 (s, 1H)

Intermediate L124 tert-Butyl N-{(2R)-2-amino-3-oxo-3-[2-(trimethylsilyl)ethoxy]propyl}-N -(tert-butoxycarbonyl)-L-aspartate

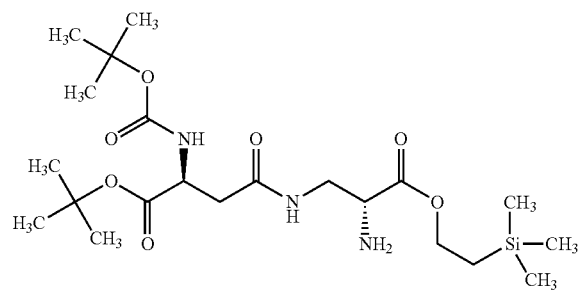 [SMILES: CC(C)(C)OC(=O)N[C@@H](CC(=O)NC[C@@H](N)C(=O)OCC[Si](C)(C)C)C(=O)OC(C)(C)C]

4.0 g (13.8 mmol) of Boc-Asp-OtBu and 1.8 g (15.2 mmol) of N-hydroxysuccinimide were dissolved in 100 ml of ethyl acetate, and 3.1 g (15.2 mmol) of 1,3-dicyclohexylcarbodiimide were added at 0° C. The reaction mixture was stirred at 0° C. for 2 hours and then at RT overnight. The reaction mixture was subsequently filtered and concentrated under reduced pressure. This gave 4.1 g (77% of theory) of the compound 1-tert-butyl 4-(2,5-dioxopyrrolidin-1-yl)-N-(tert-butoxycarbonyl)-L-aspartate.

3-Amino-N-[(benzyloxy)carbonyl]-D-alanine (2.53 g, 10.6 mmol) was dissolved in 30 ml of DMF, and N,N-diisopropylethylamine (2.74 g, 21.2 mmol) and 1-tert-butyl 4-(2,5-dioxopyrrolidin-1-yl)-N-(tert-butoxycarbonyl)-L-aspartate (4.10 g, 10.6 mmol) were added. The reaction mixture was stirred at RT overnight and concentrated under reduced pressure. This gave 4.9 g (90% of theory) of the compound (2R)-2-{[(benzyloxy)carbonyl]amino}-3-({(3S)-4-tert-butoxy-3-[(tert-butoxycarbonyl)amino]-4-oxobutanoyl}amino)propanoic acid.

(2R)-2-{[(Benzyloxy)carbonyl]amino}-3-({(3S)-4-tert-butoxy-3-[(tert-butoxycarbonyl)amino]-4-oxobutanoyl}amino)propanoic acid (4.90 g, 9.62 mmol) was dissolved in 100 ml of acetonitrile, and pyridine (1.6 ml, 19 mmol), 2-(trimethylsilyl)ethanol (1.7 ml, 12 mmol) and dicyclohexylcarbodiimide (2.38 g, 11.5 mmol) were added at RT. The reaction mixture was stirred at 0° C. for 1 hour and then at RT overnight. The reaction mixture was subsequently filtered and concentrated under reduced pressure. The residue was purified by prep. RP-HPLC. The solvents were evaporated under reduced pressure and the residue was dried under high vacuum. This gave 3.9 g (66% of theory) of the compound tert-butyl N-{(2R)-2-{[(benzyloxy)carbonyl]amino}-3-oxo-3-[2-(trimethylsilyl)ethoxy]propyl}-N2-(tert-butoxycarbonyl)-L-aspartate. tert-Butyl N-{(2R)-2-{[(benzyloxy)carbonyl]amino}-3-oxo-3-[2-(trimethylsilyl)ethoxy]propyl}-N$^2$-(tert-butoxycarbonyl)-L-aspartate (3.80 g, 6.23 mmol) was dissolved in 120 ml of methanol, and 380 mg of palladium on carbon (10%) were added. The reaction mixture was hydrogenated at RT with hydrogen under standard pressure for 2 hours and then filtered. The solvent was removed under reduced pressure. This gave 2.9 g (84% of theory) of the title compound $^1$H-NMR (400 MHz, DMSO-d$_6$): δ[ppm]=0.04 (s, 9H), 0.97 (m, 2H), 1.38 (s, 9H), 1.39 (s, 9H), 1.89 (bs, 2H), 2.43 (m, 1H), 3.18 (m, 3H), 3.38 (m, 1H), 4.11 (m, 3H), 6.93 (d, 1H), 7.91 (bt, 1H)

Intermediate L125

Trifluoroacetic acid/tert-butyl-N-(2-aminoethyl)-N$^2$-(bromoacetyl)-D-alpha-glutaminate (1:1)

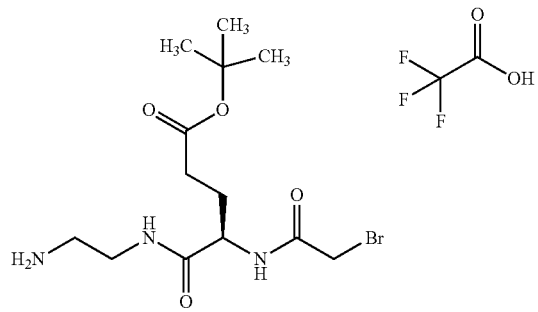 [SMILES: CC(C)(C)OC(=O)CC[C@@H](NC(=O)CBr)C(=O)NCCN ; O=C(O)C(F)(F)F]

This intermediate was prepared starting with (2R)-2-{[(benzyloxy)carbonyl]amino}-5-tert-butoxy-5-oxopentanoic acid and tert-butyl (2-aminoethyl)carbamate by classical methods of peptide chemistry.

LC-MS (Method 1): R$_t$=0.49 min; MS (ESIpos): m/z=366 und 368 (M+H)$^+$.

Intermediate F104

Trifluoroacetic acid/(2S)-2-amino-4-[{(1R)-1-[1-benzyl-4-(2,5-difluorophenyl)-1H-pyrrol-2-yl]-2,2-dimethylpropyl}(glycoloyl)amino]-N-(2-{[(2,5-dioxo-2,5-dihydro-1H-pyrrol-1-yl)acetyl]amino}ethyl)butanamide (1:1)

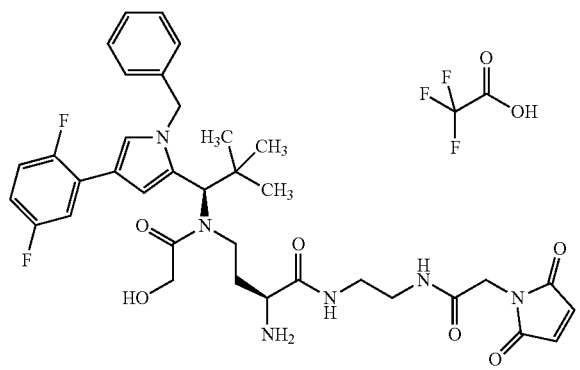 [SMILES: CC(C)(C)[C@H](c1cc(-c2cc(F)ccc2F)cn1Cc1ccccc1)N(CC[C@H](N)C(=O)NCCNC(=O)CN1C(=O)C=CC1=O)C(=O)CO ; O=C(O)C(F)(F)F]
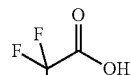

10 mg (0.014 mmol) of Intermediate C53 were dissolved in 3.3 ml of DMF, and 8.5 mg (0.027 mmol) of Intermediate L1, 7.8 mg (0.02 mmol) of HATU and 12 µl of N,N-diisopropylethylamine were added. The reaction was stirred at RT for 15 min and then concentrated. The residue was purified by preparative HPLC giving, after lyophilization, 5.6 mg (38% of theory) of the protected intermediate.

LC-MS (Method 1): $R_t$=1.32 min; MS (ESIpos): m/z=915 (M+H)$^+$.

5.6 mg (0.006 mmol) of this intermediate were taken up in 2 ml of DMF, and 69 mg (0.61 mmol) of 1,4-diazabicyclo[2.2.2]octane were added. The reaction was treated in an ultrasonic bath for 2 h. 35 µl of acetic acid were then added and the reaction was concentrated under high vacuum. The residue was purified by preparative HPLC. This gave 2.4 mg (48% of theory) of the title compound.

LC-MS (Method 1): $R_t$=0.84 min; MS (EIpos): m/z=693 [M+H]$^+$.

HPLC (Method 11): $R_t$=1.91 min;

Alternatively, the title compound was also prepared from Intermediate C58. 15 mg (0.023 mmol) of Intermediate C58 were initially reacted with 11 mg (0.036 mmol) of Intermediate L1 in the presence of 13 mg (0.034 mmol) of HATU and 10 µl of N,N-diisopropylethylamine. After 60 min of stirring at RT, the mixture was concentrated and the residue was purified by preparative HPLC. This gave 12.3 mg (63% of theory) of the protected intermediate.

LC-MS (Method 1): $R_t$=1.3 min; MS (EIpos): m/z=837 [M+H]$^+$.

In the second step, this intermediate was dissolved in 3 ml of 2,2,2-trifluoroethanol. 12 mg (0.088 mmol) of zinc chloride were added, and the reaction was stirred at 50° C. for 2 h. 26 mg (0.088 mmol) of ethylenediamine-N,N,N',N'-tetraacetic acid and 2 ml of a 0.1% strength aqueous trifluoroacetic acid solution were then added. The reaction was purified by preparative HPLC. Concentration of the appropriate fractions and lyophilization of the residue from acetonitrile/water gave 8.1 mg (68% of theory) of the title compound.

LC-MS (Method 1): $R_t$=0.89 min; MS (ESIpos): m/z=693 (M+H)$^+$.

Intermediate F119

Trifluoroacetic acid/(2S)-2-amino-4-[{(1R)-1-[1-benzyl-4-(2,5-difluorophenyl)-1H-pyrrol-2-yl]-2,2-dimethylpropyl}(glycoloyl)amino]-N-{2-[(bromoacetyl)amino]ethyl}butanamide (1:1)

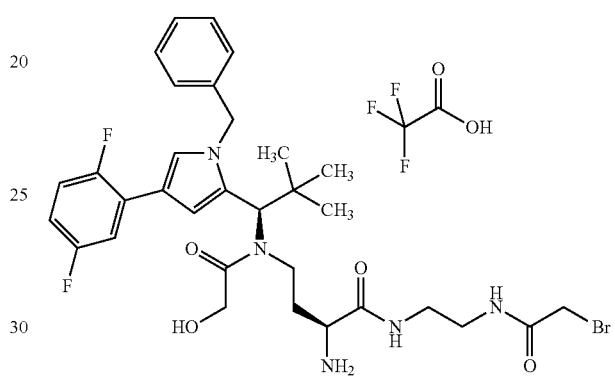

29 mg (0.044 mmol) of Intermediate C58 were taken up in 3.4 ml of DMF, and 36 mg (0.087 mmol) of Intermediate L52, 25 mg (0.065 mmol) of HATU and 19 µl of N,N-diisopropylethylamine were added. After 60 min of stirring at RT, the mixture was concentrated and the residue was purified by preparative HPLC. This gave 26.4 mg (73% of theory) of the intermediate.

LC-MS (Method 1): $R_t$=1.34 min; MS (ESIpos): m/z=820 and 822 (M+H)$^+$.

This intermediate was dissolved in 3 ml of 2,2,2-trifluoroethanol. 6.5 mg (0.048 mmol) of zinc chloride were added, and the reaction was stirred at 50° C. for 4 h. 13.9 mg (0.048 mmol) of ethylenediamine-N,N,N',N'-tetraacetic acid and 2 ml of a 0.1% strength aqueous trifluoroacetic acid solution were added. The reaction was purified by preparative HPLC. Concentration of the appropriate fractions and lyophilization of the residue from acetonitrile/water gave 14.4 mg (58% of theory) of the title compound.

LC-MS (Method 1): $R_t$=0.88 min; MS (ESIpos): m/z=676 and 678 (M+H)$^+$.

Intermediate F127

Trifluoroacetic acid/(2S)-2-amino-4-({(1R)-1-[1-benzyl-4-(2,5-difluorophenyl)-1H-pyrrol-2-yl]-2,2-dimethylpropyl}[(2S)-2-methoxypropanoyl]amino)-N-(2-{[(2,5-dioxo-2,5-dihydro-1H-pyrrol-1-yl)acetyl]amino}ethyl)butanamide (1:1)

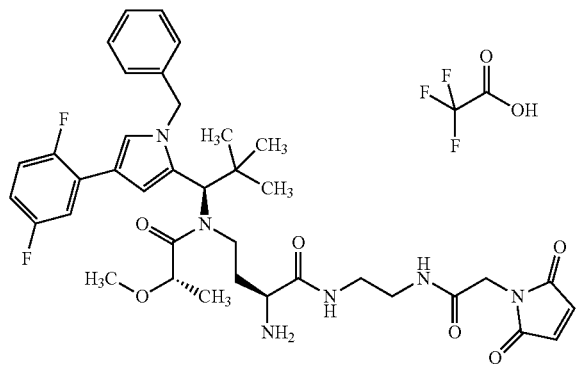 [SMILES: CO[C@@H](C)C(=O)N(CC[C@H](N)C(=O)NCCNC(=O)CN1C(=O)C=CC1=O)[C@@H](c1cc(-c2cc(F)ccc2F)cn1Cc1ccccc1)C(C)(C)C ; O=C(O)C(F)(F)F]

12 mg (0.015 mmol) of Intermediate C59 were dissolved in 2.4 ml of DMF, and 14.6 mg (0.046 mmol) of Intermediate L1, 6 mg (0.031 mmol) of 1-(3-dimethylaminopropyl)-3-ethylcarbodiimide hydrochloride, 5.9 mg (0.039 mmol) of 1-hydroxy-1H-benzotriazole hydrate and 8 µl of N,N-diisopropylethylamine were added. After 1 h of stirring at RT, the mixture was concentrated and the residue was purified by preparative HPLC. This gave 11 mg (70% of theory) of this intermediate.

LC-MS (Method 1): $R_t$=1.34 min; MS (ESIpos): m/z=942 (M+H)$^+$.

11 mg (0.011 mmol) of this intermediate were taken up in 2 ml of DMF, and 123 mg (1.1 mmol) of 1,4-diazabicyclo[2.2.2]octane were added. The reaction was treated in an ultrasonic bath for 2 h. 63 µl of acetic acid were then added and the reaction was concentrated under high vacuum. The residue was purified by preparative HPLC. This gave 2 mg (22% of theory) of the title compound.

LC-MS (Method 1): $R_t$=0.89 min; MS (EIpos): m/z=721 [M+H]$^+$.

HPLC (Method 11): $R_t$=1.95 min;

Intermediate F153

Trifluoroacetic acid/(2S)-2-amino-4-({(1R)-1-[1-benzyl-4-(2,5-difluorophenyl)-1H-pyrrol-2-yl]-2,2-dimethylpropyl}[(2S)-2-hydroxypropanoyl]amino)-N-(2-{[(2,5-dioxo-2,5-dihydro-1H-pyrrol-1-yl)acetyl]amino}ethyl)butanamide (1:1)

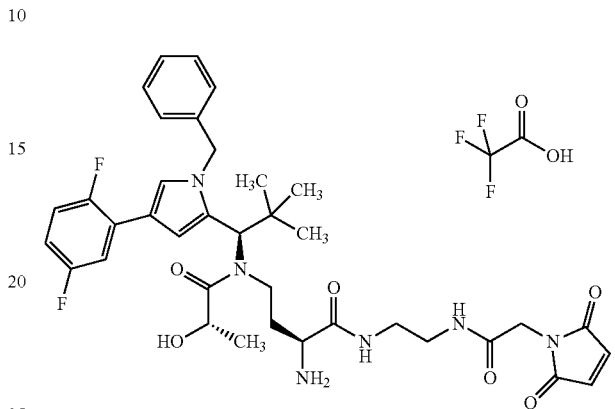

The synthesis was carried out analogously to Intermediate F104 from Intermediate C60.

LC-MS (Method 1): $R_t$=1.1 min; MS (ESIpos): m/z=707 (M+H)$^+$.

Intermediate F155

N$^6$—(N-{(2S)-2-Amino-4-[{(1R)-1-[1-benzyl-4-(2,5-difluorophenyl)-1H-pyrrol-2-yl]-2,2-dimethylpropyl}(glycoloyl)amino]butanoyl}-beta-alanyl)-N$^2$-{N-[6-(2,5-dioxo-2,5-dihydro-1H-pyrrol-1-yl)hexanoyl]-L-valyl-L-alanyl}-L-lysine/trifluoroacetic acid (1:1)

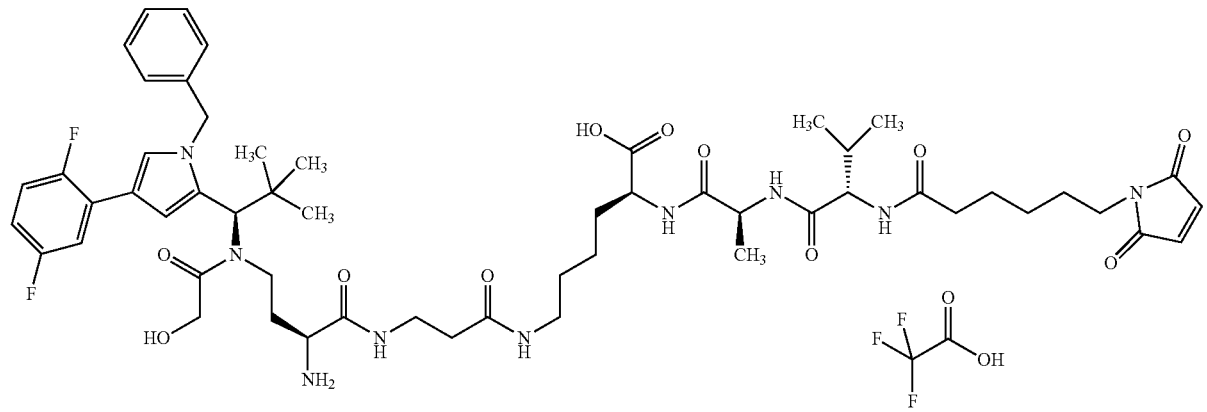 [SMILES: CC(C)[C@H](NC(=O)CCCCCN1C(=O)C=CC1=O)C(=O)N[C@@H](C)C(=O)N[C@@H](CCCCNC(=O)CCNC(=O)[C@@H](N)CCN(C(=O)CO)[C@@H](c1cc(-c2cc(F)ccc2F)cn1Cc1ccccc1)C(C)(C)C)C(=O)O ; O=C(O)C(F)(F)F]

The title compound was prepared by coupling of 14 mg (0.019 mmol) of Intermediate C61 with 15 mg (0.021 mmol) of Intermediate L61 in the presence of 8.7 mg (0.023 mmol) of HATU and 17 μl of N,N-diisopropylethylamine and subsequent deprotection with zinc chloride in trifluoroethanol as described for Intermediate F119. Purification by preparative HPLC gave 13 mg (59% of theory over 2 steps) of the title compound.

LC-MS (Method 1): $R_t$=0.86 min; MS (ESIpos): m/z=1076 (M+H)$^+$.

Intermediate F173

N-[6-(2,5-Dioxo-2,5-dihydro-1H-pyrrol-1-yl)hexanoyl]-L-valyl-L-alanyl-N-[2-({(2S)-2-amino-4-[{(1R)-1-[1-benzyl-4-(2,5-difluorophenyl)-1H-pyrrol-2-yl]-2,2-dimethylpropyl}(glycoloyl)amino]butanoyl}amino)ethyl]-L-glutamine/trifluoroacetic acid (1:1)

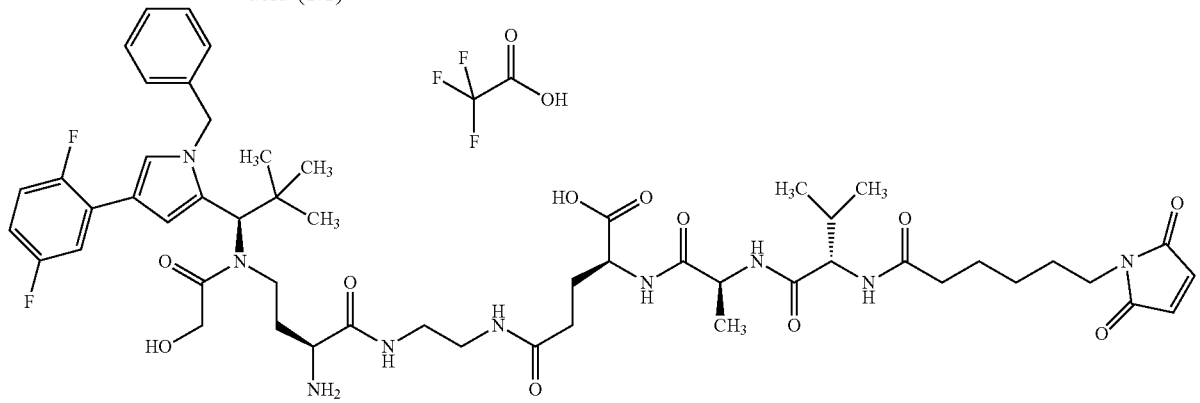

The title compound was prepared from 15 mg (0.018 mmol) of Intermediate C64 by coupling with 12 mg (0.02 mmol) of Intermediate L63 in the presence of 7.7 mg (0.02 mmol) of HATU and 16 μl of N,N-diisopropylethylamine and subsequent deprotection with zinc chloride in trifluoroethanol as described for Intermediate F119. Purification by preparative HPLC gave 12 mg (58% of theory over 2 steps) of the title compound.

LC-MS (Method 1): $R_t$=0.91 min; MS (EIpos): m/z=1048 [M+H]$^+$.

Intermediate F178

Trifluoroacetic acid/(1R,2S)-2-({(2S)-2-amino-4-[{(1R)-1-[1-benzyl-4-(2,5-difluorophenyl)-1H-pyrrol-2-yl]-2,2-dimethylpropyl}(glycoloyl)amino]butanoyl}amino)-N-{2-[(bromoacetyl)amino]ethyl}cyclopentanecarboxamide (1:1)

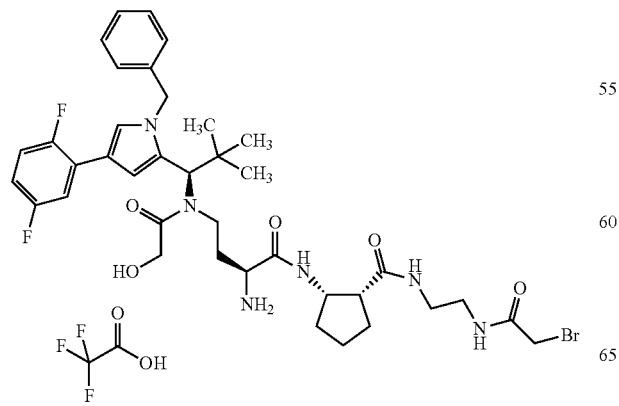

The title compound was prepared analogously to Intermediate F177 using, instead of Intermediate L1, the Intermediate L52.

LC-MS (Method 1): $R_t$=0.89 min; MS (EIpos): m/z=787 and 789 [M+H]$^+$.

Intermediate F180

N-[2-({(2S)-2-Amino-4-[{(1R)-1-[1-benzyl-4-(2,5-difluorophenyl)-1H-pyrrol-2-yl]-2,2-dimethylpropyl}(glycoloyl)amino]butanoyl}amino)ethyl]-N2-[(2,5-dioxo-2,5-dihydro-1H-pyrrol-1-yl)acetyl]-L-glutamine/trifluoroacetic acid (1:1)

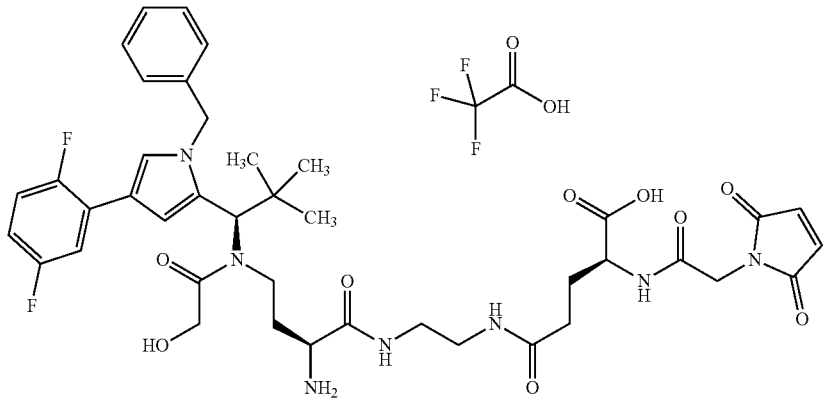 [SMILES: CC(C)(C)[C@H](c1cc(-c2cc(F)ccc2F)cn1Cc1ccccc1)N(CC[C@H](N)C(=O)NCCNC(=O)CC[C@H](NC(=O)CN1C(=O)C=CC1=O)C(=O)O)C(=O)CO ; O=C(O)C(F)(F)F]

The title compound was prepared by coupling of 9.6 mg (0.012 mmol) of Intermediate C64 with 5 mg (0.013 mmol) of Intermediate L64 in the presence of 7 mg (0.018 mmol) of HATU and 6 µl of N,N-diisopropylethylamine and subsequent deprotection with zinc chloride in trifluoroethanol as described for Intermediate F119. Purification by preparative HPLC gave 3.1 mg (28% of theory over 2 steps) of the title compound.

LC-MS (Method 1): $R_t$=0.85 min; MS (EIpos): m/z=822 [M+H]$^+$.

Intermediate F192

N-{(2S)-2-Amino-4-[{(1R)-1-[1-benzyl-4-(2,5-difluorophenyl)-1H-pyrrol-2-yl]-2,2-dimethylpropyl}(glycoloyl)amino]butanoyl}-3-{[(2,5-dioxo-2,5-dihydro-1H-pyrrol-1-yl)acetyl]amino}-L-alanine/trifluoroacetic acid (1:1)

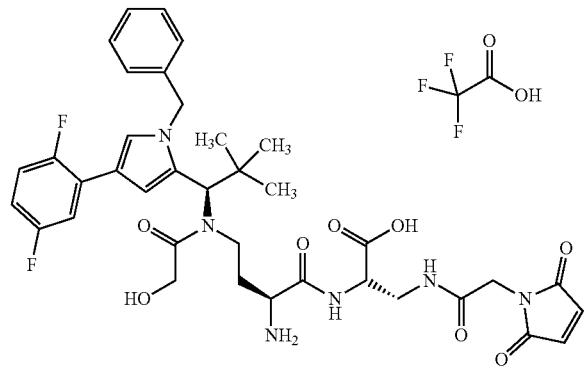

60 mg (0.091 mmol) of Intermediate C58 were taken up in 8 ml of DMF and coupled with 45 mg (0.100 mmol) of Intermediate L65 in the presence of 42 mg (0.11 mmol) of HATU and 64 µl of N,N-diisopropylethylamine. After purification by preparative HPLC, the intermediate was taken up in 10 ml of ethanol and hydrogenated over 10% palladium on activated carbon at RT under hydrogen standard pressure for 45 min. The catalyst was then filtered off, the solvent was removed under reduced pressure and the product was purified by preparative HPLC. Lyophilization from acetonitrile/water 1:1 gave 24.5 mg (31% of theory over 2 steps) of 2-(trimethylsilyl)ethyl 3-amino-N-[(2S)-4-[{(1R)-1-[1-benzyl-4-(2,5-difluorophenyl)-1H-pyrrol-2-yl]-2,2-dimethylpropyl}(glycoloyl)amino]-2-({[2-(trimethylsilyl)ethoxy]carbonyl}amino)butanoyl]-L-alaninate.

LC-MS (Method 1): $R_t$=1.17 min; MS (EIpos): m/z=844 [M+H]$^+$.

The title compound was then prepared by coupling of 10 mg (0.012 mmol) of this intermediate with 2 mg (0.013 mmol) of commercially available (2,5-dioxo-2,5-dihydro-1H-pyrrol-1-yl)acetic acid intermediate in the presence of 5.4 mg (0.014 mmol) of HATU and 8 µl of N,N-diisopropylethylamine and subsequent deprotection with zinc chloride in trifluoroethanol as described for Intermediate F119. Purification by preparative HPLC gave 3.5 mg (33% of theory over 2 steps) of the title compound.

LC-MS (Method 1): $R_t$=0.81 min; MS (ESIpos): m/z=737 (M+H)$^+$.

Intermediate F193

N-{(2S)-2-Amino-4-[{(1R)-1-[1-benzyl-4-(2,5-difluorophenyl)-1H-pyrrol-2-yl]-2,2-dimethylpropyl}(glycoloyl)amino]butanoyl}-3-{[(2,5-dioxo-2,5-dihydro-1H-pyrrol-1-yl)acetyl]amino}-D-alanine/trifluoroacetic acid (1:1)

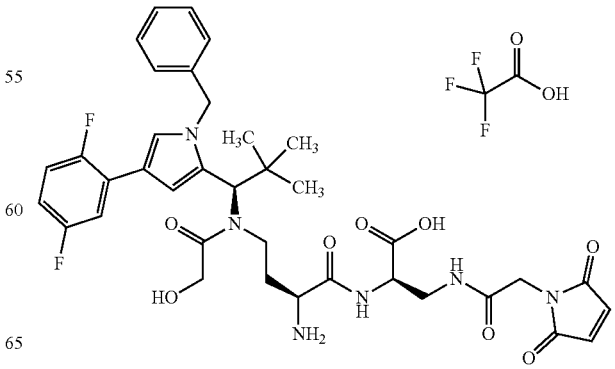

The synthesis of the title compound was carried out analogously to Intermediate F192 from 3-{[(benzyloxy)carbonyl]amino}-N-(tert-butoxycarbonyl)-D-alanine/N-cyclohexylcyclohexanamine (1:1).

LC-MS (Method 1): $R_t$=0.87 min; MS (ESIpos): m/z=737 (M+H)⁺.

Intermediate F194

N-{5-[(2,5-Dioxopyrrolidin-1-yl)oxy]-5-oxopentanoyl}-L-valyl-N-{3-[{(1R)-1-[1-benzyl-4-(2,5-difluorophenyl)-1H-pyrrol-2-yl]-2,2-dimethylpropyl}(glycoloyl)amino]propyl}-L-alaninamide

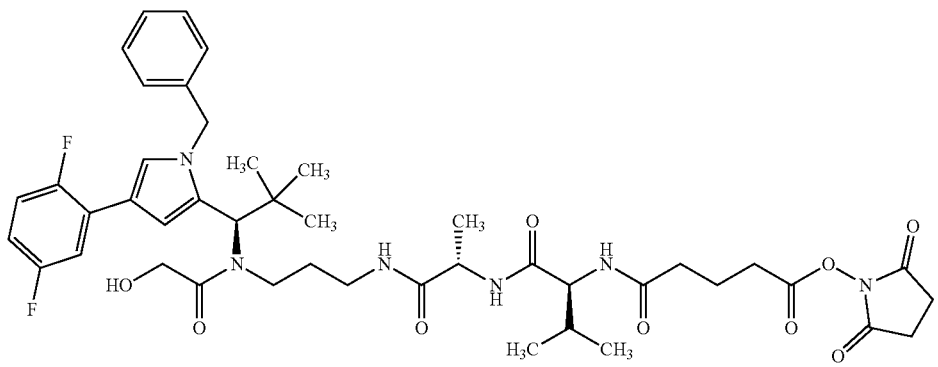 [SMILES: CC(C)[C@H](NC(=O)CCCC(=O)ON1C(=O)CCC1=O)C(=O)N[C@@H](C)C(=O)NCCCN(C(=O)CO)[C@@H](c1cc(-c2cc(F)ccc2F)cn1Cc1ccccc1)C(C)(C)C]

The title compound was prepared from Example M9 first by coupling with N-[(benzyloxy)carbonyl]-L-valyl-L-alanine in the presence of HATU and N,N-diisopropylethylamine. In the next step, the Z protective group was removed by hydrogenating for 1 hour over 10% palladium on activated carbon at RT under hydrogen standard pressure and then converting the deprotected intermediate by reaction with 1,1'-[(1,5-dioxopentane-1,5-diyl)bis(oxy)]dipyrrolidine-2,5-dione into the title compound.

LC-MS (Method 1): $R_t$=1.19 min; MS (ESIpos): m/z=851 [M+H]⁺.

Intermediate F207

N⁶—(N-{(2S)-2-Amino-4-[{(1R)-1-[1-benzyl-4-(2,5-difluorophenyl)-1H-pyrrol-2-yl]-2,2-dimethylpropyl}(glycoloyl)amino]butanoyl}-beta-alanyl)-N²-{N-[(2,5-dioxo-2,5-dihydro-1H-pyrrol-1-yl)acetyl]-L-valyl-L-alanyl}-L-lysine/trifluoroacetic acid (1:1)

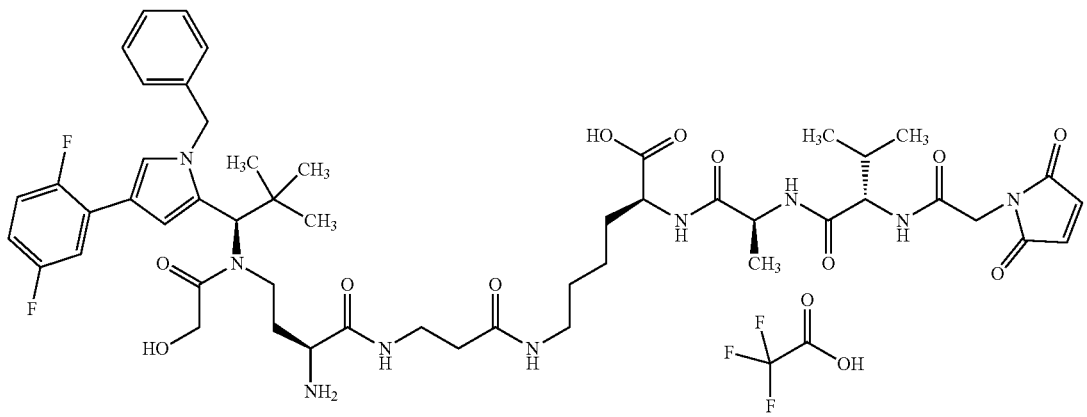

The title compound was prepared analogously to Intermediate F155.

LC-MS (Method 1): $R_t$=0.81 min; MS (ESIpos): m/z=1020 (M+H)⁺.

Intermediate F216

S-{2-[(3-Aminopropyl){(1R)-1-[1-benzyl-4-(2,5-difluorophenyl)-1H-pyrrol-2-yl]-2,2-dimethylpropyl}amino]-2-oxoethyl}-N-[19-(2,5-dioxo-2,5-dihydro-1H-pyrrol-1-yl)-17-oxo-4,7,10,13-tetraoxa-16-azanonadecan-1-oyl]-L-cysteinyl-beta-alanine/trifluoroacetic acid (1:1)

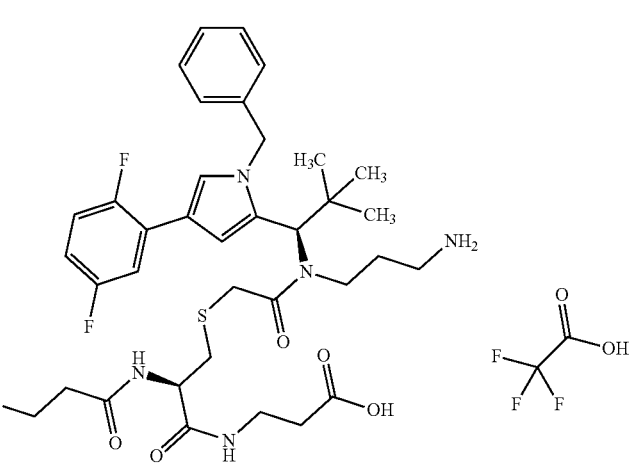

Under argon, 30.2 mg (0.06 mmol) of N,N'-bis[(benzyloxy)carbonyl]-L-cystine were initially charged in 2.0 ml of water and 2.0 ml of isopropanol, and 56.7 mg (0.20 mmol) of TCEP were added. The reaction mixture was stirred at RT for 30 min. 50.0 mg (0.08 mmol) of 2-(trimethylsilyl)ethyl {3-[{(1R)-1-[1-benzyl-4-(2,5-difluorophenyl)-1H-pyrrol-2-yl]-2,2-dimethylpropyl}(chloroacetyl)amino]propyl}carbamate (Intermediate C70), dissolved in 2.0 ml of isopropanol, and 122.2 mg (0.48 mmol) of 1,8-diazabicyclo[5.4.0]undec-7-ene were then added, and the reaction mixture was stirred at 50° C. for 7 h. Another 122.2 mg (0.48 mmol) of 1,8-diazabicyclo[5.4.0]undec-7-ene were then added, and the reaction mixture was stirred at 50° C. for 1 h. The mixture was diluted with ethyl acetate and the organic phase was extracted with water and saturated sodium bicarbonate solution and washed with saturated NaCl solution. The organic phase was dried over magnesium sulphate and the solvent was evaporated under reduced pressure. The residue was purified by preparative RP-HPLC (column: Reprosil 250×30; 10µ, flow rate: 50 ml/min, MeCN/water, 0.1% TFA). The solvents were evaporated under reduced pressure and the residue was dried under high vacuum. This gave 43.1 mg (64% of theory) of the compound S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-N-[(benzyloxy)carbonyl]-L-cysteine.

LC-MS (Method 1): $R_t$=1.46 min; MS (ESIpos): m/z=851 (M+H)⁺.

16.5 mg (0.05 mmol) of 4-methylbenzenesulphonic acid/benzyl beta-alaninate (1:1) were initially charged together with 14.0 mg (0.11 mmol) of N,N-diisopropylethylamine in 1.5 ml of acetonitrile. The reaction mixture was stirred at RT for 3 min, and 30.8 mg (0.04 mmol) of S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-N-[(benzyloxy)carbonyl]-L-cysteine dissolved in 1.5 ml of acetonitrile, 23.4 mg (0.18 mmol) of N,N-diisopropylethylamine and 29.9 mg (0.05 mmol) of T3P (50% in ethyl acetate) were then added. The reaction mixture was stirred at RT overnight. Water was added, and the reaction mixture was purified directly by preparative RP-HPLC (column: Reprosil 250×30; 10µ, flow rate: 50 ml/min, MeCN/water, 0.1% TFA). The solvents were evaporated under reduced pressure and the residue was dried under high vacuum. The compound obtained was benzyl S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-N-[(benzyloxy)carbonyl]-L-cysteinyl-beta-alaninate.

LC-MS (Method 1): $R_t$=1.59 min; MS (ESIpos): m/z=1012 (M+H)⁺.

43.8 mg (43.3 µmol) of benzyl S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-N-[(benzyloxy)carbonyl]-L-cysteinyl-beta-alaninate were dissolved in 8.0 ml of ethanol, 4.4 mg of palladium on activated carbon (10%) were added and the mixture was hydrogenated at RT and standard pressure overnight. The reaction mixture was filtered through a cardboard filter and the filter cake was washed with ethanol. The solvent was evaporated under reduced pressure. Two more times, the residue was treated as just described. The residue was purified by preparative RP-HPLC (column: Reprosil 250×30; 10µ, flow rate: 50 ml/min, MeCN/water, 0.1% TFA). The solvents were evaporated under reduced pressure and the residue was dried under high vacuum. This gave 14.5 mg (37% of theory) of the compound S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-L-cysteinyl-beta-alanine/trifluoroacetic acid (1:1).

LC-MS (Method 1): R$_t$=1.08 min; MS (ESIpos): m/z=788 (M+H)$^+$.

14.5 mg (16.1 μmol) of S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-L-cysteinyl-beta-alanine/trifluoroacetic acid (1:1) were initially charged together with 9.1 mg (17.7 μmol) of 3-(2,5-dioxo-2,5-dihydro-1H-pyrrol-1-yl)-N-{15-[(2,5-dioxopyrrolidin-1-yl)oxy]-15-oxo-3,6,9,12-tetraoxapentadec-1-yl}propanamide in 1.0 ml of DMF, and 4.9 mg (48.2 μmol) of 4-methylmorpholine were added. The reaction mixture was stirred at RT overnight, and 3.4 mg (0.06 mmol) of acetic acid were then added. The reaction mixture was purified directly by preparative RP-HPLC (column: Reprosil 250×30; 10μ, flow rate: 50 ml/min, MeCN/water, 0.1% TFA). The solvents were evaporated under reduced pressure and the residue was dried under high vacuum. This gave 4.9 mg (50% of theory) of the compound S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-L-cysteinyl-beta-alanine/trifluoroacetic acid (1:1).

LC-MS (Method 1): R$_t$=1.28 min; MS (ESIpos): m/z=1186 (M+H)$^+$.

14.1 mg (11.9 μmol) of S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-N-[19-(2,5-dioxo-2,5-dihydro-1H-pyrrol-1-yl)-17-oxo-4,7,10,13-tetraoxa-16-azanonadecan-1-oyl]-L-cysteinyl-beta-alanine/trifluoroacetic acid (1:1) were dissolved in 1.5 ml of trifluoroethanol, and 9.7 mg (71.3 μmol) of zinc dichloride were added. The reaction mixture was stirred at 50° C. for 3 h. Another 9.7 mg (71.3 μmol) of zinc dichloride were added and the reaction mixture was stirred at 50° C. for 3 h. Another 9.7 mg (71.3 μmol) of zinc dichloride were added and the reaction mixture was stirred at 70° C. for 4 h. 20.8 mg (0.07 mmol) of ethylenediamine-N,N,N',N'-tetraacetic acid were added and the reaction mixture was stirred for 10 min, and water (0.1% TFA) was then added. Purification was carried out directly by preparative RP-HPLC (column: Reprosil 125×30; 10μ, flow rate: 50 ml/min, MeCN/water, 0.1% TFA). The solvents were evaporated under reduced pressure and the residue was lyophilized. This gave 6.2 mg (44% of theory) of the title compound.

LC-MS (Method 1): R$_t$=0.82 min; MS (ESIpos): m/z=1042 (M+H)$^+$.

Intermediate F239

S-{2-[(3-Aminopropyl){(1R)-1-[1-benzyl-4-(2,5-difluorophenyl)-1H-pyrrol-2-yl]-2,2-dimethylpropyl}amino]-2-oxoethyl}-N-[(2,5-dioxo-2,5-dihydro-1H-pyrrol-1-yl)acetyl]-L-cysteine/trifluoroacetic acid (1:1)

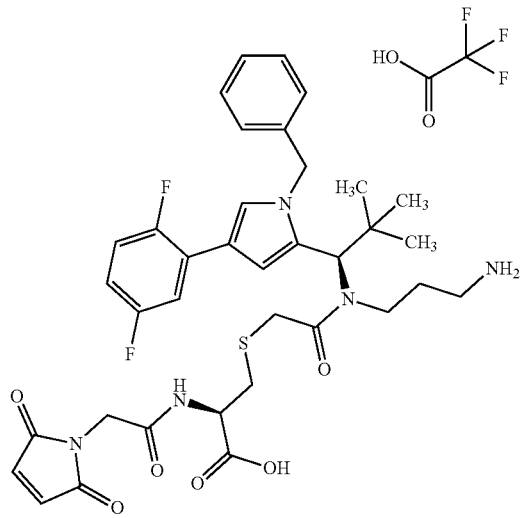 [SMILES: CC(C)(C)[C@H](c1cc(-c2cc(F)ccc2F)cn1Cc1ccccc1)N(CCCN)C(=O)CSC[C@H](NC(=O)CN1C(=O)C=CC1=O)C(=O)O ; O=C(O)C(F)(F)F]

Under argon, 7.5 mg (0.05 mmol) of (2,5-dioxo-2,5-dihydro-1H-pyrrol-1-yl)acetic acid were initially charged in 1.5 ml of DMF, and 7.5 mg (0.05 mmol) of HOBt, 15.5 mg (0.05 mmol) of TBTU and 6.2 mg (0.05 mmol) of N,N-diisopropylethylamine were added. The reaction mixture was stirred at RT for 10 min. 40.0 mg (0.05 mmol) of S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-L-cysteine/trifluoroacetic acid (1:1) (Intermediate C71), dissolved in 1.5 ml of DMF, and 18.7 mg (0.14 mmol) of N,N-diisopropylethylamine were then added, and the reaction mixture was stirred at RT overnight. The reaction mixture was purified directly by preparative RP-HPLC (column: Reprosil 250×30; 10μ, flow rate: 50 ml/min, MeCN/water, 0.1% TFA). The solvents were evaporated under reduced pressure and the residue was dried under high vacuum. This gave 11.2 mg (25% of theory) of the compound S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-N-[(2,5-dioxo-2,5-dihydro-1H-pyrrol-1-yl)acetyl]-L-cysteine.

LC-MS (Method 1): R$_t$=1.37 min; MS (ESIpos): m/z=854 (M+H)$^+$.

10.9 mg (12.8 μmol) of S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-N-[(2,5-dioxo-2,5-dihydro-1H-pyrrol-1-yl)acetyl]-L-cysteine were dissolved in 2.0 ml of trifluoroethanol, and 10.4 mg (76.6 μmol) zinc dichloride were added. The reaction mixture was stirred at 50° C. for 4 h. 22.4 mg (0.08 mmol) of ethylenediamine-N,N,N',N'-tetraacetic acid were added, the reaction mixture was stirred for 10 min and water (0.1% TFA) was then added. Purification was carried out directly by preparative RP-HPLC (column: Reprosil 250×30; 10μ, flow rate: 50 ml/min, MeCN/water, 0.1% TFA). The solvents were evaporated under reduced pressure and the residue was lyophilized. This gave 7.5 mg (65% of theory) of the title compound.

LC-MS (Method 1): R$_t$=0.92 min; MS (ESIpos): m/z=710 (M+H)$^+$.

Intermediate F240

Trifluoroacetic acid/3-({2-[(3-aminopropyl){(1R)-1-[1-benzyl-4-(2,5-difluorophenyl)-1H-pyrrol-2-yl]-2,2-dimethylpropyl}amino]-2-oxoethyl}sulphanyl)-N-(2-{[(2,5-dioxo-2,5-dihydro-1H-pyrrol-1-yl)acetyl]amino}ethyl)propanamide (1:1)

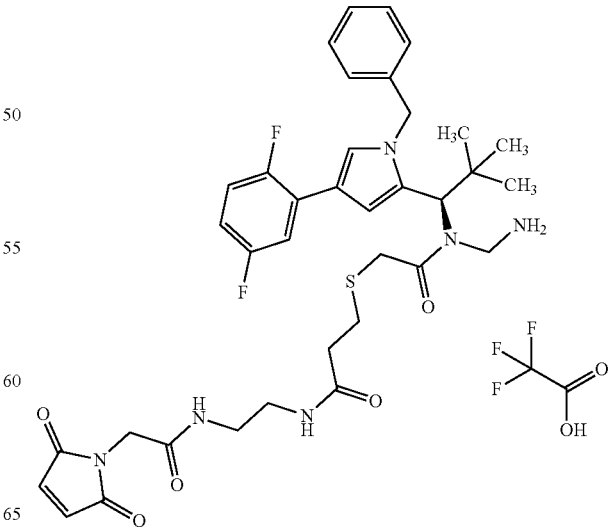

27.5 mg (0.04 mmol) of 11-{(1R)-1-[1-benzyl-4-(2,5-difluorophenyl)-1H-pyrrol-2-yl]-2,2-dimethylpropyl}-2,2-dimethyl-6,12-dioxo-5-oxa-14-thia-7,11-diaza-2-silaheptadecan-17-oic acid (Intermediate C69) were initially charged together with 15.9 mg (0.05 mmol) of trifluoroacetic acid/N-(2-aminoethyl)-2-(2,5-dioxo-2,5-dihydro-1H-pyrrol-1-yl)acetamide (1:1) (Intermediate L1) in 1.8 ml of acetonitrile. 32.4 mg (0.31 mmol) of N,N-diisopropylethylamine were then added, and 32.4 mg (0.05 mmol) of T3P (50% in ethyl acetate) were added dropwise. The reaction mixture was stirred at RT overnight. The reaction mixture was purified directly by preparative RP-HPLC (column: Reprosil 125×30; 10μ, flow rate: 50 ml/min, MeCN/water). The solvents were evaporated under reduced pressure and the residue was dried under high vacuum. This gave 11.9 mg (35% of theory) of the compound 2-(trimethylsilyl)ethyl [13-{(1R)-1-[1-benzyl-4-(2,5-difluorophenyl)-1H-pyrrol-2-yl]-2,2-dimethylpropyl}-1-(2,5-dioxo-2,5-dihydro-1H-pyrrol-1-yl)-2,7,12-trioxo-10-thia-3,6,13-triazahexadecan-16-yl]carbamate.

LC-MS (Method 1): $R_t$=1.39 min; MS (ESIpos): m/z=881 $(M+H)^+$.

11.9 mg (0.01 mol) of 2-(trimethylsilyl)ethyl [13-{(1R)-1-[1-benzyl-4-(2,5-difluorophenyl)-1H-pyrrol-2-yl]-2,2-dimethylpropyl}-1-(2,5-dioxo-2,5-dihydro-1H-pyrrol-1-yl)-2,7,12-trioxo-10-thia-3,6,13-triazahexadecan-16-yl]carbamate were dissolved in 1.0 ml of trifluoroethanol, and 5.5 mg (0.04 mmol) of zinc dichloride were added. The reaction mixture was stirred at 50° C. overnight. 11.8 mg (0.04 mmol) of ethylenediamine-N,N,N',N'-tetraacetic acid were added, the reaction mixture was stirred for 10 min and water (0.1% TFA) was then added. Purification was carried out directly by preparative RP-HPLC (column: Reprosil 125×30; 10μ, flow rate: 50 ml/min, MeCN/water, 0.1% TFA). The solvents were evaporated under reduced pressure and the residue was dried under high vacuum. This gave 7.4 mg (60% of theory) of the title compound.

LC-MS (Method 5): $R_t$=2.75 min; MS (ESIpos): m/z=737 $(M+H)^+$.

Intermediate F241

Trifluoroacetic acid/(2S)-2-amino-4-[{(1R)-1-[1-benzyl-4-(2,5-difluorophenyl)-1H-pyrrol-2-yl]-2,2-dimethylpropyl}(glycoloyl)amino]-N-(2-{[N-(bromoacetyl)glycyl]amino}ethyl)butanamide (1:1)

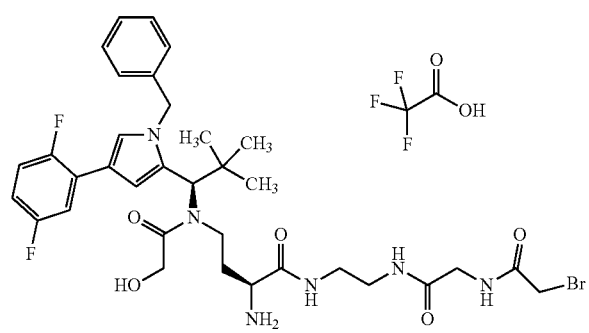 [SMILES: CC(C)(C)[C@H](c1cc(-c2cc(F)ccc2F)cn1Cc1ccccc1)N(CC[C@H](N)C(=O)NCCNC(=O)CNC(=O)CBr)C(=O)CO ; O=C(O)C(F)(F)F]

The title compound was prepared from Intermediate C66 by coupling with commercially available 1-(2-bromoacetoxy)pyrrolidine-2,5-dione and subsequent deblocking with zinc chloride.

LC-MS (Method 1): $R_t$=0.84 min; MS (EIpos): m/z=733 and 735 $[M+H]^+$.

Intermediate F242

Trifluoroacetic acid/(2S)-2-amino-4-[{(1R)-1-[1-benzyl-4-(2,5-difluorophenyl)-1H-pyrrol-2-yl]-2,2-dimethylpropyl}(glycoloyl)amino]-N-(3-{[(2,5-dioxo-2,5-dihydro-1H-pyrrol-1-yl)acetyl]amino}propyl)butanamide (1:1)

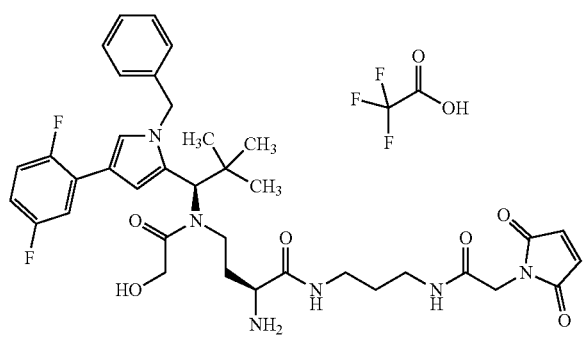 [SMILES: CC(C)(C)[C@H](c1cc(-c2cc(F)ccc2F)cn1Cc1ccccc1)N(CC[C@H](N)C(=O)NCCCNC(=O)CN1C(=O)C=CC1=O)C(=O)CO ; O=C(O)C(F)(F)F]

The synthesis of the title compound was carried out analogously to Intermediate F104.

LC-MS (Method 1): $R_t$=0.84 min; MS (ESIpos): m/z=707 $(M+H)^+$.

Intermediate F243

Trifluoroacetic acid/(2S)-2-amino-4-[{(1R)-1-[1-benzyl-4-(2,5-difluorophenyl)-1H-pyrrol-2-yl]-2,2-dimethylpropyl}(glycoloyl)amino]-N-[2-(2-{[(2,5-dioxo-2,5-dihydro-1H-pyrrol-1-yl)acetyl]amino}ethoxy)ethyl]butanamide (1:1)

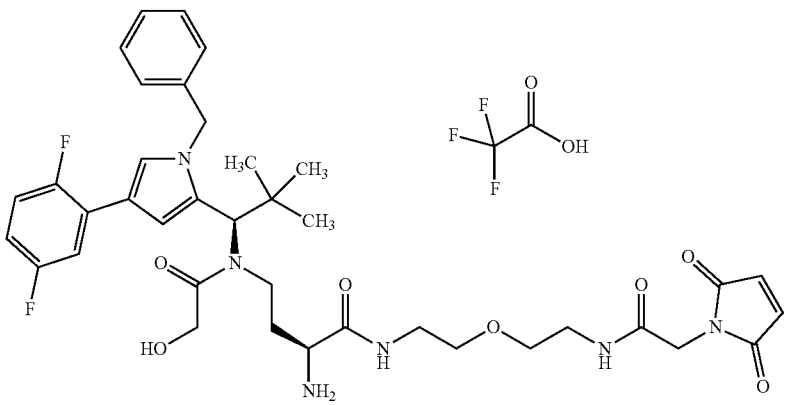 [SMILES: CC(C)(C)[C@H](c1cc(-c2cc(F)ccc2F)cn1Cc1ccccc1)N(CC[C@H](N)C(=O)NCCOCCNC(=O)CN1C(=O)C=CC1=O)C(=O)CO ; O=C(O)C(F)(F)F]

The synthesis of the title compound was carried out analogously to Intermediate F242.

LC-MS (Method 1): $R_t$=0.81 min; MS (ESIpos): m/z=737 (M+H)$^+$.

Intermediate F245

Trifluoroacetic acid/N-({(2S)-2-amino-4-[{(1R)-1-[1-benzyl-4-(2,5-difluorophenyl)-1H-pyrrol-2-yl]-2,2-dimethylpropyl}(glycoloyl)amino]butyl}-N'-(2-{[(2,5-dioxo-2,5-dihydro-1H-pyrrol-1-yl)acetyl]amino}ethyl)succinamide (1:1)

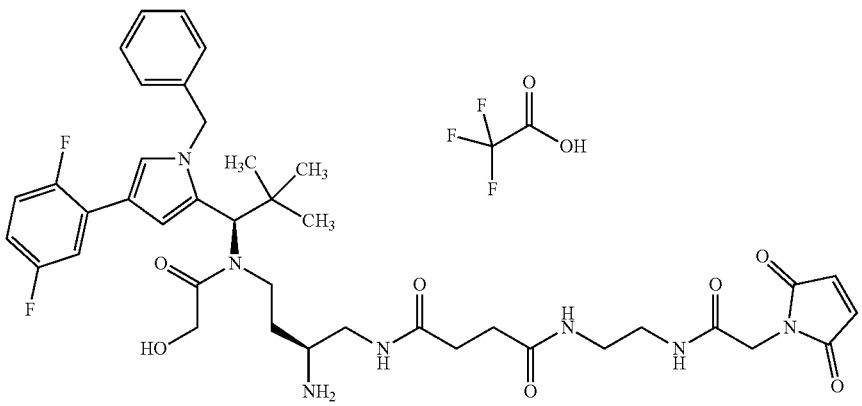 [SMILES: CC(C)(C)[C@H](c1cc(-c2cc(F)ccc2F)cn1Cc1ccccc1)N(CC[C@H](N)CNC(=O)CCC(=O)NCCNC(=O)CN1C(=O)C=CC1=O)C(=O)CO ; O=C(O)C(F)(F)F]

The title compound was prepared by coupling of 10 mg (0.0135 mmol) of Intermediate C65 with 8 mg (0.027 mmol) of Intermediate L1 in 8 ml of DMF in the presence of 15 mg (0.04 mmol) of HATU and 9 μl of N,N-diisopropylethylamine and subsequent deprotection with zinc chloride in trifluoroethanol as described for Intermediate F119. Purification by preparative HPLC gave 8.8 mg (58% of theory over 2 steps) of the title compound.

LC-MS (Method 1): $R_t$=0.84 min; MS (ESIpos): m/z=778 (M+H)$^+$.

Intermediate F247

Trifluoroacetic acid/methyl 4-[(2-{[2-({(2S)-2-amino-4-[{(1R)-1-[1-benzyl-4-(2,5-difluorophenyl)-1H-pyrrol-2-yl]-2,2-dimethylpropyl}(glycoloyl)amino]butanoyl}amino)ethyl]amino}-2-oxoethyl)amino]-2-bromo-4-oxobutanoate (1:1)

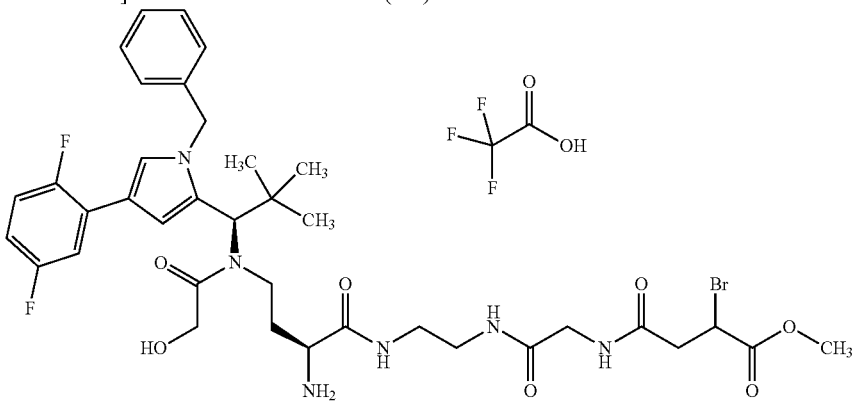

14 mg (0.018 mmol) of Intermediate C66 were dissolved in 14 ml of DCM, and with 10.1 mg (0.037 mmol) of 2-bromo-1-ethylpyridinium tetrafluoroborate (BEP) and, a little at a time, a total of 250 µl of pyridine were added, the pH being kept between 5 and 6. The pH was then adjusted to 4 with acetic acid, the reaction was concentrated and the residue was purified by preparative HPLC. Combination of the appropriate fractions, lyophilization and drying gave 4 mg (21% of theory) of the protected intermediate, which were then deprotected at the amino function with zinc chloride. HPLC purification and lyophilization gave 3 mg (72% of theory) of the title compound as a colourless foam.

LC-MS (Method 1): $R_t$=0.88 min; MS (ESIpos): m/z=805 and 807 (M+H)$^+$.

Intermediate F248

Trifluoroacetic acid/(2S)-2-amino-4-[{(1R)-1-[1-benzyl-4-(2,5-difluorophenyl)-1H-pyrrol-2-yl]-2,2-dimethylpropyl}(glycoloyl)amino]-N-{2-[2-(2,5-dioxo-2,5-dihydro-1H-pyrrol-1-yl)ethoxy]ethyl}butanamide (1:1)

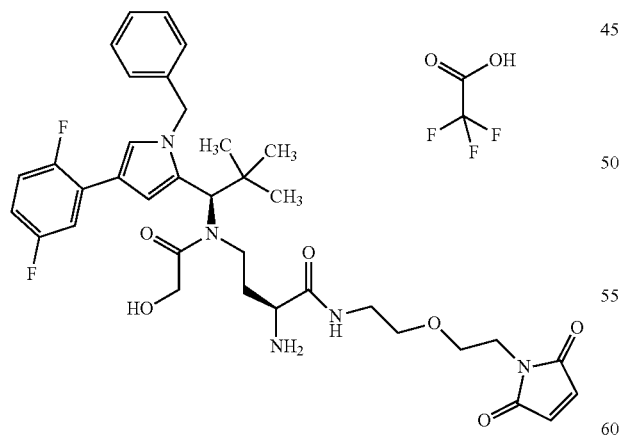

The title compound was prepared by coupling of 10 mg (0.015 mmol) of Intermediate C58 with 5 mg (0.017 mmol) of Intermediate L12 in the presence of HATU and subsequent deprotection with zinc chloride. This gave 6.5 mg (52% of theory over 2 steps) of the title compound.

LC-MS (Method 1): $R_t$=0.91 min; MS (ESIpos): m/z=680 (M+H)$^+$.

Intermediate F254

Trifluoroacetic acid/methyl (3S)-4-[(2-{[2-({(2S)-2-amino-4-[{(1R)-1-[1-benzyl-4-(2,5-difluorophenyl)-1H-pyrrol-2-yl]-2,2-dimethylpropyl}(glycoloyl)amino]butanoyl}amino)ethyl]amino}-2-oxoethyl)amino]-3-bromo-4-oxobutanoate (1:1)

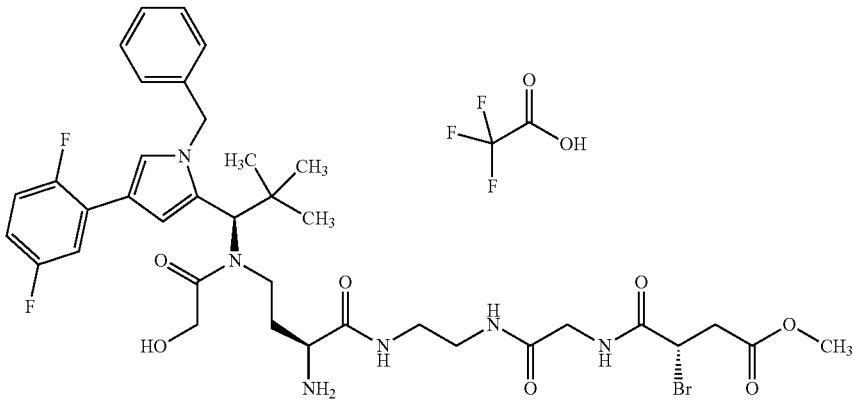 [SMILES: COC(=O)C[C@H](Br)C(=O)NCC(=O)NCCNC(=O)[C@@H](N)CCN(C(=O)CO)[C@@H](c1cc(-c2cc(F)ccc2F)cn1Cc1ccccc1)C(C)(C)C ; O=C(O)C(F)(F)F]

The title compound was prepared analogously to Intermediate 247 by coupling of 15 mg (0.02 mmol) of Intermediate C66 with 21 mg (0.099 mmol) of (2S)-2-bromo-4-methoxy-4-oxobutanoic acid which had been synthesized as described in (J. Org. Chem. 200, 65, 517-522) from (2S)-2-amino-4-methoxy-4-oxobutanoic acid hydrochloride (1:1).

LC-MS (Method 1): $R_t$=0.89 min; MS (ESIpos): m/z=805 and 807 (M+H)$^+$.

Intermediate F255

R/S—(N-[19-(2,5-Dioxo-2,5-dihydro-1H-pyrrol-1-yl)-17-oxo-4,7,10,13-tetraoxa-16-azanonadecan-1-oyl]-L-alpha-glutamyl-S-{2-[(3-aminopropyl){(1R)-1-[1-benzyl-4-(2,5-difluorophenyl)-1H-pyrrol-2-yl]-2,2-dimethylpropyl}amino]-2-oxoethyl})homocysteine/trifluoroacetic acid (1:1)

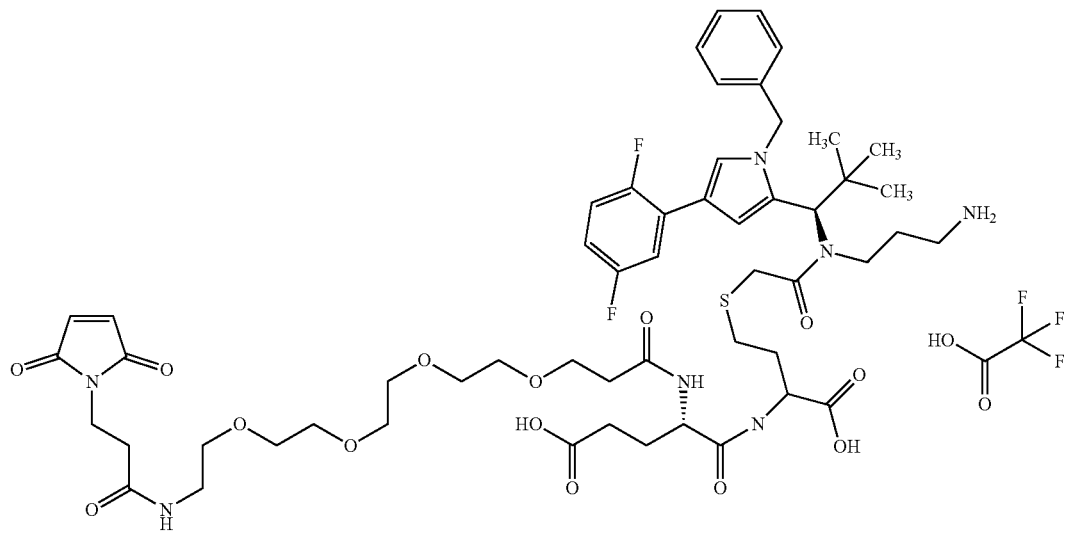 [SMILES: CC(C)(C)[C@H](c1cc(-c2cc(F)ccc2F)cn1Cc1ccccc1)N(CCCN)C(=O)CSCCC(NC(=O)[C@H](CCC(=O)O)NC(=O)CCOCCOCCOCCOCCNC(=O)CCN1C(=O)C=CC1=O)C(=O)O ; O=C(O)C(F)(F)F]

13.1 mg (0.04 mmol) of (2S)-5-(benzyloxy)-2-{[(benzyloxy)carbonyl]amino}-5-oxopentanoic acid were initially charged in 1.0 ml of DMF, and 5.4 mg (0.04 mmol) of HOBt, 11.4 mg (0.04 mmol) of TBTU and 4.6 mg (0.04 mmol) of N,N-diisopropylethylamine were added. The reaction mixture was stirred at RT for 10 min. 30.0 mg (0.04 mmol) of R/S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)homocysteine/trifluoroacetic acid (1:1) (Intermediate C11) dissolved in 12.9 mg (0.1 mmol) of N,N-diisopropylethylamine and 1 ml of DMF were then added. The reaction mixture was stirred at RT overnight. The reaction mixture was purified directly by preparative RP-HPLC (column: Reprosil 250×30; 10μ, flow rate: 50 ml/min, MeCN/water, 0.1% TFA). The solvents were evaporated under reduced pressure and the residue was dried under high vacuum. This gave 32 mg (73%) of the compound 4-[2-[[(1R)-1-[1-benzyl-4-(2,5-difluorophenyl)pyrrol-2-yl]-2,2-dimethylpropyl]-[3-(2-trimethylsilylethoxycarbonylamino)propyl]amino]-2-oxoethyl]sulphanyl-2-[[(2S)-5-benzyloxy-2-(benzyloxycarbonylamino)-5-oxo-pentanoyl]amino]butanoic acid.

LC-MS (Method 1): $R_t$=1.53 min; MS (ESIpos): m/z=1084 (M+H)$^+$.

41.4 mg (0.038 mmol) of 4-[2-[[(1R)-1-[1-benzyl-4-(2,5-difluorophenyl)pyrrol-2-yl]-2,2-dimethylpropyl]-[3-(2-trimethylsilylethoxycarbonylamino)propyl]amino]-2-oxoethyl]sulphanyl-2-[[(2S)-5-benzyloxy-2-(benzyloxycarbonylamino)-5-oxo-pentanoyl]amino]butanoic acid was dissolved in 10 ml of ethanol, 4.2 mg of Pd/C were added and the mixture was hydrogenated under standard pressure. The reaction mixture was filtered through a cardboard filter and the filter cake was washed with ethanol. The solvent was evaporated under reduced pressure without heating. The residue was purified by preparative RP-HPLC (column: Reprosil 250×40; 10μ, flow rate: 50 ml/min, MeCN/water, 0.1% TFA). The solvents were evaporated under reduced pressure and the residue was dried under high vacuum. This gave 21.1 mg (56%) of the compound R/S-(L-alpha-glutamyl-S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)homocysteine/trifluoroacetic acid (1:1).

LC-MS (Method 1): $R_t$=1.11 min; MS (ESIpos): m/z=860 (M+H)$^+$.

20.4 mg (20.94 μmol) of R/S-(L-alpha-glutamyl-S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl))homocysteine/trifluoroacetic acid (1:1) were initially charged together with 11.8 mg (23.04 μmol) of 3-(2,5-dioxo-2,5-dihydro-1H-pyrrol-1-yl)-N-{15-[(2,5-dioxopyrrolidin-1-yl)oxy]-15-oxo-3,6,9,12-tetraoxapentadec-1-yl}propanamide in 1.0 ml of DMF, and 4.2 mg (41.88 μmol) of 4-methylmorpholine were added. The reaction mixture was stirred at RT overnight, and 3.1 mg (0.05 mmol) of acetic acid were then added. The reaction mixture was purified directly by preparative RP-HPLC (column: Reprosil 250×30; 10μ, flow rate: 50 ml/min, MeCN/water, 0.1% TFA). The solvents were evaporated under reduced pressure and the residue was dried under high vacuum.

This gave 9.5 mg (36%) of the compound R/S—(N-[19-(2,5-dioxo-2,5-dihydro-1H-pyrrol-1-yl)-17-oxo-4,7,10,13-tetraoxa-16-azanonadecan-1-oyl]-L-alpha-glutamyl-S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl))homocysteine.

LC-MS (Method 1): $R_t$=1.66 min; MS (ESIpos): m/z=1259 (M+H)$^+$.

9.4 mg (7.47 μmol) of R/S—(N-[19-(2,5-dioxo-2,5-dihydro-1H-pyrrol-1-yl)-17-oxo-4,7,10,13-tetraoxa-16-azanonadecan-1-oyl]-L-alpha-glutamyl-S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl))homocysteine were dissolved in 1.5 ml of trifluoroethanol, and 6.1 mg (44.81 μmol) of zinc dichloride were added. The reaction mixture was stirred at 50° C. for 3 h. 13.1 mg (0.05 mmol) of ethylenediamine-N,N,N',N'-tetraacetic acid were added, the reaction mixture was stirred for 10 min and water (0.1% TFA) was then added. Purification was carried out directly by preparative RP-HPLC (column: Reprosil 125×30; 10μ, flow rate: 50 ml/min, MeCN/water, 0.1% TFA). The solvents were evaporated under reduced pressure and the residue was dried under high vacuum. This gave 6.9 mg (75%) of the title compound.

LC-MS (Method 1): $R_t$=0.87 min; MS (ESIpos): m/z=1114 (M+H)$^+$.

Intermediate F256

Trifluoroacetic acid/N-({(2S)-2-amino-4-[{(1R)-1-[1-benzyl-4-(2,5-difluorophenyl)-1H-pyrrol-2-yl]-2,2-dimethylpropyl}(glycoloyl)amino]butyl}-N'-[2-(2-{[(2,5-dioxo-2,5-dihydro-1H-pyrrol-1-yl)acetyl]amino}ethoxy)ethyl]succinamide (1:1)

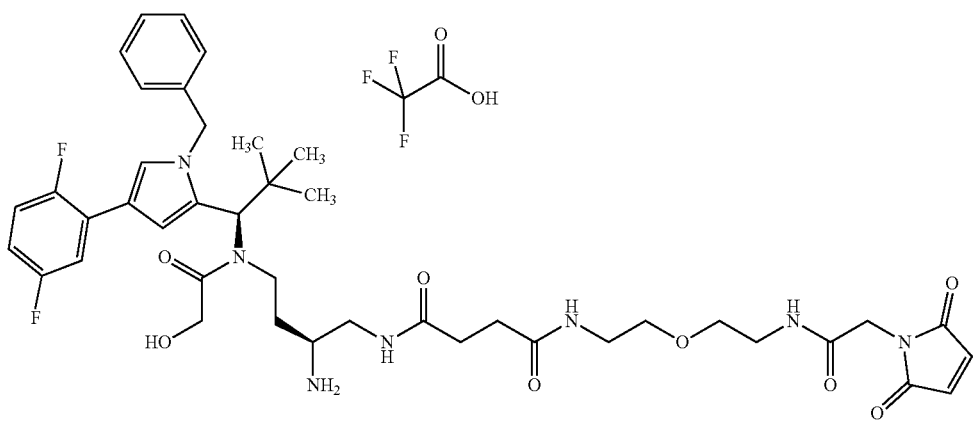 [SMILES: CC(C)(C)[C@H](c1cc(-c2cc(F)ccc2F)cn1Cc1ccccc1)N(CC[C@H](N)CNC(=O)CCC(=O)NCCOCCNC(=O)CN1C(=O)C=CC1=O)C(=O)CO ; O=C(O)C(F)(F)F]

The title compound was prepared by coupling of 10 mg (0.014 mmol) of Intermediate C65 and 9.6 mg (0.027 mmol) of trifluoroacetic acid/N-[2-(2-aminoethoxy)ethyl]-2-(2,5-dioxo-2,5-dihydro-1H-pyrrol-1-yl)acetamide (1:1) in the presence of HATU and N,N-diisopropylethylamine and subsequent deprotection with zinc chloride in trifluoroethanol as described for Intermediate F119. Purification by preparative HPLC gave 8 mg (64% of theory over 2 steps) of the title compound.

LC-MS (Method 1): $R_t$=0.84 min; MS (ESIpos): m/z=822 (M+H)$^+$.

Intermediate F257

R-{2-[(3-Aminopropyl){(1R)-1-[1-benzyl-4-(2,5-difluorophenyl)-1H-pyrrol-2-yl]-2,2-dimethylpropyl}amino]-2-oxoethyl}-N-[18-(2,5-dioxo-2,5-dihydro-1H-pyrrol-1-yl)-17-oxo-4,7,10,13-tetraoxa-16-azaoctadecan-1-oyl]-L-cysteine/trifluoroacetic acid (1:1)

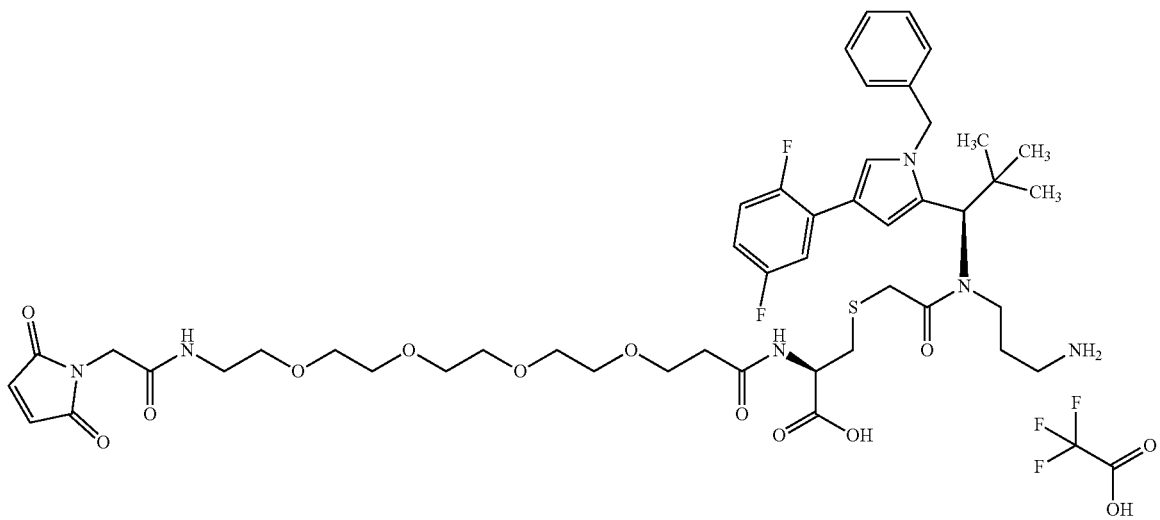

50.0 mg (0.06 mmol) of R-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-L-cysteine/trifluoroacetic acid (1:1) (Intermediate C71) and 29 mg (0.07 mmol) of 3-[2-[2-[2-[2-[[2-(2,5-dioxopyrrol-1-yl)acetyl]amino]ethoxy]ethoxy]ethoxy]ethoxy]propanoic acid (Intermediate L74) were dissolved in 3.0 ml of DMF, and 27.3 mg (0.07 mmol) of HATU and 23.3 mg (0.18 mmol) of N,N-diisopropylethylamine were added. The reaction mixture was stirred at RT for 2 hours. The reaction mixture was purified directly by preparative RP-HPLC (column: Reprosil 125×30; 10µ, flow rate: 50 ml/min, MeCN/water/0.1% TFA). The solvents were evaporated under reduced pressure and the residue was dried under high vacuum. This gave 17.4 mg (26%) of the compound R-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-N-[18-(2,5-dioxo-2,5-dihydro-1H-pyrrol-1-yl)-17-oxo-4,7,10,13-tetraoxa-16-azaoctadecan-1-oyl]-L-cysteine.

LC-MS (Method 6): $R_t$=1.34 min; MS (ESIpos): m/z=1101 (M+H)$^+$.

17 mg (0.02 mmol) of R-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-N-[18-(2,5-dioxo-2,5-dihydro-1H-pyrrol-1-yl)-17-oxo-4,7,10,13-tetraoxa-16-azaoctadecan-1-oyl]-L-cysteine were dissolved in 1.0 ml of trifluoroethanol, and 6.3 mg (0.05 mmol) of zinc dichloride were added. The reaction mixture was stirred at 50° C. overnight. 13.5 mg (0.05 mmol) of ethylenediamine-N,N,N',N'-tetraacetic acid were added, the reaction mixture was stirred for 10 min and water (0.1% TFA) was then added. Purification was carried out directly by preparative RP-HPLC (column: Reprosil 125×30; 10µ, flow rate: 50 ml/min, MeCN/water, 0.1% TFA). The solvents were evaporated under reduced pressure and the residue was dried under high vacuum. This gave 7.6 mg (46%) of the title compound.

LC-MS (Method 1): $R_t$=0.91 min; MS (ESIpos): m/z=957 (M+H)$^+$.

Intermediate F258

Trifluoroacetic acid/(2S)-2-amino-4-[{(1R)-1-[1-benzyl-4-(2,5-difluorophenyl)-1H-pyrrol-2-yl]-2,2-dimethylpropyl}(glycoloyl)amino]-N-[3-{2-[(bromoacetyl)amino]ethyl}amino)-3-oxopropyl] butanamide (1:1)

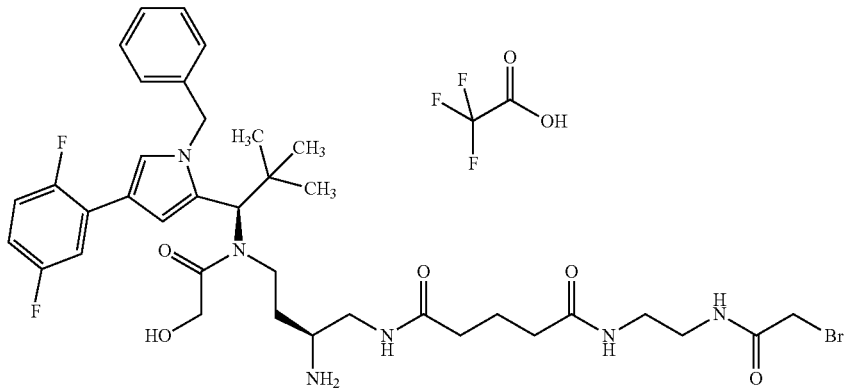 [SMILES: CC(C)(C)[C@H](c1cc(-c2cc(F)ccc2F)cn1Cc1ccccc1)N(CC[C@H](N)CNC(=O)CCCC(=O)NCCNC(=O)CBr)C(=O)CO ; O=C(O)C(F)(F)F]

The title compound was prepared by coupling of Intermediate C58 with trifluoroacetic acid/benzyl [2-(beta-alanylamino)ethyl]carbamate (1:1) using HATU, subsequent hydrogenolysis, followed by coupling with 1-(2-bromoacetoxy)pyrrolidine-2,5-dione and finally by deprotection with zinc chloride.

LC-MS (Method 1): $R_t$=0.86 min; MS (ESIpos): m/z=747 and 749 (M+H)$^+$.

Intermediate F259

N-{(2S)-2-Amino-4-[{(1R)-1-[1-benzyl-4-(2,5-difluorophenyl)-1H-pyrrol-2-yl]-2,2-dimethyl propyl}(glycoloyl)amino]butanoyl}-3-1 {[N-(bromoacetyl)glycyl]amino}-D-alanine/trifluoroacetic acid (1:1)

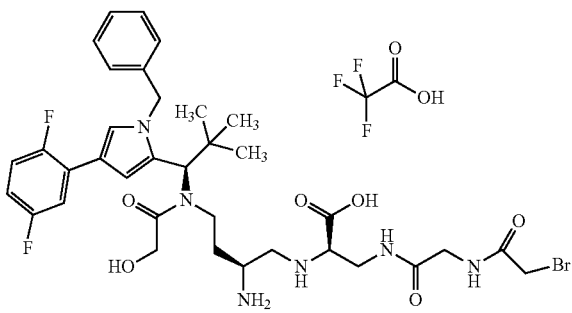 [SMILES: CC(C)(C)[C@H](c1cc(-c2cc(F)ccc2F)cn1Cc1ccccc1)N(CC[C@H](N)CN[C@H](CNC(=O)CNC(=O)CBr)C(=O)O)C(=O)CO ; O=C(O)C(F)(F)F]

75 mg (0.114 mmol) of Intermediate C58 were taken up in 12.5 ml of DMF and coupled with 78 mg (0.171 mmol) of Intermediate L75 in the presence of 65 mg (0.11 mmol) of HATU and 79 µl of N,N-diisopropylethylamine. After purification by preparative HPLC, the intermediate was taken up in 20 ml of ethanol and hydrogenated over 10% palladium on activated carbon at RT under hydrogen standard pressure for 1 h. The catalyst was then filtered off, the solvent was removed under reduced pressure and the product was purified by preparative HPLC. Lyophilization from acetonitrile/water 1:1 gave 63 mg (64% of theory over 2 steps) of 2-(trimethylsilyl)ethyl 3-amino-N-[(2S)-4-[{(1R)-1-[1-benzyl-4-(2,5-difluorophenyl)-1H-pyrrol-2-yl]-2,2-dimethylpropyl}(glycoloyl)amino]-2-({[2-(trimethylsilyl)ethoxy]carbonyl}amino)butanoyl]-D-alaninate.

LC-MS (Method 1): $R_t$=1.16 min; MS (EIpos): m/z=844 [M+H]$^+$.

40 mg (0.047 mmol) of this intermediate were then coupled as described above with N-[(benzyloxy)carbonyl]glycine in the presence of HATU and then once more hydrogenolytically deprotected.

The title compound was then prepared by coupling of 10 mg (0.012 mmol) of this intermediate with 7.7 mg (0.032 mmol) of commercially available 1-(2-bromoacetoxy)pyrrolidine-2,5-dione in the presence of 4 µl of N,N-diisopropylethylamine and subsequent deprotection with zinc chloride in trifluoroethanol as described for Intermediate F119. Purification by preparative HPLC gave 1.3 mg of the title compound.

LC-MS (Method 1): $R_t$=0.83 min; MS (ESIpos): m/z=777 and 779 (M+H)$^+$.

Intermediate F260

$N^6$—(N-{(2S)-2-Amino-4-[{(1R)-1-[1-benzyl-4-(2,5-difluorophenyl)-1H-pyrrol-2-yl]-2,2-dimethylpropyl}(glycoloyl)amino]butanoyl}-beta-alanyl)-$N^2$—{N-[(2,5-dioxo-2,5-dihydro-1H-pyrrol-1-yl)acetyl]-L-valyl-L-alanyl}-L-lysine/trifluoroacetic acid (1:1)

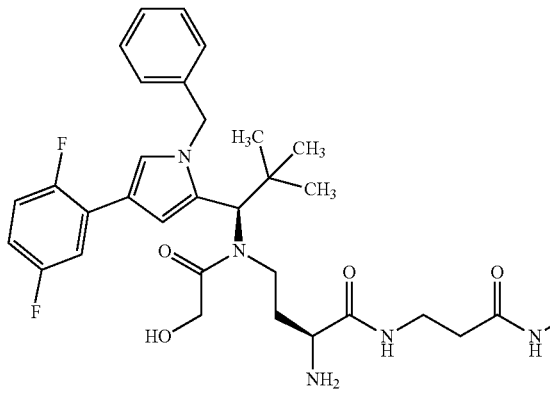
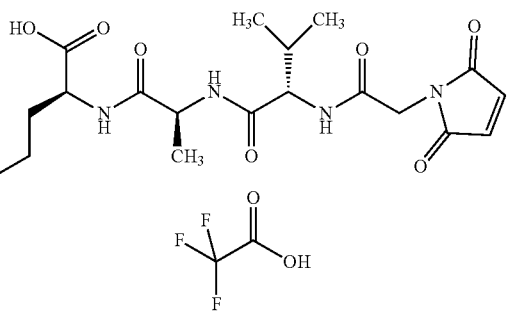

The title compound was prepared analogously to Intermediate F155.

LC-MS (Method 1): $R_t$=0.81 min; MS (ESIpos): m/z=1020 (M+H)$^+$.

Intermediate F261

Trifluoroacetic acid/(2S)-2-amino-4-[{(1R)-1-[1-benzyl-4-(2,5-difluorophenyl)-1H-pyrrol-2-yl]-2,2-dimethylpropyl}(glycoloyl)amino]-N-(2-{2-[(bromoacetyl)amino]ethoxy}ethyl)butanamide (1:1)

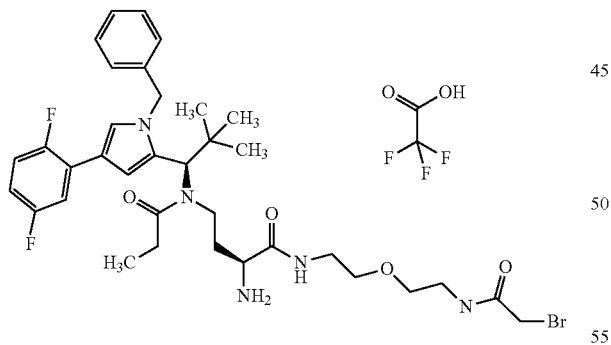

The title compound was prepared by coupling of 20 mg (0.03 mmol) of Intermediate C58 with 25.8 mg (0.061 mmol) of Intermediate L77 in the presence of HATU and subsequent deprotection with zinc chloride. This gave 11.9 mg (47% of theory over 2 steps) of the title compound.

LC-MS (Method 1): $R_t$=0.84 min; MS (ESIpos): m/z=722 and 720 (M+H)$^+$.

Intermediate F262

S-{2-[(3-Aminopropyl){(1R)-1-[1-benzyl-4-(2,5-difluorophenyl)-1H-pyrrol-2-yl]-2,2-dimethylpropyl}amino]-2-oxoethyl}-N-{3-[2-(2-{[3-(2,5-dioxo-2,5-dihydro-1H-pyrrol-1-yl)propanoyl]amino}ethoxy)ethoxy]propanoyl}-L-cysteine/trifluoroacetic acid (1:1)

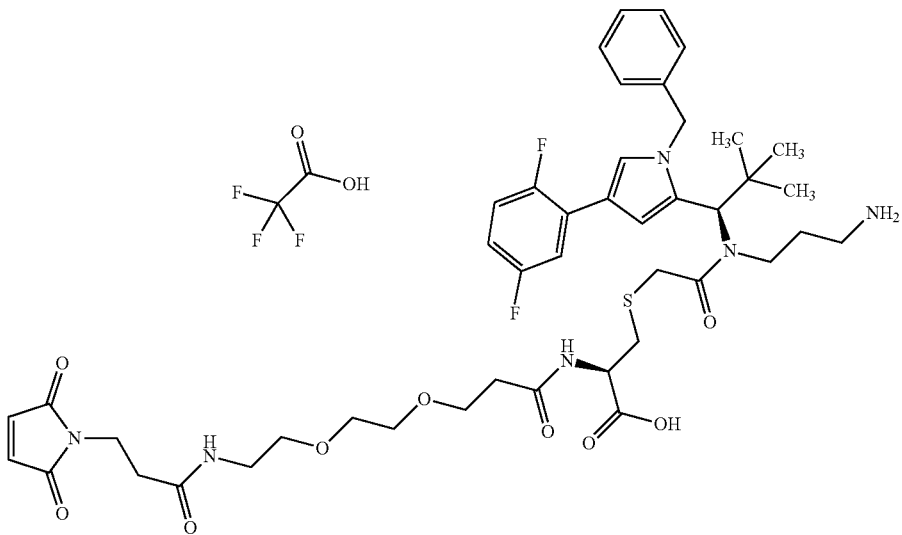 [SMILES: CC(C)(C)[C@H](c1cc(-c2cc(F)ccc2F)cn1Cc1ccccc1)N(CCCN)C(=O)CSC[C@H](NC(=O)CCOCCOCCNC(=O)CCN1C(=O)C=CC1=O)C(=O)O ; O=C(O)C(F)(F)F]

30 mg (36 µmol) of S-{2-[(3-aminopropyl){(1R)-1-[1-benzyl-4-(2,5-difluorophenyl)-1H-pyrrol-2-yl]-2,2-dimethylpropyl}amino]-2-oxoethyl}-L-cysteine/trifluoroacetic acid (1:1) (Intermediate C71) together with 16.9 mg (40 µmol) of 3-(2,5-dioxo-2,5-dihydro-1H-pyrrol-1-yl)-N-[2-(2-{3-[(2,5-dioxopyrrolidin-1-yl)oxy]-3-oxopropoxy}ethoxy)ethyl]propanamide were initially charged in 1.5 ml of DMF, and 10.9 mg (108 µmol) of 4-methylmorpholine were added. The reaction mixture was stirred at RT overnight, and 7.58 mg (0.13 mmol) of acetic acid were then added. The reaction mixture was purified directly by preparative RP-HPLC (column: Reprosil 250×30; 10µ, flow rate: 50 ml/min, MeCN/water, 0.1% TFA). The solvents were evaporated under reduced pressure and the residue was dried under high vacuum. This gave 33.4 mg (80% of theory) of the compound S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-N-{3-[2-(2-{[3-(2,5-dioxo-2,5-dihydro-1H-pyrrol-1-yl)propanoyl]amino}ethoxy)ethoxy]propanoyl}-L-cysteine.

LC-MS (Method 1): $R_t$=1.34 min; MS (ESIpos): m/z=1027 (M+H)$^+$.

32.8 mg (32 µmol) of S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-N-{3-[2-(2-{[3-(2,5-dioxo-2,5-dihydro-1H-pyrrol-1-yl)propanoyl]amino}ethoxy)ethoxy]propanoyl}-L-cysteine were dissolved in 3.0 ml of trifluoroethanol, and 26.1 mg (192 µmol) of zinc dichloride were added. The reaction mixture was stirred at 50° C. for 2 h. 56.0 mg (0.192 mmol) of ethylenediamine-N,N,N',N'-tetraacetic acid were added, the reaction mixture was stirred for 10 min and water (0.1% TFA) was then added. Purification was carried out directly by preparative RP-HPLC (column: Reprosil 250×30; 10µ, flow rate: 50 ml/min, MeCN/water, 0.1% TFA). The solvents were evaporated under reduced pressure and the residue was lyophilized. This gave 22.9 mg (71% of theory) of the title compound.

LC-MS (Method 1): $R_t$=0.88 min; MS (ESIpos): m/z=883 (M+H)$^+$.

Intermediate F263

N-[(2,5-Dioxo-2,5-dihydro-1H-pyrrol-1-yl)acetyl]-beta-alanyl-S-{2-[(3-aminopropyl){(1R)-1-[1-benzyl-4-(2,5-difluorophenyl)-1H-pyrrol-2-yl]-2,2-dimethylpropyl}amino]-2-oxoethyl}-L-cysteine/trifluoroacetic acid (1:1)

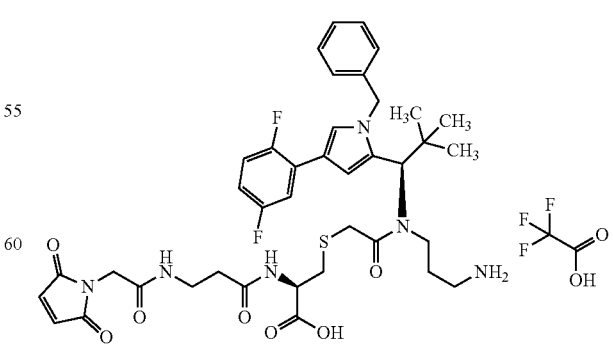

30.0 mg (0.036 mmol) of R-(11-{(1R)-1-[1-benzyl-4-(2,5-difluorophenyl)-1H-pyrrol-2-yl]-2,2-dimethylpropyl}-2, 2-dimethyl-6,12-dioxo-5-oxa-7,11-diaza-2-silatridecan-13-yl)-L-cysteine/trifluoroacetic acid (1:1) (Intermediate C71) and 9.8 mg (0.04 mmol) of N-[(2,5-dioxo-2,5-dihydro-1H-pyrrol-1-yl)acetyl]-beta-alanine (Intermediate L78) were dissolved in 1.0 ml of DMF, and 16.4 mg (0.04 mmol) of HATU and 14.0 mg (0.11 mmol) of N,N-diisopropylethylamine were added.

The reaction mixture was stirred at RT for 2 hours. The reaction mixture was purified directly by preparative RP-HPLC (column: Reprosil 125×30; 10μ, flow rate: 50 ml/min, MeCN/water/0.1% TFA). The solvents were evaporated under reduced pressure and the residue was dried under high vacuum. This gave 4.2 mg (13%) of the compound N-[(2,5-dioxo-2,5-dihydro-1H-pyrrol-1-yl)acetyl]-beta-alanyl-S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-L-cysteine.

LC-MS (Method 6): $R_t$=1.31 min; MS (ESIpos): m/z=925 (M+H)$^+$.

11.3 mg (0.011 mmol) of N-[(2,5-dioxo-2,5-dihydro-1H-pyrrol-1-yl)acetyl]-beta-alanyl-S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-L-cysteine were dissolved in 2.0 ml of trifluoroethanol, and 5.0 mg (0.04 mmol) of zinc dichloride were added. The reaction mixture was stirred at 50° C. for 2 hours. 10.7 mg (0.04 mmol) of ethylenediamine-N,N,N',N'-tetraacetic acid were added, the reaction mixture was stirred for 10 min and water (0.1% TFA) was then added. Purification was carried out directly by preparative RP-HPLC (column: Reprosil 125×30; 10μ, flow rate: 50 ml/min, MeCN/water, 0.1% TFA). The solvents were evaporated under reduced pressure and the residue was dried under high vacuum. This gave 4.4 mg (40%) of the title compound.

LC-MS (Method 1): $R_t$=0.91 min; MS (ESIpos): m/z=781 (M+H)$^+$.

Intermediate F264

N-[6-(2,5-Dioxo-2,5-dihydro-1H-pyrrol-1-yl)hexanoyl]-beta-alanyl-S-{2-[(3-aminopropyl){(1R)-1-[1-benzyl-4-(2,5-difluorophenyl)-1H-pyrrol-2-yl]-2,2-dimethylpropyl}amino]-2-oxoethyl}-L-cysteine/trifluoroacetic acid (1:1)

30.0 mg (0.036 mmol) of R-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-L-cysteine/trifluoroacetic acid (1:1) (Intermediate C71) and 12.2 mg (0.04 mmol) of N-[6-(2,5-dioxo-2,5-dihydro-1H-pyrrol-1-yl)hexanoyl]-beta-alanine (Intermediate L79) were dissolved in 1.0 ml of DMF, and 16.4 mg (0.04 mmol) of HATU and 14.0 mg (0.11 mmol) of N,N-diisopropylethylamine were added. The reaction mixture was stirred at RT for 2 hours. The reaction mixture was purified directly by preparative RP-HPLC (column: Reprosil 125×30; 10μ, flow rate: 50 ml/min, MeCN/water/0.1% TFA). The solvents were evaporated under reduced pressure and the residue was dried under high vacuum. This gave 8.9 mg (24%) of the compound N-[6-(2,5-dioxo-2,5-dihydro-1H-pyrrol-1-yl)hexanoyl]-beta-alanyl-S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-L-cysteine.

LC-MS (Method 6): $R_t$=1.38 min; MS (ESIpos): m/z=981 (M+H)$^+$.

15.3 mg (0.015 mmol) of N-[6-(2,5-dioxo-2,5-dihydro-1H-pyrrol-1-yl)hexanoyl]-beta-alanyl-S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-L-cysteine were dissolved in 2.0 ml of trifluoroethanol, and 6.3 mg (0.045 mmol) of zinc dichloride were added. The reaction mixture was stirred at 50° C. for 2 hours. 13.5 mg (0.045 mmol) of ethylenediamine-N,N,N',N'-tetraacetic acid were added, the reaction mixture was stirred for 10 min and water (0.1% TFA) was then added. Purification was carried out directly by preparative RP-HPLC (column: Reprosil 125×30; 10μ, flow rate: 50 ml/min, MeCN/water, 0.1% TFA). The solvents were evaporated under reduced pressure and the residue was dried under high vacuum. This gave 9.1 mg (62%) of the title compound.

LC-MS (Method 1): $R_t$=0.92 min; MS (ESIpos): m/z=837 (M+H)$^+$.

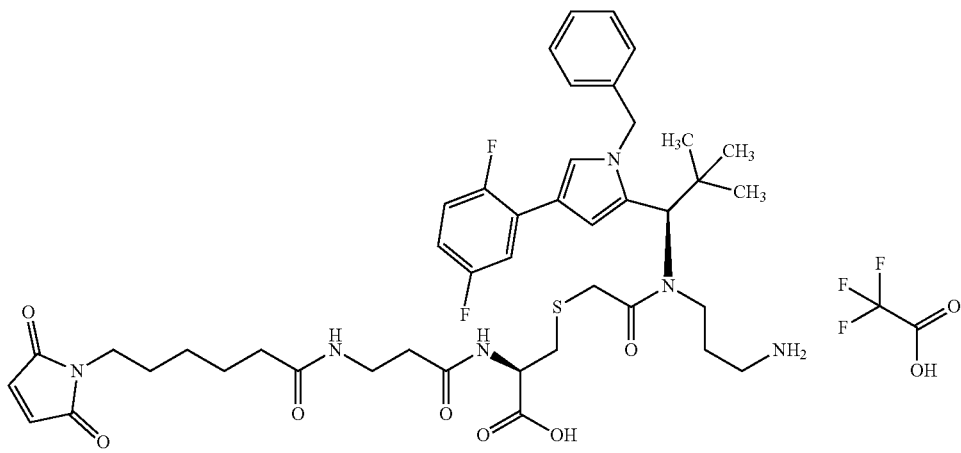 [SMILES: CC(C)(C)[C@H](c1cc(-c2cc(F)ccc2F)cn1Cc1ccccc1)N(CCCN)C(=O)CSC[C@H](NC(=O)CCNC(=O)CCCCCN1C(=O)C=CC1=O)C(=O)O ; O=C(O)C(F)(F)F]

Intermediate F265

Trifluoroacetic acid/N-(3-aminopropyl)-N-{(1R)-1-[1-benzyl-4-(2,5-difluorophenyl)-1H-pyrrol-2-yl]-2,2-dimethylpropyl}-22-(2,5-dioxo-2,5-dihydro-1H-pyrrol-1-yl)-6,17-dioxo-10,13-dioxa-3-thia-7,16-diazadocosane-1-amide (1:1)

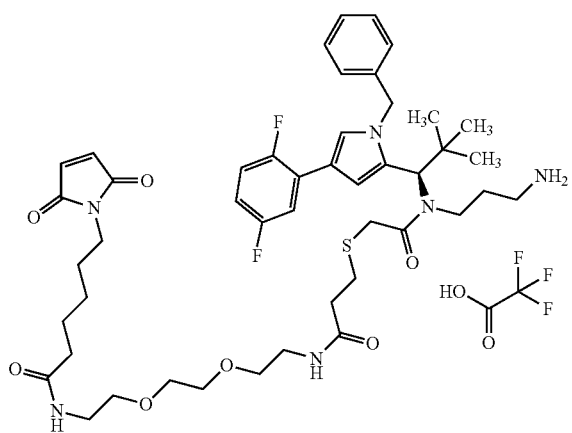 [SMILES: CC(C)(C)[C@H](c1cc(-c2cc(F)ccc2F)cn1Cc1ccccc1)N(CCCN)C(=O)CSCCC(=O)NCCOCCOCCNC(=O)CCCCCN1C(=O)C=CC1=O ; O=C(O)C(F)(F)F]

30.0 mg (42.7 µmol) of 11-{(1R)-1-[1-benzyl-4-(2,5-difluorophenyl)-1H-pyrrol-2-yl]-2,2-dimethylpropyl}-2,2-dimethyl-6,12-dioxo-5-oxa-14-thia-7,11-diaza-2-silaheptadecan-17-oic acid (Intermediate C69) and 25.3 mg (55.6 µmol) of trifluoroacetic acid/N-{2-[2-(2-aminoethoxy)ethoxy]ethyl}-6-(2,5-dioxo-2,5-dihydro-1H-pyrrol-1-yl)hexanamide (1:1) (Intermediate L82) were initially charged in 1.9 ml of acetonitrile, and 60 µl (340 µmol) of N,N-diisopropylethylamine and 33 µl (56 µmol) of 2,4,6-tripropyl-1,3,5,2,4,6-trioxatriphosphinane 2,4,6-trioxide 50% in ethyl acetate were added. The reaction mixture was stirred at RT overnight. Water (2.0 ml) was added, and purification was carried out directly by preparative RP-HPLC (column: Reprosil 250×30; 10µ, flow rate: 50 ml/min, MeCN/water, 0.1% TFA). The solvents were evaporated under reduced pressure and the residue was dried under high vacuum. This gave 26.7 mg (60% of theory) of the compound 2-(trimethylsilyl)ethyl [4-{(1R)-1-[1-benzyl-4-(2,5-difluorophenyl)-1H-pyrrol-2-yl]-2,2-dimethylpropyl}-26-(2,5-dioxo-2,5-dihydro-1H-pyrrol-1-yl)-5,10,21-trioxo-14,17-dioxa-7-thia-4,11,20-triazahexacos-1-yl]carbamate.

LC-MS (Method 1): $R_t$=1.40 min; MS (ESIpos): m/z=1025 (M+H)$^+$.

25.3 mg (24.7 µmol) of 2-(trimethylsilyl)ethyl [4-{(1R)-1-[1-benzyl-4-(2,5-difluorophenyl)-1H-pyrrol-2-yl]-2,2-dimethylpropyl}-26-(2,5-dioxo-2,5-dihydro-1H-pyrrol-1-yl)-5,10,21-trioxo-14,17-dioxa-7-thia-4,11,20-triazahexacos-1-yl]carbamate were dissolved in 2.0 ml of trifluoroethanol, and 20.2 mg (148 µmol) of zinc dichloride were added. The reaction mixture was stirred at 50° C. for 1 h. 43.3 mg (148 µmol) of ethylenediamine-N,N,N',N'-tetraacetic acid were added, the reaction mixture was stirred for 10 min and water (0.1% TFA) was then added. Purification was carried out directly by preparative RP-HPLC (column: Reprosil 250×30; 10µ, flow rate: 50 ml/min, MeCN/water, 0.1% TFA). The solvents were evaporated under reduced pressure and the residue was dried under high vacuum. This gave 23.4 mg (95% of theory) of the title compound.

LC-MS (Method 1): $R_t$=0.89 min; MS (ESIpos): m/z=881 (M+H)$^+$.

Intermediate F266

Trifluoroacetic acid/N-(3-aminopropyl)-N-{(1R)-1-[1-benzyl-4-(2,5-difluorophenyl)-1H-pyrrol-2-yl]-2,2-dimethylpropyl}-1-(2,5-dioxo-2,5-dihydro-1H-pyrrol-1-yl)-2,13-dioxo-6,9-dioxa-16-thia-3,12-diazaoctadecan-18-amide (1:1)

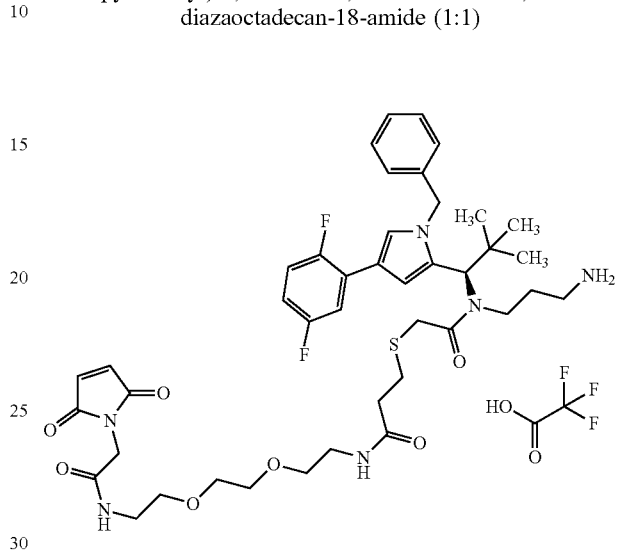

30.0 mg (0.043 mmol) of 11-{(1R)-1-[1-benzyl-4-(2,5-difluorophenyl)-1H-pyrrol-2-yl]-2,2-dimethylpropyl}-2,2-dimethyl-6,12-dioxo-5-oxa-14-thia-7,11-diaza-2-silaheptadecan-17-oic acid (Intermediate C69) were initially charged together with 22.2 mg (0.056 mmol) of trifluoroacetic acid/N-{2-[2-(2-aminoethoxy)ethoxy]ethyl}-2-(2,5-dioxo-2,5-dihydro-1H-pyrrol-1-yl)acetamide (1:1) (Intermediate L83) in 1.9 ml of acetonitrile. 60 µl (0.34 mmol) of N,N-diisopropylethylamine were then added, and 33 µl (0.056 mmol) of T3P (50% in ethyl acetate) were added dropwise. The reaction mixture was stirred at RT overnight. Water (2.0 ml) was added. The reaction mixture was purified directly by preparative RP-HPLC (column: Reprosil 125×30; 10µ, flow rate: 50 ml/min, MeCN/water, 0.1% TFA). The solvents were evaporated under reduced pressure and the residue was dried under high vacuum. This gave 20.5 mg (49% of theory) of the compound 2-(trimethylsilyl)ethyl [19-{(1R)-1-[1-benzyl-4-(2,5-difluorophenyl)-1H-pyrrol-2-yl]-2,2-dimethylpropyl}-1-(2,5-dioxo-2,5-dihydro-1H-pyrrol-1-yl)-2,13,18-trioxo-6,9-dioxa-16-thia-3,12,19-triazadocosan-22-yl]carbamate.

LC-MS (Method 1): $R_t$=1.38 min; MS (ESIpos): m/z=969 (M+H)$^+$.

19.1 mg (19.7 µmol) of 2-(trimethylsilyl)ethyl [19-{(1R)-1-[1-benzyl-4-(2,5-difluorophenyl)-1H-pyrrol-2-yl]-2,2-dimethylpropyl}-1-(2,5-dioxo-2,5-dihydro-1H-pyrrol-1-yl)-2,13,18-trioxo-6,9-dioxa-16-thia-3,12,19-triazadocosan-22-yl]carbamate were dissolved in 2.0 ml of trifluoroethanol, and 16.1 mg (118 µmol) of zinc dichloride were added. The reaction mixture was stirred at 50° C. for 1 h. 34.6 mg (118 µmol) of ethylenediamine-N,N,N',N'-tetraacetic acid were added, the reaction mixture was stirred for 10 min and water (0.1% TFA) was then added. Purification was carried out directly by preparative RP-HPLC (column: Reprosil 250×30; 10µ, flow rate: 50 ml/min, MeCN/water, 0.1% TFA). The solvents were evaporated under reduced pressure and the residue was dried under high vacuum. This gave 13.9 mg (75% of theory) of the title compound.

LC-MS (Method 1): $R_t$=0.86 min; MS (ESIpos): m/z=825 (M+H)$^+$.

Intermediate F267

S-{2-[(3-Aminopropyl){(1R)-1-[1-benzyl-4-(2,5-difluorophenyl)-1H-pyrrol-2-yl]-2,2-dimethylpropyl}amino]-2-oxoethyl}-N-[1-(2,5-dioxo-2,5-dihydro-1H-pyrrol-1-yl)-2,18-dioxo-6,9,12,15-tetraoxa-3-azaoctadecan-18-yl]-L-cysteinyl-beta-alanine/trifluoroacetic acid (1:1)

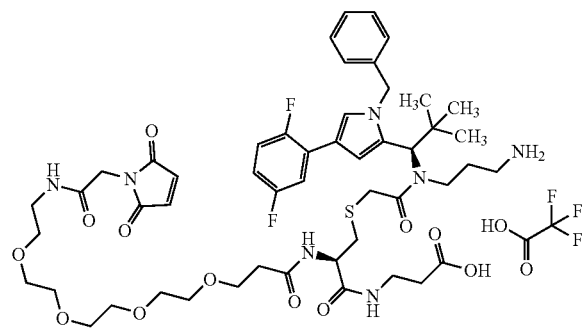 [SMILES: CC(C)(C)[C@H](c1cc(-c2cc(F)ccc2F)cn1Cc1ccccc1)N(CCCN)C(=O)CSC[C@H](NC(=O)CCOCCOCCOCCOCCNC(=O)CN1C(=O)C=CC1=O)C(=O)NCCC(=O)O ; O=C(O)C(F)(F)F]

Under argon, 13.4 mg (33.3 μmol) of 1-(2,5-dioxo-2,5-dihydro-1H-pyrrol-1-yl)-2-oxo-6,9,12,15-tetraoxa-3-azaoctadecan-18-oic acid (Intermediate L74) were initially charged in 1.0 ml of DMF, and 9.3 μl (54.4 μmol) of N,N-diisopropylethylamine and 12.6 mg (33.3 μmol) of HATU were added. The reaction mixture was stirred at RT for 10 min. 25.0 mg (27.7 μmol) of S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-L-cysteinyl-beta-alanine/trifluoroacetic acid (1:1) (see synthesis of Intermediate F216) dissolved in 4.7 μl (27.7 μmol) of N,N-diisopropylethylamine and 1.0 ml of DMF were then added. The reaction mixture was stirred at RT for 90 minutes. The reaction mixture was purified directly by preparative RP-HPLC (column: Reprosil 250×30; 10μ, flow rate: 50 ml/min, MeCN/water, 0.1% TFA). The solvents were evaporated under reduced pressure and the residue was dried under high vacuum. This gave 6.90 mg (19% of theory) of the compound S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-N-[1-(2,5-dioxo-2,5-dihydro-1H-pyrrol-1-yl)-2,18-dioxo-6,9,12,15-tetraoxa-3-azaoctadecan-18-yl]-L-cysteinyl-beta-alanine.

LC-MS (Method 5): $R_t$=4.44 min; MS (ESIpos): m/z=1172 (M+H)$^+$.

6.70 mg (5.71 μmol) of S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-N-[1-(2,5-dioxo-2,5-dihydro-1H-pyrrol-1-yl)-2,18-dioxo-6,9,12,15-tetraoxa-3-azaoctadecan-18-yl]-L-cysteinyl-beta-alanine were dissolved in 1.0 ml of trifluoroethanol, and 4.67 mg (34.3 μmol) of zinc dichloride were added. The reaction mixture was stirred at 50° C. for 1 h. 10 mg (34.3 μmol) of ethylenediamine-N,N,N',N'-tetraacetic acid were added, the reaction mixture was stirred for 10 min and water (0.1% TFA) was then added. Purification was carried out directly by preparative RP-HPLC (column: Reprosil 250×30; 10μ, flow rate: 50 ml/min, MeCN/water, 0.1% TFA). The solvents were evaporated under reduced pressure and the residue was dried under high vacuum. This gave 4.4 mg (67% of theory) of the title compound.

LC-MS (Method 1): $R_t$=0.85 min; MS (ESIpos): m/z=1028 (M+H)$^+$.

Intermediate F268

Trifluoroacetic acid/N-(3-aminopropyl)-N-{(1R)-1-[1-benzyl-4-(2,5-difluorophenyl)-1H-pyrrol-2-yl]-2,2-dimethylpropyl}-28-(2,5-dioxo-2,5-dihydro-1H-pyrrol-1-yl)-6,23-dioxo-10,13,16,19-tetraoxa-3-thia-7,22-diazaoctacosane-1-amide (1:1)

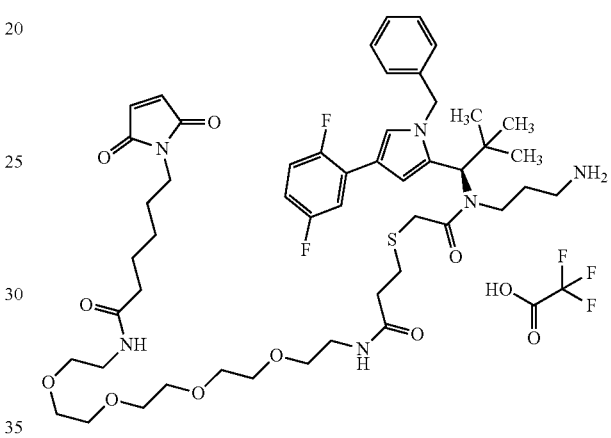

30.0 mg (0.043 mmol) of 11-{(1R)-1-[1-benzyl-4-(2,5-difluorophenyl)-1H-pyrrol-2-yl]-2,2-dimethylpropyl}-2,2-dimethyl-6,12-dioxo-5-oxa-14-thia-7,11-diaza-2-silaheptadecan-17-oic acid (Intermediate C69) were initially charged together with 30.2 mg (0.056 mmol) of trifluoroacetic acid/N-(14-amino-3,6,9,12-tetraoxatetradec-1-yl)-6-(2,5-dioxo-2,5-dihydro-1H-pyrrol-1-yl)hexanamide (1:1) (Intermediate L84) in 2.0 ml of acetonitrile. 60 μl (0.34 mmol) of N,N-diisopropylethylamine were then added, and 33 μl (0.056 mmol) of T3P (50% in ethyl acetate) were added dropwise. The reaction mixture was stirred at RT overnight. Water (2.0 ml) was added.

The reaction mixture was purified directly by preparative RP-HPLC (column: Reprosil 250×30; 10μ, flow rate: 50 ml/min, MeCN/water, 0.1% TFA). The solvents were evaporated under reduced pressure and the residue was dried under high vacuum. This gave 27.9 mg (59% of theory) of the compound 2-(trimethylsilyl)ethyl [4-{(1R)-1-[1-benzyl-4-(2,5-difluorophenyl)-1H-pyrrol-2-yl]-2,2-dimethylpropyl}-32-(2,5-dioxo-2,5-dihydro-1H-pyrrol-1-yl)-5,10,27-trioxo-14,17,20,23-tetraoxa-7-thia-4,11,26-triazadotriacont-1-yl]carbamate.

LC-MS (Method 1): $R_t$=1.41 min; MS (ESIpos): m/z=1114 (M+H)$^+$.

25.6 mg (23.0 μmol) of 2-(trimethylsilyl)ethyl [4-{(1R)-1-[1-benzyl-4-(2,5-difluorophenyl)-1H-pyrrol-2-yl]-2,2-dimethylpropyl}-32-(2,5-dioxo-2,5-dihydro-1H-pyrrol-1-yl)-5,10,27-trioxotrioxo-14,17,20,23-tetraoxa-7-thia-4,11,26-triazadotriacont-1-yl]carbamate were dissolved in 2.5 ml of trifluoroethanol, and 18.8 mg (138 μmol) of zinc dichloride were added. The reaction mixture was stirred at 50° C. for 1 h. 40.3 mg (138 µmol) of ethylenediamine-N,N,N',N'-tetraacetic acid were added, the reaction mixture was stirred for 10 min and water (0.1% TFA) was then added. Purification was carried out directly by preparative RP-HPLC (column: Reprosil 250×30; 10µ, flow rate: 50 ml/min, MeCN/water, 0.1% TFA). The solvents were evaporated under reduced pressure and the residue was dried under high vacuum. This gave 22.2 mg (88% of theory) of the title compound.

LC-MS (Method 1): $R_t$=0.94 min; MS (ESIpos): m/z=969 (M+H)$^+$.

Intermediate F269

4-{[(8R,14R)-13-(3-Aminopropyl)-14-[1-benzyl-4-(2,5-difluorophenyl)-1H-pyrrol-2-yl]-1-(2,5-dioxo-2,5-dihydro-1H-pyrrol-1-yl)-15,15-dimethyl-2,7,12-trioxo-10-thia-3,6,13-triazahexadecan-8-yl]amino}-4-oxobutanoic acid/trifluoroacetic acid (1:1)

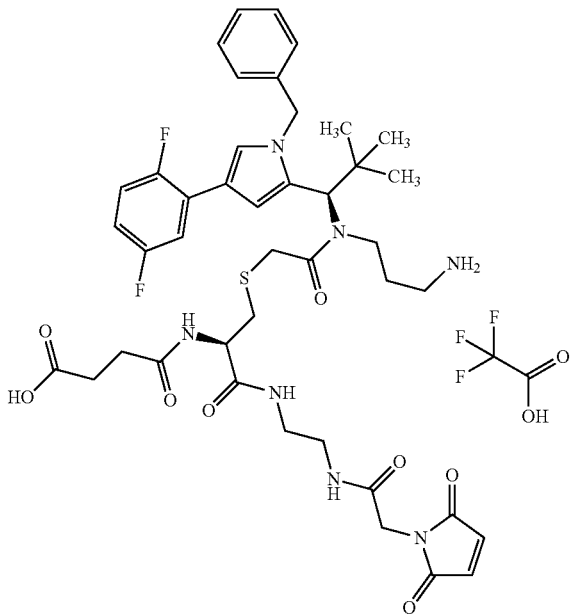 [SMILES: CC(C)(C)[C@H](c1cc(-c2cc(F)ccc2F)cn1Cc1ccccc1)N(CCCN)C(=O)CSC[C@H](NC(=O)CCC(=O)O)C(=O)NCCNC(=O)CN1C(=O)C=CC1=O ; O=C(O)C(F)(F)F]

17.0 mg (0.0195 mmol) of S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-N-(4-tert-butoxy-4-oxobutanoyl)-L-cysteine (Intermediate C77) were initially charged together with 4.99 mg (0.0253 mmol) of N-(2-aminoethyl)-2-(2,5-dioxo-2,5-dihydro-1H-pyrrol-1-yl)acetamide (Intermediate L1) in 1.0 ml of acetonitrile. 27 µl (0.16 mmol) of N,N-diisopropylethylamine were then added, and 15 µl (0.025 mmol) of T3P (50% in ethyl acetate) were added dropwise. The reaction mixture was stirred at RT overnight. Water (2.0 ml) was added. The reaction mixture was purified directly by preparative RP-HPLC (column: Reprosil 125×30; 10µ, flow rate: 50 ml/min, MeCN/water, 0.1% TFA). The solvents were evaporated under reduced pressure and the residue was dried under high vacuum. This gave 9.5 mg (46% of theory) of the compound tert-butyl 4-{[(16R)-11-{(1R)-1-[1-benzyl-4-(2,5-difluorophenyl)-1H-pyrrol-2-yl]-2,2-dimethylpropyl}-23-(2,5-dioxo-2,5-dihydro-1H-pyrrol-1-yl)-2,2-dimethyl-6,12,17,22-tetraoxo-5-oxa-14-thia-7,11,18,21-tetraaza-2-silatricosan-16-yl]amino}-4-oxobutanoate.

LC-MS (Method 1): $R_t$=1.47 min; MS (ESIpos): m/z=1052 (M+H)$^+$.

8.3 mg (7.89 µmol) of tert-butyl 4-{[(16R)-11-{(1R)-1-[1-benzyl-4-(2,5-difluorophenyl)-1H-pyrrol-2-yl]-2,2-dimethylpropyl}-23-(2,5-dioxo-2,5-dihydro-1H-pyrrol-1-yl)-2,2-dimethyl-6,12,17,22-tetraoxo-5-oxa-14-thia-7,11,18,21-tetraaza-2-silatricosan-16-yl]amino}-4-oxobutanoate were dissolved in 1.0 ml of trifluoroethanol, and 6.45 mg (47.3 µmol) of zinc dichloride were added. The reaction mixture was stirred at 50° C. for 6 h. 6.45 mg (47.3 µmol) of zinc dichloride were added and the reaction mixture was stirred at 50° C. overnight. 27.7 mg (94.6 µmol) of ethylenediamine-N,N,N',N'-tetraacetic acid were added and the reaction mixture was stirred for 10 min, and water (0.1% TFA) was then added. Purification was carried out directly by preparative RP-HPLC (column: Reprosil 125×30; 10µ, flow rate: 50 ml/min, MeCN/water, 0.1% TFA). The solvents were evaporated under reduced pressure and the residue was dried under high vacuum. This gave 1.10 mg (14% of theory) of the title compound.

LC-MS (Method 1): $R_t$=0.89 min; MS (ESIpos): m/z=852 (M+H)$^+$.

Intermediate F270

Trifluoroacetic acid/N-(3-aminopropyl)-N-{(1R)-1-[1-benzyl-4-(2,5-difluorophenyl)-1H-pyrrol-2-yl]-2,2-dimethylpropyl}-N'-(2-{[(2,5-dioxo-2,5-dihydro-1H-pyrrol-1-yl)acetyl]amino}ethyl)succinamide (1:1)

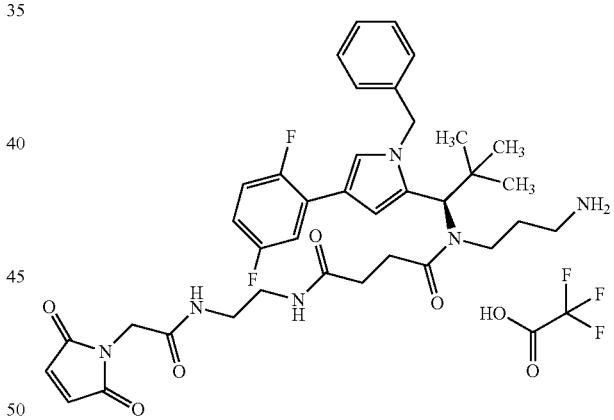

Under argon, 15.0 mg (22.9 µmol) of 11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silapentadecan-15-oic acid (Intermediate C78) were initially charged in 1.0 ml of DMF, and 8.0 µl (45.8 µmol) of N,N-diisopropylethylamine and 10.4 mg (27.4 µmol) of HATU were added. The reaction mixture was stirred at RT for 10 min. 8.54 mg (27.4 µmol) of trifluoroacetic acid/N-(2-aminoethyl)-2-(2,5-dioxo-2,5-dihydro-1H-pyrrol-1-yl)acetamide (1:1) (Intermediate L1) dissolved in 4.0 µl (22.9 µmol) of N,N-diisopropylethylamine and 1.0 ml of DMF were then added. The reaction mixture was stirred at RT for 1 h. The reaction mixture was purified directly by preparative RP-HPLC (column: Reprosil 250×30; 10μ, flow rate: 50 ml/min, MeCN/water, 0.1% TFA). The solvents were evaporated under reduced pressure and the residue was dried under high vacuum. This gave 14.7 mg (77% of theory) of the compound 2-(trimethylsilyl)ethyl [3-({(1R)-1-[1-benzyl-4-(2,5-difluorophenyl)-1H-pyrrol-2-yl]-2,2-dimethylpropyl}{4-[(2-{[(2,5-dioxo-2,5-dihydro-1H-pyrrol-1-yl)acetyl]amino}ethyl)amino]-4-oxobutanoyl}amino)propyl]carbamate.

LC-MS (Method 5): $R_t$=1.33 min; MS (ESIpos): m/z=835 (M+H)$^+$.

13.2 mg (15.8 μmol) of 2-(trimethylsilyl)ethyl [3-({(1R)-1-[1-benzyl-4-(2,5-difluorophenyl)-1H-pyrrol-2-yl]-2,2-dimethylpropyl}{4-[(2-{[(2,5-dioxo-2,5-dihydro-1H-pyrrol-1-yl)acetyl]amino}ethyl)amino]-4-oxobutanoyl}amino)propyl]carbamate were dissolved in 2.0 ml of trifluoroethanol, and 12.9 mg (94.8 μmol) of zinc dichloride were added. The reaction mixture was stirred at 50° C. for 1 h. 27.7 mg (94.6 μmol) of ethylenediamine-N,N,N',N'-tetraacetic acid were added, the reaction mixture was stirred for 10 min and water (0.1% TFA) was then added. Purification was carried out directly by preparative RP-HPLC (column: Reprosil 250×30; 10μ, flow rate: 50 ml/min, MeCN/water, 0.1% TFA). The solvents were evaporated under reduced pressure and the residue was dried under high vacuum. This gave 10.9 mg (83% of theory) of the title compound.

LC-MS (Method 1): $R_t$=0.83 min; MS (ESIpos): m/z=691 (M+H)$^+$.

Intermediate F271

4-{[(20R,26R)-25-(3-Aminopropyl)-26-[1-benzyl-4-(2,5-difluorophenyl)-1H-pyrrol-2-yl]-1-(2,5-dioxo-2,5-dihydro-1H-pyrrol-1-yl)-27,27-dimethyl-2,19,24-trioxo-6,9,12,15-tetraoxa-22-thia-3,18,25-triazaoctacosane-20-yl]amino}-4-oxobutanoic acid/trifluoroacetic acid (1:1)

Under argon, 19.4 mg (22.2 μmol) of S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-N-(4-tert-butoxy-4-oxobutanoyl)-L-cysteine (Intermediate C77) were initially charged in 2.0 ml of DMF, and 21.7 mg (44.4 μmol) of trifluoroacetic acid/N-(14-amino-3,6,9,12-tetraoxatetradec-1-yl)-2-(2,5-dioxo-2,5-dihydro-1H-pyrrol-1-yl)acetamide (1:1) (Intermediate L74), 12 μl (67 μmol) of N,N-diisopropylethylamine and 16.9 mg (44.4 μmol) of HATU were added. The reaction mixture was stirred at RT for 1 h. The reaction mixture was purified directly by preparative RP-HPLC (column: Reprosil 125×30; 10μ, flow rate: 50 ml/min, MeCN/water, 0.1% TFA). The solvents were evaporated under reduced pressure and the residue was dried under high vacuum. This gave 18.1 mg (66% of theory) of the compound tert-butyl 4-{[(16R)-11-{(1R)-1-[1-benzyl-4-(2,5-difluorophenyl)-1H-pyrrol-2-yl]-2,2-dimethylpropyl}-35-(2,5-dioxo-2,5-dihydro-1H-pyrrol-1-yl)-2,2-dimethyl-6,12,17,34-tetraoxo-5,21,24,27,30-pentaoxa-14-thia-7,11,18,33-tetraaza-2-silapentatriacontan-16-yl]amino}-4-oxobutanoate.

LC-MS (Method 4): $R_t$=1.79 min; MS (ESIpos): m/z=1250 (M+Na)$^+$.

18.1 mg (14.7 μmol) of tert-butyl 4-{[(16R)-11-{(1R)-1-[1-benzyl-4-(2,5-difluorophenyl)-1H-pyrrol-2-yl]-2,2-dimethylpropyl}-35-(2,5-dioxo-2,5-dihydro-1H-pyrrol-1-yl)-2,2-dimethyl-6,12,17,34-tetraoxo-5,21,24,27,30-pentaoxa-14-thia-7,11,18,33-tetraaza-2-silapentatriacontan-16-yl]amino}-4-oxobutanoate were dissolved in 2.0 ml of trifluoroethanol, and 12.0 mg (88.4 μmol) of zinc dichloride were added. The reaction mixture was stirred at 50° C. for 4 h. 25.8 mg (88.4 μmol) of ethylenediamine-N,N,N',N'-tetraacetic acid were added, the reaction mixture was stirred for 10 min and water (0.1% TFA) was then added. Purification was carried out directly by preparative RP-HPLC (column: Reprosil 125×30; 10μ, flow rate: 50 ml/min, MeCN/water, 0.1% TFA). The solvents were evaporated under reduced pressure and the residue was dried under high vacuum. This gave 12.3 mg (73% of theory) of the title compound.

LC-MS (Method 1): $R_t$=0.87 min; MS (ESIpos): m/z=1028 (M+H)$^+$.

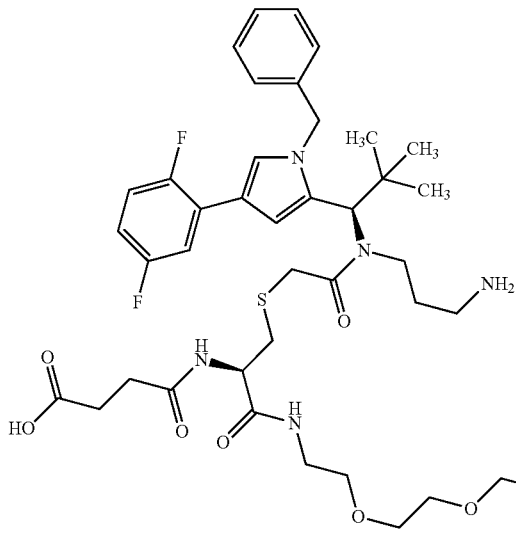
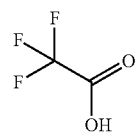
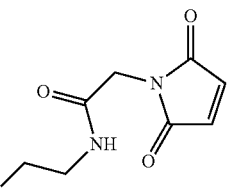

Intermediate F272

Trifluoroacetic acid/N-(3-aminopropyl)-N-{(1R)-1-[1-benzyl-4-(2,5-difluorophenyl)-1H-pyrrol-2-yl]-2,2-dimethylpropyl}-N'-[17-(2,5-dioxo-2,5-dihydro-1H-pyrrol-1-yl)-16-oxo-3,6,9,12-tetraoxa-15-azaheptadec-1-yl]succinamide (1:1)

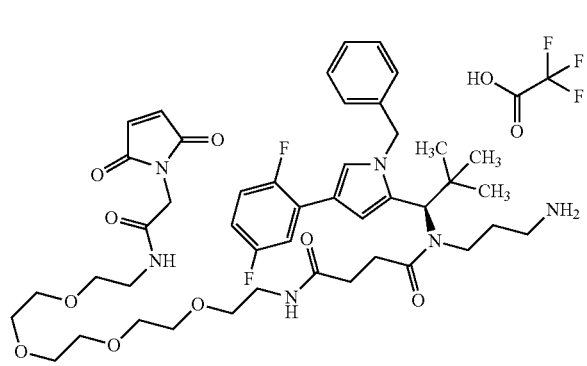

Under argon, 15.0 mg (22.9 μmol) of 11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silapentadecan-15-oic acid (Intermediate C78) were initially charged in 1.0 ml of DMF, and 8.0 μl (45.8 μmol) of N,N-diisopropylethylamine and 10.4 mg (27.4 μmol) of HATU were added. The reaction mixture was stirred at RT for 10 min. 13.4 mg (27.4 μmol) of trifluoroacetic acid/N-(14-amino-3,6,9,12-tetraoxatetradec-1-yl)-2-(2,5-dioxo-2,5-dihydro-1H-pyrrol-1-yl)acetamide (1:1) (Intermediate L85) dissolved in 4.0 μl (22.9 μmol) of N,N-diisopropylethylamine and 1.0 ml of DMF were then added. The reaction mixture was stirred at RT for 1 h. The reaction mixture was purified directly by preparative RP-HPLC (column: Reprosil 250×30; 10μ, flow rate: 50 ml/min, MeCN/water, 0.1% TFA). The solvents were evaporated under reduced pressure and the residue was dried under high vacuum. This gave 15.8 mg (68% of theory) of the compound 2-(trimethylsilyl)ethyl [23-{(1R)-1-[1-benzyl-4-(2,5-difluorophenyl)-1H-pyrrol-2-yl]-2,2-dimethylpropyl}-1-(2,5-dioxo-2,5-dihydro-1H-pyrrol-1-yl)-2,19,22-trioxo-6,9,12,15-tetraoxa-3,18,23-triazahexacosan-26-yl]carbamate.

LC-MS (Method 1): $R_t$=1.35 min; MS (ESIpos): m/z=1011 (M+H)$^+$.

15.1 mg (14.9 μmol) of 2-(trimethylsilyl)ethyl [23-{(1R)-1-[1-benzyl-4-(2,5-difluorophenyl)-1H-pyrrol-2-yl]-2,2-dimethylpropyl}-1-(2,5-dioxo-2,5-dihydro-1H-pyrrol-1-yl)-2,19,22-trioxotrioxo-6,9,12,15-tetraoxa-3,18,23-triazahexacosan-26-yl]carbamate were dissolved in 2.0 ml of trifluoroethanol, and 12.2 mg (89.6 μmol) of zinc dichloride were added. The reaction mixture was stirred at 50° C. for 1 h. 26.2 mg (89.6 μmol) of ethylenediamine-N,N,N',N'-tetraacetic acid were added, the reaction mixture was stirred for 10 min and water (0.1% TFA) was then added. Purification was carried out directly by preparative RP-HPLC (column: Reprosil 250×30; 10μ, flow rate: 50 ml/min, MeCN/water, 0.1% TFA). The solvents were evaporated under reduced pressure and the residue was dried under high vacuum. This gave 10.3 mg (70% of theory) of the title compound.

LC-MS (Method 1): $R_t$=0.88 min; MS (ESIpos): m/z=867 (M+H)$^+$.

Intermediate F273

Trifluoroacetic acid/N-(3-aminopropyl)-N-{(1R)-1-[1-benzyl-4-(2,5-difluorophenyl)-1H-pyrrol-2-yl]-2,2-dimethylpropyl}-1-(2,5-dioxo-2,5-dihydro-1H-pyrrol-1-yl)-2,19-dioxo-6,9,12,15-tetraoxa-22-thia-3,18-diazatetracosane-24-amide (1:1)

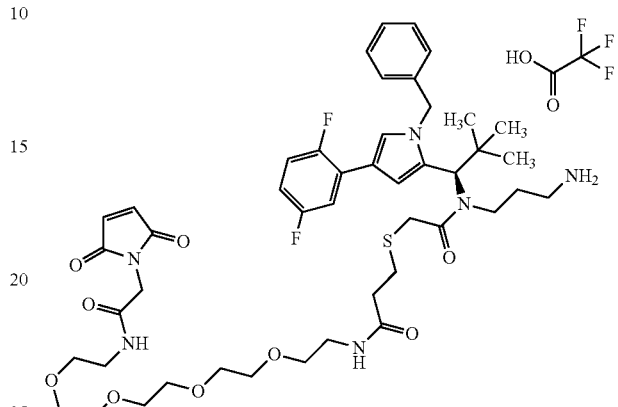

Under argon, 20.0 mg (28.5 μmol) of 11-{(1R)-1-[1-benzyl-4-(2,5-difluorophenyl)-1H-pyrrol-2-yl]-2,2-dimethylpropyl}-2,2-dimethyl-6,12-dioxo-5-oxa-14-thia-7,11-diaza-2-silaheptadecan-17-oic acid (Intermediate C69) were initially charged in 1.0 ml of DMF, and 10.0 μl (57.0 mol) of N,N-diisopropylethylamine and 13.0 mg (34.2 μmol) of HATU were added. The reaction mixture was stirred at RT for 10 min. 16.7 mg (34.2 μmol) of trifluoroacetic acid/N-(14-amino-3,6,9,12-tetraoxatetradec-1-yl)-2-(2,5-dioxo-2,5-dihydro-1H-pyrrol-1-yl)acetamide (1:1) (Intermediate L85) dissolved in 5.0 μl (28.5 μmol) of N,N-diisopropylethylamine and 1.0 ml of DMF were then added. The reaction mixture was stirred at RT for 1 h. The reaction mixture was purified directly by preparative RP-HPLC (column: Reprosil 250×30; 10μ, flow rate: 50 ml/min, MeCN/water, 0.1% TFA). The solvents were evaporated under reduced pressure and the residue was dried under high vacuum. This gave 18.6 mg (62% of theory) of the compound 2-(trimethylsilyl)ethyl [25-{(1R)-1-[1-benzyl-4-(2,5-difluorophenyl)-1H-pyrrol-2-yl]-2,2-dimethylpropyl}-1-(2,5-dioxo-2,5-dihydro-1H-pyrrol-1-yl)-2,19,24-trioxo-6,9,12,15-tetraoxa-22-thia-3,18,25-triazaoctacosan-28-yl] carbamate.

LC-MS (Method 1): $R_t$=1.37 min; MS (ESIpos): m/z=1057 (M+H)$^+$.

17.1 mg (16.2 μmol) of 2-(trimethylsilyl)ethyl [25-{(1R)-1-[1-benzyl-4-(2,5-difluorophenyl)-1H-pyrrol-2-yl]-2,2-dimethylpropyl}-1-(2,5-dioxo-2,5-dihydro-1H-pyrrol-1-yl)-2,19,24-trioxotrioxo-6,9,12,15-tetraoxa-22-thia-3,18,25-triazaoctacosan-28-yl]carbamate were dissolved in 2.0 ml of trifluoroethanol, and 13.2 mg (97.0 μmol) of zinc dichloride were added. The reaction mixture was stirred at 50° C. for 1 h. 28.4 mg (97.0 μmol) of ethylenediamine-N,N,N',N'-tetraacetic acid were added, the reaction mixture was stirred for 10 min and water (0.1% TFA) was then added. Purification was carried out directly by preparative RP-HPLC (column: Reprosil 250×30; 10μ, flow rate: 50 ml/min, MeCN/water, 0.1% TFA). The solvents were evaporated under reduced pressure and the residue was dried under high vacuum. This gave 9.80 mg (59% of theory) of the title compound.

LC-MS (Method 1): $R_t$=0.88 min; MS (ESIpos): m/z=913 (M+H)$^+$.

Intermediate F274

N-[(2,5-Dioxo-2,5-dihydro-1H-pyrrol-1-yl)acetyl]-L-valyl-L-alanyl-S-{2-[(3-aminopropyl){(1R)-1-[1-benzyl-4-(2,5-difluorophenyl)-1H-pyrrol-2-yl]-2,2-dimethylpropyl}amino]-2-oxoethyl}-L-cysteine/trifluoroacetic acid (1:1)

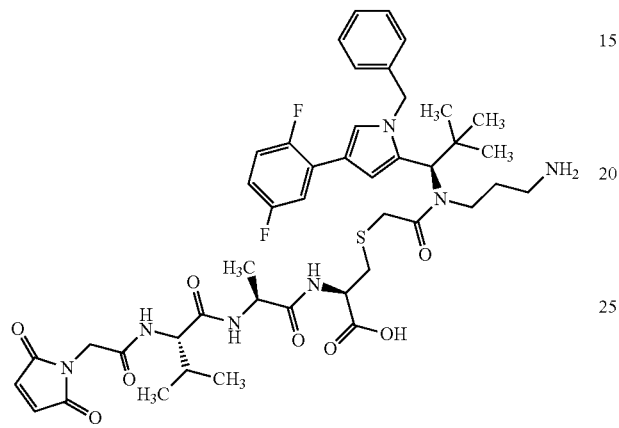

13.9 mg (0.0167 mmol) of S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-L-cysteine/trifluoroacetic acid (1:1) (Intermediate C71) were initially charged together with 7.07 mg (0.0217 mmol) of N-[(2,5-dioxo-2,5-dihydro-1H-pyrrol-1-yl)acetyl]-L-valyl-L-alanine (Intermediate L86) in 2.0 ml of acetonitrile. 23 μl (0.13 mmol) of N,N-diisopropylethylamine were then added, and 13 μl (0.022 mmol) of T3P (50% in ethyl acetate) were added dropwise. The reaction mixture was stirred at RT overnight. The reaction mixture was purified directly by preparative RP-HPLC (column: Reprosil 125×30; 10μ, flow rate: 50 ml/min, MeCN/water, 0.1% TFA). The solvents were evaporated under reduced pressure and the residue was dried under high vacuum. This gave 3.70 mg (19% of theory) of the compound N-[(2,5-dioxo-2,5-dihydro-1H-pyrrol-1-yl)acetyl]-L-valyl-L-alanyl-S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-L-cysteine.

LC-MS (Method 1): $R_t$=1.34 min; MS (ESIpos): m/z=1024 (M+H)$^+$.

10.6 mg (10.3 μmol) of N-[(2,5-dioxo-2,5-dihydro-1H-pyrrol-1-yl)acetyl]-L-valyl-L-alanyl-S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-L-cysteine were dissolved in 2.0 ml of trifluoroethanol, and 8.46 mg (62.1 μmol) of zinc dichloride were added. The reaction mixture was stirred at 50° C. for 1 h. 18.1 mg (62.1 μmol) of ethylenediamine-N,N,N',N'-tetraacetic acid were added, the reaction mixture was stirred for 10 min and water (0.1% TFA) was then added. Purification was carried out directly by preparative RP-HPLC (column: Reprosil 125×30; 10μ, flow rate: 50 ml/min, MeCN/water, 0.1% TFA). The solvents were evaporated under reduced pressure and the residue was dried under high vacuum. This gave 5.60 mg (54% of theory) of the title compound.

LC-MS (Method 12): $R_t$=1.69 min; MS (ESIpos): m/z=880 (M+H)$^+$.

Intermediate F275

N-[3-({2-[(3-Aminopropyl){(1R)-1-[1-benzyl-4-(2,5-difluorophenyl)-1H-pyrrol-2-yl]-2,2-dimethylpropyl}amino]-2-oxoethyl}sulphanyl)propanoyl]-N-(2-{[(2,5-dioxo-2,5-dihydro-1H-pyrrol-1-yl)acetyl]amino}ethyl)-L-alpha-glutamine/trifluoroacetic acid (1:1)

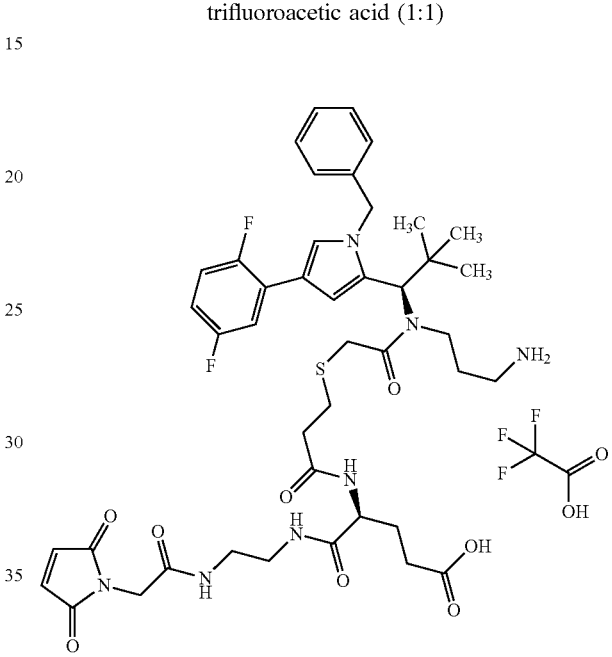

39.0 mg (55.6 μmol) of 11-{(1R)-1-[1-benzyl-4-(2,5-difluorophenyl)-1H-pyrrol-2-yl]-2,2-dimethylpropyl}-2,2-dimethyl-6,12-dioxo-5-oxa-14-thia-7,11-diaza-2-silaheptadecan-17-oic acid (Intermediate C69) were initially charged in 4.0 ml of DMF, 41.6 mg (111 μmol) of 1-benzyl-5-[2-(trimethylsilyl)ethyl]-L-glutamate hydrochloride (1:1) (Intermediate L89), 29 μl (170 μmol) of N,N-diisopropylethylamine and 42.3 mg (111 μmol) of HATU were added and the mixture was stirred at RT for 1 hour. The reaction mixture was stirred at RT for 1 hour, quenched with acetic acid and purified directly by preparative RP-HPLC (column: Reprosil 250×30; 10μ, flow rate: 50 ml/min, MeCN/water, 0.1% TFA). The solvents were evaporated under reduced pressure and the residue was dried under high vacuum. This gave 53.1 mg (93% of theory) of the compound 1-benzyl-5-[2-(trimethylsilyl)ethyl]-N-(11-{(1R)-1-[1-benzyl-4-(2,5-difluorophenyl)-1H-pyrrol-2-yl]-2,2-dimethylpropyl}-2,2-dimethyl-6,12,17-trioxo-5-oxa-14-thia-7,11-diaza-2-silaheptadecan-17-yl)-L-glutamate.

LC-MS (Method 1): $R_t$=1.71 min; MS (ESIpos): m/z=1021 [M+H]$^+$

Under argon, 7.60 mg (33.9 μmol) of palladium(II) acetate were initially charged in 3.0 ml of dichloromethane, and 14 μl (100 μmol) of triethylamine and 110 μl (680 μmol) of triethylsilane were added. The reaction mixture was stirred at RT for 5 min, and 69.2 mg (67.7 μmol) of 1-benzyl-5-[2-(trimethylsilyl)ethyl]-N-(11-{(1R)-1-[1-benzyl-4-(2,5-difluorophenyl)-1H-pyrrol-2-yl]-2,2-dimethylpropyl}-2,2-dimethyl-6,12,17-trioxo-5-oxa-14-thia-7,11-diaza-2-silaheptadecan-17-yl)-L-glutamate dissolved in 3.0 ml of dichloromethane were added. The reaction mixture was stirred at RT overnight. The reaction mixture was filtered through a cardboard filter and the filter cake was washed with dichloromethane. The solvent was evaporated under reduced pressure. The residue was purified by preparative RP-HPLC (column: Reprosil 250×30; 10μ, flow rate: 50 ml/min, MeCN/water, 0.1% TFA). The solvents were evaporated under reduced pressure and the residue was dried under high vacuum. This gave 38.4 mg (61% of theory) of the compound (19S)-11-{(1R)-1-[1-benzyl-4-(2,5-difluorophenyl)-1H-pyrrol-2-yl]-2,2-dimethylpropyl}-2,2-dimethyl-6,12,17-trioxo-19-{3-oxo-3-[2-(trimethylsilyl)ethoxy]propyl}-5-oxa-14-thia-7,11,18-triaza-2-silaicosan-20-oic acid.

LC-MS (Method 1): $R_t$=1.53 min; MS (ESIpos): m/z=931 (M+H)$^+$.

10.0 mg (10.7 μmol) of (19S)-11-{(1R)-1-[1-benzyl-4-(2,5-difluorophenyl)-1H-pyrrol-2-yl]-2,2-dimethylpropyl}-2,2-dimethyl-6,12,17-trioxo-19-{3-oxo-3-[2-(trimethylsilyl)ethoxy]propyl}-5-oxa-14-thia-7,11,18-triaza-2-silaicosan-20-oic acid (Intermediate C69) were initially charged in 1.0 ml of DMF, 6.73 mg (21.5 μmol) of N-(2-aminoethyl)-2-(2,5-dioxo-2,5-dihydro-1H-pyrrol-1-yl)acetamide/2,2,2-trifluoroethane-1,1-diol (1:1) (Intermediate L1), 5.6 μl (32 μmol) of N,N-diisopropylethylamine and 8.17 mg (21.5 μmol) of HATU were added and the mixture was stirred at RT for 1 hour. The reaction mixture was stirred at RT for 3 hour, quenched with acetic acid and purified directly by preparative RP-HPLC (column: Reprosil 125×30; 10μ, flow rate: 50 ml/min, MeCN/water, 0.1% TFA). The solvents were evaporated under reduced pressure and the residue was dried under high vacuum. This gave 6.90 mg (58% of theory) of the compound 2-(trimethylsilyl)ethyl N2-(11-{(1R)-1-[1-benzyl-4-(2,5-difluorophenyl)-1H-pyrrol-2-yl]-2,2-dimethylpropyl}-2,2-dimethyl-6,12,17-trioxo-5-oxa-14-thia-7,11-diaza-2-silaheptadecan-17-yl)-N-(2-{[(2,5-dioxo-2,5-dihydro-1H-pyrrol-1-yl) acetyl]amino}ethyl)-L-alpha-glutaminate.

LC-MS (Method 1): $R_t$=1.57 min; MS (ESIpos): m/z=1110 [M+H]$^+$ 6.90 mg (6.21 μmol) of 2-(trimethylsilyl)ethyl N²-(11-{(1R)-1-[1-benzyl-4-(2,5-difluorophenyl)-1H-pyrrol-2-yl]-2,2-dimethylpropyl}-2,2-dimethyl-6,12,17-trioxo-5-oxa-14-thia-7,11-diaza-2-silaheptadecan-17-yl)-N-(2-{[(2,5-dioxo-2,5-dihydro-1H-pyrrol-1-yl)acetyl]amino}ethyl)-L-alpha-glutaminate were dissolved in 2.0 ml of trifluoroethanol, and 5.1 mg (37.2 μmol) zinc dichloride were added. The reaction mixture was stirred at 50° C. for 3 h. 5.1 mg (37.2 μmol) of zinc dichloride were added and the reaction mixture was stirred at 50° C. for 3 h. 5.1 mg (37.2 μmol) of zinc dichloride were added and the reaction mixture was stirred at 50° C. for 3 h. 10.1 mg (74.4 μmol) of zinc dichloride were added and the reaction mixture was stirred at 50° C. overnight and at RT for 72 h. 54.5 mg (186 μmol) of ethylenediamine-N,N,N',N'-tetraacetic acid were added, the reaction mixture was stirred for 10 min and water (0.1% TFA) was then added. Purification was carried out directly by preparative RP-HPLC (column: Reprosil 125×30; 10μ, flow rate: 50 ml/min, MeCN/water, 0.1% TFA). The solvents were evaporated under reduced pressure and the residue was dried under high vacuum. This gave 2.4 mg (39% of theory) of the title compound.

LC-MS (Method 1): $R_t$=0.86 min; MS (ESIpos): m/z=866 (M+H)$^+$.

Intermediate F276

S-{2-[(3-Aminopropyl){(1R)-1-[1-benzyl-4-(2,5-difluorophenyl)-1H-pyrrol-2-yl]-2,2-dimethylpropyl}amino]-2-oxoethyl}-N-{3-[2-(2-{[(2,5-dioxo-2,5-dihydro-1H-pyrrol-1-yl)acetyl]amino}ethoxy)ethoxy]propanoyl}-L-cysteine/trifluoroacetic acid (1:1)

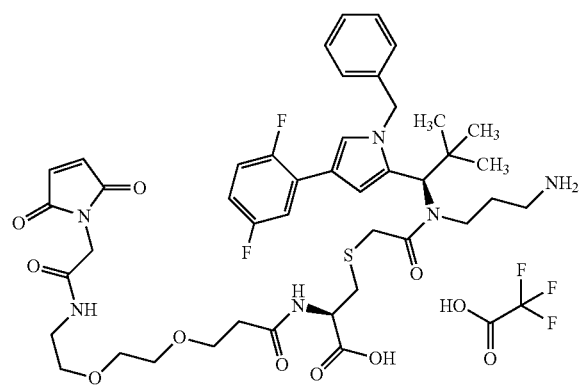 [SMILES: CC(C)(C)[C@H](c1cc(-c2cc(F)ccc2F)cn1Cc1ccccc1)N(CCCN)C(=O)CSC[C@H](NC(=O)CCOCCOCCNC(=O)CN1C(=O)C=CC1=O)C(=O)O ; O=C(O)C(F)(F)F]

Under argon, 9.08 mg (28.9 μmol) of 3-[2-(2-{[(2,5-Dioxo-2,5-dihydro-1H-pyrrol-1-yl)acetyl]amino}ethoxy)ethoxy]propanoic acid (Intermediate L87) were initially charged in 1.0 ml of DMF, and 8.33 μl (48.2 μmol) of N,N-diisopropylethylamine and 11.0 mg (28.9 μmol) of HATU were added. The reaction mixture was stirred at RT for 10 min. 20.0 mg (27.7 μmol) of S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-L-cysteine/trifluoroacetic acid (1:1) (Intermediate C71) dissolved in 4.67 μl (24.1 μmol) of N,N-diisopropylethylamine and 1.0 ml of DMF were then added. The reaction mixture was stirred at RT for 1 h. The reaction mixture was purified directly by preparative RP-HPLC (column: Reprosil 250×30; 10μ, flow rate: 50 ml/min, MeCN/water, 0.1% TFA). The solvents were evaporated under reduced pressure and the residue was dried under high vacuum. This gave 4.70 mg (19% of theory) of the compound S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-N-{3-[2-(2-{[(2,5-dioxo-2,5-dihydro-1H-pyrrol-1-yl) acetyl]amino}ethoxy)ethoxy]propanoyl}-L-cysteine.

LC-MS (Method 12): $R_t$=2.47 min; MS (ESIpos): m/z=1013 (M+H)$^+$.

13.9 mg (13.7 μmol) of S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-N-{3-[2-(2-{[(2,5-dioxo-2,5-dihydro-1H-pyrrol-1-yl)acetyl]amino}ethoxy)ethoxy]propanoyl}-L-cysteine were dissolved in 2.0 ml of trifluoroethanol, and 5.6 mg (41.2 μmol) of zinc dichloride were added. The reaction mixture was stirred at 50° C. for 1 h. 5.6 mg (41.2 μmol) of zinc dichloride were added and the reaction mixture was stirred at 50° C. for 30 minutes. 24.1 mg (82.4 μmol) of ethylenediamine-N,N,N',N'-tetraacetic acid were added and the reaction mixture was stirred for 10 min, and water (0.1% TFA)

was then added. Purification was carried out directly by preparative RP-HPLC (column: Reprosil 250×30; 10μ, flow rate: 50 ml/min, MeCN/water, 0.1% TFA). The solvents were evaporated under reduced pressure and the residue was dried under high vacuum. This gave 10.8 mg (80% of theory) of the title compound.

LC-MS (Method 12): $R_t$=1.58 min; MS (ESIpos): m/z=869 (M+H)$^+$.

Intermediate F277

N-[3-({2-[(3-Aminopropyl){(1R)-1-[1-benzyl-4-(2,5-difluorophenyl)-1H-pyrrol-2-yl]-2,2-dimethylpropyl}amino]-2-oxoethyl}sulphanyl)propanoyl]-3-[(bromoacetyl)amino]-D-alanine/trifluoroacetic acid (1:1)

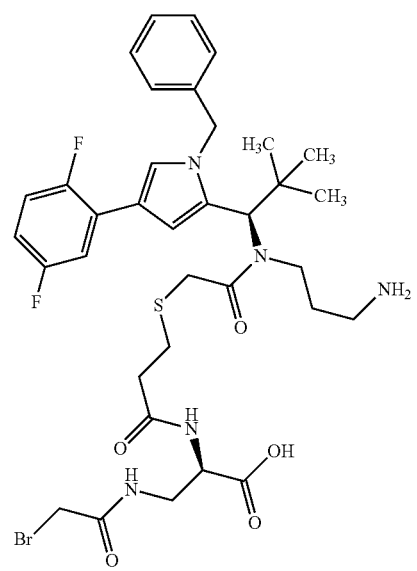

8.90 mg (8.88 μmol) of trifluoroacetic acid/2-(trimethylsilyl)ethyl 3-amino-N-(11-{(1R)-1-[1-benzyl-4-(2,5-difluorophenyl)-1H-pyrrol-2-yl]-2,2-dimethylpropyl}-2,2-dimethyl-6,12,17-trioxo-5-oxa-14-thia-7,11-diaza-2-silaheptadecan-17-yl)-D-alaninate (1:1) (Intermediate C80) and 2.31 mg (9.77 μmol) of 1-(2-bromoacetoxy)pyrrolidine-2,5-dione were dissolved in 1 ml of dimethylformamide, and 2.9 μl (27 μmol) of N-methylmorpholine were added. The reaction mixture was stirred at RT for 1 h. The reaction mixture was purified directly by preparative RP-HPLC (column: Reprosil 125×30; 10μ, flow rate: 50 ml/min, MeCN/water/0.1% TFA). The solvents were evaporated under reduced pressure and the residue was dried under high vacuum. This gave 5.80 mg (65% of theory) of the compound 2-(trimethylsilyl)ethyl N-(11-{(1R)-1-[1-benzyl-4-(2,5-difluorophenyl)-1H-pyrrol-2-yl]-2,2-dimethylpropyl}-2,2-dimethyl-6,12,17-trioxo-5-oxa-14-thia-7,11-diaza-2-silaheptadecan-17-yl)-3-[(bromoacetyl)amino]-D-alaninate.

LC-MS (Method 1): $R_t$=1.57 min; MS (ESIpos): m/z=1008 (M+H)$^+$.

5.80 mg (5.75 μmol) of 2-(trimethylsilyl)ethyl N-(11-{(1R)-1-[1-benzyl-4-(2,5-difluorophenyl)-1H-pyrrol-2-yl]-2,2-dimethylpropyl}-2,2-dimethyl-6,12,17-trioxo-5-oxa-14-thia-7,11-diaza-2-silaheptadecan-17-yl)-3-[(bromoacetyl)amino]-D-alaninate were dissolved in 2.0 ml of trifluoroethanol, and 4.70 mg (34.5 μmol) of zinc dichloride were added. The reaction mixture was stirred at 50° C. for 3 h. 4.70 mg (34.5 μmol) of zinc dichloride were added and the reaction mixture was stirred at 50° C. for 5 h. 20.2 mg (69.0 μmol) of ethylenediamine-N,N,N',N'-tetraacetic acid were added and the reaction mixture was stirred for 10 min, and water (0.1% TFA) was then added. Purification was carried out directly by preparative RP-HPLC (column: Reprosil 125×30; 10μ, flow rate: 50 ml/min, MeCN/water, 0.1% TFA). The solvents were evaporated under reduced pressure and the residue was dried under high vacuum. This gave 1.70 mg (34% of theory) of the title compound.

LC-MS (Method 1): $R_t$=0.90 min; MS (ESIpos): m/z=764 (M+H)$^+$.

Intermediate F278

N-[3-({2-[(3-Aminopropyl){(1R)-1-[1-benzyl-4-(2,5-difluorophenyl)-1H-pyrrol-2-yl]-2,2-dimethylpropyl}amino]-2-oxoethyl}sulphanyl)propanoyl]-3-{[(2,5-dioxo-2,5-dihydro-1H-pyrrol-1-yl)acetyl]amino}-D-alanine/trifluoroacetic acid (1:1)

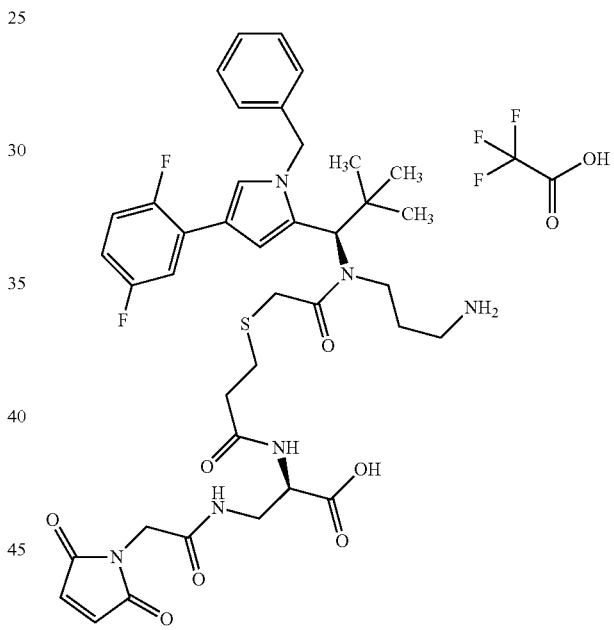

10.0 mg (9.98 μmol) of trifluoroacetic acid/2-(trimethylsilyl)ethyl 3-amino-N-(11-{(1R)-1-[1-benzyl-4-(2,5-difluorophenyl)-1H-pyrrol-2-yl]-2,2-dimethylpropyl}-2,2-dimethyl-6,12,17-trioxo-5-oxa-14-thia-7,11-diaza-2-silaheptadecan-17-yl)-D-alaninate (1:1) (Intermediate C80) and 2.77 mg (11.0 μmol) of 1-{2-[(2,5-dioxopyrrolidin-1-yl)oxy]-2-oxoethyl}-1H-pyrrole-2,5-dione were dissolved in 1 ml of dimethylformamide, and 3.3 μl (30 μmol) of N-methylmorpholine were added. The reaction mixture was stirred at RT overnight. 2.0 μl (35 μmol) of acetic acid were added, and the reaction mixture was purified directly by preparative RP-HPLC (column: Reprosil 125×30; 10μ, flow rate: 50 ml/min, MeCN/water/0.1% TFA). The solvents were evaporated under reduced pressure and the residue was dried under high vacuum. This gave 5.50 mg (54% of theory) of the compound 2-(trimethylsilyl)ethyl N-(11-{(1R)-1-[1-benzyl-4-(2,5-difluorophenyl)-1H-pyrrol-2-yl]-2,2-dimethylpropyl}-2,2-dimethyl-6,12,17-trioxo-5-oxa- 14-thia-7,11-diaza-2-silaheptadecan-17-yl)-3-{[(2,5-dioxo-2,5-dihydro-1H-pyrrol-1-yl)acetyl]amino}-D-alaninate.

LC-MS (Method 1): $R_t$=1.51 min; MS (ESIpos): m/z=1024 (M+H)$^+$.

5.50 mg (5.36 μmol) of 2-(trimethylsilyl)ethyl N-(11-{(1R)-1-[1-benzyl-4-(2,5-difluorophenyl)-1H-pyrrol-2-yl]-2,2-dimethylpropyl}-2,2-dimethyl-6,12,17-trioxo-5-oxa-14-thia-7,11-diaza-2-silaheptadecan-17-yl)-3-{[(2,5-dioxo-2,5-dihydro-1H-pyrrol-1-yl)acetyl]amino}-D-alaninate were dissolved in 1.0 ml of trifluoroethanol, and 4.39 mg (32.2 μmol) of zinc dichloride were added. The reaction mixture was stirred at 50° C. for 1 h. 4.39 mg (32.2 μmol) of zinc dichloride were added and the reaction mixture was stirred at 50° C. for 1 h. 4.39 mg (32.2 μmol) of zinc dichloride were added and the reaction mixture was stirred at 50° C. for 4 h. 28.2 mg (96.5 μmol) of ethylenediamine-N,N,N',N'-tetraacetic acid were added and the reaction mixture was stirred for 10 min, and water (0.1% TFA) was then added. Purification was carried out directly by preparative RP-HPLC (column: Reprosil 125×30; 10μ, flow rate: 50 ml/min, MeCN/water, 0.1% TFA). The solvents were evaporated under reduced pressure and the residue was dried under high vacuum.

This gave 2.70 mg (56% of theory) of the title compound.

LC-MS (Method 1): $R_t$=0.89 min; MS (ESIpos): m/z=781 (M+H)$^+$.

Intermediate F279

N-[6-(2,5-Dioxo-2,5-dihydro-1H-pyrrol-1-yl)hexanoyl]-L-valyl-N-[3-({(1R)-1-[1-benzyl-4-(2,5-difluorophenyl)-1H-pyrrol-2-yl]-2,2-dimethylpropyl}[({(2R)-2-carboxy-2-[(3-carboxypropanoyl)amino]ethyl}sulphanyl)acetyl]amino)propyl]-L-alaninamide 12.2 mg (14 μmol) of S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-N-(4-tert-butoxy-4-oxobutanoyl)-L-cysteine (Intermediate C77) were dissolved in 2.0 ml of trifluoroethanol, and 11.4 mg (83.8 μmol) of zinc dichloride were added. The reaction mixture was stirred at 50° C. for 3 h. 24.5 mg (83.8 μmol) of ethylenediamine-N,N,N',N'-tetraacetic acid were added, the reaction mixture was stirred for 10 min and water (0.1% TFA) was then added. Purification was carried out directly by preparative RP-HPLC (column: Reprosil 125×30; 10μ, flow rate: 50 ml/min, MeCN/water, 0.1% TFA). The solvents were evaporated under reduced pressure and the residue was dried under high vacuum. This gave 4.60 mg (42% of theory) of the compound 4-{[(1R)-2-({2-[(3-aminopropyl){(1R)-1-[1-benzyl-4-(2,5-difluorophenyl)-1H-pyrrol-2-yl]-2,2-dimethylpropyl}amino]-2-oxoethyl}sulphanyl)-1-carboxyethyl]amino}-4-oxobutanoic acid/trifluoroacetic acid (1:1).

LC-MS (Method 1): $R_t$=0.88 min; MS (ESIpos): m/z=673 (M+H)$^+$.

10.0 mg (12.7 μmol) of 4-{[(1R)-2-({2-[(3-aminopropyl){(1R)-1-[1-benzyl-4-(2,5-difluorophenyl)-1H-pyrrol-2-yl]-2,2-dimethylpropyl}amino]-2-oxoethyl}sulphanyl)-1-carboxyethyl]amino}-4-oxobutanoic acid/trifluoroacetic acid (1:1) and 7.41 mg (12.7 μmol) of 2,5-dioxopyrrolidin-1-yl N-[6-(2,5-dioxo-2,5-dihydro-1H-pyrrol-1-yl)hexanoyl]-L-valyl-L-alaninate (Intermediate L88) were dissolved in 1.5 ml of dimethylformamide, and 4.4 μl (25 μmol) of N,N-diisopropylethylamine were added. The reaction mixture was stirred at RT for 2 h. 2.0 μl (35 μmol) of acetic acid were added, and the reaction mixture was purified directly by preparative RP-HPLC (column: Reprosil 250×30; 10μ, flow rate: 50 ml/min, MeCN/water/0.1% TFA). The solvents were evaporated under reduced pressure and the residue was dried under high vacuum. This gave 5.20 mg (39% of theory) of the title compound.

LC-MS (Method 1): $R_t$=1.11 min; MS (ESIpos): m/z=1036 (M+H)$^+$.

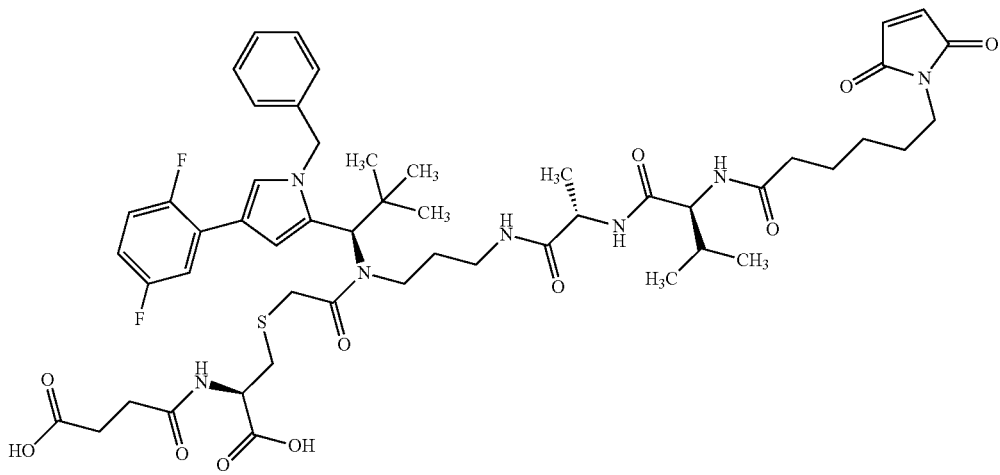 [SMILES: CC(C)[C@H](NC(=O)CCCCCN1C(=O)C=CC1=O)C(=O)N[C@@H](C)C(=O)NCCCN(C(=O)CSC[C@H](NC(=O)CCC(=O)O)C(=O)O)[C@@H](c1cc(-c2cc(F)ccc2F)cn1Cc1ccccc1)C(C)(C)C]

Intermediate F280

Trifluoroacetic acid/N-[2-({(2S)-2-amino-4-[{(1R)-1-[1-benzyl-4-(2,5-difluorophenyl)-1H-pyrrol-2-yl]-2,2-dimethylpropyl}(glycoloyl)amino]butanoyl}amino)ethyl]-3-(2,5-dioxo-2,5-dihydro-1H-pyrrol-1-yl)benzamide (1:1)

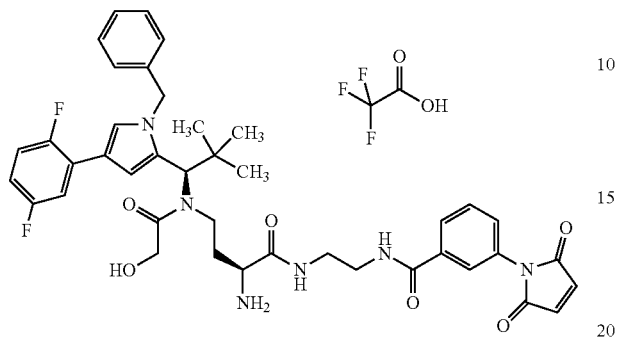

The title compound was prepared from Intermediate C64 by coupling with commercially available 1-(3-{[(2,5-dioxopyrrolidin-1-yl)oxy]carbonyl}phenyl)-1H-pyrrole-2,5-dione and subsequent deprotection with zinc chloride.

LC-MS (Method 1): $R_t$=0.88 min; MS (ESIpos): m/z=755 $(M+H)^+$.

Intermediate F281

N-{(2S)-2-Amino-4-[{(1R)-1-[1-benzyl-4-(2,5-difluorophenyl)-1H-pyrrol-2-yl]-2,2-dimethylpropyl}(glycoloyl)amino]butanoyl}-3-{[N-(bromoacetyl)-beta-alanyl]amino}-D-alanine/trifluoroacetic acid (1:1)

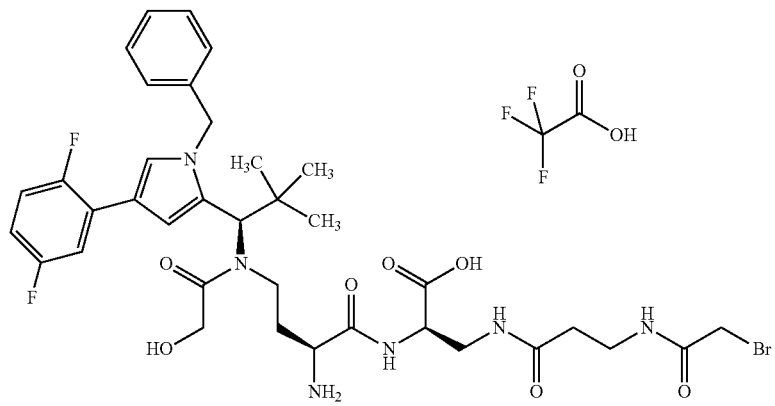 [SMILES: CC(C)(C)[C@H](c1cc(-c2cc(F)ccc2F)cn1Cc1ccccc1)N(CC[C@H](N)C(=O)N[C@H](CNC(=O)CCNC(=O)CBr)C(=O)O)C(=O)CO ; O=C(O)C(F)(F)F]

First, the modified amino acid building blocks N-(bromoacetyl)-beta-alanine and 2-(trimethylsilyl)ethyl-3-amino-N-(tert-butoxycarbonyl)-D-alaninate were prepared by classical methods of peptide chemistry. These were then coupled in the presence of HATU and morpholine. The tert-butoxycarbonyl protective group was then removed using 10% strength trifluoroacetic acid in dichloromethane, giving the intermediate 2-(trimethylsilyl)ethyl 3-{[N-(bromoacetyl)-beta-alanyl]amino}-D-alaninate.

Finally, the title compound was prepared by coupling this intermediate with intermediate C58 in the presence of HATU and 4-methylmorpholine, followed by deprotection with zinc chloride.

LC-MS (Method 1): $R_t$=0.87 min; MS (ESIpos): m/z=791 and 793 $(M+H)^+$.

Intermediate F282

Trifluoroacetic acid/(2S)-2-amino-4-[{(1R)-1-[1-benzyl-4-(2,5-difluorophenyl)-1H-pyrrol-2-yl]-2,2-dimethylpropyl}(glycoloyl)amino]-N-(3-{[N-(bromoacetyl)glycyl]amino}propyl)butanamide (1:1)

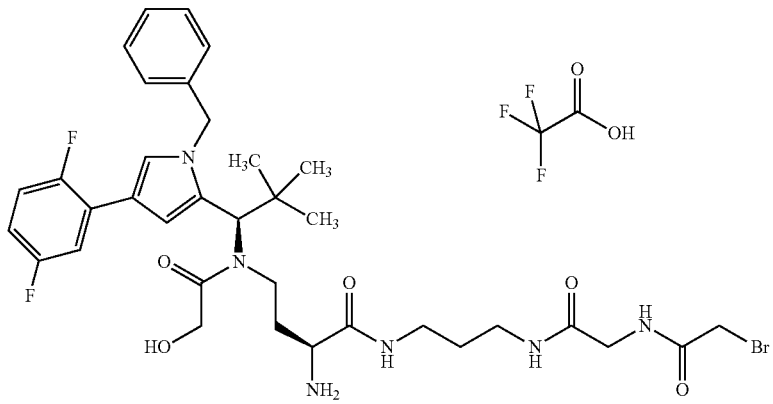 [SMILES: CC(C)(C)[C@H](c1cc(-c2cc(F)ccc2F)cn1Cc1ccccc1)N(CC[C@H](N)C(=O)NCCCNC(=O)CNC(=O)CBr)C(=O)CO ; O=C(O)C(F)(F)F]

First, the intermediate trifluoroacetic acid/N-(3-aminopropyl)-N2-(bromoacetyl)glycinamide (1:1) was prepared from tert-butyl glycinate and bromoacetic anhydride by classical methods of peptide chemistry.

Finally, the title compound was prepared by coupling this intermediate with intermediate C58 in the presence of HATU and 4-methylmorpholine, followed by deprotection with zinc chloride.

LC-MS (Method 1): $R_t$=0.83 min; MS (ESIpos): m/z=747 and 749 (M+H)$^+$.

Intermediate F283

N-[(2R)-2-({(2S)-2-Amino-4-[{(1R)-1-[1-benzyl-4-(2,5-difluorophenyl)-1H-pyrrol-2-yl]-2,2-dimethylpropyl}(glycoloyl)amino]butanoyl}amino)-2-carboxyethyl]-N$^2$-(bromoacetyl)-L-alpha-asparagine/trifluoroacetic acid (1:1)

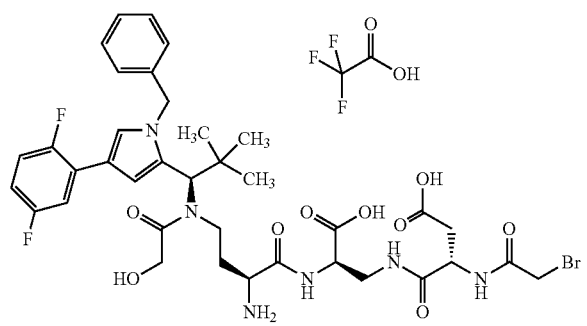 [SMILES: CC(C)(C)[C@H](c1cc(-c2cc(F)ccc2F)cn1Cc1ccccc1)N(CC[C@H](N)C(=O)N[C@H](CNC(=O)[C@H](CC(=O)O)NC(=O)CBr)C(=O)O)C(=O)CO ; O=C(O)C(F)(F)F]

First, the modified amino acid building block (2S)-2-[(bromoacetyl)amino]-4-oxo-4-[2-(trimethylsilyl)ethoxy]butanoic acid and bromoacetic anhydride was prepared from (2S)-2-amino-4-oxo-4-[2-(trimethylsilyl)ethoxy]butanoic acid and bromoacetic anhydride and the amino acid building block 2-(trimethylsilyl)ethyl-3-amino-N-(tert-butoxycarbonyl)-D-alaninate was prepared from commercially available 3-{[(benzyloxy)carbonyl]amino}-N-(tert-butoxycarbonyl)-D-alanine/N-cyclohexylcyclohexanamine (1:1). Both building blocks were coupled in the presence of HATU and morpholine and the tert-butoxycarbonyl protective group was then removed using 5% strength trifluoroacetic acid in dichloromethane, giving the silylethyl ester protective groups and thus the intermediate trifluoroacetic acid/2-(trimethylsilyl)ethyl-N-{(2R)-2-amino-3-oxo-3-[2-(trimethylsilyl)ethoxy]propyl}-N2-(bromoacetyl)-L-alpha-asparaginate (1:1).

Finally, the title compound was prepared by coupling this intermediate with intermediate C58 in the presence of HATU and 4-methylmorpholine, followed by deprotection with zinc chloride.

LC-MS (Method 1): $R_t$=0.84 min; MS (ESIpos): m/z=835 and 837 (M+H)$^+$.

Intermediate F284

N-{(2S)-2-Amino-4-[{(1R)-1-[1-benzyl-4-(2,5-difluorophenyl)-1H-pyrrol-2-yl]-2,2-dimethylpropyl}(glycoloyl)amino]butanoyl}-3-{[1-(2,5-dioxo-2,5-dihydro-1H-pyrrol-1-yl)-2,18-dioxo-6,9,12,15-tetraoxa-3-azaoctadecan-18-yl]amino}-D-alanine/trifluoracetic Acid (1:1)

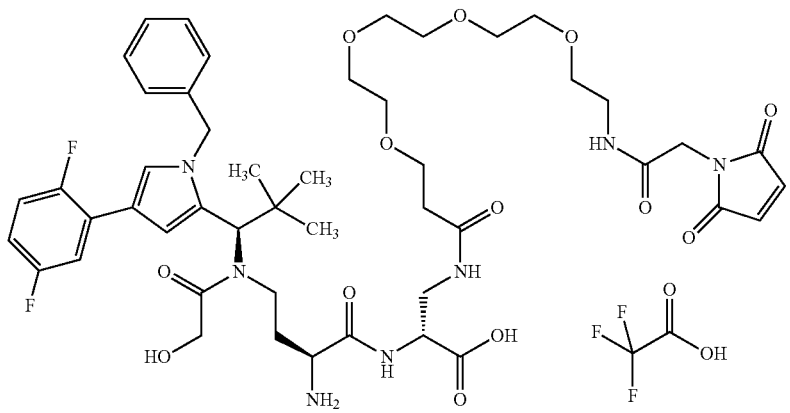

First, intermediate L80 was coupled with commercially available (2,5-dioxo-2,5-dihydro-1H-pyrrol-1-yl)acetic acid in the presence of HATU and N,N-diisopropylethylamine, and the tert-butoxycarbonyl protective group was then removed using 16% strength trifluoroacetic acid in dichloromethane, giving the silylethyl ester protective group.

Finally, the title compound was prepared by coupling this intermediate with intermediate C58 in the presence of HATU and N,N-diisopropylethylamine, followed by deprotection with zinc chloride.

LC-MS (Method 12): $R_t$=1.46 min; MS (ESIpos): m/z=984.45 (M+H)$^+$.

Intermediate F285

N-{(2S)-2-Amino-4-[{(1R)-1-[1-benzyl-4-(2,5-difluorophenyl)-1H-pyrrol-2-yl]-2,2-dimethylpropyl}(glycoloyl)amino]butanoyl}-3-[(18-bromo-17-oxo-4,7,10,13-tetraoxa-16-azaoctadecan-1-oyl)amino]-D-alanine/trifluoroacetic acid (1:1)

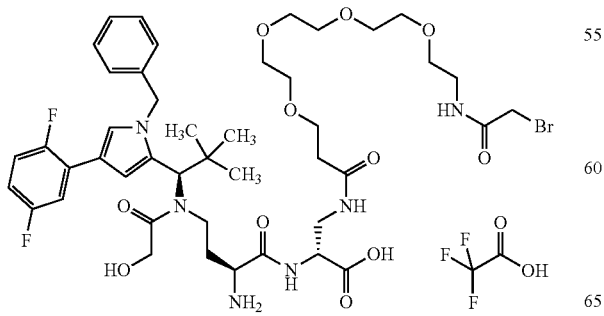

First, intermediate L80 was acylated with commercially available bromoacetic anhydride, and the tert-butoxycarbonyl protective group was then removed using 20% strength trifluoroacetic acid in dichloromethane, giving the silylethyl ester protective group.

Finally, the title compound was prepared by coupling this intermediate with intermediate C58 in the presence of HATU and N,N-diisopropylethylamine, followed by deprotection with zinc chloride.

LC-MS (Method 1): $R_t$=0.85 min; MS (ESIpos): m/z=967 and 969 (M+H)$^+$.

Intermediate F286

1-[(N-{(2S)-2-Amino-4-[{(1R)-1-[1-benzyl-4-(2,5-difluorophenyl)-1H-pyrrol-2-yl]-2,2-dimethylpropyl}(glycoloyl)amino]butanoyl}-3-{[(2,5-dioxo-2,5-dihydro-1H-pyrrol-1-yl) acetyl]amino}-D-alanyl) amino]-3,6,9,12-tetraoxapentadecan-15-oic acid/ trifluoroacetic acid (1:1)

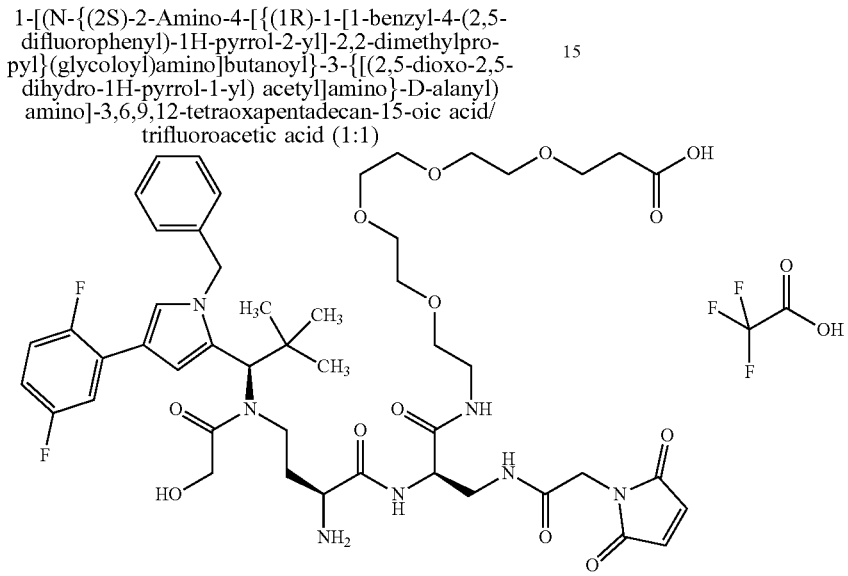

First, intermediate L91 was coupled with (2,5-dioxo-2,5-dihydro-1H-pyrrol-1-yl)acetic acid in the presence of HATU and N,N-diisopropylethylamine, and the Boc protective group was then removed using 12.5% strength TFA in DCM. The resulting intermediate was coupled with intermediate C58 in the presence of HATU and N,N-diisopropylethylamine and then converted into the title compound by deprotection with zinc chloride.

LC-MS (Method 1): $R_t$=0.84 min; MS (ESIpos): m/z=984 (M+H)$^+$.

Intermediate F288

N-{(2S)-2-Amino-4-[{(1R)-1-[1-benzyl-4-(2,5-difluorophenyl)-1H-pyrrol-2-yl]-2,2-dimethylpropyl}(glycoloyl)amino]butanoyl}-3-({N-[(2,5-dioxo-2,5-dihydro-1H-pyrrol-1-yl)acetyl]-L-seryl}amino)-D-alanine/trifluoroacetic acid (1:1)

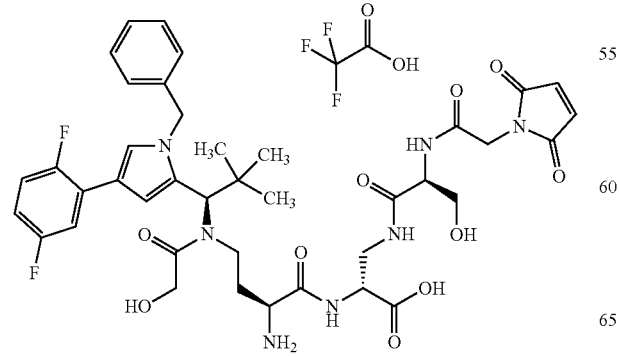

35 mg (39 μmol) of intermediate C74 were coupled in the presence of HATU and N,N-diisopropyethylamine with N-[(2,5-dioxo-2,5-dihydro-1H-pyrrol-1-yl)acetyl]-L-serine which had been prepared beforehand from tert-butyl O-tert-butyl-L-serinate and (2,5-dioxo-2,5-dihydro-1H-pyrrol-1-yl)acetic acid. Deprotection with zinc chloride and purification by HPLC gave 14 mg (38% of theory) of the title compound.

LC-MS (Method 12): $R_t$=1.43 min; MS (ESIpos): m/z=824.34 (M+H)$^+$.

Intermediate F289

$N^2$-{(2S)-2-Amino-4-[{(1R)-1-[1-benzyl-4-(2,5-difluorophenyl)-1H-pyrrol-2-yl]-2,2-dimethylpropyl}(glycoloyl)amino]butanoyl}-$N^6$-[(2,5-dioxo-2,5-dihydro-1H-pyrrol-1-yl)acetyl]-D-lysine/trifluoroacetate (1:1)

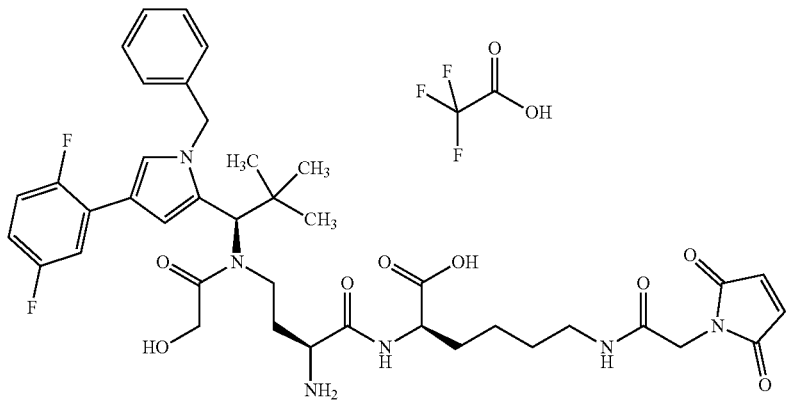 [SMILES: CC(C)(C)[C@H](c1cc(-c2cc(F)ccc2F)cn1Cc1ccccc1)N(CC[C@H](N)C(=O)N[C@H](CCCCNC(=O)CN1C(=O)C=CC1=O)C(=O)O)C(=O)CO ; O=C(O)C(F)(F)F]

First, trifluoroacetic acid/2-(trimethylsilyl)ethyl-$N^6$-[(2,5-dioxo-2,5-dihydro-1H-pyrrol-1-yl)acetyl]-D-lysinate (1:1) was prepared by classical methods of peptide chemistry from $N^6$-[(benzyloxy)carbonyl]-$N^2$-(tert-butoxycarbonyl)-D-lysine. 12.5 mg (25 μmol) of this intermediate were then coupled in the presence of HATU and 4-methylmorpholine with 15 mg (23 μmol) of Intermediate C58. Deprotection with zinc chloride and purification by HPLC gave 14 mg (53% of theory) of the title compound.

LC-MS (Method 1): $R_t$=0.83 min; MS (ESIpos): m/z=779 (M+H)$^+$.

Intermediate F290

$N^2$-{(2S)-2-Amino-4-[{(1R)-1-[1-benzyl-4-(2,5-difluorophenyl)-1H-pyrrol-2-yl]-2,2-dimethylpropyl}(glycoloyl)amino]butanoyl}-$N^6$-(bromoacetyl)-D-lysine/trifluoroacetic acid (1:1)

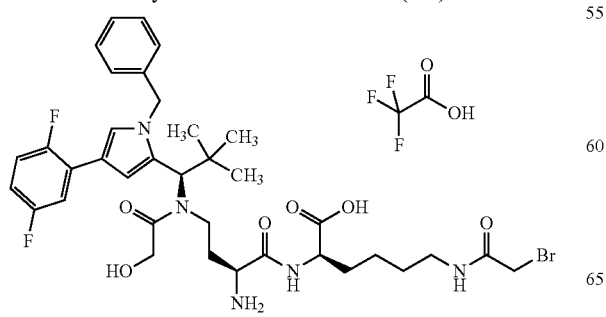

First, trifluoroacetic acid/2-(trimethylsilyl)ethyl-N6-(bromoacetyl)-D-lysinate (1:1) was prepared by classical methods of peptide chemistry from $N^6$-[(benzyloxy)carbonyl]-$N^2$-(tert-butoxycarbonyl)-D-lysine.

12 mg (25 μmol) of this intermediate were then coupled in the presence of HATU and 4-methylmorpholine with 15 mg (23 μmol) of Intermediate C58. Deprotection with zinc chloride and purification by HPLC gave 7 mg (36% of theory) of the title compound.

LC-MS (Method 1): $R_t$=0.86 min; MS (ESIpos): m/z=762 and 764 $(M+H)^+$.

Intermediate F291

N-[(2,5-Dioxo-2,5-dihydro-1H-pyrrol-1-yl)acetyl]-L-valyl-N-{3-[{(1R)-1-[1-benzyl-4-(2,5-difluorophenyl)-1H-pyrrol-2-yl]-2,2-dimethylpropyl}(glycoloyl)amino]propyl}-L-alaninamide

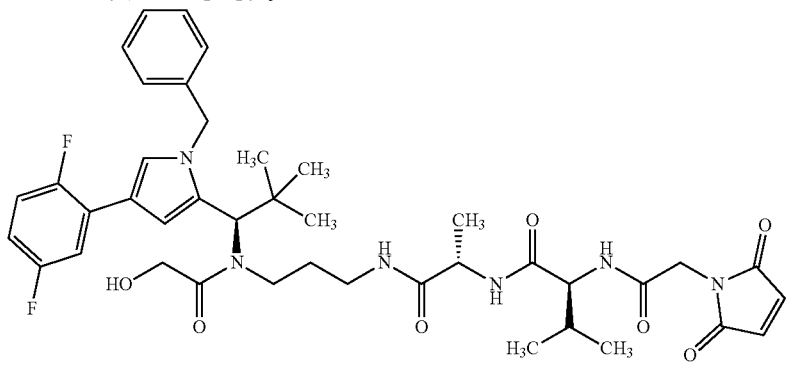

The title compound was prepared from Example M9 first by coupling with N-[(benzyloxy)carbonyl]-L-valyl-L-alanine in the presence of HATU and N,N-diisopropylethylamine. In the next step, the Z protective group was removed by hydrogenating for 1 hour over 10% palladium on activated carbon at RT under hydrogen standard pressure and then converting the deprotected intermediate into the title compound by coupling with (2,5-dioxo-2,5-dihydro-1H-pyrrol-1-yl)acetic acid in the presence of HATU and N,N-diisopropylethylamine.

LC-MS (Method 1): $R_t$=1.21 min; MS (ESIpos): m/z=777 $(M+H)^+$.

Intermediate F293

N-{(2S)-2-Amino-4-[{(1R)-1-[1-benzyl-4-(2,5-difluorophenyl)-1H-pyrrol-2-yl]-2,2-dimethylpropyl}(glycoloyl)amino]butanoyl}-3-{[(2,5-dioxo-2,5-dihydro-1H-pyrrol-1-yl)benzoyl]amino}-D-alanine/trifluoroacetic acid (1:1)

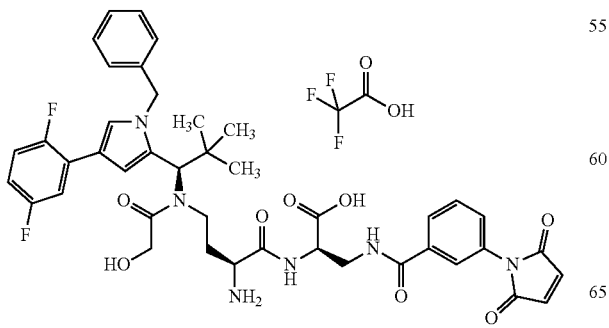

LC-MS (Method 12): $R_t$=0.93 min; MS (ESIpos): m/z=799 (M+H)+.

Intermediate F294

N-{5-[(2,5-Dioxopyrrolidin-1-yl)oxy]-5-oxopentanoyl}-L-valyl-N-{(1S)-3-[{(1R)-1-[1-benzyl-4-(2,5-difluorophenyl)-1H-pyrrol-2-yl]-2,2-dimethylpropyl}(glycoloyl)amino]-1-carboxypropyl}-L-alaninamide

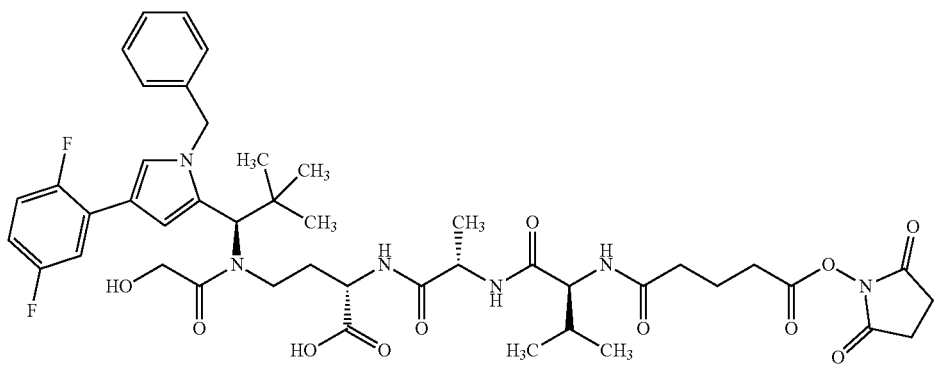 [SMILES: CC(C)[C@H](NC(=O)CCCC(=O)ON1C(=O)CCC1=O)C(=O)N[C@@H](C)C(=O)N[C@@H](CCN(C(=O)CO)[C@@H](c1cc(-c2cc(F)ccc2F)cn1Cc1ccccc1)C(C)(C)C)C(=O)O]

41 mg (0.05 mmol) of Intermediate C76 dissolved in 12 ml of methanol were hydrogenated over 10 mg of 10% palladium on activated carbon at RT for 1 h under hydrogen standard pressure. The catalyst was then filtered off and the solvent was removed under reduced pressure. This gave 32 mg (92% of theory) of the deprotected intermediate.

15 mg (0.022 mmol) of this intermediate were dissolved in DMF, and 13 mg (0.039 mmol) of 1,1'-[(1,5-dioxopentan-1,5-diyl)bis(oxy)]dipyrrolidine-2,5-dione and 7 µl of N,N-diisopropylethylamine were added. After 1 h of stirring at RT, the reaction was concentrated and the residue was purified by HPLC. This gave 9 mg (45% of theory) of the title compound.

LC-MS (Method 1): $R_t$=1.08 min; MS (ESIpos): m/z=895 (M+H)+.

Intermediate F295

N-[(2,5-Dioxo-2,5-dihydro-1H-pyrrol-1-yl)acetyl]-L-valyl-N-{(1S)-3-[{(1R)-1-[1-benzyl-4-(2,5-difluorophenyl)-1H-pyrrol-2-yl]-2,2-dimethylpropyl}(glycoloyl)amino]-1-carboxypropyl}-L-alaninamide

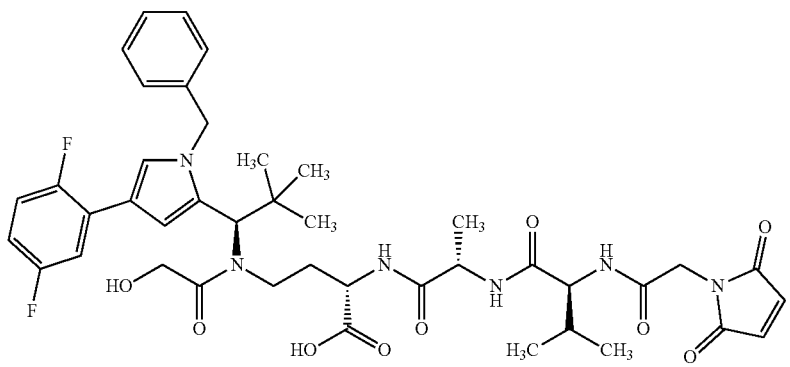 [SMILES: CC(C)[C@H](NC(=O)CN1C(=O)C=CC1=O)C(=O)N[C@@H](C)C(=O)N[C@@H](CCN(C(=O)CO)[C@@H](c1cc(-c2cc(F)ccc2F)cn1Cc1ccccc1)C(C)(C)C)C(=O)O]

415

41 mg (0.05 mmol) of Intermediate C76 dissolved in 12 ml of methanol were hydrogenated over 10 mg of 10% palladium on activated carbon at RT for 1 h under hydrogen standard pressure. The catalyst was then filtered off and the solvent was removed under reduced pressure. This gave 32 mg (92% of theory) of the deprotected intermediate.

15 mg (0.022 mmol) of this intermediate were dissolved in 4 ml of DMF, and 10 mg (0.039 mmol) of 1-{2-[(2,5-dioxopyrrolidin-1-yl)oxy]-2-oxoethyl}-1H-pyrrole-2,5-dione and 7 µl of N,N-diisopropylethylamine were added. After 2 h of stirring at RT, the reaction was concentrated and the residue was purified by HPLC. This gave 10 mg (56% of theory) of the title compound.

LC-MS (Method 1): $R_t$=1.08 min; MS (ESIpos): m/z=821 (M+H)⁺.

Intermediate F296

Trifluoroacetic acid/(2S)-2-amino-4-[{(1R)-1-[1-benzyl-4-(2,5-difluorophenyl)-1H-pyrrol-2-yl]-2,2-dimethylpropyl}(glycoloyl)amino]-N-{2-[(2-{[(2,5-dioxo-2,5-dihydro-1H-pyrrol-1-yl)acetyl]amino}ethyl)sulphonyl]ethyl}butanamide (1:1)

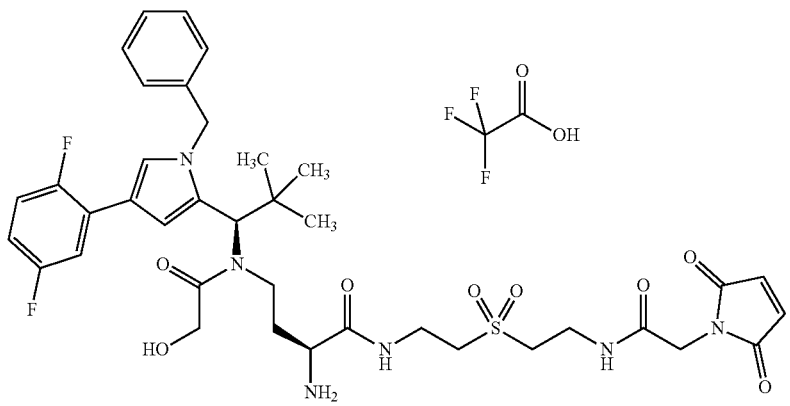 [SMILES: CC(C)(C)[C@H](c1cc(-c2cc(F)ccc2F)cn1Cc1ccccc1)N(CC[C@H](N)C(=O)NCCS(=O)(=O)CCNC(=O)CN1C(=O)C=CC1=O)C(=O)CO ; O=C(O)C(F)(F)F]

The title compound was prepared from Intermediate L81 by coupling with Intermediate C58 in the presence of HATU and N,N-diisopropylethylamine. In the next step, the Z protective group was removed by hydrogenation over 10% palladium on activated carbon in DCM/methanol 1:1 at RT under hydrogen standard pressure for 30 min. The deprotected intermediate was then converted by coupling with (2,5-dioxo-2,5-dihydro-1H-pyrrol-1-yl)acetic acid in the presence of HATU and N,N-diisopropylethylamine and finally by deprotection with zinc chloride into the title compound.

LC-MS (Method 1): $R_t$=0.83 min; MS (ESIpos): m/z=785 (M+H)⁺.

Intermediate F297

S-{2-[{(1R)-1-[1-Benzyl-4-(2,5-difluorophenyl)-1H-pyrrol-2-yl]-2,2-dimethylpropyl}(pyrrolidin-3-ylmethyl)amino]-2-oxoethyl}-N-[6-(2,5-dioxo-2,5-dihydro-H-pyrrol-1-yl)hexanoyl]-L-cysteine/trifluoroacetic acid (1:1) (Isomer 1)

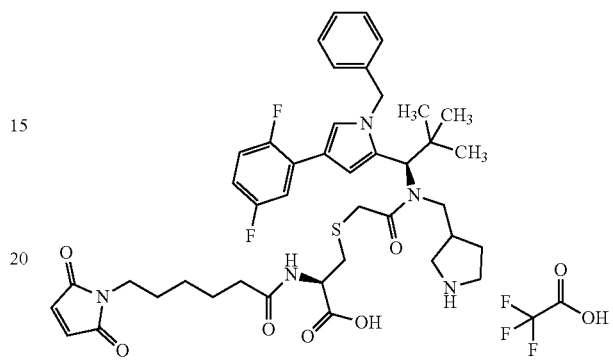

Under argon, 15 mg (0.11 mmol) of zinc chloride were added to a solution of 36 mg (0.03 mmol, 68% pure) of S-[2-({(1R)-1-[1-benzyl-4-(2,5-difluorophenyl)-1H-pyrrol-2-yl]-2,2-dimethylpropyl}{[1-(tert-butoxycarbonyl)pyrrolidin-3-yl]methyl}amino)-2-oxoethyl]-N-[6-(2,5-dioxo-2,5-dihydro-1H-pyrrol-1-yl)hexanoyl]-L-cysteine (Intermediate C92) in 0.74 ml of 2,2,2-trifluoroethanol, and the reaction mixture was stirred at 50° C. for 7 h. 32 mg (0.11 mmol) of EDTA were then added and the mixture was stirred for 15 minutes. Ethyl acetate was added to the reaction mixture and the organic phase was washed repeatedly with water and with saturated NaCl solution. The organic phase was dried over magnesium sulphate and the solvent was evaporated under reduced pressure. The residue was purified by preparative HPLC. This gave 6.4 mg (25% of theory) of the title compound.

LC-MS (Method 1): $R_t$=0.95 min; MS (ESIpos): m/z=792 (M+H-CF₃CO₂H)+.

Intermediate F298

S-{2-[{(1R)-1-[1-Benzyl-4-(2,5-difluorophenyl)-1H-pyrrol-2-yl]-2,2-dimethylpropyl}(pyrrolidin-3-ylmethyl)amino]-2-oxoethyl}-N-[6-(2,5-dioxo-2,5-dihydro-1H-pyrrol-1-yl)hexanoyl]-L-cysteine/trifluoroacetic acid (1:1) (isomer 2)

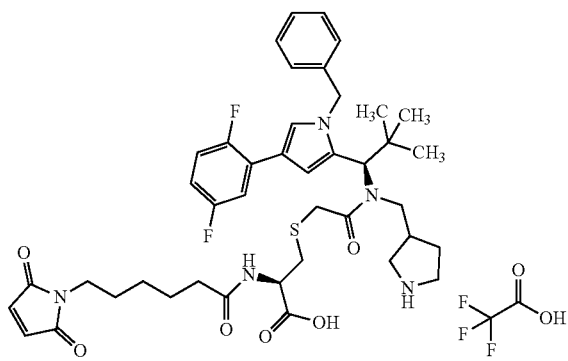

Under argon, 19 mg (0.14 mmol) of zinc chloride were added to a solution of 45 mg (0.04 mmol, 71% pure) of S-[2-({(1R)-1-[1-benzyl-4-(2,5-difluorophenyl)-1H-pyrrol-2-yl]-2,2-dimethylpropyl}{[1-(tert-butoxycarbonyl)pyrrolidin-3-yl]methyl}amino)-2-oxoethyl]-N-[6-(2,5-dioxo-2,5-dihydro-1H-pyrrol-1-yl)hexanoyl]-L-cysteine (intermediate C91) in 0.94 ml of 2,2,2-trifluoroethanol, and the reaction mixture was stirred at 50° C. for 3 h. 42 mg (0.14 mmol) of EDTA were then added, and the mixture was stirred for 15 minutes. Ethyl acetate was added to the reaction mixture and the organic phase was washed repeatedly with water and sat. NaCl solution. The organic phase was dried over magnesium sulphate and the solvent was evaporated under reduced pressure. The residue was purified by preparative HPLC. This gave 5.7 mg (18% of theory) of the title compound.

LC-MS (Method 1): $R_t$=0.96 min; MS (ESIpos): m/z=791 (M+H-CF$_3$CO$_2$H)+.

Intermediate F299

S-(2-{(3-Aminopropyl)[(R)-[1-benzyl-4-(2,5-difluorophenyl)-1H-pyrrol-2-yl](cyclohexyl)methyl]amino}-2-oxoethyl)-N-[6-(2,5-dioxo-2,5-dihydro-1H-pyrrol-1-yl)hexanoyl]-L-cysteine/trifluoroacetic acid (1:1)

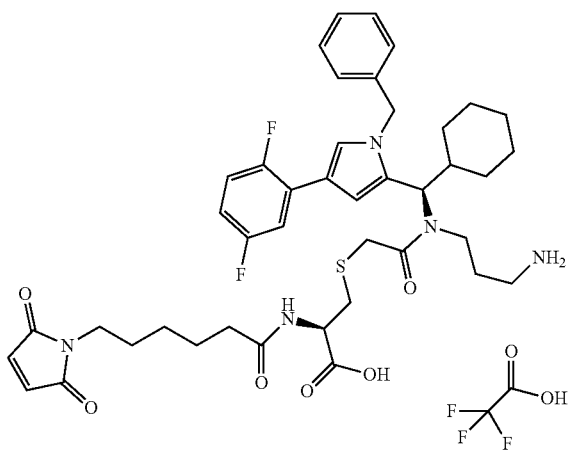 [SMILES: NCCCN(C(=O)CSC[C@H](NC(=O)CCCCCN1C(=O)C=CC1=O)C(=O)O)[C@@H](c1cc(-c2cc(F)ccc2F)cn1Cc1ccccc1)C1CCCCC1 ; O=C(O)C(F)(F)F]

76.8 mg (0.57 mmol) of zinc chloride were added to a solution of 88.0 mg (0.09 mmol) of S-{11-[(R)-[1-benzyl-4-(2,5-difluorophenyl)-1H-pyrrol-2-yl](cyclohexyl)methyl]-2,2-dimethyl-6,12-dioxo-5-oxa-7,11-diaza-2-silatridecan-13-yl}-N-[6-(2,5-dioxo-2,5-dihydro-1H-pyrrol-1-yl)hexanoyl]-L-cysteine (intermediate C84) in 1.88 ml of 2,2,2-trifluoroethanol, and the reaction mixture was stirred at 50° C. for 3 h. 164.6 mg (0.57 mmol) of EDTA were then added, and the mixture was stirred for 15 minutes. Ethyl acetate was added to the reaction mixture and the org. phase was washed repeatedly with water and with sat. NaCl solution. The organic phase was dried over sodium sulphate and the solvent was evaporated under reduced pressure. The residue was purified by preparative HPLC. This gave 31 mg (35% of theory) of the title compound.

LC-MS (Method 12): $R_t$=1.82 min; MS (ESIpos): m/z=792 (M+H)+.

Intermediate F300

(2S)-2-Amino-4-[{(1R)-1-[1-benzyl-4-(2,5-difluorophenyl)-1H-pyrrol-2-yl]-2,2-dimethylpropyl}(glycoloyl)amino]-N-(2-{[(2R)-2-(2,5-dioxo-2,5-dihydro-1H-pyrrol-1-yl)propanoyl]amino}ethyl)butanamide

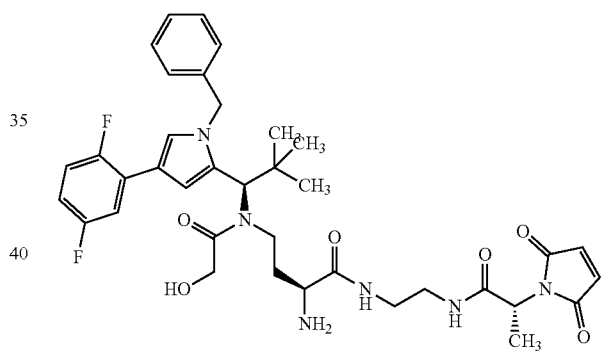

Under argon, 11 mg (0.08 mmol) of zinc chloride were added to a solution of 7 mg (0.08 mmol) of 2-(trimethylsilyl)ethyl-{(2S)-4-[{(1R)-1-[1-benzyl-4-(2,5-difluorophenyl)-1H-pyrrol-2-yl]-2,2-dimethylpropyl}(glycoloyl)amino]-1-[(2-{[(2R)-2-(2,5-dioxo-2,5-dihydro-1H-pyrrol-1-yl)propanoyl]amino}ethyl)amino]-1-oxobutan-2-yl}carbamate (intermediate C100) in 0.2 ml of 2,2,2-trifluoroethanol, and the reaction mixture was stirred at 50° C. for 8 h. 14 mg (0.05 mmol) of EDTA were then added, and the mixture was stirred for 15 minutes. Ethyl acetate was added to the reaction mixture and the organic phase was washed repeatedly with water and with sat. NaCl solution. The organic phase was dried over magnesium sulphate and the solvent was evaporated under reduced pressure. The residue was purified by preparative HPLC. This gave 1.6 mg (27% of theory) of the title compound.

LC-MS (Method 1): $R_t$=0.88 min; MS (ESIpos): m/z=707 (M+H-CF$_3$CO$_2$H)+.

Intermediate F302

S-{2-[{(1R)-1-[1-Benzyl-4-(2,5-difluorophenyl)-1H-pyrrol-2-yl]-2,2-dimethylpropyl}(pyrrolidin-3-ylmethyl)amino]-2-oxoethyl}-N-[(2,5-dioxo-2,5-dihydro-1H-pyrrol-1-yl)acetyl]-L-cysteine/trifluoroacetate (1:1) (isomer 1)

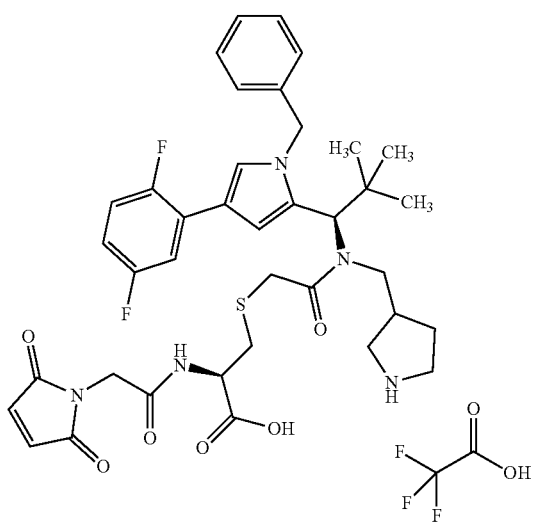

Under argon, 31.7 mg (0.23 mmol) of zinc chloride were added to a mixture of 56.9 mg (58.2 mmol, 85% pure) of S-[2-({(1R)-1-[1-benzyl-4-(2,5-difluorophenyl)-1H-pyrrol-2-yl]-2,2-dimethylpropyl}{[(1-(tert-butoxycarbonyl)pyrrolidin-3-yl]methyl}amino)-2-oxoethyl]-N-[(2,5-dioxo-2,5-dihydro-1H-pyrrol-1-yl)acetyl]-L-cysteine (intermediate C94) in 1.4 ml of 2,2,2-trifluoroethanol, and the reaction mixture was stirred at 50° C. for 3 h. 68.0 mg (0.23 mmol) of EDTA were then added, and the mixture was stirred for 15 minutes. Ethyl acetate was added to the reaction mixture and the organic phase was washed repeatedly with water and with sat. NaCl solution. The organic phase was dried over magnesium sulphate and the solvent was evaporated under reduced pressure. The residue was purified by preparative HPLC. This gave 7 mg (13% of theory) of the title compound.

LC-MS (Method 1): $R_t$=0.91 min; MS (ESIpos): m/z=736 (M+H-CF$_3$CO$_2$H)$^+$.

Intermediate F304

N-(2-{[3-({2-[{(1R)-1-[1-Benzyl-4-(2,5-difluorophenyl)-1H-pyrrol-2-yl]-2,2-dimethylpropyl}(pyrrolidin-3-ylmethyl)amino]-2-oxoethyl}sulphanyl)propanoyl]amino}ethyl)-6-(2,5-dioxo-2,5-dihydro-1H-pyrrol-1-yl)hexanamide (1:1) trifluoroacetic acid (isomer 2)

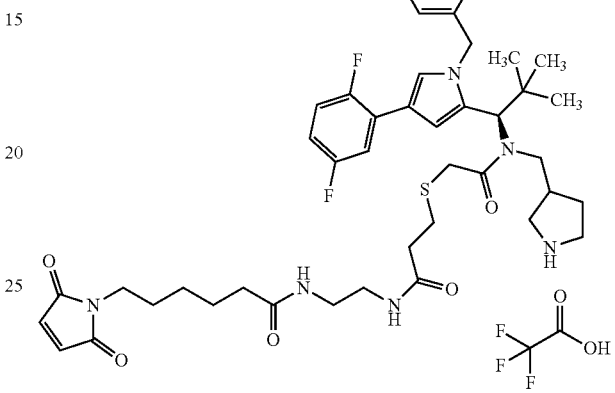

13.2 mg (0.10 mmol) of zinc chloride were added to a solution of 22.3 mg (0.02 mmol) of tert-butyl 3-[2-{(1R)-1-[1-benzyl-4-(2,5-difluorophenyl)-1H-pyrrol-2-yl]-2,2-dimethylpropyl}-18-(2,5-dioxo-2,5-dihydro-1H-pyrrol-1-yl)-3,8,13-trioxo-5-thia-2,9,12-triazaoctadec-1-yl]pyrrolidine-1-carboxylate (intermediate 98) in 0.64 ml of 2,2,2-trifluoroethanol, and the reaction mixture was stirred at 50° C. for 8 h. 28.36 mg (0.10 mmol) of EDTA were then added, and the mixture was stirred for 15 minutes. Ethyl acetate was added to the reaction mixture and the organic phase was washed repeatedly with water and with sat. NaCl solution. The organic phase was dried over magnesium sulphate and the solvent was evaporated under reduced pressure. The residue was purified by prep. HPLC. This gave 5 mg (24% of theory) of the title compound.

LC-MS (Method 5): $R_t$ 3.05 min; MS (ESIpos): m/z=819 (M+H-CF$_3$CO$_2$H)+.

Intermediate F305

N-{(1R)-1-[1-Benzyl-4-(2,5-difluorophenyl)-1H-pyrrol-2-yl]-2,2-dimethylpropyl}-22-(2,5-dioxo-2,5-dihydro-1H-pyrrol-1-yl)-6,17-dioxo-N-(pyrrolidin-3-ylmethyl)-10,13-dioxa-3-thia-7,16-diazadocosane-1-amide (1:1) trifluoroacetic acid (isomer 2)

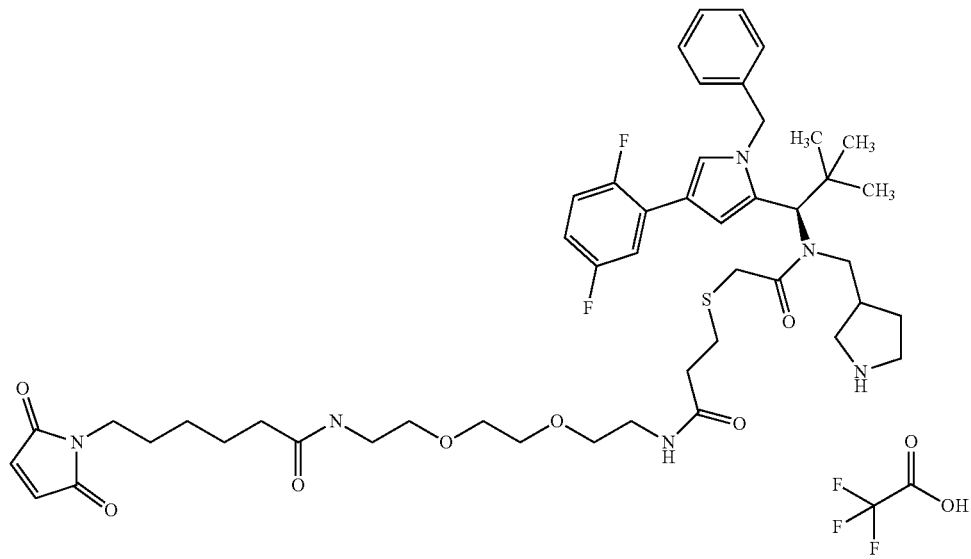 [SMILES: CC(C)(C)[C@H](c1cc(-c2cc(F)ccc2F)cn1Cc1ccccc1)N(CC1CCNC1)C(=O)CSCCC(=O)NCCOCCOCCNC(=O)CCCCCN1C(=O)C=CC1=O ; O=C(O)C(F)(F)F]

13.42 mg (0.10 mmol) of zinc chloride were added to a solution of 24.80 mg (0.02 mmol) of tert-butyl 3-[2-{(1R)-1-[1-benzyl-4-(2,5-difluorophenyl)-1H-pyrrol-2-yl]-2,2-dimethylpropyl}-24-(2,5-dioxo-2,5-dihydro-1H-pyrrol-1-yl)-3,8,19-trioxo-12,15-dioxa-5-thia-2,9,18-triazatetracos-1-yl] pyrrolidine-1-carboxylate (intermediate C99) in 0.65 ml of 2,2,2-trifluoroethanol, and the reaction mixture was stirred at 50° C. for 8 h. 28.78 mg (0.10 mmol) of EDTA were then added, and the mixture was stirred for 15 minutes. Ethyl acetate was added to the reaction mixture and the org. phase was washed repeatedly with water and with sat. NaCl solution. The organic phase was dried over magnesium sulphate and the solvent was evaporated under reduced pressure. The residue was purified by preparative HPLC. This gave 10 mg (44% of theory) of the title compound.

LC-MS (Method 5): $R_t$=3.11 min; MS (ESIpos): m/z=907 $(M+H-CF_3CO_2H)^+$.

Intermediate F306

$N^6$—(N-{(2S)-2-Amino-4-[{(1R)-1-[1-benzyl-4-(2,5-difluorophenyl)-1H-pyrrol-2-yl]-2,2-dimethylpropyl}(glycoloyl)amino]butanoyl}-beta-alanyl)-$N^2$—{N-[(2,5-dioxo-2,5-dihydro-1H-pyrrol-1-yl)acetyl]-L-valyl-L-alanyl-beta-alanyl}-L-lysine/trifluoroacetic acid (1:1)

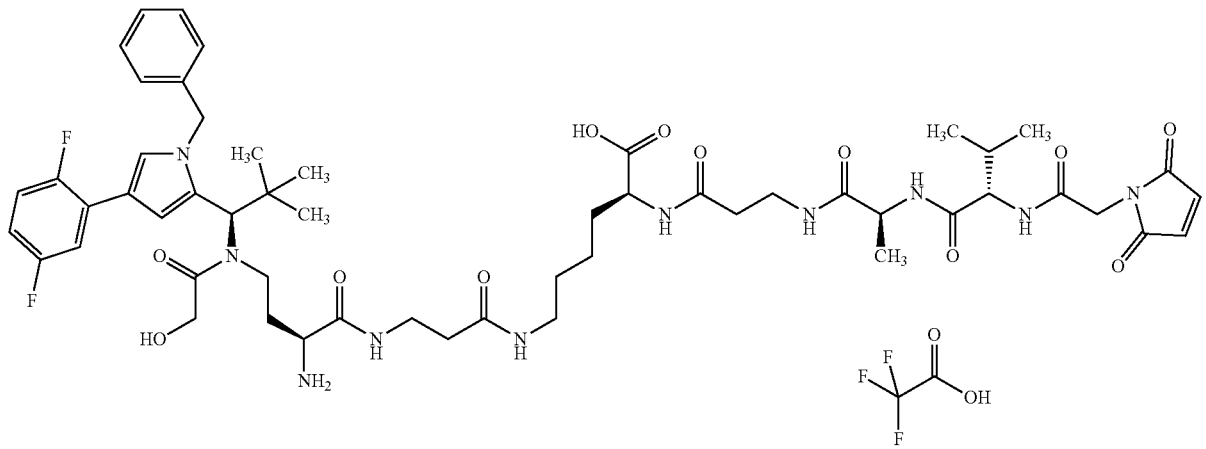 [SMILES: CC(C)[C@H](NC(=O)CN1C(=O)C=CC1=O)C(=O)N[C@@H](C)C(=O)NCCC(=O)N[C@@H](CCCCNC(=O)CCNC(=O)[C@@H](N)CCN(C(=O)CO)[C@@H](c1cc(-c2cc(F)ccc2F)cn1Cc1ccccc1)C(C)(C)C)C(=O)O ; O=C(O)C(F)(F)F]

The title compound was prepared by coupling 24 mg (0.029 mmol) of the intermediate C61 with 30 mg (0.035 mmol) of intermediate L99 in the presence of 16.7 mg (0.044 mmol) of HATU and 15 µl of N,N-diisopropylethylamine and subsequent deprotection with zinc chloride in trifluoroethanol as described for intermediate F119. Purification by preparative HPLC gave 19 mg (52% of theory over 2 steps) of the title compound.

LC-MS (Method 1): $R_t$=0.84 min; MS (ESIpos): m/z=1091 (M+H)$^+$.

Intermediate F307

N-[6-(2,5-Dioxo-2,5-dihydro-1H-pyrrol-1-yl) hexanoyl]-L-valyl-L-alanyl-S-{(5R,14R)-13-(3-aminopropyl)-14-[1-benzyl-4-(2,5-difluorophenyl)-1H-pyrrol-2-yl]-5-carboxy-15,15-dimethyl-2,7,12-trioxo-10-thia-3,6,13-triazahexadec-1-yl}-L-cysteine/trifluoroacetic acid (1:1)

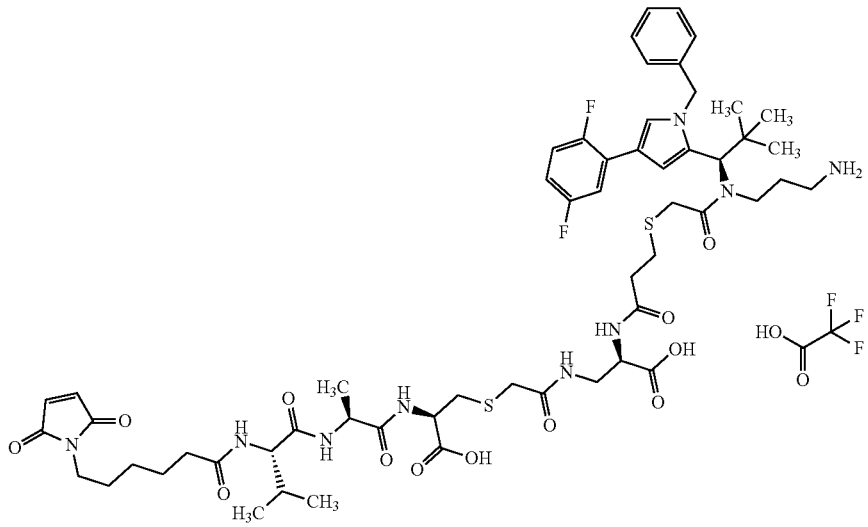 [SMILES: CC(C)[C@H](NC(=O)CCCCCN1C(=O)C=CC1=O)C(=O)N[C@@H](C)C(=O)N[C@@H](CSCC(=O)NC[C@@H](NC(=O)CCSCC(=O)N(CCCN)[C@@H](c1cc(-c2cc(F)ccc2F)cn1Cc1ccccc1)C(C)(C)C)C(=O)O)C(=O)O ; O=C(O)C(F)(F)F]

8.90 mg (8.88 µmol) of trifluoroacetic acid/2-(trimethylsilyl)ethyl 3-amino-N-(11-{(1R)-1-[1-benzyl-4-(2,5-difluorophenyl)-1H-pyrrol-2-yl]-2,2-dimethylpropyl}-2,2-dimethyl-6,12,17-trioxo-5-oxa-14-thia-7,11-diaza-2-silaheptadecan-17-yl)-D-alaninate (1:1) (intermediate C80) and 2.31 mg (9.77 µmol) of 1-(2-bromoacetoxy)pyrrolidine-2,5-dione were dissolved in 1 ml of dimethylformamide, and 2.9 µl (27 µmol) of N-methylmorpholine were added. The reaction mixture was stirred at RT for 1 h. The reaction mixture was purified directly by prep. RP-HPLC (column: Reprosil 125×30; 10µ, flow rate: 50 ml/min, MeCN/water/0.1% TFA). The solvents were evaporated under reduced pressure and the residue was dried under high vacuum. This gave 5.80 mg (65% of theory) of the compound 2-(trimethylsilyl)ethyl N-(11-{(1R)-1-[1-benzyl-4-(2,5-difluorophenyl)-1H-pyrrol-2-yl]-2,2-dimethylpropyl}-2,2-dimethyl-6,12,17-trioxo-5-oxa-14-thia-7,11-diaza-2-silaheptadecan-17-yl)-3-[(bromoacetyl)amino]-D-alaninate.

LC-MS (Method 1): $R_t$=1.57 min; MS (ESIpos): m/z=1008 (M+H)$^+$.

2-(Trimethylsilyl)ethyl N-(11-{(1R)-1-[1-benzyl-4-(2,5-difluorophenyl)-1H-pyrrol-2-yl]-2,2-dimethylpropyl}-2,2-dimethyl-6,12,17-trioxo-5-oxa-14-thia-7,11-diaza-2-silaheptadecan-17-yl)-3-[(bromoacetyl)amino]-D-alaninate (31.9 mg, 31.6 µmol) and L-cysteine (7.66 mg, 63.2 µmol) were dissolved in 3.0 ml of DMF and stirred at RT overnight. The reaction mixture was purified directly by prep. RP-HPLC (column: Reprosil 250×30; 10µ, flow rate: 50 ml/min, MeCN/water/0.1% TFA). The solvents were evaporated under reduced pressure and the residue was dried under high vacuum. This gave 28.1 mg (76% of theory) of the compound S-[(19R)-11-{(1R)-1-[1-benzyl-4-(2,5-difluorophenyl)-1H-pyrrol-2-yl]-2,2-dimethylpropyl}-2,2-dimethyl-6,12,17,22-tetraoxo-19-{[2-(trimethylsilyl)ethoxy]carbonyl}-5-oxa-14-thia-7,11,18,21-tetraaza-2-silatricosan-23-yl]-L-cysteine/trifluoroacetic acid (1:1).

LC-MS (Method 12): $R_t$=2.52 min; MS (ESIpos): m/z=1049 [M+H]$^+$

S-[(19R)-11-{(1R)-1-[1-Benzyl-4-(2,5-difluorophenyl)-1H-pyrrol-2-yl]-2,2-dimethylpropyl}-2,2-dimethyl-6,12,17,22-tetraoxo-19-{[2-(trimethylsilyl)ethoxy]carbonyl}-5-oxa-14-thia-7,11,18,21-tetraaza-2-silatricosan-23-yl]-L-cysteine/trifluoroacetic acid (1:1) (13.5 mg, 11.6 µmol) was dissolved in 1.0 ml of DMF, 2,5-dioxopyrrolidin-1-yl N-[6-(2,5-dioxo-2,5-dihydro-1H-pyrrol-1-yl)hexanoyl]-L-valyl-L-alaninate (6.76 mg, 11.6 µmol) (intermediate L88) and N,N-diisopropylethylamine (4.0 µl, 23 µmol) were added and the mixture was stirred at RT for 1 h. The reaction mixture was purified directly by prep. RP-HPLC (column: Reprosil 250×30; 10µ, flow rate: 50 ml/min, MeCN/water/0.1% TFA). The solvents were evaporated under reduced pressure and the residue was dried under high vacuum. This gave 11.1 mg (68% of theory) of the compound N-[6-(2,5-dioxo-2,5-dihydro-1H-pyrrol-1-yl)hexanoyl]-L-valyl-L-alanyl-S-[(19R)-11-{(1R)-1-[1-benzyl-4-(2,5-difluorophenyl)-1H-pyrrol-2-yl]-2,2-dimethylpropyl}-2,2-dimethyl-6,12,17,22-tetraoxo-19-{[2-(trimethylsilyl)ethoxy]carbonyl}-5-oxa-14-thia-7,11,18,21-tetraaza-2-silatricosan-23-yl]-L-cysteine.

LC-MS (Method 14): $R_t$=7.38 min; MS (ESIpos): m/z=1412 [M+H]$^+$

N-[6-(2,5-Dioxo-2,5-dihydro-1H-pyrrol-1-yl)hexanoyl]-L-valyl-L-alanyl-S-[(19R)-11-{(1R)-1-[1-benzyl-4-(2,5-difluorophenyl)-1H-pyrrol-2-yl]-2,2-dimethylpropyl}-2,2-dimethyl-6,12,17,22-tetraoxo-19-{[2-(trimethylsilyl)ethoxy]

carbonyl}-5-oxa-14-thia-7,11,18,21-tetraaza-2-silatricosan-23-yl]-L-cysteine (9.40 mg, 6.65 µmol) was dissolved in 2.0 ml of trifluoroethanol, and zinc dichloride (5.44 mg, 39.9 µmol) was added. The reaction mixture was stirred at 50° C. for 1 h. The zinc dichloride (5.44 mg, 39.9 µmol) was added, and the reaction mixture was stirred at 50° C. for 1 h. Ethylenediamine-N,N,N',N'-tetraacetic acid (23.4 mg, 79.8 µmol) was added, the reaction mixture was stirred for 10 min and water (0.1% TFA) was then added. Purification was carried out directly by prep. RP-HPLC (column: Reprosil 250×30; 10µ, flow rate: 50 ml/min, MeCN/water, 0.1% TFA). The solvents were evaporated under reduced pressure and the residue was dried under high vacuum. This gave 5.60 mg (66% of theory) of the title compound.

LC-MS (Method 1): $R_t$=0.93 min; MS (ESIpos): m/z=1168 (M+H)⁺.

Intermediate F308

N-[6-(2,5-Dioxo-2,5-dihydro-1H-pyrrol-1-yl) hexanoyl]-L-valyl-N-[(12R,19R)-19-amino-4-{(1R)-1-[1-benzyl-4-(2,5-difluorophenyl)-1H-pyrrol-2-yl]-2,2-dimethylpropyl}-12,19-dicarboxy-5,10,15-trioxo-7,17-dithia-4,11,14-triazanonadec-1-yl]-L-alaninamide/trifluoroacetic acid (1:1)

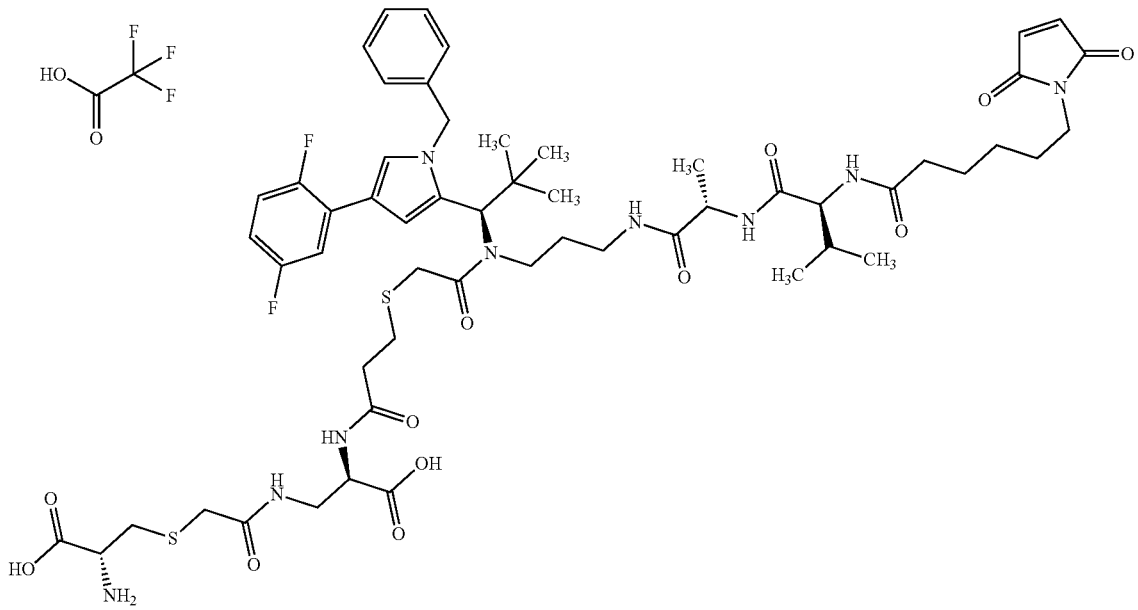 [SMILES: CC(C)[C@H](NC(=O)CCCCCN1C(=O)C=CC1=O)C(=O)N[C@@H](C)C(=O)NCCCN(C(=O)CSCCC(=O)N[C@H](CNC(=O)CSC[C@H](N)C(=O)O)C(=O)O)[C@@H](c1cc(-c2cc(F)ccc2F)cn1Cc1ccccc1)C(C)(C)C ; O=C(O)C(F)(F)F]

N-[3-({2-[(3-Aminopropyl){(1R)-1-[1-benzyl-4-(2,5-difluorophenyl)-1H-pyrrol-2-yl]-2,2-dimethylpropyl}amino]-2-oxoethyl}sulphanyl)propanoyl]-3-[(bromoacetyl)amino]-D-alanine/trifluoroacetic acid (1:1) (12.7 mg, 14.5 µmol) and N-{[2-(trimethylsilyl)ethoxy]carbonyl}-L-cysteine (3.84 mg, 14.5 µmol) were dissolved in 1.5 ml of DMF, and the mixture was stirred at RT overnight.

N,N-Diisopropylethylamine (2.5 µl, 14 µmol) was then added. The reaction mixture was stirred at RT for 3 h, and water (0.1% TFA) was then added. Purification was carried out directly by prep. RP-HPLC (column: Reprosil 250×30; 10µ, flow rate: 50 ml/min, MeCN/water, 0.1% TFA). The solvents were evaporated under reduced pressure and the residue was dried under high vacuum. This gave 7.40 mg (48% of theory) of the compound S-{(5R,14R)-13-(3-aminopropyl)-14-[1-benzyl-4-(2,5-difluorophenyl)-1H-pyrrol-2-yl]-5-carboxy-15,15-dimethyl-2,7,12-trioxo-10-thia-3,6,13-triazahexadec-1-yl}-N-{[2-(trimethylsilyl)ethoxy]carbonyl}-L-cysteine/trifluoroacetic acid (1:1).

LC-MS (Method 1): $R_t$=1.03 min; MS (ESIpos): m/z=949 [M+H]⁺

S-{(5R,14R)-13-(3-Aminopropyl)-14-[1-benzyl-4-(2,5-difluorophenyl)-1H-pyrrol-2-yl]-5-carboxy-15,15-dimethyl-2,7,12-trioxo-10-thia-3,6,13-triazahexadec-1-yl}-N-{[2-(trimethylsilyl)ethoxy]carbonyl}-L-cysteine/trifluoroacetic acid (1:1) (7.50 mg, 7.05 µmol) was dissolved in 1.0 ml of DMF, and 2,5-dioxopyrrolidin-1-yl N-[6-(2,5-dioxo-2,5-dihydro-1H-pyrrol-1-yl)hexanoyl]-L-valyl-L-alaninate (4.11 mg, 82% pure, 7.05 µmol) (intermediate L88) and N,N-diisopropylethylamine (2.5 µl, 14 µmol) were added. The reaction mixture was stirred at RT for 1 h and then purified directly by prep. RP-HPLC (column: Reprosil 250×30; 10µ, flow rate: 50 ml/min, MeCN/water/0.1% TFA). The solvents were evaporated under reduced pressure and the residue was dried under high vacuum. This gave 4.30 mg (46%) of the compound N-[6-(2,5-dioxo-2,5-dihydro-1H-pyrrol-1-yl)hexanoyl]-L-valyl-N-[(8R,15R)-23-{(1R)-1-[1-benzyl-4-(2,5-difluorophenyl)-1H-pyrrol-2-yl]-2,2-dimethylpropyl}-8,15-dicarboxy-2,2-dimethyl-6,12,17,22-tetraoxo-5-oxa-10,20-dithia-7,13,16,23-tetraaza-2-silahexacosan-26-yl]-L-alaninamide.

LC-MS (Method 14): $R_t$=6.47 min; MS (ESIpos): m/z=1312 [M+H]⁺

N-[6-(2,5-Dioxo-2,5-dihydro-1H-pyrrol-1-yl)hexanoyl]-L-valyl-N-[(8R,15R)-23-{(1R)-1-[1-benzyl-4-(2,5-difluorophenyl)-1H-pyrrol-2-yl]-2,2-dimethylpropyl}-8,15-dicarboxy-2,2-dimethyl-6,12,17,22-tetraoxo-5-oxa-10,20-dithia-7,13,16,23-tetraaza-2-silahexacosan-26-yl]-L-alaninamide (4.00 mg, 3.05 µmol) was dissolved in 1.0 ml of trifluoroethanol, and zinc dichloride (2.49 mg, 18.3 µmol) was added. The reaction mixture was stirred at 50° C. for 1 h, ethylenediamine-N,N,N',N'-tetraacetic acid (5.34 mg, 18.3 µmol) was then added, the mixture was stirred for 10 min and water (0.1% TFA) was then added. Purification was carried out directly by prep. RP-HPLC (column: Reprosil 250×30; 10μ, flow rate: 50 ml/min, MeCN/water, 0.1% TFA). The solvents were evaporated under reduced pressure and the residue was dried under high vacuum. This gave 2.50 mg (64% of theory) of the title compound.

LC-MS (Method 1): $R_t$=1.00 min; MS (ESIpos): m/z=1168 [M+H]$^+$

Intermediate F309

4-{[(11R,17R)-16-(3-Aminopropyl)-17-[1-benzyl-4-(2,5-difluorophenyl)-1H-pyrrol-2-yl]-1-(2,5-dioxo-2,5-dihydro-1H-pyrrol-1-yl)-18,18-dimethyl-6,6-dioxido-2,10,15-trioxo-6lambda$^6$,13-dithia-3,9,16-triazanonadecan-11-yl]amino}-4-oxobutanoic acid/trifluoroacetic acid (1:1)

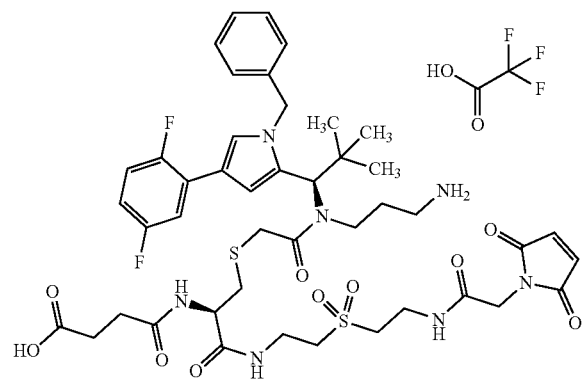 [SMILES: CC(C)(C)[C@H](c1cc(-c2cc(F)ccc2F)cn1Cc1ccccc1)N(CCCN)C(=O)CSC[C@H](NC(=O)CCC(=O)O)C(=O)NCCS(=O)(=O)CCNC(=O)CN1C(=O)C=CC1=O ; O=C(O)C(F)(F)F]

S-(11-{(1R)-1-[1-Benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-N-(4-tert-butoxy-4-oxobutanoyl)-L-cysteine (50.0 mg, 57.3 μmol) (intermediate C77) and trifluoroacetic acid/benzyl {2-[(2-aminoethyl)sulphonyl]ethyl}carbamate (1:1) (27.5 mg, 68.7 μmol) (intermediate L81) were initially charged in 4.0 ml of DMF, and HATU (26.1 mg, 68.7 μmol) and N,N-diisopropylethylamine: (30 μl, 170 μmol) were added. The reaction mixture was stirred at RT for 10 min and then purified directly by prep. RP-HPLC (column: Reprosil 250×30; 10μ, flow rate: 50 ml/min, MeCN/water/0.1% TFA). The solvents were evaporated under reduced pressure and the residue was dried under high vacuum. This gave 53.9 mg (81%) of the compound tert-butyl 4-{[(12R)-17-{(1R)-1-[1-benzyl-4-(2,5-difluorophenyl)-1H-pyrrol-2-yl]-2,2-dimethylpropyl}-26,26-dimethyl-7,7-dioxido-3,11,16,22-tetraoxo-1-phenyl-2,23-dioxa-7lambda6,14-dithia-4,10,17,21-tetraaza-26-silaheptacosan-12-yl]amino}-4-oxobutanoate.

LC-MS (Method 1): $R_t$=1.54 min; MS (ESIpos): m/z=1141 [M+H]$^+$

Under argon, palladium(II) acetate (5.12 mg, 22.8 μmol) was initially charged in 3.0 ml of DCM, triethylamine (9.5 μl, 68 μmol) and triethylsilane (73 μl, 460 μmol) were added and the mixture was stirred for 5 min. tert-Butyl 4-{[(12R)-17-{(1R)-1-[1-benzyl-4-(2,5-difluorophenyl)-1H-pyrrol-2-yl]-2,2-dimethylpropyl}-26,26-dimethyl-7,7-dioxido-3,11,16,22-tetraoxo-1-phenyl-2,23-dioxa-7lambda$^6$,14-dithia-4,10,17,21-tetraaza-26-silaheptacosan-12-yl]amino}-4-oxobutanoate (52.1 mg, 45.6 μmol) in 2.0 ml of DCM was then added. The reaction mixture was stirred at RT overnight, and 2.0 ml of water were added. The solvents were evaporated under reduced pressure. Acetonitrile was added to the residue, the mixture was filtered and the product was purified by prep. RP-HPLC (column: Reprosil 125×30; 10μ, flow rate: 50 ml/min, MeCN/water/0.1% TFA). The solvents were evaporated under reduced pressure and the residue was dried under high vacuum. This gave 43.4 mg (85%) of the compound trifluoroacetic acid/tert-butyl 4-{[(16R)-23-amino-11-{(1R)-1-[1-benzyl-4-(2,5-difluorophenyl)-1H-pyrrol-2-yl]-2,2-dimethylpropyl}-2,2-dimethyl-21,21-dioxido-6,12,17-trioxo-5-oxa-14,21lambda6-dithia-7,11,18-triaza-2-silatricosan-16-yl]amino}-4-oxobutanoate (1:1).

LC-MS (Method 1): $R_t$=1.21 min; MS (ESIpos): m/z=1007 [M+H]$^+$

Trifluoroacetic acid/tert-butyl 4-{[(16R)-23-amino-11-{(1R)-1-[1-benzyl-4-(2,5-difluorophenyl)-1H-pyrrol-2-yl]-2,2-dimethylpropyl}-2,2-dimethyl-21,21-dioxido-6,12,17-trioxo-5-oxa-14,21lambda$^6$-dithia-7,11,18-triaza-2-silatricosan-16-yl]amino}-4-oxobutanoate (1:1) (20.0 mg, 17.8 μmol) and (2,5-dioxo-2,5-dihydro-1H-pyrrol-1-yl)acetic acid (3.32 mg, 21.4 μmol) were initially charged in 2.0 ml of DMF, and HATU (8.14 mg, 21.4 μmol) and N,N-diisopropylethylamine (9.3 μl, 54 μmol) were added.

The reaction mixture was stirred at RT for 10 min. The reaction mixture was purified directly by prep. RP-HPLC (column: Reprosil 250×30; 10μ, flow rate: 50 ml/min, MeCN/water/0.1% TFA). The solvents were evaporated under reduced pressure and the residue was dried under high vacuum. This gave 17.4 mg (85%) of the compound tert-butyl 4-{[(16R)-11-{(1R)-1-[1-benzyl-4-(2,5-difluorophenyl)-1H-pyrrol-2-yl]-2,2-dimethylpropyl}-26-(2,5-dioxo-2,5-dihydro-1H-pyrrol-1-yl)-2,2-dimethyl-21,21-dioxido-6,12,17,25-tetraoxo-5-oxa-14,21lambda6-dithia-7,11,18,24-tetraaza-2-silahexacosan-16-yl]amino}-4-oxobutanoate.

LC-MS (Method 1): $R_t$=1.46 min; MS (ESIpos): m/z=1144 [M+H]$^+$ tert-Butyl 4-{[(16R)-11-{(1R)-1-[1-benzyl-4-(2,5-difluorophenyl)-1H-pyrrol-2-yl]-2,2-dimethylpropyl}-26-(2,5-dioxo-2,5-dihydro-1H-pyrrol-1-yl)-2,2-dimethyl-21,21-dioxido-6,12,17,25-tetraoxo-5-oxa-14,21lambda$^6$-dithia-7,11,18,24-tetraaza-2-silahexacosan-16-yl]amino}-4-oxobutanoate (15.9 mg, 13.9 μmol) was dissolved in 2.0 ml of trifluoroethanol, and zinc dichloride (11.4 mg, 83.4 μmol) was added. The reaction mixture was stirred at 50° C. for 1 h. Zinc dichloride (11.4 mg, 83.4 μmol) was added and the reaction mixture was stirred at 50° C. for 1 h. Zinc dichloride (11.4 mg, 83.4 μmol) was added and the reaction mixture was stirred at 50° C. for 1 h. Ethylenediamine-N,N,N',N'-tetraacetic acid (73.2 mg, 250 μmol) was added, the reaction mixture was stirred for 10 min and water (0.1% TFA) was then added. Purification was carried out directly by prep. RP-HPLC (column: Reprosil 250×30; 10μ, flow rate: 50 ml/min, MeCN/water, 0.1% TFA). The solvents were evaporated under reduced pressure and the residue was dried under high vacuum. This gave 10 mg (68% of theory) of the title compound.

LC-MS (Method 12): $R_t$=1.45 min; MS (ESIpos): m/z=944 [M+H]$^+$

Intermediate F310

Trifluoroacetic acid/N-[(8R,14R)— 13-(3-aminopropyl)-14-[1-benzyl-4-(2,5-difluorophenyl)-1H-pyrrol-2-yl]-1-(2,5-dioxo-2,5-dihydro-1H-pyrrol-1-yl)-15,15-dimethyl-2,7,12-trioxo-10-thia-3,6,13-triazahexadecan-8-yl]-2,5,8,11-tetraoxatetradecane-14-amide (1:1)

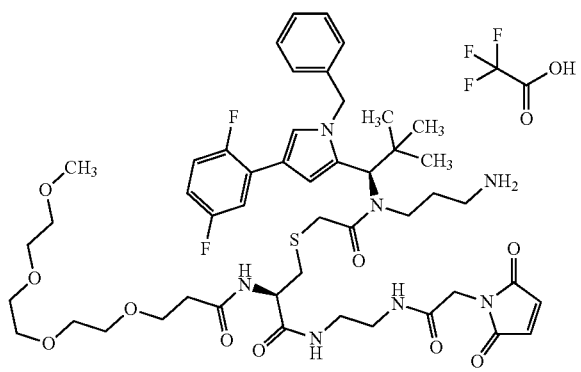 [SMILES: COCCOCCOCCOCCC(=O)N[C@@H](CSCC(=O)N(CCCN)[C@@H](c1cc(-c2cc(F)ccc2F)cn1Cc1ccccc1)C(C)(C)C)C(=O)NCCNC(=O)CN1C(=O)C=CC1=O ; O=C(O)C(F)(F)F]

S-(11-{(1R)-1-[1-Benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-L-cysteine/trifluoroacetic acid (1:1) (100 mg, 120 µmol) (intermediate C70) and 1-[(14-oxo-2,5,8,11-tetraoxatetradecan-14-yl)oxy]pyrrolidine-2,5-dione (44.1 mg, 132 µmol) were initially charged in 3.0 ml of DMF, and 4-methylmorpholine (40 µl, 360 µmol) was added. The reaction mixture was stirred at RT overnight, quenched with acetic acid (420 µmol) and purified directly by prep. RP-HPLC (column: Reprosil 125×30; 10µ, flow rate: 50 ml/min, MeCN/water/0.1% TFA). The solvents were evaporated under reduced pressure and the residue was dried under high vacuum. This gave 69.4 mg (62% of theory) of the compound S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-N-(14-oxo-2,5,8,11-tetraoxatetradecan-14-yl)-L-cysteine.

LC-MS (Method 12): $R_t$=2.61 min; MS (ESIneg): m/z=933 [M−H]⁻

S-(11-{(1R)-1-[1-Benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-N-(14-oxo-2,5,8,11-tetraoxatetradecan-14-yl)-L-cysteine (27.0 mg, 28.9 µmol) was initially charged in 2.0 ml of DMF, and N-(2-aminoethyl)-2-(2,5-dioxo-2,5-dihydro-1H-pyrrol-1-yl)acetamide (11.4 mg, 57.7 µmol) (intermediate L1), N,N-diisopropylethylamine (15 µl, 87 µmol) and HATU (22.0 mg, 57.7 µmol) were added. The reaction mixture was stirred at RT for 3 h and purified directly by prep. RP-HPLC (column: Reprosil 250×30; 10µ, flow rate: 50 ml/min, MeCN/water/0.1% TFA). The solvents were evaporated under reduced pressure and the residue was dried under high vacuum. This gave 13.7 mg (43% of theory) of the compound 2-(trimethylsilyl)ethyl {(16R)-21-{(1R)-1-[1-benzyl-4-(2,5-difluorophenyl)-1H-pyrrol-2-yl]-2,2-dimethylpropyl}-16-[(2-{[(2,5-dioxo-2,5-dihydro-1H-pyrrol-1-yl)acetyl]amino}ethyl)carbamoyl]-14,20-dioxo-2,5,8,11-tetraoxa-18-thia-15,21-diazatetracosan-24-yl}carbamate.

LC-MS (Method 12): $R_t$=2.54 min; MS (ESIpos): m/z=1114 [M+H]⁺

2-(Trimethylsilyl)ethyl {(16R)-21-{(1R)-1-[1-benzyl-4-(2,5-difluorophenyl)-1H-pyrrol-2-yl]-2,2-dimethylpropyl}-16-[(2-{[(2,5-dioxo-2,5-dihydro-1H-pyrrol-1-yl) acetyl]amino}ethyl)carbamoyl]-14,20-dioxo-2,5,8,11-tetraoxa-18-thia-15,21-diazatetracosan-24-yl}carbamate (13.7 mg, 12.3 µmol) was dissolved in 2.0 ml of trifluoroethanol, and zinc dichloride (10.1 mg, 73.8 µmol) was added. The reaction mixture was stirred at 50° C. for 4 h. Ethylenediamine-N,N,N',N'-tetraacetic acid (21.6 mg, 73.8 µmol) was added, the reaction mixture was stirred for 10 min and water (0.1% TFA) was then added. Purification was carried out directly by prep. RP-HPLC (column: Reprosil 250×30; 10µ, flow rate: 50 ml/min, MeCN/water, 0.1% TFA). The solvents were evaporated under reduced pressure and the residue was dried under high vacuum. This gave 7.30 mg (47% of theory) of the title compound.

LC-MS (Method 1): $R_t$=1.01 min; MS (ESIpos): m/z=970 [M+H]⁺

Intermediate F311

S-{2-[(3-Aminopropyl){(1R)-1-[1-benzyl-4-(2,5-difluorophenyl)-1H-pyrrol-2-yl]-2,2-dimethylpropyl}amino]-2-oxoethyl}-N-[1-(2,5-dioxo-2,5-dihydro-1H-pyrrol-1-yl)-2,30-dioxo-6,9,12,15,18,21,24,27-octaoxa-3-azatriacontan-30-yl]-L-cysteine/trifluoroacetic acid (1:1)

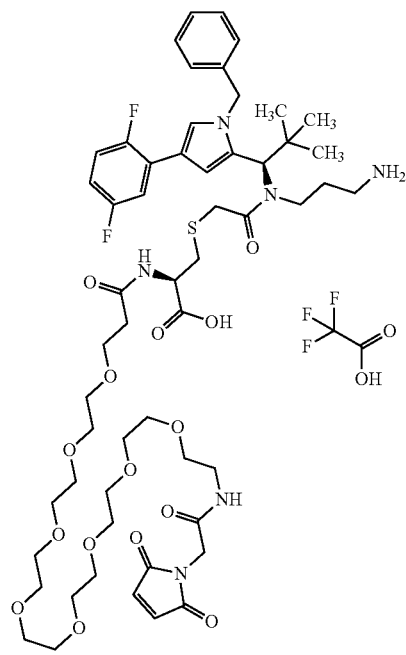 [SMILES: CC(C)(C)[C@H](c1cc(-c2cc(F)ccc2F)cn1Cc1ccccc1)N(CCCN)C(=O)CSC[C@H](NC(=O)CCOCCOCCOCCOCCOCCOCCOCCOCCNC(=O)CN1C(=O)C=CC1=O)C(=O)O ; O=C(O)C(F)(F)F]

1-(2,5-Dioxo-2,5-dihydro-1H-pyrrol-1-yl)-2-oxo-6,9,12, 15,18,21,24,27-octaoxa-3-azatriacontan-30-oic acid (10.8 mg, 18.7 µmol) (intermediate L97) was initially charged in 1.0 ml of DMF, N,N-diisopropylethylamine (5.4 µl, 31.2 µmol) and HATU (7.10 mg, 18.7 µmol) were added and the mixture was stirred for 10 min. S-(11-{(1R)-1-[1-Benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-L-cysteine/trifluoroacetic acid (1:1) (12.9 mg, 15.6 µmol) (intermediate C71), dissolved in 1.0 ml of DMF and N,N-diisopropylethylamine (2.7 µl, 15.6 µmol), was then added. The reaction mixture was stirred at RT for 2 h and then purified directly by prep. RP-HPLC (column: Reprosil 125×30; 10µ, flow rate: 50 ml/min, MeCN/water/0.1% TFA). The solvents were evaporated under reduced pressure and the residue was dried under high vacuum. This gave 3.5 mg (18%) of the compound S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-N-[1-(2,5-dioxo-2,5-dihydro-1H-pyrrol-1-yl)-2,30-dioxo-6,9,12,15,18,21,24,27-octaoxa-3-azatriacontan-30-yl]-L-cysteine.

LC-MS (Method 1): $R_t$=1.30 min; MS (ESIneg): m/z=1276 [M–H]$^-$

S-(11-{(1R)-1-[1-Benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-N-[1-(2,5-dioxo-2,5-dihydro-1H-pyrrol-1-yl)-2,30-dioxo-6,9,12,15,18,21,24,27-octaoxa-3-azatriacontan-30-yl]-L-cysteine (3.50 mg, 2.74 µmol) was dissolved in 1.0 ml of trifluoroethanol, and zinc dichloride (6.25 mg, 16.4 µmol) was added. The reaction mixture was stirred at 50° C. for 4 h. Ethylenediamine-N,N,N',N'-tetraacetic acid (47 µl, 16 µmol) was added, the reaction mixture was stirred for 10 min and water (0.1% TFA) was then added. Purification was carried out directly by prep. RP-HPLC (column: Reprosil 125×30; 10µ, flow rate: 50 ml/min, MeCN/water, 0.1% TFA). The solvents were evaporated under reduced pressure and the residue was dried under high vacuum. This gave 2.0 mg (59% of theory) of the title compound.

LC-MS (Method 1): $R_t$=0.94 min; MS (ESIpos): m/z=1133 (M+H)$^+$.

Intermediate F312

N-[(2,5-Dioxo-2,5-dihydro-1H-pyrrol-1-yl) acetyl]-L-valyl-N-[(2S)-4-[{(1R)-1-[1-benzyl-4-(2,5-difluorophenyl)-1H-pyrrol-2-yl]-2,2-dimethylpropyl}(glycoloyl)amino]-1-{[2-(L-gamma-glutamylamino)ethyl]amino}-1-oxobutan-2-yl]-L-alaninamide/trifluoroacetic acid (1:1)

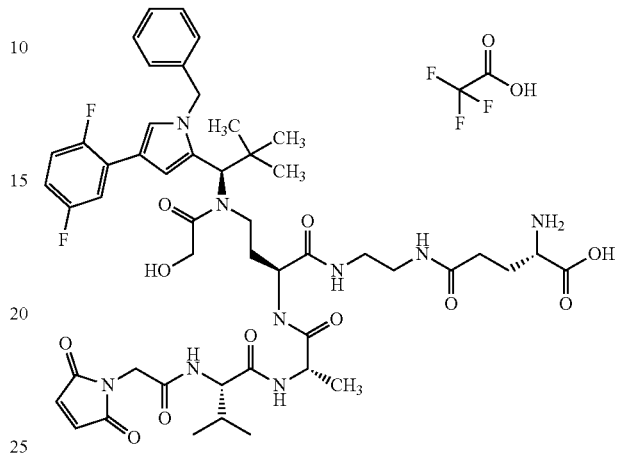

The title compound was prepared from intermediate C103 by coupling with N-[(benzyloxy)carbonyl]-L-valyl-L-alanine in the presence of HATU and N,N-diisopropylethylamine. In the next step, the Z protective group was removed by hydrogenating for 1 hour over 10% palladium on activated carbon in DCM/methanol 1:1 at RT under standard hydrogen pressure. The deprotected intermediate was then converted by coupling with (2,5-dioxo-2,5-dihydro-1H-pyrrol-1-yl)acetic acid in the presence of HATU and N,N-diisopropylethylamine and finally by deprotection with zinc chloride and purification by preparative HPLC into the title compound.

LC-MS (Method 1): $R_t$=0.9 min; MS (ESIpos): m/z=992 (M+H)$^+$.

Intermediate F313

S-[2-({(1R)-1-[1-Benzyl-4-(2,5-difluorophenyl)-1H-pyrrol-2-yl]-2,2-dimethylpropyl}{[(3R,4R)-4-fluoropyrrolidin-3-yl]methyl}amino)-2-oxoethyl]-N-[1-(2,5-dioxo-2,5-dihydro-1H-pyrrol-1-yl)-2,18-dioxo-6,9,12,15-tetraoxa-3-azaoctadecan-8-yl]-L-cysteine/trifluoroacetic acid (1:1)

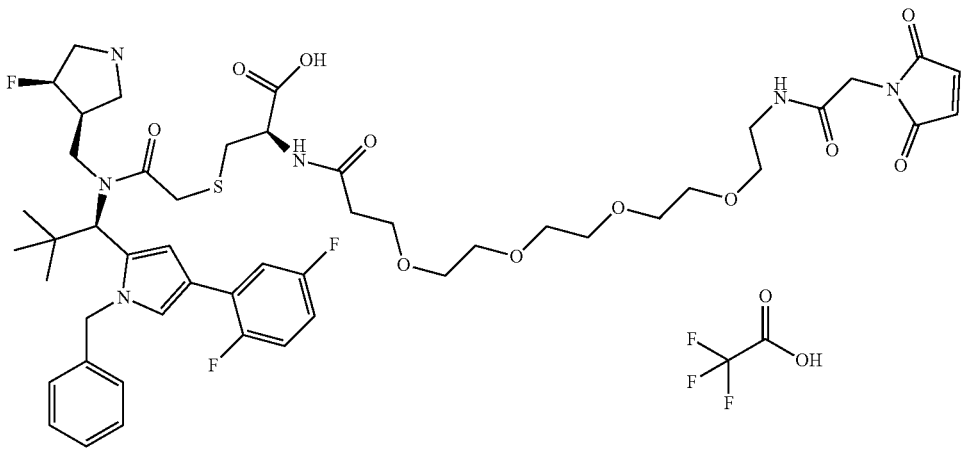 [SMILES: CC(C)(C)[C@H](c1cc(-c2cc(F)ccc2F)cn1Cc1ccccc1)N(C[C@@H]1CNC[C@@H]1F)C(=O)CSC[C@H](NC(=O)CCOCCOCCOCCOCCNC(=O)CN1C(=O)C=CC1=O)C(=O)O ; O=C(O)C(F)(F)F]

Under argon, 16.9 mg (0.13 mmol) of N,N-diisopropylethylamine and 50.0 mg (0.13 mmol) of HATU were added to a solution of 55.0 mg (0.14 mmol) of 1-(2,5-dioxo-2,5-dihydro-1H-pyrrol-1-yl)-2-oxo-6,9,12,15-tetraoxa-3-azaoctadecan-18-oic acid in 2.60 ml of DMF. The reaction mixture was stirred at RT for 10 minutes. A solution of 40.0 mg (0.05 mmol) of S-[2-({(1R)-1-[1-benzyl-4-(2,5-difluorophenyl)-1H-pyrrol-2-yl]-2,2-dimethylpropyl}{[(3R,4R)-4-fluoro-1-{[2-(trimethylsilyl)ethoxy]carbonyl}pyrrolidin-3-yl]methyl}amino)-2-oxoethyl]-L-cysteine (intermediate C107) was then added, and the mixture was stirred at RT overnight. Water was added and the mixture was extracted with dichloromethane. The organic phase was dried over magnesium sulphate and the solvent was evaporated under reduced pressure and the residue was dried under high vacuum. The residue was purified by prep. HPLC. This gave 10 mg (13% of theory, purity 82%) of the title compound.

LC-MS (Method 1): $R_t$=1.36 min; MS (ESIpos): m/z=1145 (M+H)$^+$.

4.3 mg (0.03 mmol) of zinc chloride were added to a solution of 10.9 mg (7.8 mmol, 82% pure) of S-[2-({(1R)-1-[1-benzyl-4-(2,5-difluorophenyl)-1H-pyrrol-2-yl]-2,2-dimethylpropyl}{[(3R,4R)-4-fluoro-1-{[2-(trimethylsilyl)ethoxy]carbonyl}pyrrolidin-3-yl]methyl}amino)-2-oxoethyl]-N-[1-(2,5-dioxo-2,5-dihydro-H-pyrrol-1-yl)-2,18-dioxo-6,9,12,15-tetraoxa-3-azaoctadecan-18-yl]-L-cysteine in 0.85 ml of 2,2,2-trifluoroethanol, and the reaction mixture was stirred at 50° C. for 2.5 h. 9.1 mg (0.03 mmol) of EDTA were then added, and the mixture was stirred for 15 minutes. The reaction mixture was purified by prep. HPLC. This gave 2.3 mg (26% of theory) of the title compound.

LC-MS (Method 1): $R_t$ 0.89 min; MS (ESIpos): m/z=781 (M+H-CF$_3$CO$_2$H)$^+$.

Intermediate F314

Trifluoroacetic acid/3-{[2-({(1R)-1-[1-benzyl-4-(2,5-difluorophenyl)-1H-pyrrol-2-yl]-2,2-dimethylpropyl}{[(3S,4R)-4-fluoropyrrolidin-3-yl]methyl}amino)-2-oxoethyl]sulphanyl}-N-(2-{[(2,5-dioxo-2,5-dihydro-1H-pyrrol-1-yl)acetyl]amino}ethyl)propanamide

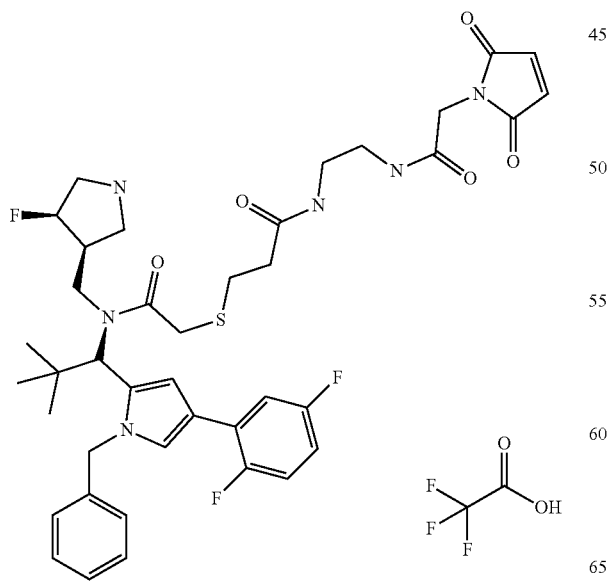

Under argon, 16.89 mg (0.13 mmol) of N,N-diisopropylethylamine and 33.13 mg (0.087 mmol) of HATU were added to a solution of 50.0 mg (0.04 mmol) of 3-{[2-({(1R)-1-[1-benzyl-4-(2,5-difluorophenyl)-1H-pyrrol-2-yl]-2,2-dimethylpropyl}{[(3R,4R)-4-fluoro-1-{[2-(trimethylsilyl)ethoxy]carbonyl}pyrrolidin-3-yl]methyl}amino)-2-oxoethyl]sulphanyl}propanoic acid (intermediate C106) in 3.14 ml of DMF. The reaction mixture was stirred at RT for 10 minutes. A solution of 27.29 mg (0.09 mmol) of N-(2-aminoethyl)-2-(2,5-dioxo-2,5-dihydro-1H-pyrrol-1-yl)acetamide (1:1) trifluoroacetic acid (intermediate L1) was then added, and the mixture was stirred at RT for 15 minutes. Water was added and the mixture was extracted with dichloromethane. The organic phase was dried over magnesium sulphate and the solvent was evaporated under reduced pressure and the residue was dried under high vacuum. The residue was purified by prep. HPLC. This gave 41 mg (68% of theory, purity 66%) of the title compound.

LC-MS (Method 12): $R_t$=2.55 min; MS (ESIneg): m/z=959 (M−H+Na)⁻.

24.7 mg (0.18 mmol) of zinc chloride were added to a solution of 41.1 mg (0.03 mmol, purity 66%) of 2-(trimethylsilyl)ethyl-(3R,4R)-3-[2-{(1R)-1-[1-benzyl-4-(2,5-difluorophenyl)-1H-pyrrol-2-yl]-2,2-dimethylpropyl}-14-(2,5-dioxo-2,5-dihydro-1H-pyrrol-1-yl)-3,8,13-trioxo-5-thia-2,9,12-triazatetradec-1-yl]-4-fluoropyrrolidine-1-carboxylate in 2.54 ml of 2,2,2-trifluoroethanol, and the reaction mixture was stirred at 50° C. for 2.5 h. 53.0 mg (0.18 mmol) of EDTA were then added, and the mixture was stirred for 15 minutes. The reaction mixture was purified by prep. HPLC. This gave 10 mg (36% of theory) of the title compound.

LC-MS (Method 1): $R_t$ 0.89 min; MS (ESIpos): m/z=781 (M+H−CF₃CO₂H)⁺.

Intermediate F315

S-{2-[(3-Aminopropyl){(1R)-1-[1-benzyl-4-(2,5-difluorophenyl)-1H-pyrrol-2-yl]-2,2-dimethylpropyl}amino]-2-oxoethyl}-N-{3-[5-(2-{[(2,5-dioxo-2,5-dihydro-1H-pyrrol-1-yl) acetyl]amino}ethyl)-1,2,4-oxadiazol-3-yl]propanoyl}-L-cysteine Under argon, 18.02 mg (0.14 mmol) of N,N-diisopropylethylamine and 31.82 mg (0.09 mmol) of HATU were added to a solution of 50.0 mg (0.07 mmol) of 3-[5-(2-{[(2,5-dioxo-2,5-dihydro-1H-pyrrol-1-yl)acetyl]amino}ethyl)-1,2,4-oxadiazol-3-yl]propanoic acid (intermediate L100) in 3.5 ml of DMF. The reaction mixture was stirred at RT for 10 minutes. A solution of 50.0 mg (0.07 mmol) of N-(2-aminoethyl)-6-(2,5-dioxo-2,5-dihydro-1H-pyrrol-1-yl)hexanamide acetate (1:1) (intermediate C107) was then added, and the mixture was stirred at RT for 2 h. Water was added and the mixture was extracted with dichloromethane. The organic phase was dried over magnesium sulphate and the solvent was evaporated under reduced pressure and the residue was dried under high vacuum. The residue was used further without purification. This gave 49 mg (21% of theory, purity 31%) of the title compound.

LC-MS (Method 1): $R_t$=1.30 min; MS (ESIpos): m/z=1022 (M+H)⁺. 8.0 mg (0.06 mmol) of zinc chloride were added to a solution of 49.0 mg (0.015 mmol, 31% pure) of S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-N-{3-[5-(2-{[(2,5-dioxo-2,5-dihydro-1H-pyrrol-1-yl)acetyl]amino}ethyl)-1,2,4-oxadiazol-3-yl]propanoyl}-L-cysteine in 0.5 ml of 2,2,2-trifluoroethanol, and the reaction mixture was stirred at 50° C. for 2 h. 17.2 mg (0.06 mmol) of EDTA were then added, and the mixture was stirred for 15 minutes. The reaction mixture was purified by prep. HPLC. This gave 3 mg (21% of theory) of the title compound.

LC-MS (Method 1): $R_t$=0.91 min; MS (ESIpos): m/z=877 (M+H−CF₃CO₂H)⁺.

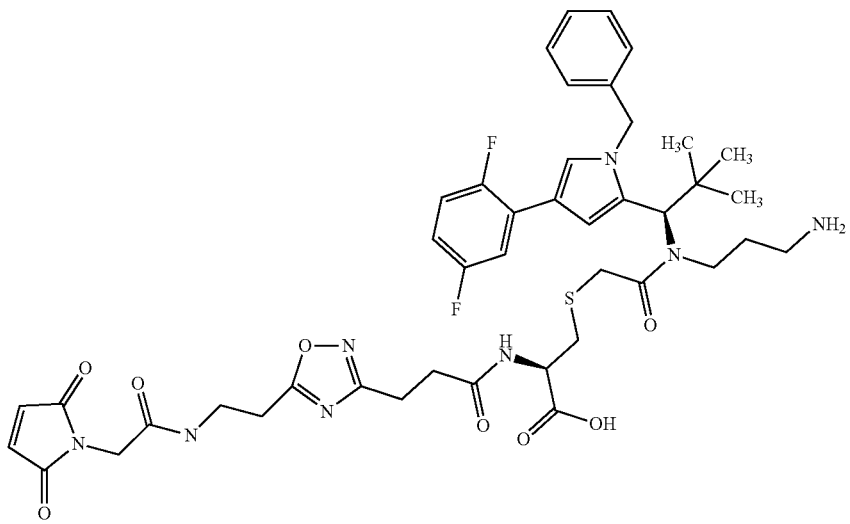 [SMILES: CC(C)(C)[C@H](c1cc(-c2cc(F)ccc2F)cn1Cc1ccccc1)N(CCCN)C(=O)CSC[C@H](NC(=O)CCc1noc(CCNC(=O)CN2C(=O)C=CC2=O)n1)C(=O)O]

Intermediate F316

Trifluoroacetic acid/N-{2-[(3-{[2-({(1R)-1-[1-benzyl-4-(2,5-difluorophenyl)-1H-pyrrol-2-yl]-2,2-dimethylpropyl}{[(3S,4R)-4-fluoropyrrolidin-3-yl]methyl}amino)-2-oxoethyl]sulphanyl}propanoyl)amino]ethyl}-6-(2,5-dioxo-2,5-dihydro-1H-pyrrol-1-yl)hexanamide (1:1)

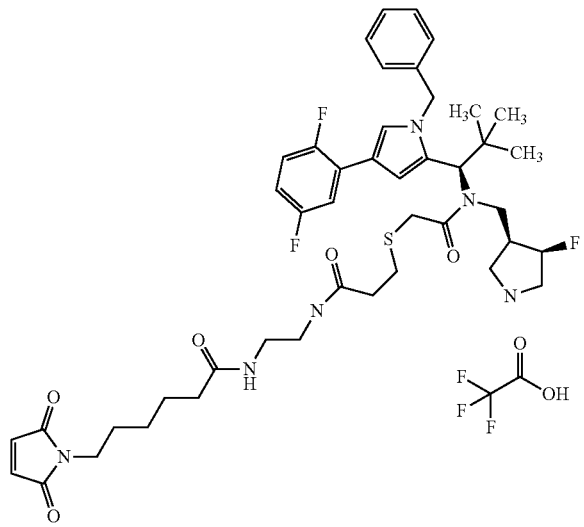 [SMILES: CC(C)(C)[C@H](c1cc(-c2cc(F)ccc2F)cn1Cc1ccccc1)N(C[C@@H]1CNC[C@@H]1F)C(=O)CSCCC(=O)NCCNC(=O)CCCCCN1C(=O)C=CC1=O ; O=C(O)C(F)(F)F]

Under argon, 16.89 mg (0.13 mmol) of N,N-diisopropylethylamine and 33.13 mg (0.087 mmol) of HATU were added to a solution of 50.0 mg (0.04 mmol, 65% purity) of 3-{[2-({(1R)-1-[1-benzyl-4-(2,5-difluorophenyl)-1H-pyrrol-2-yl]-2,2-dimethylpropyl}{[(3R,4R)-4-fluoro-1-{[2-(trimethylsilyl)ethoxy]carbonyl}pyrrolidin-3-yl]methyl}amino)-2-oxoethyl]sulphanyl}propanoic acid (intermediate 106) in 3.0 ml of DMF. The reaction mixture was stirred at RT for 10 minutes. A solution of 37.2 mg (0.09 mmol, purity 70%) of N-(2-aminoethyl)-6-(2,5-dioxo-2,5-dihydro-1H-pyrrol-1-yl)hexanamide acetate (1:1) (intermediate L73) was then added, and the mixture was stirred at RT for 7 minutes. Water was added and the mixture was extracted with dichloromethane. The organic phase was dried over magnesium sulphate and the solvent was evaporated under reduced pressure and the residue was dried under high vacuum. The residue was used further without purification. This gave 57 mg (77% of theory, purity 59%) of the title compound.

LC-MS (Method 12): $R_t$=2.60 min; MS (ESIpos): m/z=981 (M+H)$^+$.

36.0 mg (0.27 mmol) of zinc chloride were added to a solution of 56.0 mg (0.03 mmol, 59% pure) of 2-(trimethylsilyl)ethyl (3R,4R)-3-[2-{(1R)-1-[1-benzyl-4-(2,5-difluorophenyl)-1H-pyrrol-2-yl]-2,2-dimethylpropyl}-18-(2,5-dioxo-2,5-dihydro-1H-pyrrol-1-yl)-3,8,13-trioxo-5-thia-2,9,12-triazaoctadec-1-yl]-4-fluoropyrrolidine-1-carboxylate in 2.8 ml of 2,2,2-trifluoroethanol, and the reaction mixture was stirred at 50° C. for 2 h. 78.3 mg (0.27 mmol) of EDTA were then added, and the mixture was stirred for 15 minutes. The reaction mixture was purified by prep. HPLC. This gave 16 mg (44% of theory, 85% pure) of the title compound.

LC-MS (Method 1): $R_t$=0.89 min; MS (ESIpos): m/z=837 (M+H-AcOH)$^+$.

Intermediate F317

1-[(S-{2-[(3-Aminopropyl){(1R)-1-[1-benzyl-4-(2,5-difluorophenyl)-1H-pyrrol-2-yl]-2,2-dimethylpropyl}amino]-2-oxoethyl}-N-[1-(2,5-dioxo-2,5-dihydro-1H-pyrrol-1-yl)-2,18-dioxo-6,9,12,15-tetraoxa-3-azaoctadecan-18-yl]-L-cysteinyl)amino]-3,6,9,12-tetraoxapentadecan-15-oic acid/trifluoroacetic acid (1:1)

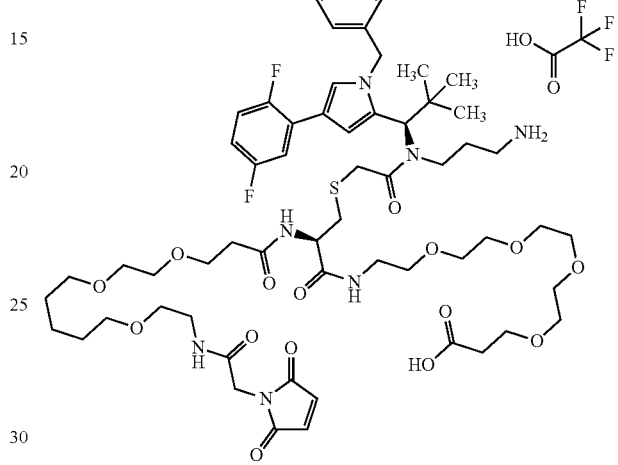

Under argon, 30.2 mg (0.06 mmol) of N,N'-bis[(benzyloxy)carbonyl]-L-cystine were initially charged in 2.0 ml of water and 2.0 ml of isopropanol, and 56.7 mg (0.20 mmol) of TCEP were added. The reaction mixture was stirred at RT for 30 min. 50.0 mg (0.08 mmol) of 2-(trimethylsilyl)ethyl {3-[{(1R)-1-[1-benzyl-4-(2,5-difluorophenyl)-1H-pyrrol-2-yl]-2,2-dimethylpropyl}(chloroacetyl)amino]propyl}carbamate (intermediate C70), dissolved in 2.0 ml of isopropanol, and 122.2 mg (0.48 mmol) of 1,8-diazabicyclo[5.4.0]undec-7-ene were then added, and the reaction mixture was stirred at 50° C. for 7 h. Another 122.2 mg (0.48 mmol) of 1,8-diazabicyclo[5.4.0]undec-7-ene were then added, and the reaction mixture was stirred at 50° C. for 1 h. The mixture was diluted with ethyl acetate and the organic phase was extracted with water and sat. sodium bicarbonate solution and washed with sat. NaCl solution. The organic phase was dried over magnesium sulphate and the solvent was evaporated under reduced pressure. The residue was purified by prep. RP-HPLC (column: Reprosil 250×30; 10μ, flow rate: 50 ml/min, MeCN/water, 0.1% TFA). The solvents were evaporated under reduced pressure and the residue was dried under high vacuum. This gave 43.1 mg (64% of theory) of the compound S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-N-[(benzyloxy)carbonyl]-L-cysteine.

LC-MS (Method 1): $R_t$=1.46 min; MS (ESIpos): m/z=851 (M+H)$^+$.

Under argon, S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-N-[(benzyloxy)carbonyl]-L-cysteine (50.0 mg, 59 μmol) was dissolved in 1.0 ml of DMF, and N,N-diisopropylethylamine (20.5 μl, 117 μmol) and HATU (26.8 mg, 70 μmol) were added. The reaction mixture was stirred for 10 min. tert- Butyl 1-amino-3,6,9,12-tetraoxapentadecan-15-oate (22.6 mg, 70 µmol) was then added. The reaction mixture was stirred for 1 hour and then purified directly by prep. RP-HPLC (column: Reprosil 250×30; 10µ, flow rate: 50 ml/min, MeCN/water). The solvents were evaporated under reduced pressure and the residue was dried under high vacuum. This gave 59.3 mg (87.5% of theory) of the compound tert-butyl 1-({S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-N-[(benzyloxy)carbonyl]-L-cysteinyl}amino)-3,6,9,12-tetraoxapentadecan-15-oate.

LC-MS (Method 12): $R_t$=2.97 min; MS (ESIpos): m/z=1154 [M+H]+

Under argon, palladium(II) acetate (6.74 mg, 30.0 µmol) was initially charged in 3.0 ml of dichloromethane, and triethylamine (13 µl, 90 µmol) and triethylsilane (96 µl, 600 µmol) were added. The reaction mixture was stirred for 5 min, and tert-butyl 1-({S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-N-[(benzyloxy)carbonyl]-L-cysteinyl}amino)-3,6,9,12-tetraoxapentadecan-15-oate (69.3 mg, 60.0 µmol) in 1.0 ml of dichloromethane was then added. The reaction mixture was stirred at RT for 2 hours, and triethylsilane (48 µl, 300 µmol) was then added. The reaction mixture was stirred at RT for 2 hours, and 2.0 ml of water (0.1% TFA) were added. The solvent was evaporated under reduced pressure without heating. The residue was taken up in acetonitrile, filtered through a syringe filter and purified by prep. RP-HPLC (column: Reprosil 250×30; 10µ, flow rate: 50 ml/min, MeCN/water, 0.1% TFA). The solvents were evaporated under reduced pressure and the residue was dried under high vacuum. This gave 65.9 mg (97% of theory) of the compound trifluoroacetic acid/tert-butyl 1-{[S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-L-cysteinyl]amino}-3,6,9,12-tetraoxapentadecan-15-oate (1:1).

LC-MS (Method 1): $R_t$=1.22 min; MS (ESIpos): m/z=1020 [M+H]+

Under argon, 1-(2,5-dioxo-2,5-dihydro-1H-pyrrol-1-yl)-2-oxo-6,9,12,15-tetraoxa-3-azaoctadecan-18-oic acid (4.26 mg, 10.6 µmol) was initially charged in 1.0 ml of DMF, and N,N-diisopropylethylamine (3.2 µl, 18 µmol) and HATU (4.02 mg, 10.6 µmol) were added. The reaction mixture was stirred for 10 min, and trifluoroacetic acid/tert-butyl 1-{[S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-L-cysteinyl]amino}-3,6,9,12-tetraoxapentadecan-15-oate (1:1) (10.0 mg, 8.82 µmol), dissolved in 1.0 ml of DMF and N,N-diisopropylethylamine (1.5 µl, 8.8 µmol), was then added. The reaction mixture was stirred at RT for 1 hour and purified directly by prep. RP-HPLC (column: Reprosil 250×30; 10µ, flow rate: 50 ml/min, MeCN/water, 0.1% TFA). The solvents were evaporated under reduced pressure and the residue was dried under high vacuum. This gave 10.9 mg (93% of theory) of the compound tert-butyl 1-({S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-N-[1-(2,5-dioxo-2,5-dihydro-1H-pyrrol-1-yl)-2,18-dioxo-6,9,12,15-tetraoxa-3-azaoctadecan-18-yl]-L-cysteinyl}amino)-3,6,9,12-tetraoxapentadecan-15-oate.

LC-MS (Method 1): $R_t$=1.44 min; MS (ESIpos): m/z=1404 [M+H]+ tert-Butyl 1-({S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-N-[1-(2,5-dioxo-2,5-dihydro-1H-pyrrol-1-yl)-2,18-dioxo-6,9,12,15-tetraoxa-3-azaoctadecan-18-yl]-L-cysteinyl}amino)-3,6,9,12-tetraoxapentadecan-15-oate (8.20 mg, 5.84 µmol) was dissolved in 2.0 trifluoroethanol, and zinc chloride (4.77 mg, 35.0 µmol) was added. The reaction mixture was stirred at 50° C. for 1 hour.

Zinc chloride (4.77 mg, 35.0 µmol) was added and the reaction mixture was stirred at 50° C. for 1 hour. Ethylenediamine-N,N,N',N'-tetraacetic acid (10.2 mg, 35.0 µmol) was added, the reaction mixture was stirred for 10 min and water (0.1% TFA) was then added. Purification was carried out directly by prep. RP-HPLC (column: Reprosil 250×30; 10µ, flow rate: 50 ml/min, MeCN/water, 0.1% TFA). The solvents were evaporated under reduced pressure and the residue was dried under high vacuum. This gave 4.1 mg (53% of theory) of the title compound.

LC-MS (Method 1): $R_t$=0.90 min; MS (ESIpos): m/z=1204 [M+H]$^+$

Intermediate F318

Trifluoroacetic acid/3-{[2-([3-amino-4-fluorobutyl]{(1R)-1-[1-benzyl-4-(2,5-difluorophenyl)-1H-pyrrol-2-yl]-2,2-dimethylpropyl}amino)-2-oxoethyl]sulphanyl}-N-(2-{[(2,5-dioxo-2,5-dihydro-1H-pyrrol-1-yl)acetyl]amino}ethyl)propanamide (1:1)

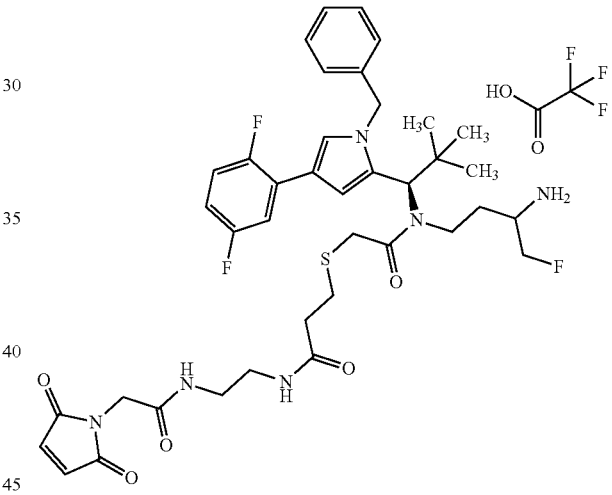

(1R)-1-[1-Benzyl-4-(2,5-difluorophenyl)-1H-pyrrol-2-yl]-2,2-dimethylpropane-1-amine (124 mg, 350 µmol) (intermediate C52) was initially charged in 5.0 ml of dichloromethane, and sodium triacetoxyborohydride (104 mg, 491 µmol) and acetic acid (23 µl, 400 µmol) were added. The reaction mixture was stirred at RT for 5 min, and tert-butyl [1-fluoro-4-oxobutan-2-yl]carbamate (82.7 mg, 403 µmol) (intermediate L123), dissolved in 3.0 ml of dichloromethane, was then added. The reaction mixture was stirred at RT overnight, and ethyl acetate was then added. The mixture was washed twice with saturated sodium bicarbonate solution and then with saturated sodium chloride solution. The organic phase was dried over magnesium sulphate and then concentrated. The residue was purified by column chromatography on Biotage/Isolera (SNAP 25 g) using the mobile phase cyclohexane/ethyl acetate 95:5. The solvents were evaporated under reduced pressure and the residue was dried under high vacuum. This gave 146 mg (77% of theory) of the compound tert-butyl [4-({(1R)-1-[1-benzyl-4-(2,5-difluorophenyl)-1H-pyrrol-2-yl]-2,2-dimethylpropyl}amino)-1-fluorobutan-2-yl]carbamate.

LC-MS (Method 13): $R_t$=2.57 min; MS (ESIneg): m/z=588 [M+CHOOH-H]$^-$ tert-Butyl [4-({(1R)-1-[1-benzyl-4-(2,5-difluorophenyl)-1H-pyrrol-2-yl]-2,2-dimethylpropyl}amino)-1-fluorobutan-2-yl]carbamate (100 mg, 184 µmol) was dissolved in 6.0 ml of DCM, and triethylamine (85 µl, 610 µmol) and chloroacetyl chloride (47 µl, 590 µmol) were added at 0° C. The reaction mixture was stirred at RT overnight. The solvent was evaporated under reduced pressure. The residue was taken up in acetonitrile/water and purified by prep. RP-HPLC (column: Reprosil 250×30; 10µ, flow rate: 50 ml/min, MeCN/water, 0.1% TFA). The solvents were evaporated under reduced pressure and the residue was dried under high vacuum. This gave 80 mg (70% of theory) of the compound tert-butyl-{4-[{(1R)-1-[1-benzyl-4-(2,5-difluorophenyl)-1H-pyrrol-2-yl]-2,2-dimethylpropyl}(chloroacetyl)amino]-1-fluorobutan-2-yl}carbamate.

LC-MS (Method 12): $R_t$=2.67 min; MS (ESIneg): m/z=664 [M–H+COOH]⁻ tert-Butyl {4-[{(1R)-1-[1-benzyl-4-(2,5-difluorophenyl)-1H-pyrrol-2-yl]-2,2-dimethylpropyl}(chloroacetyl)amino]-1-fluorobutan-2-yl}carbamate (79.2 mg, 128 µmol) and 3-sulphanylpropanoic acid (12 µl, 140 µmol) were initially charged in 3.0 ml of methanol with a drop of water. Potassium carbonate (61.8 mg, 447 µmol) was added and the reaction mixture was stirred at 50° C. for 4 h. Ethyl acetate was added and the mixture was washed repeatedly with water. The organic phase was washed with saturated sodium chloride solution, dried over magnesium sulphate and then concentrated. The residue was purified by prep. RP-HPLC (column: Reprosil 250×30; 10µ, flow rate: 50 ml/min, MeCN/water, 0.1% TFA). The solvents were evaporated under reduced pressure and the residue was dried under high vacuum. This gave 68.6 mg (78% of theory) of the compound 9-{(1R)-1-[1-benzyl-4-(2,5-difluorophenyl)-1H-pyrrol-2-yl]-2,2-dimethylpropyl}-6-(fluoromethyl)-2,2-dimethyl-4,10-dioxo-3-oxa-12-thia-5,9-diazapentadecan-15-oic acid.

LC-MS (Method 12): $R_t$=2.46 min; MS (ESIneg): m/z=688 [M–H]⁻

9-{(1R)-1-[1-Benzyl-4-(2,5-difluorophenyl)-1H-pyrrol-2-yl]-2,2-dimethylpropyl}-6-(fluoromethyl)-2,2-dimethyl-4,10-dioxo-3-oxa-12-thia-5,9-diazapentadecan-15-oic acid (15.0 mg, 21.7 µmol) and trifluoroacetic acid/N-(2-aminoethyl)-2-(2,5-dioxo-2,5-dihydro-1H-pyrrol-1-yl)acetamide (1:1) (8.12 mg, 26.1 µmol) (intermediate L1) were initially charged in 1.6 ml of DMF. HATU (9.92 mg, 26.1 µmol) and N,N-diisopropylethylamine (11 µl, 65 µmol) were added and the reaction mixture was stirred at RT for 5 min. Water (0.1% TFA) was added and the reaction mixture was purified directly by prep. RP-HPLC (column: Reprosil 250×30; 10µ, flow rate: 50 ml/min, MeCN/water). The solvents were evaporated under reduced pressure and the residue was dried under high vacuum. This gave 18.6 mg (98% of theory) of the compound tert-butyl [13-{(1R)-1-[1-benzyl-4-(2,5-difluorophenyl)-1H-pyrrol-2-yl]-2,2-dimethylpropyl}-1-(2,5-dioxo-2,5-dihydro-1H-pyrrol-1-yl)-17-fluoro-2,7,12-trioxo-10-thia-3,6,13-triazaheptadecan-16-yl]carbamate.

LC-MS (Method 12): $R_t$=2.36 min; MS (ESIpos): m/z=869 [M+H]⁺ tert-Butyl [13-{(1R)-1-[1-benzyl-4-(2,5-difluorophenyl)-1H-pyrrol-2-yl]-2,2-dimethylpropyl}-1-(2,5-dioxo-2,5-dihydro-1H-pyrrol-1-yl)-7-fluoro-2,7,12-trioxo-10-thia-3,6,13-triazaheptadecan-16-yl]carbamate (17.0 mg, 19.6 µmol) was dissolved in 2.0 ml of trifluoroethanol. Zinc chloride (16.0 mg, 117 µmol) was added and the reaction mixture was stirred at 50° C. for 1 hour. Once more, zinc chloride (16.0 mg, 117 µmol) was added and the reaction mixture was stirred at 50° C. for 1 hour. Ethylenediamine-N,N,N',N'-tetraacetic acid (68.6 mg, 234 µmol) was added to the mixture, water (0.1% TFA) was then added and the mixture was subsequently concentrated under reduced pressure. The residue was purified by prep. RP-HPLC (column: Reprosil 250×30; 10µ, flow rate: 50 ml/min, MeCN/water, 0.1% TFA). The solvents were evaporated under reduced pressure and the residue was taken up in a little water and lyophilized. This gave 10.7 mg (60% of theory) of the title compound.

LC-MS (Method 14): $R_t$=5.51 min; MS (ESIpos): m/z=769 [M+H]⁺

Intermediate F319

N-(3-{[2-({(1R)-1-[1-Benzyl-4-(2,5-difluorophenyl)-1H-pyrrol-2-yl]-2,2-dimethylpropyl}[3-({N-[6-(2,5-dioxo-2,5-dihydro-1H-pyrrol-1-yl)hexanoyl]-L-valyl-L-alanyl}amino)propyl]amino)-2-oxoethyl]sulphanyl}propanoyl)-beta-alanyl-L-aspartic acid

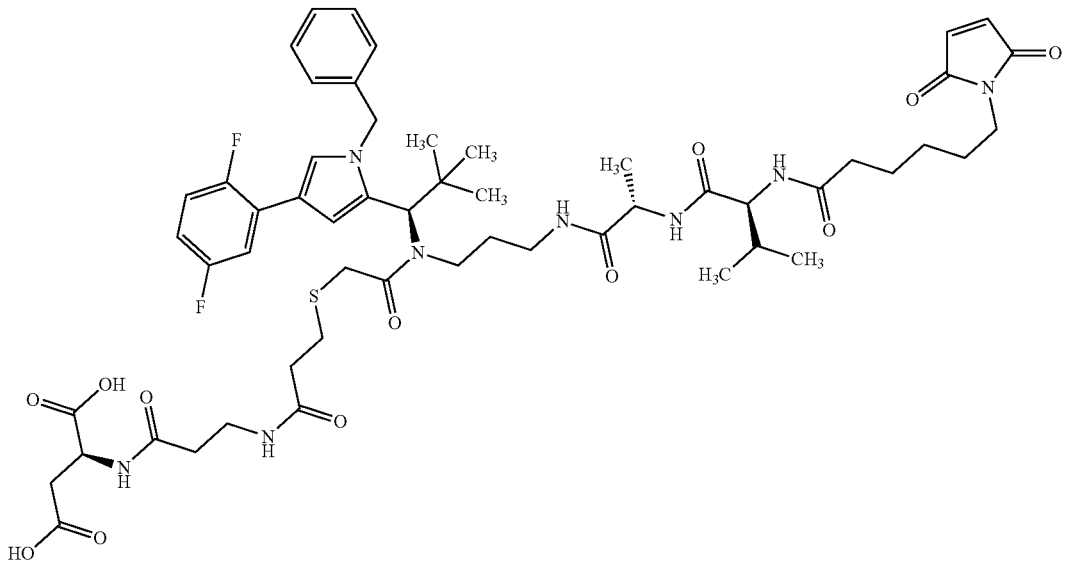 [SMILES: CC(C)[C@H](NC(=O)CCCCCN1C(=O)C=CC1=O)C(=O)N[C@@H](C)C(=O)NCCCN(C(=O)CSCCC(=O)NCCC(=O)N[C@@H](CC(=O)O)C(=O)O)[C@@H](c1cc(-c2cc(F)ccc2F)cn1Cc1ccccc1)C(C)(C)C]

Under argon, N-[6-(2,5-dioxo-2,5-dihydro-1H-pyrrol-1-yl)hexanoyl]-L-valyl-N-[3-({(1R)-1-[1-benzyl-4-(2,5-difluorophenyl)-1H-pyrrol-2-yl]-2,2-dimethylpropyl}[({3-[(2-carboxyethyl)amino]-3-oxopropyl}sulphanyl)acetyl]amino)propyl]-L-alaninamide (9.80 mg, 9.88 µmol) (intermediate C116) and di-tert-butyl L-aspartate hydrochloride (1:1) (3.34 mg, 11.9 µmol) were initially charged in 1.0 ml of DMF, and HATU (4.51 mg, 11.9 µmol) and N,N-diisopropylethylamine (5.2 µl, 30 µmol) were added. The reaction mixture was stirred at RT for 10 min and purified directly by prep. RP-HPLC (column: Reprosil 250×30; 10µ, flow rate: 50 ml/min, MeCN/water, 0.1% TFA). The solvents were LC-MS (Method 1): R$_t$=1.07 min; MS (ESIpos): m/z=1107 [M+H]$^+$ Intermediate F320

N-[6-(2,5-Dioxo-2,5-dihydro-1H-pyrrol-1-yl) hexanoyl]-L-valyl-N-[3-({(1R)-1-[1-benzyl-4-(2,5-difluorophenyl)-1H-pyrrol-2-yl]-2,2-dimethylpropyl}{[(3-{[(1S)-1,3-dicarboxypropyl]amino}-3-oxopropyl)sulphanyl]acetyl}amino)propyl]-L-alaninamide

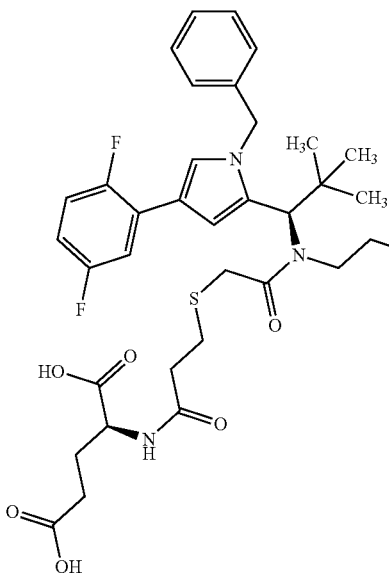
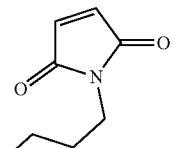

evaporated under reduced pressure and the residue was dried under high vacuum. This gave 10.5 mg (87% of theory) of the compound di-tert-butyl N-(3-{[2-({(1R)-1-[1-benzyl-4-(2,5-difluorophenyl)-1H-pyrrol-2-yl]-2,2-dimethylpropyl}[3-({N-[6-(2,5-dioxo-2,5-dihydro-1H-pyrrol-1-yl)hexanoyl]-L-valyl-L-alanyl}amino)propyl]amino)-2-oxoethyl]sulphanyl}propanoyl)-beta-alanyl-L-aspartate.

LC-MS (Method 1): R$_t$=1.33 min; MS (ESIpos): m/z=1219 [M+H]$^+$

Di-tert-butyl N-(3-{[2-({(1R)-1-[1-benzyl-4-(2,5-difluorophenyl)-1H-pyrrol-2-yl]-2,2-dimethylpropyl}[3-({N-[6-(2,5-dioxo-2,5-dihydro-1H-pyrrol-1-yl)hexanoyl]-L-valyl-L-alanyl}amino)propyl]amino)-2-oxoethyl]sulphanyl}propanoyl)-beta-alanyl-L-aspartate (9.70 mg, 7.95 µmol) was dissolved in 1.5 ml of trifluoroethanol. Zinc chloride (6.50 mg, 47.7 µmol) was added and the reaction mixture was stirred at 50° C. for 1 hour. Once more, zinc chloride (6.50 mg, 47.7 µmol) was added and the reaction mixture was stirred at 50° C. for 1 hour. Ethylenediamine-N,N,N',N'-tetraacetic acid (27.9 mg, 55.4 µmol) was added to the mixture, water (0.1% TFA) was then added and the mixture was subsequently concentrated under reduced pressure. The residue was purified by prep. RP-HPLC (column: Reprosil 250×30; 10µ, flow rate: 50 ml/min, MeCN/water, 0.1% TFA). The solvents were evaporated under reduced pressure and the residue was taken up in a little water and lyophilized. This gave 4.10 mg (47% of theory) of the title compound.

Under argon, N-[6-(2,5-dioxo-2,5-dihydro-1H-pyrrol-1-yl)hexanoyl]-L-valyl-N-[3-({(1R)-1-[1-benzyl-4-(2,5-difluorophenyl)-1H-pyrrol-2-yl]-2,2-dimethylpropyl}{[(2-carboxyethyl)sulphanyl]acetyl}amino)propyl]-L-alaninamide (20.0 mg, 21.7 µmol) (intermediate C115) and di-tert-butyl L-glutamate hydrochloride (1:1) (7.71 mg, 26.1 µmol) were initially charged in 2.0 ml of DMF, and HATU (9.91 mg, 26.1 µmol) and N,N-diisopropylethylamine (11 µl, 65 µmol) were added. The reaction mixture was stirred at RT for 10 min and then purified directly by prep. RP-HPLC (column: Reprosil 250×30; 10µ, flow rate: 50 ml/min, MeCN/water, 0.1% TFA). The solvents were evaporated under reduced pressure and the residue was dried under high vacuum. This gave 16.4 mg (65% of theory) of the compound di-tert-butyl (2S)-2-{[(13S,16S)-7-{(1R)-1-[1-benzyl-4-(2,5-difluorophenyl)-1H-pyrrol-2-yl]-2,2-dimethylpropyl}-23-(2,5-dioxo-2,5-dihydro-H-pyrrol-1-yl)-16-isopropyl-13-methyl-6,12,15,18-tetraoxo-4-thia-7,11,14,17-tetraazatricosan-1-oyl]amino}pentanedioate.

LC-MS (Method 1): R$_t$=1.40 min; MS (ESIpos): m/z=1162 [M+H]$^+$

Di-tert-butyl (2S)-2-{[(13S,16S)-7-{(1R)-1-[1-benzyl-4-(2,5-difluorophenyl)-1H-pyrrol-2-yl]-2,2-dimethylpropyl}-23-(2,5-dioxo-2,5-dihydro-1H-pyrrol-1-yl)-16-isopropyl-13-methyl-6,12,15,18-tetraoxo-4-thia-7,11,14,17-tetraazatricosan-1-oyl]amino}pentanedioate (14.7 mg, 12.6 µmol) was dissolved in 1.5 ml of trifluoroethanol. Zinc chloride (10.3 mg, 75.9 µmol) was added and the reaction mixture was stirred at 50° C. for 1 hour. Once more, zinc chloride (10.3 mg, 75.9 µmol) was added and the reaction mixture was stirred at 50° C. for 1 hour. Ethylenediamine-N,N,N',N'-tetraacetic acid (44.4 mg, 152 µmol) was added to the mixture, water (0.1% TFA) was then added and the mixture was subsequently concentrated under reduced pressure. The residue was purified by prep. RP-HPLC (column: Reprosil 250×30; 10µ, flow rate: 50 ml/min, MeCN/water, 0.1% TFA). The solvents were evaporated under reduced pressure and the residue was taken up in a little water and lyophilized. This gave 6.0 mg (45% of theory) of the title compound.

LC-MS (Method 1): R, =1.10 min; MS (ESIneg): m/z=1048 [M−H]⁻

Intermediate F321

N-(3-{[2-({(1R)-1-[1-Benzyl-4-(2,5-difluorophenyl)-1H-pyrrol-2-yl]-2,2-dimethylpropyl}[3-({N-[6-(2,5-dioxo-2,5-dihydro-1H-pyrrol-1-yl)hexanoyl]-L-valyl-L-alanyl}amino)propyl]amino)-2-oxoethyl]sulphanyl}propanoyl)-beta-alanyl-D-glutamic acid 50 ml/min, MeCN/water, 0.1% TFA). The solvents were evaporated under reduced pressure and the residue was dried under high vacuum. This gave 11.7 mg (96% of theory) of the compound di-tert-butyl N-(3-{[2-({(1R)-1-[1-benzyl-4-(2,5-difluorophenyl)-1H-pyrrol-2-yl]-2,2-dimethylpropyl}[3-({N-[6-(2,5-dioxo-2,5-dihydro-1H-pyrrol-1-yl)hexanoyl]-L-valyl-L-alanyl}amino)propyl]amino)-2-oxoethyl]sulphanyl}propanoyl)-beta-alanyl-D-glutamate.

LC-MS (Method 1): R_f=1.34 min; MS (ESIpos): m/z=1233 [M+H]⁺

Di-tert-butyl N-(3-{[2-({(1R)-1-[1-benzyl-4-(2,5-difluorophenyl)-1H-pyrrol-2-yl]-2,2-dimethylpropyl}[3-({N-[6-(2,5-dioxo-2,5-dihydro-1H-pyrrol-1-yl)hexanoyl]-L-valyl-L-alanyl}amino)propyl]amino)-2-oxoethyl]sulphanyl}propanoyl)-beta-alanyl-D-glutamate (11.5 mg, 9.32 µmol) was dissolved in 1.5 ml of trifluoroethanol. (7.62 mg, 55.9 µmol) was added and the reaction mixture was stirred at 50° C. for 1 hour. Once more, zinc chloride (7.62 mg, 55.9 µmol) was added and the reaction mixture was stirred at 50° C. for 1 hour. Ethylenediamine-N,N,N',N'-

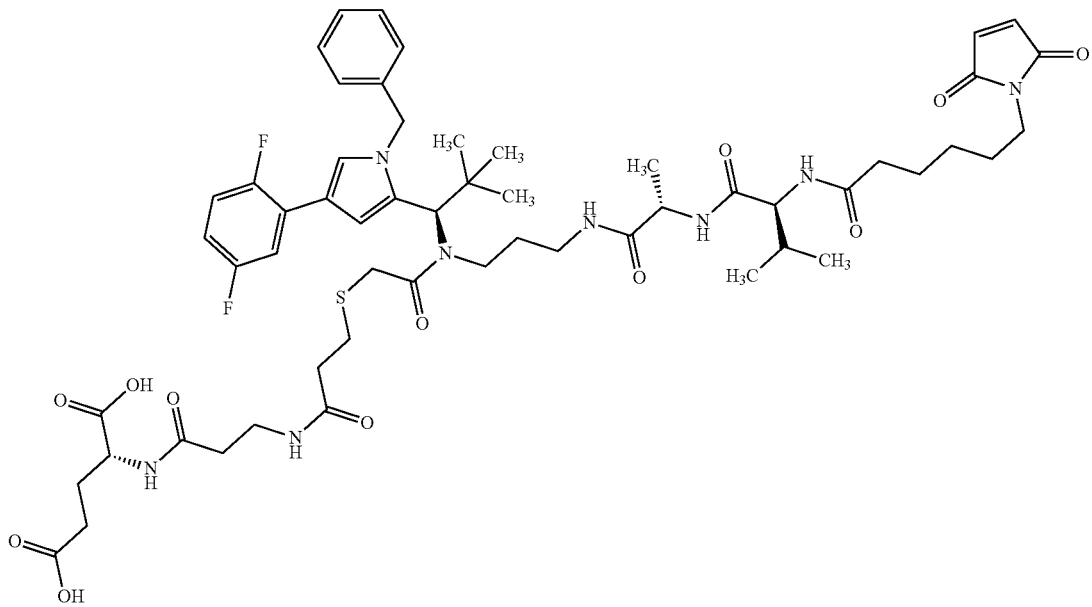 [SMILES: CC(C)[C@H](NC(=O)CCCCCN1C(=O)C=CC1=O)C(=O)N[C@@H](C)C(=O)NCCCN(C(=O)CSCCC(=O)NCCC(=O)N[C@H](CCC(=O)O)C(=O)O)[C@@H](c1cc(-c2cc(F)ccc2F)cn1Cc1ccccc1)C(C)(C)C]

Under argon, N-[6-(2,5-dioxo-2,5-dihydro-1H-pyrrol-1-yl)hexanoyl]-L-valyl-N-[3-({(1R)-1-[1-benzyl-4-(2,5-difluorophenyl)-1H-pyrrol-2-yl]-2,2-dimethylpropyl}[({3-[(2-carboxyethyl)amino]-3-oxopropyl}sulphanyl)acetyl]amino)propyl]-L-alaninamide (9.80 mg, 9.88 µmol) (intermediate C116) and di-tert-butyl D-glutamate hydrochloride (1:1) (3.51 mg, 11.9 µmol) were initially charged in 1.0 ml of DMF, and HATU (4.51 mg, 11.9 µmol) and N,N-diisopropylethylamine (5.2 µl, 30 µmol) were added. The reaction mixture was stirred at RT for 10 min and purified directly by prep. RP-HPLC (column: Reprosil 250×30; 10µ, flow rate:

tetraacetic acid (32.6 mg, 112 µmol) was added to the mixture, water (0.1% TFA) was then added and the mixture was subsequently concentrated under reduced pressure. The residue was purified by prep. RP-HPLC (column: Reprosil 250×30; 10µ, flow rate: 50 ml/min, MeCN/water, 0.1% TFA). The solvents were evaporated under reduced pressure and the residue was taken up in a little water and lyophilized. This gave 6.5 mg (62% of theory) of the title compound.

LC-MS (Method 1): R_f=1.07 min; MS (ESIpos): m/z=1121 [M+H]⁺

Intermediate F322

N-(3-{[2-({(1R)-1-[1-Benzyl-4-(2,5-difluorophenyl)-1H-pyrrol-2-yl]-2,2-dimethylpropyl}[3-({N-[6-(2,5-dioxo-2,5-dihydro-1H-pyrrol-1-yl)hexanoyl]-L-valyl-L-alanyl}amino)propyl]amino)-2-oxoethyl]sulphanyl}propanoyl)-beta-alanyl-L-glutamic acid

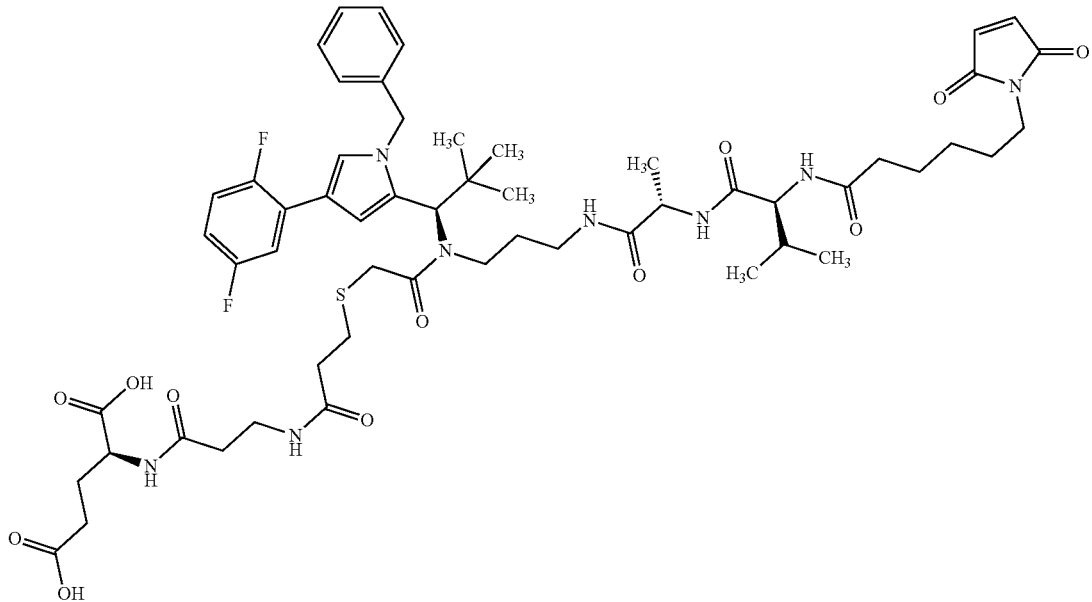 [SMILES: CC(C)[C@H](NC(=O)CCCCCN1C(=O)C=CC1=O)C(=O)N[C@@H](C)C(=O)NCCCN(C(=O)CSCCC(=O)NCCC(=O)N[C@@H](CCC(=O)O)C(=O)O)[C@@H](c1cc(-c2cc(F)ccc2F)cn1Cc1ccccc1)C(C)(C)C]

Under argon, N-[6-(2,5-dioxo-2,5-dihydro-1H-pyrrol-1-yl)hexanoyl]-L-valyl-N-[3-({(1R)-1-[1-benzyl-4-(2,5-difluorophenyl)-1H-pyrrol-2-yl]-2,2-dimethylpropyl}[({3-[(2-carboxyethyl)amino]-3-oxopropyl}sulphanyl)acetyl]amino)propyl]-L-alaninamide (9.80 mg, 9.88 μmol) (intermediate C116) and di-tert-butyl L-glutamate hydrochloride (1:1) (3.51 mg, 11.9 μmol) were initially charged in 1.0 ml of DMF, and HATU (4.51 mg, 11.9 μmol) and N,N-diisopropylethylamine (5.2 μl, 30 μmol) were added. The reaction mixture was stirred at RT for 10 min and purified directly by prep. RP-HPLC (column: Reprosil 250×30; 10μ, flow rate: 50 ml/min, MeCN/water, 0.1% TFA). The solvents were evaporated under reduced pressure and the residue was dried under high vacuum. This gave 11.3 mg (93% of theory) of the compound of di-tert-butyl N-(3-{[2-({(1R)-1-[1-benzyl-4-(2,5-difluorophenyl)-1H-pyrrol-2-yl]-2,2-dimethylpropyl}[3-({N-[6-(2,5-dioxo-2,5-dihydro-1H-pyrrol-1-yl)hexanoyl]-L-valyl-L-alanyl}amino)propyl]amino)-2-oxoethyl]sulphanyl}propanoyl)-beta-alanyl-L-glutamate.

LC-MS (Method 1): $R_t$=1.34 min; MS (ESIpos): m/z=1233 [M+H]$^+$

Di-tert-butyl N-(3-{[2-({(1R)-1-[1-benzyl-4-(2,5-difluorophenyl)-1H-pyrrol-2-yl]-2,2-dimethylpropyl}[3-({N-[6-(2,5-dioxo-2,5-dihydro-1H-pyrrol-1-yl)hexanoyl]-L-valyl-L-alanyl}amino)propyl]amino)-2-oxoethyl]sulphanyl}propanoyl)-beta-alanyl-L-glutamate (11.0 mg, 8.92 μmol) was dissolved in 1.5 ml of trifluoroethanol. Zinc chloride (7.29 mg, 53.5 μmol) was added and the reaction mixture was stirred at 50° C. for 1 hour. Once more, zinc chloride (7.29 mg, 53.5 μmol) was added and the reaction mixture was stirred at 50° C. for 1 hour. Ethylenediamine-N,N,N',N'-tetraacetic acid (31.2 mg, 107 μmol) was added to the mixture, water (0.1% TFA) was then added and the mixture was subsequently concentrated under reduced pressure. The residue was purified by prep. RP-HPLC (column: Reprosil 250×30; 10μ, flow rate: 50 ml/min, MeCN/water, 0.1% TFA). The solvents were evaporated under reduced pressure and the residue was taken up in a little water and lyophilized. This gave 5.10 mg (51% of theory) of the title compound.

LC-MS (Method 1): $R_t$=1.07 min; MS (ESIpos): m/z=1121 [M+H]$^+$

Intermediate F323

N-[6-(2,5-Dioxo-2,5-dihydro-1H-pyrrol-1-yl)hexanoyl]-L-valyl-N-[3-({[(3-{[(1R)-2-(L-beta-asparagylamino)-1-carboxyethyl]amino}-3-oxopropyl)sulphanyl]acetyl}{(1R)-1-[1-benzyl-4-(2,5-difluorophenyl)-1H-pyrrol-2-yl]-2,2-dimethylpropyl}amino)propyl]-L-alaninamide/trifluoroacetic acid (1:1)

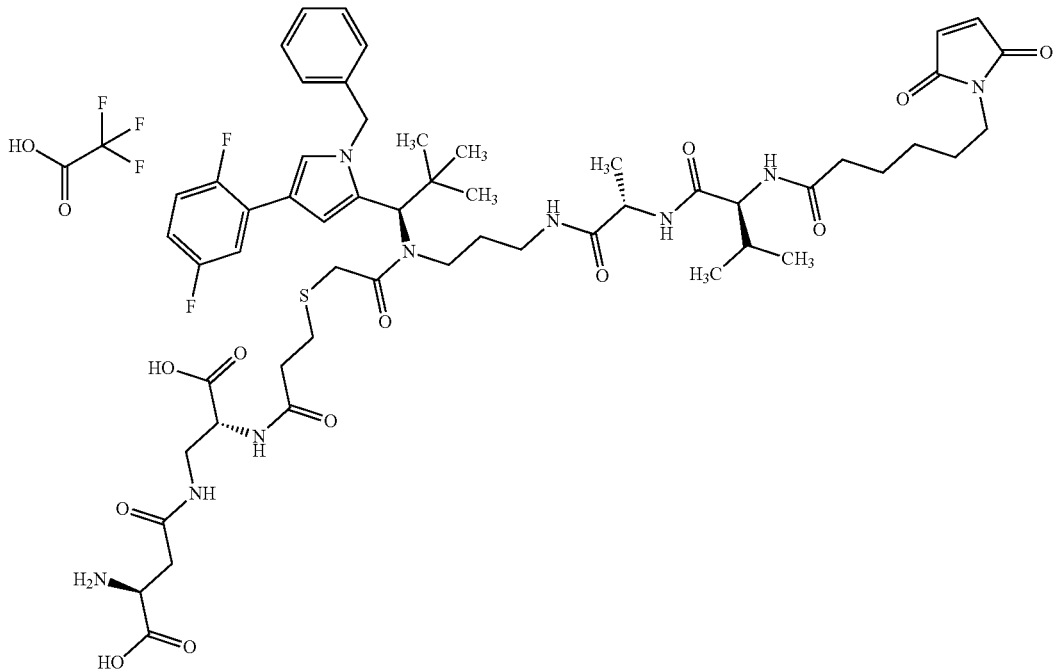

Under argon, N-[6-(2,5-dioxo-2,5-dihydro-1H-pyrrol-1-yl)hexanoyl]-L-valyl-N-[3-({(1R)-1-[1-benzyl-4-(2,5-difluorophenyl)-1H-pyrrol-2-yl]-2,2-dimethylpropyl}{[(2-carboxyethyl)sulphanyl]acetyl}amino)propyl]-L-alaninamide (10.0 mg, 7.05 μmol) (intermediate C115) and tert-butyl N-{(2R)-2-amino-3-oxo-3-[2-(trimethylsilyl)ethoxy]propyl}-$N^2$-(tert-butoxycarbonyl)-L-aspartate (4.02 mg, 8.46 μmol) (intermediate L124) were initially charged in 2.0 ml of DMF, and HATU (3.22 mg, 8.46 μmol) and N,N-diisopropylethylamine (3.7 μl, 21 μmol) were added. The reaction mixture was stirred at RT for 10 min and purified directly by prep. RP-HPLC (column: Reprosil 250×30; 10μ, flow rate: 50 ml/min, MeCN/water, 0.1% TFA). The solvents were evaporated under reduced pressure and the residue was taken up in a little water and lyophilized. This gave 4.3 mg (32% of theory) of the compound 6-tert-butyl 11-[2-(trimethylsilyl)ethyl](6S,11R,25S,28S)-19-{(1R)-1-[1-benzyl-4-(2,5-difluorophenyl)-1H-pyrrol-2-yl]-2,2-dimethylpropyl}-35-(2,5-dioxo-2,5-dihydro-1H-pyrrol-1-yl)-28-isopropyl-2,2,25-trimethyl-4,8,13,18,24,27,30-heptaoxo-3-oxa-16-thia-5,9,12,19,23,26,29-heptaazapentatriacontane-6,11-dicarboxylate.

LC-MS (Method 5): $R_t$=5.32 min; MS (ESIpos): m/z=1379 [M+H]$^+$ 6-tert-Butyl 11-[2-(trimethylsilyl)ethyl](6S,11R,25S,28S)-19-{(1R)-1-[1-benzyl-4-(2,5-difluorophenyl)-1H-pyrrol-2-yl]-2,2-dimethylpropyl}-35-(2,5-dioxo-2,5-dihydro-1H-pyrrol-1-yl)-28-isopropyl-2,2,25-trimethyl-4,8,13,18,24,27,30-heptaoxo-3-oxa-16-thia-5,9,12,19,23,26,29-heptaazapentatriacontane-6,11-dicarboxylate (4.10 mg, 73% pure, 2.17 μmol) was dissolved in 2.0 ml of trifluoroethanol. Zinc chloride (1.77 mg, 13.0 μmol) was added and the reaction mixture was stirred at 50° C. for 1 hour. Five more times, zinc chloride (1.77 mg, 13.0 μmol) was added and the reaction mixture was stirred at 50° C. for 1 hour. Ethylenediamine-N,N,N',N'-tetraacetic acid (22.0 mg, 78 μmol) was added to the mixture, water (0.1% TFA) was then added and the mixture was subsequently concentrated under reduced pressure. The residue was purified by prep. RP-HPLC (column: Reprosil 250×30; 10μ, flow rate: 50 ml/min, MeCN/water, 0.1% TFA). The solvents were evaporated under reduced pressure and the residue was taken up in a little water and lyophilized. This gave 2.1 mg (69% of theory) of the title compound.

LC-MS (Method 1): $R_t$=0.98 min; MS (ESIpos): m/z=1122 [M+H]$^+$

Intermediate F324

S-[2-({(1R)-1-[1-Benzyl-4-(2,5-difluorophenyl)-1H-pyrrol-2-yl]-2,2-dimethylpropyl}[pyrrolidin-3-ylmethyl]amino)-2-oxoethyl]-N-[1-(2,5-dioxo-2,5-dihydro-1H-pyrrol-1-yl)-2,18-dioxo-6,9,12,15-tetraoxa-3-azaoctadecan-18-yl]-L-cysteine/trifluoroacetic acid (1:1) (isomer 1)

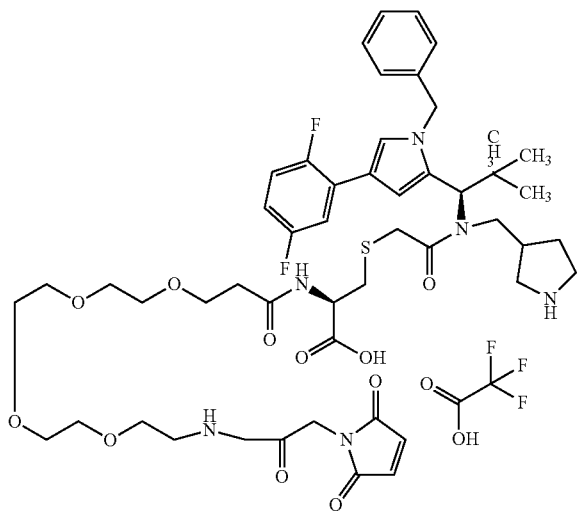

Under argon, 1-(2,5-dioxo-2,5-dihydro-1H-pyrrol-1-yl)-2-oxo-6,9,12,15-tetraoxa-3-azaoctadecan-18-oic acid (99.6 mg, 247 µmol) (intermediate L74) was initially charged in 1.4 ml of DMF, and HATU (90.4 mg, 238 µmol) and N,N-diisopropylethylamine (41 µl, 240 µmol) were added. The reaction mixture was stirred at RT for 10 min, and S-[2-({(1R)-1-[1-benzyl-4-(2,5-difluorophenyl)-1H-pyrrol-2-yl]-2,2-dimethylpropyl}[1-(tert-butoxycarbonyl)pyrrolidin-3-yl]methyl}amino)-2-oxoethyl]-L-cysteine (70.0 mg, 95.2 µmol) (intermediate C90), dissolved in 1.4 ml of DMF, was added. The reaction mixture was stirred at RT overnight and purified directly by prep. RP-HPLC (column: Reprosil 250×30; 10µ, flow rate: 50 ml/min, MeCN/water, 0.1% TFA). The solvents were evaporated under reduced pressure and the residue was taken up in a little water and lyophilized. This gave 19.0 mg (18.4% of theory) of the compound S-[2-({(1R)-1-[1-benzyl-4-(2,5-difluorophenyl)-1H-pyrrol-2-yl]-2,2-dimethylpropyl}{[(3R)-1-(tert-butoxycarbonyl)pyrrolidin-3-yl]methyl}amino)-2-oxoethyl]-N-[1-(2,5-dioxo-2,5-dihydro-1H-pyrrol-1-yl)-2,18-dioxo-6,9,12,15-tetraoxa-3-azaoctadecan-18-yl]-L-cysteine.

LC-MS (Method 12): $R_t$=2.29 min; MS (ESIpos): m/z=1082 [M+H]$^+$

S-[2-({(1R)-1-[1-Benzyl-4-(2,5-difluorophenyl)-1H-pyrrol-2-yl]-2,2-dimethylpropyl}{[1-(tert-butoxycarbonyl)pyrrolidin-3-yl]methyl}amino)-2-oxoethyl]-N-[1-(2,5-dioxo-2,5-dihydro-1H-pyrrol-1-yl)-2,18-dioxo-6,9,12,15-tetraoxa-3-azaoctadecan-18-yl]-L-cysteine (17.0 mg, 15.7 µmol) was dissolved in 2.0 ml of trifluoroethanol. Zinc chloride (8.56 mg, 62.8 µmol) was added and the reaction mixture was stirred at 50° C. for 1 hour. Once more, zinc chloride (8.56 mg, 62.8 µmol) was added and the reaction mixture was stirred at 50° C. for 2 hours. Ethylenediamine-N,N,N',N'-tetraacetic acid (36.7 mg, 126 µmol) was added to the mixture, water (0.1% TFA) was then added and the mixture was subsequently concentrated under reduced pressure. The residue was purified by prep. RP-HPLC (column: Reprosil 250×30; 10µ, flow rate: 50 ml/min, MeCN/water, 0.1% TFA). The solvents were evaporated under reduced pressure and the residue was dried under high vacuum. This gave 3.90 mg (22% of theory) of the title compound.

LC-MS (Method 1): $R_t$=0.89 min; MS (ESIpos): m/z=983 [M+H]$^+$

Intermediate F325

N-[2-({(2S)-2-Amino-4-[{(1R)-1-[1-benzyl-4-(2,5-difluorophenyl)-1H-pyrrol-2-yl]-2,2-dimethylpropyl}(glycoloyl)amino]butanoyl}amino)ethyl]-N$^2$-[(2,5-dioxo-2,5-dihydro-1H-pyrrol-1-yl)acetyl]-D-alpha-glutamine/trifluoroacetic acid (1:1)

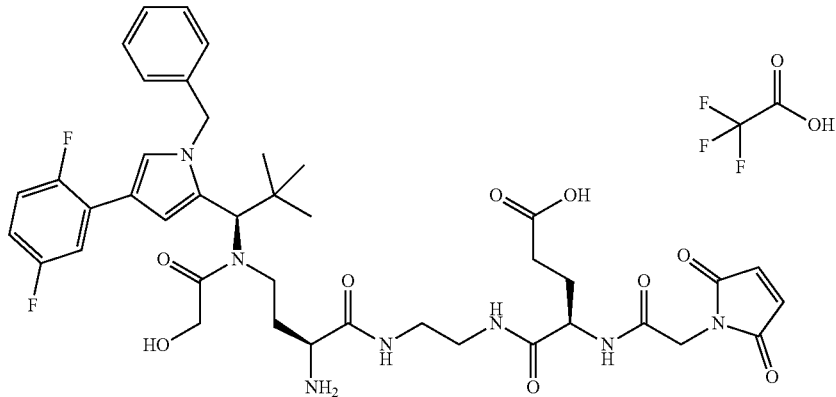 [SMILES: CC(C)(C)[C@H](c1cc(-c2cc(F)ccc2F)cn1Cc1ccccc1)N(CC[C@H](N)C(=O)NCCNC(=O)[C@@H](CCC(=O)O)NC(=O)CN1C(=O)C=CC1=O)C(=O)CO ; O=C(O)C(F)(F)F]

30 mg (0.046 mmol) of intermediate C58 were coupled with 29 mg (0.055 mmol) of trifluoroacetic acid/benzyl N-(2-aminoethyl)-N2-[(benzyloxy)carbonyl]-D-alpha-glutaminate (1:1) in the presence of 1.5 equiv. of HATU and 3 equiv. of N,N-diisopropylethylamine. Purification by preparative HPLC gave 39.5 mg (82% of theory) of the protected intermediate. First, the benzyl ester groups of this intermediate were removed hydrogenolytically. Subsequent coupling with 1-{2-[(2,5-dioxopyrrolidin-1-yl)oxy]-2-oxoethyl}-1H-pyrrole-2,5-dione in DMF in the presence of 3 equiv. of N,N-diisopropylethylamine and removal of the Teoc protective group with zinc chloride in trifluoroethanol as for intermediate F119 then gave, in 2 further steps, the title compound.

LC-MS (Method 12): $R_t$=1.44 min; MS (ESIpos): m/z=822 (M+H)$^+$.

Intermediate F326

N-[2-({(2S)-2-Amino-4-[{(1R)-1-[1-benzyl-4-(2,5-difluorophenyl)-1H-pyrrol-2-yl]-2,2-dimethylpropyl}(glycoloyl)amino]butanoyl}amino)ethyl]-N$^2$-(bromoacetyl)-D-alpha-glutamine/trifluoroacetic acid (1:1)

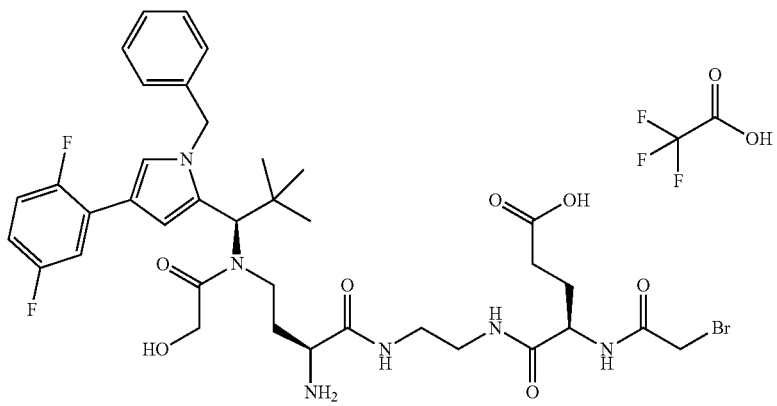 [SMILES: CC(C)(C)[C@H](c1cc(-c2cc(F)ccc2F)cn1Cc1ccccc1)N(CC[C@H](N)C(=O)NCCNC(=O)[C@@H](CCC(=O)O)NC(=O)CBr)C(=O)CO ; O=C(O)C(F)(F)F]

43 mg (0.066 mmol) of intermediate C58 were coupled with 57 mg (0.077 mmol) of intermediate L125 in the presence of 1.5 equiv. of HATU and 4 equiv. of 4-methylmorpholine. Purification by preparative HPLC gave 27 mg (34% of theory) of the protected intermediate. This was then converted into the title compound using zinc chloride in trifluoroethanol as described for intermediate F119.

LC-MS (Method 1): $R_t$=0.83 min; MS (ESIpos): m/z=805 and 807 (M+H)$^+$.

B: Preparation of Antibody Drug Conjugates (ADC)

B-1. General Process for Generating Anti-CD123 Antibodies

The anti-CD123 antibodies were obtained by CDR grafting. The sequence of the 7G3 antibody (EP2426148) represents the starting point of the humanized antibodies such as TPP-5969 and TPP-5971. Bispecific scFv immunofusion proteins based on 12F1 are disclosed in WO 2013/173820. Based on the publication of the sequences of the variable regions (VH and VL) of 12F1 (WO 2013/173820), the following antibody sequences were obtained by fusion of the variable domains of the donor immunoglobulin (VH and VL) with the constant regions of a human antibody. A chimeric variant of 12F1 was generated.

Humanization

The murine antibody sequence of the 7G3 antibody was humanized by transferring the CDRs into a human antibody skeleton. For the definition of the CDRs according to Kabat, see Andre C. R. Martin, "Protein sequence and structure analysis of antibody variable domains" in Antibody Engineering (Springer Lab Manuals), Eds.: Duebel, S. and Kontermann, R., Springer-Verlag, Heidelberg. After comparison of the murine frame sequences (without CDRs) with human germline sequences, a similar frequently occurring human frame sequence was selected. In this case, it was the heavy chain IGHV1-46-01 with the J sequence IGHJ4-03 and the light chain IGKV4-1-01 with the J segment IGKJ2. The germline sequences originated from the VBASE2 database (Retter I, Althaus HH, Münch R, Müller W: VBASE2, an integrative V gene database. Nucleic Acids Res. 2005 Jan. 1; 33 (Database issue):D671-4). The sequences were named using the IMGT system (Lefranc, M.-P., Giudicelli, V., Ginestoux, C., Jabado-Michaloud, J., Folch, G., Bellahcene, F., Wu, Y., Gemrot, E., Brochet, X., Lane, J., Regnier, L., Ehrenmann, F., Lefranc, G. and Duroux, P. IMGT®, the international ImMunoGeneTics information System®. Nucl. Acids Res, 37, D1006-D1012 (2009); doi:10.1093/nar/gkn838). The antibody variants TPP-5968, TPP-5969 and TPP-5971 described herein carry various point mutations differing from the human germline sequence which may influence their properties.

B-2. General Process for Expressing Anti-CD123 Antibodies in Mammalian Cells

The antibodies, for example TPP-6013 and TPP-5969, were produced in transient cultures of mammalian cells, as described by Tom et al., Chapter 12 in Methods Express: Expression Systems, edited by Micheal R. Dyson and Yves Durocher, Scion Publishing Ltd, 2007.

B-3. General Process for Purifying Antibodies from Cell Supernatants

The antibodies, for example TPP-6013 and TPP-5969, were obtained from the cell culture supernatants. The cell supernatants were clarified by centrifugation of cells. The cell supernatant was then purified by affinity chromatography on a MabSelect Sure (GE Healthcare) chromatography column. To this end, the column was equilibrated in DPBS pH 7.4 (Sigma/Aldrich), the cell supernatant was applied and the column was washed with about 10 column volumes of DPBS pH 7.4+500 mM sodium chloride. The antibodies were eluted in 50 mM sodium acetate pH 3.5+500 mM sodium chloride and then purified further by gel filtration chromatography on a Superdex 200 column (GE Healthcare) in DPBS pH 7.4.

The antibodies were furthermore characterized by their binding affinity to soluble IL3Ralpha (obtained from R&D Systems) via BIAcore analysis. To determine the cell binding characteristics of the anti-CD123 antibodies, binding was measured by flow cytometry on CD123-positive cancer cell lines (MOLM-13, THP-1).

B-4. General Process for Coupling to Cysteine Side Chains

The following antibodies were used for the coupling reactions:

anti-CD123 AK$_{1A}$ (TPP-5969)

anti-CD123 AK$_{1B}$ (TPP-5971)

anti-CD123 AK$_{1C}$ (TPP-6013)

anti-CD123 AK$_{1D}$ (TPP-5968)

The coupling reactions were usually carried out under argon.

Between 2 and 5 equivalents of tris(2-carboxyethyl)phosphine hydrochloride (TCEP), dissolved in PBS buffer, were added to a solution of the appropriate antibody in PBS buffer in the concentration range between 1 mg/ml and 20 mg/ml, preferably in the range of about 5 mg/ml to 15 mg/ml, and the mixture was stirred at RT for 1 h. For this purpose, the solution of the respective antibody used can be employed at the concentrations stated in the working examples, or it may optionally also be diluted with PBS buffer to about half of the stated starting concentrations in order to get into the preferred concentration range. Subsequently, depending on the intended loading, from 2 to 12 equivalents, preferably about 5-10 equivalents, of the maleinimide precursor compound or halide precursor compound to be coupled were added as a solution in DMSO. Here, the amount of DMSO should not exceed 10% of the total volume. The reaction was stirred in the case of maleinimide precursors for 60-240 min at RT and in the case of halide precursors between 8 and 24 h at RT and then applied to PBS-equilibrated PD-10 columns (Sephadex® G-25, GE Healthcare) and eluted with PBS buffer. Generally, unless indicated otherwise, 5 mg of the antibody in question in PBS buffer were used for the reduction and the subsequent coupling. Purification on the PD10 column thus in each case afforded solutions of the respective ADCs in 3.5 ml PBS buffer. The sample was then concentrated by ultracentrifugation and optionally rediluted with PBS buffer. If required, for better removal of low-molecular weight components, concentration by ultrafiltration was repeated after redilution with PBS buffer. For biological tests, if required, the concentrations of the final ADC samples were optionally adjusted to the range of 0.5-15 mg/ml by redilution. The respective protein concentrations, stated in the working examples, of the ADC solutions were determined. Furthermore, antibody loading (drug/mAb ratio) was determined using the methods described under B-7.

Depending on the linker, the ADCs shown in the examples may also be present to a lesser or higher degree in the form of the hydrolysed open-chain succinamides attached to the antibodies.

In particular the KSP-I-ADCs attached though the linker substructure

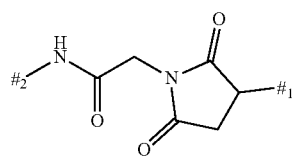

to thiol groups of the antibodies may optionally also be prepared in a targeted manner by rebuffering after the coupling and stirring at pH 8 for about 20-24 h according to Scheme 26 via the ADCs attached via open-chain succinamides.
1 represents the sulphur bridge to the antibody, and #2 the point of attachment to the modified KSP inhibitor Such ADCs where the linker is attached to the antibodies through hydrolysed open-chain succinamides may optionally also be prepared in a targeted manner by an exemplary procedure as follows:

Small Scale Coupling:

From 2 to 5 equivalents of tris(2-carboxyethyl)phosphine hydrochloride (TCEP), dissolved in PBS buffer, were added to a solution of 2-5 mg of the antibody in question in PBS buffer in a concentration range of from 1 mg/ml to 20 mg/ml, preferably in the range from about 5 mg/ml to 15 mg/ml, and the mixture was stirred at RT for 30 min to 1 h. For this purpose, the solution of the respective antibody used can be employed in the concentration given in the working examples or optionally also be diluted with PBS buffer to about half of the stated starting concentration to get to the preferred concentration range. Subsequently, depending on the intended charging, from 2 to 12 equivalents, preferably about 5-10 equivalents, of the maleinimide precursor compound to be coupled were added as a solution in DMSO. Here, the amount of DMSO should not exceed 10% of the total volume. The mixture is stirred at RT for 60-240 min and then diluted with PBS buffer, which had been adjusted to pH 8 beforehand, to a volume of 3-7 ml and stirred under argon at RT overnight. This solution was then passed over a PD-10 column (Sephadex® G-25, GE Healthcare) equilibrated with PBS buffer pH 7.2 and eluted with PBS buffer pH 7.2. The eluate was subsequently concentrated by ultracentrifugation and back-diluted with PBS buffer (pH 7.2).

Medium Scale Coupling:

Under argon, a solution of 0.344 mg TCEP in 100 μl of PBS buffer was added to 60 mg of the antibody in question in 5 ml of PBS buffer (c~12 mg/ml). The reaction was stirred at RT for 30 min, and 0.003 mmol of a maleinimide precursor compound dissolved in 600 μl of DMSO was then added. After a further 1.5 h-2 h of stirring at RT, the reaction was diluted with 1075 μl of PBS buffer which had been adjusted to pH 8 beforehand.

This solution was then applied to PD-10 columns (Sephadex® G-25, GE Healthcare) which had been equilibrated with PBS buffer pH 8 and was eluted with PBS buffer pH 8. The eluate was diluted with PBS buffer pH 8 to a total volume of 14 ml. This solution was stirred at RT under argon overnight. If required, the solution was then rebuffered to pH 7.2. The ADC solution was concentrated by ultracentrifugation, rediluted with PBS buffer (pH 7.2) and then optionally concentrated again to a concentration of about 10 mg/ml.

Other potentially hydrolysis-sensitive thianylsuccinimide bridges to the antibody in the working examples contain the following linker substructures, where #1 represents the thioether linkage to the antibody and #2 the point of attachment to the modified KSP inhibitor:

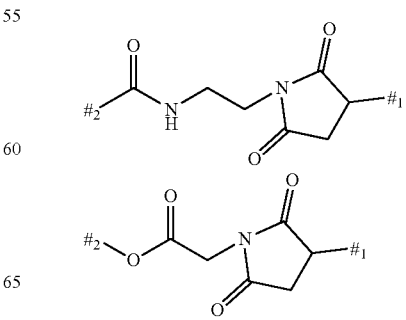

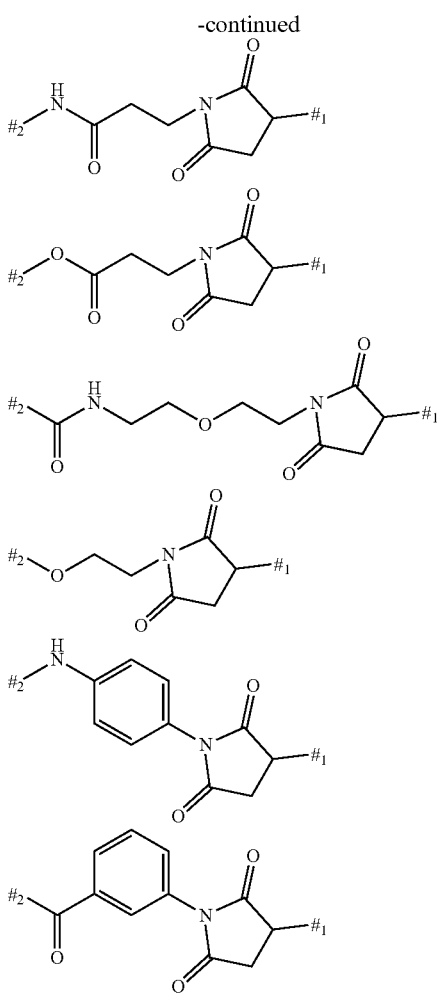

These linker substructures represent the linking unit to the antibody and have (in addition to the linker composition) a significant effect on the structure and the profile of the metabolites formed in the tumour cells.

In the structural formulae shown, $AK_{1A}$, $AK_{1B}$, $AK_{1C}$ and $AK_{1D}$ have the meaning:

$AK_{1A}$=anti-CD123 $AK_{1A}$ (TPP-5969) (partially reduced)–S$§^1$ $AK_{1B}$=anti-CD123 $AK_{1B}$ (TPP-5971) (partially reduced)–S§

$AK_{1C}$=anti-CD123 $AK_{1C}$(TPP-6013) (partially reduced)–S§

$AK_{1D}$=anti-CD123 $AK_{1D}$ (TPP-5968) (partially reduced)–S§ where
$§^1$ represents the linkage to the succinimide group or to any isomeric hydrolysed open-chain succinamides or the alkylene radical resulting therefrom,
and
S represents the sulphur atom of a cysteine residue of the partially reduced antibody.

B-5. General Process for Coupling to Lysine Side Chains

The following antibodies were used for the coupling reactions:

anti-CD123 $AK_{1A}$ (TPP-5969)
anti-CD123 $AK_{1B}$ (TPP-5971)
anti-CD123 $AK_{1C}$ (TPP-6013)
anti-CD123 $AK_{1D}$ (TPP-5968)

The coupling reactions were usually carried out under argon.

From 2 to 8 equivalents of the precursor compound to be coupled were added as a solution in DMSO to a solution of the antibody in question in PBS buffer in a concentration range between 1 mg/ml and 20 mg/ml, preferably about 10 mg/ml, depending on the intended loading. After 30 min to 6 h of stirring at RT, the same amount of precursor compound in DMSO was added again. Here, the amount of DMSO should not exceed 10% of the total volume. After a further 30 min to 6 h of stirring at RT, the reaction was applied to PD-10 columns (Sephadex® G-25, GE Healthcare) equilibrated with PBS and eluted with PBS buffer. Generally, unless indicated otherwise, 5 mg of the antibody in question in PBS buffer were used for the reduction and the subsequent coupling. Purification on the PD10 column thus in each case afforded solutions of the respective ADCs in 3.5 ml PBS buffer. The sample was then concentrated by ultracentrifugation and optionally rediluted with PBS buffer. If required, for better removal of low-molecular weight components, concentration by ultrafiltration was repeated after redilution with PBS buffer. For biological tests, if required, the concentrations of the final ADC samples were optionally adjusted to the range of 0.5-15 mg/ml by redilution.

The respective protein concentrations, stated in the working examples, of the ADC solutions were determined. Furthermore, antibody loading (drug/mAb ratio) was determined using the methods described under B-7.

In the structural formulae shown, $AK_{2A}$, $AK_{2B}$, $AK_{2C}$ and $AK_{2D}$ have the meaning $AK_{2A}$=anti-CD123 $AK_{1A}$ (TPP-5969)–NH$§^2$ $AK_{2B}$=anti-CD123 $AK_{1B}$ (TPP-5971)–NH$§^2$ $AK_{2C}$=anti-CD123 $AK_{1C}$ (TPP-6013)–NH$§^2$ $AK_{2D}$=anti-CD123 $AK_{1D}$ (TPP-5968)–NH$§^2$ where
$§^2$ represents the linkage to the carbonyl group
and
NH represents the side-chain amino group of a lysine residue of the antibody.

B-6a. General Process for Preparing Closed Succinimide-Cysteine Adducts:

In an exemplary embodiment, 10 µmol of the maleinimide precursor compounds described above were taken up in 3-5 ml of DMF, and 2.1 mg (20 µmol) of L-cysteine were added. The reaction mixture was stirred at RT for 2 h to 24 h, then concentrated under reduced pressure and then purified by preparative HPLC.

B-6aa. General Process for Preparing Isomeric Open Succinamide-Cysteine Adducts:

In an exemplary embodiment, 68 µmol of the maleinimide precursor compounds described above were taken up in 15 ml of DMF, and with 36 mg (136 µmol) of N-{[2-(trimethylsilyl)ethoxy]carbonyl}-L-cysteine were added. The reaction mixture was stirred at RT for ~20 h, then concentrated under reduced pressure and then purified by preparative HPLC. The appropriate fractions were combined and the solvents were evaporated under reduced pressure, and the residue was then dissolved in 15 ml of THF/water 1:1. 131 µl of a 2M aqueous lithium hydroxide solution were added and the reaction was stirred at RT for 1 h. The reaction was then neutralized with a 1M hydrochloric acid, the solvent was evaporated under reduced pressure and the residue was purified by preparative HPLC. This gave ~50% of theory of the regioisomeric protected intermediates as a colourless foam.

In the last step, 0.023 mmol of these regioisomeric hydrolysis products were dissolved in 3 ml of 2,2,2-trifluoroethanol. 12.5 mg (0.092 mmol) of zinc chloride were added, and the reaction was stirred at 50° C. for 4 h. 27 mg (0.092 mmol) of ethylenediamine-N,N,N',N'-tetraacetic acid were then added, and the solvent was evaporated under reduced pressure. The residue was purified by preparative HPLC. Concentration of the appropriate fractions and lyophilization of the residue from acetonitrile/water gave the hydrolysed open sulphanylsuccinamides as a regioisomer mixture.

Further Purification and Characterization of the Conjugates According to the Invention After the reaction, in some instances the reaction mixture was concentrated, for example by ultrafiltration, and then desalted and purified by chromatography, for example using a Sephadex® G-25 column. Elution was carried out, for example, with phosphate-buffered saline (PBS). The solution was then sterile filtered and frozen. Alternatively, the conjugate can be lyophylized.

B-7. Determination of the Antibody, the Toxophor Loading and the Proportion of Open Cysteine Adducts For protein identification in addition to molecular weight determination after deglycosylation and/or denaturing, a tryptic digestion was carried out which, after denaturing, reduction and derivatization, confirms the identity of the protein via the tryptic peptides found.

The toxophor loading of the PBS buffer solutions obtained of the conjugates described in the working examples was determined as follows:

Determination of toxophor loading of lysine-linked ADCs was carried out by mass spectrometric determination of the molecular weights of the individual conjugate species. Here, the antibody conjugates were first deglycosylated with PNGaseF, and the sample was acidified and, after HPLC separation/desalting, analysed by mass spectrometry using ESI-MicroTofQ (Bruker Daltonik). All spectra over the signal in the TIC (Total Ion Chromatogram) were added and the molecular weight of the different conjugate species was calculated based on MaxEnt deconvolution. The DAR (=drug/antibody ratio) was then calculated after signal integration of the different species.

The toxophor loading of cysteine-linked conjugates was determined by reversed-phase chromatography of the reduced and denatured ADCs. Guanidinium hydrochloride (GuHCl) (28.6 mg) and a solution of DL-dithiothreitol (DTT) (500 mM, 3 µl) were added to the ADC solution (1 mg/ml, 50 µl). The mixture was incubated at 55° C. for one hour and analysed by HPLC.

HPLC analysis was carried out on an Agilent 1260 HPLC system with detection at 220 nm. A Polymer Laboratories PLRP-S polymeric reversed-phase column (catalogue number PL1912-3802) (2.1×150 mm, 8 µm particle size, 1000 Å) was used at a flow rate of 1 ml/min with the following gradient: 0 min, 25% B; 3 min, 25% B; 28 min, 50% B. Mobile phase A consisted of 0.05% trifluoroacetic acid (TFA) in water, mobile phase B of 0.05% trifluoroacetic acid in acetonitrile.

The detected peaks were assigned by retention time comparison with the light chain (L0) and the heavy chain (H0) of the non-conjugated antibody. Peaks detected exclusively in the conjugated sample were assigned to the light chain with one toxophor (L1) and the heavy chains with one, two and three toxophors ($H_1$, $H_2$, $H_3$).

Average loading of the antibody with toxophors was calculated from the peak areas determined by integration as double the sum of HC load and LC load, where LC load is calculated from the sum of the toxophor number-average weighed integration results of all LC peaks divided by the sum of the singly weighed integration results of all LC peaks, and where the HC-load is calculated from the sum of the toxophor number-average weighed integration results of all HC peaks divided by the sum of the singly weighed integration results of all HC peaks. In individual cases, it may not be possible to determine the toxophor load accurately owing to co-elutions of some peaks.

In the cases where light and heavy chains could not be separated sufficiently by HPLC, determination of toxophor loading of cysteine-linked conjugates was carried out by mass spectrometric determination of the molecular weights of the individual conjugate species at light and heavy chain.

Guanidinium hydrochloride (GuHCl) (28.6 mg) and a solution of DL-dithiothreitol (DTT) (500 mM, 3 µl) were added to the ADC solution (1 mg/ml, 50 µl). The mixture was incubated for one hour at 55° C. and analysed by mass spectrometry after online desalting using ESI-MicroTofQ (Bruker Daltonik).

For the DAR determination, all spectra were added over the signal in the TIC (Total Ion Chromatogram), and the molecular weight of the different conjugate species at light and heavy chain was calculated based on MaxEnt deconvolution. Average loading of the antibody with toxophors was calculated from the peak areas determined by integration as double the sum of HC load and LC load, where LC load is calculated from the sum of the toxophor number-average weighed integration results of all LC peaks divided by the sum of the singly weighed integration results of all LC peaks, and where the HC-load is calculated from the sum of the toxophor number-average weighed integration results of all HC peaks divided by the sum of the singly weighed integration results of all HC peaks.

To determine the proportion of the open cysteine adduct, the molecular weight area ratio of closed to open cysteine adduct (molecular weight delta 18 Dalton) of all singly conjugated light and heavy chain variants was determined. The mean of all variants yielded the proportion of the open cysteine adduct.

B-8. Checking the Antigen-Binding of the ADCs

The capability of the binder of binding to the target molecule was checked after coupling had taken place. The person skilled in the art is familiar with multifarious methods which can be used for this purpose; for example, the affinity of the conjugate can be checked using ELISA technology or surface plasmon resonance analysis (BIAcore™ measurement). The conjugate concentration can be measured by the person skilled in the art using customary methods, for example for antibody conjugates by protein determination. (see also Doronina et al.; Nature Biotechnol. 2003; 21:778-784 and Polson et al., Blood 2007; 1102:616-623).

METABOLITE EMBODIMENTS

Example M1

S-[1-(2-{[2-({(2S)-2-Amino-4-[{(1R)-1-[1-benzyl-4-(2,5-difluorophenyl)-1H-pyrrol-2-yl]-2,2-dimethyl-propyl}(glycoloyl)amino]butanoyl}amino)ethyl]amino}-2-oxoethyl)-2,5-dioxopyrrolidin-3-yl]-L-cysteine/trifluoroacetic acid (1:1)

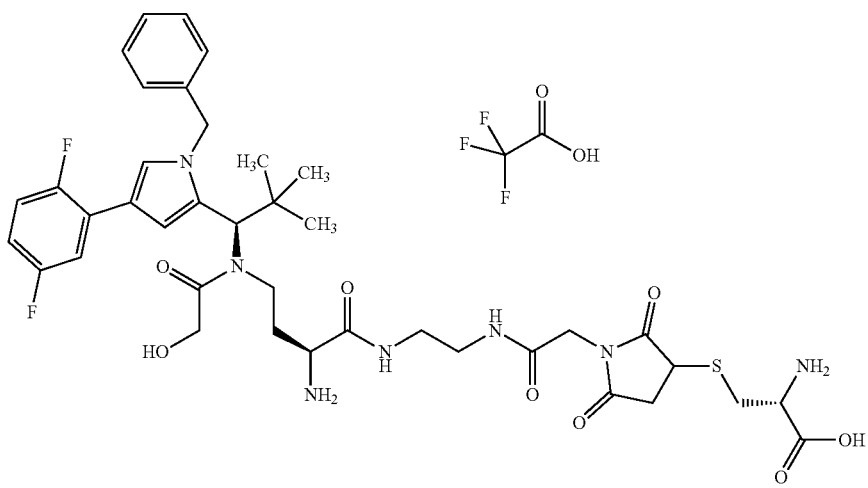 [SMILES: CC(C)(C)[C@H](c1cc(-c2cc(F)ccc2F)cn1Cc1ccccc1)N(CC[C@H](N)C(=O)NCCNC(=O)CN1C(=O)CC(SC[C@H](N)C(=O)O)C1=O)C(=O)CO ; O=C(O)C(F)(F)F]

1.8 mg (2 μmol) of Intermediate F104 were taken up in 1 ml of DMF, and 2.7 mg (22 μmol) of L-cysteine were added. The reaction mixture was stirred at RT for 20 h, then concentrated under reduced pressure and then purified by preparative HPLC. 0.6 mg (26% of theory) of the title compound remained as a colourless foam.

LC-MS (Method 1): $R_t$=0.80 min; MS (EIpos): m/z=814 [M+H]$^+$.

Example M2

4-[(2-{[2-({(2S)-2-Amino-4-[{(1R)-1-[1-benzyl-4-(2,5-difluorophenyl)-1H-pyrrol-2-yl]-2,2-dimethylpropyl}(glycoloyl)amino]butanoyl}amino)ethyl]amino}-2-oxoethyl)amino]-3-{[(2R)-2-amino-2-carboxyethyl]sulphanyl}-4-oxobutanoic acid/ trifluoroacetic acid (1:1)

and

4-[(2-{[2-({(2S)-2-amino-4-[{(1R)-1-[1-benzyl-4-(2,5-difluorophenyl)-1H-pyrrol-2-yl]-2,2-dimethylpropyl}(glycoloyl)amino]butanoyl}amino)ethyl]amino}-2-oxoethyl)amino]-2-{[(2R)-2-amino-2-carboxyethyl]sulphanyl}-4-oxobutanoic acid/ trifluoroacetic acid (1:1)

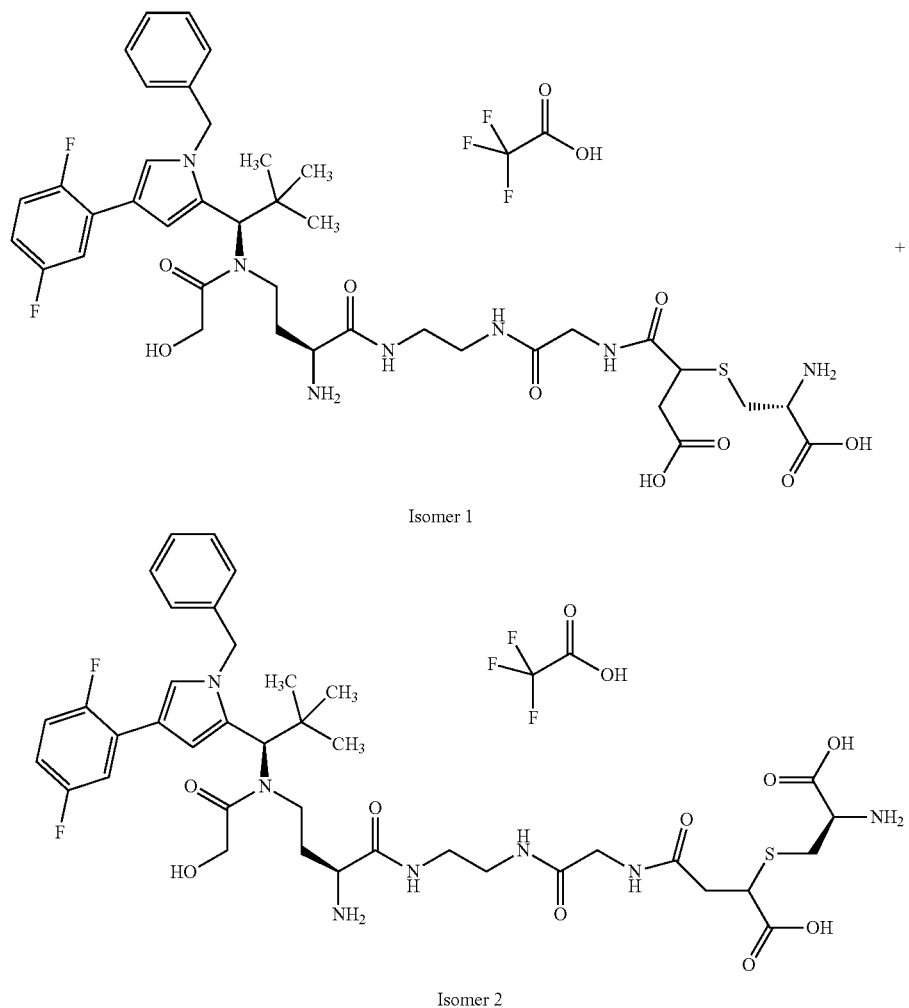

Isomer 1

Isomer 2

LC-MS (Method 1): $R_t$=0.80 min; MS (EIpos): m/z=814 [M+H]$^+$.

First, L-cysteine was converted with 1-({[2-(trimethylsilyl)ethoxy]carbonyl}oxy)pyrrolidine-2,5-dione in DMF in the presence of N,N-diisopropylethylamine into N-{[2-(trimethylsilyl)ethoxy]carbonyl}-L-cysteine.

406 mg (1.53 mmol) of N-{[2-(trimethylsilyl)ethoxy]carbonyl}-L-cysteine were dissolved in 10 ml of DMF, 157.5 mg (1.606 mmol) of maleic anhydride were added and the reaction was stirred at RT for 1 hour. 7.5 mg (0.01 mmol) of intermediate C66 were added to 130 µl of this solution, and the reaction was stirred at RT for 5 min. The mixture was then concentrated under reduced pressure, and the residue was purified by preparative HPLC. The solvent was evaporated under reduced pressure and the residue was dried under high vacuum. This gave 10 mg (89%) of the protected intermediate; it was not possible to separate the regioisomers neither by HPLC nor by LC-MS.

LC-MS (Method 1): $R_t$=1.38 min; MS (EIpos): m/z=1120 [M+H]$^+$.

In the last step, the 10 mg of this intermediate were dissolved in 2 ml of 2,2,2-trifluoroethanol. 12 mg (0.088 mmol) of zinc chloride were added, and the reaction was stirred at 50° C. for 30 min. 26 mg (0.088 mmol) of ethylenediamine-N,N,N',N'-tetraacetic acid were then added, and the solvent was evaporated under reduced pressure. The residue was purified by preparative HPLC. Concentration of the appropriate fractions and lyophilization of the residue from acetonitrile/water gave 8.3 mg (99% of theory) of the title compound as a regioisomer mixture in a ratio of 87:13.

LC-MS (Method 5): $R_t$=2.3 min and 2.43 min; MS (ESIpos): m/z=832 (M+H)$^+$.

$^1$H-NMR main regioisomer: (500 MHz, DMSO-d$_6$): δ=8.7 (m, 1H), 8.5 (m, 2H), 8.1 (m, 1H), 7.6 (m, 1H), 7.5 (s, 1H) 7.4-7.15 (m, 6H), 6.9-7.0 (m, 1H), 6.85 (s, 1H), 5.61 (s, 1H), 4.9 and 5.2 (2d, 2H), 4.26 and 4.06 (2d, 2H), 3.5-3.8 (m, 5H), 3.0-3.4 (m, 5H), 2.75-3.0 (m, 3H), 2.58 and 2.57 (dd, 1H), 0.77 and 1.5 (2m, 2H), 0.81 (s, 9H).

Alternatively, the regioisomeric title compounds were prepared as follows:

To this end, first L-cysteine was converted with 1-({[2-(trimethylsilyl)ethoxy]carbonyl}oxy)pyrrolidine-2,5-dione in DMF in the presence of N,N-diisopropylethylamine into N-{[2-(trimethylsilyl)ethoxy]carbonyl}-L-cysteine.

55 mg (0.068 mmol) of Intermediate F104 and 36 mg (0.136 mmol) of N-{[2-(trimethylsilyl) ethoxy]carbonyl}-L-cysteine were dissolved in 15 ml of DMF, and the mixture was stirred at RT for 20 h. The mixture was then concentrated and the residue was purified by preparative HPLC. The appropriate fractions were combined and the solvents were evaporated under reduced pressure, and the residue was then dissolved in 15 ml of THF/water 1:1. 131 µl of a 2M aqueous lithium hydroxide solution were added and the reaction was stirred at RT for 1 h. The reaction was then neutralized with a 1M hydrochloric acid, the solvent was evaporated under reduced pressure and the residue was purified by preparative HPLC. This gave 37 mg (50% of theory) of the regioisomeric protected intermediates as a colourless foam.

LC-MS (Method 5): $R_t$=3.33 min and 3.36 min; MS (ESIpos): m/z=976 (M+H)$^+$.

In the last step, 25 mg (0.023 mmol) of this intermediate were dissolved in 3 ml of 2,2,2-trifluoroethanol. 12.5 mg (0.092 mmol) of zinc chloride were added, and the reaction was stirred at 50° C. for 4 h. 27 mg (0.092 mmol) of ethylenediamine-N,N,N',N'-tetraacetic acid were then added, and the solvent was evaporated under reduced pressure. The residue was purified by preparative HPLC. Concentration of the appropriate fractions and lyophilization of the residue from acetonitrile/water gave 18.5 mg (85% of theory) of the title compound as a regioisomer mixture in a ratio of 21:79.

LC-MS (Method 5): $R_t$=2.37 min and 3.44 min; MS (ESIpos): m/z=832 (M+H)$^+$.

Example M3

4-[(2-{[(2R)-2-({(2S)-2-Amino-4-[{(1R)-1-[1-benzyl-4-(2,5-difluorophenyl)-1H-pyrrol-2-yl]-2,2-dimethylpropyl}(glycoloyl)amino]butanoyl}amino)-2-carboxyethyl]amino}-2-oxoethyl)amino]-3-{[(2R)-2-amino-2-carboxyethyl]sulphanyl}-4-oxobutanoic acid/trifluoroacetic acid (1:1)

and

4-[(2-{[(2R)-2-({(2S)-2-amino-4-[{(1R)-1-[1-benzyl-4-(2,5-difluorophenyl)-1H-pyrrol-2-yl]-2,2-dimethylpropyl}(glycoloyl)amino]butanoyl}amino)-2-carboxyethyl]amino}-2-oxoethyl)amino]-2-{[(2R)-2-amino-2-carboxyethyl]sulphanyl}-4-oxobutanoic acid/trifluoroacetic acid (1:1)

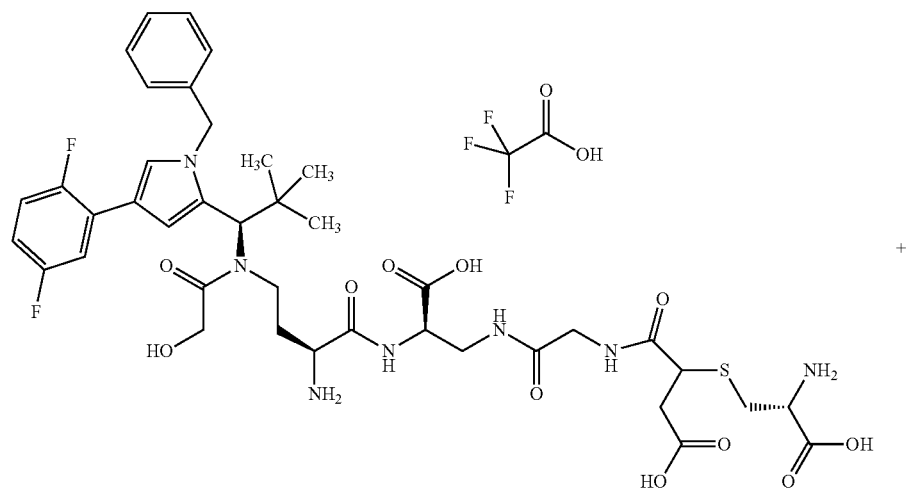

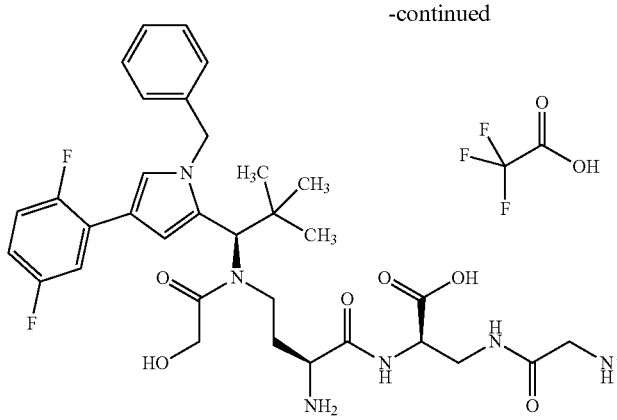
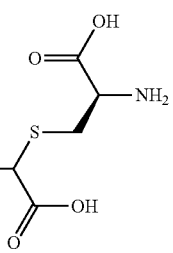

First, L-cysteine was converted with 1-({[2-(trimethylsilyl)ethoxy]carbonyl}oxy)pyrrolidine-2,5-dione in DMF in the presence of N,N-diisopropylethylamine into N-{[2-(trimethylsilyl)ethoxy]carbonyl}-L-cysteine.

11 mg (0.013 mmol) of Intermediate F193 and 8 mg (0.016 μmol) of N-{[2-(trimethylsilyl) ethoxy]carbonyl}-L-cysteine were dissolved in 3 ml of DMF, and the mixture was stirred at RT for 20 h. The mixture was then concentrated and the residue was purified by preparative HPLC.

The appropriate fractions were combined and the solvents were evaporated under reduced pressure, and the residue was then dissolved in 2 ml of THF/water 1:1. 19 μl of a 2M aqueous lithium hydroxide solution were added and the reaction was stirred at RT for 1 h. Another 19 μl of the 2M aqueous lithium hydroxide solution were then added and the reaction was stirred at RT overnight.

The mixture was then neutralized with a 1M hydrochloric acid, the solvent was evaporated under reduced pressure and the residue was purified by preparative HPLC. This gave 4.1 mg (38% of theory) of the regioisomeric protected intermediates as a colourless foam.

LC-MS (Method 1): $R_t$=1.03 min (breit); MS (ESIpos): m/z=1020 (M+H)$^+$.

In the last step, 4.1 mg (0.004 mmol) of this intermediate were dissolved in 3 ml of 2,2,2-trifluoroethanol. 3 mg (0.022 mmol) of zinc chloride were added, and the reaction was stirred at 50° C. for 1 h. 6 mg (0.022 mmol) of ethylenediamine-N,N,N',N'-tetraacetic acid and 2 m of a 0.1% strength aqueous trifluoroacetic acid were then added, and the solvent was evaporated under reduced pressure. The residue was purified by preparative HPLC. Concentration of the appropriate fractions and lyophilization of the residue from acetonitrile/water gave 5 mg (quant.) of the title compound as a regioisomer mixture in a ratio of 20:80.

LC-MS (Method 1): $R_t$=0.78 min (breit); MS (ESIpos): m/z=876 (M+H)$^+$.

LC-MS (Method 5): $R_t$=2.36 min and 2.39 min; MS (ESIpos): m/z=876 (M+H)$^+$.

Example M4

S-(1-{2-[2-({(2S)-2-Amino-4-[{(1R)-1-[1-benzyl-4-(2,5-difluorophenyl)-1H-pyrrol-2-yl]-2,2-dimethylpropyl}(glycoloyl)amino]butanoyl}amino)ethoxy]ethyl}-2,5-dioxopyrrolidin-3-yl)-L-cysteine/trifluoroacetic acid (1:1)

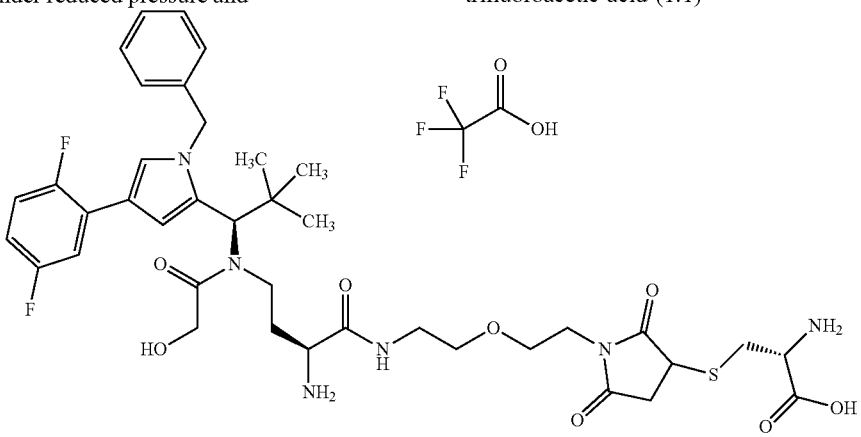

3 mg (4 μmol) of Intermediate F248 were taken up in 2 ml of DMF, and 0.9 mg (8 μmol) of L-cysteine were added. The reaction mixture was stirred at RT for 18 h and then concentrated under reduced pressure. The residue was purified by preparative HPLC. The appropriate fractions were concentrated, giving, after lyophilization of the residue from acetonitrile/water, 1.1 mg (32% of theory) of the title compound as a white solid.

LC-MS (Method 1): $R_t$=0.78 min; MS (EIpos): m/z=801 [M+H]$^+$.

Example M5

(3R,7S)-7-Amino-17-{[(2R)-2-amino-2-carboxy-ethyl]sulphanyl}-3-[1-benzyl-4-(2,5-difluorophenyl)-1H-pyrrol-2-yl]-4-glycoloyl-2,2-dimethyl-8,16-dioxo-12-oxa-4,9,15-triazanonadecane-19-oic acid/ trifluoroacetic acid (1:1)

and (3R,7S)-7-amino-18-{[(2R)-2-amino-2-carboxy-ethyl]sulphanyl}-3-[1-benzyl-4-(2,5-difluorophenyl)-1H-pyrrol-2-yl]-4-glycoloyl-2,2-dimethyl-8,16-dioxo-12-oxa-4,9,15-triazanonadecan-19-oic acid/ trifluoroacetic acid (1:1)

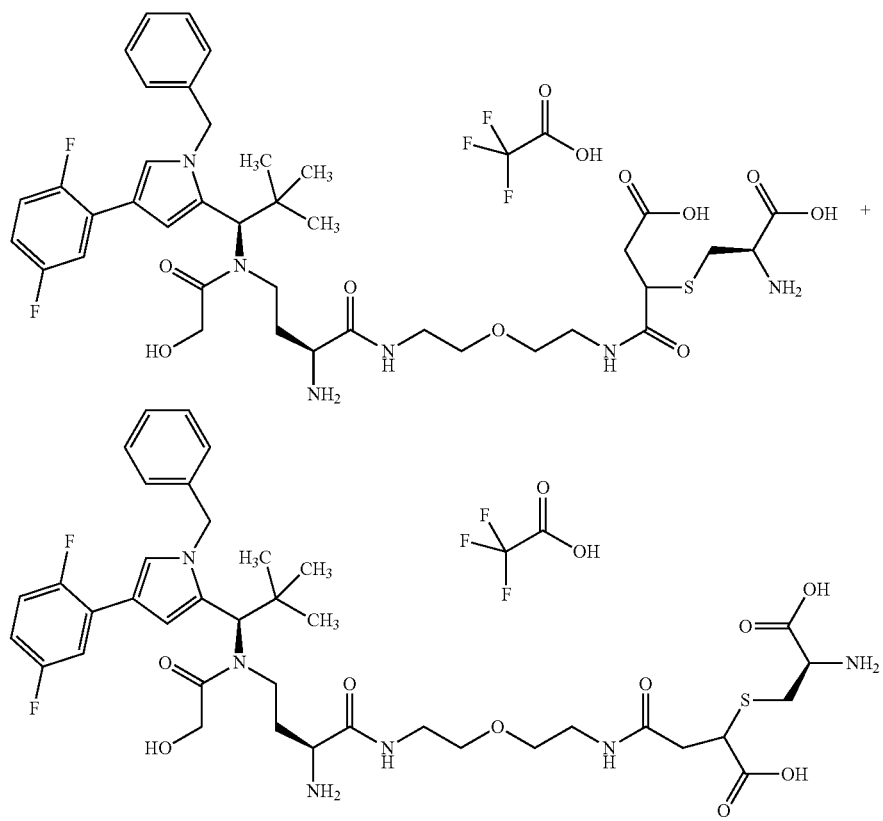

8 mg (0.010 mmol) of the protected intermediate of Intermediate F248 and 5.1 mg (0.02 mmol) of N-{[2-(trimethylsilyl)ethoxy]carbonyl}-L-cysteine were dissolved in 3 ml of DMF, and the mixture was stirred at RT for 18 h and then treated in an ultrasonic bath for 2 h. The mixture was then concentrated and the residue was purified by preparative HPLC. The appropriate fractions were combined and the solvents were evaporated under reduced pressure, and the residue was then dissolved in 2 ml of THF/water 1:1. 15 µl of a 2M aqueous lithium hydroxide solution were added and the reaction was stirred at RT for 15 min. The reaction was then adjusted to a pH of ~3 with a 1M hydrochloric acid, diluted with 20 ml of sodium chloride solution and extracted twice with 20 ml of ethyl acetate. The organic phase was dried over magnesium sulphate and concentrated, and the residue was lyophilized from acetonitrile/water. This gave 8.4 mg (78% of theory over 2 steps) of the regioisomeric protected intermediates as a colourless foam.

LC-MS (Method 1): $R_t$=1.44 min and 3.43 min; MS (ESIpos): m/z=1107 (M+H)$^+$.

In the last step, 8 mg (0.007 mmol) of this intermediate were dissolved in 5 ml of 2,2,2-trifluoroethanol. 9.8 mg (0.072 mmol) of zinc chloride were added, and the reaction was stirred at 50° C. for 1.5 h. Ethylenediamine-N,N,N',N'-tetraacetic acid were then added, and the solvent was evaporated under reduced pressure. The residue was purified by preparative HPLC. Concentration of the appropriate fractions and lyophilization of the residue from acetonitrile/water gave 4 mg (59% of theory) of the title compound as a regioisomer mixture in a ratio of 31:67.

LC-MS (Method 1): $R_t$=0.79 min and 0.81 min; MS (ESIpos): m/z=819 (M+H)$^+$.

Example M6

2-{[(2R)-2-Amino-2-carboxyethyl]sulphanyl}-4-({(14R)-13-(3-aminopropyl)-14-[1-benzyl-4-(2,5-difluorophenyl)-1H-pyrrol-2-yl]-15,15-dimethyl-2,7,12-trioxo-10-thia-3,6,13-triazahexadec-1-yl}amino)-4-oxobutanoic acid/trifluoroacetic acid (1:2) and 3-{[(2R)-2-amino-2-carboxyethyl]sulphanyl}-4-({(14R)— 13-(3-aminopropyl)-14-[1-benzyl-4-(2,5-difluorophenyl)-1H-pyrrol-2-yl]-15,15-dimethyl-2,7,12-trioxo-10-thia-3,6,13-triazahexadec-1-yl}amino)-4-oxobutanoic acid/trifluoroacetic acid (1:2)

18 mg (0.021 mmol) of Intermediate F213 and 11.2 mg (0.04 mmol) of N-{[2-(trimethylsilyl) ethoxy]carbonyl}-L-cysteine were dissolved in 2 ml of DMF, and the mixture was stirred at RT for 18 h. The reaction mixture was concentrated under reduced pressure. The residue (21.2 mg) was dissolved in 3 ml of THF/water 1:1. 0.04 ml of a 2M aqueous lithium hydroxide solution were added and the reaction was stirred at RT for 3 hours. 0.02 ml of a 2M aqueous lithium hydroxide solution were added and the reaction was stirred at RT for 1 hour. The reaction was then adjusted to a pH of ~7 using 7.2 mg (0.12 mmol) of acetic acid. The reaction mixture was purified directly by preparative RP-HPLC (column: Reprosil 125×30; 10µ, flow rate: 50 ml/min, MeCN/water; 0.1% TFA). The solvents were evaporated under reduced pressure and the residue was dried under high vacuum. This gave 13 mg (57% over 2 steps) of the regioisomeric protected intermediates.

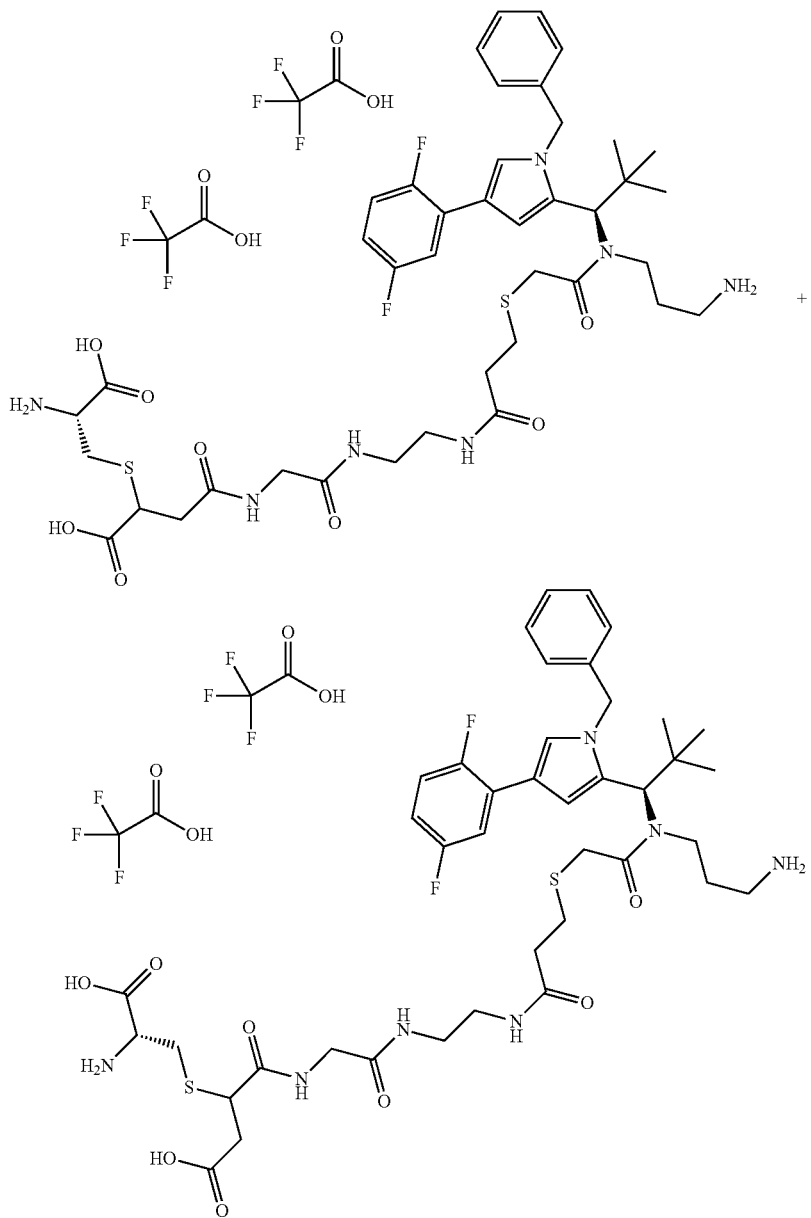

LC-MS (Method 1): $R_t$=1.03 min; MS (ESIpos): m/z=1020 (M+H)$^+$.

In the last step, 13 mg (0.01 mmol) of this intermediate were dissolved in 2 ml of 2,2,2-trifluoroethanol. 6.2 mg (0.05 mmol) of zinc chloride were added, and the reaction was stirred at 50° C. for 7 h. 13.3 mg (0.05 mmol) of ethylenediamine-N,N,N',N'-tetraacetic acid were then added, and the product was purified by preparative HPLC. Concentration of the appropriate fractions and lyophilization of the residue from acetonitrile/water gave 10.3 mg (81.4%) of the title compound as a regioisomer mixture.

LC-MS (Method 1): $R_t$=1.03 min; MS (ESIpos): m/z=875 (M+H)$^+$.

Example M7

S-(2-{[2-({(2S)-2-Amino-4-[{(1R)-1-[1-benzyl-4-(2,5-difluorophenyl)-1H-pyrrol-2-yl]-2,2-dimethylpropyl}(glycoloyl)amino]butanoyl}amino)ethyl]amino}-2-oxoethyl)-L-cysteine/trifluoroacetic acid (1:1)

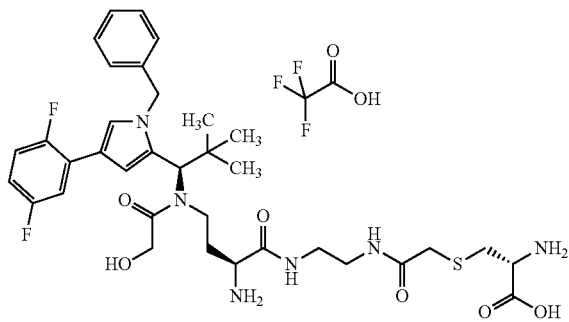 [SMILES: CC(C)(C)[C@H](c1cc(-c2cc(F)ccc2F)cn1Cc1ccccc1)N(CC[C@H](N)C(=O)NCCNC(=O)CSC[C@H](N)C(=O)O)C(=O)CO ; O=C(O)C(F)(F)F]

6 mg (8 μmol) of Intermediate F119 were taken up in 3 ml of DMF, and 1.8 mg (15 μmol) of L-cysteine were added. The reaction mixture was stirred at RT for 6 h and then allowed to stand at RT for 3 days. The reaction was then concentrated under reduced pressure, and the product was purified by preparative HPLC.

LC-MS (Method 1): $R_t$=0.81 min; MS (ESIpos): m/z=717 (M+H)$^+$.

Example M8

(3R)-6-{(11S,15R)-11-Amino-15-[1-benzyl-4-(2,5-difluorophenyl)-1H-pyrrol-2-yl]-14-glycoloyl-16,16-dimethyl-2,5,10-trioxo-3,6,9,14-tetraazaheptadec-1-yl}-5-oxothiomorpholine-3-carboxylic acid/trifluoroacetic acid (1:1)

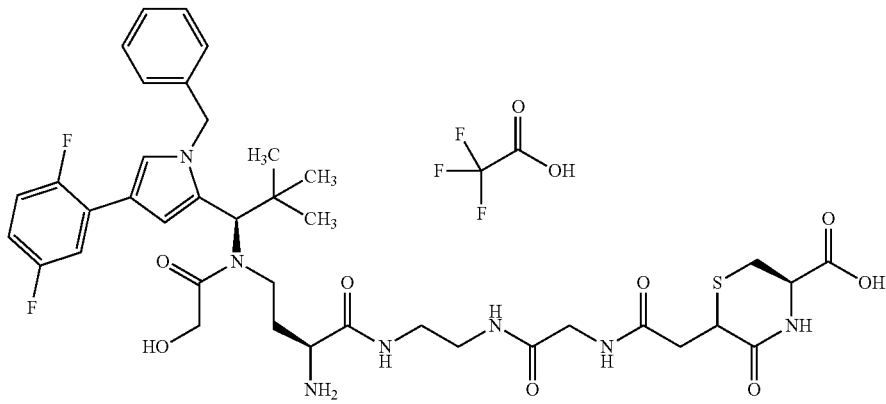

4 mg (0.004 mmol) of the compound from Example 135 were dissolved in 4 ml of THF/water, and 48 μl of a 2-molar aqueous lithium hydroxide solution were added. The reaction was stirred at RT for 1 h and then concentrated and purified by preparative HPLC. Combination, concentration and lyophilization of the appropriate fractions from acetonitrile/water gave 2.4 mg (60% of theory) of the title compound.

LC-MS (Method 1): $R_t$=0.86 min; MS (EIpos): m/z=814 [M+H]$^+$.

Example M9

N-(3-Aminopropyl)-N-{(1R)-1-[1-benzyl-4-(2,5-difluorophenyl)-1H-pyrrol-2-yl]-2,2-dimethylpropyl}-2-hydroxyacetamide

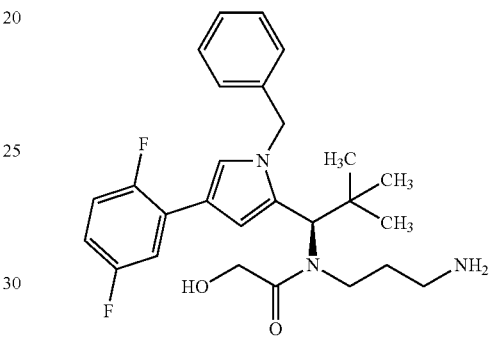

150.0 mg (0.42 mmol) of (1R)-1-[1-benzyl-4-(2,5-difluorophenyl)-1H-pyrrol-2-yl]-2,2-dimethylpropan-1-amine (Intermediate C52) were initially charged in 2.0 ml of dichloromethane, and 29.2 mg (0.49 mmol) of HOAc and 125.6 mg (0.59 mmol) of sodium triacetoxyborohydride were added and the mixture was stirred at RT for 5 min. 98.9 mg (0.49 mmol) of 3-(1,3-dioxo-1,3-dihydro-2H-isoindol-2-yl)propanal were added. The reaction mixture was stirred at RT overnight. The reaction mixture was diluted with ethyl acetate and the organic phase was washed twice with saturated sodium carbonate solution and once with saturated NaCl solution. After drying over magnesium sulphate, the solvent was evaporated under reduced pressure and the residue was purified on silica gel (mobile phase: dichloromethane/methanol 100:1). The solvents were evaporated under reduced pressure and the residue was dried under high vacuum. This gave 188.6 mg (74%) of the compound 2-[3-({(1R)-1-[1-benzyl-4-(2,5-difluorophenyl)-1H-pyrrol-2-yl]-2,2-dimethylpropyl}amino)propyl]-1H-isoindole-1,3(2H)-dione.

LC-MS (Method 1): $R_t$=1.00 min; MS (ESIpos): m/z=541 [M+H]$^+$.

171.2 mg (0.32 mmol) of 2-[3-({(1R)-1-[1-benzyl-4-(2,5-difluorophenyl)-1H-pyrrol-2-yl]-2,2-dimethylpropyl}amino)propyl]-1H-isoindole-1,3(2H)-dione were initially charged in 5.0 ml of dichloromethane, and 73.6 mg (0.73 mmol) of triethylamine were added. At 0° C., 94.9 mg (0.70 mmol) of acetoxyacetyl chloride were added, and the reaction mixture was stirred at RT overnight.

The reaction mixture was diluted with ethyl acetate and the organic phase was washed twice with saturated sodium bicarbonate solution and once with sat. NaCl solution. After drying over magnesium sulphate, the solvent was evaporated under reduced pressure and the residue was purified using Biotage Isolera (silica gel, column 10 g SNAP, flow rate 12 ml/min, ethyl acetate/cyclohexane 1:3). The solvents were evaporated under reduced pressure and the residue was dried under high vacuum. This gave 159.0 mg (77%) of the compound 2-({(1R)-1-[1-benzyl-4-(2,5-difluorophenyl)-1H-pyrrol-2-yl]-2,2-dimethylpropyl}[3-(1,3-dioxo-1,3-dihydro-2H-isoindol-2-yl)propyl]amino)-2-oxoethyl acetate.

LC-MS (Method 1): $R_t$=1.35 min; MS (ESIpos): m/z=642 [M+H]$^+$.

147.2 mg (0.23 mmol) of 2-({(1R)-1-[1-benzyl-4-(2,5-difluorophenyl)-1H-pyrrol-2-yl]-2,2-dimethylpropyl}[3-(1,3-dioxo-1,3-dihydro-2H-isoindol-2-yl)propyl]amino)-2-oxoethyl acetate were initially charged in 4.0 ml of ethanol, and 356.2 mg (4.59 mmol) of methanamine (40% in water) were added. The reaction mixture was stirred at 50° C. overnight. The solvent was evaporated under reduced pressure and the residue co-distilled three times with toluene. The residue was purified on silica gel (mobile phase: dichloromethane/methanol=10:1). The solvents were evaporated under reduced pressure and the residue was dried under high vacuum. This gave 67.4 mg (63%) of the title compound.

LC-MS (Method 1): $R_t$=0.91 min; MS (ESIpos): m/z=470 [M+H]$^+$.

Example M10

(2R,28R)-28-Amino-2-[({2-[(3-aminopropyl){(1R)-1-[1-benzyl-4-(2,5-difluorophenyl)-1H-pyrrol-2-yl]-2,2-dimethylpropyl}amino]-2-oxoethyl}sulphanyl)methyl]-25-(carboxymethyl)-4,20,24-trioxo-7,10,13,16-tetraoxa-26-thia-3,19,23-triazanonacosan-1,29-dioic acid/trifluoroacetic acid (1:2) and (1R,28R,34R)-1-amino-33-(3-aminopropyl)-34-[-benzyl-4-(2,5-difluorophenyl)-H-pyrrol-2-yl]-35,35-dimethyl-6,10,26,32-tetraoxo-14,17,20,23-tetraoxa-3,30-dithia-7,11,27,33-tetraazahexatriacontane-1,4,28-tricarboxylic acid/trifluoroacetic acid (1:2)

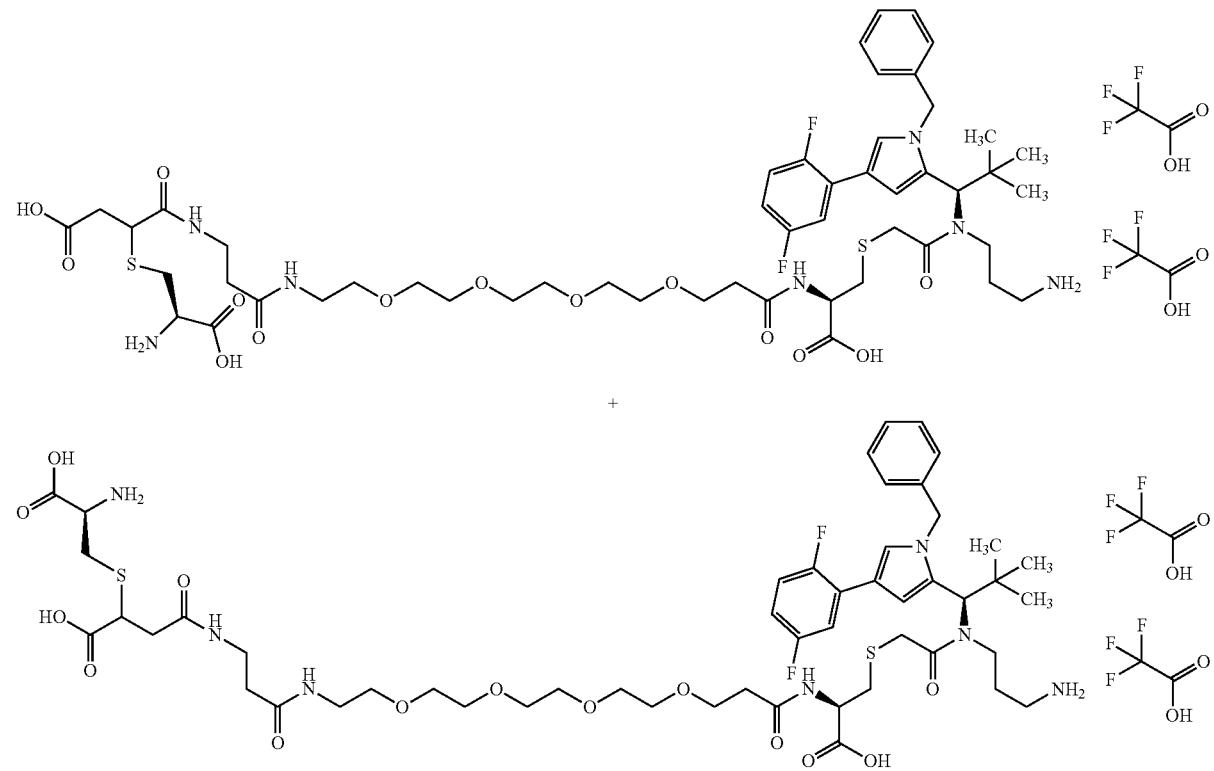

20 mg (0.018 mmol) of R-{2-[(3-aminopropyl){(1R)-1-[1-benzyl-4-(2,5-difluorophenyl)-1H-pyrrol-2-yl]-2,2-dimethylpropyl}amino]-2-oxoethyl}-N-[19-(2,5-dioxo-2,5-dihydro-1H-pyrrol-1-yl)-17-oxo-4,7,10,13-tetraoxa-16-azanonadecan-1-oyl]-L-cysteine/trifluoroacetic acid (1:1) (Intermediate F209) and 9.78 mg (0.036 mmol) of N-{[2-(trimethylsilyl)ethoxy]carbonyl}-L-cysteine were dissolved in 2 ml of DMF, and the mixture was stirred at RT for 18 h. The reaction mixture was concentrated under reduced pressure. The residue (47.7 mg) was dissolved in 3 ml of THF/water 1:1. 0.08 ml of a 2M aqueous lithium hydroxide solution were added and the reaction was stirred at RT for 1 hour. The reaction was then adjusted to a pH of ~7 using 9.26 mg (0.15 mmol) of acetic acid. The reaction mixture was purified directly by preparative RP-HPLC (column: Reprosil 125×30; 10μ, flow rate: 50 ml/min, MeCN/water; 0.1% TFA). The solvents were evaporated under reduced pressure and the residue was dried under high vacuum. This gave 15.3 mg (29% over 2 steps) of the regioisomeric protected intermediates.

LC-MS (Method 6): $R_t$=12.26 min and 12.30 min; MS (ESIpos): m/z=1254 (M+H)$^+$.

In the last step, 15.3 mg (0.01 mmol) of this intermediate were dissolved in 2 ml of 2,2,2-trifluoroethanol. 6.1 mg (0.05 mmol) of zinc chloride were added, and the reaction was stirred at 50° C. for 2 h. 13.1 mg (0.05 mmol) of ethylenediamine-N,N,N',N'-tetraacetic acid were then added, and the product was purified by preparative HPLC. Concentration of the appropriate fractions and lyophilization of the residue from acetonitrile/water gave 11.9 mg (79.5%) of the title compound as a regioisomer mixture.

LC-MS (Method 1): $R_t$=0.85 min; MS (ESIpos): m/z=1110 (M+H)$^+$.

Example M11

S-{2-[(3-Aminopropyl){(1R)-1-[1-benzyl-4-(2,5-difluorophenyl)-1H-pyrrol-2-yl]-2,2-dimethylpropyl}amino]-2-oxoethyl}-L-cysteine/trifluoroacetic acid (1:2)

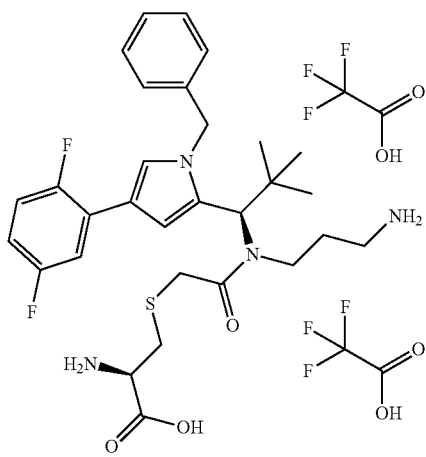

15.0 mg (0.018 mmol) of S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-L-cysteine/trifluoroacetic acid (1:1) (Intermediate C71) were dissolved in 1.0 ml of trifluoroethanol, and 7.4 mg (0.054 mmol) of zinc dichloride were added. The reaction mixture was stirred at 50° C. overnight. 15.8 mg (0.054 mmol) of ethylenediamine-N,N,N',N'-tetraacetic acid were added, the reaction mixture was stirred for 10 min and water (0.1% TFA) was then added. Purification was carried out directly by preparative RP-HPLC (column: Reprosil 125×30; 10μ, flow rate: 50 ml/min, MeCN/water, 0.1% TFA). The solvents were evaporated under reduced pressure and the residue was dried under high vacuum. This gave 11.1 mg (77%) of the title compound.

LC-MS (Method 1): $R_t$=0.83 min; MS (ESIpos): m/z=573 (M+H)$^+$.

Example M12

4-{[(1R)-2-({2-[(3-Aminopropyl){(1R)-1-[1-benzyl-4-(2,5-difluorophenyl)-1H-pyrrol-2-yl]-2,2-dimethylpropyl}amino]-2-oxoethyl}sulphanyl)-1-carboxyethyl]amino}-4-oxobutanoic acid/trifluoroacetic acid (1:1)

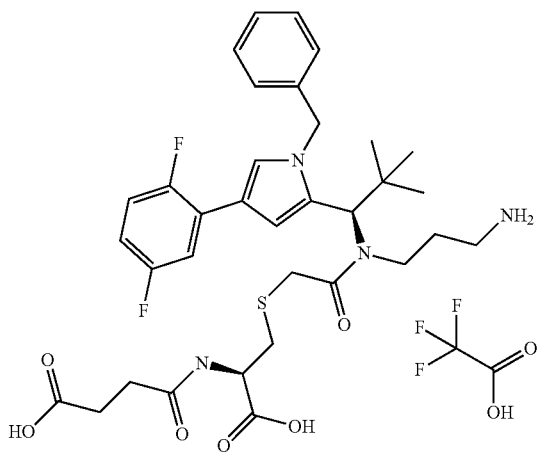 [SMILES: CC(C)(C)[C@H](c1cc(-c2cc(F)ccc2F)cn1Cc1ccccc1)N(CCCN)C(=O)CSC[C@H](NC(=O)CCC(=O)O)C(=O)O ; O=C(O)C(F)(F)F]

12.2 mg (0.014 mmol) of S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-N-(4-tert-butoxy-4-oxobutanoyl)-L-cysteine (Intermediate C77) were dissolved in 2.0 ml of trifluoroethanol, and 11.4 mg (0.084 mmol) of zinc dichloride were added. The reaction mixture was stirred at 50° C. for 3 h. 24.5 mg (0.084 mmol) of ethylenediamine-N,N,N',N'-tetraacetic acid were added, the reaction mixture was stirred for 10 min and water (0.1% TFA) was then added. Purification was carried out directly by preparative RP-HPLC (column: Reprosil 125×30; 10μ, flow rate: 50 ml/min, MeCN/water, 0.1% TFA). The solvents were evaporated under reduced pressure and the residue was dried under high vacuum. This gave 4.6 mg (42%) of the title compound.

LC-MS (Method 1): $R_t$=0.88 min; MS (ESIpos): m/z=673 (M+H)$^+$.

Example M13

4-[(2-{[2-({(2S)-2-Amino-4-[{(1R)-1-[1-benzyl-4-(2,5-difluorophenyl)-1H-pyrrol-2-yl]-2,2-dimethyl-propyl}(glycoloyl)amino]butanoyl}amino)ethyl]amino}-2-oxoethyl)amino]-2-{[(2R)-2-amino-2-carboxyethyl]sulphanyl}-4-oxobutanoic acid/trifluoroacetic acid (1:1)

Regioisomer 1, Epimer 1 (2R) or (2S)

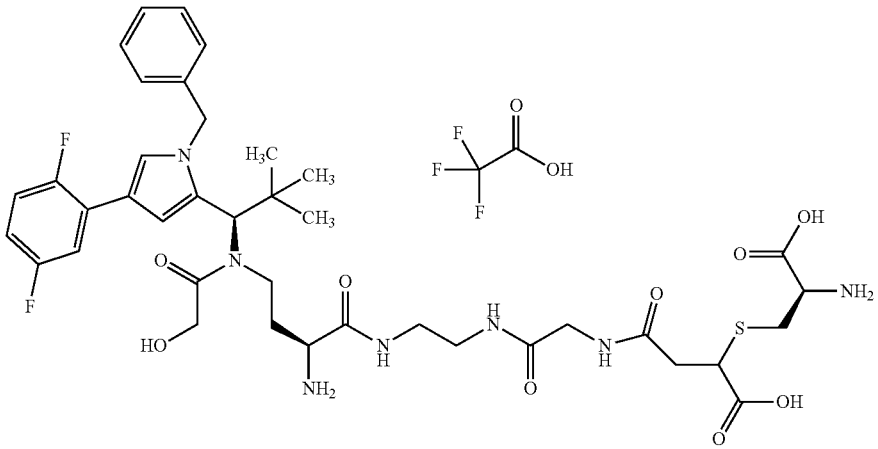 [SMILES: CC(C)(C)[C@H](c1cc(-c2cc(F)ccc2F)cn1Cc1ccccc1)N(CC[C@H](N)C(=O)NCCNC(=O)CNC(=O)CC(SC[C@H](N)C(=O)O)C(=O)O)C(=O)CO ; O=C(O)C(F)(F)F]

LC-MS (Method 5): $R_t$=2.44 min; MS (ESIpos): m/z=832 [M+H]$^+$.

First, methyl L-cysteinate hydrochloride (1:1) was converted with 1-({[2-(trimethylsilyl)ethoxy]carbonyl}oxy)pyrrolidine-2,5-dione in DMF in the presence of N,N-diisopropylethylamine into methyl N-{[2-(trimethylsilyl)ethoxy]carbonyl}-L-cysteinate.

408 mg (1.93 mmol) of commercially available 3-bromo-4-methoxy-4-oxobutanoic acid and 180 mg (0.644 mmol) of methyl N-{[2-(trimethylsilyl)ethoxy]carbonyl}-L-cysteinate were dissolved in 8 ml of DMF, and 147 mg (0.97 mmol) of 1,8-diazabicyclo[5.4.0]undec-7-ene were added. After 18 h of stirring at RT, another 136 mg (0.64 mmol) of 3-bromo-4-methoxy-4-oxobutanoic acid and 147 mg (0.97 mmol) of 1,8-diazabicyclo[5.4.0]undec-7-ene were added, and the mixture was stirred at RT for a further 12 h and then concentrated under reduced pressure. The residue was purified by preparative HPLC. Combination of the appropriate fractions and evaporation of the solvents under reduced pressure gave 151 mg (57% of theory) of 4-methoxy-3-{[(2R)-3-methoxy-3-oxo-2-({[2-(trimethylsilyl)ethoxy]carbonyl}amino)propyl]sulphanyl}-4-oxobutanoic acid.

LC-MS (Method 12): $R_t$=1.74 min; MS (ESIneg): m/z=408 (M−H)$^-$.

Of this intermediate, 145 mg were separated by supercritical fluid chromatography via chiral columns into the individual diastereomers (SFC; column: DAICEL, AD-H 5 u 250×20 mm; flow rate: 80 ml/min; method: AD-25% ETOH-80 ml; pressure: 100 bar; wavelength: 210 nM), giving 63 mg (43%) of Epimer 1 and 58 mg (40%) of Epimer 2.

Epimer 1 was characterized as follows:

LC-MS (Method 5): $R_t$=2.94 min; MS (ESIneg): m/z=408 (M−H)$^-$.

$^1$H-NMR: (400 MHz, DMSO-$d_6$): δ=7.57 (d, 1H), 4.24 (m, 1H), 4.05 (t, 2H), 3.67 (t, 1H), 3.65 (s, 3H), 3.62 (s, 3H), 3.05 (dd, 1H), 2.70-2.88 (m, 2H), 2.59 (dd, 1H), 0.93 (t, 2H), 0.02 (s, 9H).

Epimer 2 was characterized as follows:

LC-MS (Method 5): $R_t$=2.95 min; MS (ESIneg): m/z=408 (M−H)$^-$.

$^1$H-NMR: (400 MHz, DMSO-$d_6$): δ=7.58 (d, 1H), 4.16-4.23 (m, 1H), 4.05 (t, 2H), 3.67 (dd, 1H), 3.65 (s, 3H), 3.64 (s, 3H), 3.04 (dd, 1H), 2.88 (dd, 1H), 2.77 (dd, 1H), 2.61 (dd, 1H), 0.92 (t, 2H), 0.02 (s, 9H).

32.5 mg (0.079 mmol) of Epimer 1 were coupled in the presence of 30 mg (0.079 mmol) of HATU and 13.4 mg (0.132 mmol) of 4-methylmorpholine with 50 mg (0.066 mmol) of Intermediate C66, giving, after HPLC purification, 43 mg (57% of theory) of the fully protected intermediate methyl 4-{[(8S)-8-{2-[{(1R)-1-[1-benzyl-4-(2,5-difluoro-phenyl)-1H-pyrrol-2-yl]-2,2-dimethylpropyl}(glycoloyl)amino]ethyl}-2,2-dimethyl-6,9,14-trioxo-5-oxa-7,10,13-triaza-2-silapentadecan-15-yl]amino}-2-{[(2R)-3-methoxy-3-oxo-2-({[2-(trimethylsilyl)ethoxy]carbonyl}amino)propyl]sulphanyl}-4-oxobutanoate. 40 mg (0.035 mmol) of this intermediate were then stirred at RT with 0.9 ml of a 2-molar lithium hydroxide solution in 11 ml of methanol for 20 min, resulting in the cleavage of both methyl ester groups. Purification by HPLC gave 12 mg (31% of theory) of the dicarboxylic acid derivative.

LC-MS (Method 5): $R_t$=4.74 min; MS (ESIpos): m/z=1120 [M+H]$^+$.

Finally, 10 mg (0.009 mmol) of this intermediate were completely deprotected with zinc chloride in trifluoroethanol as described above. The residue was purified by preparative HPLC. Concentration of the appropriate fractions and lyophilization of the residue from acetonitrile/water gave 2.6 mg (30% of theory) of the title compound.

LC-MS (Method 5): $R_t$=2.44 min; MS (ESIpos): m/z=832 [M+H]$^+$.

Example M14

4-[(2-{[2-({(2S)-2-Amino-4-[{(1R)-1-[1-benzyl-4-(2,5-difluorophenyl)-1H-pyrrol-2-yl]-2,2-dimethylpropyl}(glycoloyl)amino]butanoyl}amino)ethyl]amino}-2-oxoethyl)amino]-2-{[(2R)-2-amino-2-carboxyethyl]sulphanyl}-4-oxobutanoic acid/trifluoroacetic acid (1:1)

Regioisomer 1, Epimer 2 (2R or 2S)

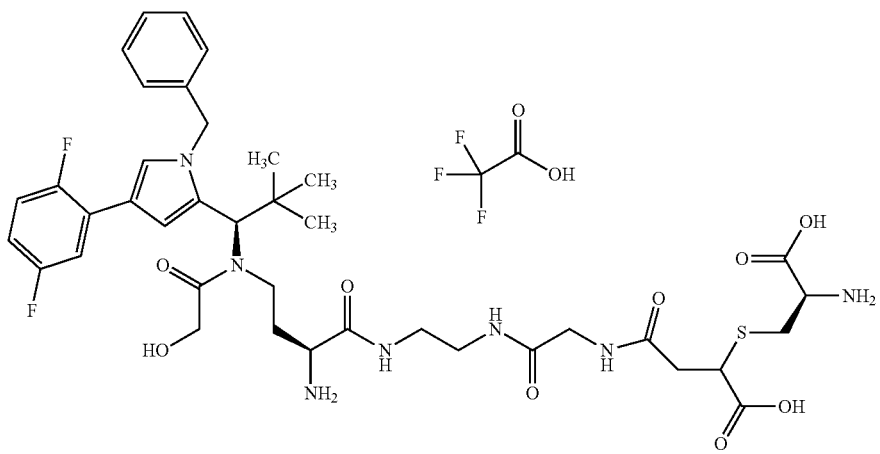 [SMILES: CC(C)(C)[C@H](c1cc(-c2cc(F)ccc2F)cn1Cc1ccccc1)N(CC[C@H](N)C(=O)NCCNC(=O)CNC(=O)CC(SC[C@H](N)C(=O)O)C(=O)O)C(=O)CO ; O=C(O)C(F)(F)F]

LC-MS (Method 5): $R_t$=2.44 min; MS (EIpos): m/z=832 [M+H]$^+$.

The intermediate Epimer 2 described in Example M13 was reacted analogously to the description in Example M13:

32.5 mg (0.079 mmol) of Epimer 2 were coupled in the presence of 30 mg (0.079 mmol) of HATU and 13.4 mg (0.132 mmol) of 4-methylmorpholine with 50 mg (0.066 mmol) of Intermediate C66, giving, after HPLC purification, 43 mg (57% of theory) of the fully protected intermediate methyl 4-{[(8S)-8-{2-[{(1R)-1-[1-benzyl-4-(2,5-difluorophenyl)-1H-pyrrol-2-yl]-2,2-dimethylpropyl}(glycoloyl)amino]ethyl}-2,2-dimethyl-6,9,14-trioxo-5-oxa-7,10,13-triaza-2-silapentadecan-15-yl]amino}-2-{[(2R)-3-methoxy-3-oxo-2-({[2-(trimethylsilyl)ethoxy]carbonyl}amino)propyl]sulphanyl}-4-oxobutanoate.

40 mg (0.035 mmol) of this intermediate were then stirred at RT with 0.9 ml of a 2-molar lithium hydroxide solution in 11 ml of methanol for 20 min, resulting in the cleavage of both methyl ester groups. Purification by HPLC gave 11 mg (28% of theory) of the dicarboxylic acid derivative.

LC-MS (Method 5): $R_t$=4.74 min; MS (ESIpos): m/z=1120 [M+H]$^+$.

Finally, 10 mg (0.009 mmol) of this intermediate were completely deprotected with zinc chloride in trifluoroethanol as described above. The residue was purified by preparative HPLC. Concentration of the appropriate fractions and lyophilization of the residue from acetonitrile/water gave 4.4 mg (52% of theory) of the title compound.

LC-MS (Method 5): $R_t$=2.44 min; MS (ESIpos): m/z=832 [M+H]$^+$.

Example M15

4-[(2-{[2-({(2S)-2-Amino-4-[{(1R)-1-[1-benzyl-4-(2,5-difluorophenyl)-1H-pyrrol-2-yl]-2,2-dimethylpropyl}(glycoloyl)amino]butanoyl}amino)ethyl]amino}-2-oxoethyl)amino]-3-{[(2R)-2-amino-2-carboxyethyl]sulphanyl}-4-oxobutanoic acid/trifluoroacetic acid (1:1)

Regioisomer 2, Epimer 1 (3R or 3S)

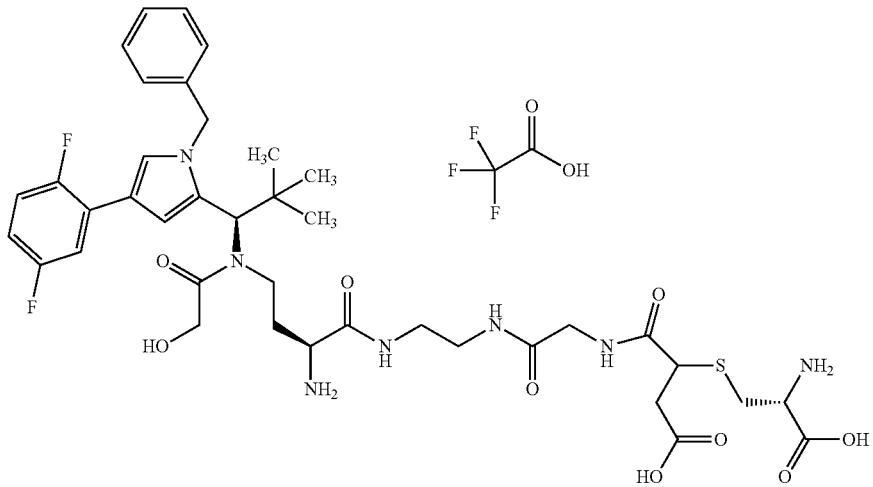 [SMILES: CC(C)(C)[C@H](c1cc(-c2cc(F)ccc2F)cn1Cc1ccccc1)N(CC[C@H](N)C(=O)NCCNC(=O)CNC(=O)C(CC(=O)O)SC[C@H](N)C(=O)O)C(=O)CO ; O=C(O)C(F)(F)F]

LC-MS (Method 5): $R_t$=2.45 min; MS (EIpos): m/z=832 [M+H]$^+$.

742.8 mg (3.3 mmol) of commercially available 2-bromo-4-ethoxy-4-oxobutanoic acid and 802 mg (2.87 mmol) of methyl N-{[2-(trimethylsilyl)ethoxy]carbonyl}-L-cysteinate were dissolved in 32 ml of DMF, and 655.4 mg (4.31 mmol) of 1,8-diazabicyclo[5.4.0]undec-7-ene were added. After 20 h of stirring at RT, the reaction was concentrated under reduced pressure and the residue was purified by preparative HPLC. Combination of the appropriate fractions and evaporation of the solvents under reduced pressure gave 521 mg (43% of theory) of 4-ethoxy-2-{[(2R)-3-methoxy-3-oxo-2-({[2-(trimethylsilyl)ethoxy]carbonyl}amino)propyl]sulphanyl}-4-oxobutanoic acid.

LC-MS (Method 5): $R_t$=3.13 min; MS (ESIpos): m/z=424 (M+H)$^+$.

Of this intermediate, 510 mg were separated by supercritical fluid chromatography via chiral columns into the individual diastereomers (SFC; column: DAICEL, AD-H 5 u 250×20 mm; flow rate: 80 ml/min; method: AD-10% ETOH-80 ml; pressure: 100 bar; wavelength: 210 nM), giving 100 mg (20%) of Epimer 1 and 141 mg (28%) of Epimer 2.

Epimer 1 was characterized as follows:
LC-MS (Method 1): $R_t$=0.99 min; MS (ESIneg): m/z=422 (M−H)$^-$.

$^1$H-NMR: (400 MHz, DMSO-d$_6$): δ=7.60 (d, 1H), 4.18-4.26 (m, 1H), 4.01-4.08 (m, 4H), 3.63 (s, 3H), 3.59 (dd, 1H), 3.04 (dd, 1H), 2.92 (dd, 1H), 2.80 (dd, 1H), 2.63 (dd, 1H), 1.17 (t, 3H), 0.92 (t, 2H), 0.02 (s, 9H).

Epimer 2 was characterized as follows:
LC-MS (Method 5): $R_t$=2.95 min; MS (ESIneg): m/z=408 (M−H)$^-$.

$^1$H-NMR: (400 MHz, DMSO-d$_6$): δ=7.56 (d, 1H), 4.21-4.29 (m, 1H), 4.01-4.1 (m, 4H), 3.64 (s, 3H), 3.58 (dd, 1H), 3.08 (dd, 1H), 2.85 (dd, 1H), 2.78 (dd, 1H), 2.60 (dd, 1H), 1.17 (t, 3H), 0.93 (t, 2H), 0.02 (s, 9H).

33.6 mg (0.079 mmol) of Epimer 1 were coupled in the presence of 30 mg (0.079 mmol) of HATU and 13.4 mg (0.132 mmol) of 4-methylmorpholine with 50 mg (0.066 mmol) of Intermediate C66, giving, after HPLC purification, 51 mg (63% of theory) of the fully protected intermediate ethyl 4-{[(8S)-8-{2-[{(1R)-1-[1-benzyl-4-(2,5-difluorophenyl)-1H-pyrrol-2-yl]-2,2-dimethylpropyl}(glycoloyl)amino]ethyl}-2,2-dimethyl-6,9,14-trioxo-5-oxa-7,10,13-triaza-2-silapentadecan-15-yl]amino}-3-{[(2R)-3-methoxy-3-oxo-2-({[2-(trimethylsilyl)ethoxy]carbonyl}amino)propyl]sulphanyl}-4-oxobutanoate.

49 mg (0.042 mmol) of this intermediate were then stirred at RT with 0.5 ml of a 2-molar lithium hydroxide solution in 12 ml of THF/water 1:1 for 30 min, resulting in the cleavage of both methyl ester groups. Acidification and purification by HPLC gave 11 mg (24% of theory) of the dicarboxylic acid derivative.

LC-MS (Method 5): $R_t$=4.68 min; MS (ESIpos): m/z=1120 [M+H]$^+$.

Finally, 11 mg (0.01 mmol) of this intermediate were completely deprotected with zinc chloride in trifluoroethanol as described above. The residue was purified by preparative HPLC. Concentration of the appropriate fractions and lyophilization of the residue from acetonitrile/water gave 3.7 mg (39% of theory) of the title compound.

LC-MS (Method 5): $R_t$=2.45 min; MS (ESIpos): m/z=832 [M+H]$^+$.

Example M16

4-[(2-{[2-({(2S)-2-Amino-4-[{(1R)-1-[1-benzyl-4-(2,5-difluorophenyl)-1H-pyrrol-2-yl]-2,2-dimethylpropyl}(glycoloyl)amino]butanoyl}amino)ethyl]amino}-2-oxoethyl)amino]-3-{[(2R)-2-amino-2-carboxyethyl]sulphanyl}-4-oxobutanoic acid/trifluoroacetic acid (1:1)

Regioisomer 2, Epimer 2 (3R or 3S)

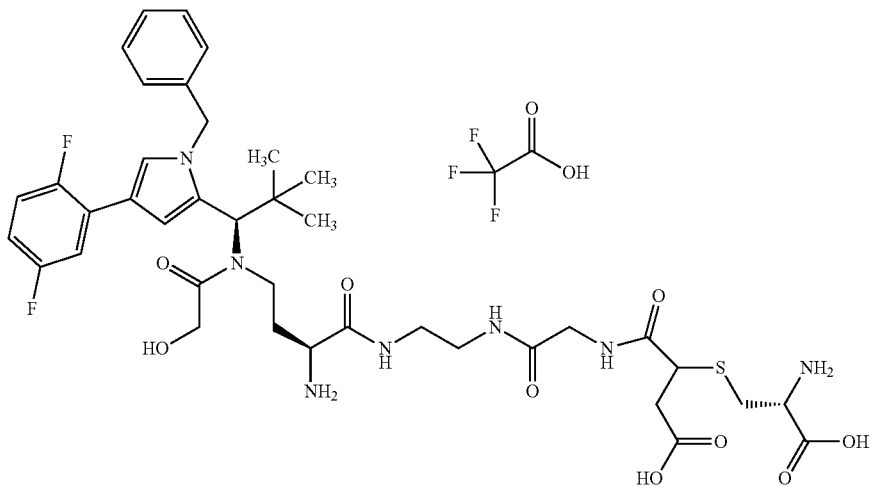 [SMILES: CC(C)(C)[C@H](c1cc(-c2cc(F)ccc2F)cn1Cc1ccccc1)N(CC[C@H](N)C(=O)NCCNC(=O)CNC(=O)C(CC(=O)O)SC[C@H](N)C(=O)O)C(=O)CO ; O=C(O)C(F)(F)F]

LC-MS (Method 5): $R_t$=2.44 min; MS (EIpos): m/z=832 [M+H]$^+$.

The intermediate Epimer 2 described in Example M15 was reacted analogously to the description in Example M15:

33.6 mg (0.079 mmol) of Epimer 2 were coupled in the presence of 30 mg (0.079 mmol) of HATU and 13.4 mg (0.132 mmol) of 4-methylmorpholine with 50 mg (0.066 mmol) of Intermediate C66, giving, after HPLC purification, 51 mg (63% of theory) of the fully protected intermediate ethyl 4-{[(8S)-8-{2-[{(1R)-1-[1-benzyl-4-(2,5-difluorophenyl)-1H-pyrrol-2-yl]-2,2-dimethylpropyl}(glycoloyl)amino]ethyl}-2,2-dimethyl-6,9,14-trioxo-5-oxa-7,10,13-triaza-2-silapentadecan-15-yl]amino}-3-{[(2R)-3-methoxy-3-oxo-2-({[2-(trimethylsilyl)ethoxy]carbonyl}amino)propyl]sulphanyl}-4-oxobutanoate.

49 mg (0.042 mmol) of this intermediate were then stirred at RT with 0.5 ml of a 2-molar lithium hydroxide solution in 12 ml of THF/water 1:1 for 30 min, resulting in the cleavage of both methyl ester groups. Acidification and purification by HPLC gave 13.4 mg (28% of theory) of the dicarboxylic acid derivative.

LC-MS (Method 5): $R_t$=4.66 min; MS (ESIpos): m/z=1120 [M+H]$^+$.

Finally, 13.4 mg (0.012 mmol) of this intermediate were completely deprotected with zinc chloride in trifluoroethanol as described above. The residue was purified by preparative HPLC. Concentration of the appropriate fractions and lyophilization of the residue from acetonitrile/water gave 7.5 mg (66% of theory) of the title compound.

LC-MS (Method 5): $R_t$=2.44 min; MS (ESIpos): m/z=832 [M+H]$^+$.

Example M17

(2S)-2-Amino-4-[{(1R)-1-[1-benzyl-4-(2,5-difluorophenyl)-1H-pyrrol-2-yl]-2,2-dimethylpropyl}(glycoloyl)amino]butanoic acid hydrochloride (1:1)

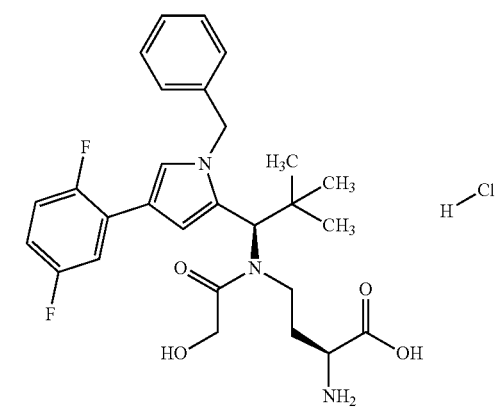 [SMILES: CC(C)(C)[C@H](c1cc(-c2cc(F)ccc2F)cn1Cc1ccccc1)N(CC[C@H](N)C(=O)O)C(=O)CO ; Cl]

150 mg (0.2 mmol) of Intermediate C53 were dissolved in 15 ml of DMF, and 2.29 g (20.39 mmol) of DABCO. The reaction was treated in an ultrasonic bath for 30 min. By addition of 1.17 ml of acetic acid, the reaction was then adjusted to pH 3-4, and the mixture was concentrated under reduced pressure. The residue was purified by preparative HPLC and the appropriate fractions were concentrated at RT under reduced pressure. The residue was taken up in acetonitrile/water (1:1), 5 ml of a 4N hydrochloric acid were added and the mixture was then lyophilized. This gave 81 mg (68% of theory) of the title compound.

LC-MS (Method 5): $R_t$=2.69 min; MS (EIpos): m/z=514 [M+H]$^+$.

Example M18

N-[2-({(2S)-2-Amino-4-[{(1R)-1-[1-benzyl-4-(2,5-difluorophenyl)-1H-pyrrol-2-yl]-2,2-dimethylpropyl}(glycoloyl)amino]butanoyl}amino)ethyl]-L-glutamine/trifluoroacetic acid (1:1)

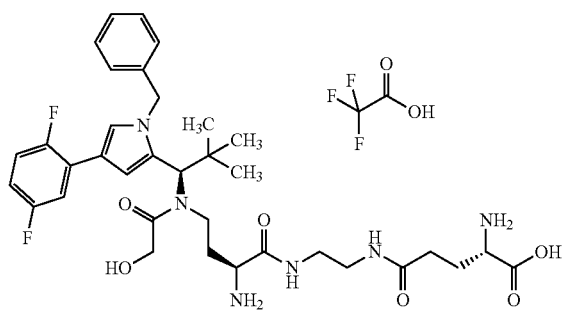 [SMILES: CC(C)(C)[C@H](c1cc(-c2cc(F)ccc2F)cn1Cc1ccccc1)N(CC[C@H](N)C(=O)NCCNC(=O)CC[C@H](N)C(=O)O)C(=O)CO ; O=C(O)C(F)(F)F]

First, trifluoroacetic acid/benzyl N-(2-aminoethyl)-N$^2$-[(benzyloxy)carbonyl]-L-glutaminate (1:1) was prepared using classical methods of peptide chemistry. In the presence of HATU, this intermediate was then coupled with Intermediate C58. Subsequently, first the benzyloxycarbonyl protective group and the benzyl ester were removed by hydrogenolytic cleavage, and then the 2-(trimethylsilyl)ethoxycarbonyl protective group was removed using zinc chloride.

LC-MS (Method 6): $R_t$=1.91 min; MS (EIpos): m/z=685 [M+H]$^+$.

Example M19

N$^6$—(N-{(2S)-2-Amino-4-[{(1R)-1-[1-benzyl-4-(2,5-difluorophenyl)-1H-pyrrol-2-yl]-2,2-dimethylpropyl}(glycoloyl)amino]butanoyl}-beta-alanyl)-L-lysine/trifluoroacetic acid (1:1)

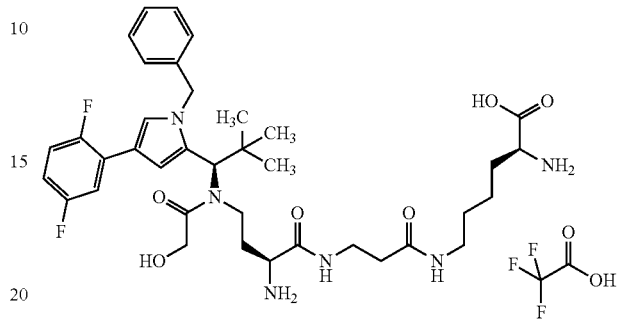

Initially, trifluoroacetic acid/2-(trimethylsilyl)ethyl-N2-[(benzyloxy)carbonyl]-L-lysinate (1:1) was prepared using classical protective group operations known in peptide chemistry. In the presence of HATU, this intermediate was then coupled with Intermediate C61. Subsequently, first the 2-(trimethylsilyl)ethoxycarbonyl protective group and the 2-(trimethylsilyl)ethyl ester were cleaved using zinc chloride. Finally, the title compound was obtained by hydrogenolytical cleavage of the benzyloxycarbonyl protective group and purification by preparative HPLC.

HPLC (Method 11): $R_t$=1.65 min;

Example M20

(1R,4R,27R,33R)-1-Amino-32-(3-aminopropyl)-33-[1-benzyl-4-(2,5-difluorophenyl)-1H-pyrrol-2-yl]-34,34-dimethyl-6,9,25,31-tetraoxo-13,16,19,22-tetraoxa-3,29-dithia-7,10,26,32-tetraazapentatriacontane-1,4,27-tricarboxylic acid/trifluoroacetic acid (1:2)

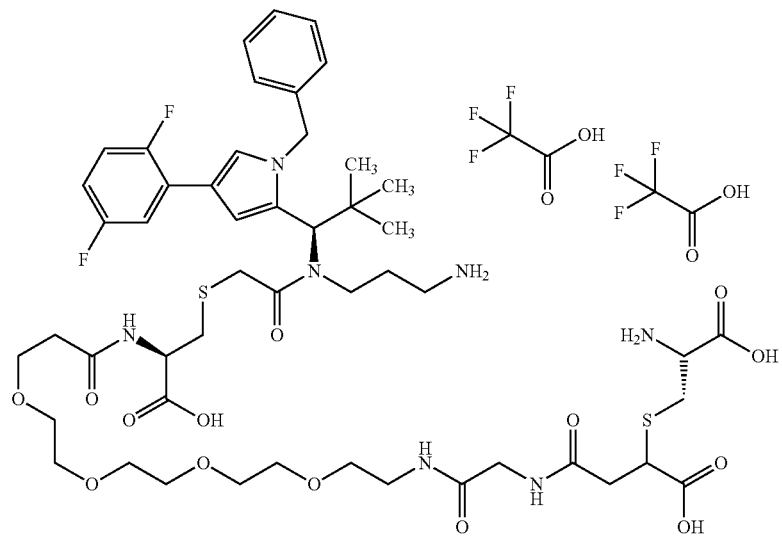

First, methyl L-cysteinate hydrochloride (1:1) was converted with 1-({[2-(trimethylsilyl)ethoxy]carbonyl}oxy)pyrrolidine-2,5-dione in DMF in the presence of N,N-diisopropylethylamine into methyl N-{[2-(trimethylsilyl)ethoxy]carbonyl}-L-cysteinate.

408 mg (1.93 mmol) of commercially available 3-bromo-4-methoxy-4-oxobutanoic acid and 180 mg (0.644 mmol) of methyl N-{[2-(trimethylsilyl)ethoxy]carbonyl}-L-cysteinate were dissolved in 8 ml of DMF, and 147 mg (0.97 mmol) of 1,8-diazabicyclo[5.4.0]undec-7-ene were added. After 18 h of stirring at RT, another 136 mg (0.64 mmol) of 3-bromo-4-methoxy-4-oxobutanoic acid and 147 mg (0.97 mmol) of 1,8-diazabicyclo[5.4.0]undec-7-ene were added, and the mixture was stirred at RT for a further 12 h and then concentrated under reduced pressure. The residue was purified by preparative HPLC. Combination of the appropriate fractions and evaporation of the solvents under reduced pressure gave 151 mg (57% of theory) of 4-methoxy-3-{[(2R)-3-methoxy-3-oxo-2-({[2-(trimethylsilyl)ethoxy]carbonyl}amino)propyl]sulphanyl}-4-oxobutanoic acid.

LC-MS (Method 12): $R_t$=1.74 min; MS (ESIneg): m/z=408 (M−H)⁻.

3.66 mg (8.93 µmol) of 4-methoxy-3-{[(2R)-3-methoxy-3-oxo-2-({[2-(trimethylsilyl)ethoxy]carbonyl}amino)propyl]sulphanyl}-4-oxobutanoic acid were coupled in the presence of 3.66 mg (8.93 µmol) of HATU and 1.6 µl (15 µmol) of 4-methylmorpholine with 13.0 mg (7.44 µmol) of S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-N-[15-(glycylamino)-4,7,10,13-tetraoxapentadecan-1-oyl]-L-cysteine/trifluoroacetic acid (1:1) (Intermediate C80), giving, after HPLC purification, 3.9 mg (37% of theory) of the fully protected intermediate S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-N-[15-({N-[(8R,11R)-8,11-bis(methoxycarbonyl)-2,2-dimethyl-6,13-dioxo-5-oxa-10-thia-7-aza-2-silatridecan-13-yl]glycyl}amino)-4,7,10,13-tetraoxapentadecan-1-oyl]-L-cysteine. 3.90 mg (2.76 µmol) of this intermediate were then stirred at RT with 35 µl of a 2-molar lithium hydroxide solution in 1.0 ml of THF/water 3:1 for 15 min, resulting in the cleavage of both methyl ester groups. Purification by HPLC gave 3.60 mg (94% of theory) of the dicarboxylic acid derivative.

LC-MS (Method 5): $R_t$=4.83 min; MS (ESIpos): m/z=1385 [M+H]⁺.

Finally, 3.6 mg (2.6 µmol) of this intermediate were completely deprotected with zinc chloride in trifluoroethanol as described above. The residue was purified by preparative HPLC. Concentration of the appropriate fractions and lyophilization of the residue from acetonitrile/water gave 1.92 mg (55% of theory) of the title compound.

LC-MS (Method 5): $R_t$=2.72 min; MS (ESIneg): m/z=1094 [M−H]⁻.

Example M21

(2R,24S,27R)-27-Amino-2-[({2-[(3-aminopropyl){(1R)-1-[1-benzyl-4-(2,5-difluorophenyl)-1H-pyrrol-2-yl]-2,2-dimethylpropyl}amino]-2-oxoethyl}sulphanyl)methyl]-24-(carboxymethyl)-4,20,23-trioxo-7,10,13,16-tetraoxa-25-thia-3,19,22-triazaoctacosane-1,28-dioic acid trifluoroacetic acid (1:2)

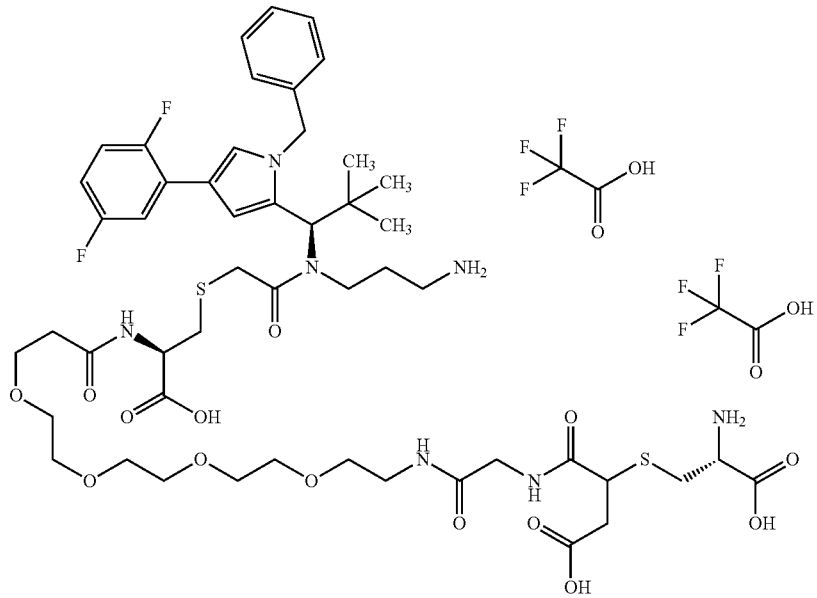

742.8 mg (3.3 mmol) of commercially available 2-bromo-4-ethoxy-4-oxobutanoic acid and 802 mg (2.87 mmol) of methyl N-{[2-(trimethylsilyl)ethoxy]carbonyl}-L-cysteinate were dissolved in 32 ml of DMF, and 655.4 mg (4.31 mmol) of 1,8-diazabicyclo[5.4.0]undec-7-ene were added. After 20 h of stirring at RT, the reaction was concentrated under reduced pressure and the residue was purified by preparative HPLC. Combination of the appropriate fractions and evaporation of the solvents under reduced pressure gave 521 mg (43% of theory) of 4-ethoxy-2-{[(2R)-3-methoxy-3-oxo-2-({[2-(trimethylsilyl)ethoxy]carbonyl}amino)propyl]sulphanyl}-4-oxobutanoic acid.

LC-MS (Method 5): $R_t$=3.13 min; MS (ESIpos): m/z=424 (M+H)⁺.

4.36 mg (10.3 µmol) of 4-ethoxy-2-{[(2R)-3-methoxy-3-oxo-2-({[2-(trimethylsilyl)ethoxy]carbonyl}amino)propyl]sulphanyl}-4-oxobutanoic acid were coupled in the presence of 3.92 mg (10.3 µmol) of HATU and 1.9 µl (17 µmol) of 4-methylmorpholine with 15.0 mg (8.59 µmol) of S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-N-[15-(glycylamino)-4,7,10,13-tetraoxapentadecan-1-oyl]-L-cysteine/trifluoroacetic acid (1:1) (Intermediate C80), giving, after HPLC purification, 3.6 mg (26% of theory) of the fully protected intermediate S-(11-{(1R)-1-[1-benzyl-4-(2,5-difluorphenyl)-1H-pyrrol-2-yl]-2,2-dimethylpropyl}-2,2-dimethyl-6,12-dioxo-5-oxa-7,11-diaza-2-silatridecan-13-yl)-N-[15-({N-[(8R,11S)-11-(2-ethoxy-2-oxoethyl)-8-(methoxycarbonyl)-2,2-dimethyl-6,12-dioxo-5-oxa-10-thia-7-aza-2-siladodecan-12-yl]glycyl}amino)-4,7,10,13-tetraoxapentadecan-1-oyl]-L-cysteine. 6.20 mg (2.82 µmol) of this intermediate were then stirred at RT with 35 µl of a 2-molar lithium hydroxide solution in 1.0 ml of THF/water 1:1 for 15 min, resulting in the cleavage of both ester groups. Acidification and purification by HPLC gave 3.60 mg (92% of theory) of the dicarboxylic acid derivative.

LC-MS (Method 5): $R_t$=4.71 min; MS (ESIpos): m/z=1385 [M+H]$^+$.

Finally, 3.60 mg (1.69 µmol) of this intermediate were completely deprotected with zinc chloride in trifluoroethanol as described above. The residue was purified by preparative HPLC. Concentration of the appropriate fractions and lyophilization of the residue from acetonitrile/water gave 0.88 mg (39% of theory) of the title compound.

LC-MS (Method 5): $R_t$=2.72 min; MS (ESIneg): m/z=1094 [M−H]$^−$.

Example M22

(2R,27R)-27-Amino-2-[({2-[(3-aminopropyl){(1R)-1-[1-benzyl-4-(2,5-difluorophenyl)-1H-pyrrol-2-yl]-2,2-dimethylpropyl}amino]-2-oxoethyl}sulphanyl)methyl]-24-(carboxymethyl)-4,20,23-trioxo-7,10,13,16-tetraoxa-25-thia-3,19,22-triazaoctacosane-1,28-dioic acid/trifluoroacetic acid (1:2) and (1R,27R,33R)-1-amino-32-(3-aminopropyl)-33-[-benzyl-4-(2,5-difluorophenyl)-H-pyrrol-2-yl]-34,34-dimethyl-6,9,25,31-tetraoxo-13,16,19,22-tetraoxa-3,29-dithia-7,10,26,32-tetraazapentatriacontane-1,4,27-tricarboxylic acid/trifluoroacetic acid (1:2)

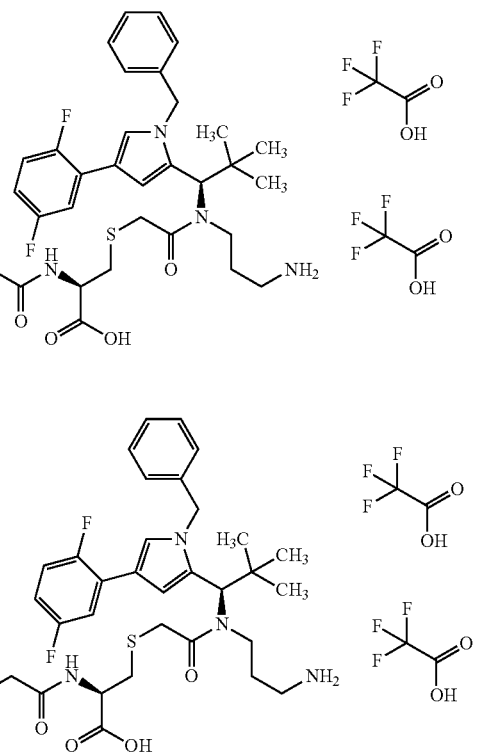

16.5 mg (0.015 mmol) of S-{2-[(3-aminopropyl){(1R)-1-[1-benzyl-4-(2,5-difluorophenyl)-1H-pyrrol-2-yl]-2,2-dimethylpropyl}amino]-2-oxoethyl}-N-[1-(2,5-dioxo-2,5-dihydro-H-pyrrol-1-yl)-2,18-dioxo-6,9,12,15-tetraoxa-3-azaoctadecan-18-yl]-L-cysteine/trifluoroacetic acid (1:1) (intermediate F257) and 8.18 mg (0.031 mmol) of N-{[2-(trimethylsilyl)ethoxy]carbonyl}-L-cysteine were dissolved in 2 ml of DMF, and the mixture was stirred at RT for 18 h. The reaction mixture was concentrated under reduced pressure. The residue (28.9 mg) was dissolved in 3 ml of THF/water 1:1. 0.046 ml of a 2M aqueous lithium hydroxide solution was added and the mixture was stirred at RT for 3 hours. The mixture was then adjusted to a pH of ~7 using 5.2 µl (0.092 mmol) of acetic acid. The reaction mixture was purified directly by prep. RP-HPLC (column: Reprosil 125×30; 10µ, flow rate: 50 ml/min, MeCN/water; 0.1% TFA). The solvents were evaporated under reduced pressure and the residue was dried under high vacuum. This gave 12.1 mg (58% over 2 steps) of the regioisomeric protected intermediates.

LC-MS (Method 12): $R_t$=1.82 min; MS (ESIpos): m/z=1240 (M+H)$^+$.

In the last step, 12.1 mg (0.009 mmol) of this intermediate were dissolved in 2 ml of 2,2,2-trifluoroethanol. 7.3 mg (0.054 mmol) of zinc chloride were added, and the mixture was stirred at 50° C. for 2 h. 15.7 mg (0.054 mmol) of ethylenediamine-N,N,N',N'-tetraacetic acid were then added, and the solvent was purified by preparative HPLC. Concentration of the appropriate fractions and lyophilization of the residue from acetonitrile/water gave 6.4 mg (59%) of the title compound as a regioisomer mixture.

LC-MS (Method 1): $R_t$=0.86 min; MS (ESIpos): m/z=1096 (M+H)$^+$.

Example M23

N-{(2S)-2-Amino-4-[{(1R)-1-[1-benzyl-4-(2,5-difluorophenyl)-1H-pyrrol-2-yl]-2,2-dimethyl propyl}(glycoloyl)amino]butanoyl}-beta-alanyl-L-glutamic acid/trifluoroacetic acid (1:1)

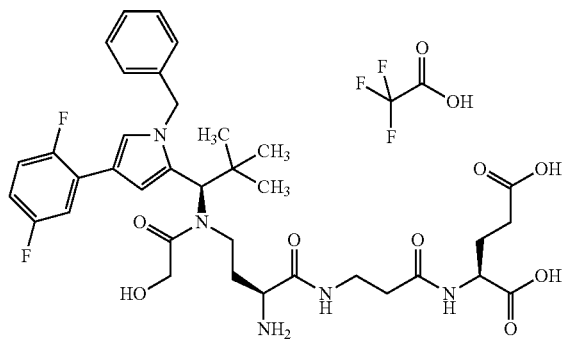 [SMILES: CC(C)(C)[C@H](c1cc(-c2cc(F)ccc2F)cn1Cc1ccccc1)N(CC[C@H](N)C(=O)NCCC(=O)N[C@@H](CCC(=O)O)C(=O)O)C(=O)CO ; O=C(O)C(F)(F)F]

First, di-tert-butyl L-glutamate hydrochloride (1:1) was coupled with intermediate C61 in the presence of HATU and N,N-diisopropylethylamine. The protected intermediate was then taken up in trifluoroethanol and, by stirring at 50° C. in the presence of zinc chloride overnight, deprotected completely. Work-up was carried out after addition of EDTA by purification by preparative HPLC.

LC-MS (Method 12): $R_t$=1.45 min; MS (ESIpos): m/z=714 [M+H]$^+$.

Example M24

N-{(2S)-2-Amino-4-[{(1R)-1-[1-benzyl-4-(2,5-difluorophenyl)-1H-pyrrol-2-yl]-2,2-dimethylpropyl}(glycoloyl)amino]butanoyl}-beta-alanyl-D-glutamic acid/trifluoroacetic acid (1:1)

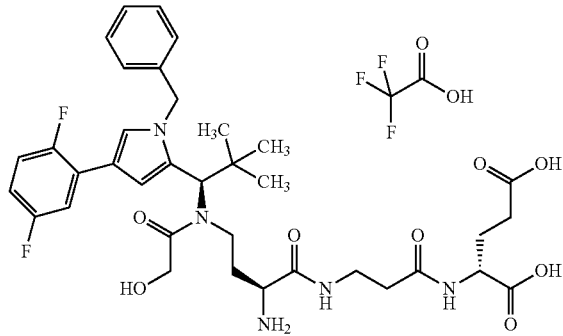 [SMILES: CC(C)(C)[C@H](c1cc(-c2cc(F)ccc2F)cn1Cc1ccccc1)N(CC[C@H](N)C(=O)NCCC(=O)N[C@H](CCC(=O)O)C(=O)O)C(=O)CO ; O=C(O)C(F)(F)F]

First, di-tert-butyl D-glutamate hydrochloride (1:1) was coupled with intermediate C61 in the presence of HATU and N,N-diisopropylethylamine. The protected intermediate was then taken up in trifluoroethanol and, by stirring at 50° C. in the presence of zinc chloride, deprotected completely. Work-up was carried out after addition of EDTA by purification by preparative HPLC.

LC-MS (Method 12): $R_t$=1.41 min; MS (ESIpos): m/z=714 [M+H]$^+$.

Example M25

N-{(2S)-2-Amino-4-[{(1R)-1-[1-benzyl-4-(2,5-difluorophenyl)-1H-pyrrol-2-yl]-2,2-dimethyl propyl}(glycoloyl)amino]butanoyl}-L-glutamic acid/trifluoroacetic acid (1:1)

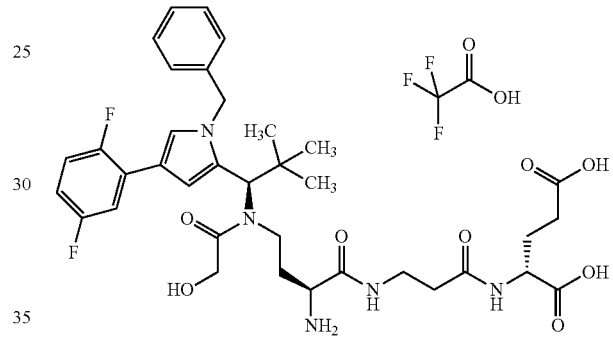

First, di-tert-butyl L-glutamate hydrochloride (1:1) was coupled with intermediate C61 in the presence of HATU and N,N-diisopropylethylamine. In the next step, the Z protective group was removed by hydrogenation over 10% palladium on activated carbon in methanol at RT under standard hydrogen pressure for 45 minutes. The partially protected intermediate was then taken up in trifluoroethanol and deprotected completely by stirring at 50° C. in the presence of zinc chloride for 7 hours. Work-up was carried out after addition of EDTA by purification by preparative HPLC.

LC-MS (Method 12): $R_t$=1.44 min; MS (ESIpos): m/z=643 [M+H]$^+$.

Example M26

4-[(2-{[2-({(2S)-2-Amino-4-[{(1R)-1-[1-benzyl-4-(2,5-difluorophenyl)-1H-pyrrol-2-yl]-2,2-dimethyl-propyl}(glycoloyl)amino]butanoyl}amino)ethyl]amino]-2-oxoethyl)amino]-2-{[(2R)-2-amino-2-carboxyethyl]sulphanyl}-4-oxobutanoic acid/ trifluoroacetic acid (1:1)

Regioisomer 1, Mixture of Epimers

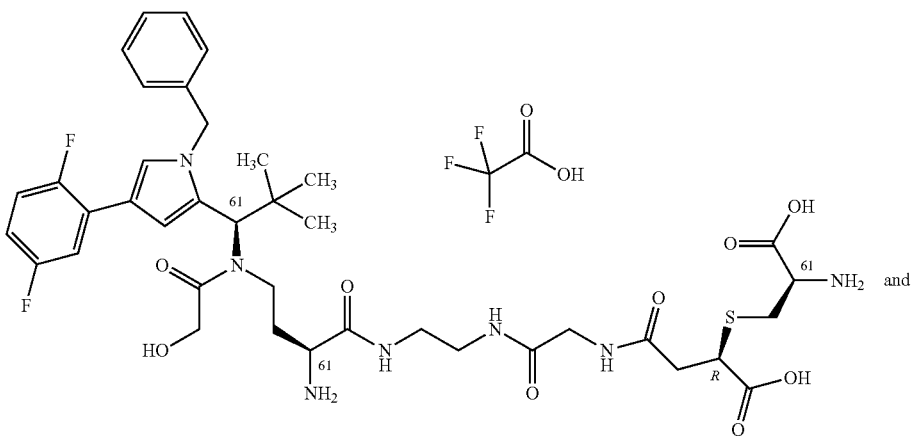

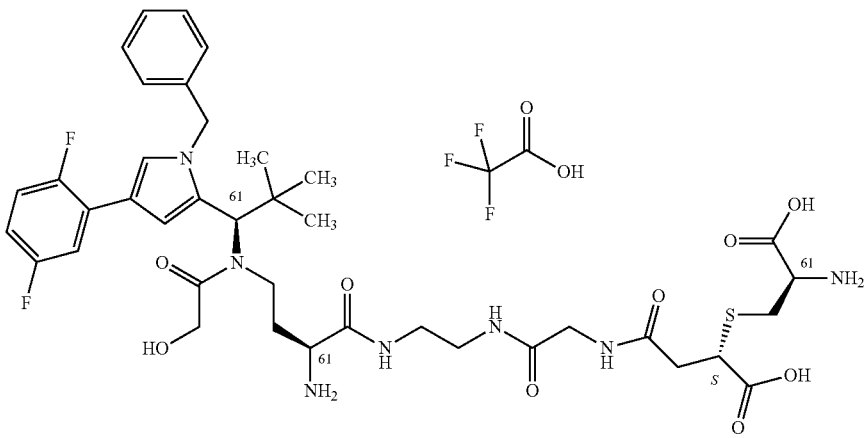

This example describes the epimer mixture of the compounds of Example 13 and Example 14. The synthesis was carried out analogously to Example 13, where the separation of the two epimers by supercritical fluid chromatography was dispensed with and the title compound was prepared as a mixture of epimers.

LC-MS (Method 5): $R_t$=2.43 min; MS (ESIpos): m/z=832 [M+H]$^+$.

Example M27

4-[(2-{[2-({(2S)-2-Amino-4-[{(1R)-1-[1-benzyl-4-(2,5-difluorophenyl)-1H-pyrrol-2-yl]-2,2-dimethyl-propyl}(glycoloyl)amino]butanoyl}amino)ethyl]amino}-2-oxoethyl)amino]-3-{[(2R)-2-amino-2-carboxyethyl]sulphanyl}-4-oxobutanoic acid/trifluoroacetic acid (1:1)

Regioisomer 2, Mixture of Epimers

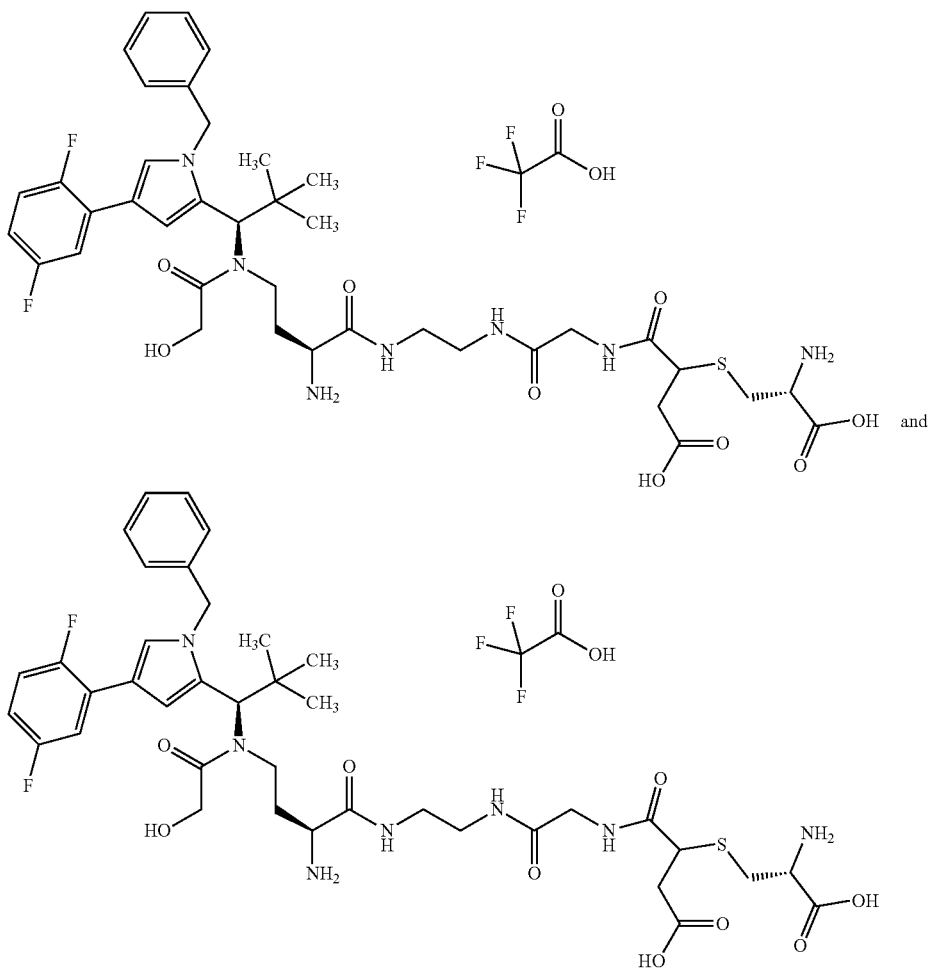

This example describes the epimer mixture of the compounds of Example 15 and Example 16. The synthesis was carried out analogously to Example 15, where the separation of the two epimers by supercritical fluid chromatography was dispensed with and the title compound was prepared as a mixture of epimers.

LC-MS (Method 5): $R_t$=2.45 min; MS (EIpos): m/z=832 [M+H]$^+$.

Working Examples ADCs

The ADCs shown in the structural formulae of the Working examples, which were coupled to the cystein side chains of the antibodies via maleimide radicals, are, depending on the linker and the coupling procedure, mainly present in the ring-opened or ring-closed forms shown in each case. However, the preparation may comprise a small proportion of the respective other form.

Example 194m1

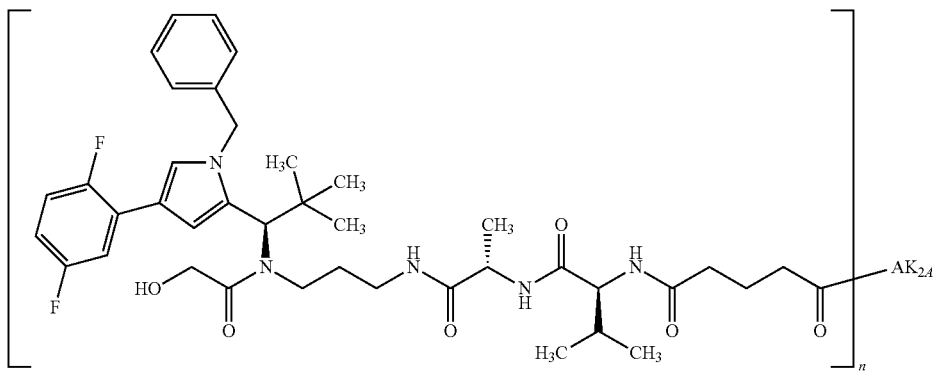

Here, 5 mg of anti-CD123 $AK_{1A}$ (TPP-5969) in 500 µl of PBS (c=10 mg/ml) were used for coupling with Intermediate F194. First, 5 eq of Intermediate F194 dissolved in 100 µl of DMSO were added, and after 1 h of stirring at RT the same amount was added again and the reaction was stirred at RT for a further hour. The reaction was subsequently purified on a Sephadex column, then concentrated by ultracentrifugation and rediluted with PBS.

Protein concentration: 1.28 mg/ml
Drug/mAb ratio: 3.3

Example 194m2

Here, 5 mg of anti-CD123 $AK_{1B}$ (TPP-5971) in 500 µl of PBS (c=10 mg/ml) were used for coupling with Intermediate F194. First, 5 eq of Intermediate F194 dissolved in 100 µl of DMSO were added, and after 1 h of stirring at RT the same amount was added again and the reaction was stirred at RT for a further hour. The reaction was subsequently purified on a Sephadex column, then concentrated by ultracentrifugation and rediluted with PBS.

Protein concentration: 1.18 mg/ml
Drug/mAb ratio: 3.2

Example 194m3

Here, 5 mg of anti-CD123 $AK_{1C}$ (TPP-6013) in 500 µl of PBS (c=10 mg/ml) were used for coupling with Intermediate F194. First, 5 eq of Intermediate F194 dissolved in 100 µl of DMSO were added, and after 1 h of stirring at RT the same amount was added again and the reaction was stirred at RT for a further hour. The reaction was subsequently purified on a Sephadex column, then concentrated by ultracentrifugation and rediluted with PBS.

Protein concentration: 0.42 mg/ml
Drug/mAb ratio: 2.9

Example 208m1

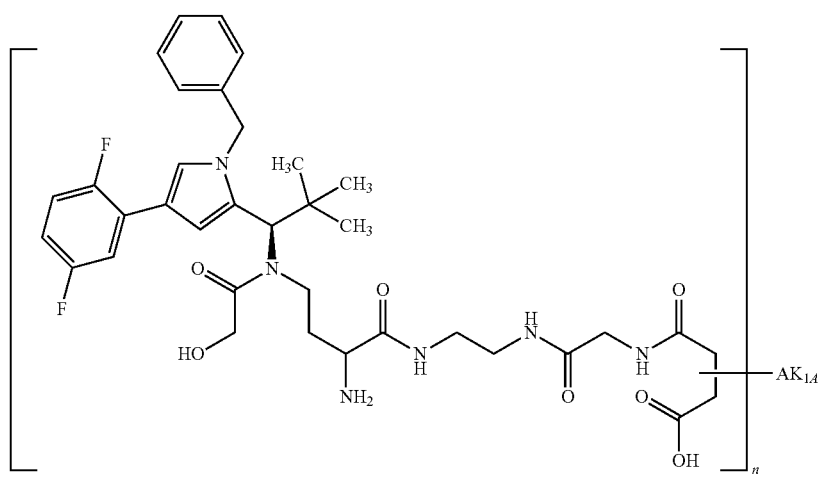

Under argon, a solution of 0.006 mg of TCEP in 10 µl of PBS buffer was added to 1 mg of anti-CD123 $AK_{1A}$ (TPP-5969) in 93 µl of PBS (c=10.2 mg/ml). The reaction was stirred at RT for 30 min, and 0.043 mg (0.053 µmol) of Intermediate F104 dissolved in 10 µl of DMSO were then added. After a further 90 min of stirring at RT, the reaction was diluted with 2387 µl of PBS buffer which had been adjusted to pH 8 beforehand.

This solution was then applied to PD-10 columns (Sephadex® G-25, GE Healthcare) which had been equilibrated with PBS buffer pH 8 and was eluted with PBS buffer pH 8. The eluate was diluted with PBS buffer pH 8 to a total volume of 15 ml. This solution was stirred under argon at RT overnight and then re-buffered to pH 7.2 using PD-10 columns. The eluate was then concentrated by ultracentrifugation, rediluted with PBS buffer (pH 7.2) and concentrated again. The ADC batch obtained was characterized as follows:
Protein concentration: 0.54 mg/ml
Drug/mAb ratio: 2.5

Example 208m1 (TV)

Under argon, a solution of 1.4 mg of TCEP in 0.83 ml of PBS buffer was added to 250 mg of anti-CD123 $AK_{1A}$ (TPP-5969) in 21.7 ml of PBS (c=11.5 mg/ml). The reaction was stirred at RT for 30 min, and 10.76 mg (0.0133 mmol) of Intermediate F104 dissolved in 2500 µl of DMSO were then added. After a further 90 min of stirring at RT, the reaction was re-buffered to pH 8 using PD-10 columns. The combined eluates were then stirred under argon at RT overnight.

The reaction was then re-buffered with PBS buffer to a pH of 7.2 using PD-10 columns and the eluate was diluted with PBS to a total volume of 125 ml. The eluate was then concentrated by ultracentrifugation, rediluted with PBS buffer (pH 7.2) and concentrated again. The ADC batch obtained was characterized as follows:
Protein concentration: 9.79 mg/ml
Drug/mAb ratio: 2.9

Example 208m2

Under argon, a solution of 0.287 mg of TCEP in 0.05 ml of PBS buffer was added to 5 mg of anti-CD123 $AK_{1B}$ (TPP-5971) in 450 µl of PBS (c=11.1 mg/ml). The reaction was stirred at RT for 30 min, and 0.215 mg (0.000267 mmol) of Intermediate F104 dissolved in 50 µl of DMSO were then added. After a further 90 min of stirring at RT, the reaction was diluted with 1950 µl of PBS buffer which had been adjusted to pH 8 beforehand.

This solution was then applied to PD-10 columns (Sephadex® G-25, GE Healthcare) which had been equilibrated with PBS buffer pH 8 and was eluted with PBS buffer pH 8. The eluate was diluted with PBS buffer pH 8 to a total volume of 15 ml. This solution was stirred under argon at RT overnight and then re-buffered to pH 7.2 using PD-10 columns. The eluate was then concentrated by ultracentrifugation and rediluted with PBS buffer (pH 7.2). The ADC batch obtained was characterized as follows:
Protein concentration: 1.76 mg/ml
Drug/mAb ratio: 2.8

Example 208m3

Under argon, a solution of 0.29 mg of TCEP in 0.05 ml of PBS buffer was added to 5 mg of anti-CD123 $AK_{1C}$ (TPP-6013) in 450 µl of PBS (c=11.1 mg/ml). The reaction was stirred at RT for 30 min, and 0.215 mg (0.000267 mmol) of Intermediate F104 dissolved in 50 µl of DMSO were then added. After a further 90 min of stirring at RT, the reaction was diluted with 1950 µl of PBS buffer which had been adjusted to pH 8 beforehand.

This solution was then applied to PD-10 columns (Sephadex® G-25, GE Healthcare) which had been equilibrated with PBS buffer pH 8 and was eluted with PBS buffer pH 8. The eluate was diluted with PBS buffer pH 8 to a total volume of 15 ml. This solution was stirred under argon at RT overnight and then re-buffered to pH 7.2 using PD-10 columns. The eluate was then concentrated by ultracentrifugation and rediluted with PBS buffer (pH 7.2). The ADC batch obtained was characterized as follows:
Protein concentration: 1.99 mg/ml
Drug/mAb ratio: 2.9

Example 208m3 (TV)

Under argon, a solution of 1.4 mg of TCEP in 0.83 ml of PBS buffer was added to 250 mg of anti-CD123 $AK_{1C}$ (TPP-6013) in 21.7 ml of PBS (c=11.5 mg/ml). The reaction was stirred at RT for 30 min, and 10.76 mg (0.0133 mmol) of Intermediate F104 dissolved in 2500 µl of DMSO were then added. After a further 90 min of stirring at RT, the reaction was re-buffered to pH 8 using PD-10 columns.

The combined eluates were then stirred under argon at RT overnight.

The reaction was then re-buffered with PBS buffer to a pH of 7.2 using PD-10 columns and the eluate was diluted with PBS to a total volume of 125 ml. The eluate was then concentrated by ultracentrifugation, rediluted with PBS buffer (pH 7.2) and concentrated again. The ADC batch obtained was characterized as follows:
Protein concentration: 11.06 mg/ml
Drug/mAb ratio: 3.4

For this ADC preparation, a proportion of 86.1% was determined for the ring-opened succinamide form.

Example 208m4

Under argon, a solution of 0.29 mg of TCEP in 0.05 ml of PBS buffer was added to 5 mg of anti-CD123 $AK_{1D}$ (TPP-5968) in 450 µl of PBS (c=11.1 mg/ml). The reaction was stirred at RT for 30 min, and 0.215 mg (0.000267 mmol) of Intermediate F104 dissolved in 50 µl of DMSO were then added. After a further 90 min of stirring at RT, the reaction was diluted with 1950 µl of PBS buffer which had been adjusted to pH 8 beforehand.

This solution was then applied to PD-10 columns (Sephadex® G-25, GE Healthcare) which had been equilibrated with PBS buffer pH 8 and was eluted with PBS buffer pH 8. The eluate was diluted with PBS buffer pH 8 to a total volume of 15 ml. This solution was stirred under argon at RT overnight and then re-buffered to pH 7.2 using PD-10 columns. The eluate was then concentrated by ultracentrifugation and rediluted with PBS buffer (pH 7.2). The ADC batch obtained was characterized as follows:
Protein concentration: 1.41 mg/ml
Drug/mAb ratio: 3.8

Example 240m1

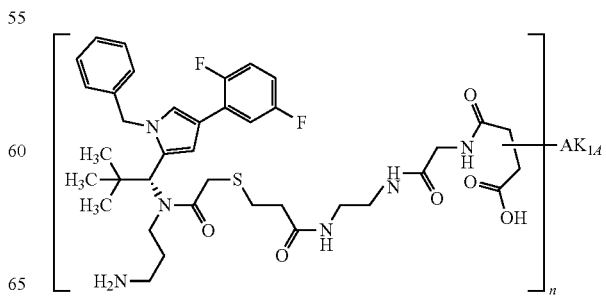

Under argon, a solution of 0.029 mg of TCEP in 50 μl of PBS buffer was added to 5 mg of anti-CD123 AK$_{1A}$ (TPP-5969) in 366 μl of PBS (c=13.66 mg/ml). The reaction was diluted with 1984 μl of PBS buffer which had been adjusted to pH 8 beforehand and stirred at RT for 1 h. 0.199 mg (0.00023 mmol) of Intermediate F240 dissolved in 100 μl of DMSO were then added. After a further 90 min of stirring at RT, the reaction was applied to PD-10 columns (Sephadex® G-25, GE Healthcare) which had been equilibrated with PBS buffer pH 8 and was eluted with PBS buffer pH 8. The eluate was stirred under argon at RT overnight and then concentrated by ultracentrifugation and rediluted with PBS buffer (pH 7.2). Under these conditions, some of the ADCs may also be present in the ring-closed form. The ADC batch obtained was characterized as follows:

Protein concentration: 1.84 mg/ml
Drug/mAb ratio: 2.7

DMSO were then added. After a further 90 min of stirring at RT, the reaction was applied to PD-10 columns (Sephadex® G-25, GE Healthcare) which had been equilibrated with PBS buffer pH 8 and was eluted with PBS buffer pH 8. The eluate was stirred under argon at RT overnight and then concentrated by ultracentrifugation and rediluted with PBS buffer (pH 7.2). Under these conditions, some of the ADCs may also be present in the ring-closed form. The ADC batch obtained was characterized as follows:

Protein concentration: 1.58 mg/ml
Drug/mAb ratio: 2.3

For this ADC preparation, a proportion of 92.9% was determined for the ring-opened succinamide form.

Example 257m1

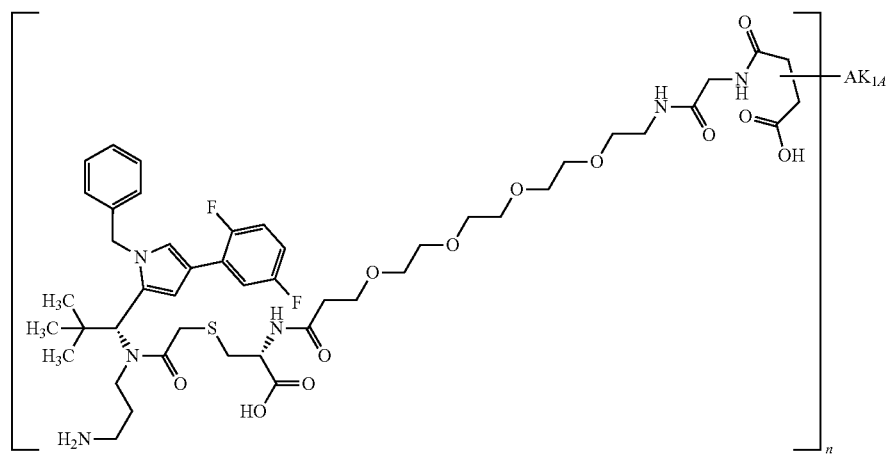

Example 240m2

Under argon, a solution of 0.029 mg of TCEP in 50 μl of PBS buffer was added to 5 mg of anti-CD123 AK$_{1B}$ (TPP-5971) in 337 μl of PBS (c=14.85 mg/ml). The reaction was diluted with 2013 μl of PBS buffer which had been adjusted to pH 8 beforehand and stirred at RT for 1 h. 0.199 mg (0.00023 mmol) of Intermediate F240 dissolved in 100 μl of DMSO were then added. After a further 90 min of stirring at RT, the reaction was applied to PD-10 columns (Sephadex® G-25, GE Healthcare) which had been equilibrated with PBS buffer pH 8 and was eluted with PBS buffer pH 8. The eluate was stirred under argon at RT overnight and then concentrated by ultracentrifugation and rediluted with PBS buffer (pH 7.2). Under these conditions, some of the ADCs may also be present in the ring-closed form. The ADC batch obtained was characterized as follows:

Protein concentration: 1.74 mg/ml
Drug/mAb ratio: 2.7

Example 240m3

Under argon, a solution of 0.029 mg of TCEP in 50 μl of PBS buffer was added to 5 mg of anti-CD123 AK$_{1C}$ (TPP-6013) in 371 μl of PBS (c=13.49 mg/ml). The reaction was diluted with 1979 μl of PBS buffer which had been adjusted to pH 8 beforehand and stirred at RT for 1 h. 0.199 mg (0.00023 mmol) of Intermediate F240 dissolved in 100 μl of Under argon, a solution of 0.029 mg of TCEP in 50 μl of PBS buffer was added to 5 mg of anti-CD123 AK$_{1A}$ (TPP-5969) in 366 μl of PBS (c=13.66 mg/ml). The reaction was diluted with 1984 μl of PBS buffer which had been adjusted to pH 8 beforehand and stirred at RT for 1 h. 0.290 mg (0.00023 mmol) of Intermediate F257 dissolved in 100 μl of DMSO were then added. After a further 90 min of stirring at RT, the reaction was applied to PD-10 columns (Sephadex® G-25, GE Healthcare) which had been equilibrated with PBS buffer pH 8 and was eluted with PBS buffer pH 8. The eluate was stirred under argon at RT overnight and then concentrated by ultracentrifugation and rediluted with PBS buffer (pH 7.2). Under these conditions, some of the ADCs may also be present in the ring-closed form. The ADC batch obtained was characterized as follows:

Protein concentration: 1.78 mg/ml
Drug/mAb ratio: 3.2

Example 257m1 (TV)

Under argon, a solution of 1.4 mg of TCEP in 0.83 ml of PBS buffer was added to 250 mg of anti-CD123 AK$_{1A}$ (TPP-5969) in 21.7 ml of PBS (c=11.5 mg/ml). The reaction was stirred at RT for 30 min and 8.92 mg (0.0083 mmol) of Intermediate F257 dissolved in 2500 μl of DMSO were then added. After a further 90 min of stirring at RT, the reaction was re-buffered to pH 8 using PD-10 columns. The combined eluates were then stirred under argon at RT overnight.

The reaction was then re-buffered with PBS buffer to a pH of 7.2 using PD-10 columns and the eluate was diluted with PBS to a total volume of 125 ml. The eluate was then concentrated by ultracentrifugation, rediluted with PBS buffer (pH 7.2) and concentrated again. The ADC batch obtained was characterized as follows:
Protein concentration: 11.27 mg/ml
Drug/mAb ratio: 3.6

Example 257m2

Under argon, a solution of 0.029 mg of TCEP in 50 µl of PBS buffer was added to 5 mg of anti-CD123 $AK_{1B}$ (TPP-5971) in 337 µl of PBS (c=14.85 mg/ml). The reaction was diluted with 2013 µl of PBS buffer which had been adjusted to pH 8 beforehand and stirred at RT for 1 h. 0.290 mg (0.00023 mmol) of Intermediate F257 dissolved in 100 µl of DMSO were then added. After a further 90 min of stirring at RT, the reaction was applied to PD-10 columns (Sephadex® G-25, GE Healthcare) which had been equilibrated with PBS buffer pH 8 and was eluted with PBS buffer pH 8. The eluate was stirred under argon at RT overnight and then concentrated by ultracentrifugation and rediluted with PBS buffer (pH 7.2). Under these conditions, some of the ADCs may also be present in the ring-closed form. The ADC batch obtained was characterized as follows:
Protein concentration: 1.54 mg/ml
Drug/mAb ratio: 3.1

Example 257m3

Under argon, a solution of 0.029 mg of TCEP in 50 µl of PBS buffer was added to 5 mg of anti-CD123 $AK_{1C}$ (TPP-6013) in 371 µl of PBS (c=13.49 mg/ml). The reaction was diluted with 1979 µl of PBS buffer which had been adjusted to pH 8 beforehand and stirred at RT for 1 h. 0.290 mg (0.00023 mmol) of Intermediate F257 dissolved in 100 µl of DMSO were then added. After a further 90 min of stirring at RT, the reaction was applied to PD-10 columns (Sephadex® G-25, GE Healthcare) which had been equilibrated with PBS buffer pH 8 and was eluted with PBS buffer pH 8. The eluate was stirred under argon at RT overnight and then concentrated by ultracentrifugation and rediluted with PBS buffer (pH 7.2). Under these conditions, some of the ADCs may also be present in the ring-closed form. The ADC batch obtained was characterized as follows:
Protein concentration: 1.59 mg/ml
Drug/mAb ratio: 2.4

Example 257m3 (TV)

Under argon, a solution of 1.4 mg of TCEP in 0.83 ml of PBS buffer was added to 250 mg of anti-CD123 $AK_{1C}$ (TPP-6013) in 21.7 ml of PBS (c=11.5 mg/ml). The reaction was stirred at RT for 30 min and 8.93 mg (0.0083 mmol) of Intermediate F257 dissolved in 2500 µl of DMSO were then added. After a further 90 min of stirring at RT, the reaction was re-buffered to pH 8 using PD-10 columns. The combined eluates were then stirred under argon at RT overnight.
The reaction was then re-buffered with PBS buffer to a pH of 7.2 using PD-10 columns and the eluate was diluted with PBS to a total volume of 125 ml. The eluate was then concentrated by ultracentrifugation, rediluted with PBS buffer (pH 7.2) and concentrated again. The ADC batch obtained was characterized as follows:
Protein concentration: 13.36 mg/ml
Drug/mAb ratio: 3.3
For this ADC preparation, a proportion of 78.7% was determined for the ring-opened succinamide form.

Example 259m1

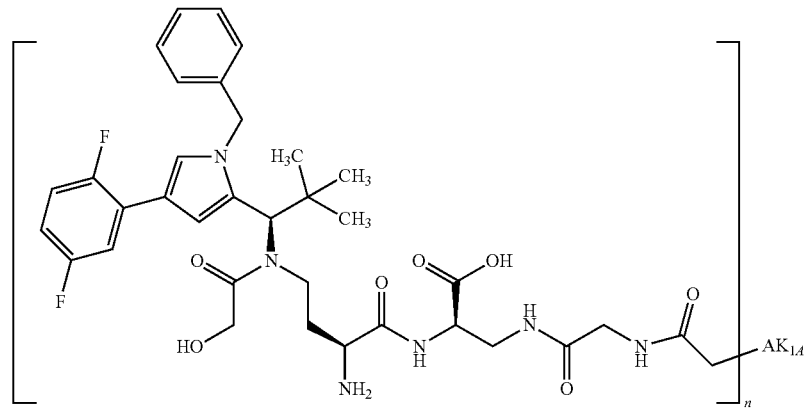

Here, 5 mg of anti-CD123 $AK_{1A}$ (TPP-5969) in 450 µl of PBS (c=11.1 mg/ml) were used for coupling with Intermediate F259. The reduction time of the antibody was 30 min, and after addition of 0.245 mg (0.267 µmol) of F259, the reaction was stirred at RT for 20 h and then purified on Sephadex. The eluate was finally concentrated by ultracentrifugation and rediluted with PBS.
Protein concentration: 1.70 mg/ml
Drug/mAb ratio: 1.7

Example 259m2

Here, 5 mg of anti-CD123 $AK_{1B}$ (TPP-5971) in 450 µl of PBS (c=11.1 mg/ml) were used for coupling with Intermediate F259. The reduction time of the antibody was 30 min, and after addition of 0.245 mg (0.267 µmol) of F259, the reaction was stirred at RT for 20 h and then purified on Sephadex. The eluate was finally concentrated by ultracentrifugation and rediluted with PBS.
Protein concentration: 1.72 mg/ml
Drug/mAb ratio: 1.8

Example 259m3

Here, 5 mg of anti-CD123 $AK_{1C}$(TPP-6013) in 450 μl of PBS (c=11.1 mg/ml) were used for coupling with Intermediate F259. The reduction time of the antibody was 30 min, and after addition of 0.245 mg (0.267 μmol) of F259, the reaction was stirred at RT for 20 h and then purified on Sephadex. The eluate was finally concentrated by ultracentrifugation and rediluted with PBS.
Protein concentration: 1.57 mg/ml
Drug/mAb ratio: 2.0

Example 260m1

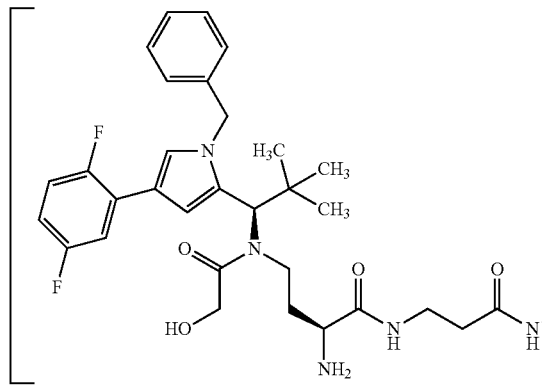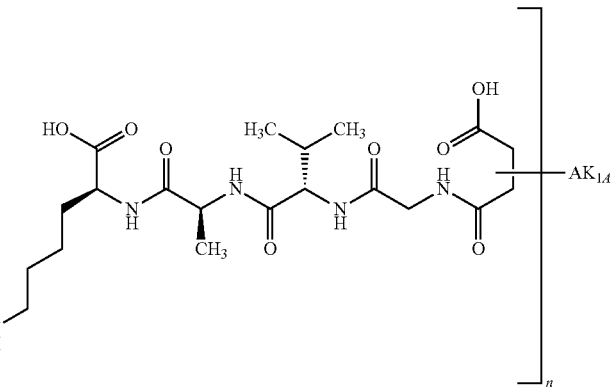

Example 260m1 (TV)

Under argon, a solution of 1.4 mg of TCEP in 0.83 ml of PBS buffer was added to 250 mg of anti-CD123 $AK_{1A}$ (TPP-5969) in 21.7 ml of PBS (c=11.5 mg/ml). The reaction was stirred at RT for 30 min, and 15.1 mg (0.0133 mmol) of Intermediate F260 dissolved in 2500 μl of DMSO were then added. After a further 90 min of stirring at RT, the reaction was re-buffered to pH 8 using PD-10 columns. The combined eluates were then stirred under argon at RT overnight.

The reaction was then re-buffered with PBS buffer to a pH of 7.2 using PD-10 columns and the eluate was diluted with PBS to a total volume of 125 ml. The eluate was then concentrated by ultracentrifugation, rediluted with PBS buffer (pH 7.2) and concentrated again. The ADC batch obtained was characterized as follows:
Protein concentration: 9.47 mg/ml
Drug/mAb ratio: 3.0

Example 260m2

Under argon, a solution of 0.029 mg of TCEP in 50 μl of PBS buffer was added to 5 mg of anti-CD123 $AK_{1B}$ (TPP-5971) in 450 μl of PBS (c=11.1 mg/ml). The reaction was stirred at RT for 30 min, and 0.302 mg (0.00027 mmol) of Intermediate F260 dissolved in 50 μl of DMSO were then added. After a further 90 min of stirring at RT, the reaction was diluted with 1950 μl of PBS buffer which had been adjusted to pH 8 beforehand.

This solution was then applied to PD-10 columns (Sephadex® G-25, GE Healthcare) which had been equilibrated with PBS buffer pH 8 and was eluted with PBS buffer pH 8. The eluate was stirred under argon at RT overnight and then concentrated by ultracentrifugation and rediluted with PBS buffer (pH 7.2). Under these conditions, some of the ADCs may also be present in the ring-closed form. The ADC batch obtained was characterized as follows:
Protein concentration: 1.62 mg/ml
Drug/mAb ratio: 3.5

Example 260m3 (TV)

Under argon, a solution of 1.4 mg of TCEP in 0.83 ml of PBS buffer was added to 250 mg of anti-CD123 $AK_{1C}$ (TPP-6013) in 21.7 ml of PBS (c=11.5 mg/ml). The reaction was stirred at RT for 30 min, and 15.1 mg (0.0133 mmol) of Intermediate F260 dissolved in 2500 μl of DMSO were then added. After a further 90 min of stirring at RT, the reaction was re-buffered to pH 8 using PD-10 columns. The combined eluates were then stirred under argon at RT overnight.

The reaction was then re-buffered with PBS buffer to a pH of 7.2 using PD-10 columns and the eluate was diluted with PBS to a total volume of 125 ml. The eluate was then concentrated by ultracentrifugation, rediluted with PBS buffer (pH 7.2) and concentrated again. The ADC batch obtained was characterized as follows:
Protein concentration: 12.08 mg/ml
Drug/mAb ratio: 2.8

For this ADC preparation, a proportion of 84.5% was determined for the ring-opened succinamide form.

Example 270m1

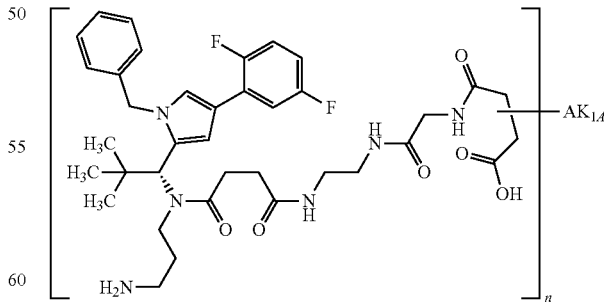

Under argon, a solution of 0.029 mg of TCEP in 50 μl of PBS buffer was added to 5 mg of anti-CD123 $AK_{1A}$ (TPP-5969) in 366 μl of PBS (c=13.66 mg/ml). The reaction was diluted with 1984 μl of PBS buffer which had been adjusted to pH 8 beforehand and stirred at RT for 1 h. 0.188 mg (0.00023 mmol) of Intermediate F270 dissolved in 100 µl of DMSO were then added. After a further 90 min of stirring at RT, the reaction was applied to PD-10 columns (Sephadex® G-25, GE Healthcare) which had been equilibrated with PBS buffer pH 8 and was eluted with PBS buffer pH 8. The eluate was stirred under argon at RT overnight and then concentrated by ultracentrifugation and rediluted with PBS buffer (pH 7.2). Under these conditions, some of the ADCs may also be present in the ring-closed form. The ADC batch obtained was characterized as follows:
Protein concentration: 1.71 mg/ml
Drug/mAb ratio: 2.7

Example 270m2

Under argon, a solution of 0.029 mg of TCEP in 50 µl of PBS buffer was added to 5 mg of anti-CD123 $AK_{1B}$ (TPP-5971) in 337 µl of PBS (c=14.85 mg/ml). The reaction was diluted with 2013 µl of PBS buffer which had been adjusted to pH 8 beforehand and stirred at RT for 1 h. 0.188 mg (0.00023 mmol) of Intermediate F270 dissolved in 100 of DMSO were then added. After a further 90 min of stirring at RT, the reaction was applied to PD-10 columns (Sephadex® G-25, GE Healthcare) which had been equilibrated with PBS buffer pH 8 and was eluted with PBS buffer pH 8. The eluate was stirred under argon at RT overnight and then concentrated by ultracentrifugation and rediluted with PBS buffer (pH 7.2). Under these conditions, some of the ADCs may also be present in the ring-closed form. The ADC batch obtained was characterized as follows:
Protein concentration: 1.65 mg/ml
Drug/mAb ratio: 2.9

Example 270m3

Under argon, a solution of 0.029 mg of TCEP in 50 µl of PBS buffer was added to 5 mg of anti-CD123 $AK_{1C}$ (TPP-6013) in 371 µl of PBS (c=13.49 mg/ml). The reaction was diluted with 1979 µl of PBS buffer which had been adjusted to pH 8 beforehand and stirred at RT for 1 h. 0.188 mg (0.00023 mmol) of Intermediate F270 dissolved in 100 of DMSO were then added. After a further 90 min of stirring at RT, the reaction was applied to PD-10 columns (Sephadex® G-25, GE Healthcare) which had been equilibrated with PBS buffer pH 8 and was eluted with PBS buffer pH 8. The eluate was stirred under argon at RT overnight and then concentrated by ultracentrifugation and rediluted with PBS buffer (pH 7.2). Under these conditions, some of the ADCs may also be present in the ring-closed form. The ADC batch obtained was characterized as follows:
Protein concentration: 1.51 mg/ml
Drug/mAb ratio: 2.4
For this ADC preparation, a proportion of 94.4% was determined for the ring-opened succinamide form.

Example 271m1

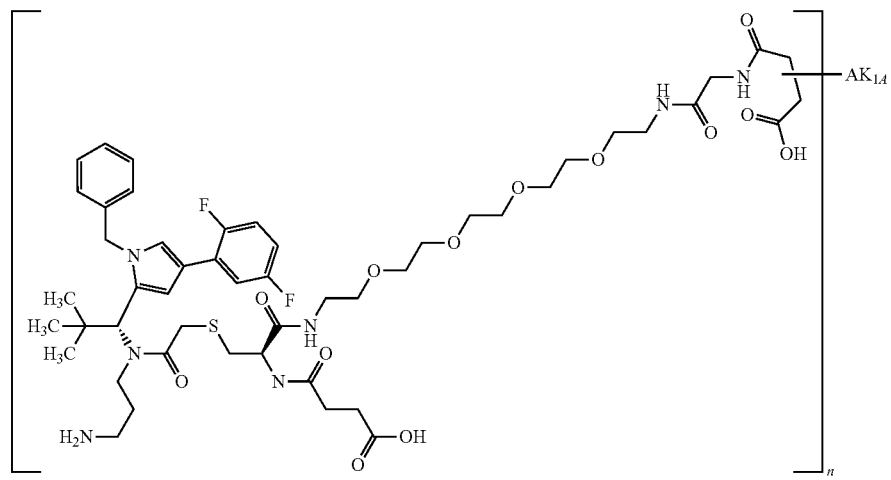

Under argon, a solution of 0.172 mg of TCEP in 0.30 ml of PBS buffer was added to 30 mg of anti-CD123 $AK_{1A}$ (TPP-5969) in 3.0 ml of PBS (c=10.0 mg/ml). The mixture was stirred at RT for 30 min, and 1.14 mg (0.001 mmol) of intermediate F271, dissolved in 300 µl of DMSO, were then added. After a further 90 min of stirring at RT, the mixture was re-buffered to pH 8 using PD-10 columns. The combined eluates were then stirred under argon at RT overnight.
The mixture was then re-buffered with PBS buffer to a pH of 7.2 using PD-10 columns and the eluate was diluted with PBS to a total volume of 14 ml. The eluate was then concentrated by ultracentrifugation, rediluted with PBS buffer (pH 7.2) and concentrated again. The ADC batch obtained was characterized as follows:
Protein concentration: 11.82 mg/ml
Drug/mAb ratio: 3.1

Example 271m3

Under argon, a solution of 0.029 mg of TCEP in 50 µl of PBS buffer was added to 5 mg of anti-CD123 $AK_{1C}$(TPP-6013) in 450 µl of PBS (c=11.11 mg/ml). The reaction was stirred at RT for 30 min. 0.267 mg (0.00023 mmol) of intermediate F271, dissolved in 50 µl of DMSO, were then added. After a further 90 min of stirring at RT, the mixture was diluted with 1950 µl of PBS buffer, which had been adjusted to pH 8 beforehand, and then applied to PD-10 columns (Sephadex® G-25, GE Healthcare) which had been equilibrated with PBS buffer pH 8 and was eluted with PBS buffer pH 8. The eluate was stirred under argon at RT overnight and then concentrated by ultracentrifugation and rediluted with PBS buffer (pH 7.2). Under these conditions, some of the ADCs may also be present in the ring-closed form. The ADC batch obtained was characterized as follows:
Protein concentration: 1.33 mg/ml
Drug/mAb ratio: 4.2 concentrated by ultracentrifugation and rediluted with PBS buffer (pH 7.2). Under these conditions, some of the ADCs may also be present in the ring-closed form. The ADC batch obtained was characterized as follows:
Protein concentration: 1.84 mg/ml
Drug/mAb ratio: 3.2

Example 274m3

Under argon, a solution of 0.029 mg of TCEP in 50 µl of PBS buffer was added to 5 mg of anti-CD123 $AK_{1C}$ (TPP-6013) in 371 µl of PBS (c=13.49 mg/ml). The reaction was diluted with 1979 µl of PBS buffer which had been adjusted to pH 8 beforehand and stirred at RT for 1 h. 0.232 mg (0.00023 mmol) of Intermediate F274 dissolved in 100 µl of DMSO were then added. After a further 90 min of stirring at RT, the reaction was applied to PD-10 columns (Sepha- Example 274m1

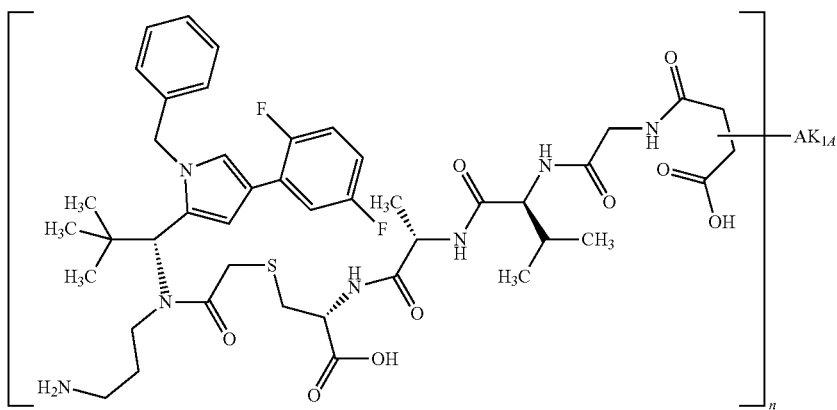

Under argon, a solution of 0.029 mg of TCEP in 50 µl of PBS buffer was added to 5 mg of anti-CD123 $AK_{1A}$ (TPP-5969) in 366 µl of PBS (c=13.66 mg/ml). The reaction was diluted with 1984 µl of PBS buffer which had been adjusted to pH 8 beforehand and stirred at RT for 1 h. 0.232 mg (0.00023 mmol) of Intermediate F274 dissolved in 100 µl of DMSO were then added. After a further 90 min of stirring at RT, the reaction was applied to PD-10 columns (Sephadex® G-25, GE Healthcare) which had been equilibrated with PBS buffer pH 8 and was eluted with PBS buffer pH 8. The eluate was stirred under argon at RT overnight and then concentrated by ultracentrifugation and rediluted with PBS buffer (pH 7.2). Under these conditions, some of the ADCs may also be present in the ring-closed form. The ADC batch obtained was characterized as follows:
Protein concentration: 1.92 mg/ml
Drug/mAb ratio: 3.2

Example 274m2

Under argon, a solution of 0.029 mg of TCEP in 50 µl of PBS buffer was added to 5 mg of anti-CD123 $AK_{1B}$ (TPP-5971) in 337 µl of PBS (c=14.85 mg/ml). The reaction was diluted with 2013 µl of PBS buffer which had been adjusted to pH 8 beforehand and stirred at RT for 1 h. 0.232 mg (0.00023 mmol) of Intermediate F274 dissolved in 100 µl of DMSO were then added. After a further 90 min of stirring at RT, the reaction was applied to PD-10 columns (Sephadex® G-25, GE Healthcare) which had been equilibrated with PBS buffer pH 8 and was eluted with PBS buffer pH 8. The eluate was stirred under argon at RT overnight and then dex® G-25, GE Healthcare) which had been equilibrated with PBS buffer pH 8 and was eluted with PBS buffer pH 8. The eluate was stirred under argon at RT overnight and then concentrated by ultracentrifugation and rediluted with PBS buffer (pH 7.2). Under these conditions, some of the ADCs may also be present in the ring-closed form. The ADC batch obtained was characterized as follows:
Protein concentration: 1.69 mg/ml
Drug/mAb ratio: 3.0
For this ADC preparation, a proportion of 89.5% was determined for the ring-opened succinamide form.

Example 276m1

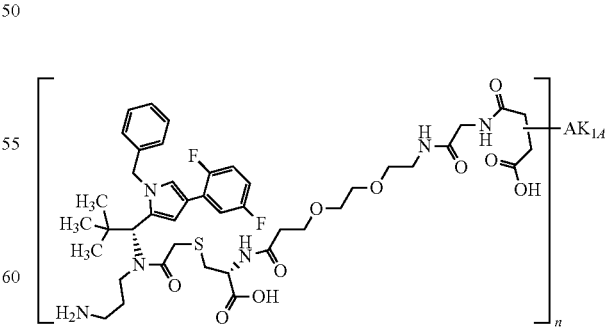

Under argon, a solution of 0.029 mg of TCEP in 50 µl of PBS buffer was added to 5 mg of anti-CD123 $AK_{1A}$ (TPP-5969) in 450 µl of PBS (c=11.11 mg/ml). The reaction was stirred at RT for 30 min. 0.229 mg (0.00023 mmol) of intermediate F276, dissolved in 50 µl of DMSO, was then added. After a further 90 min of stirring at RT, the reaction was diluted with 1950 µl of PBS buffer, which had been adjusted to pH 8 beforehand, and then applied to PD-10 columns (Sephadex® G-25, GE Healthcare) equilibrated with PBS buffer pH 8 and eluted with PBS buffer pH 8. The eluate was stirred under argon at RT overnight and then concentrated by ultracentrifugation and rediluted with PBS buffer (pH 7.2). Under these conditions, some of the ADCs may also be present in the ring-closed form. The ADC batch obtained was characterized as follows:

Protein concentration: 1.26 mg/ml
Drug/mAb ratio: 3.8

Example 276m3

Under argon, a solution of 0.029 mg of TCEP in 50 µl of PBS buffer was added to 5 mg of anti-CD123 $AK_{1C}$(TPP-6013) in 450 µl of PBS (c=11.11 mg/ml). The reaction was stirred at RT for 30 min. 0.229 mg (0.00023 mmol) of intermediate F276, dissolved in 50 µl of DMSO, was then added. After a further 90 min of stirring at RT, the reaction was diluted with 1950 µl of PBS buffer, which had been adjusted to pH 8 beforehand, and then applied to PD-10 columns (Sephadex® G-25, GE Healthcare) equilibrated with PBS buffer pH 8 and eluted with PBS buffer pH 8. The eluate was stirred under argon at RT overnight and then concentrated by ultracentrifugation and rediluted with PBS buffer (pH 7.2). Under these conditions, some of the ADCs may also be present in the ring-closed form. The ADC batch obtained was characterized as follows:

Protein concentration: 1.39 mg/ml
Drug/mAb ratio: 4.0

Example 281m3

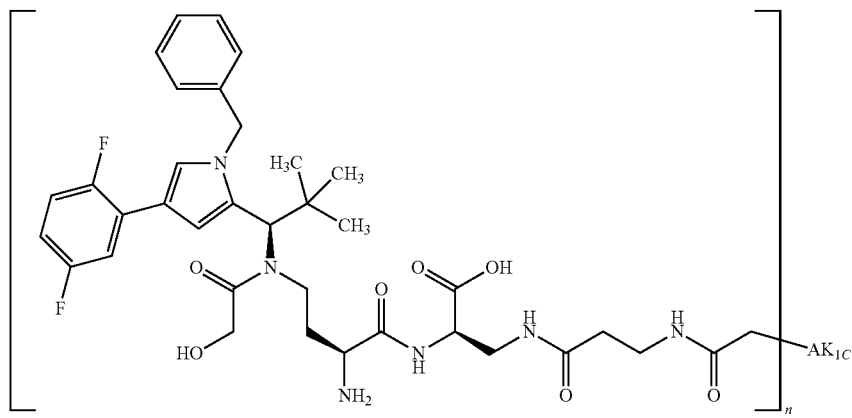

Here, 5 mg of anti-CD123 $AK_{1C}$(TPP-6013) in 500 µl of PBS were used for coupling with intermediate F281 at pH 7.2 (c=10 mg/ml). The reduction time of the antibody in the presence of 0.029 mg of TCEP was 30 min. The mixture was then, after addition of 0.25 mg (0.27 µmol) of F281, stirred in 50 µl of DMSO at RT for 20 h and subsequently purified on Sephadex. Finally, the eluate was concentrated by ultracentrifugation and rediluted with PBS.

Protein concentration: 1.42 mg/ml
Drug/mAb ratio: 3.8

Example 284m1

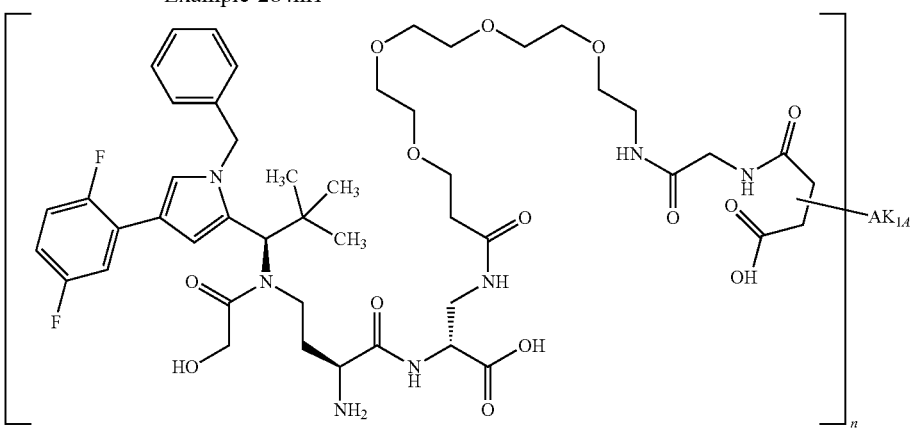

Under argon, a solution of 0.029 mg of TCEP in 50 μl of PBS buffer was added to 5 mg of anti-CD123 $AK_{1A}$ (TPP-5969) in 450 μl of PBS (c=11.1 mg/ml). The reaction was stirred at RT for 30 min, and 0.256 mg (0.00023 mmol) of Intermediate F284 dissolved in 50 μl of DMSO were then added. After a further 90 min of stirring at RT, the reaction was diluted with 1950 μl of PBS buffer which had been adjusted to pH 8 beforehand.

This solution was then applied to PD-10 columns (Sephadex® G-25, GE Healthcare) which had been equilibrated with PBS buffer pH 8 and was eluted with PBS buffer pH 8. The eluate was stirred under argon at RT overnight and then concentrated by ultracentrifugation and rediluted with PBS buffer (pH 7.2). Under these conditions, some of the ADCs may also be present in the ring-closed form. The ADC batch obtained was characterized as follows:
Protein concentration: 1.78 mg/ml
Drug/mAb ratio: 2.7

Example 284m2

Under argon, a solution of 0.029 mg of TCEP in 50 μl of PBS buffer was added to 5 mg of anti-CD123 $AK_{1B}$ (TPP-5971) in 450 μl of PBS (c=11.1 mg/ml). The reaction was stirred at RT for 30 min, and 0.256 mg (0.000233 mmol) of Intermediate F284 dissolved in 50 μl of DMSO were then added. After a further 90 min of stirring at RT, the reaction was diluted with 1950 μl of PBS buffer which had been adjusted to pH 8 beforehand.

This solution was then applied to PD-10 columns (Sephadex® G-25, GE Healthcare) which had been equilibrated with PBS buffer pH 8 and was eluted with PBS buffer pH 8. The eluate was stirred under argon at RT overnight and then concentrated by ultracentrifugation and rediluted with PBS buffer (pH 7.2). Under these conditions, some of the ADCs may also be present in the ring-closed form. The ADC batch obtained was characterized as follows:
Protein concentration: 1.83 mg/ml
Drug/mAb ratio: 3.3

Example 284m3

Under argon, a solution of 0.029 mg of TCEP in 50 μl of PBS buffer was added to 5 mg of anti-CD123 $AK_{1C}$ (TPP-6013) in 510 μl of PBS (c=9.8 mg/ml), and the mixture was stirred at RT for 30 min. 0.26 mg (0.23 μmol) of Intermediate F284 dissolved in 50 μl of DMSO were then added. After a further 90 min of stirring at RT, the mixture was made up to 2.5 ml with PBS buffer pH 8 and passed through a PD-10 column (Sephadex® G-25, GE Healthcare) equilibrated with PBS buffer pH 8, eluted with PBS buffer pH 8 and then stirred at RT overnight. The eluate was then concentrated by ultracentrifugation and rediluted with PBS buffer (pH 7.2). The ADC batch obtained was characterized as follows:
Protein concentration: 1.54 mg/ml
Drug/mAb ratio: 2.2

Example 296m1

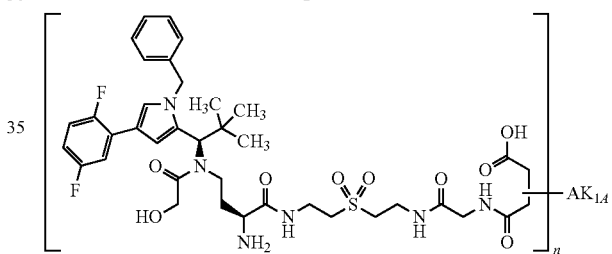

Under argon, a solution of 0.14 mg of TCEP in 0.25 ml of PBS buffer was added to 25 mg of anti-CD123 $AK_{1A}$ (TPP-5969) in 2.5 ml of PBS (c=10 mg/ml). The reaction was stirred at RT for 30 min and 1.05 mg (0.0012 mmol) of Intermediate F296 dissolved in 250 μl of DMSO were then added. After a further 90 min of stirring at RT, the mixture was diluted with 2 ml of PBS buffer which was adjusted to pH 8, and the reaction was stirred under argon at RT overnight.

The reaction was then re-buffered with PBS buffer to a pH of 7.2 using PD-10 columns. The mixture was then concentrated by ultracentrifugation, rediluted with PBS buffer (pH 7.2) and concentrated again. The ADC batch obtained was characterized as follows:
Protein concentration: 7.66 mg/ml
Drug/mAb ratio: 2.8

Example 296m2

Under argon, a solution of 0.029 mg of TCEP in 50 μl of PBS buffer was added to 5 mg of anti-CD123 $AK_{1B}$ (TPP-5971) in 500 μl of PBS (c=10 mg/ml), and the mixture was stirred at RT for 30 min. 0.21 mg (0.23 μmol) of Intermediate F296 dissolved in 50 μl of DMSO were then added. After a further 90 min of stirring at RT, the mixture was made up to 2.5 ml with PBS buffer pH 8 and passed through a PD-10 column (Sephadex® G-25, GE Healthcare) equilibrated with PBS buffer pH 8, eluted with PBS buffer pH 8 and then stirred under argon at RT overnight. The eluate was then concentrated by ultracentrifugation and rediluted with PBS buffer (pH 7.2). The ADC batch obtained was characterized as follows:

Protein concentration: 1.7 mg/ml
Drug/mAb ratio: 2.8

Example 296m3

Under argon, a solution of 0.029 mg of TCEP in 50 µl of PBS buffer was added to 5 mg of anti-CD123 $AK_{1C}$ (TPP-6013) in 500 µl of PBS (c=10 mg/ml), and the mixture was stirred at RT for 30 min. 0.21 mg (0.23 µmol) of Intermediate F296 dissolved in 50 µl of DMSO were then added. After a further 90 min of stirring at RT, the mixture was made up to 2.5 ml with PBS buffer pH 8 and passed through a PD-10 column (Sephadex® G-25, GE Healthcare) equilibrated with PBS buffer pH 8, eluted with PBS buffer pH 8 and then stirred under argon at RT overnight. The eluate was then concentrated by ultracentrifugation and rediluted with PBS buffer (pH 7.2). The ADC batch obtained was characterized as follows:

Protein concentration: 1.51 mg/ml
Drug/mAb ratio: 2.1

Example 297m1

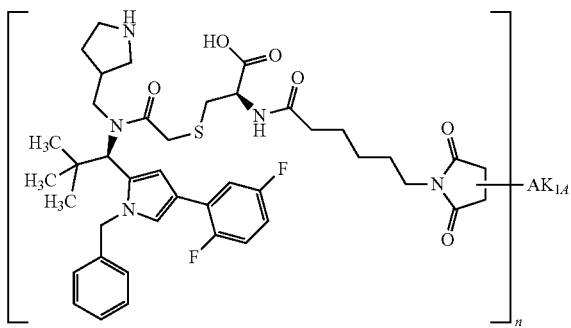

Here, 5 mg of anti-CD123 $AK_{1A}$ (TPP-5969) in 427 µl of PBS at pH 7.2 (c=13.66 mg/ml) were used for coupling with Intermediate F297. The reduction time of the antibody in the presence of 0.029 mg of TCEP was 30 min. After addition of 0.23 mg (0.26 µmol) of F297 in 50 µl of DMSO, the reaction was then stirred at RT for 2 h and subsequently purified on Sephadex. The eluate was finally concentrated by ultracentrifugation and rediluted with PBS.

Protein concentration: 1.81 mg/ml
Drug/mAb ratio: 2.5

Example 297m2

Here, 5 mg of anti-CD123 $AK_{1B}$ (TPP-5971) in 427 µl of PBS at pH 7.2 (c=14.85 mg/ml) were used for coupling with Intermediate F297. The reduction time of the antibody in the presence of 0.029 mg of TCEP was 30 min. After addition of 0.23 mg (0.26 µmol) of F297 in 50 µl of DMSO, the reaction was then stirred at RT for 2 h and subsequently purified on Sephadex. The eluate was finally concentrated by ultracentrifugation and rediluted with PBS.

Protein concentration: 1.64 mg/ml
Drug/mAb ratio: 2.4

Example 297m3

Here, 5 mg of anti-CD123 $AK_{1C}$(TPP-6013) in 427 µl of PBS at pH 7.2 (c=13.49 mg/ml) were used for coupling with Intermediate F297. The reduction time of the antibody in the presence of 0.029 mg of TCEP was 30 min. After addition of 0.23 mg (0.26 µmol) of F297 in 50 µl of DMSO, the reaction was then stirred at RT for 2 h and subsequently purified on Sephadex. The eluate was finally concentrated by ultracentrifugation and rediluted with PBS.

Protein concentration: 1.81 mg/ml
Drug/mAb ratio: 2.1

Example 309m1

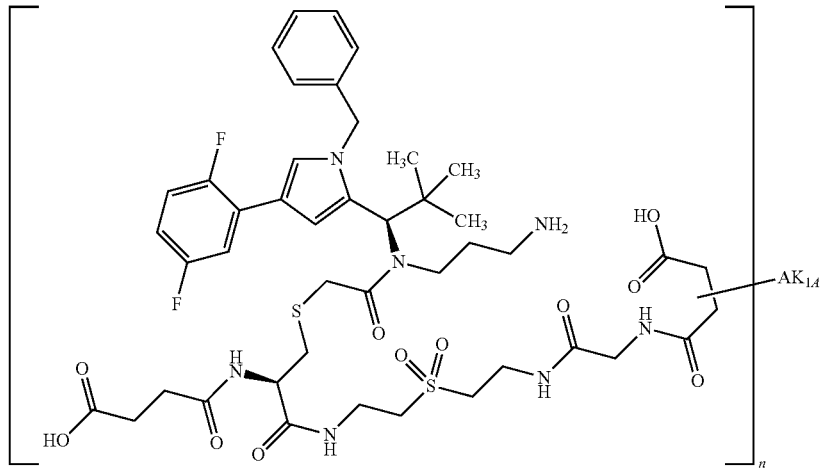

Under argon, a solution of 0.029 mg of TCEP in 50 μl of PBS buffer was added to 5 mg of anti-CD123 $AK_{1A}$ (TPP-5969) in 450 μl of PBS (c=11.11 mg/ml). The mixture was stirred at RT for 30 min. 0.247 mg (0.00023 mmol) of intermediate F309, dissolved in 50 μl of DMSO, was then added. After a further 90 min of stirring at RT, the mixture was diluted with 1950 μl of PBS buffer which had been adjusted to pH 8 beforehand and was then applied to PD-10 columns (Sephadex® G-25, GE Healthcare) which had been equilibrated with PBS buffer pH 8 and was eluted with PBS buffer pH 8. The eluate was stirred under argon at RT overnight and then concentrated by ultracentrifugation and rediluted with PBS buffer (pH 7.2). Under these conditions, some of the ADCs may also be present in the ring-closed form. The ADC batch obtained was characterized as follows:
Protein concentration: 0.77 mg/ml
Drug/mAb ratio: 4.1

Example 309m3

Under argon, a solution of 0.029 mg of TCEP in 50 μl of PBS buffer was added to 5 mg of anti-CD123 $AK_{1C}$(TPP-6013) in 450 μl of PBS (c=11.11 mg/ml). The mixture was stirred at RT for 30 min. 0.247 mg (0.00023 mmol) of intermediate F309, dissolved in 50 μl of DMSO, was then added. After a further 90 min of stirring at RT, the mixture was diluted with 1950 μl of PBS buffer which had been adjusted to pH 8 beforehand and was then applied to PD-10 columns (Sephadex® G-25, GE Healthcare) which had been equilibrated with PBS buffer pH 8 and was eluted with PBS buffer pH 8. The eluate was stirred under argon at RT overnight and then concentrated by ultracentrifugation and rediluted with PBS buffer (pH 7.2). Under these conditions, some of the ADCs may also be present in the ring-closed form. The ADC batch obtained was characterized as follows:
Protein concentration: 1.15 mg/ml
Drug/mAb ratio: 4.2

Example 310m1

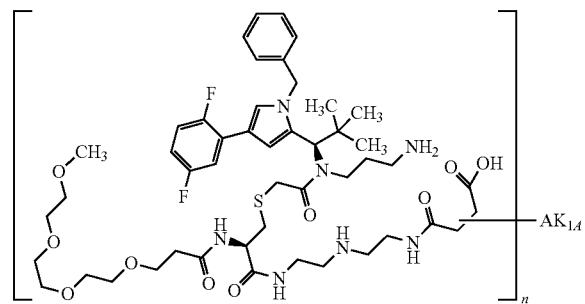

Under argon, a solution of 0.172 mg of TCEP in 0.30 ml of PBS buffer was added to 30 mg of anti-CD123 $AK_{1A}$ (TPP-5969) in 3.0 ml of PBS (c=10.0 mg/ml). The mixture was stirred at RT for 30 min and 1.08 mg (0.001 mmol) of intermediate F310, dissolved in 300 μl of DMSO, were then added. After a further 90 min of stirring at RT, the mixture was re-buffered to pH 8 using the PD-10 columns. The combined eluates were then stirred under argon at RT overnight.
Using PD-10 columns with PBS buffer, the mixture was then re-buffered to a pH of 7.2 and the eluate was diluted with PBS to a total volume of 14 ml. The mixture was then concentrated by ultracentrifugation, rediluted with PBS buffer (pH 7.2) and concentrated again. The ADC batch obtained was characterized as follows:
Protein concentration: 13.04 mg/ml
Drug/mAb ratio: 3.0

Example 310m3

Under argon, a solution of 0.029 mg of TCEP in 50 μl of PBS buffer was added to 5 mg of anti-CD123 $AK_{1C}$ (TPP-6013) in 450 μl of PBS (c=11.11 mg/ml). The mixture was stirred at RT for 30 min. 0.253 mg (0.00023 mmol) of intermediate F310, dissolved in 50 μl of DMSO, was then added. After a further 90 min of stirring at RT, the mixture was diluted with 1950 μl of PBS buffer which had been adjusted to pH 8 beforehand and was then applied to PD-10 columns (Sephadex® G-25, GE Healthcare) which had been equilibrated with PBS buffer pH 8 and was eluted with PBS buffer pH 8. The eluate was stirred under argon at RT overnight and then concentrated by ultracentrifugation and rediluted with PBS buffer (pH 7.2). Under these conditions, some of the ADCs may also be present in the ring-closed form. The ADC batch obtained was characterized as follows:
Protein concentration: 1.84 mg/ml
Drug/mAb ratio: 4.4

Example 314m1

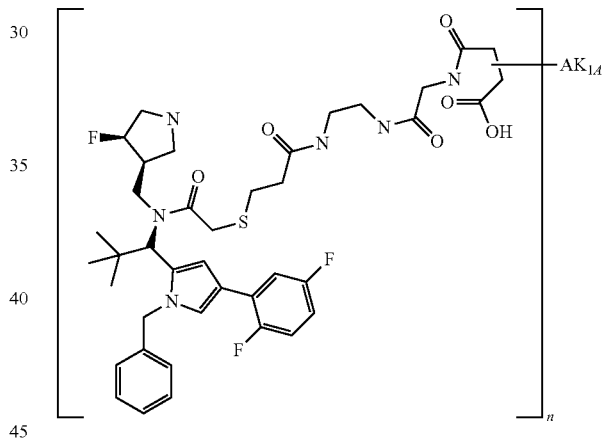

Under argon, a solution of 0.029 mg of TCEP in 50 μl of PBS buffer was added to 5 mg of anti-CD123 $AK_{1A}$ (TPP-5969) in 450 μl of PBS (c=11.11 mg/ml). The mixture was stirred at RT for 30 min. 0.209 mg (0.00023 mmol) of intermediate F314, dissolved in 50 μl of DMSO, was then added. After a further 90 min of stirring at RT, the mixture was diluted with 1950 μl of PBS buffer which had been adjusted to pH 8 beforehand and was then applied to PD-10 columns (Sephadex® G-25, GE Healthcare) which had been equilibrated with PBS buffer pH 8 and was eluted with PBS buffer pH 8. The eluate was stirred under argon at RT overnight and then concentrated by ultracentrifugation and rediluted with PBS buffer (pH 7.2). Under these conditions, some of the ADCs may also be present in the ring-closed form. The ADC batch obtained was characterized as follows:
Protein concentration: 1.42 mg/ml
Drug/mAb ratio: 4.0

Example 314m3

Under argon, a solution of 0.029 mg of TCEP in 50 μl of PBS buffer was added to 5 mg of anti-CD123 $AK_{1C}$ (TPP- 6013) in 450 μl of PBS (c=11.11 mg/ml). The mixture was stirred at RT for 30 min. 0.209 mg (0.00023 mmol) of intermediate F314, dissolved in 50 μl of DMSO, was then added. After a further 90 min of stirring at RT, the mixture was diluted with 1950 μl of PBS buffer which had been adjusted to pH 8 beforehand and was then applied to PD-10 columns (Sephadex® G-25, GE Healthcare) which had been equilibrated with PBS buffer pH 8 and was eluted with PBS buffer pH 8. The eluate was stirred under argon at RT overnight and then concentrated by ultracentrifugation and rediluted with PBS buffer (pH 7.2). Under these conditions, some of the ADCs may also be present in the ring-closed form. The ADC batch obtained was characterized as follows:

Protein concentration: 1.29 mg/ml
Drug/mAb ratio: 4.3

Example 317m1 intermediate F317, dissolved in 50 μl of DMSO, was then added. After a further 90 min of stirring at RT, the mixture was diluted with 1950 μl of PBS buffer which had been adjusted to pH 8 beforehand and was then applied to PD-10 columns (Sephadex® G-25, GE Healthcare) which had been equilibrated with PBS buffer pH 8 and was eluted with PBS buffer pH 8. The eluate was stirred under argon at RT overnight and then concentrated by ultracentrifugation and rediluted with PBS buffer (pH 7.2). Under these conditions, some of the ADCs may also be present in the ring-closed form. The ADC batch obtained was characterized as follows:

Protein concentration: 1.61 mg/ml
Drug/mAb ratio: 2.7

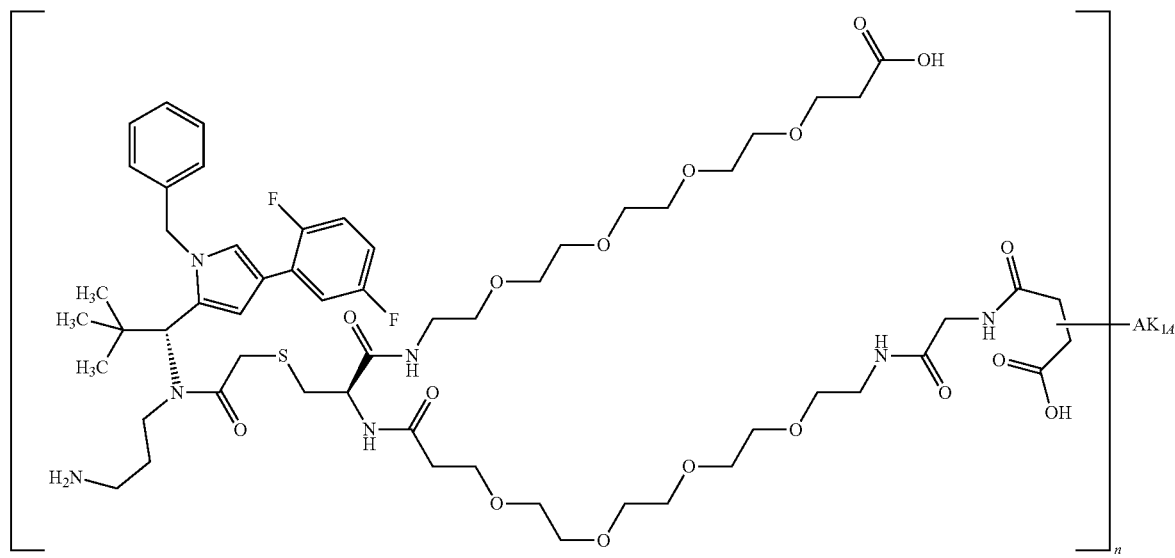

Under argon, a solution of 0.029 mg of TCEP in 50 μl of PBS buffer was added to 5 mg of anti-CD123 $AK_{1A}$ (TPP-5969) in 450 μl of PBS (c=11.11 mg/ml). The mixture was stirred at RT for 30 min. 0.308 mg (0.00023 mmol) of intermediate F317, dissolved in 50 μl of DMSO, was then added. After a further 90 min of stirring at RT, the mixture was diluted with 1950 μl of PBS buffer which had been adjusted to pH 8 beforehand and was then applied to PD-10 columns (Sephadex® G-25, GE Healthcare) which had been equilibrated with PBS buffer pH 8 and was eluted with PBS buffer pH 8. The eluate was stirred under argon at RT overnight and then concentrated by ultracentrifugation and rediluted with PBS buffer (pH 7.2). Under these conditions, some of the ADCs may also be present in the ring-closed form. The ADC batch obtained was characterized as follows:

Protein concentration: 1.59 mg/ml
Drug/mAb ratio: 2.5

Example 317m3

Under argon, a solution of 0.029 mg of TCEP in 50 μl of PBS buffer was added to 5 mg of anti-CD123 $AK_{1C}$ (TPP-6013) in 450 μl of PBS (c=11.11 mg/ml). The reaction was stirred at RT for 30 min. 0.308 mg (0.00023 mmol) of Example 318m1

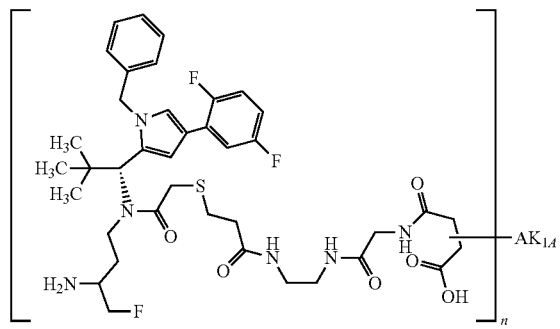

Under argon, a solution of 0.029 mg of TCEP in 50 μl of PBS buffer was added to 5 mg of anti-CD123 $AK_{1A}$ (TPP-5969) in 450 μl of PBS (c=11.11 mg/ml). The mixture was stirred at RT for 30 min. 0.206 mg (0.00023 mmol) of intermediate F318, dissolved in 50 μl of DMSO, was then added. After a further 90 min of stirring at RT, the mixture was diluted with 1950 μl of PBS buffer which had been adjusted to pH 8 beforehand and was then applied to PD-10 columns (Sephadex® G-25, GE Healthcare) which had been equilibrated with PBS buffer pH 8 and was eluted with PBS buffer pH 8. The eluate was stirred under argon at RT overnight and then concentrated by ultracentrifugation and rediluted with PBS buffer (pH 7.2). Under these conditions, some of the ADCs may also be present in the ring-closed form. The ADC batch obtained was characterized as follows:
Protein concentration: 1.39 mg/ml
Drug/mAb ratio: 5.2

Example 318m3

Under argon, a solution of 0.029 mg of TCEP in 50 µl of PBS buffer was added to 5 mg of anti-CD123 $AK_{1C}$ (TPP-6013) in 450 µl of PBS (c=11.11 mg/ml). The mixture was stirred at RT for 30 min. 0.206 mg (0.00023 mmol) of intermediate F318, dissolved in 50 µl of DMSO, was then added. After a further 90 min of stirring at RT, the mixture was diluted with 1950 µl of PBS buffer which had been adjusted to pH 8 beforehand and was then applied to PD-10 columns (Sephadex® G-25, GE Healthcare) which had been equilibrated with PBS buffer pH 8 and was eluted with PBS buffer pH 8. The eluate was stirred under argon at RT overnight and then concentrated by ultracentrifugation and rediluted with PBS buffer (pH 7.2). Under these conditions, some of the ADCs may also be present in the ring-closed form. The ADC batch obtained was characterized as follows:
Protein concentration: 1.46 mg/ml
Drug/mAb ratio: 4.0

Example 319m1

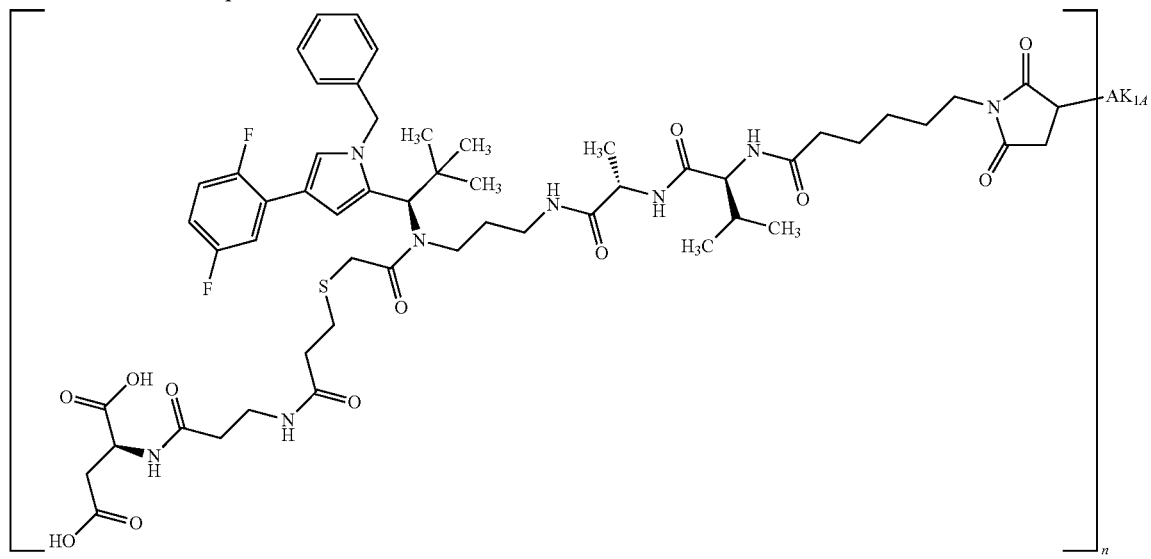

Under argon, a solution of 0.143 mg of TCEP in 0.25 ml of PBS buffer was added to 25 mg of anti-CD123 $AK_{1A}$ (TPP-5969) in 2.5 ml of PBS (c=10.0 mg/ml). The mixture was stirred at RT for 30 min and 0.923 mg (0.00083 mmol) of intermediate F319, dissolved in 250 µl of DMSO, were then added. After a further 90 min of stirring at RT, the mixture was diluted with 2 ml of PBS buffer.

The mixture was then purified on PD-10 columns and the eluate was diluted with PBS to a total volume of 14 ml. Subsequently, the mixture was concentrated by ultracentrifugation, rediluted with PBS buffer and concentrated again. The ADC batch obtained was characterized as follows:
Protein concentration: 12.79 mg/ml
Drug/mAb ratio: 3.9

Example 320m1

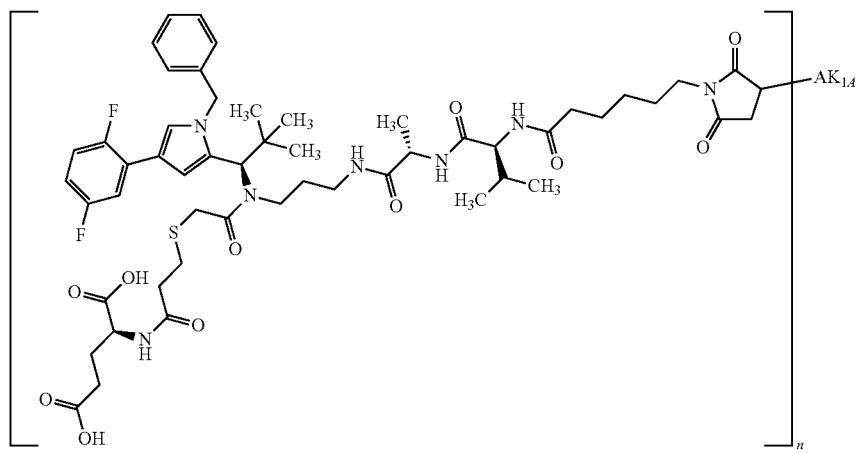

Here, 5 mg of anti-CD123 AK$_{1A}$ (TPP-5969) in 374 µl of PBS at pH 7.2 (c=13.36 mg/ml) were used for coupling with intermediate F320. The reduction time of the antibody in the presence of 0.029 mg of TCEP was 30 min. After addition of 0.245 mg (0.23 µmol) of F320 in 100 µl of DMSO, the mixture was then stirred at RT for 90 min and subsequently purified on Sephadex. The mixture was then concentrated by ultracentrifugation and rediluted with PBS.

Protein concentration: 1.84 mg/ml
Drug/mAb ratio: 1.8

Example 321m1

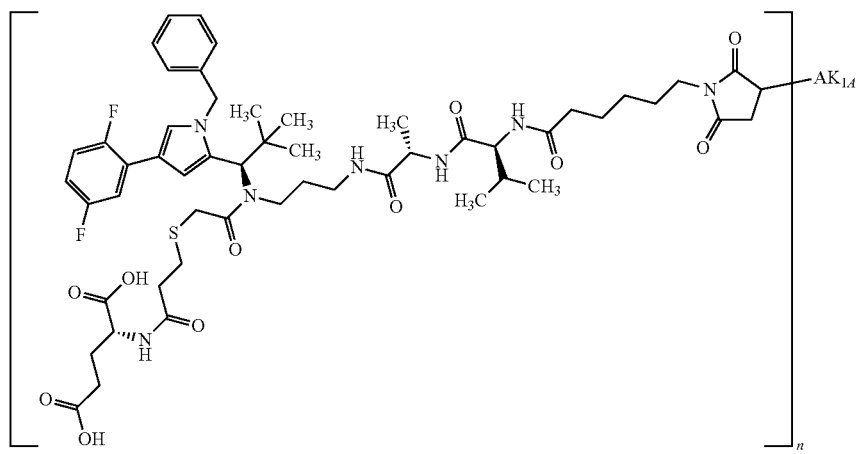

Here, 5 mg of anti-CD123 AK$_{1A}$ (TPP-5969) in 374 µl of PBS at pH 7.2 (c=13.36 mg/ml) were used for coupling with intermediate F321. The reduction time of the antibody in the presence of 0.029 mg of TCEP was 30 min. After addition of 0.262 mg (0.23 µmol) of F321 in 100 µl of DMSO, the mixture was then stirred at RT for 90 min and subsequently purified on Sephadex. The mixture was then concentrated by ultracentrifugation and rediluted with PBS.

Protein concentration: 1.93 mg/ml
Drug/mAb ratio: 1.9

Example 322m1

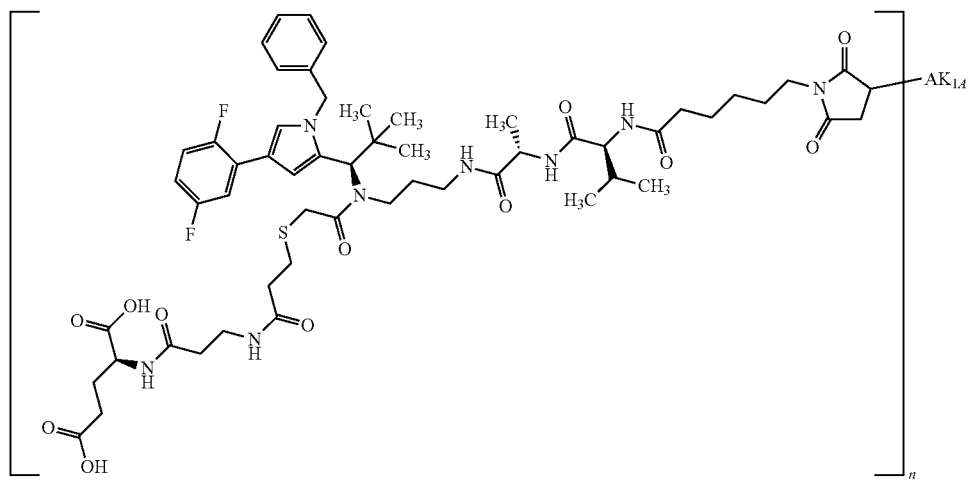

Here, 5 mg of anti-CD123 $AK_{1A}$ (TPP-5969) in 374 μl of PBS at pH 7.2 (c=13.36 mg/ml) were used for coupling with intermediate F322. The reduction time of the antibody in the presence of 0.029 mg of TCEP was 30 min. After addition of 0.262 mg (0.23 μmol) of F322 in 100 μl of DMSO, the mixture was then stirred at RT for 90 min and subsequently purified on Sephadex. The mixture was then concentrated by ultracentrifugation and rediluted with PBS.
Protein concentration: 1.88 mg/ml
Drug/mAb ratio: 1.8

Example 323m1

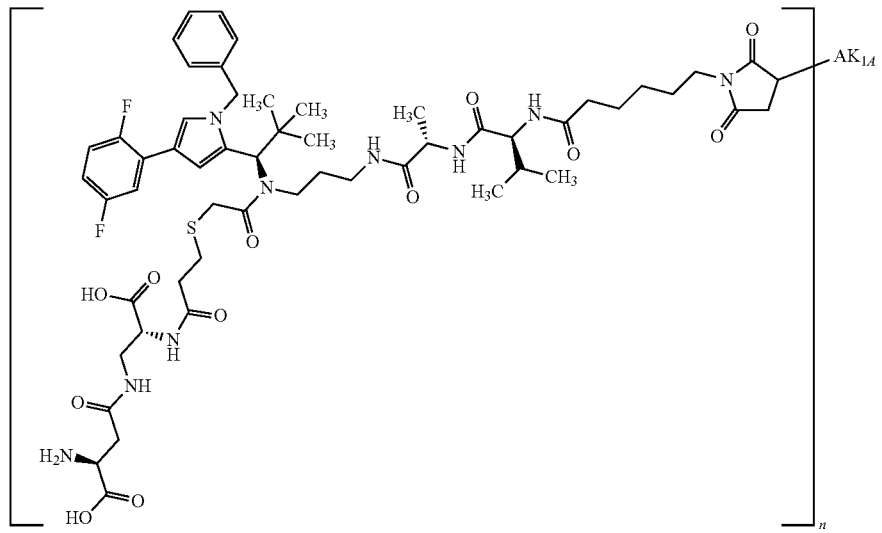

Under argon, a solution of 0.029 mg of TCEP in 50 μl of PBS buffer was added to 5 mg of anti-CD123 $AK_{1A}$ (TPP-5969) in 450 μl of PBS (c=11.11 mg/ml). The mixture was stirred at RT for 30 min. 0.328 mg (0.00023 mmol) of intermediate F323, dissolved in 50 μl of DMSO, was then added. After a further 90 min of stirring at RT, the mixture was diluted with 1950 μl of PBS buffer and then purified on PD-10 columns (Sephadex® G-25, GE Healthcare). The mixture was then concentrated by ultracentrifugation and rediluted with PBS buffer. The ADC batch obtained was characterized as follows:
Protein concentration: 2.03 mg/ml
Drug/mAb ratio: 2.9

Example 323m3

Under argon, a solution of 0.029 mg of TCEP in 50 μl of PBS buffer was added to 5 mg of anti-CD123 $AK_{1C}$ (TPP-6013) in 450 μl of PBS (c=11.11 mg/ml). The mixture was stirred at RT for 30 min. 0.328 mg (0.00023 mmol) of intermediate F323, dissolved in 50 μl of DMSO, was then added. After a further 90 min of stirring at RT, the mixture was diluted with 1950 μl of PBS buffer and then purified on PD-10 columns (Sephadex® G-25, GE Healthcare). The mixture was then concentrated by ultracentrifugation and rediluted with PBS buffer. The ADC batch obtained was characterized as follows:
Protein concentration: 2.06 mg/ml
Drug/mAb ratio: 4.2

Example 324m1

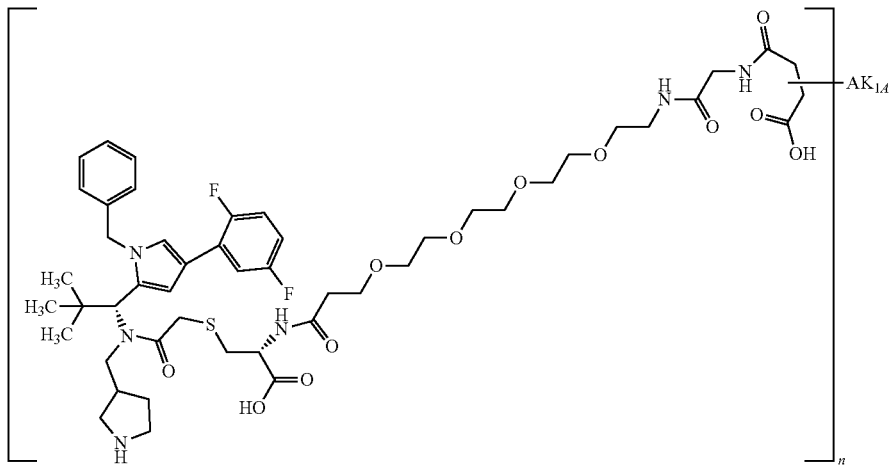

Under argon, a solution of 0.029 mg of TCEP in 50 µl of PBS buffer was added to 5 mg of anti-CD123 $AK_{1A}$ (TPP-5969) in 450 µl of PBS (c=11.11 mg/ml). The mixture was stirred at RT for 30 min. 0.256 mg (0.00023 mmol) of intermediate F324, dissolved in 50 µl of DMSO, was then added. After a further 90 min of stirring at RT, the mixture was diluted with 1950 µl of PBS buffer, which had been adjusted to pH 8 beforehand, and was then applied to PD-10 columns (Sephadex® G-25, GE Healthcare) which had been equilibrated with PBS buffer pH 8 and was eluted with PBS buffer pH 8. The eluate was stirred under argon at RT overnight and then concentrated by ultracentrifugation and rediluted with PBS buffer (pH 7.2). Under these conditions, some of the ADCs may also be present in the ring-closed form. The ADC batch obtained was characterized as follows:
Protein concentration: 1.48 mg/ml
Drug/mAb ratio: 3.1

Example 324m3

Under argon, a solution of 0.029 mg of TCEP in 50 µl of PBS buffer was added to 5 mg of anti-CD123 $AK_{1C}$ (TPP-6013) in 450 µl of PBS (c=11.11 mg/ml). The mixture was stirred at RT for 30 min. 0.256 mg (0.00023 mmol) of intermediate F324, dissolved in 50 µl of DMSO, was then added. After a further 90 min of stirring at RT, the mixture was diluted with 1950 µl of PBS buffer, which had been adjusted to pH 8 beforehand, and was then applied to PD-10 columns (Sephadex® G-25, GE Healthcare) which had been equilibrated with PBS buffer pH 8 and was eluted with PBS buffer pH 8. The eluate was stirred under argon at RT overnight and then concentrated by ultracentrifugation and rediluted with PBS buffer (pH 7.2). Under these conditions, some of the ADCs may also be present in the ring-closed form. The ADC batch obtained was characterized as follows:
Protein concentration: 1.42 mg/ml
Drug/mAb ratio: 4.4

Example 325m3

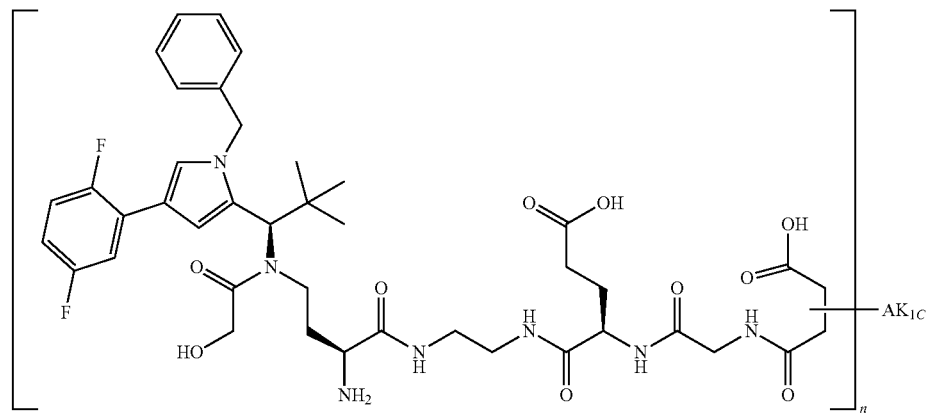

Under argon, a solution of 0.029 mg of TCEP in 50 µl of PBS buffer was added to 5 mg of anti-CD123 AK$_{1C}$ (TPP-6013) in 0.400 ml of PBS (c=12.5 mg/ml). The mixture was stirred at RT for 30 min and 0.22 mg (0.00023 mmol) of intermediate F325, dissolved in 50 µl of DMSO, was then added. After a further 90 min of stirring at RT, the mixture was made up to 2.5 ml with PBS buffer pH 8 and applied to a PD-10 column (Sephadex® G-25, GE Healthcare) equilibrated with PBS buffer pH 8, was eluted with PBS buffer pH 8 and was then stirred under argon at RT overnight. The eluate was then concentrated by ultracentrifugation and rediluted with PBS buffer (pH 7.2). The ADC batch obtained was characterized as follows:

Protein concentration: 1.87 mg/ml
Drug/mAb ratio: 4.1

Example 326m3

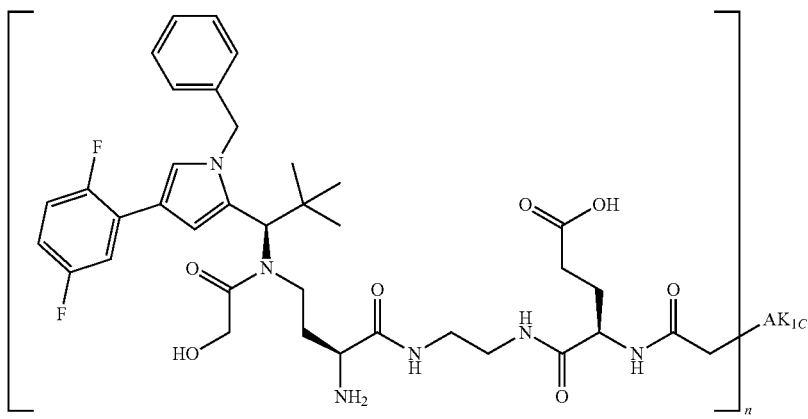

Under argon, a solution of 0.029 mg of TCEP in 50 µl of PBS buffer was added to 5 mg of anti-CD123 AK$_{1C}$ (TPP-6013) in 0.400 ml of PBS (c=12.5 mg/ml). The mixture was stirred at RT for 30 min and 0.22 mg (0.00023 mmol) of intermediate F326, dissolved in 50 µl of DMSO, was then added. The mixture was then stirred under argon at RT overnight, then made up to 2.5 ml with PBS buffer (pH 7.2) and applied to a PD-10 column (Sephadex® G-25, GE Healthcare) equilibrated with PBS buffer pH 7.2. The mixture was then concentrated by ultracentrifugation and rediluted with PBS buffer (pH 7.2). The ADC batch obtained was characterized as follows:

Protein concentration: 1.33 mg/ml
Drug/mAb ratio: 6.0

C: Assessment of Biological Efficacy

The biological activity of the compounds according to the invention can be shown in the assays described below:

C-1a Determination of the Cytotoxic Effects of the ADCs Directed Against CD123

The analysis of the cytotoxic effects of the anti-CD123 ADCs and the corresponding metabolites was carried out with various cell lines:

NCI-H292: human mucoepidermoid lung carcinoma cells, ATCC-CRL-1848, standard medium: RPMI 1640 (Biochrom; # FG1215, stab. glutamine)+10% FCS (Biochrom; # S0415).

MOLM-13: human acute monocytic leukaemia cells (AML-M5a), DSMZ, No. ACC 554, standard medium: RPMI 1640 (Gibco; #21875-059, stab. L-glutamine)+20% heat inactivated FCS (Gibco, No. 10500-064); CD123-positive.

THP-1: human monocytic leukaemia cells, ATCC, NO. TIB-202, standard medium: RPMI 1640 (Gibco; #21875-059, stab. L-glutamine)+10% heat inactivated FCS (Gibco, No. 10500-064)+2.5 g of glucose (20% glucose solution, Gibco, No. 19002); CD123-positive.

KG-1: human acute myeloid leukaemia cells obtained from bone marrow, DSMZ, No. ACC 14, standard medium: RPMI 1640 (Gibco; #21875-059, stab. L-glutamine)+10% heat inactivated FCS (Gibco, No. 10500-064)+2.5 g of glucose (20% glucose solution, Gibco, No. 19002); CD123-positive.

The cells were cultivated by the standard method as stated by the American Tissue Culture Collection (ATCC) or the Leibniz-Institut DSMZ-Deutsche Sammlung von Mikroorganismen und Zellkulturen GmbH (DSMZ) for the cell lines in question.

MTT Assay

The cells were cultivated according to the standard method using the growth media listed under C-1. The test is carried out by detaching the cells with a solution of Accutase in PBS (Biochrom AG # L2143), pelleting, resuspending in culture medium, counting and sowing into a 96-well culture plate with white bottom (Costar #3610) (NCI H292: 2500 cells/well; MOLM-13: 2000 cells/well; THP-1: 8000 cells/well; KG-1: 5000 cells/well in a total volume of 100 µl). The cells were then incubated in an incubator at 37° C. and 5% carbon dioxide. After 48 h, the medium was replaced.

The antibody drug conjugates or the metabolites in 10 µl of culture medium in concentrations from $10^{-5}$M to $10^{-13}$M were then pipetted to the cells (in triplicate), and the assay was then incubated in an incubator at 37° C. and 5% carbon dioxide. After 96 h, the cell proliferation was detected using the MTT assay (ATCC, Manassas, Va., USA, catalogue No. 30-1010K). To this end, the MTT reagent was incubated with the cells for 4 h, followed by lysis of the cells overnight by addition of the detergent. The dye formed was detected at 570 nm (Infinite M1000 pro, Tecan). The measured data were used to calculate the IC$_{50}$ of the growth inhibition using the DRC (dose response curve).

The proliferation of cells which were not treated with test substance but were otherwise identically treated was defined as the 100% figure.

Table 1 below lists the IC$_{50}$ values of representative working examples for different anti-CD123 antibodies from this assay:

TABLE 1

| Example | MOLM 13 IC$_{50}$ [M] MTT assay | THP-1 IC$_{50}$ [M] MTT assay | KG-1 IC$_{50}$ [M] MTT assay |
|---|---|---|---|
| 194m1 | 5.25E−08 | 2.56E−10 | 1.23E−08 |
| 194m2 | 4.82E−08 | 2.05E−10 | 1.92E−08 |
| 194m3 | 1.24E−07 | 1.77E−10 | 1.24E−08 |
| 208m1 | 1.00E−08 | 1.39E−09 | |
| 208m1 TV | 3.28E−09 | 1.03E−10 | |
| 208m2 | 9.85E−08 | 9.15E−10 | |
| 208m3 | 4.62E−08 | 2.75E−09 | |
| 208m3 TV | 2.37E−09 | 2.70E−09 | |
| 208m4 | 6.95E−09 | 8.80E−10 | |
| 240m1 | 2.47E−08 | 1.51E−09 | |
| 240m2 | 2.20E−08 | 2.00E−09 | |
| 240m3 | 2.30E−08 | 1.70E−09 | |
| 257m1 | 2.39E−08 | 3.42E−10 | 4.05E−08 |
| 257m2 | 2.27E−08 | 3.50E−10 | 1.92E−07 |
| 257m3 | 2.02E−08 | 1.11E−09 | 2.07E−07 |
| 257m3 TV | 1.23E−10 | 2.23E−10 | |
| 259m1 | 1.90E−07 | 1.50E−08 | |
| 259m2 | 5.00E−07 | 7.51E−08 | |
| 259m3 | 5.00E−07 | 4.08E−08 | |
| 260m1 | 2.01E−08 | 2.86E−09 | |
| 260m1 TV | 5.09E−09 | 4.00E−09 | |
| 260m2 | 2.07E−08 | 1.14E−09 | |
| 260m3 TV | 1.35E−08 | 4.95E−10 | |
| 270m1 | 2.26E−07 | 1.50E−08 | |
| 270m2 | 7.50E−08 | 7.20E−08 | |
| 270m3 | 1.37E−07 | 2.60E−08 | |
| 271m1 | 4.60E−09 | 4.69E−09 | |
| 271m3 | 1.03E−09 | 9.58E−10 | |
| 274m1 | 2.13E−07 | 1.85E−08 | |
| 274m2 | 2.26E−07 | 1.18E−09 | |
| 274m3 | 2.95E−07 | 5.63E−10 | |
| 276m1 | 3.35E−09 | 1.35E−09 | |
| 276m3 | 4.83E−10 | 6.62E−10 | |
| 281m3 | 2.15E−10 | | 4.37E−09 |
| 284m1 | 2.62E−07 | 5.001E−07 | |
| 284m2 | 2.39E−07 | 2.43E−07 | |
| 284m3 | 1.66E−08 | 7.13E−09 | |
| 296m1 | 1.28E−08 | 2.74E−09 | |
| 296m2 | 9.44E−09 | 1.34E−09 | |
| 296m3 | 1.42E−08 | 2.61E−09 | |
| 297m1 | 3.64E−07 | 5.72E−09 | |
| 297m2 | 1.70E−07 | 4.72E−09 | |
| 297m3 | 4.65E−07 | 2.54E−09 | |
| 309m1 | 9.40E−09 | 3.22E−09 | |
| 309m3 | 4.36E−09 | 9.09E−10 | |
| 310m1 | 3.58E−09 | 4.11E−09 | |
| 310m3 | 3.19E−10 | 3.50E−10 | |
| 314m1 | 5.12E−9 | 4.78E−10 | |
| 314m3 | 1.88E−9 | 2.59E−10 | |
| 317m1 | 1.66E−08 | 7.13E−09 | |
| 317m3 | 1.60E−08 | 7.68E−09 | |
| 318m1 | 1.61E−08 | 3.71E−09 | |
| 318m3 | 4.41E−09 | 2.92E−09 | |
| 319m1 | 2.51E−10 | 1.15E−09 | |
| 320m1 | 7.69E−09 | 1.91E−09 | |
| 321m1 | 3.29E−09 | 1.48E−09 | |
| 322m1 | 3.26E−09 | 9.70E−10 | |
| 323m1 | 2.71E−09 | 1.07E−09 | |
| 323m3 | 1.93E−10 | 7.76E−10 | |
| 324m1 | 2.50E−09 | 3.57E−10 | |
| 324m3 | 4.43E−10 | 4.49E−10 | |
| 325m3 | 3.22E−10 | | |
| 326m3 | 1.66E−09 | | |

The activity data reported relate to the working examples described in the present experimental section, with the drug/mAB ratios indicated. The values may possibly deviate for different drug/mAB ratios. The IC$_{50}$ values are means of several independent experiments or individual values. The action of the CD123 antibody drug conjugates was selective for the respective isotype control comprising the respective linker and toxophor.

C-1b Determination of the Inhibition of the Kinesin Spindle Protein KSP/Eg5 by Selected Examples The motor domain of the human kinesin spindle protein KSP/Eg5 (tebu-bio/Cytoskeleton Inc, No. 027EG01-XL) was incubated in a concentration of 10 nM with microtubuli (bovine or porcine, tebu-bio/Cytoskeleton Inc) stabilized with 50 µg/ml taxol (Sigma No. T7191-5MG) for 5 min at RT in 15 mM PIPES, pH 6.8 (5 mM MgCl$_2$ and 10 mM DTT, Sigma). The freshly prepared mixture was aliquoted into a 384 MTP (Greiner bio-one REF 781096). The inhibitors to be examined at concentrations of 1.0×10-6 M to 1.0×10-13 M and ATP (final concentration 500 µM, Sigma) were then added. Incubation was at RT for 2 h. ATPase activity was detected by detecting the inorganic phosphate formed using malachite green (Biomol). After addition of the reagent, the assay was incubated at RT for 50 min prior to detection of the absorption at a wavelength of 620 nm. The positive controls used were monastrol (Sigma, M8515-1 mg) and ispinesib (AdooQ Bioscience A10486). The individual data of the dose-activity curve are eight-fold determinations. The IC$_{50}$ values are means of two independent experiments. The 100% control was the sample which had not been treated with inhibitors.

Table 2 below lists the IC$_{50}$ values of representative working examples from the assay described and the corresponding cytotoxicity data (MTT assay).

TABLE 2

| Examples | KSP assay IC$_{50}$ [M] | NCI-H292 IC$_{50}$ [M] MTT assay | KPL4 IC$_{50}$ [M] MTT assay |
|---|---|---|---|
| M1 | 2.01E−09 | 5.00E−07 | 5.00E−07 |
| M2 | 2.45E−09 | 2.04E−07 | 1.63E−07 |
| M3 | 1.52E−09 | 3.21E−08 | 9.00E−08 |
| M4 | 2.71E−10 | 4.43E−08 | 1.76E−07 |
| M5 | 4.57E−10 | 7.94E−08 | 2.22E−07 |
| M6 | 1.78E−09 | 4.63E−08 | 1.93E−07 |
| M7 | 6.21E−10 | 2.22E−08 | 9.25E−08 |
| M9 | 1.07E−09 | 7.74E−10 | 2.57E−10 |
| M10 | 4.70E−10 | 3.03E−07 | 2.26E−07 |
| M11 | 1.11E−09 | 4.32E−11 | |
| M12 | 4.46E−10 | 3.3E−08 | |
| M13 | 1.50E−09 | 1.52E−07 | 1.69E−07 |
| M14 | 2.16E−09 | 1.74E−07 | 1.82E−07 |
| M15 | 9.64E−10 | 1.33E−07 | 1.69E−07 |
| M16 | 1.48E−09 | 1.43E−07 | 1.95E−07 |
| M17 | 4.17E−09 | 7.35E−09 | |
| M18 | 5.17E−09 | 3.55E−08 | |
| M19 | 2.58E−09 | 1.21E−07 | |
| M20 | 1.50E−09 | 1.49E−07 | 2.13E−07 |
| M21 | 2.31E−09 | | |
| M22 | 8.27E−10 | 2.89E−08 | 1.82E−07 |
| M23 | 1.26E−09 | 5.00E−07 | 5.00E−07 |
| M24 | 2.90E−09 | 1.67E−07 | 5.00E−07 |
| M25 | 2.91E−09 | 5.00E−07 | 5.00E−07 |
| M26 | 9.44E−10 | 6.38E−08 | |
| M27 | 2.03E−09 | 2.76E−07 | |

The activity data reported relate to the working examples described in the present experimental section.

C-2a Internalisation Assay

Internalisation is a key process which enables specific and efficient provision of the cytotoxic payload in antigen-expressing cancer cells via antibody drug conjugates (ADC). This process is monitored via fluorescent labelling of specific CD123 antibodies and an isotype control antibody labelled with a pH-sensitive fluorophor. First, the fluorescent dye was conjugated to lysines of the antibody. Conjugation was carried out using a two-fold molar excess of CypHer 5E mono NHS ester (Batch 357392, GE Healthcare) at pH 8.3.

After the coupling, the reaction mixture was purified by gel chromatography (Zeba Spin Desalting Columns, 40K, Thermo Scientific, No. 87768; elution buffer: DULBECCO'S PBS, Sigma-Aldrich, No. D8537), to eliminate excess dye and to adjust the pH. The protein solution was concentrated using VIVASPIN 500 columns (Sartorius stedim biotec VS0131). The dye load of the antibody was determined by spectrophotometric analysis (NanoDrop) and subsequent calculation using the following equation D: $P = A_{dye} \varepsilon_{protein}$: $(A_{280} - 0.16 A_{dye}) \varepsilon_{dye}$. The dye load of the CD123 antibodies examined here and the isotype control were of a comparable order. In cell binding assays, it was confirmed that the conjugation did not lead to a change in the affinity of the antibodies. The antigen to be examined is expressed by haematopoietic suspension cells, and the internalisation of the labelled CD123 antibodies was therefore examined in an FACS-based internalisation assay. To this end, cell lines with different expression levels of the receptor were selected and tested. The cells ($5 \times 10^4$/well) were sown in a 96-MTP in a total volume of 100 µl (Greiner bio-one, CELLSTAR, 650 180, U-bottom). After addition of the anti-CD123 antibody to be examined in a final concentration of 10 µg/ml, the cell batches were incubated at 37° C. for different periods (1 h, 2 h, 6 h, in triplicate). The same treatment protocol was applied to the labelled isotype control (negative control). In parallel, identical test batches were processed at 4° C. (negative control). FACS analysis was then carried out using the Guava flow cytometer (Millipore). Kinetic evaluation was via measurement of the fluorescence intensity using the guavaSoft 2.6 software (Millipore). A target-mediated specific internalisation of the anti-CD123 antibodies was observed in various cancer cell lines (MOLM-13, THP-1, KG-1), whereas the isotype control and the 4° C. batches showed no internalisation.

C-2b Determination of the Co-Localisation of the Internalised CD123 Antibody in the Lysosome The toxic active compound of the antibody drug conjugates is released in the lysosome, owing to the linker selected. The transport of the antibody to this organelle is therefore crucial. By co-localisation of the antibody with marker proteins specific for the lysosome (e.g. surface protein or small GTPasen), it is possible to identify antibodies having a suitable profile. To this end, the CD123-positive cells ($5 \times 10^4$/well) in 100 µl of medium were initially sown into a 96-MTP (Greiner bio-one, CELLSTAR, 650 180, U-bottom). After addition of the CypHer5E-labelled anti-CD123 antibody (final concentration 20 µg/ml), the batches were incubated in duplicate at 37° C. for 6 h. In each case 30 min prior to the end of the incubation time, a lysosome-specific live dye was added to the samples. The lysomes were stained using the CytoPainter LysoGreen indicator reagent (final concentration 1:2000; abcam, ab176826). After incubation, 200 µl of ice-cold FACS buffer (DULBECCO'S PBS, Sigma-Aldrich, No. D8537+3% FBS heat inactivated FBS, Gibco, No. 10500-064) were pipetted into the batch and the cell suspension was centrifuged at 400×g and 4° C. for 5 min. The pellet was then resuspended in 300 µl ice-cold FACS buffer and centrifuged again (4 min, 400×g at 4° C.). After the centrifugation, the supernatant was discarded and the pellet was taken up in 30 µl of ice-cold FACS buffer. The samples prepared in this manner were immediately subjected to FACS/image analysis (FlowSight amnis, Millipore). Co-localisation was evaluated using the specific co-localisation software IDEAS Application v6.1. Table 3 summarizes the data from this assay for the anti-CD123 antibodies examined.

TABLE 3

| Examples | Co-localisation [%] |
|---|---|
| TPP-6013 | 43.5 |
| TPP-5969 | 26.0 |
| 7G3 | 10.0 |
| Isotype control | 0.2 |

C-3 In Vitro Tests for Determining Cell Permeability

The cell permeability of a substance can be investigated by means of in vitro testing in a flux assay using Caco-2 cells [M. D. Troutman and D. R. Thakker, Pharm. Res. 20 (8), 1210-1224 (2003)]. For this purpose, the cells were cultured for 15-16 days on 24-well filter plates. For the determination of permeation, the respective test substance was applied in a HEPES buffer to the cells either apically (A) or basally (B) and incubated for 2 hours. After 0 hours and after 2 hours, samples were taken from the cis and trans compartments. The samples were separated by HPLC (Agilent 1200, Biblingen, Germany) using reverse phase columns. The HPLC system was coupled via a Turbo Ion Spray Interface to a Triple Quadropol mass spectrometer API 4000 (AB SCIEX Deutschland GmbH, Darmstadt, Germany). The permeability was evaluated on the basis of a $P_{app}$ value, which was calculated using the formula published by Schwab et al. [D. Schwab et al., J. Med. Chem. 46, 1716-1725 (2003)]. A substance was classified as actively transported when the ratio of $P_{app}$ (B-A) to $P_{app}$ (A-B) (efflux ratio) was >2 or ≤0.5.

Of critical importance for toxophores which are released intracellularly is the permeability from B to A [$P_{app}$ (B-A)] and the ratio of $P_{app}$ (B-A) to $P_{app}$ (A-B) (efflux ratio): the lower this permeability, the slower the active and passive transport processes of the substance through the monolayer of Caco-2 cells. If additionally the efflux ratio does not indicate any active transport, the substance may, following intracellular release, remain longer in the cell. Hence, there is also more time available for interaction with the biochemical target (in this case: kinesin spindle protein, KSP/Eg5).

Table 4 below sets out permeability data for representative working examples from this assay:

TABLE 4

| Working Example | $P_{app}$ (B-A) [nm/s] | Efflux ratio |
|---|---|---|
| M1 | 7.8 | 4 |
| M2 | 4.8 | 6.4 |
| M3 | 1.4 | 1.3 |
| M4 | 21.3 | 18.7 |
| M5 | 20.3 | 26.5 |
| M6 | 1.7 | 0.7 |
| M7 | 5.6 | 2.2 |
| M9 | 213 | 16 |
| M11 | 24.3 | 27.7 |
| M12 | 3.3 | 1.8 |
| M13 | 7.1 | 3.6 |
| M14 | 12.7 | 6.6 |
| M15 | 6.4 | 4.4 |
| M16 | 9.0 | 7.0 |
| M17 | 93.6 | 81.5 |
| M18 | 1.6 | 2.9 |
| M19 | 1.9 | 2.9 |
| M21 | 0.5 | 1.5 |
| M22 | 0.9 | 0.9 |
| M23 | 2.8 | 2.0 |

TABLE 4-continued

| Working Example | $P_{app}$ (B-A) [nm/s] | Efflux ratio |
|---|---|---|
| M24 | 3.9 | 1.0 |
| M25 | 8.1 | 3.6 |
| M26 | 13.0 | 9.6 |
| M27 | 13.2 | 11.9 |

C-4 In Vitro Tests for Determining the Substrate Properties for P-Glycoprotein (P-Gp)

Many tumour cells express transporter proteins for drugs, and this frequently accompanies the development of resistance towards cytostatics. Substances which are not substrates of such transporter proteins, such as P-glycoprotein (P-gp) or BCRP, for example, could therefore exhibit an improved activity profile.

The substrate properties of a substance for P-gp (ABCB1) were determined by means of a flux assay using LLC-PK1 cells which overexpress P-gp (L-MDR1 cells) [A. H. Schinkel et al., *J. Clin. Invest.* 96, 1698-1705 (1995)]. For this purpose, the LLC-PK1 cells or L-MDR1 cells were cultured on 96-well filter plates for 3-4 days. For determination of the permeation, the respective test substance, alone or in the presence of an inhibitor (such as ivermectin or verapamil, for example), was applied in a HEPES buffer to the cells either apically (A) or basally (B) and incubated for 2 hours. After 0 hours and after 2 hours, samples were taken from the cis and trans compartments. The samples were separated by HPLC using reverse phase columns. The HPLC system was coupled via a Turbo Ion Spray Interface to a Triple Quadropol mass spectrometer API 3000 (Applied Biosystems Applera, Darmstadt, Germany). The permeability was evaluated on the basis of a $P_{app}$ value, which was calculated using the formula published by Schwab et al. [D. Schwab et al., *J. Med. Chem.* 46, 1716-1725 (2003)]. A substance was classified as P-gp substrate when the efflux ratio of $P_{app}$ (B-A) to $P_{app}$ (A-B) was >2.

As further criteria for the evaluation of the P-gp substrate properties, the efflux ratios in L-MDR1 and LLC-PK1 cells or the efflux ratio in the presence or absence of an inhibitor may be compared. If these values differ by a factor of more than 2, the substance in question is a P-gp substrate.

C-5 Pharmacokinetics

C5a: Identification of the ADC Metabolites after Internalisation In Vitro

Description of the Method:

Internalisation studies with immunoconjugates are carried out to analyse metabolites formed intracellularly. To this end, human lung tumour cells NCI H292 ($3\times10^5$/well) are sown in 6-well plates and incubated overnight (37° C., 5% $CO_2$). The cells are treated with 10 µg/ml (66 nM) of the ADC to be examined. Internalisation was carried out at 37° C. and 5% $CO_2$. At various time points (0, 4, 24, 48, 72 h), cell samples are taken for further analysis. First, the supernatants (about 5 ml) are harvested and, after centrifugation (2 min, RT, 1000 rpm Heraeus Variofuge 3.0R), stored at −80° C. The cells are washed with PBS and detached with Accutase, and the cell number is determined. After another washing, a defined number of cells ($2\times10^5$) is treated with 100 ml of lysis buffer (Mammalian Cell Lysis Kit (Sigma MCL1) and incubated with continuous shaking (Thermomixer, 15 min, 4° C., 650 rpm) in Protein LoBind tubes (Eppendorf Cat. No. 0030 108.116). After the incubation, the lysate is centrifuged (10 min, 4° C., 12000 g, Eppendorf 5415R) and the supernatant is harvested. The supernatant obtained is stored at −80° C. All samples are then analysed as follows.

Measurement of the compounds in the culture supernatant or cell lysate is carried out after precipitation of the proteins with methanol or acetonitrile by high-pressure liquid chromatography (HPLC) coupled to a triple-quadrupole mass spectrometer (MS).

For work-up of 50 µl of culture supernatant/cell lysate, 150 µl of precipitation reagent (generally acetonitrile) are added and the mixture is shaken for 10 seconds. The precipitation reagent contains an internal standard (ISTD) in a suitable concentration (generally in the range of 20-100 ng/ml). After 3 minutes of centrifugation at 16000 g, the supernatant is transferred into an autosampler vial, made up with 500 µl of a buffer suitable for the mobile phase and shaken again.

The two matrix samples are then measured using the HPLC-coupled triple-quadrupol mass spectrometer API6500 from AB SCIEX Deutschland GmbH.

For calibration, concentrations of 0.5-2000 µg/l are added to plasma samples. The detection limit (LOQ) is about 2 µg/l. The linear range extends from 2 to 1000 µg/l.

For calibration of the tumour samples, concentrations of 0.5-200 µg/l are added to the supernatant of untreated tumours. The detection limit is 4 µg/l. The linear range extends from 4 to 200 µg/l.

Quality controls for testing validity contain 5 and 50 µg/l.

C5b: Identification of the ADC Metabolites In Vivo

After i.v. administration of 3-30 mg/kg of different ADCs, the plasma and tumour concentrations of the ADCs and any metabolites occurring can be measured, and the pharmacokinetic parameters such as clearance (CL), area under the curve (AUC) and half-times ($t_{1/2}$) can be calculated.

Analysis for Quantification of any Metabolites Occurring

Measurement of the compounds in plasma and tumour is carried out after precipitation of the proteins with methanol or acetonitrile by high-pressure liquid chromatography (HPLC) coupled to a triple-quadrupole mass spectrometer (MS).

For work-up of 50 µl of plasma, 250 µl of precipitation reagent (generally acetonitrile) are added and the mixture is shaken for 10 seconds. The precipitation reagent contains an internal standard (ISTD) in a suitable concentration (generally in the range of 20-100 ng/ml). After 3 minutes of centrifugation at 16000 g, the supernatant is transferred into an autosampler vial, made up with 500 µl of a buffer suitable for the mobile phase and shaken again.

During the work-up of a tumour, the latter is treated with 3 times the amount of extraction buffer. The extraction buffer contains 50 ml of Tissue Protein Extraction Reagent (Pierce, Rockford, Ill.), two pellets of Complete-Protease-Inhibitor-Cocktail (Roche Diagnostics GmbH, Mannheim, Germany) and phenylmethylsulphonyl fluoride (Sigma, St. Louis, Mo.) in a final concentration of 1 mM. The sample is homogenized twice for 20 minutes in a Tissuelyser II (Qiagen), at maximum stroke number. 50 µl of the homogenate are transferred into an autosampler vial and made up with 150 µl of methanol including ISTD. After 3 minutes of centrifugation at 16000 g, 10 µl of the supernatant are made up with 180 µl of a buffer suitable for the mobile phase and shaken again. The tumour sample is then ready for measuring.

The two matrix samples are then measured using the HPLC-coupled triple-quadrupol mass spectrometer API6500 from AB SCIEX Deutschland GmbH.

For calibration, concentrations of 0.5-2000 µg/l are added to plasma samples. The detection limit (LOQ) is about 2 µg/l. The linear range extends from 2 to 1000 µg/l.

For calibration of the tumour samples, concentrations of 0.5-200 µg/l are added to the supernatant of untreated tumours. The detection limit is 5 µg/l. The linear range extends from 5 to 200 µg/l.

Quality controls for testing validity contain 5 and 50 µg/l, in plasma additionally 500 µg/l.

Analysis for Quantification of the Antibodies Used

The antibody part of the ADCs was determined using a ligand binding assay (ELISA) as total IgG concentration in plasma samples and tumour lysates. Here, the sandwich ELISA format was used. This ELISA had been qualified and validated for the determination in plasma and tumour samples. The ELISA plates were coated with anti-human goat IgG Fc antibodies. After incubation with the sample, the plates were washed and incubated with a detector conjugate of simian anti-human IgG(H+L) antibody and horseradish peroxidase (HRP). After a further washing step, the HRP substrate was added to OPD and the colour development was monitored via absorption at 490 nm.

Standard samples having a known IgG concentration were fitted using a 4-parameter equation. Within the lower (LLOQ) and upper (ULOQ) quantification limits, the unknown concentrations were determined by interpolation.

C-6 Efficacy Test In Vivo

The efficacy of the conjugates according to the invention could be tested in vivo using, for example, xenograft models. The person skilled in the art is familiar with prior art methods which can be used to test the efficacy of the compounds according to the invention (see, for example, WO 2005/081711; Polson et al., Cancer Res. 2009 Mar. 15; 69(6):2358-64).

To this end, for example, a tumour cell line expressing the target molecule of the binder was implanted into rodents (e.g. mice). A conjugate according to the invention, an isotype antibody control conjugate or a control antibody or isotonic saline was then administered to the implant animals. Administration was carried out once or more than once. After an incubation time of several days, the tumour size was determined by comparison of conjugate-treated animals and the control group (control conjugate). The conjugate-treated animals showed a smaller tumour size.

C-6a. Growth Inhibition/Regression of Experimental Tumours in Mice

Human tumour cells expressing the antigen for the antibody drug conjugate were inoculated subcutaneously into the flank of immunosuppressed mice, for example NMRi nude or SCID mice. 1-10 million cells were detached from the cell culture, centrifuged and resuspended in medium or medium/Matrigel. The cell suspension was injected under the skin of the mouse.

Within a number of days, a tumour grew. Treatment was initiated after the tumour had established, at a tumour size of approximately 40 mm². To examine the effect on larger tumours, it is also possible to initiate the treatment only at a tumour size of 50-100 mm².

The treatment of the mouse with the ADCs was carried out via the intraperitoneal (i.p.) route. The ADC was administered in a volume of 5 ml/kg.

The treatment protocol depended on the pharmacokinetics of the antibody conjugate. As a standard, there were four successive treatments on every fourth day. For a quick assessment, it is also possible to use a protocol with a single treatment. However, the treatment may also be continued, or a second cycle of three treatment days may follow at a later stage.

As standard, 8 animals were used per treatment group. In addition to the groups which received the active substances, one group, as control group, was treated only with buffer, following the same protocol.

During the course of the experiment, the tumour area was measured regularly in two dimensions (length/width) using a caliper. The tumour area was determined as length×width. The comparison of the mean tumour area of the treatment group to that of the control group was stated as T/C area.

If all groups of the experiment were terminated at the same time at the end of the treatment, the tumours could be removed and weighed. The comparison of the mean tumour weight of the treatment group to that of the control group was stated as T/C weight.

C-6b. Efficacy in Human Tumour Xenograft Models

The tumour cells in question were inoculated subcutaneously into the flank of female NMRI-nude mice (Janvier). At a tumour size of ~40 mm², the animals were treated intravenously with the antibody drug conjugate. Subsequent to the treatment, tumour growth was optionally monitored further.

Treatment with the anti CD123 antibody drug conjugates resulted in a marked and long-lasting growth inhibition of the tumours compared to the control group and the isotype drug conjugates. The T/C values, determined over the tumour area on the day with the last measured value of the isotype group, calculated after inoculation, are stated in Table 5.

TABLE 5

| Example | Tumour model | Dose | Dosage protocol | T/C area |
|---|---|---|---|---|
| 257-m1 (TV) | THP-1 (human acute myeloid leukaemia) | 10 mg/kg | Q4dx4 | 0.41 (day 33) |
| 257-m3 (TV) | THP-1 (human acute myeloid leukaemia) | 10 mg/kg | Q4dx4 | 0.3 (day 33) |
| 257-m1 (TV) | MOLM-13 (human acute myeloid leukaemia) | 10 mg/kg | Q4dx4 | 0.26 (day 26) |
| 257-m3 (TV) | MOLM-13 (human acute myeloid leukaemia) | 10 mg/kg | Q4dx4 | 0.22 (day 26) |
| 208-m1 (TV) | MOLM-13 (human acute myeloid leukaemia) | 10 mg/kg | Q4dx4 | 0.28 (day 22) |
| 208-m3 (TV) | MOLM-13 (human acute myeloid leukaemia) | 10 mg/kg | Q4dx4 | 0.38 (day 22) |

Working Examples of Anti-CD123 Antibodies

All examples were carried out using standard methods known to the person skilled in the art, unless described here in detail. Routine methods of molecular biology of the examples that follow can be carried out as described in standard laboratory textbooks such as Sambrook et al., Molecular Cloning: a Laboratory Manual, 2. Edition; Cold Spring Harbor Laboratory Press, Cold Spring Harbor, N.Y., 1989.

Determination of the Binding Affinity of the Antibodies by Surface Plasmon Resonance:

Surface plasmon resonance experiments for quantitative binding analysis were carried out using a Biacore T200 instrument (GE Healthcare Biacore, Inc.). Here the antibodies to be examined were fixed with the aid of an anti-human Fc antibody ("Human Antibody Capture Kit", BR-1008-39, GE Healthcare Biacore, Inc.) amine-coupled to the sensor chip surface. Amine coupling was performed according to the manufacturer's instructions using 1-ethyl-3-(3-dimethylaminopropyl)carbodiimide hydrochloride (EDC), N-hydroxysuccinimide (NHS) and ethanolamine HCl pH 8.5 ("Amine Coupling Kit" BR-1000-50, GE Healthcare Biacore, Inc.). For the analyses, Series S sensor chips CM5 (GE Healthcare Biacore, Inc.) were used with the mobile buffer HBS-EP+ (10 mM HEPES pH 7.4, 150 mM NaCl, 3 mM EDTA, 0.05% Surfactant P20). All experimental steps were carried out at 25° C. After fixation of the anti-CD123 antibodies to be examined, injections of the extracellular domain of IL3Ra (Analyt, R&D Systems) in a concentration range of from 1.56 to 200 nM were carried out, and after each antigen injection the sensor surface was regenerated with glycine HCl pH 2.0. Prior to another analyte injection, antibodies were in each case fixed as above, under identical conditions. For all measurements, an upstream flow cell only containing immobilized amine-coupled anti-human Fc antibody was used as reference cell. Evaluation of the sensorgrams obtained was, after double referencing (subtraction of the reference flow cell signal and a buffer injection), carried out by a global fit based on a 1:1 Langmuir binding model with the aid of the Biacore T200 evaluation software (GE Healthcare Biacore, Inc.).

TABLE 6a

Recombinant antigen (IL3R3alpha/CD123) used for affinity determination

| Nomenclature | Description | Origin | Cat. No. (R&D) |
|---|---|---|---|
| TPP-5521 | IL3Ra aa20-305 | murine | 203-IL |

TABLE 6b

Monovalent $K_D$ values of the anti-CD123 antibodies determined with Biacore using IL3Ra protein (TPP-5521 as analyte)

| | ka (1/Ms) | kd (1/s) | $K_D$ (nM) |
|---|---|---|---|
| TPP-6013 | 3.0E+05 | 1.9E−04 | 0.6E−09 |

Binding of Anti-CD123 Antibodies to Various Antigen-Expressing Cancer Cell Lines Binding of the anti-CD123 antibodies was examined by flow cytometry using different human haematological cell lines (MOLM-13, THP-1, KG-1). To this end, the cells ($5 \times 10^5$ cells/well) were incubated in FACS buffer (PBS without Ca/Mg, 3% FCS, Biochrom) with 10 µg/ml primary antibody solution (start concentration) on ice for 30-45 min protected from light. A dose activity curve (1:5 dilution) was plotted. After the incubation, 200 µl of ice-cold FACS buffer were added using a pipette, and the cell suspension was centrifuged at 4° C., 400 g, for 4 min. The cell pellet was washed with 300 µl of ice-cold FACS buffer and the pellet obtained was then resuspended in 100 µl FACS buffer and incubated again with secondary antibody (monoclonal anti-kappa light chains-FITC antibody, Sigma, No. SAB4700605) in a 1:10 dilution on ice for 30 min. The cells were then washed with ice-cold FACS buffer and adjusted to a cell concentration of $0.5 \times 10^6$ cell/ml prior to flow cytometry using a Guava flow cytometer (Millipore). Propidium iodide (final concentration 1 µg/ml) was used for live staining. The EC50 values of the antibodies to be examined were determined by means of titration curves (Table 7).

TABLE 7

FACS analysis: Binding of the anti-CD123 antibodies to different cancer cell lines.

| Cell Line | Source | TPP-6013 | TPP-5969 |
|---|---|---|---|
| KG1 | ATCC CCL-246 | 3.0E−09 | 2.8E−09 |
| MOLM-13 | DSMZ No. ACC 554 | 2.4E−09 | 5.3E−09 |
| THP-1 | ATCC No. TIB-202 | 34.1E−09 | 8.9E−09 |
| MV-4-11 | ATCC No. CRL 9591 | 1.0E−09 | 2.6E−092 |
| L428 | DSMZ No. ACC197 | 2.2E−09 | |

---

The invention claimed is:
1. A conjugate of an antibody with one or more drug molecules of the formula below:

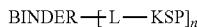

wherein
BINDER is an anti-CD 123 antibody which is a chimeric or humanized variant of the antibody 7G3 or 12F1 or is an antigen-binding fragment thereof;
L is a linker;
n is a number from 1 to 50; and
KSP is a compound of the formula (I) below:
Formula (I):

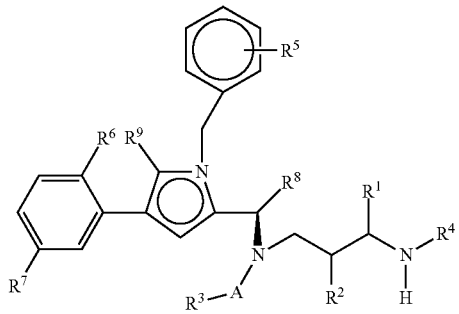

wherein
$R^1$ is —H, -L-#1, -MOD or —$(CH_2)_{0-3}$Z,
wherein
Z is —H, —$NHY^3$, —$OY^3$, —$SY^3$, halogen, —C(=O)—$NY^1Y^2$ or —C(=O)—$OY^3$,
$Y^1$ and $Y^2$ are independently of one another —H, —$NH_2$, —$(CH_2CH_2O)_{0-3}$—$(CH_2)_{0-3}$Z' or —CH$(CH_2W)Z'$,
$Y^3$ is —H or —$(CH_2)_{0-3}$Z',
Z' is —H, —$NH_2$, —$SO_3H$, —COOH, —NH—C(=O)—$CH_2$—$CH_2$—CH($NH_2$)COOH or —(CO—NH—$CHY^4)_{1-3}$COOH,
W is H or OH, and
$Y^4$ is straight-chain or branched $C_{1-6}$ alkyl which is optionally substituted by —NH—C(=O)—$NH_2$, or represents aryl or benzyl which are optionally substituted by —$NH_2$;
$R^2$ is —H, -MOD, —C(=O)—$CHY^4$—$NHY^5$ or —$(CH_2)_{0-3}$Z,
wherein
Z is —H, halogen, —$OY^3$, —$SY^3$, —$NHY^3$, —C(=O)—$NY^1Y^2$ or —C(=O)—$OY^3$,
$Y^1$ and $Y^2$ are independently of one another —H, —$NH_2$ or —$(CH_2)_{0-3}$Z',
$Y^3$ is —H or —$(CH_2)_{0-3}$Z',
Z' is —H, —$SO_3H$, —$NH_2$ or —COOH;
$Y^4$ is straight-chain or branched $C_{1-6}$-alkyl which is optionally substituted by —NH—C(=O)—$NH_2$, or represents aryl or benzyl which are optionally substituted by —$NH_2$,
$Y^5$ is —H or —C(=O)—$CHY^6$—$NH_2$, and
$Y^6$ is straight-chain or branched $C_{1-6}$-alkyl;
$R^4$ is —H, -L-#1, -$SG_{lys}$-$(C=O)_{0-1}$—$R^{4'}$, —C(=O)—$CHY^4$—$NHY^5$ or —$(CH_2)_{0-3}$Z, wherein $SG_{lys}$ is a group which can be cleaved by lysosomal enzymes,
wherein $R^{4'}$ is a $C_{1-10}$-alkyl, $C_{5-10}$-aryl or $C_{6-10}$-aralkyl, $C_{5-10}$-heteroalkyl, $C_{1-10}$-alkyl-O—$C_{6-10}$-aryl, $C_{5-10}$-heterocycloalkyl, heteroaryl, heteroarylalkyl, heteroarylalkoxy, $C_{1-10}$-alkoxy, $C_{6-10}$-aryloxy or $C_{6-10}$-aralkoxy,
$C_{5-10}$-heteroaralkoxy, $C_{1-10}$-alkyl-O—$C_{6-10}$-aryloxy, $C_{5-10}$-heterocycloalkoxy group which may be mono- or polysubstituted by —$NH_2$, —NH-alkyl, —N(alkyl)$_2$, —NH—C(=O)-alkyl, —N(alkyl)-C(=O)-alkyl, —$SO_3H$, —$S(=O)_2$—$NH_2$, —$S(=O)_2$—N(alkyl)$_2$, —COOH, —C(=O)—$NH_2$, —C(=O)—N(Alkyl)$_2$ or —OH, —H or a group —$O_x$—$(CH_2CH_2O)_v$—$R^{4''}$,
wherein x is 0 or 1,
wherein v is a number from 1 to 20,
wherein $R^{4''}$ is —H, -alkyl,
—$CH_2$—COOH, —$CH_2$—$CH_2$—COOH, or —$CH_2$—$CH_2$—$NH_2$;
wherein Z is —H, halogen, —$OY^3$, —$SY^3$, —$NHY^3$, —C(=O)—$NY^1Y^2$ or —C(=O)—$OY^3$,
wherein $Y^1$ and $Y^2$ are independently of one another —H, —$NH_2$ or —$(CH_2)_{0-3}$Z',
wherein $Y^3$ is —H or —$(CH_2)_{0-3}$Z',
wherein Z' is —H, —$SO_3H$, —$NH_2$ or —COOH;
wherein $Y^4$ is straight-chain or branched $C_{1-6}$-alkyl which is optionally substituted by —NH—C(=O)—$NH_2$, or represents aryl or benzyl which are optionally substituted by —$NH_2$,
wherein $Y^5$ is —H or —C(=O)—$CHY^6$—$NH_2$, and
wherein $Y^6$ is straight-chain or branched $C_{1-6}$-alkyl;
or
$R^2$ and $R^4$ taken together (with formation of a pyrrolidine ring) are —$CH_2$—$CHR^{11}$— or —$CHR^{11}$—$CH_2$—,
wherein
$R^{11}$ is —H, —$NH_2$, —$SO_3H$, —COOH, —SH, halogen, $C_{1-4}$-alkyl, $C_{1-4}$-haloalkyl, $C_{1-4}$-alkoxy, hydroxyl-substituted
$C_{1-4}$-alkyl, C(=O)—O—($C_{1-4}$-alkyl) or —OH;
A is —C(=O)—, —S(=O)—, —$S(=O)_2$—, —$S(=O)_2$—NH— or —C(=N—$NH_2$)—;
$R^3$ is -L-#1, -MOD or an optionally substituted alkyl, cycloalkyl, aryl, heteroaryl, heteroalkyl, or heterocycloalkyl group,
$R^5$ is —H, —$NH_2$, —$NO_2$, halogen, —CN, $CF_3$, —$OCF_3$, —$CH_2F$, —$CH_2F$, SH or —$(CH_2)_{0-3}$Z, wherein
Z is —H, —$OY^3$, —$SY^3$, halogen, —$NHY^3$, —C(=O)—$NY^1Y^2$ or —C(=O)—$OY^3$
$Y^1$ and $Y^2$ are independently of one another —H, —$NH_2$ or —$(CH_2)_{0-3}$Z',
$Y^3$ is —H or —$(CH_2)_{0-3}$Z', and
Z' is —H, —$SO_3H$, —$NH_2$ or —COOH;
$R^6$ and $R^7$ are independently of one another —H, cyano, $C_{1-10}$-alkyl, fluoro-$C_{1-10}$-alkyl, $C_{2-10}$-alkenyl, fluoro-$C_{2-10}$-alkenyl, $C_{2-10}$-alkynyl, fluoro-$C_{2-10}$-alkynyl, hydroxy, —$NO_2$, —$NH_2$, —COOH or halogen;
$R^8$ is $C_{1-10}$-alkyl, fluoro-$C_{1-10}$-alkyl, $C_{2-10}$-alkenyl, fluoro-$C_{2-10}$-alkyl, $C_{2-10}$-alkynyl, fluoro-$C_{2-10}$-alkynyl, $C_{4-10}$-cycloalkyl, fluoro-$C_{4-10}$-cycloalkyl or —$(CH_2)_{0-2}$—($HZ^2$), which may be mono- or disubstituted, identically or differently, by —OH, —COOH or —$NH_2$, and
wherein
$HZ^2$ is a 4- to 7-membered heterocycle having up to two heteroatoms selected from the group consisting of N, O and S;

$R^9$ is —H, —F, —CH$_3$, —CF$_3$, —CH$_2$F or —CHF$_2$;
wherein
one of the substituents $R^1$, $R^3$ or $R^4$ is -L-#1,
L is the linker and #1 is the bond to the antibody,
MOD is —(NR$^{10}$)$_n$-(G1)$_o$-G2-G3,
wherein
$R^{10}$ is —H or C$_1$-C$_3$-alkyl;
G1 is —NH—C(=O)— or —C(=O)—NH— (wherein, if G1 is —NH—C(=O)—, $R^{10}$ is not —NH$_2$);
n is 0 or 1;
o is 0 or 1; and
G2 is a straight-chain or branched hydrocarbon chain which has 1 to 10 carbon atoms and which may be interrupted once or more than once by one or more of the groups —O—, —S—, —S(=O)—, S(=O)$_2$, —NR$^y$—, —NR$^y$C(=O)—, C(=O)—NR$^y$—, —NR$^y$NR$^y$—, —S(=O)$_2$—NR$^y$NR$^y$—, or —C(=O)—NR$^y$NR$^y$—
wherein
$R^y$ is —H, phenyl, C$_1$-C$_{10}$-alkyl, C$_2$-C$_{10}$-alkenyl or C$_2$-C$_0$-alkynyl, each of which may be mono- or disubstituted, identically or differently, by —NH—C(=O)—NH$_2$, —COOH, —OH, —NH$_2$, —NH—CNNH$_2$, sulphonamide, sulphone, sulphoxide or sulphonic acid,
and/or which may be interrupted once or more than once, identically or differently, by —C(=O)—, —CR$^x$=N—O—, wherein
$R^x$ is —H, C$_1$-C$_3$-alkyl or phenyl, and
wherein
the hydrocarbon chain including a C$_1$-C$_{10}$-alkyl group optionally substituted on the hydrocarbon group as side chain may be substituted by —NH—C(=O)NH$_2$, —COOH, —OH, —NH$_2$, —NH—CN—NH$_2$, sulphonamide, sulphone, sulphoxide or sulphonic acid, G3 is —H or —COOH, and
wherein the group -MOD has at least one group —COOH;
or a salt, a solvate, a salt of a solvate, or an epimer thereof.

2. The conjugate according to claim 1, wherein A is —C(=O)—.

3. The conjugate according to claim 1, wherein $R^1$ is —H, -L-#1, —COOH, —C(=O)—NHNH$_2$, —(CH$_2$)$_{1-3}$NH$_2$, —C(=O)—NZ"(CH$_2$)$_{1-3}$ NH$_2$ or —C(=O)—NZ"CH$_2$COOH, and wherein Z" is —H or —NH$_2$.

4. The conjugate according to claim 1, wherein
$R^2$ and $R^4$ are —H; or
$R^2$ and $R^4$ together (with formation of a pyrrolidine ring) are —CHR$^{11}$—CH$_2$— or —CH$_2$—CHR$^{11}$—,
wherein $R^{11}$ is —H, —COOH, —F, methyl, —CH$_2$F, —O-methyl, —CH$_2$OH, —C(=O)—O—(C$_{1-4}$-alkyl) or —OH.

5. The conjugate according to claim 1, wherein
$R^3$ is -L-#1; or
$R^3$ is a phenyl group which may be mono- or polysubstituted by halogen, C$_{1-3}$-alkyl or fluoro-C$_{1-3}$-alkyl; or
$R^3$ is a C$_{1-10}$-alkyl group or fluoro-C1-10-alkyl group which may optionally be substituted by —OY$^4$, —SY$^4$, —O—C(=O)—Y$^4$, —O—C(=O)—NH—Y$^4$, —NH—C(=O)—Y$^4$, —NH—C(=O)—NH—Y$^4$, —S(O)$_n$—Y$^4$, —S(=O)$_2$—NH—Y$^4$, —NH—Y$^4$ or —N(Y$^4$)$_2$,
wherein
n is 0, 1 or 2, and
$Y^4$ is —H, phenyl which is optionally mono- or polysubstituted by halogen, C$_{1-3}$-alkyl or fluoro-C$_{1-3}$-alkyl, or is alkyl which may be substituted by —OH, —COOH and/or —NH—C(=O)—C$_{1-3}$-alkyl.

6. The conjugate according to claim 5, wherein the conjugate has the formula (IIj) below:

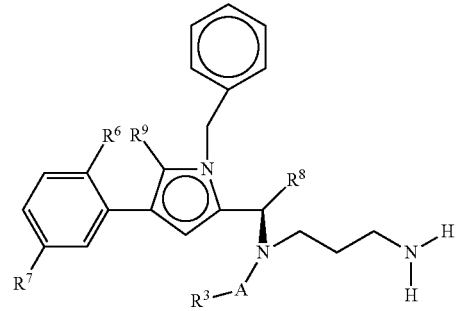

(IIj)

wherein
$R^3$ is -L-#1;
A is —C(=O)—; and
$R^6$ and $R^7$ are independently of one another —H, cyano, C$_{1-10}$-alkyl, fluoro-C$_{1-10}$-alkyl, C$_{2-10}$-alkenyl, fluoro-C$_{2-10}$-alkenyl, C$_2$-o-alkynyl, fluoro-C$_{2-10}$-alkynyl, hydroxy, —NO$_2$, —NH$_2$, —COOH or halogen;
$R^8$ is C$_{1-10}$-alkyl, fluoro-C$_{1-10}$-alkyl, C$_{2-10}$-alkenyl, fluoro-C$_{2-10}$-alkenyl, C$_{2-10}$-alkynyl, fluoro-C$_{2-10}$-alkynyl, C$_{4-10}$-cycloalkyl, fluoro-C$_{4-10}$-cycloalkyl or —(CH$_2$)$_{0-2}$—(HZ$^2$), which may be mono- or disubstituted, identically or differently, by —OH, —COOH or —NH$_2$,
wherein
HZ$^2$ is a 4- to 7-membered heterocycle having up to two heteroatoms selected from the group consisting of N, O and S; and
$R^9$ is —H, —F, —CH$_3$, —CF$_3$, —CH$_2$F or —CHF$_2$.

7. The conjugate according to claim 1, wherein the substituent $R^1$ is -L-#1.

8. The conjugate according to claim 7, where the conjugate has the formula (IIk):

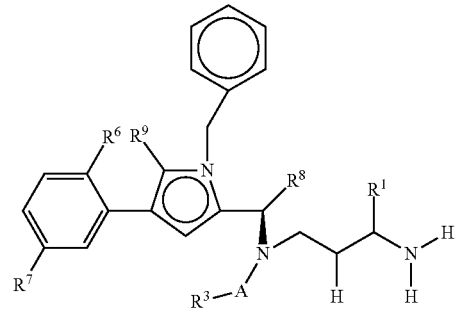

(IIk)

wherein
$R^1$ is -L-#1;
A is —C(=O)—;
$R^3$ is —CH$_2$OH;
$R^6$ and $R^7$ are independently of one another —H, cyano, C$_{1-10}$-alkyl, fluoro-C$_{1-10}$-alkyl, C$_{2-10}$-alkenyl, fluoro-C$_{2-10}$-alkenyl, C$_{2-10}$-alkynyl, fluoro-C$_{2-10}$-alkynyl, hydroxy, —NO$_2$, —NH$_2$, —COOH or halogen, $R^8$ is $C_{1-10}$-alkyl, fluoro-$C_{1-10}$-alkyl, $C_{2-10}$-alkenyl, fluoro-$C_{2-10}$-alkyl, $C_{2-10}$-alkynyl, fluoro-$C_{2-10}$-alkynyl, $C_{4-10}$-cycloalkyl, fluoro-$C_{4-10}$-cycloalkyl or —$(CH_2)_{0-2}$—$(HZ^2)$, which may be mono- or disubstituted, identically or differently, by —OH, —COOH or —NH$_2$,
  wherein
  $HZ^2$ is a 4- to 7-membered heterocycle having up to two heteroatoms selected from the group consisting of N, O and S; and
$R^9$ is —H, —F, —CH$_3$, —CF$_3$, —CH$_2$F or —CHF$_2$.

9. The conjugate according to claim 1, wherein $R^5$ is —H or —F.

10. The conjugate according to claim 1, wherein $R^6$ and $R^7$ are independently of one another —H, $C_{1-3}$-alkyl, fluoro-$C_{1-3}$-alkyl, $C_{2-4}$-alkenyl, fluoro-$C_{2-4}$-alkenyl, $C_{2-4}$-alkynyl, fluoro-$C_{2-4}$-alkynyl, hydroxy or halogen.

11. The conjugate according to claim 1, wherein $R^8$ is a branched $C_1$-s-alkyl group or cyclohexyl.

12. The conjugate according to claim 1, wherein $R^9$ is —H or fluorine.

13. The conjugate according to claim 1, wherein the linker -L- has one of the basic structures (i) to (iv) below:

—(CO)$_m$-SG1-L1-L2;-      (i)

—(CO)$_m$-L1-SG-L1-L2-;      (ii)

—(CO)$_m$-L1-L2-; or      (iii)

—(CO)$_m$-L1-SG-L2;      (iv)

wherein
m is 0 or 1;
SG and SG1 are in vivo cleavable groups;
each L1 is independently of one another an organic group not cleavable in vivo;
and
L2 is a coupling group to the binder.

14. The conjugate according to claim 13, wherein the in vivo cleavable group SG is a 2-8 oligopeptide group, or a disulphide, a hydrazone, an acetal or an aminal; and SG1 is a 2-8 oligopeptide group.

15. The conjugate according to claim 1,
  wherein the linker L is attached to a cysteine side chain or a cysteine residue and has the formula below:

§ —(C(=O)-)$_m$-L1-L2- § § wherein
m is 0 or 1;
§ is the bond to the active compound molecule;
§ § is the bond to the antibody;
-L2-is

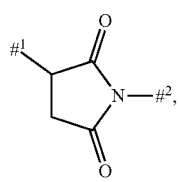

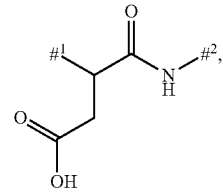

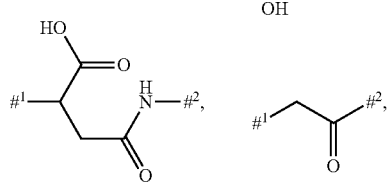

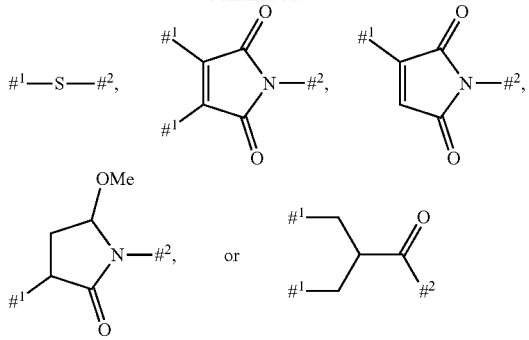

wherein
$^1$ denotes the point of attachment to the sulphur atom of the antibody;
$^2$ denotes the point of attachment to group L1;
$L^1$ is —(NR$^{10}$)$_n$-(G1)o-G2-,
  wherein
  $R^{10}$ is —H, —NH$_2$ or $C_1$-$C_3$-alkyl;
  G1 is —NH—C(=O)—;
  n is 0 or 1;
  o is 0 or 1; and
  G2 is a straight-chain or branched hydrocarbon chain having 1 to 100 carbon atoms from aryl groups, and/or straight-chain and/or branched alkyl groups, and/or cyclic alkyl groups and which may be interrupted once or more than once, identically or differently by —O—, —S—, —S(=O)—, S(=O)$_2$—, —NH—, —C(=O)—, —N—CH$_3$—, —NHNH—, —S(=O)$_2$—NHNH—, —NH—C(=O)—, —C(=O)—NH—, —C(=O)—NHNH— and a 5- to 10-membered aromatic or non-aromatic heterocycle having 1 to 4 identical or different heteroatoms and/or hetero groups selected from N, O and S, —S(=O)— or —S(=O)$_2$—,
  where the straight-chain or branched hydrocarbon chain may optionally be substituted by —NH—C(=O)—NH$_2$, —COOH, —OH, —NH$_2$, —NH—CNNH$_2$, sulphonamide, sulphone, sulphoxide or sulphonic acid,
  or represents one of the groups below:

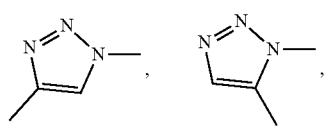

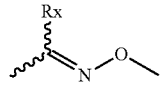

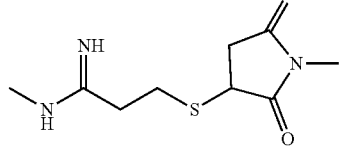

wherein $R^x$ is —H, $C_1$-$C_3$-alkyl or phenyl.

16. The conjugate according to claim 15, wherein L2 is represented by one or both of the formulae below:

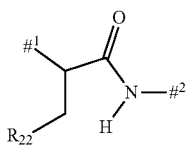

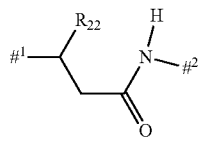

wherein
¹ denotes the point of attachment to the sulphur atom of the binder;
² denotes the point of attachment to group L;
R²² is —COOH; and
wherein more than 80% (based on the total number of bonds of the linker to the binder) of the bonds to the sulphur atom of the binder are present in one of these two structures.

17. The conjugate according to claim 15, wherein L has the formulae below:

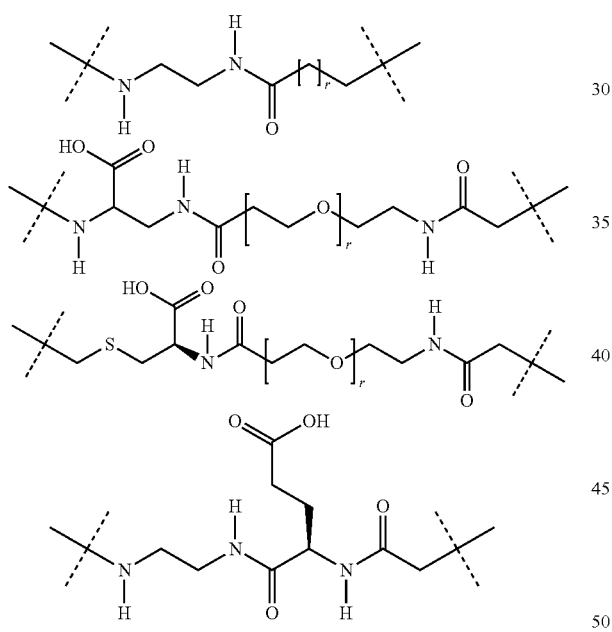

wherein
r is a number from 0 to 8.

18. The conjugate according to claim 1, wherein the linker -L- is attached to a cysteine side chain or a cysteine residue and has the formula below:

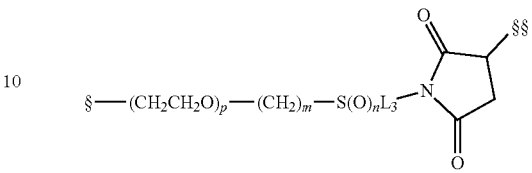

wherein
§ is the bond to the active compound molecule;
§ § is the bond to the antibody;
m is 0, 1, 2 or 3;
n is 0, 1 or 2;
p is 0 to 20; and
L3 is

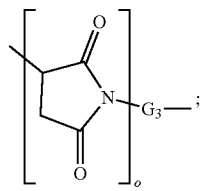

wherein
o is 0 or 1; and
G3 is a straight-chain or branched hydrocarbon chain having 1 to 100 carbon atoms from aryl groups, and/or straight-chain and/or branched alkyl groups, and/or cyclic alkyl groups and which may be interrupted once or more than once, identically of differently by —O—, —S—, —S(=O)—, S(=O)₂—, —NH—, —C(=O)—, —N—CH₃—, —NHNH—, —S(=O)₂—NHNH—, —NH—C(=O)—, —C(=O)—NH—, —C(=O)—NHNH— and a 5- to 10-membered aromatic or non-aromatic heterocycle having 1 to 4 identical or different heteroatoms and/or hetero groups selected from N, O and S, —S(=O)— or —S(=O)₂—,
where the straight-chain or branched hydrocarbon chain may optionally be substituted by —NH—C(=O)—NH₂, —COOH, —OH, —NH₂—, —NH—CN—NH₂, sulphonamide, sulphone, sulphoxide or sulphonic acid.

19. The conjugate according to claim 1, wherein the conjugate has one of the formulae below:

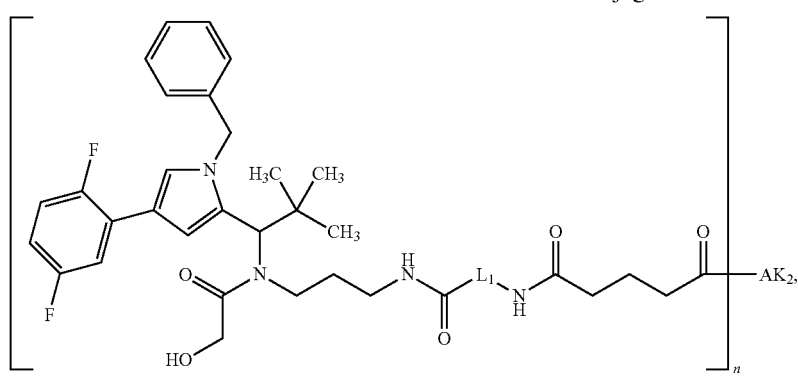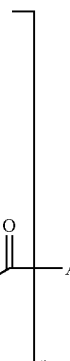

-continued
585
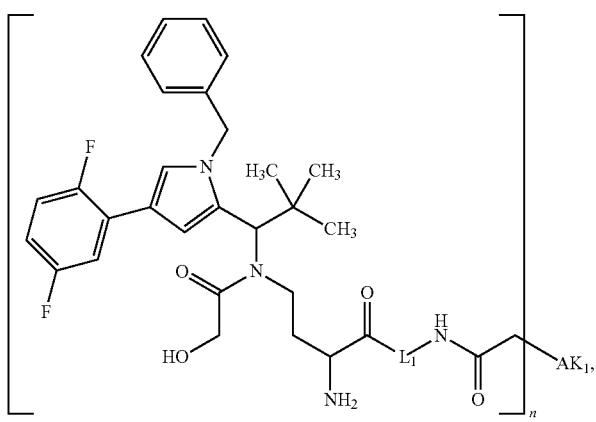
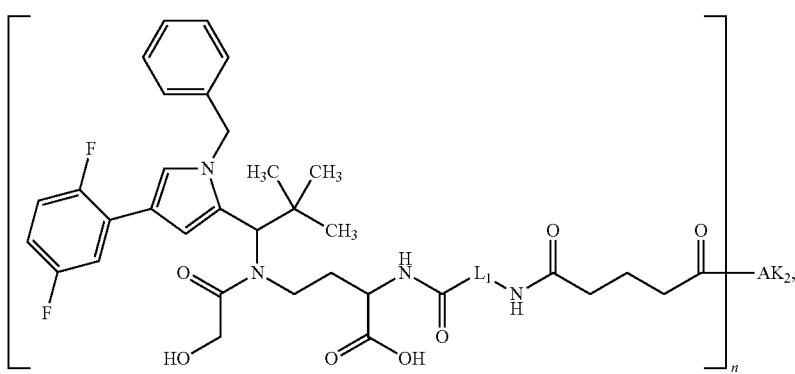
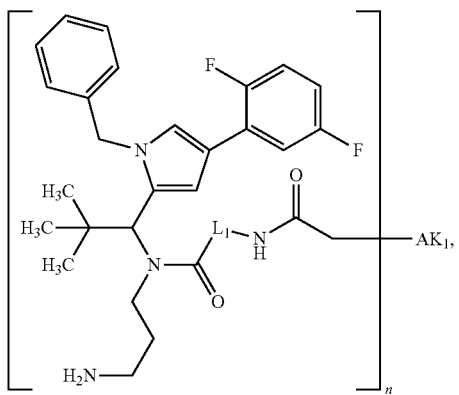
586
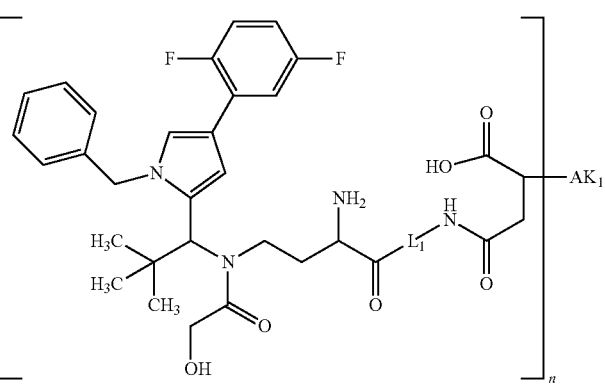
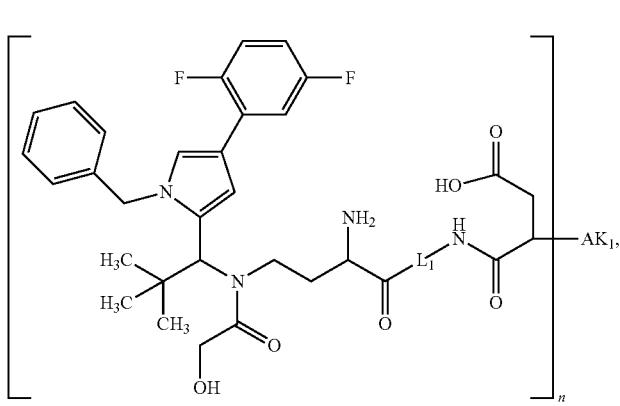
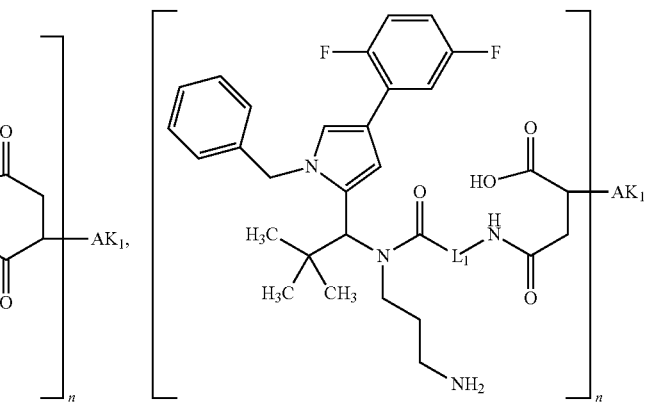

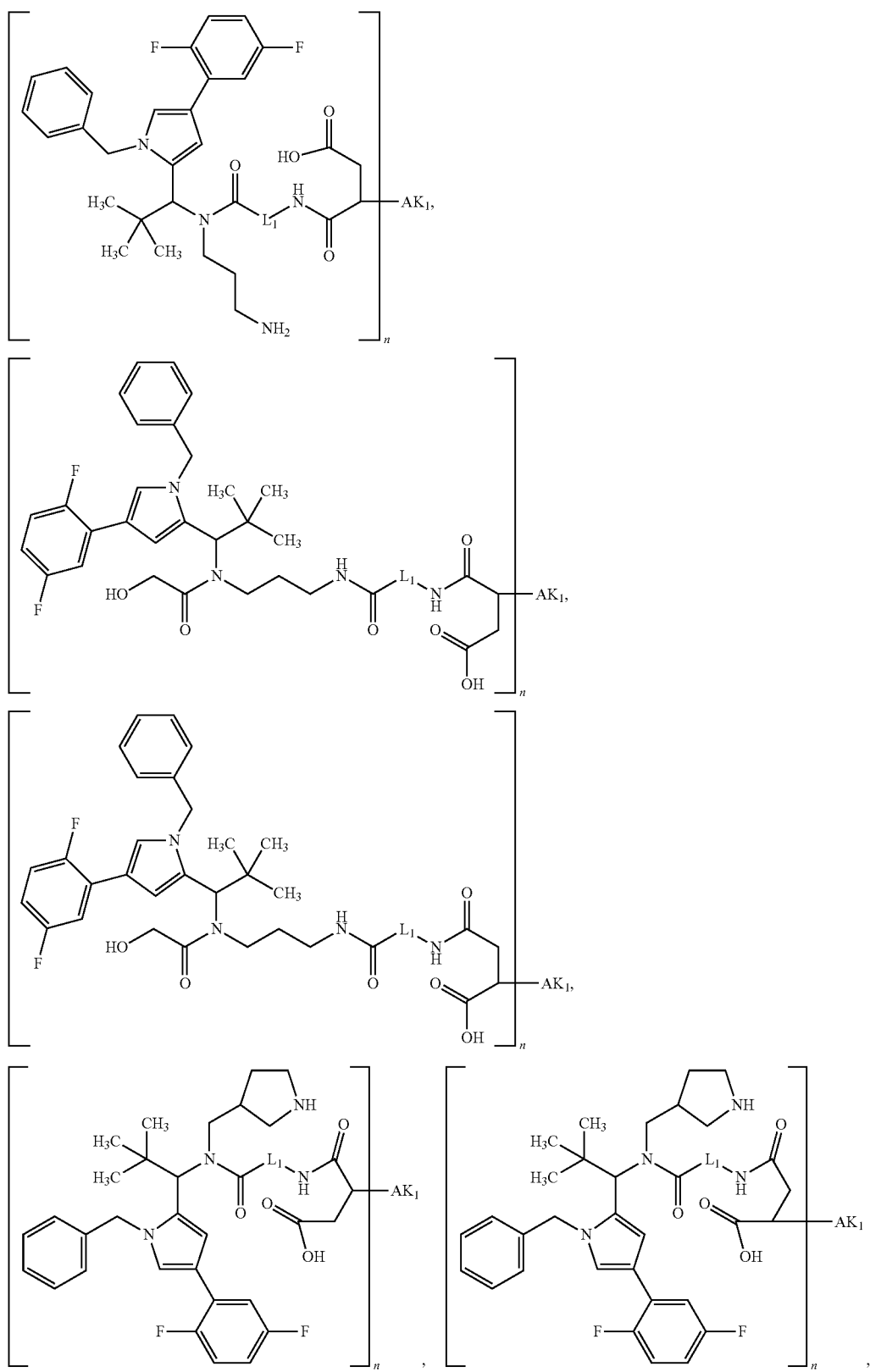

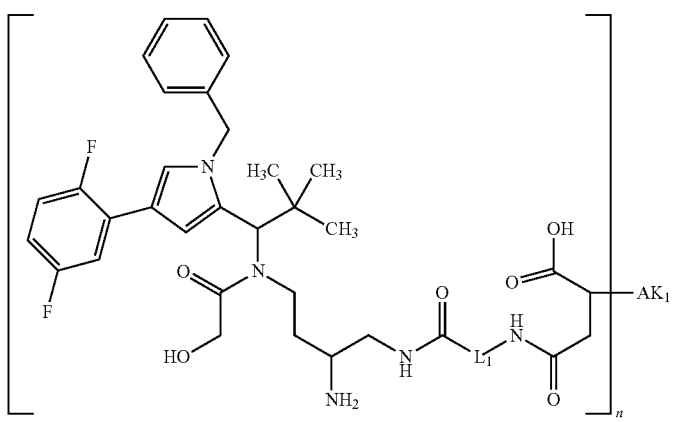
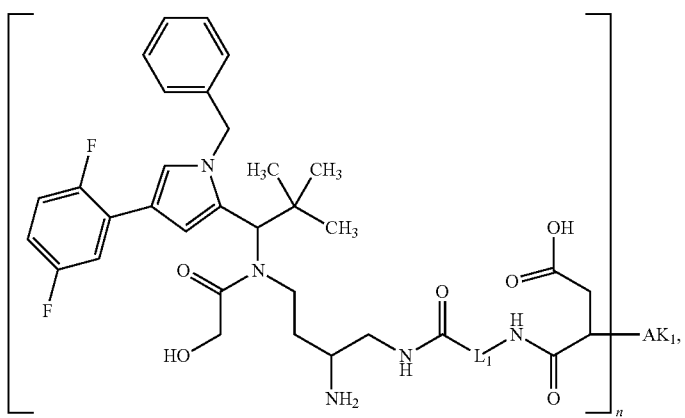
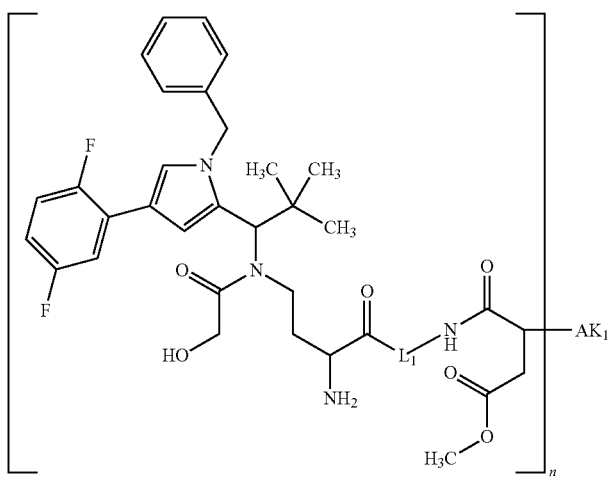

591
-continued
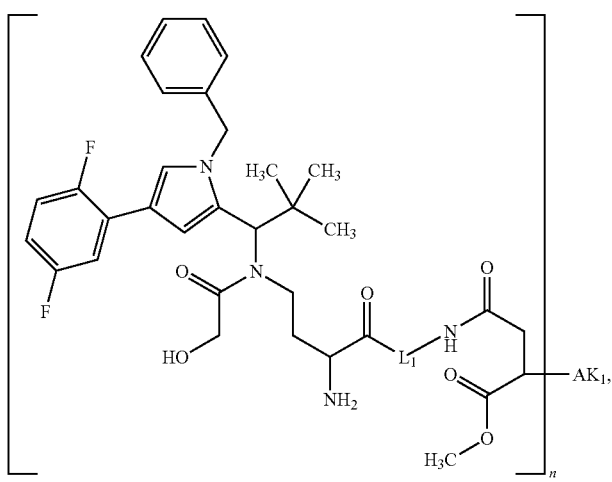
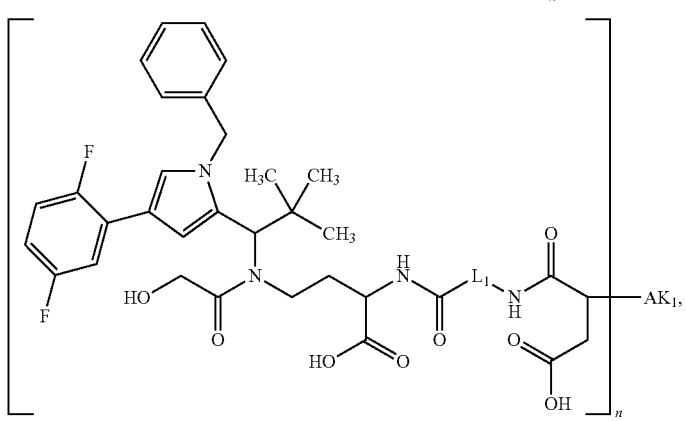
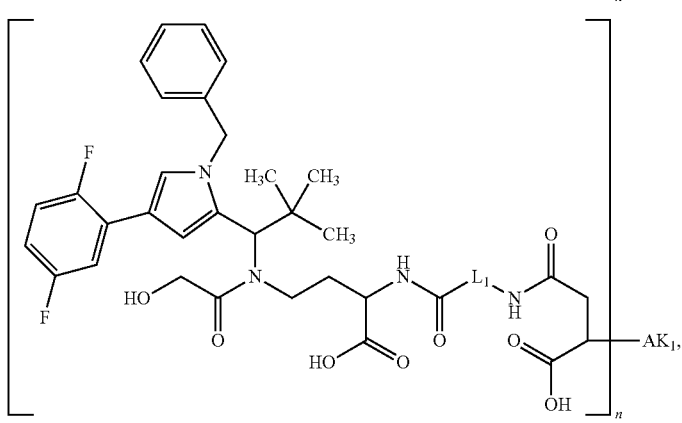
592
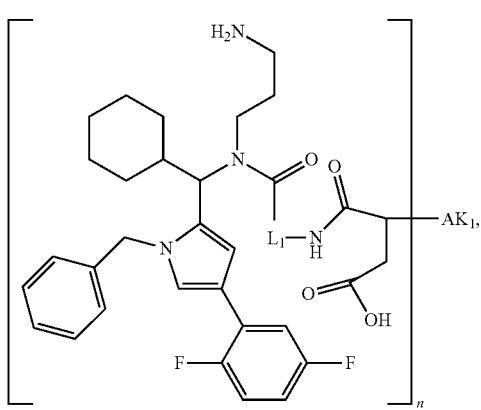
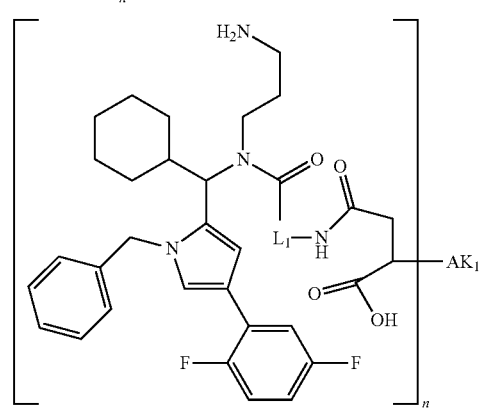

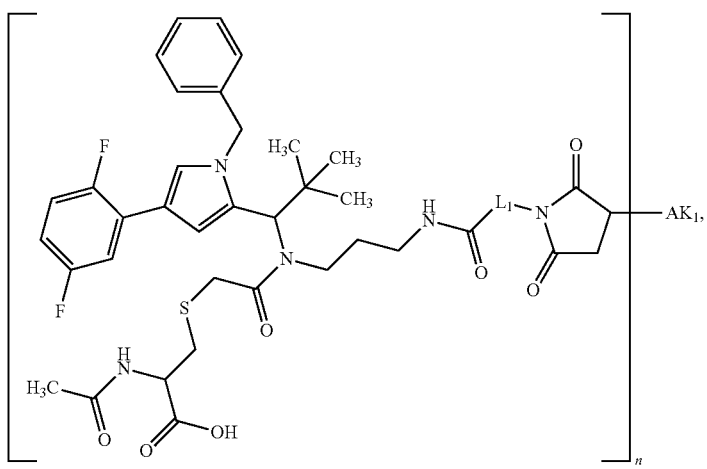
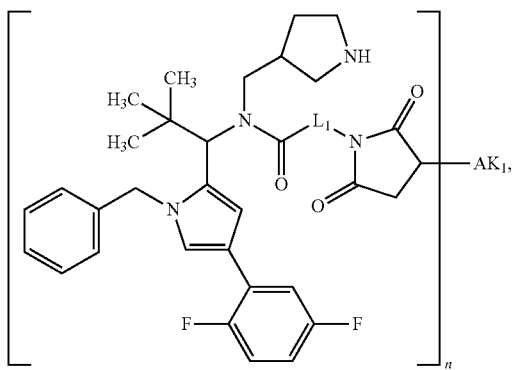
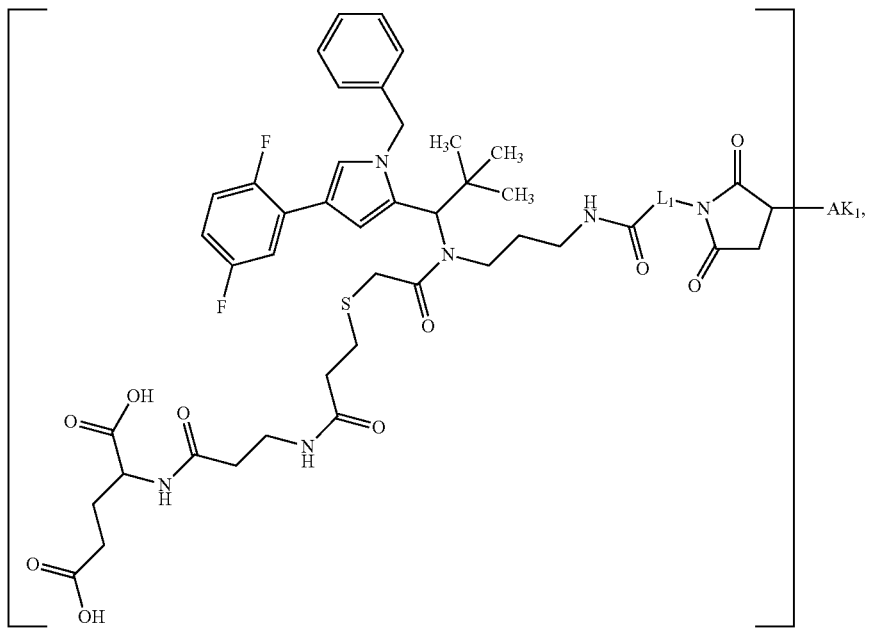

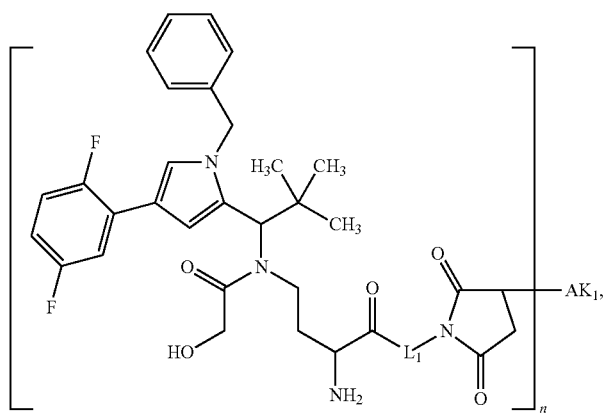
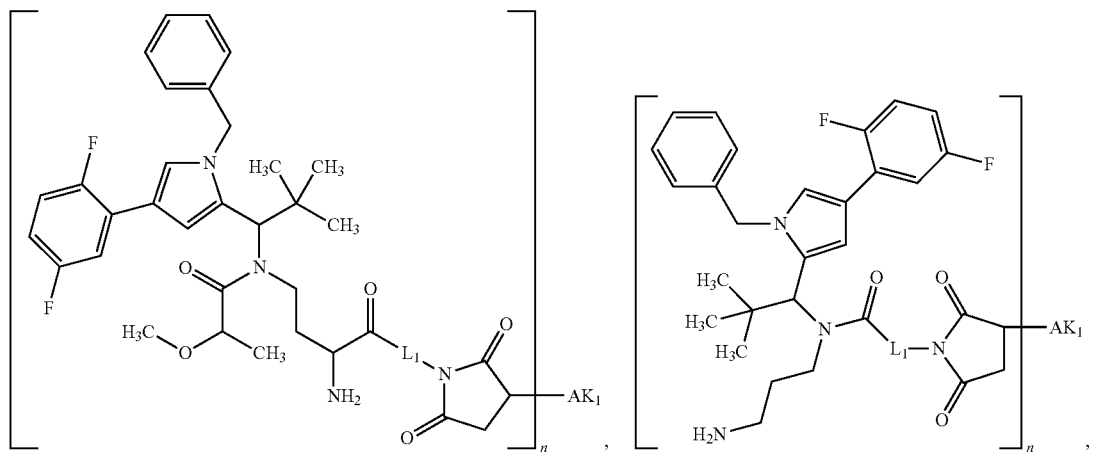
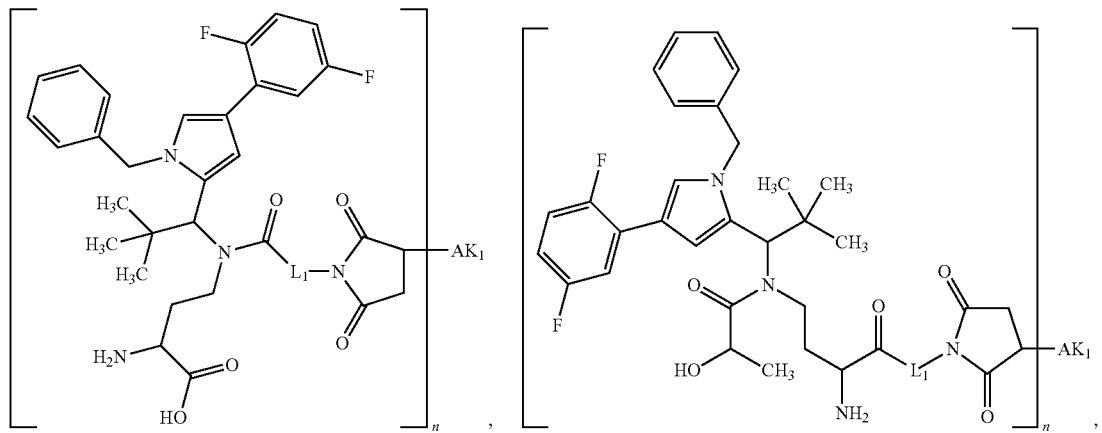

-continued
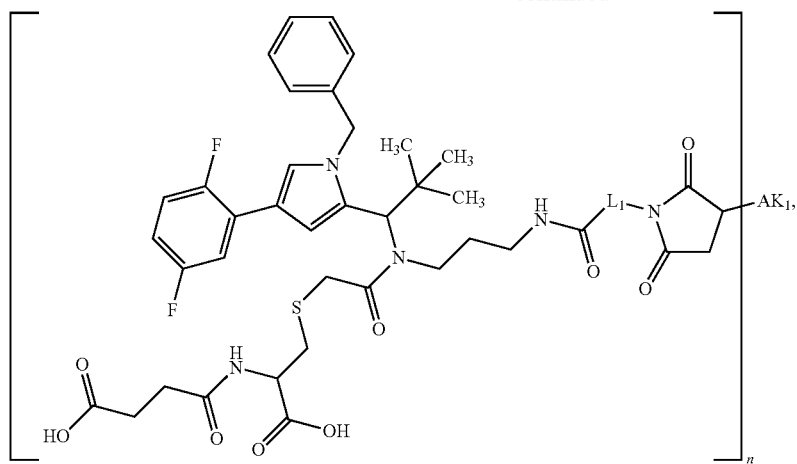
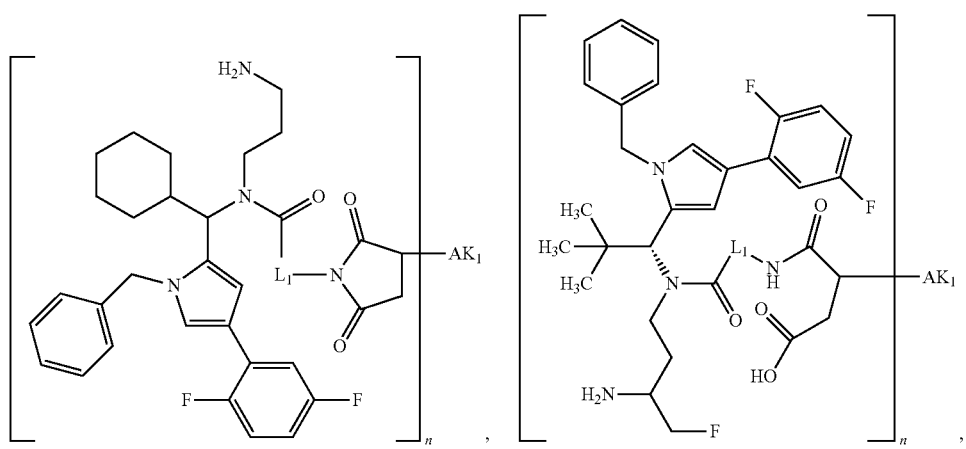
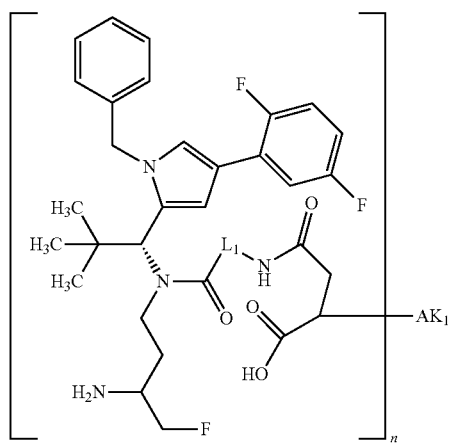

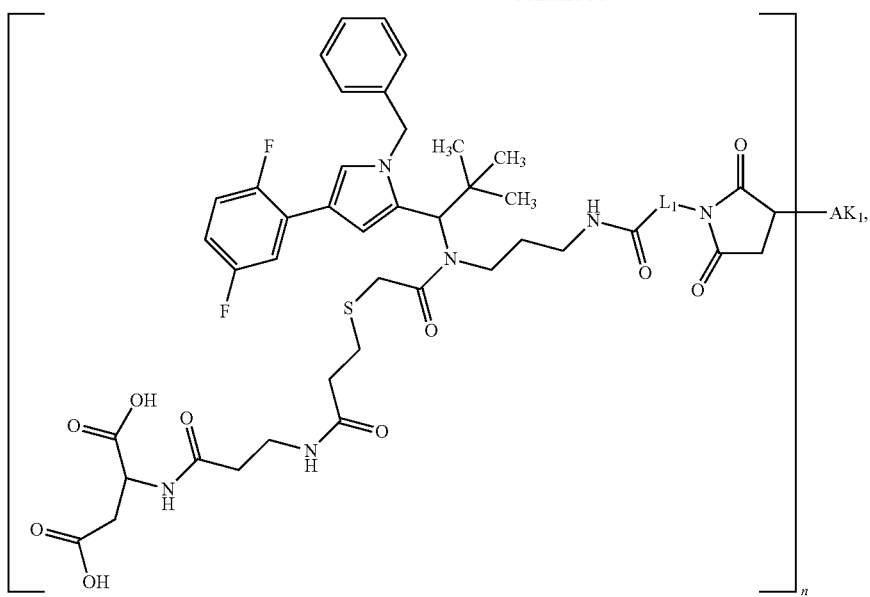
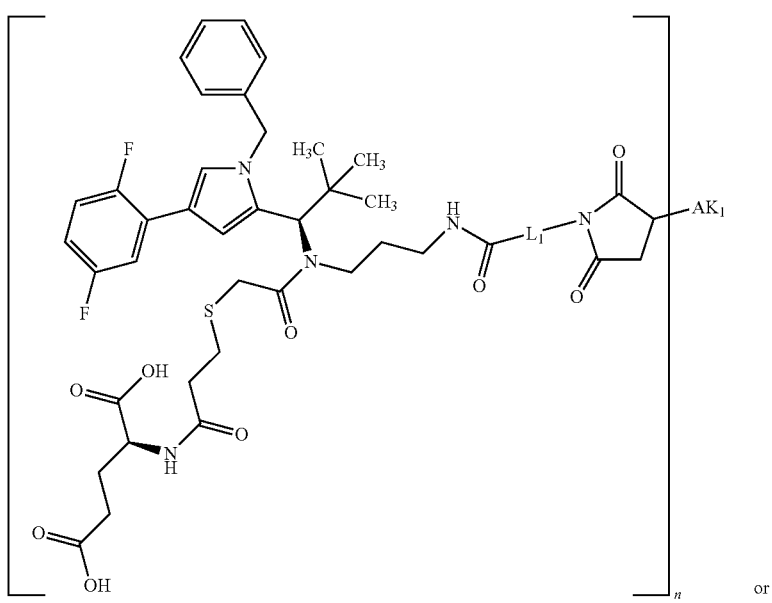
or

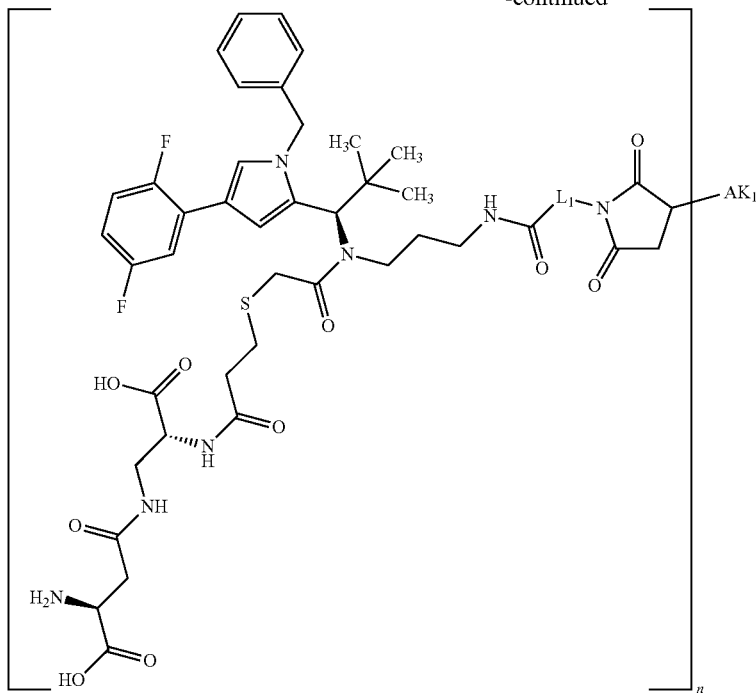

wherein
- AK1 is an anti-CD123 antibody attached via cysteine and AK2 is an anti-CD123 antibody attached via lysine, which antibody is a chimeric or humanized variant of the antibody 7G3 or 12F1;
- n is a number from 1 to 20; and
- $L_1$ is a straight-chain or branched hydrocarbon chain having 1 to 30 carbon atoms which may be interrupted once or more than once, identically or differently, by —O—, —S—, —C(=O)—, —S(=O)$_2$—, —NH—, cyclopentyl, piperidinyl, or phenyl,
  - wherein the straight-chain or branched hydrocarbon chain may be substituted by —COOH or —NH$_2$, or a salt, a solvate, a salt of a solvate, or an epimer thereof.

20. The conjugate according to claim 19, wherein the linker $L_1$ is the group

- § —NH—(CH$_2$)$_2$—§ §;
- § —NH—(CH$_2$)$_6$—§ §;
- § —NH—(CH$_2$)$_2$—O—(CH$_2$)$_2$—§ §;
- § —NH—CH(COOH)—(CH$_2$)$_4$—§ §
- § —NH—NH—C(=O)—(CH$_2$)$_5$—§ §;
- § —NH—(CH$_2$)$_2$—C(=O)—O—(CH$_2$)$_2$—§ §;
- § —NH—(CH$_2$)$_2$—C(=O)—NH—(CH$_2$)$_2$—§ §;
- § —NH—(CH$_2$)$_2$—NH—C(=O)—CH$_2$—§ §;
- § —NH—(CH$_2$)$_3$—NH—C(=O)—CH$_2$—§ §;
- § —NH—(CH$_2$)$_2$—NH—C(=O)—(CH$_2$)$_2$—§ §;
- § —NH—(CH$_2$)$_2$—NH—C(=O)—(CH$_2$)$_5$—§ §;
- § —NH—(CH$_2$)$_2$—NH—C(=O)—CH(CH$_3$)—§ §;
- § —NH—(CH$_2$)$_2$—O—(CH$_2$)$_2$—NH—C(=O)—CH$_2$—§ §;
- § —NH—CH(COOH)—CH$_2$—NH—C(=O)—CH$_2$—§ §;
- § —NH—CH(COOH)—(CH$_2$)$_2$—NH—C(=O)—CH$_2$—§ §;
- § —NH—CH(COOH)—(CH$_2$)$_4$—NH—C(=O)—CH$_2$—§ §;
- § —NH—CH(COOH)—CH$_2$—NH—C(=O)—(CH$_2$)$_2$—§ §;
- § —NH—(CH$_2$)$_2$—NH—C(=O)—CH(C$_2$H$_4$COOH)—§ §;
- § —NH—(CH$_2$)$_2$—NH—C(=O)—((CH$_2$)$_2$—O)$_3$—(CH$_2$)$_2$—§ §;
- § —NH—(CH$_2$)$_2$—S(=O)$_2$—(CH$_2$)$_2$—NH—C(=O)—CH$_2$—§ §;
- § —NH—(CH$_2$)$_2$—NH—C(=O)—CH$_2$—NH—C(=O)—CH$_2$—§ §;
- § —NH—(CH$_2$)$_3$—NH—C(=O)—CH$_2$—NH—C(=O)—CH$_2$—§ §;
- § —NH—CH(COOH)—CH$_2$—NH—C(=O)—CH(CH$_2$COOH)—§ §;
- § —NH—(CH$_2$)$_2$—NH—C(=O)—CH(C$_2$H$_4$COOH)—NH—C(=O)—CH$_2$—§ §;
- § —NH—CH(COOH)—CH$_2$—NH—C(=O)—(CH$_2$)$_2$—NH—C(=O)—CH$_2$—§ §;
- § —NH—(CH$_2$)$_2$—NH—C(=O)—(CH$_2$)$_2$—CH(COOH)—NH—C(=O)—CH$_2$—§ §;
- § —NH—CH(COOH)—CH$_2$—NH—C(=O)—CH(CH$_2$OH)—NH—C(=O)—CH$_2$—§ §;
- § —NH—CH[C(=O)—NH—(CH$_2$)$_2$—O)$_4$—(CH$_2$)$_2$COOH]—CH$_2$—NH—C(=O)—CH$_2$—§ §;
- § —NH—CH(COOH)—CH$_2$—NH—C(=O)—((CH$_2$)$_2$—O)$_4$—(CH$_2$)$_2$—NH—C(=O)—CH$_2$—§ §;
- § —NH—(CH$_2$)$_4$—CH(COOH)—NH—C(=O)—CH(CH$_3$)—NH—C(=O)—CH(isoC$_3$H$_7$)—§ §;
- § —NH—(CH$_2$)$_4$—CH(COOH)—NH—C(=O)—CH(CH$_3$)—NH—C(=O)—CH(isoC$_3$H$_7$)—NH—C(=O)—(CH$_2$)$_5$—§ §;
- § —NH—(CH$_2$)$_2$—C(=O)—NH—(CH$_2$)$_4$—CH(COOH)—NH—C(=O)—CH(CH$_3$)—NH—C(=O)—CH(isoC$_3$H$_7$)—NH—C(=O)—CH$_2$—§ §;
- § —NH—(CH$_2$)$_2$—C(=O)—NH—(CH$_2$)$_4$—CH(COOH)—NH—C(=O)—CH(CH$_3$)—NH—C(=O)—CH(isoC$_3$H$_7$)—NH—C(=O)—(CH$_2$)$_5$—§ §;

603

§ —NH—(CH$_2$)$_4$—CH(COOH)—NH—C(=O)—CH[(CH$_2$)$_3$—NH—C(=O)—NH$_2$]—NH—C(=O)—CH(isoC$_3$H$_7$)—NH—C(=O)—(CH$_2$)$_5$—§ §;

§ —NH—(CH$_2$)$_2$—NH—C(=O)—(CH$_2$)$_2$—CH(COOH)—NH—C(=O)—CH(CH$_3$)—NH—C(=O)—CH(isoC$_3$H$_7$)—NH—C(=O)—(CH$_2$)$_5$—§ §;

§ —NH—CH(CH$_3$)—C(=O)—NH—(CH$_2$)$_4$—CH(COOH)—NH—C(=O)—CH(CH$_3$)—NH—C(=O)—CH(isoC$_3$H$_7$)—NH—C(=O)—(CH$_2$)$_5$—§ §;

§ —NH—(CH$_2$)$_2$—C(=O)—NH—(CH$_2$)$_4$—CH(COOH)—NH—C(=O)—CH[(CH$_2$)$_3$—NH—C(=O)—NH$_2$]—NH—C(=O)—CH(isoC$_3$H$_7$)—NH—C(=O)—(CH$_2$)$_5$—§ §;

604

§ —CH$_2$—S—(CH$_2$)$_2$—C(=O)—NH—(CH$_2$)$_2$—§ §;
§ —CH$_2$—S—(CH$_2$)$_5$—C(=O)—NH—(CH$_2$)$_2$—§ §;
§ —CH$_2$—S—CH$_2$CH(COOH)—NH—C(=O)—CH$_2$—§ §;
§ —CH$_2$—S—CH$_2$CH(COOH)—NH—C(=O)—(CH$_2$)$_5$—§ §;
§ —CH$_2$—S—(CH$_2$)$_2$—C(=O)—NH—((CH$_2$)$_2$—O)$_2$—(CH$_2$)$_2$—§ §;
§ —CH$_2$—S—(CH$_2$)$_2$—C(=O)—NH—((CH$_2$)$_2$—O)$_2$—(CH$_2$)$_5$—§ §;
§ —CH$_2$—S—(CH$_2$)$_2$—C(=O)—NH—(CH$_2$)$_2$—NH—C(=O)—CH$_2$—§ §;

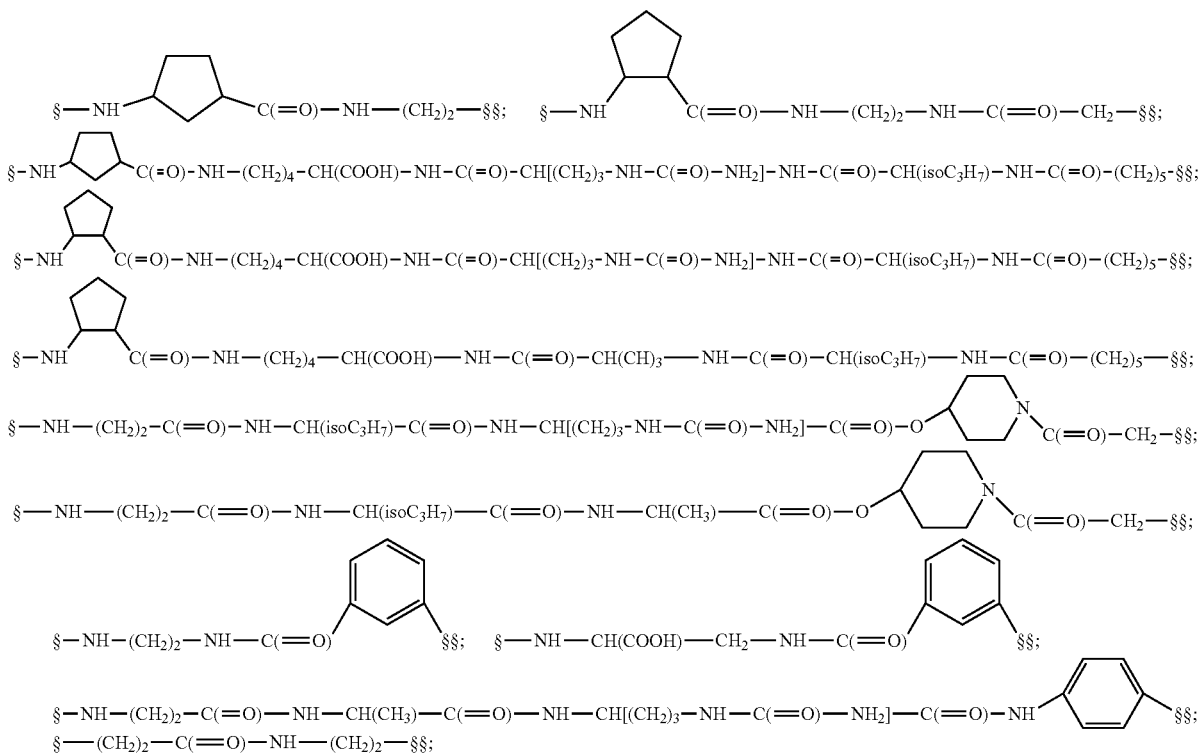

§ —(CH$_2$)$_2$—C(=O)—NH—(CH$_2$)$_2$—§ §;
§ —(CH$_2$)$_2$—C(=O)—NH—(CH$_2$)$_2$—NH—C(=O)—CH$_2$—§ §;
§ —CH(CH$_3$)—NH—C(=O)—CH(isoC$_3$H$_7$)—§ §;
§ —CH(CH$_3$)—NH—C(=O)—CH(isoC$_3$H$_7$)—NH—C(=O)—CH$_2$—§ §;
§ —CH(CH$_3$)—NH—C(=O)—CH(isoC$_3$H$_7$)—NH—C(=O)—(CH$_2$)$_5$—§ §;
§ —(CH$_2$)$_2$—C(=O)—NH—((CH$_2$)$_2$—O)$_4$—(CH$_2$)$_2$—NH—C(=O)—CH$_2$—§ §;
§ —CH(CH$_3$)—NH—C(=O)—CH(isoC$_3$H$_7$)—NH—C(=O)—((CH$_2$)$_2$—O)$_4$—(CH$_2$)$_2$—NH—C(=O)—(CH$_2$)$_2$—§ §;

§ —CH$_2$—S—(CH$_2$)$_2$—C(=O)—NH—(CH$_2$)$_2$—NH—C(=O)—CH$_5$—§ §;
§ —CH$_2$—S—(CH$_2$)$_2$—C(=O)—NH—CH(COOH)—CH$_2$—NH—C(=O)—CH$_2$—§ §;
§ —CH$_2$—S—CH$_2$CH(NH$_2$)—C(=O)—NH—(CH$_2$)$_2$—NH—C(=O)—(CH$_2$)$_5$—§ §;
§ —CH$_2$—S—(CH$_2$)$_2$—C(=O)—NH—((CH$_2$)$_2$—O)$_2$—(CH$_2$)$_2$—NH—C(=O)—CH$_2$—§ §;
§ —CH$_2$—S—(CH$_2$)$_2$—C(=O)—NH—((CH$_2$)$_2$—O)$_4$—(CH$_2$)$_2$—NH—C(=O)—CH$_2$—§ §;
§ —CH$_2$—S—(CH$_2$)$_2$—C(=O)—NH—((CH$_2$)$_2$—O)$_2$—(CH$_2$)$_2$—NH—C(=O)—(CH$_2$)$_5$—§ §;

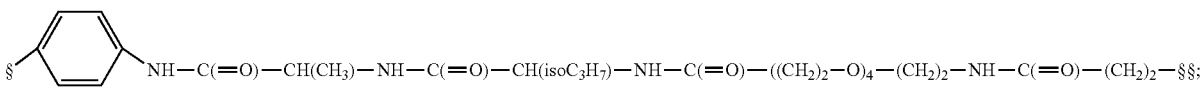

§ —CH₂—S—(CH₂)₂—C(=O)—NH—((CH₂)₂—O)₄—(CH₂)₂—NH—C(=O)—(CH₂)₅—§ §;
§ —CH₂—S—CH₂CH(COOH)—NH—C(=O)—((CH₂)₂—O)₂—(CH₂)₂—NH—C(=O)—CH₂—§ §;
§ —CH₂—S—CH₂CH(COOH)—NH—C(=O)—((CH₂)₂—O)₄—(CH₂)₂—NH—C(=O)—CH₂—§ §;
§ —CH₂—S—CH₂CH(COOH)—NH—C(=O)—((CH₂)₂—O)₄—(CH₂)₂—NH—C(=O)—(CH₂)₂—§ §;
§ —CH₂—S—(CH₂)₂—CH(COOH)—NH—C(=O)—((CH₂)₂—O)₄—(CH₂)₂—NH—C(=O)—(CH₂)₂—§ §;
§ —CH₂—S—(CH₂)₂—C(=O)—NH—CH(C₂H₄COOH)—C(=O)—NH—(CH₂)₂—NH—C(=O)—CH₂—§ §;
§ —CH₂—S—CH₂CH[NH—C(=O)—(CH₂)₂—COOH]—C(=O)—NH—(CH₂)₂—NH—C(=O)—CH₂—§§;
§ —CH₂—S—CH₂CH[NH—C(=O)—((CH₂)₂—O)₄—CH₃]—C(=O)—NH—(CH₂)₂—NH—C(=O)—CH₂—§ §;
§ —CH₂—S—CH₂CH(COOH)—NH—C(=O)—CH(CH₃)—NH—C(=O)—CH(isoC₃H₇)—NH—C(=O)—CH₂—§ §;
§ —CH₂—S—CH₂CH[NH—C(=O)—(CH₂)₂—COOH]—C(=O)—NH—(CH₂)₂—S(=O)₂—(CH₂)₂—NH—C(=O)—CH₂—§ §;
§ —CH₂—S—CH₂CH[NH—C(=O)—(CH₂)₂—COOH]—C(=O)—NH—((CH₂)₂—O)₄—(CH₂)₂—NH—C(=O)—CH₂—§ §;
§ —CH₂—S—CH₂CH[C(=O)—NH—(CH₂)₂—COOH]—NH—C(=O)—((CH₂)₂—O)₄—(CH₂)₂—NH—C(=O)—CH₂—§ §;
§ —CH₂—S—CH₂CH[C(=O)—NH—(CH₂)₂—COOH]—NH—C(=O)—((CH₂)₂—O)₄—(CH₂)₂—NH—C(=O)—(CH₂)₂—§ §;
§ —CH₂—S—CH₂CH(COOH)—NH—C(=O)—(CH₂)₂CH(COOH)—NH—C(=O)—((CH₂)₂—O)₄—(CH₂)₂—NH—C(=O)—CH₂—§ §
§ —CH₂—S—CH₂CH[C(=O)—NH—((CH₂)₂—O)₄—(CH₂)₂—COOH]—NH—C(=O)—((CH₂)₂—O)₄—(CH₂)₂—NH—C(=O)—CH₂—§ §;
or
§ —CH₂—S—CH₂CH(COOH)—NH—C(=O)—CH[(CH₂)₂—COOH]—NH—C(=O)—((CH₂)₂—O)₄—(CH₂)₂—NH—C(=O)—(CH₂)₂—§ §, wherein
§ is the bond to the active compound molecule;
§ § is the bond to the antibody; and
isoC₃H₇ is an isopropyl radical,
or a salt, a solvate, a salt of a solvate, or an epimer thereof.

21. The conjugate according to claim 1, wherein the conjugate has one of the formulae below:

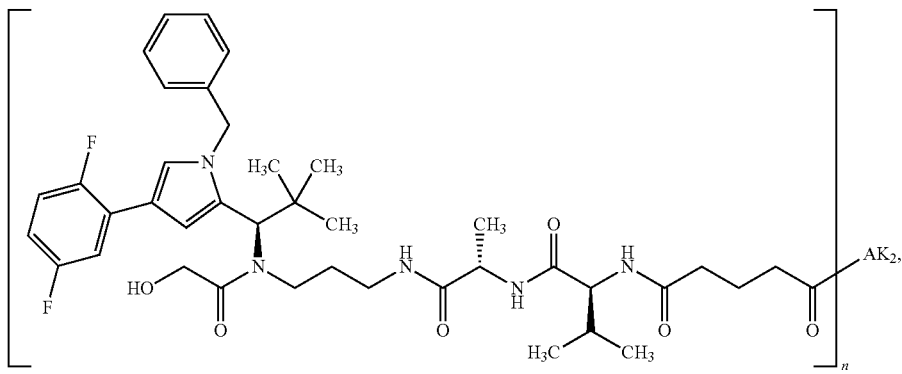

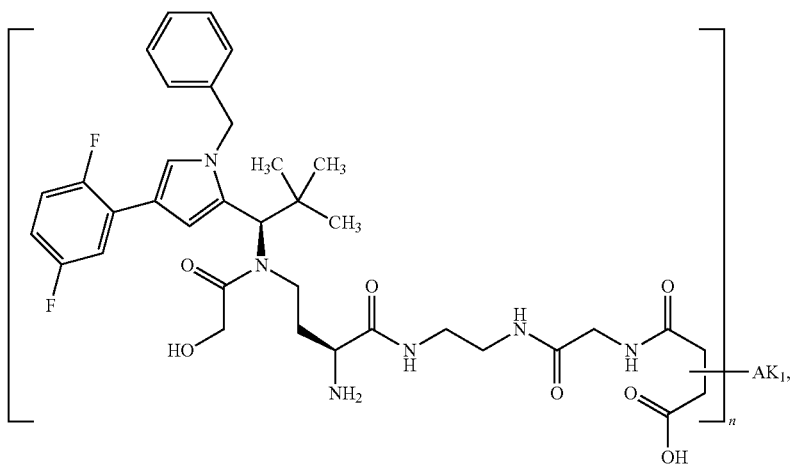

-continued
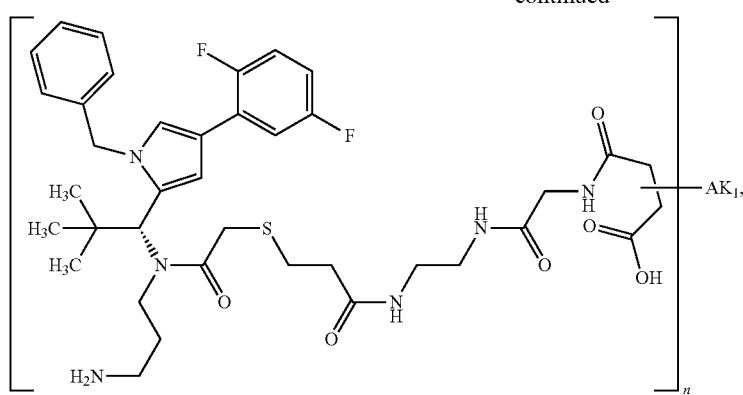
607
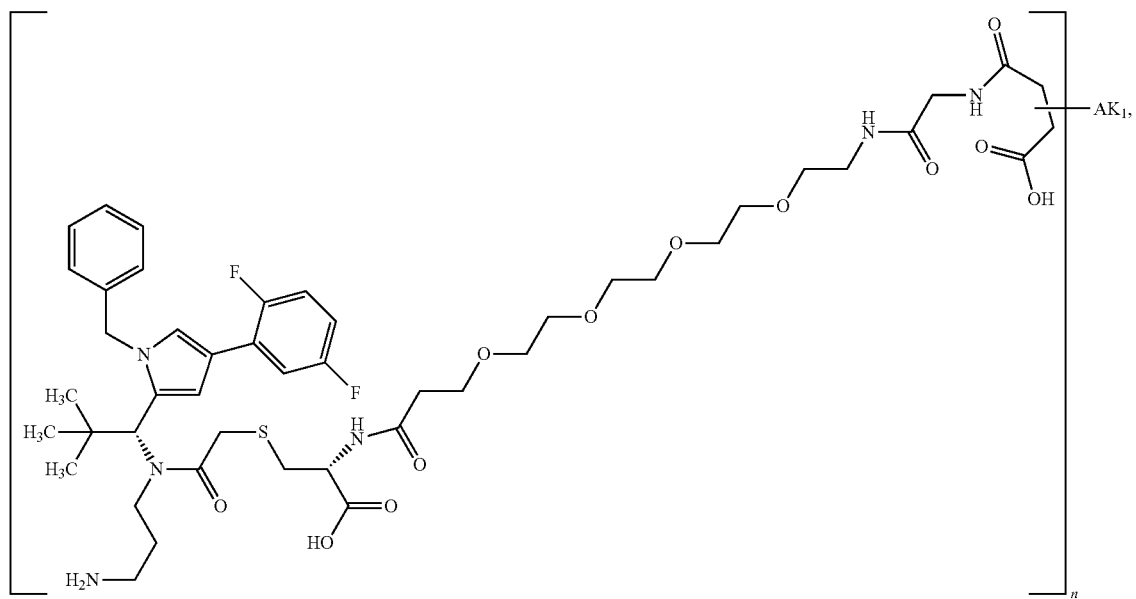
608
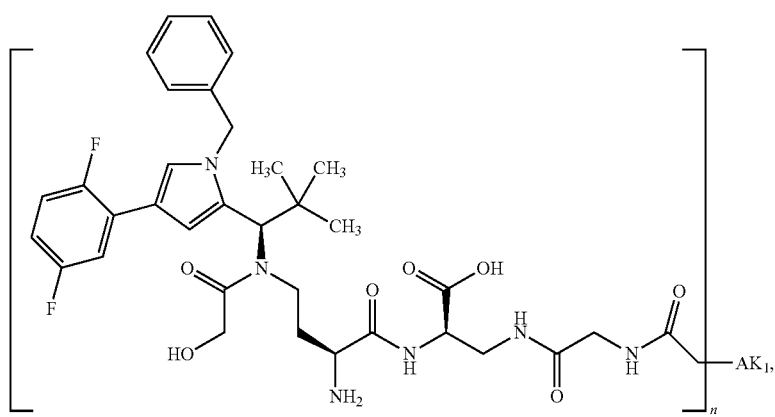

609
-continued
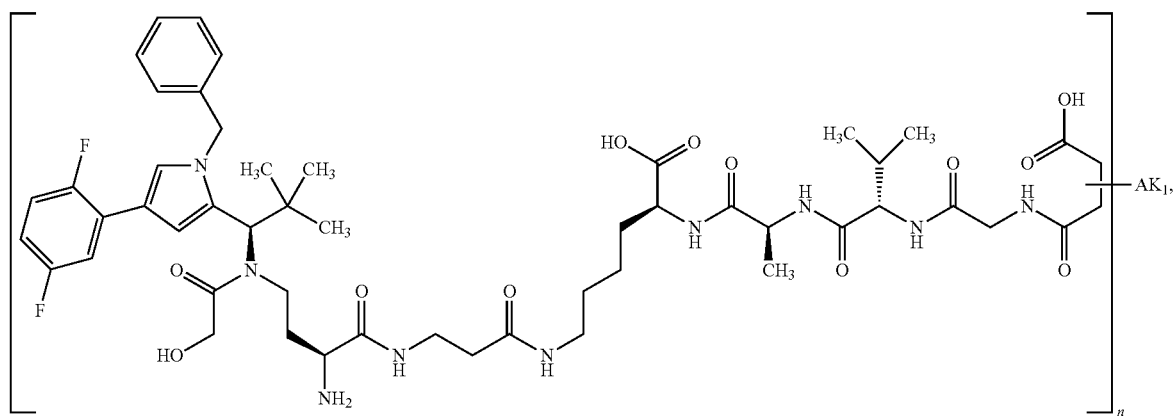
610
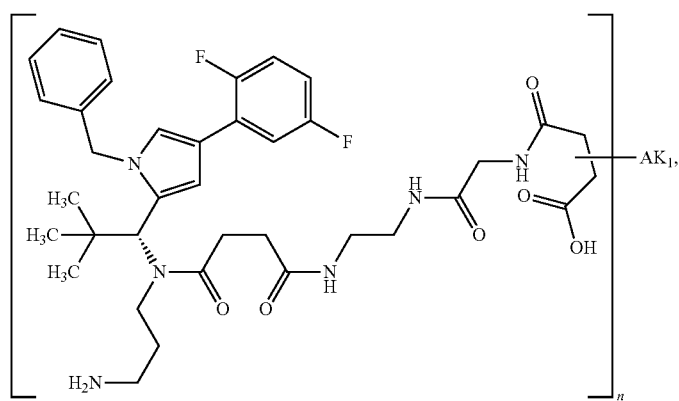
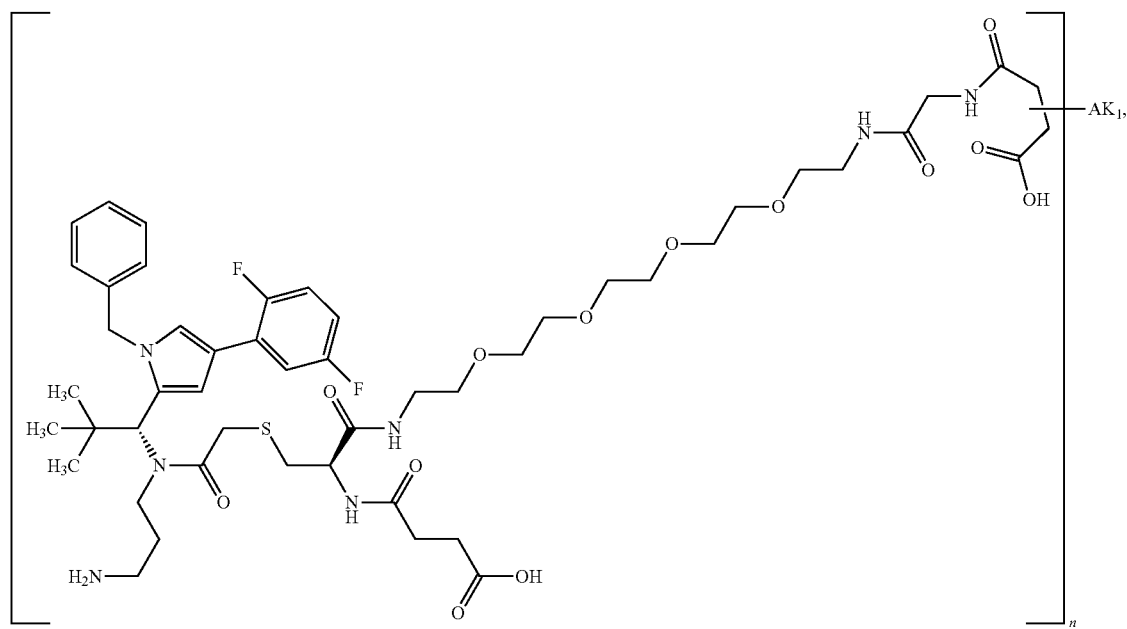

-continued
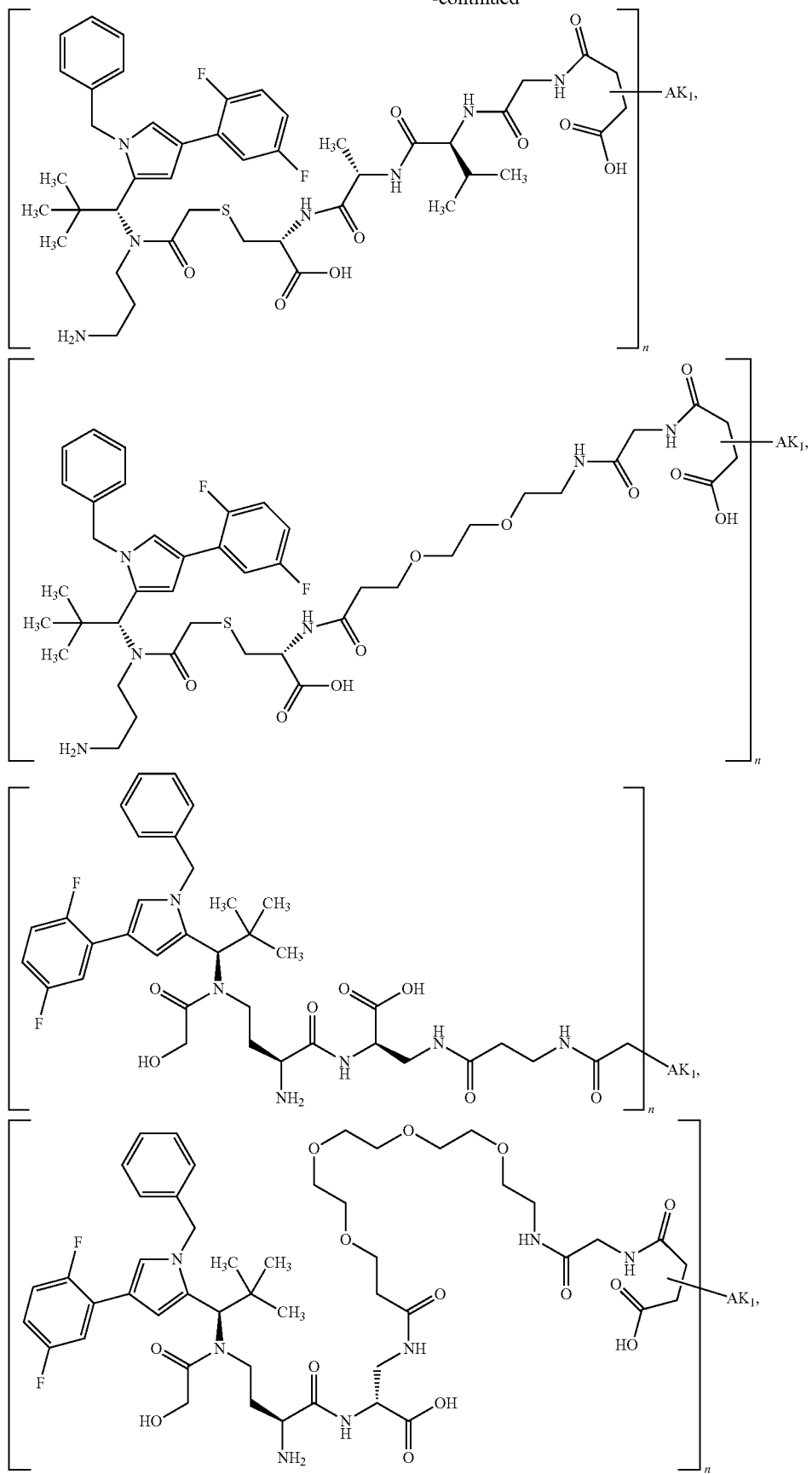

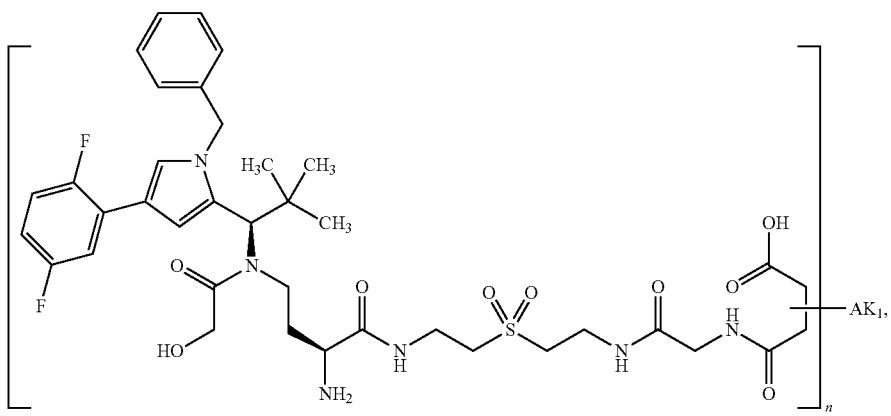
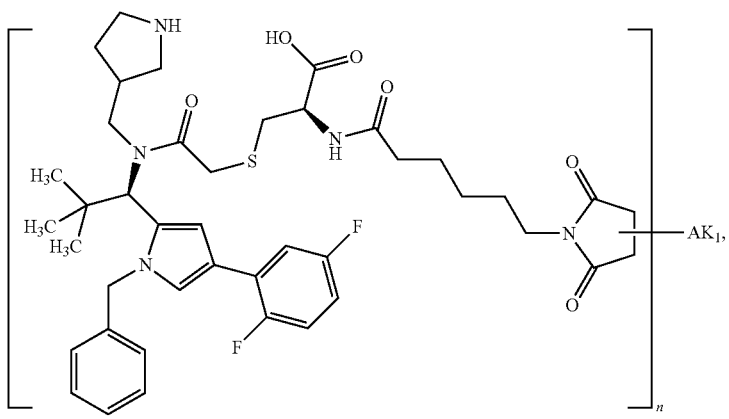
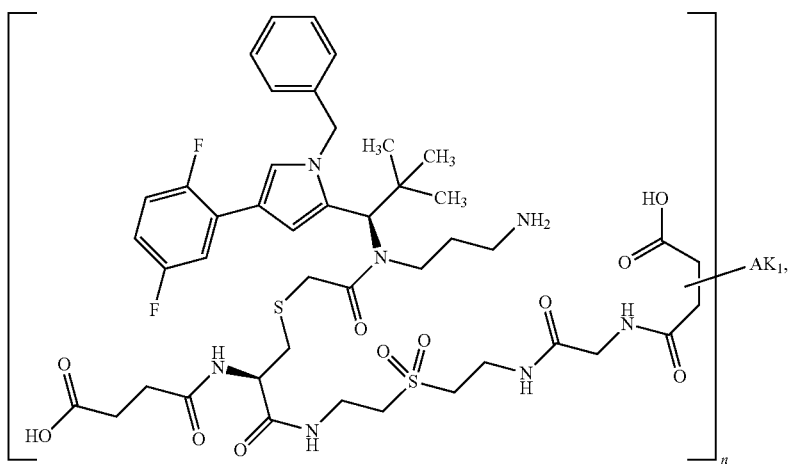

-continued
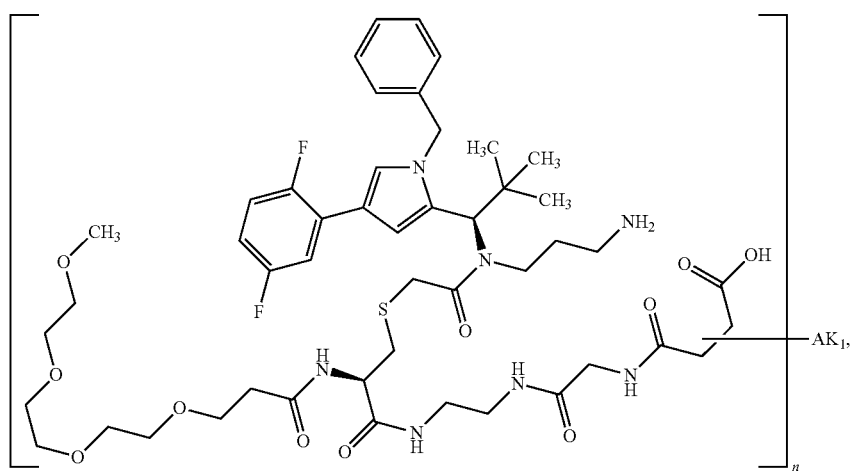
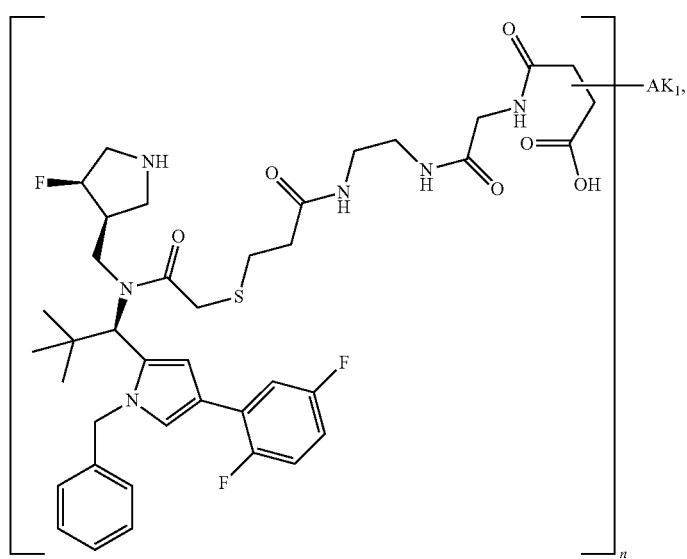
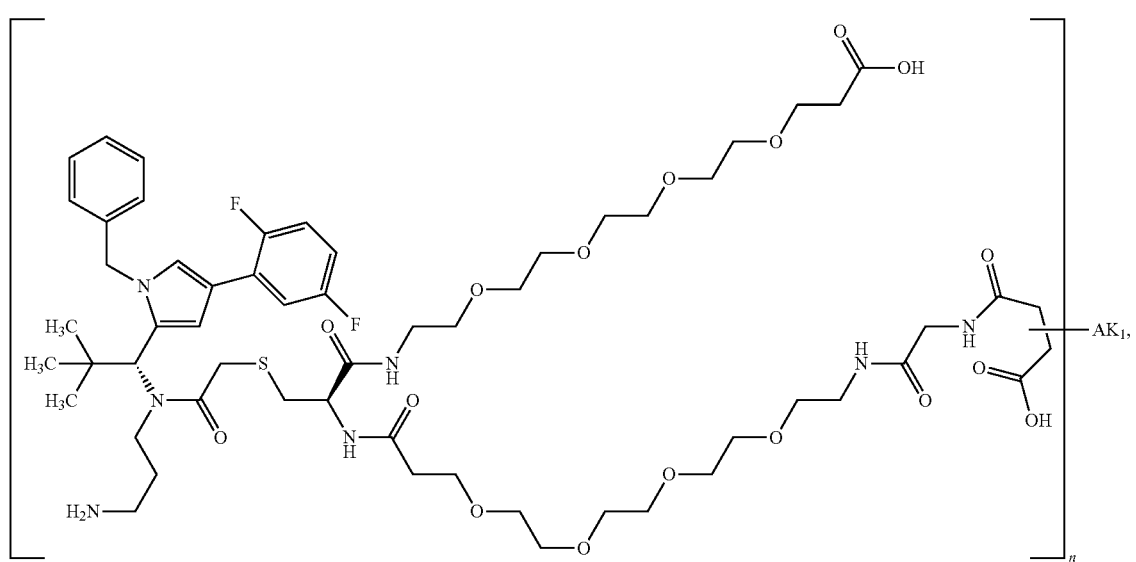

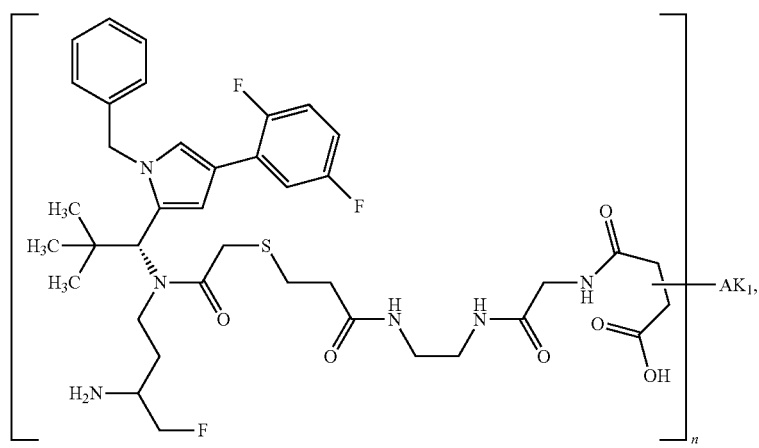
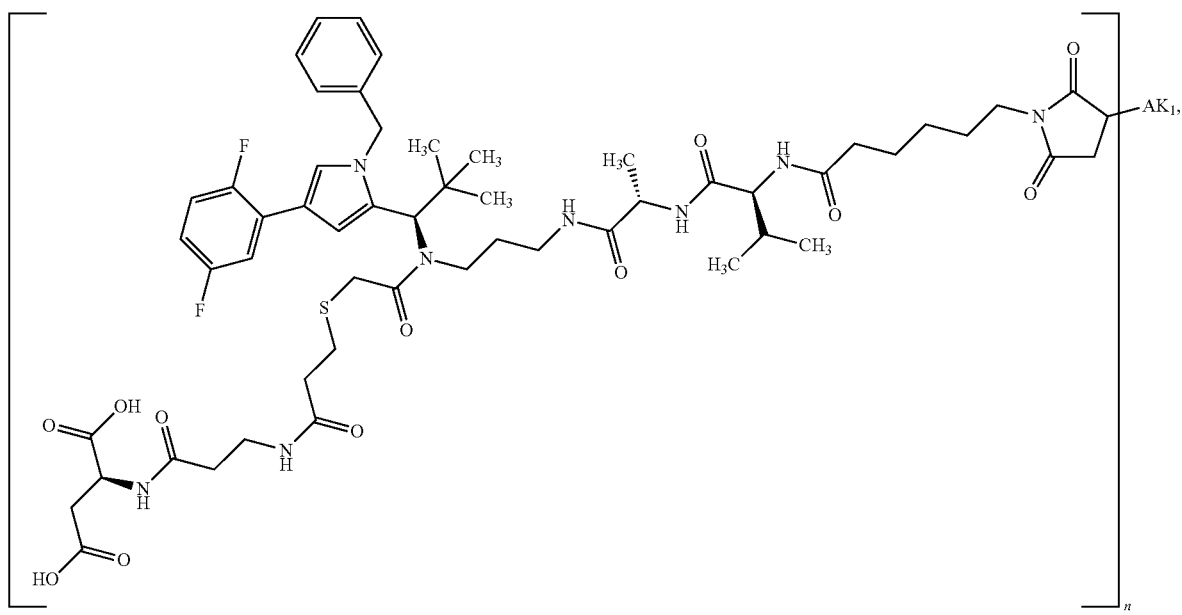
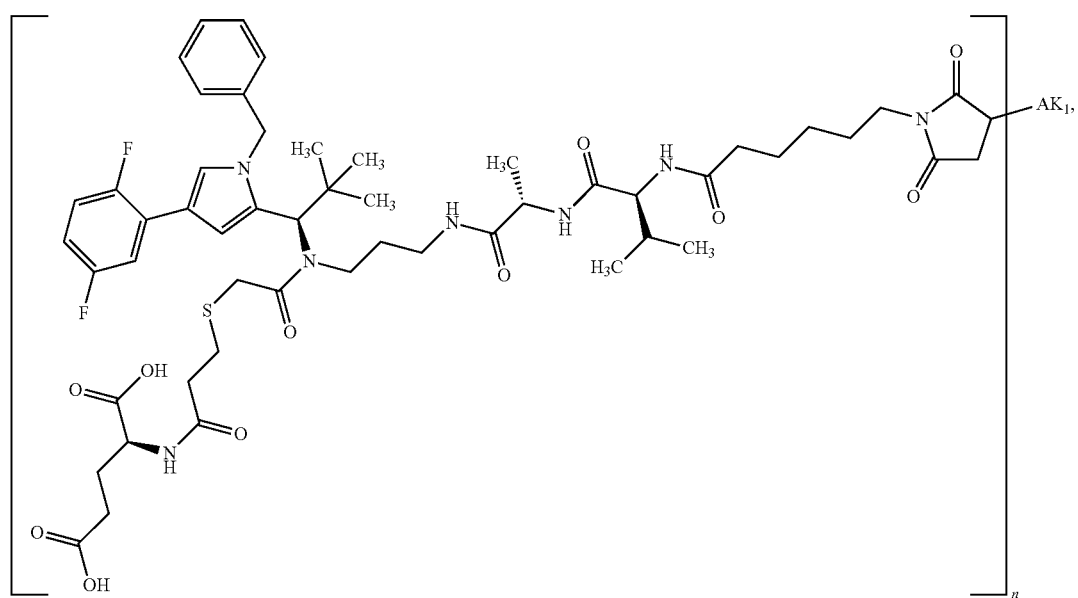

619
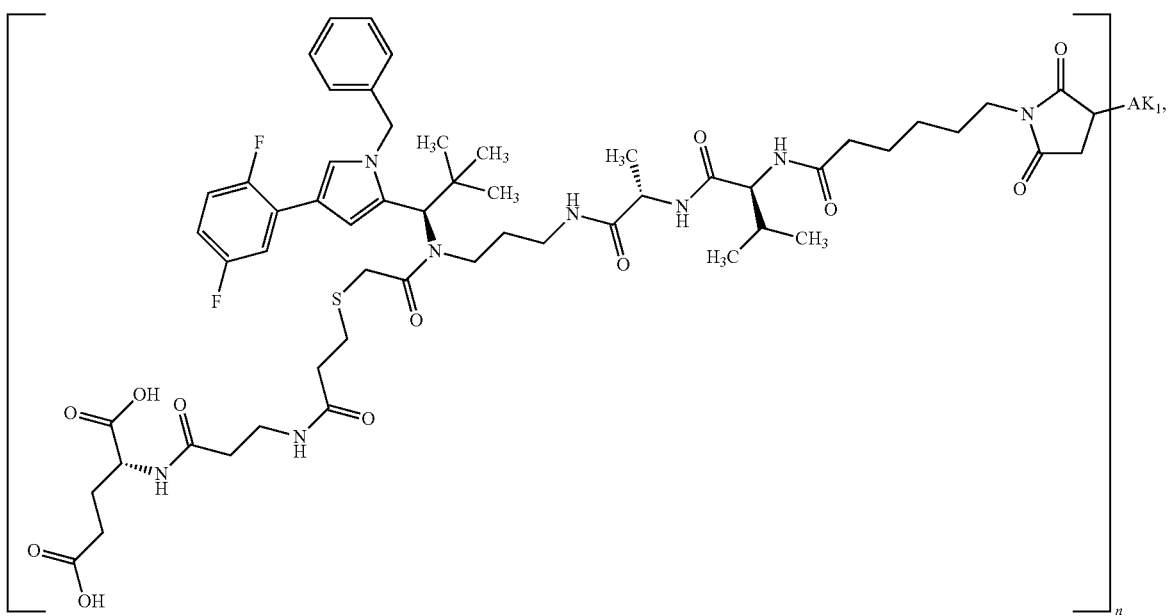
620
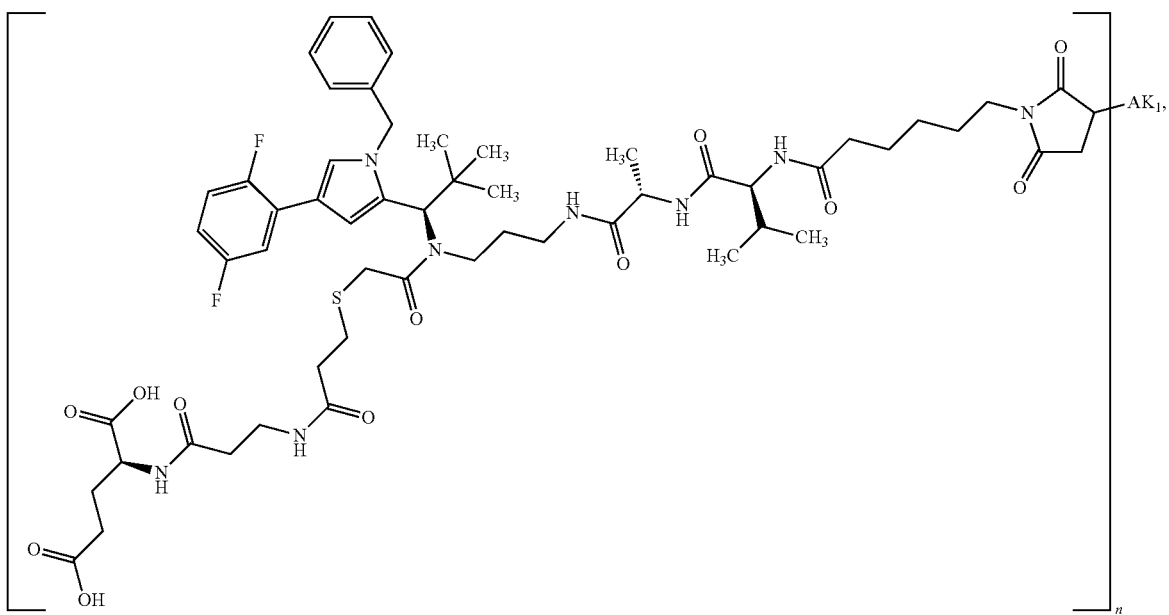

621
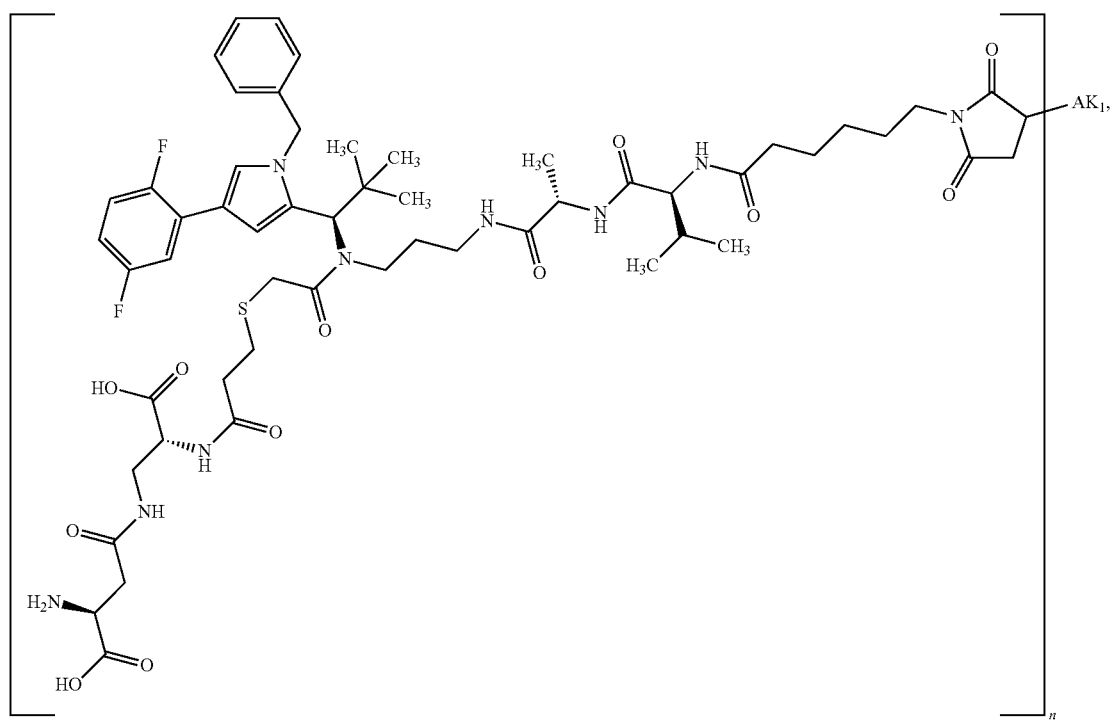
622
-continued
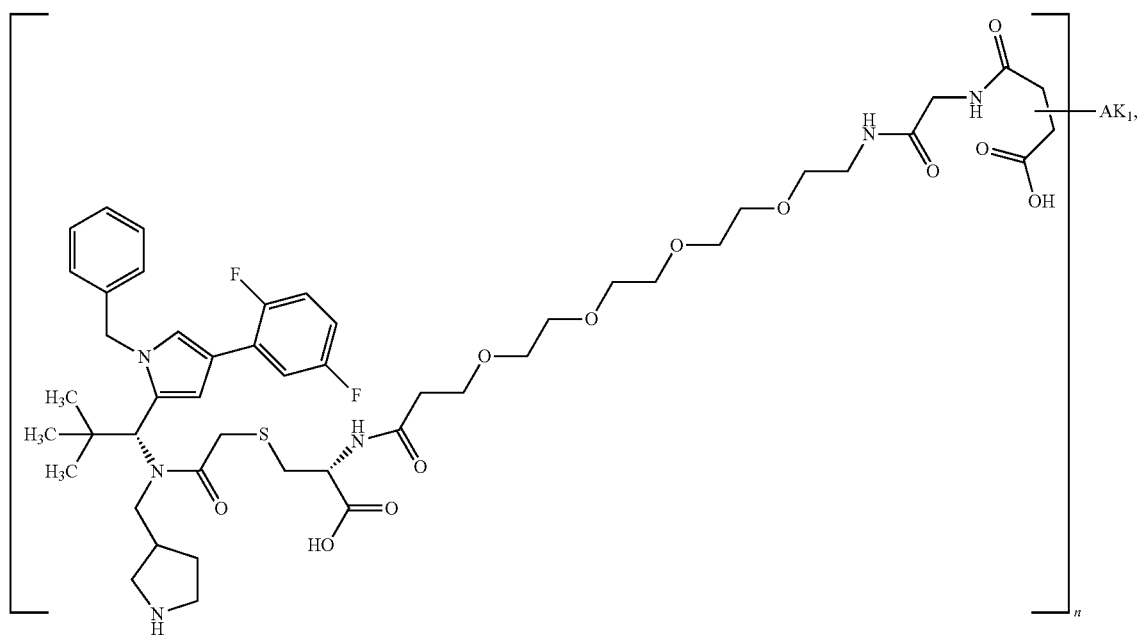

-continued

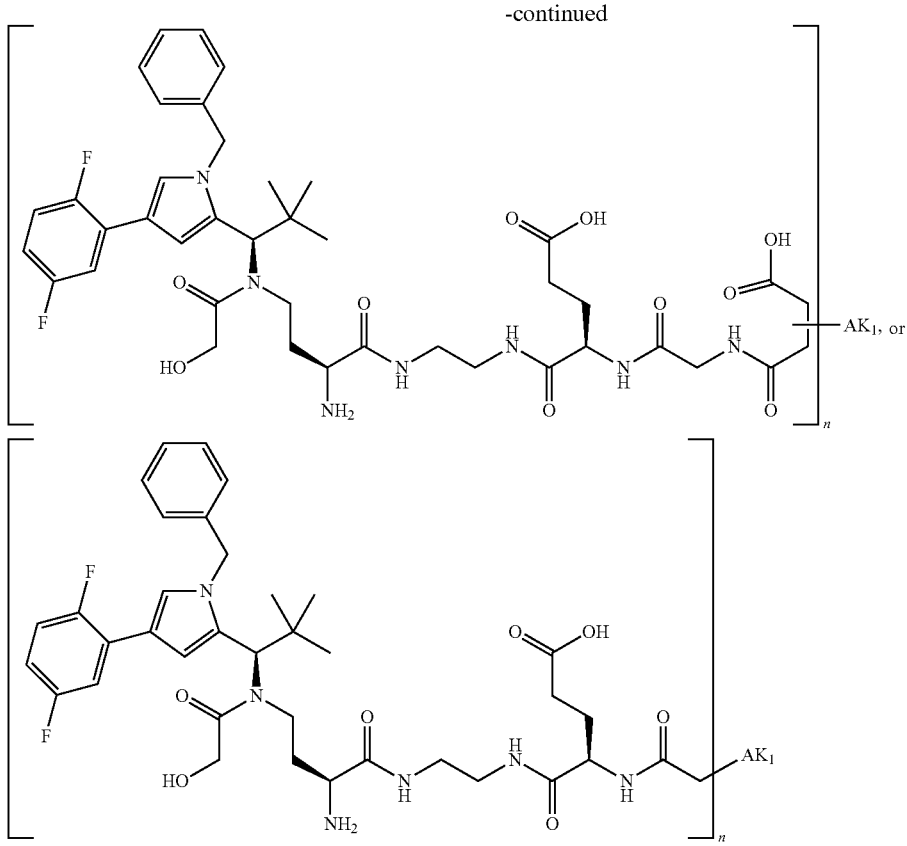

wherein
AK1 is an anti-CD123 antibody attached via cysteine and AK2 is an anti-CD123 antibody attached via lysine, which antibody is a chimeric or humanized variant of the antibody 7G3 or 12F1, and
n is a number from 1 to 20.

22. The conjugate according to claim 1, wherein the anti-CD123 antibody or an antigen-binding fragment thereof comprises:
   a variable heavy chain comprising the variable CDR1 sequence of the heavy chain, as shown in SEQ ID NO: 2, the variable CDR2 sequence of the heavy chain, as shown in SEQ ID NO: 3, and the variable CDR3 sequence of the heavy chain, as shown in SEQ ID NO: 4, and
   a variable light chain comprising the variable CDR1 sequence of the light chain, as shown in SEQ ID NO: 6, the variable CDR2 sequence of the light chain, as shown in SEQ ID NO: 7, and the variable CDR3 sequence of the light chain, as shown in SEQ ID NO: 8; or
   a variable heavy chain comprising the variable CDR1 sequence of the heavy chain, as shown in SEQ ID NO: 12, the variable CDR2 sequence of the heavy chain, as shown in SEQ ID NO: 13, and the variable CDR3 sequence of the heavy chain, as shown in SEQ ID NO: 14, and
   a variable light chain comprising the variable CDR1 sequence of the light chain, as shown in SEQ ID NO: 16, the variable CDR2 sequence of the light chain, as shown in SEQ ID NO: 17, and the variable CDR3 sequence of the light chain, as shown in SEQ ID NO: 18; or
   a variable heavy chain comprising the variable CDR1 sequence of the heavy chain, as shown in SEQ ID NO: 22, the variable CDR2 sequence of the heavy chain, as shown in SEQ ID NO: 23, and the variable CDR3 sequence of the heavy chain, as shown in SEQ ID NO: 24, and
   a variable light chain comprising the variable CDR1 sequence of the light chain, as shown in SEQ ID NO: 26, the variable CDR2 sequence of the light chain, as shown in SEQ ID NO: 27, and the variable CDR3 sequence of the light chain, as shown in SEQ ID NO: 28; or
   a variable heavy chain comprising the variable CDR1 sequence of the heavy chain, as shown in SEQ ID NO: 32, the variable CDR2 sequence of the heavy chain, as shown in SEQ ID NO: 33, and the variable CDR3 sequence of the heavy chain, as shown in SEQ ID NO: 34, and
   a variable light chain comprising the variable CDR1 sequence of the light chain, as shown in SEQ ID NO: 36, the variable CDR2 sequence of the light chain, as shown in SEQ ID NO: 37, and the variable CDR3 sequence of the light chain, as shown in SEQ ID NO: 38.

23. The conjugate according to claim 1, wherein the anti-CD123 antibody or an antigen-binding fragment thereof comprises:
   a variable sequence of the heavy chain, as shown in SEQ ID NO:1, and also a variable sequence of the light chain, as shown in SEQ ID NO:5; or
   a variable sequence of the heavy chain, as shown in SEQ ID NO:11, and also a variable sequence of the light chain, as shown in SEQ ID NO: 15; or a variable sequence of the heavy chain, as shown in SEQ ID NO:21, and also a variable sequence of the light chain, as shown in SEQ ID NO:25; or a variable sequence of the heavy chain, as shown in SEQ ID NO:31, and also a variable sequence of the light chain, as shown in SEQ ID NO:35.

24. The conjugate according to claim 1, wherein the anti-CD123 antibody is an IgG antibody.

25. The conjugate according to claim 1, wherein the anti-CD123 antibody comprises:

a sequence of the heavy chain, as shown in SEQ ID NO:9, and also a sequence of the light chain, as shown in SEQ ID NO:10; or a sequence of the heavy chain, as shown in SEQ ID NO: 19, and also a sequence of the light chain, as shown in SEQ ID NO:20; or a sequence of the heavy chain, as shown in SEQ ID NO:29, and also a sequence of the light chain, as shown in SEQ ID NO:30; or a sequence of the heavy chain, as shown in SEQ ID NO:39, and also a sequence of the light chain, as shown in SEQ ID NO:40.

26. A pharmaceutical composition comprising a conjugate according to claim 1, in combination with an inert non-toxic pharmaceutically suitable auxiliary.

27. A method for treatment of lung cancer, leukemia, myeloma, Hodgkin's lymphoma or breast cancer, comprising administering to a patient in need thereof a conjugate according to claim 1.

28. The conjugate of claim 1, wherein $R^3$ is -L-#1 or a $C_{1-10}$-alkyl, $C_{6-10}$-aryl or $C_{6-10}$-aralkyl, $C_{5-10}$-heteroalkyl, $C_{1-10}$-alkyl-O—$C_{6-10}$-aryl or $C_{5-10}$-heterocycloalkyl group which may in each case be substituted by 1-3-OH groups, 1-3 halogen atoms, 1-3 halogenated alkyl groups (each having 1-3 halogen atoms), 1-3-O-alkyl groups, 1-3-SH groups, 1-3-S-alkyl groups, 1-3-O—C(=O)-alkyl groups, 1-3-O—C(=O)—NH-alkyl groups, 1-3-NH—C(=O)-alkyl groups, 1-3-NH—C(=O)—NH-alkyl groups, 1-3-S(=O)$_n$-alkyl groups, 1-3-S(=O)$_2$—NH-alkyl groups, 1-3-NH-alkyl groups, 1-3-N(alkyl)$_2$ groups, 1-3-NH$_2$ groups or 1-3-(CH$_2$)$_{0-3}$Z groups, wherein n is 0, 1 or 2, Z is —H, halogen, —OY$^3$, —SY$^3$, —NHY$^3$, —C(=O)—NY$^1$Y$^2$ or —C(=O)—OY$^3$, Y$^1$ and Y$^2$ are independently of one another —H, —NH$_2$ or —(CH$_2$)$_{0-3}$Z'

Y$^3$ is —H, —(CH$_2$)$_{0-3}$—CH(NH—C(=O)—CH$_3$)Z', —(CH$_2$)$_{0-3}$—CH(NH$_2$)Z' or —(CH$_2$)$_{0-3}$Z', and Z' is —H, —SO$_3$H, —NH$_2$ or —COOH.

* * * * *

SEQUENCE LISTING

```
<160> NUMBER OF SEQ ID NOS: 43

<210> SEQ ID NO 1
<211> LENGTH: 120
<212> TYPE: PRT
<213> ORGANISM: Artificial Sequence
<220> FEATURE:
<223> OTHER INFORMATION: TPP-5968 - VH

<400> SEQUENCE: 1

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
                20                  25                  30

Tyr Met Lys Trp Val Arg Gln Ala Pro Gly Gln Gly Leu Glu Trp Met
            35                  40                  45

Gly Asp Ile Ile Pro Ser Asn Gly Ala Thr Phe Tyr Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
```

```
                    85                  90                  95
Ala Arg Ser His Leu Leu Arg Ala Ser Trp Phe Ala Tyr Trp Gly Gln
            100                 105                 110

Gly Thr Leu Val Thr Val Ser Ser
        115                 120

<210> SEQ ID NO 2
<211> LENGTH: 5
<212> TYPE: PRT
<213> ORGANISM: Artificial Sequence
<220> FEATURE:
<223> OTHER INFORMATION: TPP-5968 - HCDR1

<400> SEQUENCE: 2

Asp Tyr Tyr Met Lys
1               5

<210> SEQ ID NO 3
<211> LENGTH: 17
<212> TYPE: PRT
<213> ORGANISM: Artificial Sequence
<220> FEATURE:
<223> OTHER INFORMATION: TPP-5968 - HCDR2

<400> SEQUENCE: 3

Asp Ile Ile Pro Ser Asn Gly Ala Thr Phe Tyr Ala Gln Lys Phe Gln
1               5                   10                  15

Gly

<210> SEQ ID NO 4
<211> LENGTH: 13
<212> TYPE: PRT
<213> ORGANISM: Artificial Sequence
<220> FEATURE:
<223> OTHER INFORMATION: TPP-5968 - HCDR3

<400> SEQUENCE: 4

Ala Arg Ser His Leu Leu Arg Ala Ser Trp Phe Ala Tyr
1               5                   10

<210> SEQ ID NO 5
<211> LENGTH: 113
<212> TYPE: PRT
<213> ORGANISM: Artificial Sequence
<220> FEATURE:
<223> OTHER INFORMATION: TPP-5968 - VL

<400> SEQUENCE: 5

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asp Tyr Ser Tyr Pro Tyr Thr Phe Gly Gln Gly Thr Lys Leu Glu Ile
            100                 105                 110
```

Lys

<210> SEQ ID NO 6
<211> LENGTH: 17
<212> TYPE: PRT
<213> ORGANISM: Artificial Sequence
<220> FEATURE:
<223> OTHER INFORMATION: TPP-5968 - LCDR1

<400> SEQUENCE: 6

Lys Ser Ser Gln Ser Leu Leu Asn Ser Gly Asn Gln Lys Asn Tyr Leu
1               5                   10                  15

Thr

<210> SEQ ID NO 7
<211> LENGTH: 7
<212> TYPE: PRT
<213> ORGANISM: Artificial Sequence
<220> FEATURE:
<223> OTHER INFORMATION: TPP-5968 - LCDR2

<400> SEQUENCE: 7

Trp Ala Ser Thr Arg Glu Ser
1               5

<210> SEQ ID NO 8
<211> LENGTH: 9
<212> TYPE: PRT
<213> ORGANISM: Artificial Sequence
<220> FEATURE:
<223> OTHER INFORMATION: TPP-5968 - LCDR3

<400> SEQUENCE: 8

Gln Asn Asp Tyr Ser Tyr Pro Tyr Thr
1               5

<210> SEQ ID NO 9
<211> LENGTH: 449
<212> TYPE: PRT
<213> ORGANISM: Artificial Sequence
<220> FEATURE:
<223> OTHER INFORMATION: TPP-5968 - Heavy Chain

<400> SEQUENCE: 9

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
                20                  25                  30

Tyr Met Lys Trp Val Arg Gln Ala Pro Gly Gln Gly Leu Glu Trp Met
            35                  40                  45

Gly Asp Ile Ile Pro Ser Asn Gly Ala Thr Phe Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser His Leu Leu Arg Ala Ser Trp Phe Ala Tyr Trp Gly Gln
                100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala

```
                130             135             140
Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
        290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Arg Asp Glu Leu Thr Lys Asn Gln Val Ser Leu
            355                 360                 365

Thr Cys Leu Val Lys Gly Phe Tyr Pro Ser Asp Ile Ala Val Glu Trp
        370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
            435                 440                 445

Gly

<210> SEQ ID NO 10
<211> LENGTH: 220
<212> TYPE: PRT
<213> ORGANISM: Artificial Sequence
<220> FEATURE:
<223> OTHER INFORMATION: TPP-5968 - Light Chain

<400> SEQUENCE: 10

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45
```

```
Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asp Tyr Ser Tyr Pro Tyr Thr Phe Gly Gln Gly Thr Lys Leu Glu Ile
            100                 105                 110

Lys Arg Thr Val Ala Ala Pro Ser Val Phe Ile Phe Pro Pro Ser Asp
            115                 120                 125

Glu Gln Leu Lys Ser Gly Thr Ala Ser Val Val Cys Leu Leu Asn Asn
            130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
            195                 200                 205

Ser Pro Val Thr Lys Ser Phe Asn Arg Gly Glu Cys
            210                 215                 220

<210> SEQ ID NO 11
<211> LENGTH: 120
<212> TYPE: PRT
<213> ORGANISM: Artificial Sequence
<220> FEATURE:
<223> OTHER INFORMATION: TPP-5969 - VH

<400> SEQUENCE: 11

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asp Tyr
            20                  25                  30

Tyr Met Lys Trp Val Arg Gln Ala Pro Gly Gln Gly Leu Glu Trp Met
        35                  40                  45

Gly Asp Ile Ile Pro Ser Asn Gly Ala Thr Phe Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser His Leu Leu Arg Ala Ser Trp Phe Ala Tyr Trp Gly Gln
            100                 105                 110

Gly Thr Leu Val Thr Val Ser Ser
            115                 120

<210> SEQ ID NO 12
<211> LENGTH: 5
<212> TYPE: PRT
<213> ORGANISM: Artificial Sequence
<220> FEATURE:
<223> OTHER INFORMATION: TPP-5969 - HCDR1

<400> SEQUENCE: 12

Asp Tyr Tyr Met Lys
```

```
<210> SEQ ID NO 13
<211> LENGTH: 17
<212> TYPE: PRT
<213> ORGANISM: Artificial Sequence
<220> FEATURE:
<223> OTHER INFORMATION: TPP-5969 - HCDR2

<400> SEQUENCE: 13

Asp Ile Ile Pro Ser Asn Gly Ala Thr Phe Tyr Ala Gln Lys Phe Gln
1               5                   10                  15
Gly

<210> SEQ ID NO 14
<211> LENGTH: 13
<212> TYPE: PRT
<213> ORGANISM: Artificial Sequence
<220> FEATURE:
<223> OTHER INFORMATION: TPP-5969 - HCDR3

<400> SEQUENCE: 14

Ala Arg Ser His Leu Leu Arg Ala Ser Trp Phe Ala Tyr
1               5                   10

<210> SEQ ID NO 15
<211> LENGTH: 113
<212> TYPE: PRT
<213> ORGANISM: Artificial Sequence
<220> FEATURE:
<223> OTHER INFORMATION: TPP-5969 - VL

<400> SEQUENCE: 15

Asp Ile Val Met Thr Gln Ser Pro Asp Ser Leu Ala Val Ser Leu Gly
1               5                   10                  15

Glu Arg Ala Thr Ile Asn Cys Glu Ser Ser Gln Ser Leu Leu Asn Ser
                20                  25                  30

Gly Asn Gln Lys Asn Tyr Leu Thr Trp Tyr Gln Gln Lys Pro Gly Gln
            35                  40                  45

Pro Pro Lys Leu Leu Ile Tyr Trp Ala Ser Thr Arg Glu Ser Gly Val
        50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asp Tyr Ser Tyr Pro Tyr Thr Phe Gly Gln Gly Thr Lys Leu Glu Ile
            100                 105                 110
Lys

<210> SEQ ID NO 16
<211> LENGTH: 17
<212> TYPE: PRT
<213> ORGANISM: Artificial Sequence
<220> FEATURE:
<223> OTHER INFORMATION: TPP-5969 - LCDR1

<400> SEQUENCE: 16

Glu Ser Ser Gln Ser Leu Leu Asn Ser Gly Asn Gln Lys Asn Tyr Leu
1               5                   10                  15
Thr
```

-continued

```
<210> SEQ ID NO 17
<211> LENGTH: 7
<212> TYPE: PRT
<213> ORGANISM: Artificial Sequence
<220> FEATURE:
<223> OTHER INFORMATION: TPP-5969 - LCDR2

<400> SEQUENCE: 17

Trp Ala Ser Thr Arg Glu Ser
1               5

<210> SEQ ID NO 18
<211> LENGTH: 9
<212> TYPE: PRT
<213> ORGANISM: Artificial Sequence
<220> FEATURE:
<223> OTHER INFORMATION: TPP-5969 - LCDR3

<400> SEQUENCE: 18

Gln Asn Asp Tyr Ser Tyr Pro Tyr Thr
1               5

<210> SEQ ID NO 19
<211> LENGTH: 449
<212> TYPE: PRT
<213> ORGANISM: Artificial Sequence
<220> FEATURE:
<223> OTHER INFORMATION: TPP-5969 - Heavy Chain

<400> SEQUENCE: 19

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asp Tyr
            20                  25                  30

Tyr Met Lys Trp Val Arg Gln Ala Pro Gly Gln Gly Leu Glu Trp Met
        35                  40                  45

Gly Asp Ile Ile Pro Ser Asn Gly Ala Thr Phe Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser His Leu Leu Arg Ala Ser Trp Phe Ala Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240
```

```
Pro Ser Val Phe Leu Phe Pro Pro Lys Pro Lys Asp Thr Leu Met Ile
            245                 250                 255

Ser Arg Thr Pro Glu Val Thr Cys Val Val Asp Val Ser His Glu
        260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly

<210> SEQ ID NO 20
<211> LENGTH: 220
<212> TYPE: PRT
<213> ORGANISM: Artificial Sequence
<220> FEATURE:
<223> OTHER INFORMATION: TPP-5969 - Light Chain

<400> SEQUENCE: 20

Asp Ile Val Met Thr Gln Ser Pro Asp Ser Leu Ala Val Ser Leu Gly
1               5                   10                  15

Glu Arg Ala Thr Ile Asn Cys Glu Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asp Tyr Ser Tyr Pro Tyr Thr Phe Gly Gln Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140
```

-continued

```
Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
            165                 170                 175

Ser Thr Tyr Ser Leu Ser Ser Thr Leu Thr Leu Ser Lys Ala Asp Tyr
        180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
        210                 215                 220

<210> SEQ ID NO 21
<211> LENGTH: 120
<212> TYPE: PRT
<213> ORGANISM: Artificial Sequence
<220> FEATURE:
<223> OTHER INFORMATION: TPP-5971 - VH

<400> SEQUENCE: 21

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asp Tyr
            20                  25                  30

Tyr Met Lys Trp Val Arg Gln Ala Pro Gly Gln Gly Leu Glu Trp Met
        35                  40                  45

Gly Asp Ile Ile Pro Ser Asn Gly Ala Thr Phe Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser His Leu Leu Arg Ala Ser Trp Phe Ala Tyr Trp Gly Gln
            100                 105                 110

Gly Thr Leu Val Thr Val Ser Ser
        115                 120

<210> SEQ ID NO 22
<211> LENGTH: 5
<212> TYPE: PRT
<213> ORGANISM: Artificial Sequence
<220> FEATURE:
<223> OTHER INFORMATION: TPP-5971 - HCDR1

<400> SEQUENCE: 22

Asp Tyr Tyr Met Lys
1               5

<210> SEQ ID NO 23
<211> LENGTH: 17
<212> TYPE: PRT
<213> ORGANISM: Artificial Sequence
<220> FEATURE:
<223> OTHER INFORMATION: TPP-5971 - HCDR2

<400> SEQUENCE: 23

Asp Ile Ile Pro Ser Asn Gly Ala Thr Phe Tyr Ala Gln Lys Phe Gln
1               5                   10                  15

Gly

<210> SEQ ID NO 24
```

```
<211> LENGTH: 13
<212> TYPE: PRT
<213> ORGANISM: Artificial Sequence
<220> FEATURE:
<223> OTHER INFORMATION: TPP-5971 - HCDR3

<400> SEQUENCE: 24

Ala Arg Ser His Leu Leu Arg Ala Ser Trp Phe Ala Tyr
1               5                   10

<210> SEQ ID NO 25
<211> LENGTH: 113
<212> TYPE: PRT
<213> ORGANISM: Artificial Sequence
<220> FEATURE:
<223> OTHER INFORMATION: TPP-5971 - VL

<400> SEQUENCE: 25

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asp Tyr Ser Tyr Pro Tyr Thr Phe Gly Gln Gly Thr Lys Leu Glu Ile
            100                 105                 110

Lys

<210> SEQ ID NO 26
<211> LENGTH: 17
<212> TYPE: PRT
<213> ORGANISM: Artificial Sequence
<220> FEATURE:
<223> OTHER INFORMATION: TPP-5971 - LCDR1

<400> SEQUENCE: 26

Lys Ser Ser Gln Ser Leu Leu Asn Ser Gly Asn Gln Lys Asn Tyr Leu
1               5                   10                  15

Thr

<210> SEQ ID NO 27
<211> LENGTH: 7
<212> TYPE: PRT
<213> ORGANISM: Artificial Sequence
<220> FEATURE:
<223> OTHER INFORMATION: TPP-5971 - LCDR2

<400> SEQUENCE: 27

Trp Ala Ser Thr Arg Glu Ser
1               5

<210> SEQ ID NO 28
<211> LENGTH: 9
<212> TYPE: PRT
<213> ORGANISM: Artificial Sequence
<220> FEATURE:
<223> OTHER INFORMATION: TPP-5971 - LCDR3
```

-continued

<400> SEQUENCE: 28

Gln Asn Asp Tyr Ser Tyr Pro Tyr Thr
1               5

<210> SEQ ID NO 29
<211> LENGTH: 449
<212> TYPE: PRT
<213> ORGANISM: Artificial Sequence
<220> FEATURE:
<223> OTHER INFORMATION: TPP-5971 - Heavy Chain

<400> SEQUENCE: 29

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asp Tyr
            20                  25                  30

Tyr Met Lys Trp Val Arg Gln Ala Pro Gly Gln Gly Leu Glu Trp Met
        35                  40                  45

Gly Asp Ile Ile Pro Ser Asn Gly Ala Thr Phe Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser His Leu Leu Arg Ala Ser Trp Phe Ala Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

```
Lys Thr Ile Ser Lys Ala Lys Gly Gln Pro Arg Glu Pro Gln Val Tyr
                340                 345                 350

Thr Leu Pro Pro Ser Arg Asp Glu Leu Thr Lys Asn Gln Val Ser Leu
            355                 360                 365

Thr Cys Leu Val Lys Gly Phe Tyr Pro Ser Asp Ile Ala Val Glu Trp
        370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly

<210> SEQ ID NO 30
<211> LENGTH: 220
<212> TYPE: PRT
<213> ORGANISM: Artificial Sequence
<220> FEATURE:
<223> OTHER INFORMATION: TPP-5971 - Light Chain

<400> SEQUENCE: 30

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asp Tyr Ser Tyr Pro Tyr Thr Phe Gly Gln Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 31
<211> LENGTH: 117
<212> TYPE: PRT
```

<213> ORGANISM: Artificial Sequence
<220> FEATURE:
<223> OTHER INFORMATION: TPP-6013 - VH

<400> SEQUENCE: 31

Gln Val Gln Leu Gln Glu Ser Gly Pro Gly Leu Val Lys Pro Ser Gln
1               5                   10                  15

Ser Leu Ser Leu Thr Cys Ser Val Thr Asp Tyr Ser Ile Thr Ser Gly
            20                  25                  30

Tyr Tyr Trp Asn Trp Ile Arg Gln Phe Pro Gly Asn Lys Leu Glu Trp
        35                  40                  45

Met Gly Tyr Ile Ser Tyr Asp Gly Ser Asn Asn Tyr Asn Pro Ser Leu
    50                  55                  60

Lys Asn Arg Ile Ser Ile Thr Arg Asp Thr Ser Lys Asn Gln Phe Phe
65                  70                  75                  80

Leu Lys Leu Ser Ser Val Thr Thr Glu Asp Thr Ala Thr Tyr Tyr Cys
                85                  90                  95

Ser Arg Gly Glu Gly Phe Tyr Phe Asp Ser Trp Gly Gln Gly Thr Thr
            100                 105                 110

Leu Thr Val Ser Ser
        115

<210> SEQ ID NO 32
<211> LENGTH: 6
<212> TYPE: PRT
<213> ORGANISM: Artificial Sequence
<220> FEATURE:
<223> OTHER INFORMATION: TPP-6013 - HCDR1

<400> SEQUENCE: 32

Ser Gly Tyr Tyr Trp Asn
1               5

<210> SEQ ID NO 33
<211> LENGTH: 16
<212> TYPE: PRT
<213> ORGANISM: Artificial Sequence
<220> FEATURE:
<223> OTHER INFORMATION: TPP-6013 - HCDR2

<400> SEQUENCE: 33

Tyr Ile Ser Tyr Asp Gly Ser Asn Asn Tyr Asn Pro Ser Leu Lys Asn
1               5                   10                  15

<210> SEQ ID NO 34
<211> LENGTH: 10
<212> TYPE: PRT
<213> ORGANISM: Artificial Sequence
<220> FEATURE:
<223> OTHER INFORMATION: TPP-6013 - HCDR3

<400> SEQUENCE: 34

Ser Arg Gly Glu Gly Phe Tyr Phe Asp Ser
1               5                   10

<210> SEQ ID NO 35
<211> LENGTH: 113
<212> TYPE: PRT
<213> ORGANISM: Artificial Sequence
<220> FEATURE:
<223> OTHER INFORMATION: TPP-6013 - VL

<400> SEQUENCE: 35

Asp Ile Met Met Ser Gln Ser Pro Ser Ser Leu Ala Val Ser Val Gly
1               5                   10                  15

Glu Lys Phe Thr Met Thr Cys Lys Ser Ser Gln Ser Leu Phe Phe Gly
            20                  25                  30

Ser Thr Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Ala
65                  70                  75                  80

Ile Ser Ser Val Met Pro Glu Asp Leu Ala Val Tyr Tyr Cys Gln Gln
                85                  90                  95

Tyr Tyr Asn Tyr Pro Trp Thr Phe Gly Gly Gly Thr Lys Leu Glu Ile
            100                 105                 110

Lys

<210> SEQ ID NO 36
<211> LENGTH: 17
<212> TYPE: PRT
<213> ORGANISM: Artificial Sequence
<220> FEATURE:
<223> OTHER INFORMATION: TPP-6013 - LCDR1

<400> SEQUENCE: 36

Lys Ser Ser Gln Ser Leu Phe Phe Gly Ser Thr Gln Lys Asn Tyr Leu
1               5                   10                  15

Ala

<210> SEQ ID NO 37
<211> LENGTH: 7
<212> TYPE: PRT
<213> ORGANISM: Artificial Sequence
<220> FEATURE:
<223> OTHER INFORMATION: TPP-6013 - LCDR2

<400> SEQUENCE: 37

Trp Ala Ser Thr Arg Glu Ser
1               5

<210> SEQ ID NO 38
<211> LENGTH: 9
<212> TYPE: PRT
<213> ORGANISM: Artificial Sequence
<220> FEATURE:
<223> OTHER INFORMATION: TPP-6013 - LCDR3

<400> SEQUENCE: 38

Gln Gln Tyr Tyr Asn Tyr Pro Trp Thr
1               5

<210> SEQ ID NO 39
<211> LENGTH: 446
<212> TYPE: PRT
<213> ORGANISM: Artificial Sequence
<220> FEATURE:
<223> OTHER INFORMATION: TPP-6013 - Heavy Chain

<400> SEQUENCE: 39

Gln Val Gln Leu Gln Glu Ser Gly Pro Gly Leu Val Lys Pro Ser Gln
1               5                   10                  15

Ser Leu Ser Leu Thr Cys Ser Val Thr Asp Tyr Ser Ile Thr Ser Gly
            20                  25                  30

-continued

```
Tyr Tyr Trp Asn Trp Ile Arg Gln Phe Pro Gly Asn Lys Leu Glu Trp
     35                  40                  45

Met Gly Tyr Ile Ser Tyr Asp Gly Ser Asn Asn Tyr Asn Pro Ser Leu
 50                  55                  60

Lys Asn Arg Ile Ser Ile Thr Arg Asp Thr Ser Lys Asn Gln Phe Phe
 65                  70                  75                  80

Leu Lys Leu Ser Ser Val Thr Thr Glu Asp Thr Ala Thr Tyr Tyr Cys
                 85                  90                  95

Ser Arg Gly Glu Gly Phe Tyr Phe Asp Ser Trp Gly Gln Gly Thr Thr
                100                 105                 110

Leu Thr Val Ser Ser Ala Ser Thr Lys Gly Pro Ser Val Phe Pro Leu
                115                 120                 125

Ala Pro Ser Ser Lys Ser Thr Ser Gly Gly Thr Ala Ala Leu Gly Cys
                130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
                180                 185                 190

Leu Gly Thr Gln Thr Tyr Ile Cys Asn Val Asn His Lys Pro Ser Asn
                195                 200                 205

Thr Lys Val Asp Lys Lys Val Glu Pro Lys Ser Cys Asp Lys Thr His
                210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
                260                 265                 270

Val Lys Phe Asn Trp Tyr Val Asp Gly Val Glu Val His Asn Ala Lys
                275                 280                 285

Thr Lys Pro Arg Glu Glu Gln Tyr Asn Ser Thr Tyr Arg Val Val Ser
                290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
                340                 345                 350

Pro Ser Arg Asp Glu Leu Thr Lys Asn Gln Val Ser Leu Thr Cys Leu
                355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
                420                 425                 430

His Asn His Tyr Thr Gln Lys Ser Leu Ser Leu Ser Pro Gly
                435                 440                 445
```

```
<210> SEQ ID NO 40
<211> LENGTH: 220
<212> TYPE: PRT
<213> ORGANISM: Artificial Sequence
<220> FEATURE:
<223> OTHER INFORMATION: TPP-6013 - Light Chain

<400> SEQUENCE: 40

Asp Ile Met Met Ser Gln Ser Pro Ser Ser Leu Ala Val Ser Val Gly
1               5                   10                  15

Glu Lys Phe Thr Met Thr Cys Lys Ser Ser Gln Ser Leu Phe Phe Gly
            20                  25                  30

Ser Thr Gln Lys Asn Tyr Leu Ala Trp Tyr Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Ala
65                  70                  75                  80

Ile Ser Ser Val Met Pro Glu Asp Leu Ala Val Tyr Tyr Cys Gln Gln
                85                  90                  95

Tyr Tyr Asn Tyr Pro Trp Thr Phe Gly Gly Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 41
<211> LENGTH: 359
<212> TYPE: PRT
<213> ORGANISM: Homo sapiens

<400> SEQUENCE: 41

Lys Glu Asp Pro Asn Pro Pro Ile Thr Asn Leu Arg Met Lys Ala Lys
1               5                   10                  15

Ala Gln Gln Leu Thr Trp Asp Leu Asn Arg Asn Val Thr Asp Ile Glu
            20                  25                  30

Cys Val Lys Asp Ala Asp Tyr Ser Met Pro Ala Val Asn Asn Ser Tyr
        35                  40                  45

Cys Gln Phe Gly Ala Ile Ser Leu Cys Glu Val Thr Asn Tyr Thr Val
    50                  55                  60

Arg Val Ala Asn Pro Pro Phe Ser Thr Trp Ile Leu Phe Pro Glu Asn
65                  70                  75                  80

Ser Gly Lys Pro Trp Ala Gly Ala Glu Asn Leu Thr Cys Trp Ile His
                85                  90                  95

Asp Val Asp Phe Leu Ser Cys Ser Trp Ala Val Gly Pro Gly Ala Pro
```

-continued

```
                100             105             110
Ala Asp Val Gln Tyr Asp Leu Tyr Leu Asn Val Ala Asn Arg Arg Gln
            115                 120                 125

Gln Tyr Glu Cys Leu His Tyr Lys Thr Asp Ala Gln Gly Thr Arg Ile
    130                 135                 140

Gly Cys Arg Phe Asp Asp Ile Ser Arg Leu Ser Ser Gly Ser Gln Ser
145                 150                 155                 160

Ser His Ile Leu Val Arg Gly Arg Ser Ala Ala Phe Gly Ile Pro Cys
                165                 170                 175

Thr Asp Lys Phe Val Val Phe Ser Gln Ile Glu Ile Leu Thr Pro Pro
            180                 185                 190

Asn Met Thr Ala Lys Cys Asn Lys Thr His Ser Phe Met His Trp Lys
            195                 200                 205

Met Arg Ser His Phe Asn Arg Lys Phe Arg Tyr Glu Leu Gln Ile Gln
    210                 215                 220

Lys Arg Met Gln Pro Val Ile Thr Glu Gln Val Arg Asp Arg Thr Ser
225                 230                 235                 240

Phe Gln Leu Leu Asn Pro Gly Thr Tyr Thr Val Gln Ile Arg Ala Arg
                245                 250                 255

Glu Arg Val Tyr Glu Phe Leu Ser Ala Trp Ser Thr Pro Gln Arg Phe
            260                 265                 270

Glu Cys Asp Gln Glu Glu Gly Ala Asn Thr Arg Ala Trp Arg Thr Ser
            275                 280                 285

Leu Leu Ile Ala Leu Gly Thr Leu Leu Ala Leu Val Cys Val Phe Val
            290                 295                 300

Ile Cys Arg Arg Tyr Leu Val Met Gln Arg Leu Phe Pro Arg Ile Pro
305                 310                 315                 320

His Met Lys Asp Pro Ile Gly Asp Ser Phe Gln Asn Asp Lys Leu Val
                325                 330                 335

Val Trp Glu Ala Gly Lys Ala Gly Leu Glu Glu Cys Leu Val Thr Glu
            340                 345                 350

Val Gln Val Val Gln Lys Thr
            355
```

<210> SEQ ID NO 42
<211> LENGTH: 286
<212> TYPE: PRT
<213> ORGANISM: Homo sapiens

<400> SEQUENCE: 42

```
Lys Glu Asp Pro Asn Pro Ile Thr Asn Leu Arg Met Lys Ala Lys
1               5                   10                  15

Ala Gln Gln Leu Thr Trp Asp Leu Asn Arg Asn Val Thr Asp Ile Glu
            20                  25                  30

Cys Val Lys Asp Ala Asp Tyr Ser Met Pro Ala Val Asn Asn Ser Tyr
            35                  40                  45

Cys Gln Phe Gly Ala Ile Ser Leu Cys Glu Val Thr Asn Tyr Thr Val
        50                  55                  60
```

```
Arg Val Ala Asn Pro Pro Phe Ser Thr Trp Ile Leu Phe Pro Glu Asn
 65                  70                  75                  80

Ser Gly Lys Pro Trp Ala Gly Ala Glu Asn Leu Thr Cys Trp Ile His
             85                  90                  95

Asp Val Asp Phe Leu Ser Cys Ser Trp Ala Val Gly Pro Gly Ala Pro
            100                 105                 110

Ala Asp Val Gln Tyr Asp Leu Tyr Leu Asn Val Ala Asn Arg Arg Gln
        115                 120                 125

Gln Tyr Glu Cys Leu His Tyr Lys Thr Asp Ala Gln Gly Thr Arg Ile
130                 135                 140

Gly Cys Arg Phe Asp Asp Ile Ser Arg Leu Ser Ser Gly Ser Gln Ser
145                 150                 155                 160

Ser His Ile Leu Val Arg Gly Arg Ser Ala Ala Phe Gly Ile Pro Cys
                165                 170                 175

Thr Asp Lys Phe Val Val Phe Ser Gln Ile Glu Ile Leu Thr Pro Pro
            180                 185                 190

Asn Met Thr Ala Lys Cys Asn Lys Thr His Ser Phe Met His Trp Lys
        195                 200                 205

Met Arg Ser His Phe Asn Arg Lys Phe Arg Tyr Glu Leu Gln Ile Gln
210                 215                 220

Lys Arg Met Gln Pro Val Ile Thr Glu Gln Val Arg Asp Arg Thr Ser
225                 230                 235                 240

Phe Gln Leu Leu Asn Pro Gly Thr Tyr Thr Val Gln Ile Arg Ala Arg
                245                 250                 255

Glu Arg Val Tyr Glu Phe Leu Ser Ala Trp Ser Thr Pro Gln Arg Phe
            260                 265                 270

Glu Cys Asp Gln Glu Glu Gly Ala Asn Thr Arg Ala Trp Arg
        275                 280                 285
```

<210> SEQ ID NO 43
<211> LENGTH: 5
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (3)..(3)
<223> OTHER INFORMATION: Xaa can be any amino acid

<400> SEQUENCE: 43

```
Trp Ser Xaa Trp Ser
1               5
```